(12) United States Patent
Nakamura et al.

(10) Patent No.: US 8,198,454 B2
(45) Date of Patent: Jun. 12, 2012

(54) AMIDE DERIVATIVES AND MEDICINAL USE THEREOF

(75) Inventors: Mitsuharu Nakamura, Tokyo (JP);
Takao Kamahori, Tokyo (JP); Seigo Ishibuchi, Tokyo (JP); Yoichi Naka, Nakatsu (JP); Hiroshi Sumichika, Tokyo (JP); Katsuhiko Itoh, Saitama (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 12/458,095

(22) Filed: Jun. 30, 2009

(65) Prior Publication Data

US 2010/0041656 A1    Feb. 18, 2010

Related U.S. Application Data

(63) Continuation of application No. 10/380,502, filed as application No. PCT/JP01/07977 on Sep. 14, 2001, now Pat. No. 7,855,297.

(30) Foreign Application Priority Data

Sep. 14, 2000   (JP) .................................. 2000-280540
Dec. 20, 2000   (JP) .................................. 2000-386813

(51) Int. Cl.
*C07D 401/00* (2006.01)
*A61K 31/44* (2006.01)
(52) U.S. Cl. ....................................... 546/256; 514/333
(58) Field of Classification Search .................. 546/146; 514/307
See application file for complete search history.

(56) References Cited

U.S. PATENT DOCUMENTS

| | | |
|---|---|---|
| 5,491,152 A | 2/1996 | Wilde et al. |
| 2008/0194640 A1 | 8/2008 | Nakamura et al. |

FOREIGN PATENT DOCUMENTS

| | | |
|---|---|---|
| EP | 181136 | 5/1986 |
| EP | 0181136 | 10/1986 |
| EP | 0 512 570 | 11/1992 |
| EP | 0978279 | 7/1999 |
| EP | 978279 | 2/2000 |
| JP | 5-294960 | 11/1993 |
| JP | 10-182648 | 7/1998 |
| WO | 94/07815 | 4/1994 |
| WO | 94/27971 | 12/1994 |
| WO | 99/00406 | 1/1999 |

OTHER PUBLICATIONS

Caplus 2000:475658 abstract, "Preparation of tetrahyro-2H-thiopyran-1,1-dioxides as inhibitors of matrix metalloproteinases or tumor necrosis factor alpha", Taniguchi et. al., 2000.*

Hardman, J., ed. Goodman and Gilman's The Pharmacological Basis of Therapeutics, 9th ed., 1996 McGraw-Hill.*
Guo, R-F. et al.,Annu. Rev. Immunol. 2005, vol. 23, 821-52.*
Theodore C. Pellas, et al., "C5a Receptor Antagonists", Current Pharmaceutical Design, 1999, vol. 5, 737-755.
Allan K. Wong, et al., "Development of C5a Receptor Antagonists", IDRUGS, 1999, vol. 2, No. 7, pp. 686-693.
Craig Gerard, et al., "C5a Anaphylatoxin and Its Seven Transmembrane-Segment Receptor", Annu. Rev. Immunol., 1994, 12:775-808.
W. Czech, et al., "Distinct Amplification of the C5a-Receptor Pathways in Normodense and Hypodense Eosinophils of Patients with Atopic Dermatitis" Scand. J. Immunol. 53, 235-239, 2001.
Ryohei F. Tsuji, et al., "Early Local Generation of C5a Initiates the Elicitation of Contact Sensitivity by Leading to Early T Cell Recruitment", The Journal of Immunology, 2000, vol. 165, pp. 1588-1598.
Edda Fiebiger, et al., "Anti-FcεRIα Autoantibodies in Autoimmune-mediated Disorders Identification of a Structure-Function Relationship" J. Clin Invest., vol. 101, No. 1, Jan. 1998, pp. 243-251.
Ulrich Baumann, et al., "A Codominant Role of FcγRI/III and C5aR in the Reverse Arthus Reaction[1]", The Journal of Immunology, 2000, vol. 164, pp. 1065-1070.

(Continued)

*Primary Examiner* — Janet Andres
*Assistant Examiner* — Heidi Reese
(74) *Attorney, Agent, or Firm* — Oblon, Spivak, McClelland, Maier & Neustadt, L.L.P.

(57) ABSTRACT

The present invention relates to an amide derivative of the formula (1), having a C5a receptor antagonistic action

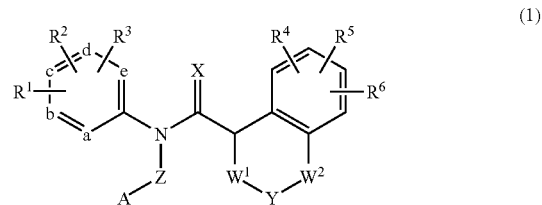

(1)

wherein each symbol is as defined in the specification.

The above-mentioned amide derivative, an optically active form thereof and a pharmaceutically acceptable salt thereof are promising as an agent for the treatment or prophylaxis of diseases or syndromes caused by inflammation caused by C5a [e.g., autoimmune diseases such as rheumatism, systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease and serious organ injury (e.g., pneumonia, nephritis, hepatitis and pancreatitis and the like) due to activation of leukocytes caused by ischemia reperfusion, trauma, burn, surgical invasion and the like]. Moreover, they are useful as a therapeutic or prophylactic agent for the infectious diseases caused by bacteria and virus that invade via a C5a receptor.

37 Claims, No Drawings

OTHER PUBLICATIONS

Toshio Fujiyoshi, et al., "The Anti-allergic Effects of EB-382, a Non-steroidal Antiinflammatory Agent", Yakugaku Zassi, 1987, vol. 107, pp. 170-174.

H. Michael Belmont, et al., Complement Activation During Systemic Lupus Erythematosus; $C3_a$ $C5_a$ Anaphylatoxins Circulate During Exacerbations of Disease; Arthritis and Rheumatism, vol. 29, No. 9 (Sep. 1986) pp. 1085-1089.

Boris J. Czermak, et al., Protective effects of C5a blockade in sepsis; Nature Medicine, vol. 5, No. 7, Jul. 1999, pp. 788-792.

Richard A Robbins, et al., Activation of the Complement System in the Adult Respiratory Distress Syndrome [1-4] ARDS: American Review of Respiratory Dieseases, 135, 1987, pp. 651-658.

Hideaki Takematsu, MD, et al., Quantification of Chemotactic Peptides ($C5_a$ Anaphylatoxin and IL-8) in Psoriatic Lesional Skin, Archives of Dermatology, vol. 129, Jan. 1993, pp. 74-80.

J. Ember et al., "Complement factors and their receptors", Immunopharmacology, vol. 38, pp. 3-15, 1997.

C. Gerard et al., "C5a Anaphylatoxin and its seven transmembrane-segement receptor", Annu. Rev. Immunol., vol. 12, pp. 775-808, 1999.

A. Wong et al., "Development of C5a receptor antagonists", Idrugs, vol. 2, No. 7, pp. 686-693, 1999.

T. Pallas et al., "C5a Receptor Antagonists", Current Pharmaceutical Design, vol. 5, pp. 737-755, 1999.

T. J. Lanza et al., "Substituted 4,6-Diaminoquinolines as inhibitors of C5a Receptor Binding", J. Med. Chem., vol. 35, pp. 252-258, 1992.

Price et al., "Some Naphtalene Analogs of Desoxycorticosterone", Journal of the American Chemical Society, vol. 69, pp. 2261-2264 (1947).

Hcaplus 133: 104964.

* cited by examiner

AMIDE DERIVATIVES AND MEDICINAL USE THEREOF

This application is a continuation of Ser. No. 10/380,502, filed May 8, 2003 now U.S. Pat. No. 7,855,297, which is a 371 U.S. national stage of International Application No. PCT/JP01/07977 filed Sep. 14, 2001, herein incorporated by reference in their entirety.

TECHNICAL FIELD

The present invention relates to an amide derivative showing a C5a receptor antagonistic action and useful for the prophylaxis or treatment of autoimmune diseases such as rheumatism, systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease or serious organ injury (e.g., pneumonia, nephritis, hepatitis and pancreatitis and the like) due to activation of leukocytes caused by ischemia reperfusion, trauma, burn, surgical invasion and the like, an optically active form thereof a pharmaceutically acceptable salt thereof and pharmaceutical use thereof.

BACKGROUND ART

When the complement system is activated, the protein of the complement system is enzymolysed and fragments having various physiological activities are produced. One of the fragments, complement component C5a, is a glycoprotein having a molecular weight of about 11,000, consists of 74 amino acids and has a strong inflammation inducing action. C5a has a broad range of actions such as smooth muscle contraction, promotion of blood vessel permeability, migration of leukocyte, degranulation of leukocyte, production of reactive oxygen species, reinforcement of antibody production, induction of production of cytokine, TNF (tumor necrosis factor) and leukotriene, and the like, and is said to be a causative substance of diseases such as autoimmune diseases (e.g., rheumatism and systemic lupus erythematosus and the like), sepsis, adult respiratory distress syndrome, chronic obstructive pulmonary disease, allergic diseases (e.g., asthma and the like), atherosclerosis, cardiac infarction, brain infarction, psoriasis, Alzheimer's disease, serious organ injuries (e.g., pneumonia, nephritis, hepatitis, pancreatitis and the like) due to activation of leukocytes caused by ischemia reperfusion, trauma, burn, surgical invasion and the like, and the like [Annu. Rev. Immunol., vol. 12, pp. 775-808 (1994), Immunopharmacology, vol. 38, pp. 3-15 (1997), Curr. Pharm. Des., vol. 5, pp. 737-755 (1999) and IDrugs, vol. 2, pp. 686-693 (1999)].

Accordingly, a non-peptide small molecular compound having a C5a receptor antagonistic action is expected as a novel non-steroid type antiinflammatory drug. In addition, it can be expected as a prophylactic or therapeutic drug of infectious diseases caused by bacteria or virus that invades via a C5a receptor.

As regards the C5a antagonist, for example, the following patent applications have been published. JP-A-10-182648 discloses TAN-2474 related compounds having a C5a antagonistic action. In addition, the specification of WO94/07815 discloses peptide derivatives having a C5a receptor antagonistic action, the specification of WO99/00406 discloses cyclic peptide derivatives having a C5a receptor antagonistic action.

Heretofore, however, a pharmaceutical drug, that prevents or treats diseases or syndromes due to the inflammation caused by C5a by inhibiting the action of C5a, has not been developed.

DISCLOSURE OF THE INVENTION

In view of the above-mentioned situation, the present inventors have conducted intensive studies with the aim of finding a non-peptide compound having a C5a receptor antagonistic action. As a result, they have found that an amide derivative according to the present invention shows a C5a receptor antagonistic action, which resulted in the completion of the present invention.

Accordingly, the present invention provides the following.
1. An amide derivative represented by the formula (1)

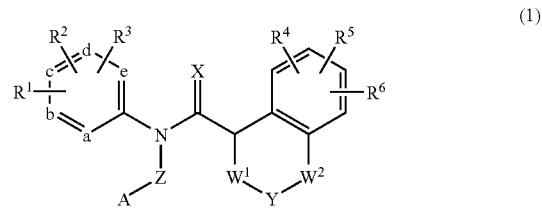

wherein
$R^1$, $R^2$ and $R^3$ are the same or different and each is hydrogen atom, alkyl group optionally having substituents, alkenyl group optionally having substituents, alkynyl group optionally having substituents, cycloalkyl group optionally having substituents, aryl group optionally having substituents, heteroaryl group optionally having substituents, arylalkyl group optionally having substituents, heteroarylalkyl group optionally having substituents, alkoxy group optionally having substituents, aryloxy group, arylalkyloxy group, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group optionally having substituents, alkoxycarbonyl group, carboxyl group, acylamino group, sulfamoyl group optionally having substituents or haloalkyl group, or any two of $R^1$, $R^2$ and $R^3$ in combination with the adjacent carbon atom may form a ring, a, b, c, d and e are each carbon atom, or 1 or 2 of a, b, c, d and e is(are) nitrogen atom(s) (provided that the nitrogen atom here may be bonded to oxygen atom to form amine oxide) and the rest are carbon atoms, $R^4$, $R^5$ and $R^6$ are the same or different and each is hydrogen atom, alkyl group optionally having substituents, alkenyl group optionally having substituents, alkynyl group optionally having substituents, cycloalkyl group optionally having substituents, aryl group optionally having substituents, heteroaryl group optionally having substituents, arylalkyl group optionally having substituents, heteroarylalkyl group optionally having substituents, alkoxy group optionally having substituents, aryloxy group, arylalkyloxy group, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group optionally having substituents, alkoxycarbonyl group, carboxyl group, acylamino group, sulfamoyl group optionally having substituents, haloalkyl group or haloalkyloxy group, A is hydrogen atom, cycloalkyl group optionally having substituents, aryl group optionally having substituents, heteroaryl group optionally having substituents or cyclic amino group optionally having substituents, $W^1$ and $W^2$ are the same or different and each is a bond or alkylene($C_n$) optionally having substituents wherein n is an integer of 1 to 3, X is oxygen atom or sulfur atom, Y is a bond, oxygen atom, —CO—, —N($R^7$)— wherein $R^7$ is hydrogen atom or alkyl group optionally having substituents, —$SO_m$— wherein m is an integer of 0 to 2, —CON($R^8$)— wherein $R^8$ is hydrogen atom or alkyl group optionally having substituents or —N($R^9$)CO— wherein $R^9$ is hydrogen atom or alkyl group optionally having substituents), and Z is a bond or alkylene group optionally having substituents (hereinafter sometimes abbreviated as amide derivative (1)), an optically active form thereof or pharmaceutically acceptable salt thereof.

2. The amide derivative of the above-mentioned 1, wherein, in the formula (1), $R^1$, $R^2$ and $R^3$ are the same or different and each is hydrogen atom, alkyl group optionally having substituents, alkenyl group optionally having substituents, alkynyl group optionally having substituents, cycloalkyl group, alkoxy group optionally having substituents, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, tetrazolyl group, oxadiazolyl group, sulfamoyl group or haloalkyl group, a, b, c, d and e are each carbon atom, or 1 or 2 of a, b, c, d and e is(are) nitrogen atom(s) and the rest are carbon atoms, $R^4$, $R^5$ and $R^6$ are the same or different and each is hydrogen atom, alkyl group optionally having substituents, alkenyl group optionally having substituents, alkynyl group optionally having substituents, cycloalkyl group, alkoxy group optionally having substituents, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, tetrazolyl group, oxadiazolyl group, sulfamoyl group or haloalkyl group, A is hydrogen atom, cycloalkyl group, aryl group optionally having substituents, heteroaryl group optionally having substituents or cyclic amino group, $W^1$ and $W^2$ are the same or different and each is a bond or alkylene ($C_n$) optionally having substituents wherein n is an integer of 1 to 3, X is oxygen atom or sulfur atom, Y is a bond, oxygen atom, —CO—, —N($R^7$)— wherein $R^7$ is hydrogen atom or alkyl group optionally having substituents, —$SO_m$— wherein m is an integer of 0 to 2, —CON($R^8$)— wherein $R^8$ is hydrogen atom or alkyl group optionally having substituents or —N($R^9$)CO— wherein $R^9$ is hydrogen atom or alkyl group optionally having substituents), and Z is a bond or alkylene group optionally having substituents, an optically active form thereof or a pharmaceutically acceptable salt thereof.

3. The amide derivative of the above-mentioned 2, wherein a, b, c, d and e in the formula (1) are all carbon atoms, an optically active form thereof or a pharmaceutically acceptable salt thereof.

4. The amide derivative of the above-mentioned 1, wherein $R^1$, $R^2$ and $R^3$ in the formula (1) are the same or different and each is hydrogen atom, alkyl group having 2 to 4 carbon atoms or alkoxy group, an optically active form thereof or a pharmaceutically acceptable salt thereof.

5. The amide derivative of the above-mentioned 1, wherein $R^1$, $R^2$ and $R^3$ in the formula (1) are the same or different and each is hydrogen atom, alkyl group having 2 to 4 carbon atoms or alkoxy group having 2 to 4 carbon atoms, an optically active form thereof or a pharmaceutically acceptable salt thereof.

6. The amide derivative of the above-mentioned 1, wherein $R^1$, $R^2$ and $R^3$ in the formula (1) are the same or different and each is hydrogen atom, alkyl group having 2 to 4 carbon atoms or methoxy group, an optically active form thereof or a pharmaceutically acceptable salt thereof.

7. The amide derivative of the above-mentioned 1, wherein $R^4$, $R^5$ and $R^6$ in the formula (1) are the same or different and each is hydrogen atom, alkyl group optionally having substituents, alkoxy group optionally having substituents, acyloxy group optionally having substituents, halogen atom, hydroxyl group, amino group, alkylamino group, dialkylamino group, cyclic amino group, carboxyl group, haloalkyl group or haloalkyloxy group, an optically active form thereof or a pharmaceutically acceptable salt thereof.

8. The amide derivative of the above-mentioned 1, wherein $R^4$, $R^5$ and $R^6$ in the formula (1) are the same or different and each is hydrogen atom, alkyl group optionally having substituents, alkoxy group optionally having substituents, acyloxy group optionally having substituents, halogen atom, hydroxyl group, amino group, alkylamino group, dialkylamino group, cyclic amino group, carboxyl group or haloalkyl group, an optically active form thereof or a pharmaceutically acceptable salt thereof.

9. The amide derivative of the above-mentioned 1, wherein Z of the formula (1) is —$CH_2$—, an optically active form thereof or a pharmaceutically acceptable salt thereof.

10. The amide derivative of the above-mentioned 1, wherein A of the formula (1) is aryl group optionally having substituents or heteroaryl group optionally having substituents, an optically active form thereof or a pharmaceutically acceptable salt thereof.

11. The amide derivative of the above-mentioned 1, wherein A of the formula (1) is phenyl group optionally having substituents, pyridyl group optionally having substituents, pyrazolyl group optionally having substituents, thiazolyl group optionally having substituents, oxazolyl group optionally having substituents or thienyl group optionally having substituents, an optically active form thereof or a pharmaceutically acceptable salt thereof.

12. The amide derivative of the above-mentioned 1, wherein A of the formula (1) is phenyl group optionally having substituents or a nitrogen-containing heterocyclic group selected from the group consisting of the following formulas (Aa)-(Ac)

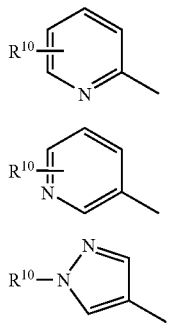

(Aa)

(Ab)

(Ac)

wherein $R^{10}$ is hydrogen atom, alkyl group optionally having substituents, alkenyl group optionally having substituents, alkynyl group optionally having substituents, cycloalkyl group, alkoxy group optionally having substituents, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, tetrazolyl group, oxadiazolyl group, sulfamoyl group or haloalkyl group, an optically active form thereof or a pharmaceutically acceptable salt thereof.

13. The amide derivative of the above-mentioned 1, wherein X of the formula (1) is oxygen atom, an optically active form thereof or a pharmaceutically acceptable salt thereof.

14. The amide derivative of the above-mentioned 1, wherein —$W^1$—Y—$W^2$— of the formula (1) is —$(CH_2)_2$—, —$(CH_2)_3$— or —$(CH_2)_2O$—, an optically active form thereof or a pharmaceutically acceptable salt thereof.

15. The amide derivative of any of the above-mentioned 1, wherein $R^1$, $R^2$ and $R^3$ of the formula (1) are the same or different and each is hydrogen atom, alkyl group having 2 to 4 carbon atoms or alkoxy group having 2 to 4 carbon atoms, a, b, c, d and e are each carbon atom, or either b or d is nitrogen atom and the rest are carbon atoms, $R^4$, $R^5$ and $R^6$ are the same or different and each is hydrogen atom, methoxy group, halogen atom or hydroxyl group, Z is —$CH_2$—, A is phenyl group optionally having substituents or nitrogen-containing heterocyclic group selected from the group consisting of the following formulas (Aa')-(Ae')

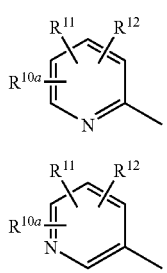

(Aa')

(Ab')

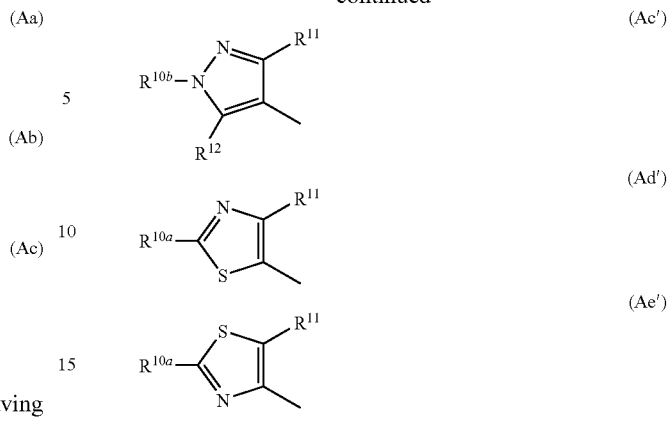

(Ac')

(Ad')

(Ae')

wherein $R^{10a}$, $R^{11}$ and $R^{12}$ are the same or different and each is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents, alkoxy group optionally having substituents, aryloxy group, arylalkyloxy group, halogen atom, hydroxyl group, nitro group, cyano group, alkylthio group, amino group, alkylamino group, dialkylamino group, cyclic amino group, haloalkyl group, haloalkyloxy group, $R^{13}O(CH_2)_jO(CH_2)_kO(CH_2)_lO$— wherein j, k and l are each independently an integer of 2 to 10, $R^{13}$ is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents or haloalkyl group, or $R^{13}O(CH_2)_jO(CH_2)_kO$— wherein j, k and $R^{13}$ are as defined above, $R^{10b}$ is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents, haloalkyl group, haloalkyloxy group, $R^{13}O(CH_2)_jO(CH_2)_kO(CH_2)_l$— wherein j, k, l and $R^{13}$ are as defined above, or $R^{13}O(CH_2)_jO(CH_2)_k$— wherein j, k and $R^{13}$ are as defined above, X is oxygen atom, and —$W^1$—Y—$W^2$— is —$(CH_2)_2$— or —$(CH_2)_3$—, an optically active form thereof or a pharmaceutically acceptable salt thereof.

16. The amide derivative of any of the above-mentioned 1 to 15, wherein the amide derivative is selected from the group consisting of N-[(4-dimethylaminophenyl)methyl]-N-(4-ethylphenyl)-1,2,3,4-tetrahydronaphthalene-1-carboxamide, N-[(4-dimethylaminophenyl)methyl]-N-(4-ethylphenyl)indan-1-carboxamide, N-[(4-dimethylaminophenyl)methyl]-N-(4-isopropylphenyl)-1,2,3,4-tetrahydronaphthalene-1-carboxamide, N-[(4-dimethylaminophenyl)methyl]-N-(4-isopropylphenyl)-7-methoxy-1,2,3,4-tetrahydronaphthalene-1-carboxamide, N-[(4-dimethylaminophenyl)methyl]-N-(4-isopropylphenyl) chroman-4-carboxamide, N-[(4-dimethylaminophenyl)methyl]-5-hydroxy-N-(4-isopropylphenyl)-1,2,3,4-tetrahydronaphthalene-1-carboxamide, N-[(4-dimethylaminophenyl)methyl]-N-(4-isopropylphenyl)-6-methoxyindan-1-carboxamide,
N-[(1-ethylpyrazol-4-yl)methyl]-N-(4-isopropylphenyl)-1,2,3,4-tetrahydronaphthalene-1-carboxamide,
N-[(4-dimethylaminophenyl)methyl]-N-(4-isopropylphenyl)-6-methoxychroman-4-carboxamide,
N-[(1,3-dioxaindan-5-yl)methyl]-N-(4-isopropylphenyl)-7-methoxy-1,2,3,4-tetrahydronaphthalene-1-carboxamide,
N-[(4-dimethylaminophenyl)methyl]-4-hydroxy-N-(4-isopropylphenyl)indan-1-carboxamide,
N-[(1-ethylpyrazol-4-yl)methyl]-5-hydroxy-N-(4-isopropylphenyl)-1,2,3,4-tetrahydronaphthalene-1-carboxamide, and
N-[(1-ethylpyrazol-4-yl)methyl]-4-hydroxy-N-(4-isopropylphenyl) indan-1-carboxamide,
an optically active form thereof or pharmaceutically acceptable salt thereof.

17. The amide derivative of the above-mentioned 1, wherein the amide derivative is
N-[(1-ethylpyrazol-4-yl)methyl]-5-hydroxy-N-(6-isopropylpyridin-3-yl)-1,2,3,4-tetrahydronaphthalene-1-carboxamide,
an optically active form thereof or a pharmaceutically acceptable salt thereof.

18. The amide derivative of any of the above-mentioned 1 to 15, wherein the amide derivative is selected from the group consisting of
N-[(2,6-dimethoxypyridin-3-yl)methyl]-5-hydroxy-N-(4-isopropylphenyl)-1,2,3,4-tetrahydronaphthalene-1-carboxamide,
5-hydroxy-N-(4-isopropylphenyl)-N-[(6-phenoxypyridin-3-yl) methyl]-1,2,3,4-tetrahydronaphthalene-1-carboxamide,
N-[(6-dimethylaminopyridin-3-yl)methyl]-5-hydroxy-N-(4-isopropylphenyl)-1,2,3,4-tetrahydronaphthalene-1-carboxamide,
N-[(4-dimethylaminophenyl)methyl]-7-ethoxy-N-(4-isopropylphenyl)-1,2,3,4-tetrahydronaphthalene-1-carboxamide,
N-[(5-ethylthiophen-2-yl)methyl]-N-(4-isopropylphenyl)-1,2,3,4-tetrahydronaphthalene-1-carboxamide,
N-[(4-dimethylaminophenyl)methyl]-7-fluoro-N-(4-isopropylphenyl)-1,2,3,4-tetrahydronaphthalene-1-carboxamide,
N-(4-bromophenyl)-N-[(4-dimethylaminophenyl)methyl]-7-fluoro-1,2,3,4-tetrahydronaphthalene-1-carboxamide,
N-[(4-dimethylaminophenyl)methyl]-8-fluoro-5-hydroxy-N-(4-isopropylphenyl)-1,2,3,4-tetrahydronaphthalene-1-carboxamide,
N-[(2,6-dimethoxypyridin-3-yl)methyl]-5-hydroxy-N-(6-isopropylpyridin-3-yl)-1,2,3,4-tetrahydronaphthalene-1-carboxamide,
N-[(4-dimethylaminophenyl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-[(6-methoxypyridin-3-yl)methyl]-1,2,3,4-tetrahydronaphthalene-1-carboxamide,
N-[(2,4-dimethylthiazol-5-yl)methyl]-5-hydroxy-N-(6-isopropylpyridin-3-yl)-1,2,3,4-tetrahydronaphthalene-1-carboxamide,
N-(4-butylphenyl)-N-[(4-dimethylaminophenyl)methyl]-5-hydroxy-1,2,3,4-tetrahydronaphthalene-1-carboxamide,
N-[(4-dimethylaminophenyl)methyl]-7-methoxy-N-(4-methoxyphenyl)-1,2,3,4-tetrahydronaphthalene-1-carboxamide,
N-(4-chlorophenyl)-N-[(4-dimethylaminophenyl)methyl]-7-methoxy-1,2,3,4-tetrahydronaphthalene-1-carboxamide,
N-[(4-dimethylaminophenyl)methyl]-7-methoxy-N-(4-methylphenyl)-1,2,3,4-tetrahydronaphthalene-1-carboxamide,
N-[(4-dimethylaminophenyl)methyl]-N-(4-ethoxyphenyl)-7-methoxy-1,2,3,4-tetrahydronaphthalene-1-carboxamide,
N-(4-bromophenyl)-N-[(4-dimethylaminophenyl)methyl]-7-methoxy-1,2,3,4-tetrahydronaphthalene-1-carboxamide,
N-(4-isopropylphenyl)-7-methoxy-N-[(4-methylaminophenyl)methyl]-1,2,3,4-tetrahydronaphthalene-1-carboxamide,
N-[(4-dimethylaminophenyl)methyl]-5-hydroxy-N-(4-methoxyphenyl)-1,2,3,4-tetrahydronaphthalene-1-carboxamide,
5-hydroxy-N-(4-isopropylphenyl)-N-[(2-methylthiazol-4-yl)methyl]-1,2,3,4-tetrahydronaphthalene-1-carboxamide,
N-(4-bromophenyl)-N-[(dimethylaminophenyl)methyl]-5-hydroxy-1,2,3,4-tetrahydronaphthalene-1-carboxamide,
N-(4-isopropylphenyl)-7-methoxy-N-(2-tolylmethyl)-1,2,3,4-tetrahydronaphthalene-1-carboxamide,
N-[(2,4-dichlorophenyl)methyl]-N-(4-isopropylphenyl)-7-methoxy-1,2,3,4-tetrahydronaphthalene-1-carboxamide,
N-(4-isopropylphenyl)-7-methoxy-N-[(4-nitrophenyl)methyl]-1,2,3,4-tetrahydronaphthalene-1-carboxamide,
N-(4-isopropylphenyl)-7-methoxy-N-[(3-tolyl)methyl]-1,2,3,4-tetrahydronaphthalene-1-carboxamide,
N-(4-isopropylphenyl)-7-methoxy-N-[(4-tolyl)methyl]-1,2,3,4-tetrahydronaphthalene-1-carboxamide,
N-[(2-fluorophenyl)methyl]-N-(4-isopropylphenyl)-7-methoxy-1,2,3,4-tetrahydronaphthalene-1-carboxamide,
N-[(4-fluorophenyl)methyl]-N-(4-isopropylphenyl)-7-methoxy-1,2,3,4-tetrahydronaphthalene-1-carboxamide,
N-[(2,4-dimethylphenyl)methyl]-N-(4-isopropylphenyl)-7-methoxy-1,2,3,4-tetrahydronaphthalene-1-carboxamide,
N-(4-isopropylphenyl)-7-methoxy-N-[(2-methoxyphenyl)methyl]-1,2,3,4-tetrahydronaphthalene-1-carboxamide,
N-[(2-chlorophenyl)methyl]-N-(4-isopropylphenyl)-7-methoxy-1,2,3,4-tetrahydronaphthalene-1-carboxamide,
N-[(2,4-difluorophenyl)methyl]-N-(4-isopropylphenyl)-7-methoxy-1,2,3,4-tetrahydronaphthalene-1-carboxamide,
N-[(2,6-difluorophenyl)methyl]-N-(4-isopropylphenyl)-7-methoxy-1,2,3,4-tetrahydronaphthalene-1-carboxamide,
N-[(4-ethoxyphenyl)methyl]-N-(4-isopropylphenyl)-7-methoxy-1,2,3,4-tetrahydronaphthalene-1-carboxamide,
N-(4-isopropylphenyl)-7-methoxy-N-[(4-oxachroman-6-yl)methyl]-1,2,3,4-tetrahydronaphthalene-1-carboxamide,
N-[(2,3-dimethoxyphenyl)methyl]-N-(4-isopropylphenyl)-7-methoxy-1,2,3,4-tetrahydronaphthalene-1-carboxamide,
N-[(2,4-dimethoxyphenyl)methyl]-N-(4-isopropylphenyl)-7-methoxy-1,2,3,4-tetrahydronaphthalene-1-carboxamide,
N-(4-isopropylphenyl)-7-methoxy-N-[(2-trifluoromethylphenyl)methyl]-1,2,3,4-tetrahydronaphthalene-1-carboxamide,
N-(4-isopropylphenyl)-7-methoxy-N-[(4-trifluoromethylphenyl)methyl]-1,2,3,4-tetrahydronaphthalene-1-carboxamide,
N-[(2-bromophenyl)methyl]-N-(4-isopropylphenyl)-7-methoxy-1,2,3,4-tetrahydronaphthalene-1-carboxamide, N-(4-isopropylphenyl)-7-methoxy-N-[(2,3,4-trimethoxyphenyl)methyl]-1,2,3,4-tetrahydronaphthalene-1-carboxamide, 5-hydroxy-N-(4-isopropylphenyl)-N-{[1-(2-pyridylmethyl)pyrazol-4-yl]methyl}-1,2,3,4-tetrahydronaphthalene-1-carboxamide, N-[(1-benzylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(2-pyridylmethyl)pyrazol-4-yl]methyl}-1,2,3,4-tetrahydronaphthalene-1-carboxamide, N-({1-[(4-fluorophenyl)methyl]pyrazol-4-yl}methyl)-5-hydroxy-N-(6-isopropylpyridin-3-yl)-1,2,3,4-tetrahydronaphthalene-1-carboxamide, N-({1-[(4-chlorophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide, 5-hydroxy-N-(6-isopropylpyridin-3-yl)-N-({1-[(4-methoxyphenyl)methyl]pyrazol-4-yl}methyl)-1,2,3,4-tetrahydronaphthalene-1-carboxamide, N-({1-[(4-bromophenyl)methyl]pyrazol-4-yl}methyl)-5-hydroxy-N-(6-isopropylpyridin-3-yl)-1,2,3,4-tetrahydronaphthalene-1-carboxamide, N-({1-[(3-chlorophenyl)methyl]pyrazol-4-yl}methyl)-5-hydroxy-N-(6-isopropylpyridin-3-yl)-1,2,3,4-tetrahydronaphthalene-1-carboxamide, N-({1-[(2-chlorophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[(4-methylphenyl)methyl]pyrazol-4-yl}methyl)-1,2,3,4-tetrahydronaphthalene-1-carboxamide, 5-hydroxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(5-methoxypyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide, 8-fluoro-5-hydroxy-N-(6-isopropylpyridin-3-yl)-N-{[1-(2-pyridylmethyl)pyrazol-4-yl]methyl}-1,2,3,4-tetrahydronaphthalene-1-carboxamide, 5-hydroxy-N-(6-isopropylpyridin-3-yl)-N-({1-[(4-trifluoromethylpyridin-2-yl)methyl]pyrazole-4-yl}methyl)-1,2,3,4-tetrahydronaphthalene-1-carboxamide, N-({1-[(6-dimethylaminopyridin-2-yl)methyl]pyrazol-4-yl}methyl)-5-hydroxy-N-(6-isopropylpyridin-3-yl)-1,2,3,4-tetrahydronaphthalene-1-carboxamide, N-({1-[3-(dimethylaminophenyl)methyl]pyrazol-4-yl}methyl)-5-hydroxy-N-(6-isopropylpyridin-3-yl)-1,2,3,4-tetrahydronaphthalene-1-carboxamide, N-[(2-ethyl-4-trifluoromethylthiazol-5-yl)methyl]-5-hydroxy-N-(6-isopropylpyridin-3-yl)-1,2,3,4-tetrahydronaphthalene-1-carboxamide, 5-benzyloxy-N-(4-isopropylphenyl)-N-[(1-isopropylpyrazol-4-yl)methyl]-1,2,3,4-tetrahydronaphthalene-1-carboxamide, 5-hydroxy-N-(4-isopropylphenyl)-N-[(1-methylpyrazol-4-yl)methyl]-1,2,3,4-tetrahydronaphthalene-1-carboxamide, 5-benzyloxy-N-(4-isopropylphenyl)-N-[(1-propylpyrazol-4-yl)methyl]-1,2,3,4-tetrahydronaphthalene-1-carboxamide, N-{[1-(cyclohexylmethyl)pyrazol-4-yl]methyl}-5-hydroxy-N-(4-isopropylphenyl)-1,2,3,4-tetrahydronaphthalene-1-carboxamide, 5-hydroxy-N-(4-isopropylphenyl)-N-{[1-(3-thienylmethyl)pyrazol-4-yl]methyl}-1,2,3,4-tetrahydronaphthalene-1-carboxamide, N-{[1-(4-fluorobenzyl)pyrazol-4-yl]methyl}-5-hydroxy-N-(4-methoxyphenyl)-1,2,3,4-tetrahydronaphthalene-1-carboxamide, N-[(1-ethylpyrazol-4-yl)methyl]-5-hydroxy-N-(4-methoxyphenyl)-1,2,3,4-tetrahydronaphthalene-1-carboxamide, N-{[1-(cyclohexylmethyl)pyrazol-4-yl]methyl}-5-hydroxy-N-(4-methoxyphenyl)-1,2,3,4-tetrahydronaphthalene-1-carboxamide, 5-hydroxy-N-(6-isopropylpyridin-3-yl)-N-{[1-(2-piperidinoethyl)pyrazol-4-yl]methyl}-1,2,3,4-tetrahydronaphthalene-1-carboxamide, N-{[1-(cyclohexylmethyl)pyrazol-4-yl]methyl}-5-hydroxy-N-(6-isopropylpyridin-3-yl)-1,2,3,4-tetrahydronaphthalene-1-carboxamide, N-[(1-heptylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(3-thienylmethyl)pyrazol-4-yl]methyl}-1,2,3,4-tetrahydronaphthalene-1-carboxamide, 5-hydroxy-N-(6-isopropylpyridin-3-yl)-N-({1-[(2-methylthiazol-4-yl)methyl]pyrazol-4-yl}methyl)-1,2,3,4-tetrahydronaphthalene-1-carboxamide, N-[(1-butylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(3-methylbutyl)pyrazol-4-yl]methyl}-1,2,3,4-tetrahydronaphthalene-1-carboxamide, N-[(1-benzylpyrazol-4-yl)methyl]-5-hydroxy-N-(6-methoxypyridin-3-yl)-1,2,3,4-tetrahydronaphthalene-1-carboxamide, 5-hydroxy-N-(6-isopropylpyridin-3-yl)-N-({1-[2-(2-pyridyl)ethyl]pyrazol-4-yl}methyl)-1,2,3,4-tetrahydronaphthalene-1-carboxamide, N-[(1-dodecylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-[(1-nonylpyrazol-4-yl)methyl]-1,2,3,4-tetrahydronaphthalene-1-carboxamide, N-{[1-(2-butoxyethyl)pyrazol-4-yl]methyl}-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[2-(2-methoxyethoxy)ethyl]pyrazol-4-yl}methyl)-1,2,3,4-tetrahydronaphthalene-1-carboxamide, 5-hydroxy-N-(4-isopropylphenyl)-N-[(6-morpholinopyridin-3-yl)methyl]-1,2,3,4-tetrahydronaphthalene-1-carboxamide, 5-hydroxy-N-(4-isopropylphenyl)-N-({1-[(4-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-methoxypyridin-2-yl)methyl]pyrazol-4-yl}methyl)-1,2,3,4-tetrahydronaphthalene-1-carboxamide, 5-hydroxy-N-[(1-isopropylpyrazol-4-yl)methyl]-N-(6-isopropylpyridin-3-yl)-1,2,3,4-tetrahydronaphthalene-1-carboxamide, N-[(4-dimethylaminophenyl)methyl]-N-(6-isopropylpyridin-3-yl)-7-methoxy-1,2,3,4-tetrahydronaphthalene-1-carboxamide, 5-hydroxy-N-(6-isopropylpyridin-3-yl)-N-{[1-(2-thienylmethyl)pyrazol-4-yl]methyl}-1,2,3,4-tetrahydronaphthalene-1-carboxamide, N-({1-[(5-chlorothiophen-2-yl)methyl]pyrazol-4-yl}methyl)-5-hydroxy-N-(6-isopropylpyridin-3-yl)-1,2,3,4-tetrahydronaphthalene-1-carboxamide, 5-benzyloxy-N-({1-[2-(2-butoxyethoxy)ethyl]pyrazol-4-yl}methyl)-N-(6-isopropylpyridin-3-yl)-1,2,3,4-tetrahydronaphthalene-1-carboxamide, N-({1-[2-(2-butoxyethoxy)ethyl]pyrazol-4-yl}methyl)-5-hydroxy-N-(6-isopropylpyridin-3-yl)-1,2,3,4-tetrahydronaphthalene-1-carboxamide, and N-({1-[2-(2-ethoxyethoxy)ethyl]pyrazol-4-yl}methyl)-N-(6-isopropylpyridin-3-yl)-5-hydroxy-1,2,3,4-tetrahydronaphthalene-1-carboxamide, an optically active form thereof or a pharmaceutically acceptable salt thereof.

19. A pharmaceutical composition comprising the amide derivative of any of the aforementioned 1 to 18, an optically active form thereof or a pharmaceutically acceptable salt thereof, and a pharmaceutically acceptable additive.

20. A prophylactic or therapeutic drug of a disease, in which C5a is involved, which comprises the amide derivative of any of the aforementioned 1 to 18, an optically active form thereof or a pharmaceutically acceptable salt thereof as an active ingredient.

21. The prophylactic or therapeutic drug of the aforementioned 20, wherein the disease, in which C5a is involved, is an autoimmune disease, sepsis, adult respiratory distress syndrome, chronic obstructive pulmonary disease, an allergic disease, atherosclerosis, cardiac infarction, brain infarction, psoriasis, Alzheimer's disease, or serious organ injury due to activation of leukocytes caused by ischemia reperfusion, trauma, burn or surgical invasion.

22. The prophylactic or therapeutic drug of the aforementioned 20, wherein the disease, in which C5a is involved, is autoimmune disease, sepsis, adult respiratory distress syndrome, an allergic disease, atherosclerosis, cardiac infarction, brain infarction, psoriasis, Alzheimer's disease, or serious organ injury due to activation of leukocytes caused by ischemia reperfusion, trauma, burn or surgical invasion.

23. A C5a receptor antagonist comprising the amide derivative of any of the aforementioned 1 to 18, an optically active form thereof or a pharmaceutically acceptable salt thereof as an active ingredient.

24. The C5a receptor antagonist of the aforementioned 23, which is a prophylactic or therapeutic drug of an infectious disease caused by bacteria or virus that invades via the C5a receptor.

25. The C5a receptor antagonist of the aforementioned 23, which is used in combination with an agent for the prophylaxis or treatment of an autoimmune disease, sepsis, adult respiratory distress syndrome, chronic obstructive pulmonary disease, an allergic disease, atherosclerosis, cardiac infarction, brain infarction, psoriasis, Alzheimer's disease, or serious organ injury due to activation of leukocytes caused by ischemia reperfusion, trauma, burn or surgical invasion.

26. A combination drug with an agent for the prophylaxis or treatment of an autoimmune disease, sepsis, adult respiratory distress syndrome, chronic obstructive pulmonary disease, an allergic disease, atherosclerosis, cardiac infarction, brain infarction, psoriasis, Alzheimer's disease, or serious organ injury due to activation of leukocytes caused by ischemia reperfusion, trauma, burn or surgical invasion, which comprises the amide derivative of any of the aforementioned 1 to 18, an optionally active form thereof or a pharmaceutically acceptable salt thereof as an active ingredient.

MODE OF EMBODIMENT OF THE INVENTION

Some of the terms to be used in the present specification are defined as follows.

The "substances that bind to a C5a receptor" means C5a, a hydrolysates of C5a (e.g., C5a desArg wherein the carboxy terminal arginine of C5a has been deleted), and known or unknown substances, which are other than C5a, having affinity for C5a receptor.

The "C5a receptor antagonist" are substances that inhibit the bond between a C5a receptor and "substances that bind to a C5a receptor".

The "C5a receptor antagonistic action" means an action that inhibits a reaction that causes some physiological changes (e.g., increase of intracellular $Ca^{2+}$, and the like) by binding, via C5a receptor, of "substances that bind to a C5a receptor" to cells that express the C5a receptor.

In the present specification, each symbol is as defined in the following.

In $R^1$-$R^{13}$, $R^{10a}$ and $R^{10b}$, the alkyl group is straight chain or branched chain alkyl having 1 to 18, preferably 1 to 12, carbon atoms, such as methyl, ethyl, propyl, isopropyl, butyl, isobutyl, secondary butyl, tertiary butyl, isopentyl, pentyl, 3-methylbutyl, neopentyl, 1-ethylpentyl, hexyl, 2-ethylbutyl, heptyl, octyl, nonyl, decyl, dodecyl, hexadecyl, octadecyl and the like.

In $R^1$-$R^6$ and $R^{10}$, the alkenyl group is straight chain or branched chain alkenyl having 2 to 18, preferably 2 to 12, more preferably 2 to 8, carbon atoms, such as vinyl, allyl, 1-propenyl, isopropenyl, 2-butenyl, 3-butenyl, 2-pentenyl, 4-pentenyl, 3-methyl-2-butenyl, 5-hexenyl, 4-methyl-3-pentenyl, 2-octenyl, 2-dodecenyl and the like.

In $R^1$-$R^6$ and $R^{10}$, the alkynyl group is straight chain or branched chain alkynyl having 2 to 18, preferably 2 to 12, more preferably 2 to 5, carbon atoms, such as ethynyl, 2-propynyl, 2-butynyl, 5-pentynyl, 2-octynyl, 2-dodecynyl and the like.

In $R^1$-$R^6$, $R^{10}$-$R^{13}$, $R^{10a}$, $R^{10b}$ and A, the cycloalkyl group, for example, is cycloalkyl preferably having 3 to 7 carbon atoms, such as cyclopropyl, cyclopentyl, cyclohexyl, cycloheptyl and the like.

In $R^1$-$R^6$, $R^{10}$-$R^{12}$ and $R^{10a}$, the alkoxy group is, for example, straight chain or branched chain alkoxy having preferably 1 to 18 carbon atoms, such as methoxy, ethoxy, propoxy, isopropoxy, butoxy, isobutoxy, secondary butoxy, tertiary butoxy, pentyloxy, 3-methylbutoxy, neopentyloxy, hexyloxy, heptyloxy, octyloxy, decyloxy, hexadecyloxy, octadecyloxy and the like, and the like.

In $R^1$-$R^6$ and $R^{10}$, the acyloxy group is, for example, alkanoyloxy having 2 to 9 carbon atoms, such as acetoxy, propionyloxy, butyryloxy, isobutyryloxy, 2-methylbutyryloxy, 2,2-dimethylbutyryloxy, 3,3-dimethylbutyryloxy, valeryloxy, isovaleryloxy, hexanoyloxy, heptanoyloxy, octanoyloxy, nonanoyloxy and the like, cycloalkylcarbonyloxy having 4 to 8 carbon atoms, such as cyclopentylcarbonyloxy, cyclohexylcarbonyloxy and the like, arylcarbonyloxy having 7 to 11 carbon atoms, such as benzoyloxy, naphthoyloxy and the like, and the like.

In $R^1$-$R^6$, $R^{10}$-$R^{12}$ and $R^{10a}$, the halogen atom is chlorine, bromine, fluorine or iodine.

In $R^1$-$R^6$ and $R^{10}$, the acyl group is, for example, alkanoyl having 1 to 8, preferably 2 to 8, carbon atoms, such as formyl, acetyl, propionyl, butyryl, isobutyryl, valeryl, isovaleryl, hexanoyl, octanoyl and the like, cycloalkylcarbonyl having 4 to 8 carbon atoms (cycloalkyl moiety is same as the aforementioned cycloalkyl), such as cyclopropylcarbonyl, cyclopentylcarbonyl, cyclohexylcarbonyl and the like, aroyl having 7 to 11 carbon atoms, such as benzoyl, toluoyl, naphthoyl and the like, heteroarylcarbonyl such as nicotinoyl, thenoyl, furoyl and the like, and the like.

In $R^1$-$R^6$, $R^{10}$-$R^{12}$ and $R^{10a}$, the alkylthio group is straight chain or branched chain alkylthio having 1 to 18, preferably 1 to 12, carbon atoms, such as methylthio, ethylthio, propylthio, isopropylthio, butylthio, isobutylthio, secondary butylthio, tertiary butylthio, pentylthio, 3-methylbutylthio, neopentylthio, 1-ethylpentylthio, hexylthio, 2-ethylbutylthio, heptylthio, octylthio, decylthio, hexadecylthio, octadecylthio and the like.

In $R^1$-$R^6$ and $R^{10}$, the alkylsulfonyl group is alkylsulfonyl group wherein the alkyl moiety is as defined for the above-mentioned "alkyl group" (straight chain or branched chain alkyl having 1 to 18, preferably 1 to 12, carbon atoms). Examples thereof include methylsulfonyl group, ethylsulfonyl group, propylsulfonyl group and the like.

In $R^1$-$R^6$, $R^{10}$-$R^{12}$ and $R^{10a}$, the alkylamino group is alkylamino group wherein the alkyl moiety is as defined for the above-mentioned "alkyl group". Examples thereof include methylamino group, ethylamino group, propylamino group, isopropylamino group and the like.

In $R^1$-$R^6$, $R^{10}$-$R^{12}$ and $R^{10a}$, the dialkylamino group is that wherein each alkyl moiety is as defined for the above-mentioned "alkyl group" and respective alkyl may be the same or different. Examples thereof include dimethylamino group, diethylamino group, dipropylamino group, diisopropylamino group, ethylmethylamino group, butylmethylamino group and the like.

The cyclic amino group in $R^1$-$R^6$, $R^{10}$-$R^{12}$, $R^{10a}$ and A is a 3 to 8-membered saturated cyclic amino group that may contain one or more oxygen atoms and sulfur atoms as ring-constituting atoms, besides carbon atom and nitrogen atom. Examples thereof include aziridinyl, azetidinyl, pyrrolizinyl, piperidino, piperidyl, piperazino, piperazinyl, azepinyl, morpholino, morpholinyl, thiomorpholinyl, imidazolidinyl, heptamethyleneimino and the like.

In $R^1$-$R^6$, the sulfamoyl group is sulfamoyl group optionally mono- or di-substituted with lower alkyl having 1 to 3 carbon atoms. Examples thereof include sulfamoyl, methylsulfamoyl, ethylsulfamoyl, dimethylsulfamoyl and the like.

In $R^1$-$R^6$, $R^{10}$-$R^{13}$, $R^{10a}$ and $R^{10b}$, the haloalkyl group is alkyl substituted by one or more halogen atoms which is as the aforementioned "halogen atom", wherein the alkyl moiety is as defined for the aforementioned "alkyl group". Examples thereof include fluoromethyl, difluoromethyl, trifluoromethyl, 2,2,2-trifluoroethyl, chloromethyl, trichloromethyl and the like.

In the haloalkyloxy group for $R^4$-$R^6$, $R^{11}$, $R^{12}$, $R^{10a}$ and $R^{10b}$, "haloalkyl" is as defined for the aforementioned haloalkyl. Examples of haloalkyloxy group include trifluoromethyloxy, 2,2,2-trifluoroethyloxy and the like.

In $R^1$-$R^6$, $R^{11}$-$R^{13}$, $R^{10a}$, $R^{10b}$ and A, the aryl group is, for example, aryl having 6 to 14 carbon atoms such as phenyl, 1-naphthyl, 2-naphthyl, 1-anthryl, 2-anthryl and the like. The aryl may have one or more substituents wherein the position of substitution is not particularly limited. The substituents may form a ring, may be condensed with aryl and may be partially reduced.

In $R^1$-$R^6$, $R^{11}$-$R^{13}$, $R^{10a}$, $R^{10b}$ and A, the heteroaryl is a 5- to 14-membered ring group that contains one or more hetero atoms such as nitrogen atom, oxygen atom, sulfur atom and the like as ring-constituting atoms, besides carbon atom, may be monocyclic or polycyclic and may be partially reduced. Examples thereof include pyridyl, thienyl, furyl, pyrrolyl, pyrazolyl, imidazolyl, oxazolyl, isoxazolyl, thiazolyl, pyridazinyl, pyrimidinyl, pyrazinyl, indolyl, indolinyl, benzofuranyl, 2,3-dihydrobenzofuranyl, benzothienyl, benzoxazolyl, benzimidazolyl, benzothiazolyl, quinolyl, isoquinolyl, quinoxalinyl, quinazolinyl, phenazinyl, tetrazolyl, oxadiazolyl, imidazothienyl, 1,3-dioxaindanyl, 4-oxachromanyl and the like. These heteroaryl groups optionally have one or more substituents, where the position of substitution is not particularly limited. In the case of a polycycle, any ring may be substituted. The bond may be present on any ring, if it is possible.

When any two of $R^1$, $R^2$ and $R^3$ in combination with the adjacent carbon atom form a ring, it may be condensed with aryl (the "aryl" here is as defined above), or partially reduced. In addition, the ring may contain one or more hetero atoms such as nitrogen atom, oxygen atom, sulfur atom and the like to form heteroaryl (the "heteroaryl" here is as defined above), and a ring wherein the heteroaryl is partially reduced is also encompassed.

In $R^1$-$R^6$ and $R^{10}$, the alkoxycarbonyl group is that wherein the alkoxy moiety is as defined for the above-mentioned "alkoxy group". The alkoxycarbonyl group is exemplified by methoxycarbonyl group, ethoxycarbonyl group, propoxycarbonyl group, isopropoxycarbonyl group, tertiary butoxycarbonyl group and the like.

In $R^1$-$R^6$, the acylamino group is that wherein the acyl group is as defined for the above-mentioned "acyl". In addition, alkylsulfonylamino and arylsulfonylamino are also encompassed in acylamino, wherein the "alkyl" and "aryl" here are as defined above. Examples of the acylamino group include acetamide, benzamide and the like.

In $W^1$, $W^2$ and Z, the alkylene group is alkylene having 1 to 10, preferably 1 or 2, carbon atoms. Examples thereof include methylene, ethylene, trimethylene, tetramethylene, pentamethylene, hexamethylene, octamethylene, nonamethylene, decamethylene and the like.

In $R^1$-$R^6$, $R^{11}$, $R^{12}$, $R^{10a}$, $R^{10b}$ and $R^{13}$, the arylalkyl is that wherein the aryl moiety is as defined for the aforementioned "aryl group" and the alkyl moiety is straight chain or branched chain alkyl having 1 to 12, preferably 1 to 3, carbon atoms. Examples of arylalkyl include benzyl, 2-phenylethyl, 3-phenylpropyl, 1-naphthylmethyl, 2-(1-naphthyl)ethyl, 2-naphthylmethyl, 2-(2-naphthyl)ethyl and the like. The aryl moiety of arylalkyl may have one or more substituents, where the position of substitution is not particularly limited.

In $R^1$-$R^6$, $R^{11}$, $R^{12}$, $R^{10a}$, $R^{10b}$ and $R^{13}$, the heteroarylalkyl group is that wherein the heteroaryl moiety is as defined for the aforementioned "heteroaryl group" and the alkyl moiety is straight chain or branched chain alkyl having 1 to 12, preferably 1 to 3, carbon atoms. Examples of heteroarylalkyl include 2-pyridylmethyl, 3-pyridylmethyl, 4-pyridylmethyl, 2-thienylmethyl, 3-thienylmethyl, 2-furylmethyl, 3-furylmethyl, 2-pyrrolylmethyl, 3-pyrrolylmethyl, 3-pyrazolylmethyl, 4-pyrazolylmethyl, 5-pyrazolylmethyl, 2-imidazolylmethyl, 4-imidazolylmethyl, 5-imidazolylmethyl, 2-oxazolylmethyl, 4-oxazolylmethyl, 5-oxazolylmethyl, 3-isoxazolylmethyl, 4-isoxazolylmethyl, 5-isoxazolylmethyl, 2-thiazolylmethyl, 4-thiazolylmethyl, 5-thiazolylmethyl, 3-isothiazolylmethyl, 4-isothiazolylmethyl, 5-isothiazolylmethyl, 2-(2-pyridyl)ethyl, 2-(3-pyridyl)ethyl, 2-(4-pyridyl)ethyl, 2-(2-thienyl)ethyl, 2-(3-thienyl)ethyl, 2-(2-thiazolyl)ethyl, 2-(4-thiazolyl)ethyl, 2-(5-thiazolyl)ethyl and the like. The heteroaryl moiety of heteroarylalkyl group may have one or more substituents, where the position of substitution is not particularly limited.

In $R^1$-$R^6$, the carbamoyl group optionally having substituents is a carbamoyl group optionally mono or di-substituted by lower alkyl having 1 to 3 carbon atoms. Examples thereof include carbamoyl, methylcarbamoyl, ethylcarbamoyl, dimethylcarbamoyl and the like.

In $R^1$-$R^6$, $R^{11}$, $R^{12}$ and $R^{10a}$, the aryloxy group is that wherein the aryl moiety is as defined for the aforementioned "aryl group". Examples of aryloxy group include phenoxy and the like.

In $R^1$-$R^6$, $R^{11}$, $R^{12}$ and $R^{10a}$, the arylalkyloxy group is that wherein the arylalkyl moiety is as defined for the aforementioned "arylalkyl". Examples of arylalkyloxy group include benzyloxy and the like.

In the present invention, specific examples of the substituent of the "optionally having substituents" include alkyl group, alkenyl group, alkynyl group, cycloalkyl group, aryl group, arylalkyl group, heteroaryl group, heteroarylalkyl group, alkoxy group, aryloxy group, arylalkyloxy group, acyloxy group, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, acylamino group, sulfamoyl group, haloalkyl group, haloalkyloxy group, oxo group (provided that when it substitutes divalent nitrogen atom, it forms amine oxide), tetrahydropyran-2-yloxy, $R^{13}O(CH_2)_jO(CH_2)_kO(CH_2)_lO$— wherein j, k, l and $R^{13}$ are as defined above, $R^{13}O(CH_2)_jO(CH_2)_kO$— wherein j, k and $R^{13}$ are as defined above, $R^{13}O(CH_2)_jO$— wherein j and $R^{13}$ are as defined above, $R^{13}O(CH_2)_jO(CH_2)_kO(CH_2)_l$— wherein j, k, l and $R^{13}$ are as defined above, $R^{13}O(CH_2)_jO(CH_2)_k$— wherein j, k and $R^{13}$ are as defined-above, $R^{13}O(CH_2)_j$— wherein j and $R^{13}$ are as defined above), and the like, which are as defined above. These substituents may be optionally substituted further by the substituents recited here. In addition, the substituted substituents are optionally substituted further by the substituents recited here.

As the amide derivative (1), an optically active form thereof or pharmaceutically acceptable salt thereof of the present invention, for example, amide derivative (1), wherein $R^1$, $R^2$ and $R^3$ are the same or different and each is hydrogen atom, alkyl group optionally having substituents, alkenyl group optionally having substituents, alkynyl group optionally having substituents, cycloalkyl group, alkoxy group optionally having substituents, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, tetrazolyl group, oxadiazolyl group, sulfamoyl group or haloalkyl group, a, b, c, d and e are each carbon atom, or one or two of a, b, c, d and e is(are) nitrogen atom(s) and the rest are carbon atoms, $R^4$, $R^5$ and $R^6$ are the same or different and each is hydrogen atom, alkyl group optionally having substituents, alkenyl group optionally having substituents, alkynyl group optionally having substituents, cycloalkyl group, alkoxy group optionally having substituents, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, tetrazolyl group, oxadiazolyl group, sulfamoyl group or haloalkyl group, A is hydrogen atom, cycloalkyl group, aryl group optionally having substituents, heteroaryl group optionally having substituents or cyclic amino group, $W^1$ and $W^2$ are the same or different and each is a bond or alkylene ($C_n$) optionally having substituents wherein n is an integer of 1 to 3, X is oxygen atom or sulfur atom, Y is a bond, oxygen atom, —CO— and —N($R^7$)— wherein $R^7$ is hydrogen atom or alkyl group optionally having substituents, —$SO_m$— wherein m is an integer of 0 to 2, —CON($R^8$)— wherein $R^8$ is hydrogen atom or alkyl group optionally having substituents, or —N($R^9$)CO— wherein $R^9$ is hydrogen atom or alkyl group optionally having substituents, and Z is a bond or alkylene group optionally having substituents, an optically active form thereof or a pharmaceutically acceptable salt thereof is preferable. At this time, a, b, c, d and e are preferably all carbon atoms.

The $R^1$, $R^2$ and $R^3$ of the formula (1) are preferably the same or different and each is hydrogen atom, alkyl group having 2 to 4 carbon atoms or alkoxy group, more preferably hydrogen atom, alkyl group having 2 to 4 carbon atoms or alkoxy group having 2 to 4 carbon atoms, still more preferably hydrogen atom, alkyl group having 2 to 4 carbon atoms or methoxy group.

As $R^1$, preferred is alkyl group having 2 to 4 carbon atoms or alkoxy group having 2 to 4 carbon atoms. As $R^2$ and $R^3$, preferred is hydrogen atom.

As $R^4$, $R^5$ and $R^6$ of the formula (1), preferred are the same or different and each is hydrogen atom, alkyl group optionally having substituents, alkoxy group optionally having substituents, acyloxy group optionally having substituents, halogen atom, hydroxyl group, amino group, alkylamino group, dialkylamino group, cyclic amino group, carboxyl group, haloalkyl group or haloalkyloxy group, more preferred is hydrogen atom, alkyl group optionally having substituents, alkoxy group optionally having substituents, acyloxy group optionally having substituents, halogen atom, hydroxyl group, amino group, alkylamino group, dialkylamino group, cyclic amino group, carboxyl group or haloalkyl group.

As A of the formula (1), preferred is aryl group optionally having substituents or heteroaryl group optionally having substituents, more preferred is phenyl group optionally having substituents, pyridyl group optionally having substituents, pyrazolyl group optionally having substituents, thiazolyl group optionally having substituents, oxazolyl group optionally having substituents or thienyl group optionally having substituents, still more preferred is phenyl group optionally having substituents or nitrogen-containing heterocyclic group selected from the group consisting of the following formulas (Aa)-(Ac)

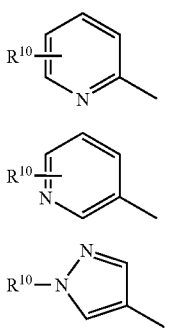
(Aa)

(Ab)

(Ac)

wherein $R^{10}$ is hydrogen atom, alkyl group optionally having substituents, alkenyl group optionally having substituents, alkynyl group optionally having substituents, cycloalkyl group, alkoxy group optionally having substituents, acyloxy group optionally having substituents, halogen atom, hydroxyl group, nitro group, cyano group, acyl group, mercapto group, alkylthio group, alkylsulfonyl group, amino group, alkylamino group, dialkylamino group, cyclic amino group, carbamoyl group, alkoxycarbonyl group, carboxyl group, tetrazolyl group, oxadiazolyl group, sulfamoyl group or haloalkyl group, or phenyl group optionally having substituents or a nitrogen-containing heterocyclic group selected from the group consisting of the following formulas (Aa')-(Ae')

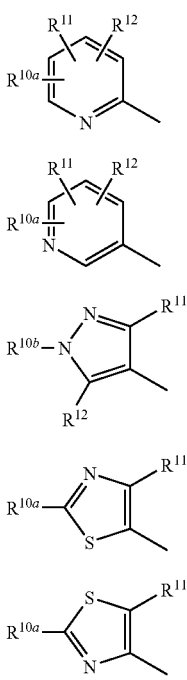
(Aa')

(Ab')

(Ac')

(Ad')

(Ae')

wherein $R^{10a}$, $R^{11}$ and $R^{12}$ are the same or different and each is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents, alkoxy group optionally having substituents, aryloxy group, arylalkyloxy group, halogen atom, hydroxyl group, nitro group, cyano group, alkylthio group, amino group, alkylamino group, dialkylamino group, cyclic amino group, haloalkyl group, haloalkyloxy group, $R^{13}O(CH_2)_jO(CH_2)_kO(CH_2)_lO-$ wherein j, k, l and $R^{13}$ are as defined above or $R^{13}O(CH_2)_jO(CH_2)_kO-$ wherein j, k and $R^{13}$ are as defined above, $R^{10b}$ is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents, haloalkyl group, $R^{13}O(CH_2)_jO(CH_2)_kO(CH_2)_l-$ wherein j, k, l and $R^{13}$ are as defined above, or $R^{13}O(CH_2)_jO(CH_2)_k-$ wherein j, k and $R^{13}$ are as defined above.

As $-W^1-Y-W^2-$ of the formula (1), $-(CH_2)_2-$, $-(CH_2)_3-$ or $-(CH_2)_2O-$ is preferable.

It is preferable that a, b, c, d and e of the formula (1) be preferably all carbon atoms, or that b (or d) be nitrogen atom and the rest be carbon atoms.

The case where the $R^1$, $R^2$ and $R^3$ of the formula (1) are the same or different and each is hydrogen atom, alkyl group having 2 to 4 carbon atoms or alkoxy group having 2 to 4 carbon atoms, a, b, c, d and e are each carbon atom, or either b or d is nitrogen atom and the rest are carbon atoms, $R^4$, $R^5$ and $R^6$ are the same or different and each is hydrogen atom, methoxy group, halogen atom or hydroxyl group, Z is $-CH_2-$, A is phenyl group optionally having substituents or a nitrogen-containing heterocyclic group selected from the group consisting of the following formulas (Aa')-(Ae')

(Aa')

(Ab')

(Ac')

(Ad')

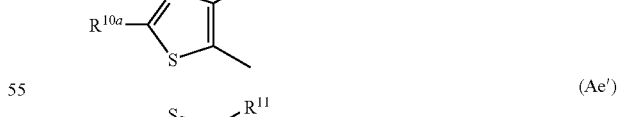
(Ae')

wherein $R^{10a}$, $R^{11}$ and $R^{12}$ are the same or different and each is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents, alkoxy group optionally having substituents, aryloxy group, arylalkyloxy group, halogen atom, hydroxyl group, nitro group, cyano group, alkylthio group, amino group, alkylamino group, dialkylamino group, cyclic amino group, haloalkyl group, haloalkyloxy group, $R^{13}O(CH_2)_jO(CH_2)_kO(CH_2)_lO$— wherein j, k, l and $R^{13}$ are as defined above or $R^{13}O(CH_2)_jO(CH_2)_kO$— wherein j, k and $R^{13}$ are as defined above, $R^{10b}$ is hydrogen atom, alkyl group optionally having substituents, cycloalkyl group optionally having substituents, aryl group optionally having substituents, heteroaryl group optionally having substituents, arylalkyl group optionally having substituents, heteroarylalkyl group optionally having substituents, haloalkyl group, haloalkyloxy group, $R^{13}O(CH_2)_jO(CH_2)_kO(CH_2)_l$— wherein j, k, l and $R^{13}$ are as defined above or $R^{13}O(CH_2)_jO(CH_2)_k$— wherein j, k and $R^{13}$ are as defined above, X is oxygen atom, and —$W^1$—Y—$W^2$— is —$(CH_2)_2$— or —$(CH_2)_3$— is particularly preferable.

As X of the formula (1), oxygen atom is preferable.

As —$W^1$—Y—$W^2$— of the formula (1), —$(CH_2)_2$— or —$(CH_2)_3$— is preferable.

As Z of the formula (1), —$CH_2$— is preferable.

Preferable examples of the amide derivative (1) are as follows:

N-[(4-dimethylaminophenyl)methyl]-N-(4-ethylphenyl)-1,2,3,4-tetrahydronaphthalene-1-carboxamide, N-[(4-dimethylaminophenyl)methyl]-N-(4-ethylphenyl)indan-1-carboxamide, N-[(4-dimethylaminophenyl)methyl]-N-(4-isopropylphenyl)-1,2,3,4-tetrahydronaphthalene-1-carboxamide, N-[(4-dimethylaminophenyl)methyl]-N-(4-isopropylphenyl)-7-methoxy-1,2,3,4-tetrahydronaphthalene-1-carboxamide, N-[(4-dimethylaminophenyl)methyl]-N-(4-isopropylphenyl)chroman-4-carboxamide, N-[(4-dimethylaminophenyl)methyl]-5-hydroxy-N-(4-isopropylphenyl)-1,2,3,4-tetrahydronaphthalene-1-carboxamide, N-[(4-dimethylaminophenyl)methyl]-N-(4-isopropylphenyl)-6-methoxyindan-1-carboxamide, N-[(1-ethylpyrazol-4-yl)methyl]-N-(4-isopropylphenyl)-1,2,3,4-tetrahydronaphthalene-1-carboxamide, N-[(4-dimethylaminophenyl)methyl]-N-(4-isopropylphenyl)-6-methoxychroman-4-carboxamide, N-[(1,3-dioxaindan-5-yl)methyl]-N-(4-isopropylphenyl)-7-methoxy-1,2,3,4-tetrahydronaphthalene-1-carboxamide, N-[(4-dimethylaminophenyl)methyl]-4-hydroxy-N-(4-isopropylphenyl)indan-1-carboxamide, N-[(1-ethylpyrazol-4-yl)methyl]-5-hydroxy-N-(4-isopropylphenyl)-1,2,3,4-tetrahydronaphthalene-1-carboxamide, and N-[(1-ethylpyrazol-4-yl)methyl]-4-hydroxy-N-(4-isopropylphenyl)indan-1-carboxamide, moreover, N-[(1-ethylpyrazol-4-yl)methyl]-5-hydroxy-N-(6-isopropylpyridin-3-yl)-1,2,3,4-tetrahydronaphthalene-1-carboxamide, and in addition, N-[(2,6-dimethoxypyridin-3-yl)methyl]-5-hydroxy-N-(4-isopropylphenyl)-1,2,3,4-tetrahydronaphthalene-1-carboxamide, 5-hydroxy-N-(4-isopropylphenyl)-N-[(6-phenoxypyridin-3-yl)methyl]-1,2,3,4-tetrahydronaphthalene-1-carboxamide, N-[(6-dimethylaminopyridin-3-yl)methyl]-5-hydroxy-N-(4-isopropylphenyl)-1,2,3,4-tetrahydronaphthalene-1-carboxamide, N-[(4-dimethylaminophenyl)methyl]-7-ethoxy-N-(4-isopropylphenyl)-1,2,3,4-tetrahydronaphthalene-1-carboxamide, N-[(5-ethylthiophen-2-yl)methyl]-N-(4-isopropylphenyl)-1,2,3,4-tetrahydronaphthalene-1-carboxamide, N-[(4-dimethylaminophenyl)methyl]-7-fluoro-N-(4-isopropylphenyl)-1,2,3,4-tetrahydronaphthalene-1-carboxamide, N-(4-bromophenyl)-N-[(4-dimethylaminophenyl)methyl]-7-fluoro-1,2,3,4-tetrahydronaphthalene-1-carboxamide, N-[(4-dimethylaminophenyl)methyl]-8-fluoro-5-hydroxy-N-(4-isopropylphenyl)-1,2,3,4-tetrahydronaphthalene-1-carboxamide, N-[(2,6-dimethoxypyridin-3-yl)methyl]-5-hydroxy-N-(6-isopropylpyridin-3-yl)-1,2,3,4-tetrahydronaphthalene-1-carboxamide, N-[(4-dimethylaminophenyl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-[(6-methoxypyridin-3-yl)methyl]-1,2,3,4-tetrahydronaphthalene-1-carboxamide, N-[(2,4-dimethylthiazol-5-yl)methyl]-5-hydroxy-N-(6-isopropylpyridin-3-yl)-1,2,3,4-tetrahydronaphthalene-1-carboxamide, N-(4-butylphenyl)-N-[(4-dimethylaminophenyl)methyl]-5-hydroxy-1,2,3,4-tetrahydronaphthalene-1-carboxamide, N-[(4-dimethylaminophenyl)methyl]-7-methoxy-N-(4-methoxyphenyl)-1,2,3,4-tetrahydronaphthalene-1-carboxamide, N-(4-chlorophenyl)-N-[(4-dimethylaminophenyl)methyl]-7-methoxy-1,2,3,4-tetrahydronaphthalene-1-carboxamide, N-[(4-dimethylaminophenyl)methyl]-7-methoxy-N-(4-methylphenyl)-1,2,3,4-tetrahydronaphthalene-1-carboxamide, N-[(4-dimethylaminophenyl)methyl]-N-(4-ethoxyphenyl)-7-methoxy-1,2,3,4-tetrahydronaphthalene-1-carboxamide, N-(4-bromophenyl)-N-[(4-dimethylaminophenyl)methyl]-7-methoxy-1,2,3,4-tetrahydronaphthalene-1-carboxamide, N-(4-isopropylphenyl)-7-methoxy-N-[(4-methylaminophenyl)methyl]-1,2,3,4-tetrahydronaphthalene-1-carboxamide, N-[(4-dimethylaminophenyl)methyl]-5-hydroxy-N-(4-methoxyphenyl)-1,2,3,4-tetrahydronaphthalene-1-carboxamide, 5-hydroxy-N-(4-isopropylphenyl)-N-[(2-methylthiazol-4-yl)methyl]-1,2,3,4-tetrahydronaphthalene-1-carboxamide, N-(4-bromophenyl)-N-[(dimethylaminophenyl)methyl]-5-hydroxy-1,2,3,4-tetrahydronaphthalene-1-carboxamide, N-(4-isopropylphenyl)-7-methoxy-N-(2-tolylmethyl)-1,2,3,4-tetrahydronaphthalene-1-carboxamide, N-[(2,4-dichlorophenyl)methyl]-N-(4-isopropylphenyl)-7-methoxy-1,2,3,4-tetrahydronaphthalene-1-carboxamide, N-(4-isopropylphenyl)-7-methoxy-N-[(4-nitrophenyl)methyl]-1,2,3,4-tetrahydronaphthalene-1-carboxamide, N-(4-isopropylphenyl)-7-methoxy-N-[(3-tolyl)methyl]-1,2,3,4-tetrahydronaphthalene-1-carboxamide, N-(4-isopropylphenyl)-7-methoxy-N-[(4-tolyl)methyl]-1,2,3,4-tetrahydronaphthalene-1-carboxamide, N-[(2-fluorophenyl)methyl]-N-(4-isopropylphenyl)-7-methoxy-1,2,3,4-tetrahydronaphthalene-1-carboxamide, N-[(4-fluorophenyl)methyl]-N-(4-isopropylphenyl)-7-methoxy-1,2,3,4-tetrahydronaphthalene-1-carboxamide, N-[(2,4-dimethylphenyl)methyl]-N-(4-isopropylphenyl)-7-methoxy-1,2,3,4-tetrahydronaphthalene-1-carboxamide,
N-(4-isopropylphenyl)-7-methoxy-N-[(2-methoxyphenyl)methyl]-1,2,3,4-tetrahydronaphthalene-1-carboxamide,
N-[(2-chlorophenyl)methyl]-N-(4-isopropylphenyl)-7-methoxy-1,2,3,4-tetrahydronaphthalene-1-carboxamide,
N-[(2,4-difluorophenyl)methyl]-N-(4-isopropylphenyl)-7-methoxy-1,2,3,4-tetrahydronaphthalene-1-carboxamide,
N-[(2,6-difluorophenyl)methyl]-N-(4-isopropylphenyl)-7-methoxy-1,2,3,4-tetrahydronaphthalene-1-carboxamide,
N-[(4-ethoxyphenyl)methyl]-N-(4-isopropylphenyl)-7-methoxy-1,2,3,4-tetrahydronaphthalene-1-carboxamide,
N-(4-isopropylphenyl)-7-methoxy-N-[(4-oxachroman-6-yl)methyl]-1,2,3,4-tetrahydronaphthalene-1-carboxamide,
N-[(2,3-dimethoxyphenyl)methyl]-N-(4-isopropylphenyl)-7-methoxy-1,2,3,4-tetrahydronaphthalene-1-carboxamide,
N-[(2,4-dimethoxyphenyl) methyl]-N-(4-isopropylphenyl)-7-methoxy-1,2,3,4-tetrahydronaphthalene-1-carboxamide,
N-(4-isopropylphenyl)-7-methoxy-N-[(2-trifluoromethylphenyl)methyl]-1,2,3,4-tetrahydronaphthalene-1-carboxamide,
N-(4-isopropylphenyl)-7-methoxy-N-[(4-trifluoromethylphenyl)methyl]-1,2,3,4-tetrahydronaphthalene-1-carboxamide,
N-[(2-bromophenyl)methyl]-N-(4-isopropylphenyl)-7-methoxy-1,2,3,4-tetrahydronaphthalene-1-carboxamide,
N-(4-isopropylphenyl)-7-methoxy-N-[(2,3,4-trimethoxyphenyl)methyl]-1,2,3,4-tetrahydronaphthalene-1-carboxamide,
5-hydroxy-N-(4-isopropylphenyl)-N-{[1-(2-pyridylmethyl)pyrazol-4-yl]methyl}-1,2,3,4-tetrahydronaphthalene-1-carboxamide,
N-[(1-benzylpyrazol-4-yl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-{[1-(2-pyridylmethyl)pyrazol-4-yl]methyl}-1,2,3,4-tetrahydronaphthalene-1-carboxamide,
N-({1-[(4-fluorophenyl)methyl]pyrazol-4-yl}methyl)-5-hydroxy-N-(6-isopropylpyridin-3-yl)-1,2,3,4-tetrahydronaphthalene-1-carboxamide,
N-({1-[(4-chlorophenyl)methyl]pyrazol-4-yl}methyl)-5-hydroxy-N-(6-isopropylpyridin-3-yl)-1,2,3,4-tetrahydronaphthalene-1-carboxamide,
5-hydroxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide,
5-hydroxy-N-(6-isopropylpyridin-3-yl)-N-({1-[(4-methoxyphenyl)methyl]pyrazol-4-yl}methyl)-1,2,3,4-tetrahydronaphthalene-1-carboxamide,
N-({1-[(4-bromophenyl)methyl]pyrazol-4-yl}methyl)-5-hydroxy-N-(6-isopropylpyridin-3-yl)-1,2,3,4-tetrahydronaphthalene-1-carboxamide,
N-({1-[(3-chlorophenyl)methyl]pyrazol-4-yl}methyl)-5-hydroxy-N-(6-isopropylpyridin-3-yl)-1,2,3,4-tetrahydronaphthalene-1-carboxamide,
N-({1-[(2-chlorophenyl)methyl]pyrazol-4-yl}methyl)-5-hydroxy-N-(6-isopropylpyridin-3-yl)-1,2,3,4-tetrahydronaphthalene-1-carboxamide,
5-hydroxy-N-(6-isopropylpyridin-3-yl)-N-({1-[(4-methylphenyl)methyl]pyrazol-4-yl}methyl)-1,2,3,4-tetrahydronaphthalene-1-carboxamide,
5-hydroxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide,
5-hydroxy-N-(6-isopropylpyridin-3-yl)-N-({1-[(5-methoxypyridine-2-yl)methyl]pyrazol-4-yl}methyl)-1,2,3,4-tetrahydronaphthalene-1-carboxamide,
5-hydroxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide,
5-hydroxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide,
8-fluoro-5-hydroxy-N-(6-isopropylpyridin-3-yl)-N-{[1-(2-pyridylmethyl)pyrazol-4-yl]methyl}-1,2,3,4-tetrahydronaphthalene-1-carboxamide,
5-hydroxy-N-(6-isopropylpyridin-3-yl)-N-({1-[(4-trifluoromethylpyridin-2-yl)methyl]pyrazol-4-yl}methyl)-1,2,3,4-tetrahydronaphthalene-1-carboxamide,
N-({1-[(6-dimethylaminopyridin-2-yl)methyl]pyrazol-4-yl}methyl)-5-hydroxy-N-(6-isopropylpyridin-3-yl)-1,2,3,4-tetrahydronaphthalene-1-carboxamide,
N-({1-[3-(dimethylaminophenyl)methyl]pyrazol-4-yl}methyl)-5-hydroxy-N-(6-isopropylpyridin-3-yl)-1,2,3,4-tetrahydronaphthalene-1-carboxamide,
N-[(2-ethyl-4-trifluoromethylthiazol-5-yl)methyl]-5-hydroxy-N-(6-isopropylpyridin-3-yl)-1,2,3,4-tetrahydronaphthalene-1-carboxamide,
5-benzyloxy-N-(4-isopropylphenyl)-N-[(1-isopropylpyrazol-4-yl)methyl]-1,2,3,4-tetrahydronaphthalene-1-carboxamide,
5-hydroxy-N-(4-isopropylphenyl)-N-[(1-methylpyrazol-4-yl)methyl]-1,2,3,4-tetrahydronaphthalene-1-carboxamide,
5-benzyloxy-N-(4-isopropylphenyl)-N-[(1-propylpyrazol-4-yl)methyl]-1,2,3,4-tetrahydronaphthalene-1-carboxamide,
N-{[1-(cyclohexylmethyl)pyrazol-4-yl]methyl}-5-hydroxy-N-(4-isopropylphenyl)-1,2,3,4-tetrahydronaphthalene-1-carboxamide,
5-hydroxy-N-(4-isopropylphenyl)-N-{[1-(3-thienylmethyl)pyrazol-4-yl]methyl}-1,2,3,4-tetrahydronaphthalene-1-carboxamide,
N-{[1-(4-fluorobenzyl)pyrazol-4-yl]methyl}-5-hydroxy-N-(4-methoxyphenyl)-1,2,3,4-tetrahydronaphthalene-1-carboxamide,
N-[(1-ethylpyrazol-4-yl)methyl]-5-hydroxy-N-(4-methoxyphenyl)-1,2,3,4-tetrahydronaphthalene-1-carboxamide,
N-{[1-(cyclohexylmethyl)pyrazol-4-yl]methyl}-5-hydroxy-N-(4-methoxyphenyl)-1,2,3,4-tetrahydronaphthalene-1-carboxamide,
5-hydroxy-N-(6-isopropylpyridin-3-yl)-N-{[1-(2-piperidinoethyl)pyrazol-4-yl]methyl}-1,2,3,4-tetrahydronaphthalene-1-carboxamide,
N-{[1-(cyclohexylmethyl)pyrazol-4-yl]methyl}-5-hydroxy-N-(6-isopropylpyridin-3-yl)-1,2,3,4-tetrahydronaphthalene-1-carboxamide,
N-[(1-heptylpyrazol-4-yl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-{[1-(3-thienylmethyl)pyrazol-4-yl]methyl}-1,2,3,4-tetrahydronaphthalene-1-carboxamide,
5-hydroxy-N-(6-isopropylpyridin-3-yl)-N-({1-[(2-methylthiazol-4-yl)methyl]pyrazol-4-yl}methyl)-1,2,3,4-tetrahydronaphthalene-1-carboxamide,
N-[(1-butylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(3-methylbutyl)pyrazol-4-yl]methyl}-1,2,3,4-tetrahydronaphthalene-1-carboxamide, N-[(1-benzylpyrazol-4-yl)methyl]-5-hydroxy-N-(6-methoxypyridin-3-yl)-1,2,3,4-tetrahydronaphthalene-1-carboxamide, 5-hydroxy-N-(6-isopropylpyridin-3-yl)-N-({1-[2-(2-pyridyl)ethyl]pyrazol-4-yl}methyl)-1,2,3,4-tetrahydronaphthalene-1-carboxamide, N-[(1-dodecylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-[(1-nonylpyrazol-4-yl)methyl]-1,2,3,4-tetrahydronaphthalene-1-carboxamide, N-{[1-(2-butoxyethyl)pyrazol-4-yl]methyl}-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[2-(2-methoxyethoxy)ethyl]pyrazol-4-yl}methyl)-1,2,3,4-tetrahydronaphthalene-1-carboxamide, 5-hydroxy-N-(4-isopropylphenyl)-N-[(6-morpholinopyridin-3-yl)methyl]-1,2,3,4-tetrahydronaphthalene-1-carboxamide, 5-hydroxy-N-(4-isopropylphenyl)-N-({1-[(4-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-methoxypyridin-2-yl)methyl]pyrazol-4-yl}methyl)-1,2,3,4-tetrahydronaphthalene-1-carboxamide, 5-hydroxy-N-[(1-isopropylpyrazol-4-yl)methyl]-N-(6-isopropylpyridin-3-yl)-1,2,3,4-tetrahydronaphthalene-1-carboxamide, N-[(4-dimethylaminophenyl)methyl]-N-(6-isopropylpyridin-3-yl)-7-methoxy-1,2,3,4-tetrahydronaphthalene-1-carboxamide, 5-hydroxy-N-(6-isopropylpyridin-3-yl)-N-{[1-(2-thienylmethyl)pyrazol-4-yl]methyl}-1,2,3,4-tetrahydronaphthalene-1-carboxamide, N-({1-[(5-chlorothiophen-2-yl)methyl]pyrazol-4-yl}methyl)-5-hydroxy-N-(6-isopropylpyridin-3-yl)-1,2,3,4-tetrahydronaphthalene-1-carboxamide, 5-benzyloxy-N-({1-[2-(2-butoxyethoxy)ethyl]pyrazol-4-yl}methyl)-N-(6-isopropylpyridin-3-yl)-1,2,3,4-tetrahydronaphthalene-1-carboxamide, N-({1-[2-(2-butoxyethoxy)ethyl]pyrazol-4-yl}methyl)-5-hydroxy-N-(6-isopropylpyridin-3-yl)-1,2,3,4-tetrahydronaphthalene-1-carboxamide, and N-({1-[2-(2-ethoxyethoxy)ethyl]pyrazol-4-yl}methyl)-N-(6-isopropylpyridin-3-yl)-5-hydroxy-1,2,3,4-tetrahydronaphthalene-1-carboxamide.

The pharmaceutically acceptable salt of the compound of the formula (1) is preferably exemplified by a salt with inorganic acid such as hydrochloric acid, hydrobromic acid, sulfuric acid, phosphoric acid, nitric acid and the like, a salt with organic acid such as acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid, ascorbic acid and the like, a salt with alkali metal (lithium, sodium, potassium and the like), a salt with alkaline earth metal (calcium, magnesium and the like), a salt with metal such as aluminum and the like, salt with organic base such as piperidine, piperazine, morpholine, diethanolamine, ethylenediamine and the like.

The present invention encompasses solvates (e.g., hydrate) of the compound of the above-mentioned formula (1) or a salt thereof, prodrug metabolized in vivo to be converted to the compound of the formula (1), and active metabolites of the compound of the formula (1).

The compound of the present invention further encompasses any form of an optically pure enantiomer, a diastereomer and a mixture of these.

While the compound of the present invention can be produced by the following methods, the production method is not limited to them. The methods exemplified here may be used alone or in combination and a conventional method may be further combined. Where necessary, each compound is protected or deprotected by a conventional method.

The compound (1a) wherein X of the formula (1) is oxygen atom can be produced by the following methods 1-3.

Method 1: Production Method 1 of Compound (1a)

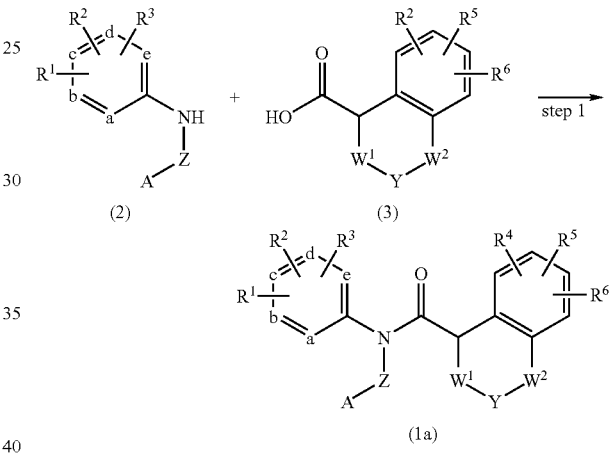

wherein $R^1$, $R^2$, $R^3$, $R^4$, $R^5$, $R^6$, a, b, c, d, e, A, $W^1$, $W^2$, Y and Z are as defined above.

For step 1, a known amidation method or peptide synthesis method and the like can be used for example, the reaction is carried out in the presence of a condensing agent (e.g., carbodiimide (N,N-dicyclohexylcarbodiimide, 1-ethyl-3-(3-dimethylaminopropyl)-carbodiimide and the like), diphenylphosphorylazide, carbonyldiimidazole, 1-benzotriazolyloxy tris(dimethylamino)phosphonium hexafluorophosphate (Bop reagent), 2-chloro-N-methylpyridinium iodide-tributylamine system (Mukaiyama Method), N-cyclohexylcarbodiimide-N'-methylpolystyrene and the like, in an inert solvent or without solvent at preferably from −20° C. to 80° C. In step 1, a deoxydation agent [e.g., organic base (e.g., triethylamine, N-methylmorpholine, pyridine, dimethylaniline and the like), inorganic base (e.g., sodium hydrogencarbonate, potassium carbonate, sodium hydroxide and the like)] and the like may be present. Generally, the reaction of step 1 is completed within 24 hr.

The compound (1a) in step 1 can be also produced by converting compound (3) to a different reactive derivative. When the reactive derivative of compound (3) is acid halide (e.g., acid chloride, acid bromide and the like) or acid anhydride (e.g., symmetric acid anhydride, mixed acid anhydride of lower alkyl carbonate, mixed acid anhydride of alkyl phosphate and the like), the reaction with compound (2) is generally carried out in an inert solvent or without solvent at from −20° C. to 80° C.

Furthermore, when what is called an active ester (4-nitrophenyl ester, 4-chlorobenzyl ester, 4-chlorophenyl ester, pentafluorophenyl ester, succinimide ester, benzotriazole ester, 4-dimethylsulfonium phenyl ester and the like) is used as the reactive derivative of compound (3), the reaction is generally carried out in an inert solvent or without solvent at a temperature of from −20° C. to the refluxing temperature of the solvent.

The inert solvent to be used in the aforementioned amidation is exemplified by hydrocarbons such as hexane, benzene, toluene, xylene and the like, halogenated hydrocarbons such as chloroform, dichloromethane, dichloroethane and the like, ethers such as tetrahydrofuran (hereinafter to be abbreviated as THF), dioxane and the like, esters such as ethyl acetate and the like, ketones such as acetone, methyl ethyl ketone and the like, alcohols such as methanol, ethanol, isopropyl alcohol and the like, amides such as N,N-dimethylformamide (hereinafter to be abbreviated as DMF), dimethylacetamide (hereinafter to be abbreviated as DMA) and the like, acetonitrile, dimethyl sulfoxide, water and a mixed solvent thereof and the like.

Method 2: Production Method 2 of Compound (1a)

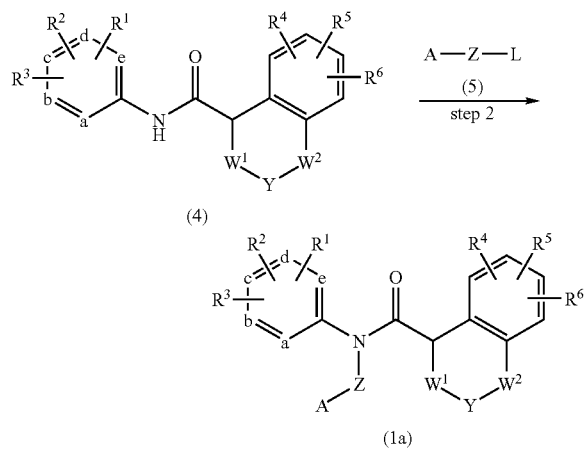

wherein $R^1$, $R^2$, $R^3$, $R^4$, $R^5$, $R^6$, a, b, c, d, e, A, $W^1$, $W^2$, Y and Z are as defined above, and L is a leaving group such as halogen atom, methanesulfonyoxy or para-toluenesulfonyloxy and the like.

The compound (1a) can be produced by reacting compound (4) with compound (5).

In step 2, the reaction is carried out in a solvent that does not inhibit the reaction, in the presence of a deoxydation agent [e.g., organic base (e.g., triethylamine, N-methylmorpholine, pyridine, dimethylaniline and the like), inorganic base (e.g., sodium hydride, sodium hydrogencarbonate, potassium carbonate, sodium hydroxide and the like)] and the like at from −20° C. to the refluxing temperature of the solvent. The solvent to be used in step 2 is exemplified by hydrocarbons such as hexane, benzene, toluene and the like, halogenated hydrocarbons such as chloroform, dichloromethane, dichloroethane and the like, ethers such as THF, dioxane and the like, esters such as acetic acid ester and the like, ketones such as acetone, methyl ethyl ketone and the like, alcohols such as methanol, ethanol, isopropyl alcohol and the like, amides such as DMF, DMA and the like, acetonitrile, DMSO, water or a mixed solvent thereof and the like.

Method 3: Production Method 3 of Compound (1a)

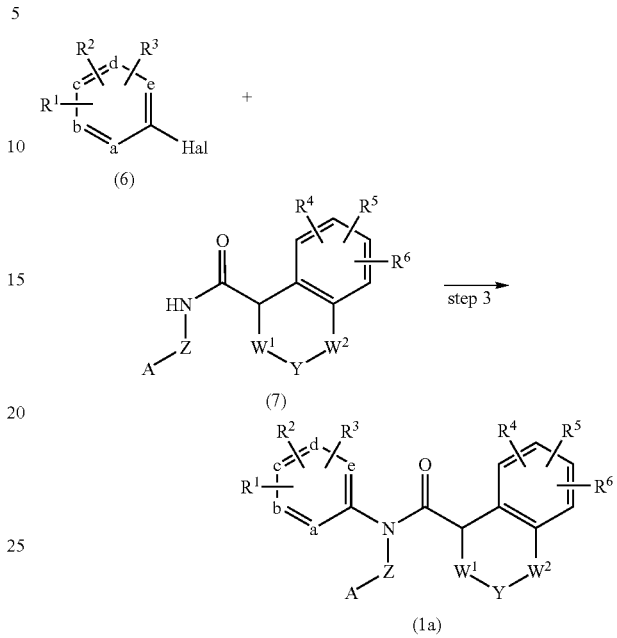

wherein $R^1$, $R^2$, $R^3$, $R^4$, $R^5$, $R^6$, a, b, c, d, e, A, $W^1$, $W^2$, Y and Z are as defined above, and Hal is iodine atom, bromine atom or chlorine atom.

By reacting compound (7) with compound (6), compound (1a) can be produced.

Step 3 is carried out in a solvent that does not inhibit the reaction in the presence of a deoxydation agent such as an organic base (e.g., triethylamine, N-methylmorpholine, pyridine, dimethylaniline and the like) or an inorganic base (e.g., sodium hydride, sodium hydrogencarbonate, potassium carbonate, sodium hydroxide and the like) and, where necessary, a catalyst such as copper, copper iodide and the like at a temperature from −20° C. to the refluxing temperature of the solvent. The solvent to be used in step 3 is exemplified by hydrocarbons such as hexane, benzene, toluene and the like, halogenated hydrocarbons such as chloroform, dichloromethane, dichloroethane and the like, ethers such as THF, dioxane and the like, esters such as acetic acid ester and the like, ketones such as acetone, methyl ethyl ketone and the like, alcohols such as methanol, ethanol, isopropyl alcohol and the like, amides such as DMF, DMA and the like, nitrobenzene, acetonitrile, DMSO, water or a mixed solvent thereof and the like.

Method 4: Production Method of Compound (1b) Wherein X of the Formula (1) is Sulfur Atom

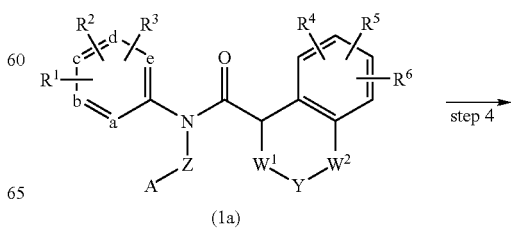

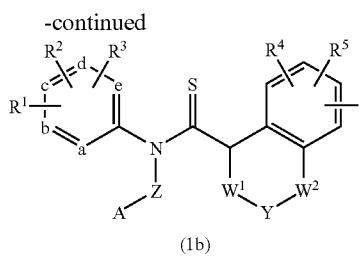

(1b)

wherein $R^1$, $R^2$, $R^3$, $R^4$, $R^5$, $R^6$, a, b, c, d, e, A, $W^1$, $W^2$, Y and Z are as defined above.

The compound (1b) can be produced from compound (1a) by the above-mentioned routes (step 4).

Step 4 is carried out in a solvent that does not inhibit the reaction in the presence of 2,4-bis(4-methoxyphenyl)-1,3-dithia-2,4-diphosphetan-2,4-disulfide (Lawesson's reagent), diphosphorus pentasulfide and the like.

The solvent to be used in step 4 is exemplified by benzene, toluene, xylene, THF, pyridine and the like. The reaction is carried out at a temperature of generally from 0° C. to the refluxing temperature of the solvent. While the reaction time varies depending on the reaction temperature, it is generally 1 hr-24 hr.

Method 5: Production Method of Compound (9) Wherein $R^4$ of the Formula (1) is Hydroxyl Group and $R^5$ and $R^6$ are Hydrogen Atoms

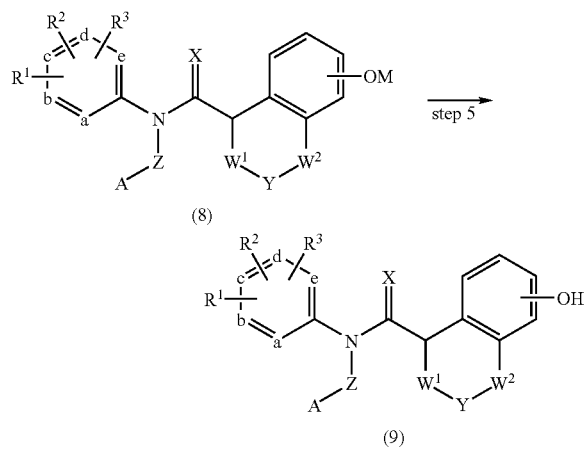

(8)

(9)

wherein $R^1$, $R^2$, $R^3$, a, b, c, d, e, A, $W^1$, $W^2$, X, Y and Z are as defined above, and M is a hydroxyl-protecting group.

The compound (9) can be produced by eliminating the protecting group M of compound (8) (step 5).

The protecting group M is exemplified by methyl, benzyl, substituted benzyl, benzyloxycarbonyl and the like.

The protecting group can be eliminated by a conventional method such as hydrolysis, acid treatment, hydrogenolysis with metal catalyst (palladium carbon, Raney-nickel and the like), depending on the kind of the protecting group, and the like.

Synthetic Method of Starting Material Compound

The compound (2) to be the starting material of method 1 can be produced by the following methods 6-8.

Method 6: Production Method of Compound (2)

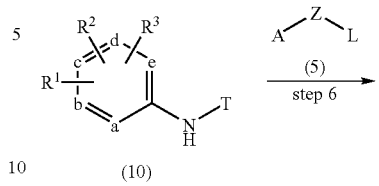

(10)

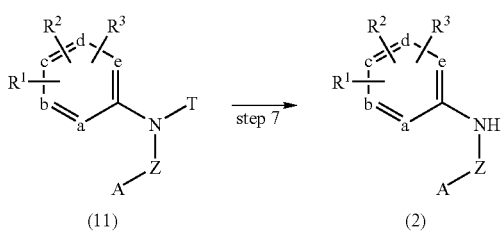

(11) (2)

wherein T is amino-protecting group such as acetyl, t-butoxycarbonyl and the like and $R^1$, $R^2$, $R^3$, a, b, c, d, e, A, Z and L are as defined above.

The compound (10) and compound (5) are reacted in a suitable solvent in the presence of a base to give compound (11), and then a protecting group is eliminated to give compound (2) (steps 6 and 7).

The solvent to be used in step 6 is exemplified by methanol, ethanol, propanol, isopropyl alcohol, methylene chloride, chloroform, THF, dioxane, benzene, toluene, xylene, DMF, DMSO and the like. The base to be used is exemplified by sodium hydride, sodium carbonate, potassium carbonate, sodium hydrogencarbonate, sodium hydroxide, potassium hydroxide, triethylamine, diisopropylethylamine, pyridine and the like. While the reaction temperature varies depending on the solvent, it is generally 0° C.-140° C., and while the reaction time varies depending on the reaction temperature, it is generally from 1 hr to 24 hr.

This reaction can be also carried out without the protecting group T (when T is hydrogen atom), whereby compound (2) can be produced.

In step 7, the protecting group can be eliminated by a conventional method such as hydrolysis, acid treatment and the like according to a conventional method, depending on the kind of the protecting group.

Method 7: Production Method of Compound (15), Wherein, in Compound (2), —Z—A is —CH($R^{11}$)—U—A (U is Alkylene Optionally Having Substituents, $R^{11}$ is Hydrogen Atom, Alkyl Optionally Having Substituents, Aryl or Heteroaryl, and A is as Defined Above

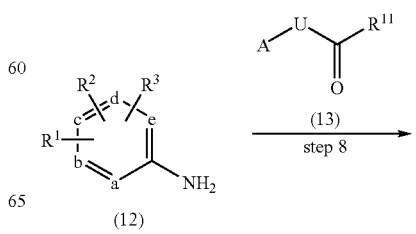

(12) (13)

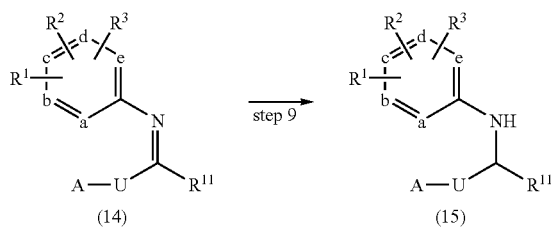

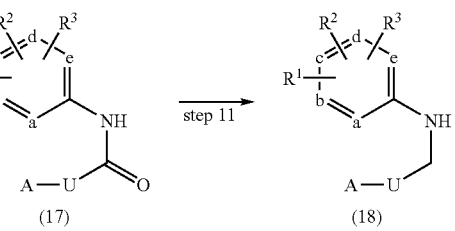

wherein $R^1$, $R^2$, $R^3$, a, b, c, d, e, A, $R^{11}$ and U are as defined above.

The compound (12) and compound (13) are subjected to dehydration condensation without solvent or in a suitable solvent to give compound (14), which compound is then reduced in a suitable solvent, whereby compound (15) can be produced (steps 8 and 9).

The dehydration condensation reaction of compound (12) and compound (13) in step 8 can be carried out in the presence of a dehydrating agent or by removing the generated water from the reaction system with Dean-Stark trap.

As the dehydrating agent to be used for this reaction, a conventional dehydrating agent can be used. Examples of the dehydrating agent include anhydrous magnesium sulfate, molecular sieves and the like. The solvent to be used for the reaction may be, for example, methylene chloride, chloroform, benzene, toluene, xylene and the like. While the reaction temperature varies depending on the solvent, it is generally from 0° C. to 150° C., and while the reaction time varies depending on the reaction temperature, it is generally 1 hr-24 hr.

The reducing agent to be used for step 9 is exemplified by sodium borohydride, sodium triacetoxyborohydride, sodium cyanoborohydride, formic acid, sodium formate and the like. When sodium triacetoxyborohydride or sodium cyanoborohydride is used as a reducing agent, removal of water using the dehydrating agent or Dean-Stark trap in step 8 can be omitted. The solvent to be used for the reaction includes, for example, water, methanol, ethanol, propanol, THF, dioxane, 1,2-dichloroethane, acetic acid and the like, and a mixed solvent thereof may be used. While the reaction temperature varies depending on the solvent, it is generally from 0° C. to 80° C., and while the reaction time varies depending on the reaction temperature, it is generally from 1 hr to 24 hr.

Method 8: Production Method of Compound (18), Wherein, in Compound (2), —Z—A is —CH$_2$—U—A Wherein A and U are as Defined Above

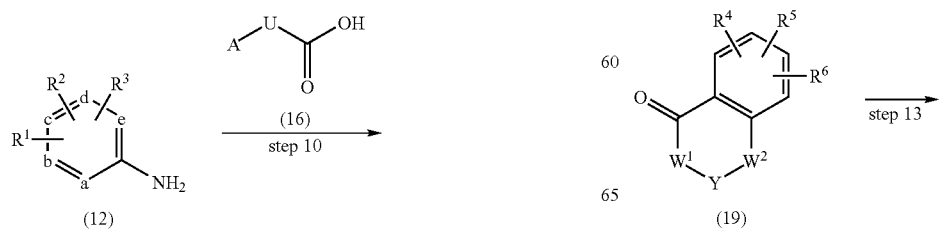

wherein $R^1$, $R^2$, $R^3$, a, b, c, d, e, A and U are as defined above.

The compound (12) or a salt thereof and compound (16) or a reactive derivative thereof are reacted without solvent or in a suitable solvent to give compound (17), which compound is then reacted with a reducing agent in a suitable solvent, whereby compound (18) can be produced (steps 10 and 11).

The reaction of compound (12) or a salt thereof with compound (16) in step 10 can be carried out in the same manner as in step 1.

The reducing agent to be used for reduction in step 11 is exemplified by lithium aluminum hydride, borane and the like. The solvent to be used for reduction is, for example, THF, diethyl ether, hexane and the like; or a mixed solvent thereof. While the reaction temperature varies depending on the solvent, it is generally from 0° C. to 65° C., and while the reaction time varies depending on the reaction temperature, it is generally from 1 hr to 24 hr.

The compound (3) to be the starting material can be produced by the following methods 9-10.

Method 9: Production Method 1 of Compound (3)

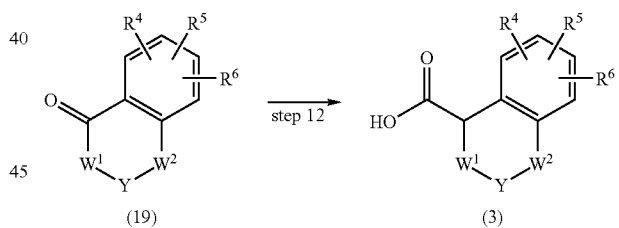

The compound (3) to be used in Method 1 can be produced from compound (19) wherein $R^4$, $R^5$, $R^6$, $W^1$, $W^2$ and Y are as defined above according to the method described in a reference (Synthetic Communications, 12(10), 763-770, 1982) (step 12).

Method 10: Production Method 2 of Compound (3)

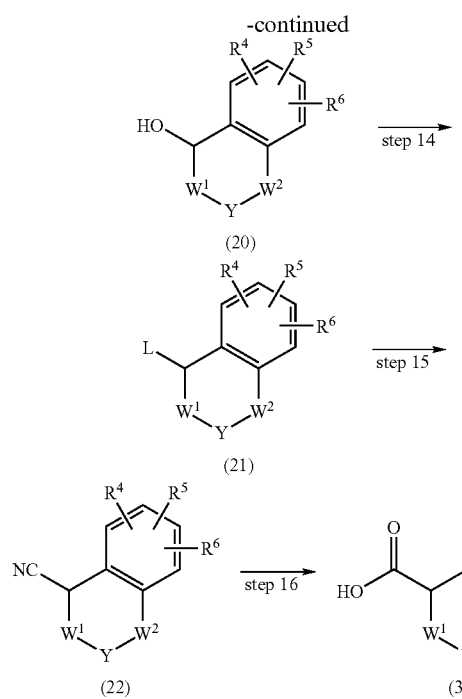

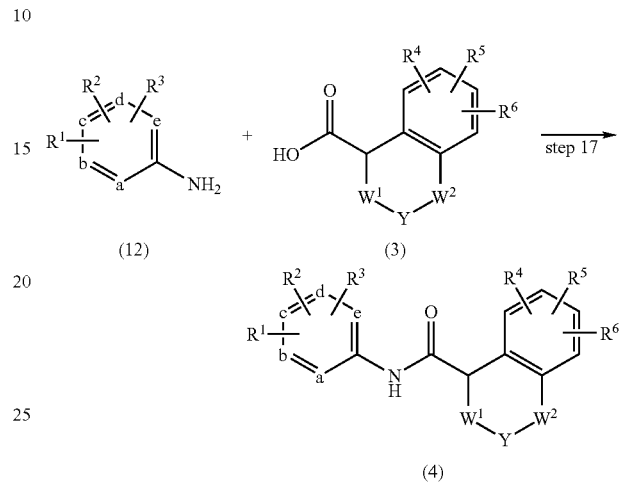

wherein $R^4$, $R^5$, $R^6$, $W^1$, $W^2$, Y and L are as defined above.

The compound (3) can be produced from compound (19) via steps 13-16.

The reducing agent to be used for the reduction in step 13 is, for example, lithium aluminum hydride, sodium borohydride, lithium borohydride, diborane and the like. The solvent to be used in step 13 is, for example, water, methanol, ethanol, propanol, ether, THF, dioxane, acetic acid and the like, or a mixed solvent thereof. While the reaction temperature varies depending on the solvent, it is generally from 0° C. to 80° C., and while the reaction time varies depending on the reaction temperature, it is generally from 1 hr to 24 hr.

When L of compound (21) in step 14 is chlorine atom, the reaction is generally carried out in an inert solvent or without solvent in the presence of thionyl chloride, methanesulfonyl chloride, para-toluenesulfonyl chloride or triphenylphosphine, as necessary, in the co-presence of an organic base such as triethylamine and the like, at from −20° C. to 80° C. The solvent to be used then is, for example, methylene chloride, chloroform, carbon tetrachloride, ether, DMF and the like; or a mixed solvent thereof and the like.

When L of compound (21) is methanesulfonyloxy or para-toluenesulfonyloxy, the reaction is generally carried out in an inert solvent or without solvent in the presence of methanesulfonyl chloride or para-toluenesulfonyl chloride in the co-presence of an organic base such as triethylamine and the like at from −20° C. to 80° C. The solvent is to be used here is, for example, methylene chloride, chloroform, ether, DMF or a mixed solvent thereof and the like.

The step 15 is carried out in a solvent that does not inhibit the reaction in the presence of sodium cyanide, potassium cyanide, tetraethylammonium cyanide and the like at a temperature of from −20° C. to the refluxing temperature of the solvent. The solvent to be used in step 15 includes water, ethanol, ethanol, propanol, ether, DMF, DMSO, acetone, acetonitrile and a mixed solvent and the like.

The step 16 is carried out in a solvent that does not inhibit the reaction in the presence of an inorganic base (e.g., sodium hydroxide, potassium hydroxide, barium hydroxide and the like) or an acid (e.g., hydrochloric acid, hydrobromic acid, sulfuric acid and the like) at a temperature of from −20° C. to the refluxing temperature of the solvent. The solvent to be used in step 16 is, for example, water, methanol, ethanol, propanol, ethylene glycol, ethylene glycol monomethyl ether, DME, acetic acid, formic acid; or a mixed solvent thereof and the like.

Method 11: Production Method of Compound (4), which is a Starting Material of Method 2 wherein $R^1$, $R^2$, $R^3$, $R^4$, $R^5$, $R^6$, a, b, c, d, e, $W^1$, $W^2$ and Y are as defined above.

The compound (4) can be produced from compound (12) and compound (3).

That is, compound (4) can be produced by reacting compound (12) or a salt thereof with compound (3) or a reactive derivative thereof without solvent or in a suitable solvent (step 17).

The reaction of compound (3) with compound (12) or a salt thereof in step 17 can be carried out in the same manner as in step 1.

Method 12: Production Method of Compound (7), which is a Starting Material of Method 3

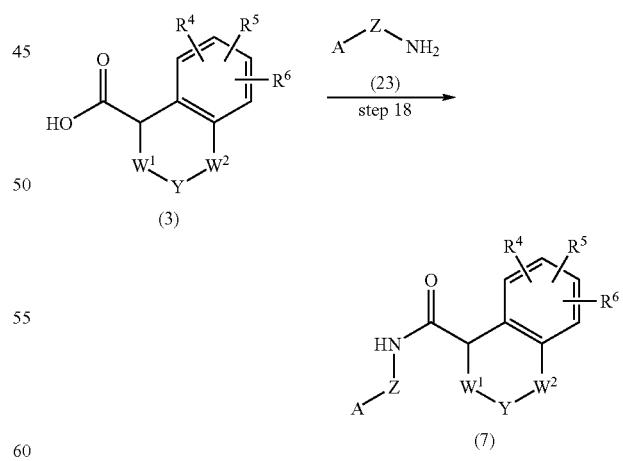

wherein $R^4$, $R^5$, $R^6$, A, $W^1$, $W^2$, Y and Z are as defined above.

The compound (7) can be produced by reacting compound (3) with compound (23) or a salt thereof (step 18).

That is, by reacting compound (23) or a salt thereof and compound (3) or a reactive derivative thereof without solvent or in a suitable solvent, compound (7) can be produced.

The reaction of compound (3) and compound (23) or a salt thereof in step 18 can be carried out in the same manner as in step 1.

The product obtained in each of the above-mentioned steps can be isolated and purified by a conventional method.

A part of the compounds of the formula (1) in the present invention can be converted to a salt as necessary by a treatment in a suitable solvent (methanol, ethanol and the like), with an acid (hydrochloric acid, sulfuric acid, hydrobromic acid, phosphoric acid, nitric acid, methanesulfonic acid, ethanesulfonic acid, fumaric acid, maleic acid, benzoic acid, citric acid, malic acid, mandelic acid, para-toluenesulfonic acid, acetic acid, succinic acid, malonic acid, lactic acid, salicylic acid, gallic acid, picric acid, carbonic acid, ascorbic acid, trifluoroacetic acid, tartaric acid and the like), an alkali metal (lithium, sodium, potassium and the like), alkaline earth metal (calcium, magnesium and the like), metal such as aluminum and the like, or an organic base (piperidine, piperazine, morpholine, diethanolamine, ethylenediamine and the like).

When the crystal of obtained the compound of the present invention is not a solvate and the like, the compound of the present invention can be converted to a solvate by treating the compound with water, water-containing solvent or other solvent.

The compound of the formula (1) of the present invention, a pharmaceutically acceptable salt thereof and a solvate thereof show a C5a receptor antagonistic action and are useful as a prophylactic or therapeutic drug of diseases, in which C5a is involved, for example, diseases or syndromes due to inflammation caused by C5a [e.g., autoimmune diseases such as rheumatism and systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; serious organ injury (e.g., pneumonia, nephritis, hepatitis and pancreatitis and the like) due to activation of leukocytes caused by ischemia reperfusion, trauma, burn, surgical invasion, and the like. In addition, they are useful as a prophylactic or therapeutic drug of infectious diseases due to bacteria or virus that invades via a C5a receptor.

When the compound of the present invention of the formula (1), pharmaceutical acceptable salt thereof and solvate thereof are used for the aforementioned prophylaxis or treatment, it is generally administered systemically or topically and orally or parenterally. The dose to patients varies depending on the age, body weight, sex, general health conditions, treatment effect, diet, administration time, administration method, clearance rate, combination of drugs, the condition of the disease under treatment and the like. It is generally desirably in the range of from 0.1 mg to 500 mg per dose for an adult by oral administration once to several times a day, or in the range of from 0.01 mg to 200 mg per dose for an adult by parenteral administration (preferably intravenous administration) once to several times a day.

Because the dose may change depending on various conditions as mentioned above, when a dose smaller than the above-mentioned range may be sufficient, a dose outside the above-mentioned range may be necessary.

The compound of the formula (1) of the present invention, a pharmaceutically acceptable salt thereof and a solvate thereof can be used orally or parenterally, for example, by inhalation, rectal administration, topical administration and the like as a pharmaceutical composition or preparation (e.g., powder, granule, tablet, pill, capsule, syrup, elixir, suspension, solution and the like), wherein at least one compound of the present invention can be used alone or used upon admixing with a pharmaceutically acceptable carrier (excipient, binder, disintegrant, corrigent, corrective, emulsifier, diluent and/or dissolution aids and the like).

A pharmaceutical composition can be prepared according to a general method. In the present specification, by the parenteral is meant subcutaneous injection, intravenous injection, intramuscular injection, intraperitoneal injection, drip and the like. A composition for injection, such as sterile suspension for injection and oil suspension can be prepared using a suitable dispersing agent, wetting agent, or suspending agent according to a method known in the art.

A solid composition for oral administration is exemplified by tablet, pill, capsule, powder, granule and the like. In the above-mentioned solid composition, one or more active compounds can be admixed with at least one additive such as sucrose, lactose, mannitol, maltitol, glucose, cornstarch, talc, hydroxypropylcellulose, microcrystalline cellulose, starch, polyvinylpyrrolidone, magnesium aluminometasilicate, dextran, starches, agar, arginates, chitins, chitosans, pectins, tragacanth gums, Acacia, gelatins, collagens, casein, albumin, synthetic or semi-synthetic polymers or glicerides.

In addition, the above-mentioned composition can contain further additives such as lubricants (e.g., magnesium stearate etc.), preservatives (e.g., parabens, sorbins etc.), antioxidants (e.g., ascorbic acid, α-tocopherol, cysteine etc.), disintegrants (e.g., carmellose calcium etc.), stabilizers (e.g., lactose etc.), dissolution aids (e.g., glutamic acid, aspartic acid etc.), binder, thickener, sweetener, flavor, perfume and the like.

Where necessary, the tablet and pill may be coated with a film of gastric or enteric coating such as sucrose, gelatin, hydroxypropylcellulose, hydroxypropylmethylcellulose phthalate and the like, or may be coated with two or more layers. In addition, they may include a capsule of absorbable material such as gelatin.

The liquid composition for oral administration includes pharmaceutically acceptable solution, suspension, syrup, elixir and the like, and may contain a generally used inactive diluent (purified water, ethanol). This composition may contain, besides the inactive diluent, auxiliaries such as wetting agent, suspending agent, sweetening agent, flavor, perfume and preservative. Other compositions for oral administration are, for example, spray agent containing one or more active substances and formulated by a method known per se.

The composition for injection for parenteral administration may include sterile aqueous or non-aqueous solution, suspension and emulsion. Examples of the aqueous solution and suspension include distilled water for injection and physiological saline. Examples of the water insoluble solution and suspension include propylene glycol, polyethylene glycol, olive oil, ethanol, polysorbate 80 and the like. The above-mentioned composition may further contain auxiliaries such as preservative, wetting agent, emulsifier, dispersing agent, stabilizer (e.g., lactose and the like) and dissolution aids (e.g., amino acid such as arginine, glutamic acid, aspartic acid, and the like). These can be sterilized by, for example, filtration through a bacteria-retaining filter, addition of microbicide or irradiation.

The composition for injection can be used by producing a sterile solid composition and dissolved, for example, the lyophilized product in sterile water or sterile solvent for injection before use.

Other composition for parenteral administration include external solution, ointment, liniment, suppository and the like, containing one or more active substances and formulated by a conventional method.

The suppository for rectal administration can be produced by admixing the drug and a suitable non-irritant vehicle, which is a substance which is solid at ambient temperature but liquid at the temperature of intestine and which melts in the rectum to release the drug, such as cocoa butter and polyethylene glycols.

The amide derivative (1), an optically active form thereof or a pharmaceutically acceptable salt thereof of the present invention are useful as an active ingredient of a C5a receptor antagonist, which C5a receptor antagonist can be used as a drug for the prophylaxis or treatment of infectious diseases caused by bacteria or viruses that invade via a C5a receptor, and can be used in combination with a prophylactic or therapeutic drugs of autoimmunity disease, sepsis, adult respiratory distress syndrome, chronic obstructive pulmonary disease, allergic disease, atherosclerosis, cardiac infarction, cerebral infarction, psoriasis, Alzheimer's disease, or serious organ injury due to activation of leucytes caused by ischemia reperfusion, external injuries, burn or surgical invasion.

The compound of the formula (1) of the present invention, optically active form thereof or a pharmaceutically acceptable salt thereof is expected to show a superior treatment effect by a combined use with an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn, surgical invasion and the like. As used herein, by the "combined use" is meant a combination composition of the compound of the present invention or a pharmaceutically acceptable salt thereof with an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn surgical invasion and the like, and the use as a potentiator of an action of an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn, surgical invasion and the like, including combined use and concurrent use, wherein two or more active ingredient compounds are simultaneously used or used in a staggered manner with or without mixing. The pharmaceutical drug of the present invention which is characterized by the combined use of the compound represented by the above-mentioned formula (1), optically active form thereof or a pharmaceutically acceptable salt thereof and an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn, surgical invasion and the like is not particularly limited in terms of the mode of use thereof as long as the compound represented by the formula (1), optically active form thereof or a pharmaceutically acceptable salt thereof and an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn, surgical invasion and the like are combined. For example, (A) the compound represented by the formula (1), optically active form thereof or a pharmaceutically acceptable salt thereof, and (B) an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn, surgical invasion and the like may be formulated as preparations to be each generally administered, or a composition wherein they are combined in advance may be used. The combined pharmaceutical drug of the present invention may be, for example, a single agent obtained by mixing the compound represented by the formula (1), optically active form thereof or a pharmaceutically acceptable salt thereof and an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn, surgical invasion and the like according to a known production method for pharmaceutical preparations using, where desired, pharmaceutically acceptable diluent, excipient and the like, or respective preparations thereof obtained using, where desired, pharmaceutically acceptable diluent, excipient and the like, or a combination preparation in a container including respective preparations thereof (set, kit, pack). For example, the combined pharmaceutical drug of the present invention can be used as a combination preparation packaging the same or different preparations of a preparation containing the compound represented by the formula (1), optically active form thereof or a pharmaceutically acceptable salt thereof, and an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn surgical invasion and the like, or as a composition containing the compound represented by the formula (1), optically active form thereof or a pharmaceutically acceptable salt thereof and an agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn surgical invasion and the like.

When the compound of the present invention, optically active form thereof or a pharmaceutically acceptable salt thereof is used as a combination composition, the ratio of the composition is optional, and the amount of the compound of the present invention or a pharmaceutically acceptable salt thereof to be mixed can be determined depending on the kind of the various pharmaceutical agents to be mixed for combination, and the factors such as titer and the like. When it is used as a combination drug, the dose of the compound of the present invention or a pharmaceutically acceptable salt thereof, and the pharmaceutical agent to be combined therewith can be determined as appropriate from the range generally employed. It is preferable to administer in a smaller dose than the dose for single use of each pharmaceutical agent, in the hope of affording a synergistic effect.

Examples of the agent for the prophylaxis or treatment of autoimmune diseases such as rheumatism, systemic lupus erythematosus and the like; sepsis; adult respiratory distress syndrome; chronic obstructive pulmonary disease; allergic diseases such as asthma and the like; atherosclerosis; cardiac infarction; brain infarction; psoriasis; Alzheimer's disease; or serious organ injury (e.g., pneumonia, nephritis, hepatitis, pancreatitis and the like) due to activation of leukocytes caused by ischemia reperfusion, trauma, burn surgical invasion and the like include antirheumatic agents (gold compound, penicillamine, bucillamine, lobenzarit, actarit, salazosulfapyridine etc.), immunosuppressants (azathioprine, cyclophosphamide, methotrexate, brequinar sodium, deoxyspergualin, mizoribine, 2-morpholinoethyl mycophenolate, cyclosporin, rapamycin, tacrolimus hydrate, leflunomide, OKT-3, anti-TNF-α antibody, anti-IL (interleukin)-6 antibody and FTY720 (EP627406-B1) etc.), steroidal drugs (predonizolone, methylpredonizolone, dexamethazone, hydrocortizone etc.) or nonsteroidal anti-inflammatory agents (aspirin, indometacin, indometacin farnesylate, diclofenac sodium, alclofenac, amfenac sodium, ibuprofen, ketoprofen, loxoprofen sodium, naproxen, pranoprofen, zaltoprofen, mefenamic acid, flufenamic acid, tolfenamic acid, phenylbutazone, ketophenylbutazone, piroxicam, tenoxicam, ampiroxicam etc.), bactericides (gentamicin, tobramycin, cefotaxim, ceftazidime, vancomycin, erythromycin, imipenem, metronidazole etc.), cerebral circulatory metabolism improvers (meclofenoxate, idebenone, indeloxazine, nicergoline, propentofylline, cytochrome C, citicoline, ifenprodil, bencyclane, cinepazide, ozagrel, nizofenone, ibudilast, pentoxifylline, propentofylline, vinpocetine, brovincamine, dihydroergotoxine, moxisylyte, dilazep, nicardipine, cinnarizine, flunarizine, nilvadipine etc.), anti-platelet aggregation inhibitors (ticlopidine, aspirin, beraprost, dipyridamole, cilostazol, ozagrel, sarpogrelate etc.), anticoagulants (heparin, warfarin etc.), thrombolytic agents (urokinase, tissue plasminogen activator etc.), antiallergic agents (cromoglic acid, pranlukast, tazanolast, seratrodast, tranilast, amlexanox, repirinast, tazanolast, pemirolast, ibudilast, supratast, ketotifen, azelastine, oxatomide, terfenadine, mequitazine, epinastine, astemizole, ramatroban, zafirlukast etc.), proteolytic enzyme inhibitors (gabexate, nafamosutat, aprotinin etc.), acetylcholinesterase inhibitors (aricept etc.) and the like.

EXAMPLES

The present invention is specifically explained in the following by referring to Preparation Examples, Examples, Formulation Examples and Test Examples, which are not to be construed as limitative.

$^1$H-NMR was measured at 300 MHz. The chemical shift of $^1$H-NMR was measured using tetramethylsilane (TMS) as the internal standard and expressed as relative delta (δ) value in parts per million (ppm). For the coupling constant, obvious multiplicity is shown using s (singlet), d (doublet), t (triplet), q (quartet), sept (septet), m (multiplet), dd (double doublet), brs (broad singlet) and the like in hertz (Hz).

Thin-layer chromatography was manufactured by Merck, and column chromatography was performed using silica gel manufactured by Fuji silysia chemical.

Preparation Example 1

To a solution of 4-dimethylaminobenzaldehyde (11 g) in toluene (200 mL) were added 4-isopropylaniline (10 g) and molecular sieves 4A (20 g) under ice-cooling, and the mixture was stirred at room temperature for one day. The molecular sieves 4A was filtered off from the reaction mixture, and the obtained filtrate was concentrated under reduced pressure. The residue was dissolved in methanol (200 mL) and sodium borohydride (2.3 g) was added under ice-cooling. The mixture was stirred at room temperature for 5 hr. After methanol was distilled away, water was added to the residue, and the mixture was extracted with chloroform. The organic layer was washed with saturated brine and dried over anhydrous sodium sulfate. The solvent was evaporated to give (4-dimethylaminophenylmethyl)(4-isopropylphenyl)amine (13.6 g). melting point: 71-73° C.

Preparation Example 2

By the reaction and treatment in the same manner as in Preparation Example 1 using 4-dimethylaminobenzaldehyde (10.0 g) and 4-methoxyaniline (8.25 g) as a starting material, (4-dimethylaminophenylmethyl) (4-methoxyphenyl)amine (5 g) was obtained. melting point: 92-94° C.

Preparation Example 3

To a solution of 1-ethylpyrazole-4-carboxylic acid (2.34 g) in 1,2-dichloroethane (50 mL) were added thionyl chloride (1.83 mL) and several drops of DMF, and the mixture was stirred at 70° C. for 1.5 hr. The reaction mixture was concentrated under reduced pressure, and methylene chloride (20 mL) was added to the residue. To this solution was added a solution of 4-isopropylaniline (2.29 mL) in methylene chloride (20 mL) under ice-cooling. The temperature of the mixture was raised to room temperature and stirred at the same temperature for 1 hr. The reaction mixture was added to saturated aqueous sodium hydrogencarbonate and extracted with chloroform. The organic layer was washed with saturated brine, and dried over anhydrous sodium sulfate. The solvent was evaporated, and ether and hexane were added to the residue. The precipitated solid was collected by filtration to give N-(4-isopropylphenyl)-1-ethylpyrazole-4-carboxamide (3.76 g) (melting point: 141.0° C.). To this compound (3.75 g) was added borane-THF complex/1 mol/L-THF solution (BH$_3$.THF complex/1M THF solution) (29 mL) and the mixture was heated under reflux for 4 hr. After cooling the reaction mixture, 1 mol/L-hydrochloric acid (60 mL) was added, and the mixture was stirred at room temperature for one day. The reaction mixture was added to saturated aqueous sodium hydrogencarbonate and extracted with chloroform. The organic layer was washed with saturated brine, and dried over anhydrous sodium sulfate. The solvent was evaporated and the residue was purified by silica gel column chromatography to give [(1-ethylpyrazol-4-yl)methyl](4-isopropylphenyl)amine (1.95 g).

$^1$H-NMR (CDCl$_3$) δ: 1.21 (6H, d, J=6.9 Hz), 1.47 (3H, t, J=7.3 Hz), 2.81 (1H, sept, 6.9 Hz), 3.57-3.78 (1H, brs), 4.14 (2H, q, J=7.3 Hz), 4.15 (2H, s), 6.62 (2H, d, J=8.4 Hz), 7.06 (2H, d, J=8.4 Hz), 7.36 (1H, s), 7.47 (1H, s).

Preparation Example 4

6-Chloronicotinic acid (3.15 g), 4-isopropylaniline (2.73 mL) and triethylamine (5.6 mL) were dissolved in DMF (150 mL). 1-Hydroxybenzotriazole monohydrate (hereinafter to be abbreviated as HOBt.H$_2$O) (3.22 g) and 1-ethyl-3-(3-dimethylaminopropyl)carbodiimide hydrochloride (hereinafter to be abbreviated as WSCI.HCl) (4.03 g) were added under ice-cooling. The mixture was stirred at room temperature for one day and the reaction mixture was partitioned between water and ethyl acetate. The organic layer was washed with saturated brine, and dried over anhydrous magnesium sulfate. The solvent was evaporated and ether was added to the residue. The precipitated solid was collected by filtration to give N-(4-isopropylphenyl)-6-chloropyridine-3-carboxamide (4.72 g).

$^1$H-NMR (CDCl$_3$) δ: 1.25 (6H, d, J=6.9 Hz), 2.91 (1H, sept, 6.9 Hz), 7.24 (2H, d, J=8.4 Hz), 7.45 (2H, d, J=8.4 Hz), 7.52 (2H, d, J=8.4 Hz), 7.72-7.87 (1H, m), 8.15 (1H, dd, J=2.4, 8.4 Hz), 8.84 (1H, d, J=2.4 Hz).

N-(4-Isopropylphenyl)-6-chloropyridine-3-carboxamide (1.00 g) was dissolved in THF (10 mL) and sodium methoxide (0.21 g) was added. The mixture was stirred at 50° C. for one day. After cooling, the reaction mixture was partitioned between water and ethyl acetate. The organic layer was washed with saturated brine and dried over anhydrous magnesium sulfate. The solvent was evaporated and the residue was purified by silica gel column chromatography to give N-(4-isopropylphenyl)-6-methoxypyridine-3-carboxamide (0.76 g).

A BH$_3$-THF complex/1M THF solution (6.3 mL) was added to N-(4-isopropylphenyl)-6-methoxypyridine-3-carboxamide (0.76 g), and the mixture was heated under reflux for 4 hr. After cooling the reaction mixture, 1 mol/L hydrochloric acid (15 mL) was added and the mixture was stirred at room temperature for one day. The reaction mixture was poured into saturated aqueous sodium hydrogencarbonate and extracted with chloroform. The organic layer was washed with saturated brine and dried over anhydrous sodium sulfate. The solvent was evaporated and the residue was purified by silica gel column chromatography to give (4-isopropylphenyl)[(6-methoxypyridin-3-yl)methyl]amine (0.62 g).

$^1$H-NMR (CDCl$_3$) δ: 1.20 (6H, d, J=6.9 Hz), 2.80 (1H, sept, 6.9 Hz), 3.73-3.87 (1H, m), 3.93 (3H, s), 4.22 (2H, s), 6.59 (2H, d, J=8.4 Hz), 6.72 (1H, d, J=8.4 Hz), 7.04 (2H, d, J=8.4 Hz), 7.59 (1H, dd, J=2.4, 8.4 Hz), 8.14. (1H, d, J=2.4 Hz).

Preparation Example 5

To a solution of 7-methoxytetralone (22.3 g) in nitromethane (5 mL) was added zinc iodide (0.65 g). While stirring the mixture, trimethylsilyl cyanide (50 mL) was added under ice-cooling. The mixture was stirred at room temperature for 1 hr, and the reaction mixture was partitioned between water and chloroform. The organic layer was washed with saturated brine and dried over anhydrous sodium sulfate. The solvent was evaporated and the residue was dissolved in a mixed solvent of acetic acid (200 mL) and conc. hydrochloric acid (200 mL). Thereto was added stannous chloride (106 g) and the mixture was heated under reflux for one day. After cooling, the reaction mixture was extracted with chloroform. The organic layer was washed with saturated brine and dried over anhydrous magnesium sulfate. The solvent was evaporated and ether was added to the residue. The precipitated solid was collected by filtration to give 7-methoxy-1,2,3,4-tetrahydronaphthalene-1-carboxylic acid (8.1 g). melting point: 126-127° C.

Preparation Example 6

By the reaction and treatment in the same manner as in Preparation Example 5 using 5-hydroxy-1-tetralone (20 g) as a starting material, 5-hydroxy-1,2,3,4-tetrahydronaphthalene-1-carboxylic acid (18.5 g) was obtained. This compound (18.5 g) was dissolved in a mixed solvent of DMF (105 mL) and toluene (42 mL). Thereto were added benzyl bromide (25.8 mL) and potassium carbonate (54 g), and the mixture was stirred at 50-60° C. for 8 hr. The reaction mixture was partitioned between water and ethyl acetate. The organic layer was washed with saturated brine and dried over anhydrous magnesium sulfate. The solvent was evaporated, and methanol (100 mL), 1,4-dioxane (100 mL) and 1 mol/L aqueous sodium hydroxide solution (116 mL) were added to the residue. The mixture was stirred at 50° C. for 5 hr. The reaction mixture was partitioned between water and ethyl acetate, and the aqueous layer was acidified with conc. hydrochloric acid. The mixture was extracted with chloroform and dried over anhydrous magnesium sulfate. The solvent was evaporated and the residue was purified by silica gel column chromatography to give 5-benzyloxy-1,2,3,4-tetrahydronaphthalene-1-carboxylic acid (20.4 g). melting point: 145-146° C.

Preparation Example 7

By the reaction and treatment in the same manner as in Preparation Example 5 using 4-chromanone (5.1 g) as a starting material, chroman-4-carboxylic acid (4.1 g) was obtained. melting point: 94.3° C.

Preparation Example 8

By the reaction and treatment in the same manner as in Preparation Example 5 using 6-methoxy-4-chromanone (6.1 g) as a starting material, 6-methoxychroman-4-carboxylic acid (1.2 g) was obtained. melting point: 97.4° C.

Preparation Example 9

By the reaction and treatment in the same manner as in Preparation Example 5 using 6-methoxy-1-indanone (5.6 g) as a starting material, 6-methoxyindan-1-carboxylic acid (2.6 g) was obtained. melting point: 101.1° C.

Preparation Example 10

By the reaction and treatment in the same manner as in Preparation Example 6 using 4-hydroxy-1-indanone (5 g) as a starting material, 4-benzyloxyindan-1-carboxylic acid (1.4 g) was obtained. melting point: 133.4° C.

Preparation Example 11

To a solution of 1,2,3,4-tetrahydronaphthalene-1-carboxylic acid (2 g) in methylene chloride (10 mL) was added thionyl chloride (1 mL) and the mixture was heated under reflux with stirring for 3 hr. The reaction mixture was concentrated under reduced pressure, and THF (5 mL) was added to the residue. This solution was added to a solution of 4-isopropylaniline (1.53 g) and triethylamine (4.6 mL) in THF (10 mL) under ice-cooling. The temperature was raised to room temperature, and the mixture was stirred at the same temperature for 1 hr. The reaction mixture was partitioned between water and ethyl acetate. The organic layer was washed with saturated brine and dried over anhydrous magnesium sulfate. The solvent was evaporated and hexane was added to the residue. The precipitated solid was collected by filtration to give N-(4-isopropylphenyl)-1,2,3,4-tetrahydronaphthalene-1-carboxamide (2.78 g). melting point: 163.1° C.

Preparation Example 12

7-Methoxy-1,2,3,4-tetrahydronaphthalene-1-carboxylic acid (0.62 g), 4-isopropylaniline (0.41 g) and triethylamine (0.84 mL) were dissolved in DMF (20 mL), and HOBt.H$_2$O (0.48 g) and WSCI.HCl (0.61 g) were added under ice-cooling. The mixture was stirred at room temperature for one day and the reaction mixture was partitioned between water and ethyl acetate. The organic layer was washed with saturated brine and dried over anhydrous magnesium sulfate. The solvent was evaporated and ether was added to the residue. The precipitated solid was collected by filtration to give N-(4-isopropylphenyl)-7-methoxy-1,2,3,4-tetrahydronaphthalene-1-carboxamide (0.70 g). melting point: 168-169° C.

Preparation Example 13

To a solution of ethyl pyrazole-4-carboxylate (13.0 g), 4-dimethylaminopyridine (0.57 g) and triethylamine (15.5 mL) in tetrahydrofuran (80 mL) was added a solution of di-tert-butyl dicarbonate (24.3 g) in tetrahydrofuran (20 mL) at room temperature. The mixture was stirred at the same temperature for 4 hr. The reaction mixture was concentrated under reduced pressure, and the residue was partitioned between water and ethyl acetate. The organic layer was washed with saturated brine and dried over anhydrous magnesium sulfate. The solvent was evaporated and the residue was purified by silica gel column chromatography to give ethyl 1-(tert-butyloxycarbonyl)pyrazole-4-carboxylate (22.1 g).
$^1$H-NMR (CDCl$_3$) δ: 1.37 (3H, t, J=7.1 Hz), 1.67 (9H, s), 4.33 (2H, q, J=7.1 Hz), 8.06 (1H, s), 8.56 (1H, s).
Ethyl (1-tert-butyloxycarbonyl)pyrazole-4-carboxylate (17.0 g) was dissolved in anhydrous tetrahydrofuran (150 mL), and 1 mol/L diisobutylaluminum hydride/toluene solution (142 mL) was added at −78° C. over 40 min. The reaction temperature was raised to 0° C. over 1.5 hr, and methanol-ether (1:9) (100 mL), saturated aqueous potassium sodium tartrate tetrahydrate (Rochelle salt) solution (70 mL), water (330 mL) and ether (1 L) were successively added to the reaction mixture at the same temperature. The mixture was stirred for one more hour. The reaction mixture was passed through Celite, and the filtrate was washed with saturated brine and dried over anhydrous sodium sulfate. The solvent was evaporated, and the residue was purified by silica gel column chromatography to give 1-(tert-butyloxycarbonyl)-4-(hydroxymethyl)pyrazole (5.92 g).
$^1$H-NMR (CDCl$_3$) δ: 1.64 (9H, s), 4.61 (2H, s), 7.69 (1H, s), 8.03 (1H, s).

Preparation Example 14

By the reaction and treatment in the same manner as in Preparation Example 11 using 5-benzyloxy-1,2,3,4-tetrahydronaphthalene-1-carboxylic acid (5.48 g) and 4-isopropylaniline (3.90 mL) as starting materials, 5-benzyloxy-N-(4-isopropylphenyl)-1,2,3,4-tetrahydronaphthalene-1-carboxamide (5.94 g) was obtained. melting point: 170.4° C.

Preparation Example 15

By the reaction and treatment in the same manner as in Preparation Example 11 using 1,2,3,4-tetrahydronaphthalene-1-carboxylic acid (1.51 g) and 5-amino-2-isopropylpyridine (1.17 g) as starting materials, N-(6-isopropylpyridin-3-yl)-1,2,3,4-tetrahydronaphthalene-1-carboxamide (2.18 g) was obtained. melting point: 155.7° C.

Preparation Example 16

By the reaction and treatment in the same manner as in Preparation Example 11 using 5-benzyloxy-1,2,3,4-tetrahydronaphthalene-1-carboxylic acid (1.06 g) and 5-amino-2-isopropylpyridine (0.50 g) as starting materials, 5-benzyloxy-N-(6-isopropylpyridin-3-yl)-1,2,3,4-tetrahydronaphthalene-1-carboxamide (1.08 g) was obtained. melting point: 157.4° C.

Preparation Example 17

By the reaction and treatment in the same manner as in Preparation Example 11 using 5-benzyloxy-8-fluoro-1,2,3,4-tetrahydronaphthalene-1-carboxylic acid (2.30 g) and 5-amino-2-isopropylpyridine (1.04 g) as starting materials, 5-benzyloxy-8-fluoro-N-(6-isopropylpyridin-3-yl)-1,2,3,4-tetrahydronaphthalene-1-carboxamide (2.83 g) was obtained. melting point: 184.0° C.

Preparation Example 18

To a solution of 8-nitrochroman-4-carboxylic acid (3.0 g) and 4-isopropylaniline (2.0 g) in dimethylformamide (30 mL) were added N-hydroxybenzotriazole hydrate (2.0 g) and 1-ethyl-3-(3'-dimethylaminopropyl)carbodiimide hydrochloride (2.8 g), and the mixture was stirred at room temperature. After the completion of the reaction, the reaction mixture was partitioned between water and ethyl acetate. The organic layer was washed with saturated brine and dried over magnesium sulfate. The solvent was evaporated, and the residue was purified by silica gel column chromatography to give N-(4-isopropylphenyl)-8-nitrochroman-4-carboxamide (4.1 g).
$^1$H-NMR (CDCl$_3$) δ: 1.22 (6H, d, J=6.9 Hz), 2.20-2.40 (1H, m), 2.50-2.70 (1H, m), 2.80-3.00 (1H, m), 3.80-3.95 (1H, m), 4.30-4.60 (2H, m), 6.90-7.60 (7H, m), 7.75-7.90 (1H, m)

Preparation Example 19

By the reaction and treatment in the same manner as in Preparation Example 18 using 4-benzyloxyindan-1-carboxylic acid (0.8 g) and 2,4-dimethoxyaniline (0.5 g) as starting materials, 4-benzyloxy-N-(2,4-dimethoxyphenyl) indan-1-carboxamide (0.96 g) was obtained. melting point: 129.7° C.

$^1$H-NMR (CDCl$_3$) δ: 2.40-2.60 (2H, m), 2.90-3.20 (2H, m), 3.75 (3H, s), 3.78 (3H, s), 4.00-4.20 (1H, m), 5.12 (2H, s), 6.40-6.50 (2H, m), 6.82 (1H, d, J=8.0 Hz), 7.01 (1H, d, J=7.5 Hz), 7.10-7.60 (6H, m), 7.73 (1H, brs), 8.24 (1H, d, J=8.6 Hz)

Preparation Example 20

By the reaction and treatment in the same manner as in Preparation Example 18 using 5-benzyloxy-8-methyl-1,2,3,4-tetrahydronaphthalene-1-carboxylic acid (1.34 g) and 5-amino-2-isopropylpyridine (0.62 g) as starting materials, 5-benzyloxy-N-(6-isopropylpyridin-3-yl)-8-methyl-1,2,3,4-tetrahydronaphthalene-1-carboxamide (1.75 g) was obtained.

$^1$H-NMR (CDCl$_3$) δ: 1.26 (6H, d, J=6.9 Hz), 1.55-1.80 (1H, m), 1.85-2.00 (2H, m), 2.20 (3H, s), 2.40-2.55 (1H, m), 2.55-2.75 (1H, m), 2.95-3.10 (2H, m), 3.80-3.90 (1H, m), 5.10 (2H, s), 6.83 (1H, d, J=8.1 Hz), 7.00-7.50 (8H, m), 7.95-8.10 (1H, m), 8.27 (1H, d, J=2.4 Hz)

Preparation Example 21

By the reaction and treatment in the same manner as in Preparation Example 18 using 5-benzyloxy-1,2,3,4-tetrahydronaphthalene-1-carboxylic acid (20.0 g) and 5-amino-2-methoxypyridine (8.72 g), as starting materials, 5-benzyloxy-N-(6-methoxypyridin-3-yl)-1,2,3,4-tetrahydronaphthalene-1-carboxamide (23.9 g) was obtained.

$^1$H-NMR (DMSO-d$_6$) δ: 1.62-1.69 (1H, m), 1.96-2.05 (3H, m), 2.64-2.69 (2H, m), 3.82 (3H, s), 3.81-3.85 (1H, m), 5.11 (2H, s), 6.71-6.89 (3H, m), 7.05-7.10 (1H, m), 7.30-7.49 (5H, m), 7.92-7.96 (1H, m), 8.39-8.40 (1H, m), 10.20 (1H, s)

Preparation Example 22

7-Methoxy-1,2,3,4-tetrahydronaphthalene-1-carboxylic acid (5.0 g) and (R)-(+)-1-phenethylamine (3.13 mL) were dissolved in methanol (50 mL), and the solvent was evaporated under reduced pressure to give crude crystals (7.33 g). This was recrystallized from a mixed solvent of methanol and isopropyl ether. The obtained crystals were partitioned between ethyl acetate and 1 mol/L-hydrochloric acid. The organic layer was washed with saturated brine and dried over magnesium sulfate.

The solvent was evaporated under reduced pressure to give (R)-7-methoxy-1,2,3,4-tetrahydronaphthalene-1-carboxylic acid (0.65 g).

optical purity>99.9% e.e.
Analysis Conditions
  column: CHIRALCEL OD (DAICEL)
  developing solvent: hexane/isopropanol/acetic acid=97/3/3
  flow rate: 0.5 mL/min
  UV detection: 254 nm
  retention time: 21.5 min Preparation Example 23

7-Methoxy-1,2,3,4-tetrahydronaphthalene-1-carboxylic acid (5.0 g) and (S)-(−)-1-phenethylamine (3.2 mL) were dissolved in methanol (50 mL), and the solvent was evaporated under reduced pressure to give crude crystals (7.33 g). This was recrystallized from a mixed solvent of methanol and isopropyl ether. The obtained crystals were partitioned between ethyl acetate and 1 mol/L-hydrochloric acid. The organic layer was washed with saturated brine and dried over magnesium sulfate. The solvent was evaporated under reduced pressure to give (S)-7-methoxy-1,2,3,4-tetrahydronaphthalene-1-carboxylic acid (0.96 g).

optical purity>99.9% e.e.
Analysis Conditions
  column: CHIRALCEL OD (DAICEL)
  developing solvent: hexane/isopropanol/acetic acid=97/3/3
  flow rate: 0.5 mL/min
  UV detection: 254 nm
  retention time: 26 min Preparation Example 24

By the reaction and treatment in the same manner as in Preparation Example 11 using 5-benzyloxy-1,2,3,4-tetrahydronaphthalene-1-carboxylic acid (2.82 g) and 2-amino-5-methylpyridine (1.08 g) as starting materials, 5-benzyloxy-N-(5-methylpyridin-2-yl)-1,2,3,4-tetrahydronaphthalene-1-carboxamide (2.00 g) was obtained.

MS (ESI) m/z: 373 [MH]$^+$

Example 1

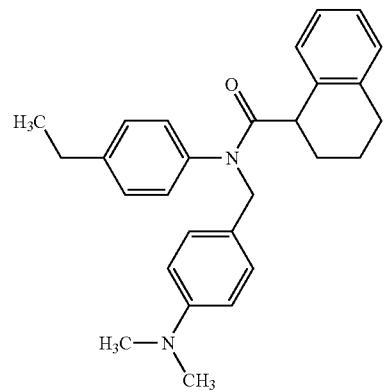

To a solution of 1,2,3,4-tetrahydronaphthalene-1-carboxylic acid (1.0 g) in methylene chloride (10 mL) was added thionyl chloride (0.68 mL), and the mixture was heated under reflux with stirring for 3 hr. The reaction mixture was concentrated under reduced pressure, and THF (6 mL) was added to the residue. This solution was added to a solution of [(4-dimethylaminophenyl)methyl](4-ethylphenyl)-amine (1.2 g) and triethylamine (2 mL) in THF (6 mL) under ice-cooling. The mixture was allowed to warm to room temperature and stirred at the same temperature for one day. The reaction mixture was partitioned between water and ethyl acetate. The organic layer was washed with saturated brine and dried over anhydrous magnesium sulfate. The solvent was evaporated, and the residue was purified by silica gel column chromatography. The obtained crystals were recrystallized from a mixed solvent of ethyl acetate and hexane to give N-[(4-dimethylaminophenyl)methyl]-N-(4-ethylphenyl)-1,2,3,4-tetrahydronaphthalene-1-carboxamide (0.28 g). melting point: 109-110° C.

Example 2

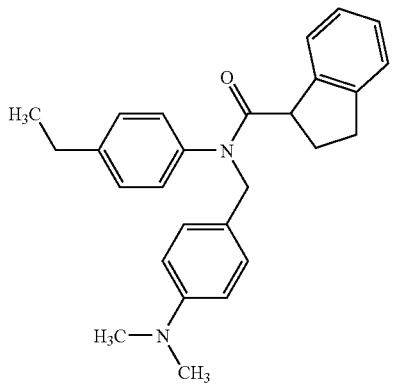

By the reaction and treatment in the same manner as in Example 1 using indan-1-carboxylic acid (0.46 g) and [(4-dimethylaminophenyl)methyl](4-ethylphenyl)amine (0.6 g) as starting materials, N-[(4-dimethylaminophenyl) methyl]-N-(4-ethylphenyl)indan-1-carboxamide (0.15 g) was obtained.

$^1$H-NMR (CDCl$_3$) δ: 1.22 (3H, t, J=7.3 Hz), 2.00-2.20 (1H, m), 2.25-2.45 (1H, m), 2.63 (2H, q, J=7.3 Hz), 2.65-2.85 (1H, m), 2.93 (6H, s), 3.00-3.15 (1H, m), 3.96 (1H, t, J=7.9 Hz), 4.73 (1H, d, J=13.9 Hz), 4.94 (1H, d, J=13.9 Hz), 6.64 (2H, d, J=8.6 Hz), 6.97 (2H, d, J=7.9 Hz), 7.00-7.20 (8H, m).

Example 3

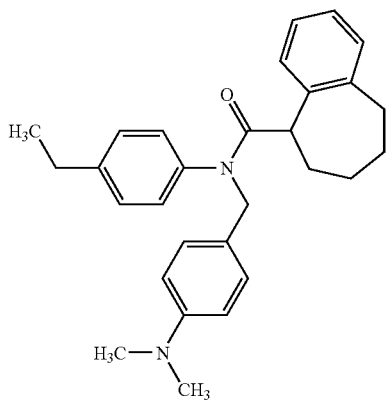

By the reaction and treatment in the same manner as in Example 1 using 6,7,8,9-tetrahydro-5H-benzocycloheptene-5-carboxylic acid (0.54 g) and [(4-dimethylaminophenyl)methyl](4-ethylphenyl)amine (0.6 g) as starting materials, N-[(4-dimethylaminophenyl)methyl]-N-(4-ethylphenyl)-6,7,8,9-tetrahydro-5H-benzocycloheptene-5-carboxamide (0.2 g) was obtained.

$^1$H-NMR (CDCl$_3$) δ: 1.17 (3H, t, J=7.3 Hz), 1.20-2.05 (6H, m), 2.10-2.30 (1H, m), 2.56 (3H, q, J=7.3 Hz), 2.92 (6H, s), 3.69 (1H, d, J=7.9 Hz), 4.78 (1H, d, J=13.9 Hz), 4.90 (1H, d, J=13.9 Hz), 6.55-6.65 (4H, m), 6.90-7.30 (8H, m).

Example 4

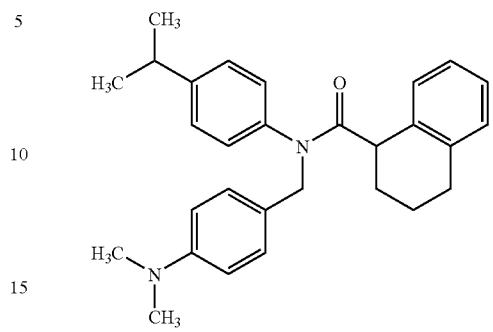

To a solution of 1,2,3,4-tetrahydronaphthalene-1-carboxylic acid (3.3 g) in 1,2-dichloroethane (20 mL) was added thionyl chloride (2.1 mL), and the mixture was heated under reflux with stirring for 3 hr. The reaction mixture was concentrated under reduced pressure, and methylene chloride (10 mL) was added to the residue. This solution was added to a solution of [(4-dimethylaminophenyl)methyl](4-isopropylphenyl)amine (5.1 g) in methylene chloride (10 mL) under ice-cooling. The reaction mixture was warmed to room temperature and stirred at the same temperature for one day. The reaction mixture was partitioned between water and ethyl acetate. The organic layer was washed with saturated brine and dried over anhydrous magnesium sulfate. The solvent was evaporated, and the residue was purified by silica gel column chromatography. The obtained crystals were recrystallized from isopropyl ether to give N-[(4-dimethylaminophenyl)methyl]-N-(4-isopropylphenyl)-1,2,3,4-tetrahydronaphthalene-1-carboxamide (4.38 g) melting point: 121° C.

Example 5

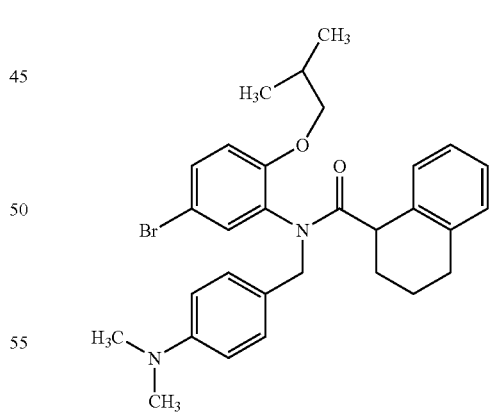

To a solution of 1,2,3,4-tetrahydronaphthalene-1-carboxylic acid (0.24 g) in methylene chloride (3 mL) was added thionyl chloride (0.15 mL), and the mixture was heated under reflux with stirring for 3 hr. The reaction mixture was concentrated under reduced pressure, and THF (2 mL) was added to the residue. This solution was added to a solution of (5-bromo-2-isobutoxyphenyl)[(4-dimethylaminophenyl) methyl]amine (0.5 g) and sodium hydride (0.07 g) in THF (3 mL). The reaction mixture was warmed to room temperature and stirred at the same temperature for one day. The reaction mixture was partitioned between water and ethyl acetate. The organic layer was washed with saturated brine and dried over anhydrous magnesium sulfate. The solvent was evaporated, and the residue was purified by silica gel column chromatography. The obtained crystals were recrystallized from ethyl acetate to give N-(5-bromo-2-isobutoxyphenyl)-N-[(4-dimethylaminophenyl)methyl]-1,2,3,4-tetrahydronaphthalene-1-carboxamide (0.3 g). melting point: 176-178° C.

Example 6

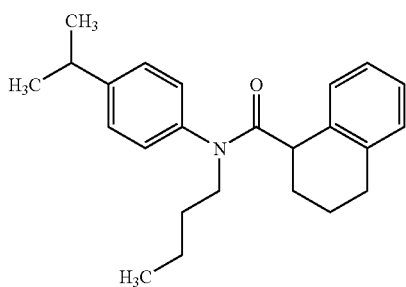

N-(4-Isopropylphenyl)-1,2,3,4-tetrahydronaphthalene-1-carboxamide (0.5 g) and butyl bromide (0.22 mL) were dissolved in DMF (3 mL), and sodium hydride (0.08 g) was added under ice-cooling. The mixture was stirred at the same temperature for 30 min and then at room temperature for 3 hr. The reaction mixture was partitioned between water and ethyl acetate. The organic layer was washed with saturated brine and dried over anhydrous magnesium sulfate. The solvent was evaporated and the residue was purified by silica gel column chromatography to give N-butyl-N-(4-isopropylphenyl)-1,2,3,4-tetrahydronaphthalene-1-carboxamide (0.53 g).

$^1$H-NMR (CDCl$_3$) δ: 0.91 (3H, t, J=7.3 Hz), 1.26 (6H, d, J=6.6 Hz), 1.20-1.65 (5H, m), 1.80-2.10 (3H, m), 2.63 (1H, dt, J=16.5 Hz, 4.6 Hz), 2.75-3.00 (2H, m), 3.65-3.80 (3H, m), 6.95-7.30 (8H, m).

Example 7

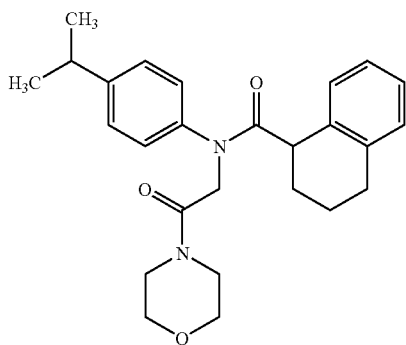

By the reaction and treatment in the same manner as in Example 6 using N-(4-isopropylphenyl)-1,2,3,4-tetrahydronaphthalene-1-carboxamide (0.5 g) and 2-morpholino-2-oxoethyl chloride (0.33 g) as starting materials, N-(4-isopropylphenyl)-N-(2-morpholino-2-oxoethyl)-1,2,3,4-tetrahydronaphthalene-1-carboxamide (0.43g) was obtained. melting point: 180° C.

Example 8

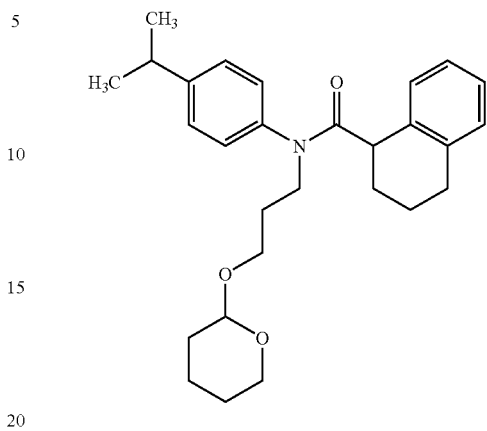

By the reaction and treatment in the same manner as in Example 6 using N-(4-isopropylphenyl)-1,2,3,4-tetrahydronaphthalene-1-carboxamide (0.75 g) and 3-(tetrahydropyran-2-yloxy)propyl bromide (0.52 mL) as starting materials, N-(4-isopropylphenyl)-N-[3-(tetrahydropyran-2-yloxy)propyl]-1,2,3,4-tetrahydronaphthalene-1-carboxamide (0.9 g) was obtained.

$^1$H-NMR (CDCl$_3$) δ: 1.26 (6H, d, J=7.3 Hz), 1.40-2.10 (13H, m), 2.63 (1H, dt, J=16.5 Hz, 4.6 Hz), 2.75-3.05 (2H, m), 3.35-3.50 (2H, m), 3.70-4.00 (4H, m), 4.12 (1H, dd, J=14.5 Hz, 7.3 Hz), 6.95-7.30 (8H, m).

Example 9

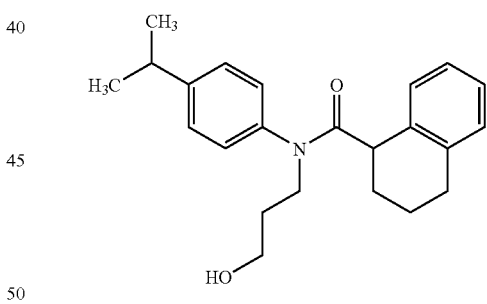

N-(4-Isopropylphenyl)-N-[3-(tetrahydropyran-2-yloxy)propyl]-1,2,3,4-tetrahydronaphthalene-1-carboxamide (0.24 g) was dissolved in a mixed solvent (7 mL) of acetic acid: THF: water (4:2:1) and stirred at room temperature for 2 hr. The reaction mixture was partitioned between water and ethyl acetate. The organic layer was washed with saturated brine and dried over anhydrous magnesium sulfate. The solvent was evaporated, and the residue was purified by silica gel column chromatography to give N-(3-hydroxypropyl)-N-(4-isopropylphenyl)-1,2,3,4-tetrahydronaphthalene-1-carboxamide (0.12 g).

$^1$H-NMR (CDCl$_3$) δ: 1.27 (6H, d, J=6.6 Hz), 1.40-2.10 (6H, m), 2.65 (1H, dt, J=16.5 Hz, 4.6 Hz), 2.75-3.05 (2H, m), 3.60-3.90 (4H, m), 3.95-4.15 (4H, m), 6.95-7.30 (8H, m).

Example 10

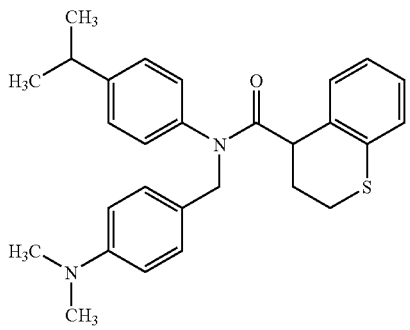

By the reaction and treatment in the same manner as in Example 1 using thiochroman-4-carboxylic acid (0.55 g) and [(4-dimethylaminophenyl)methyl](4-isopropylphenyl)amine (0.63 g) as starting materials, N-[(4-dimethylaminophenyl)methyl]-N-(4-isopropylphenyl)thiochroman-4-carboxamide (0.3 g) was obtained. melting point: 118° C.

Example 11

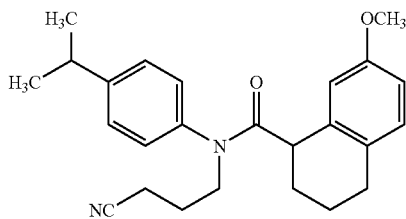

By the reaction and treatment in the same manner as in Example 1 using 7-methoxy-1,2,3,4-tetrahydronaphthalene-1-carboxylic acid (1.56 g) and (3-cyanopropyl) (4-isopropylphenyl)amine (1.79 g) as starting materials, N-(3-cyanopropyl)-N-(4-isopropylphenyl)-7-methoxy-1,2,3,4-tetrahydronaphthalene-1-carboxamide (1.56 g) was obtained. melting point: 74-750° C.

Example 12

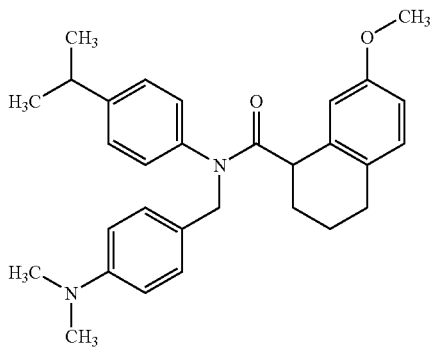

To a solution of 7-methoxy-1,2,3,4-tetrahydronaphthalene-1-carboxylic acid (1.0 g) in 1,2-dichloroethane (20 mL) was added thionyl chloride (2.1 mL), and the mixture was heated under reflux with stirring for 3 hr. The reaction mixture was concentrated under reduced pressure, and methylene chloride (10 mL) was added to the residue. This solution was added to a solution of [(4-dimethylaminophenyl)methyl](4-isopropylphenyl)amine (1.3 g) in methylene chloride (10 mL) under ice-cooling. The reaction mixture was warmed to room temperature and stirred at the same temperature for one day. The reaction mixture was partitioned between water and ethyl acetate. The organic layer was washed with saturated brine and dried over anhydrous magnesium sulfate. The solvent was evaporated, and the residue was purified by silica gel column chromatography to give N-[(4-dimethylaminophenyl)methyl]-N-(4-isopropylphenyl)-7-methoxy-1,2,3,4-tetrahydronaphthalene-1-carboxamide (0.73 g).

$^1$H-NMR (CDCl$_3$) δ: 1.22 (6H, d, J=7.3 Hz), 1.43-1.45 (1H, m), 1.86-2.01 (2H, m), 2.25 (3H, s), 2.54-2.79 (1H, m), 2.70-3.00 (2H, m), 2.93 (6H, s), 3.68 (1H, t, J=8.6 Hz), 3.68 (3H, s), 4.59 (1H, d, J=14 Hz), 6.51 (1H, d, J=2.5 Hz), 6.66 (2H, dd, J=2.6, 8.5 Hz), 6.91-6.99 (2H, m), 7.17 (2H, dd, J=8.7, 14 Hz).

Example 13

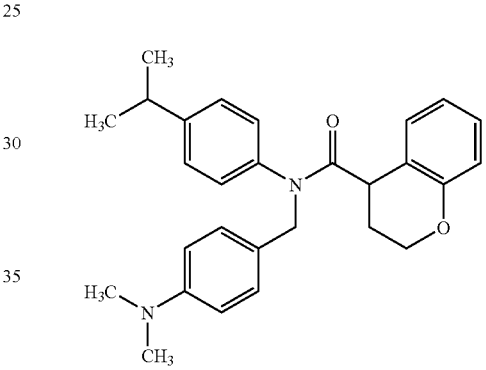

By the reaction and treatment in the same manner as in Example 1 using chroman-4-carboxylic acid (0.5 g) and [(4-dimethylaminophenyl)methyl](4-isopropylphenyl)amine (0.63 g) as starting materials, N-[(4-dimethylaminophenyl)methyl]-N-(4-isopropylphenyl)chroman-4-carboxamide (0.25 g) was obtained. melting point: 110-112° C.

Example 14

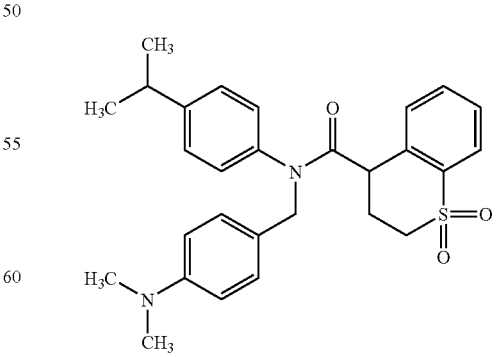

By the reaction and treatment in the same manner as in Example 1 using 1,1-dioxothiochroman-4-carboxylic acid (0.26 g) and [(4-dimethylaminophenyl)methyl](4-isopropylphenyl)amine (0.31 g) as starting materials, N-[(4-dimethylaminophenyl) methyl]-N-(4-isopropylphenyl)-1,1-dioxothiochroman-4-carboxamide (0.07 g) was obtained. melting point: 185-187° C.

Example 15

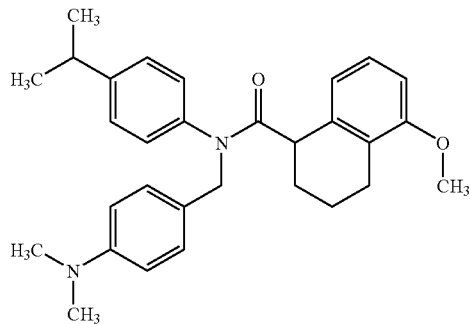

By the reaction and treatment in the same manner as in Example 12 using 5-methoxy-1,2,3,4-tetrahydronaphthalene-1-carboxylic acid (2.0 g) and [(4-dimethylaminophenyl)methyl](4-isopropylphenyl)amine (1.91 g) as starting materials, N-[(4-dimethylaminophenyl)methyl]-N-(4-isopropylphenyl)-5-methoxy-1,2,3,4-tetrahydronaphthalene-1-carboxamide (0.48 g) was obtained.

$^1$H-NMR (CDCl$_3$) δ: 1.22 (6H, d, J=7.3 Hz), 1.43-1.45 (1H, m), 1.86-2.01 (2H, m), 2.25 (3H, s), 2.63 (1H, t, 5.9 Hz), 2.80-2.99 (1H, m), 2.70-3.00 (2H, m), 2.94 (6H, s), 3.68 (1H, t, J=8.6 Hz), 3.77 (3H, s), 4.73 (1H, d, J=14 Hz), 4.95 (1H, d, J=14 Hz), 6.66 (2H, d, J=8.0 Hz), 6.68 (2H, s), 6.97 (2H, d, J=8.0 Hz), 7.04-7.30 (5H, m).

Example 16

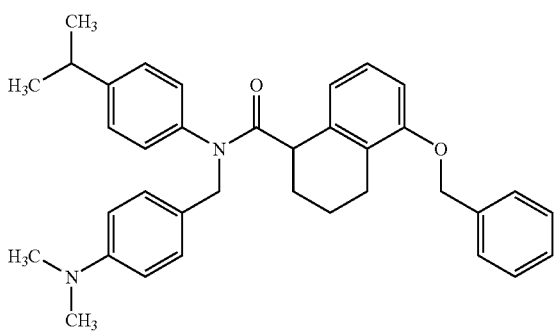

By the reaction and treatment in the same manner as in Example 12 using 5-benzyloxy-1,2,3,4-tetrahydronaphthalene-1-carboxylic acid (2.0 g) and [(4-dimethylaminophenyl)methyl](4-isopropylphenyl)amine (1.91 g) as starting materials, 5-benzyloxy-N-[(4-dimethylaminophenyl)methyl]-N-(4-isopropylphenyl)-1,2,3,4-tetrahydronaphthalene-1-carboxamide (0.76 g) was obtained.

$^1$H-NMR (CDCl$_3$) δ: 1.22 (6H, d, J=7.3 Hz), 1.39-1.53 (1H, m), 1.79-2.08 (3H, m), 2.68-2.78 (2H, m), 2.83-2.92 (1H, m), 2.94 (6H, s), 3.73 (1H, t, J=8.6 Hz), 4.72 (1H, d, J=14 Hz), 4.93 (1H, d, J=14 Hz), 5.03 (2H, s), 6.61-6.74 (4H, m), 6.94-7.20 (7H, m), 7.28-7.44 (5H, m).

Example 17

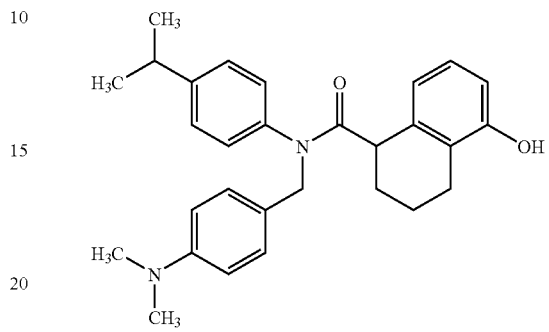

5-Benzyloxy-N-[(4-dimethylaminophenyl)methyl]-N-(4-isopropylphenyl)-1,2,3,4-tetrahydronaphthalene-1-carboxamide (0.75 g) was dissolved in methanol (60 mL), and 10% palladium carbon (0.5 g) and ammonium formate (1.5 g) were added. The mixture was stirred at room temperature for one day. The reaction mixture was filtrated, and the filtrate was concentrated. Water was added to the residue, and the precipitated crude crystals were recrystallized from ethyl acetate to give N-[(4-dimethylaminophenyl)methyl]-5-hydroxy-N-(4-isopropylphenyl)-1,2,3,4-tetrahydronaphthalene-1-carboxamide (0.5 g). melting point: 200-202° C.

Example 18

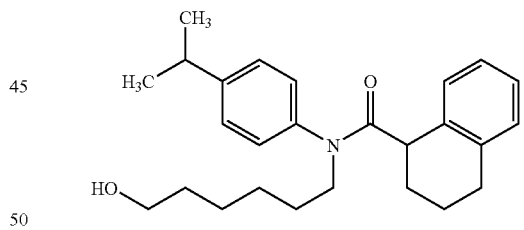

By the reaction and treatment in the same manner as in Example 1 using 1,2,3,4-tetrahydronaphthalene-1-carboxylic acid (1.1 g) and (4-isopropylphenyl)[6-(tetrahydropyran-2-yloxy)hexyl]amine (2.0 g) as starting materials, N-(4-isopropylphenyl)-N-[6-(tetrahydropyran-2-yloxy)hexyl]-1,2,3,4-tetrahydronaphthalene-1-carboxamide (1.0 g) was obtained. By the reaction and treatment of this compound in the same manner as in Example 9, N-(6-hydroxyhexyl)-N-(4-isopropylphenyl)-1,2,3,4-tetrahydronaphthalene-1-carboxamide (0.64 g) was obtained.

$^1$H-NMR (CDCl$_3$) δ: 1.26 (6H, d, J=7.3 Hz), 1.20-2.10 (13H, m), 2.63 (1H, dt, J=16.5 Hz, 4.6 Hz), 2.75-3.05 (2H, m), 3.59 (2H, t, J=5.9 Hz), 3.65-3.80 (3H, m), 6.95-7.30 (8H, m).

Example 19

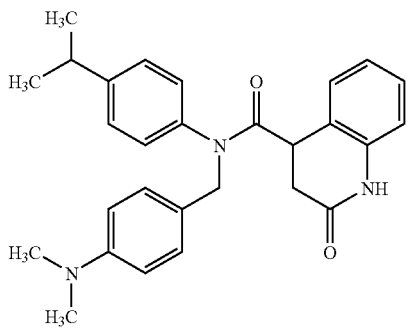

By the reaction and treatment in the same manner as in Example 1 using 2-oxo-1,2,3,4-tetrahydroquinoline-4-carboxylic acid (0.5 g) and [(4-dimethylaminophenyl)methyl](4-isopropylphenyl)amine (0.7 g) as starting materials, N-[(4-dimethylaminophenyl)methyl]-N-(4-isopropylphenyl)-2-oxo-1,2,3,4-tetrahydroquinoline-4-carboxamide (0.6 g) was obtained. melting point: 170° C.

Example 20

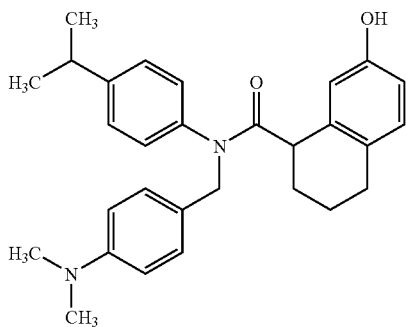

N-[(4-Dimethylaminophenyl)methyl]-N-(4-isopropylphenyl)-7-methoxy-1,2,3,4-tetrahydronaphthalene-1-carboxamide (3.2 g) was dissolved in methylene chloride (60 mL), and boron tribromide (0.72 mL) was added under ice-cooling. The mixture was stirred at room temperature for one day. The reaction mixture was partitioned between saturated aqueous sodium hydrogencarbonate and chloroform. The organic layer was washed with saturated brine and dried over anhydrous magnesium sulfate. The solvent was evaporated, and the residue was purified by silica gel column chromatography to give N-[(4-dimethylaminophenyl)methyl]-7-hydroxy-N-(4-isopropylphenyl)-1,2,3,4-tetrahydronaphthalene-1-carboxamide (0.36 g). melting point: 214-217° C.

Example 21

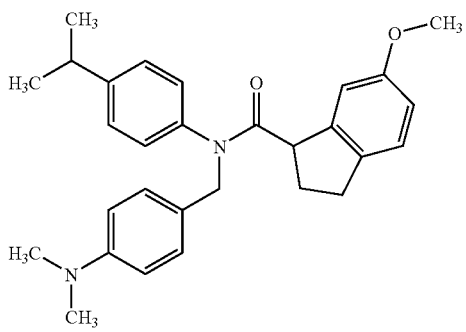

By the reaction and treatment in the same manner as in Example 12 using 6-methoxyindan-1-carboxylic acid (0.5 g) and [(4-dimethylaminophenyl)methyl](4-isopropylphenyl)amine (0.7 g) as starting materials, N-[(4-dimethylaminophenyl)methyl]-N-(4-isopropylphenyl)-6-methoxyindan-1-carboxamide (0.53 g) was obtained.

$^1$H-NMR (CDCl$_3$) δ: 1.23 (6H, d, J=6.6 Hz), 2.00-2.20 (1H, m), 2.30-2.50 (1H, m), 2.60-2.75 (1H, m), 2.80-3.10 (2H, m), 2.93 (6H, s), 3.74 (3H, s), 3.93 (1H, t, J=7.9 Hz), 4.68 (1H, d, J=13.9 Hz), 4.98 (1H, d, J=13.9 Hz), 6.60-6.75 (4H, m), 6.90-7.20 (7H, m).

Example 22

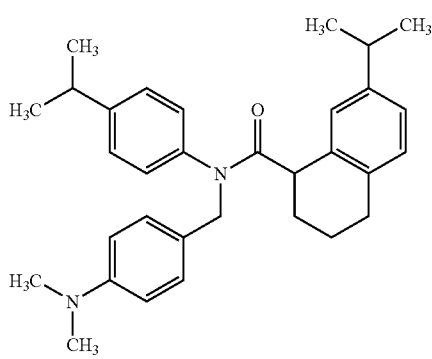

By the reaction and treatment in the same manner as in Example 1 using 7-isopropyl-1,2,3,4-tetrahydronaphthalene-1-carboxylic acid (1.0 g) and [(4-dimethylaminophenyl)methyl](4-isopropylphenyl)amine (1.07 g) as starting materials, N-[(4-dimethylaminophenyl)methyl]-7-isopropyl-N-(4-isopropylphenyl)-1,2,3,4-tetrahydronaphthalene-1-carboxamide (0.53 g) was obtained. melting point: 123-125° C.

Example 23

By the reaction and treatment in the same manner as in Example 1 using 1,2,3,4-tetrahydronaphthalene-1-carboxylic acid (0.5 g) and [(1-ethylpyrazol-4-yl)methyl](4-isopropylphenyl)amine (0.57 g) as starting materials, N-[(1-ethylpyrazol-4-yl)methyl]-N-(4-isopropylphenyl)-1,2,3,4-tetrahydronaphthalene-1-carboxamide (0.12 g) was obtained. melting point: 75-76° C.

Example 24

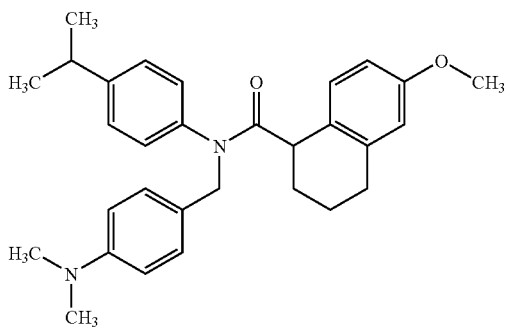

By the reaction and treatment in the same manner as in Example 12 using 6-methoxy-1,2,3,4-tetrahydronaphthalene-1-carboxylic acid (0.54 g) and [(4-dimethylaminophenyl)methyl](4-isopropylphenyl)amine (0.7 g) as starting materials, N-[(4-dimethylaminophenyl)methyl]-N-(4-isopropylphenyl)-6-methoxy-1,2,3,4-tetrahydronaphthalene-1-carboxamide (0.36 g) was obtained.

$^1$H-NMR (CDCl$_3$) δ: 1.23 (6H, d, J=6.6 Hz), 1.35-1.55 (1H, m), 1.75-2.10 (3H, m), 2.55-2.70 (1H, m), 2.75-3.00 (2H, m), 2.94 (6H, s), 3.60-3.70 (1H, m), 3.74 (3H, s), 4.70 (1H, d, J=13.9 Hz), 4.93 (1H, d, J=13.9 Hz), 6.50-6.75 (4H, m), 6.90-7.20 (7H, m).

Example 25

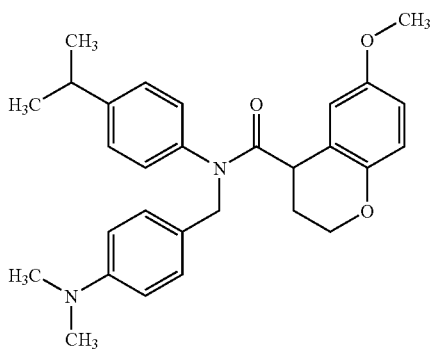

By the reaction and treatment in the same manner as in Example 1 using 6-methoxychroman-4-carboxylic acid (0.54 g) and [(4-dimethylaminophenyl)methyl](4-isopropylphenyl)amine (0.7 g) as starting materials, N-[(4-dimethylaminophenyl) methyl]-N-(4-isopropylphenyl)-6-methoxychroman-4-carboxamide (0.3 g) was obtained. melting point: 82-84° C.

Example 26

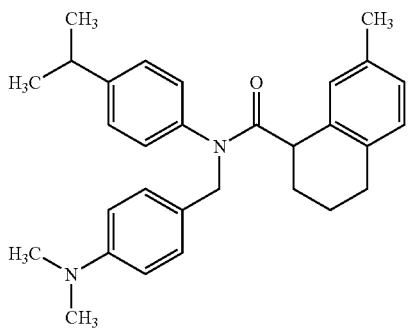

By the reaction and treatment in the same manner as in Example 12 using 7-methyl-1,2,3,4-tetrahydronaphthalene-1-carboxylic acid (1.0 g) and [(4-dimethylaminophenyl)methyl](4-isopropylphenyl) amine (1.40 g) as starting materials, N-[(4-dimethylaminophenyl)methyl]-N-(4-isopropylphenyl)-7-methyl-1,2,3,4-tetrahydronaphthalene-1-carboxamide (0.53 g) was obtained.

$^1$H-NMR (CDCl$_3$) δ: 1.22 (6H, d, J=7.3 Hz), 1.43-1.45 (1H, m), 1.86-2.01 (2H, m), 2.25 (3H, s), 2.54-2.79 (1H, m), 2.70-3.00 (2H, m), 2.93 (6H, s), 3.69 (1H, t, J=8.6 hz), 4.70 (1H, d, J=14 Hz), 4.98 (1H, d, J=14 Hz), 6.65 (2H, d, J=8.5 Hz), 6.80 (1H, s), 6.91 (2H, s), 6.96 (2H, d, J=7.9 Hz), 7.15 (4H, dd, J=6.6, 8.6 Hz).

Example 27

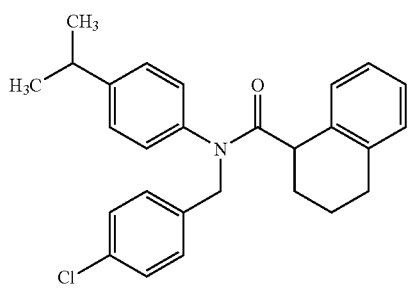

By the reaction and treatment in the same manner as in Example 1 using 1,2,3,4-tetrahydronaphthalene-1-carboxylic acid (1.0 g) and [(4-chlorophenyl)methyl](4-isopropylphenyl)amine (1.3 g) as starting materials, N-[(4-chlorophenyl) methyl]-N-(4-isopropylphenyl)-1,2,3,4-tetrahydronaphthalene-1-carboxamide (0.1 g) was obtained. melting point: 122-123° C.

Example 28

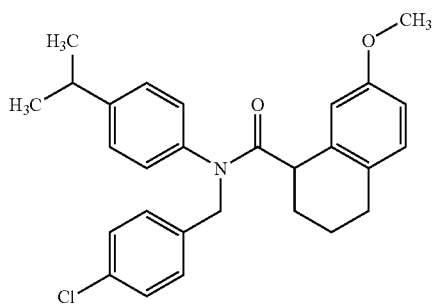

By the reaction and treatment in the same manner as in Example 1 using 7-methoxy-1,2,3,4-tetrahydronaphthalene-1-carboxylic acid (1.0 g) and [(4-chlorophenyl)methyl](4-isopropylphenyl) amine (1.5 g) as starting materials, N-[(4-chlorophenyl)methyl]-N-(4-isopropylphenyl)-7-methoxy-1,2,3,4-tetrahydronaphthalene-1-carboxamide (0.58 g) was obtained. melting point: 87-88° C.

Example 29

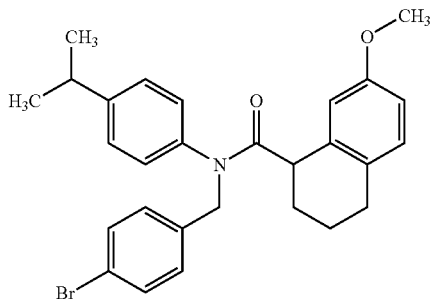

By the reaction and treatment in the same manner as in Example 1 using 7-methoxy-1,2,3,4-tetrahydronaphthalene-1-carboxylic acid (1.5 g) and [(4-bromophenyl)methyl](4-isopropylphenyl)amine (2.21 g) as starting materials, N-[(4-bromophenyl)methyl]-N-(4-isopropylphenyl)-7-methoxy-1,2,3,4-tetrahydronaphthalene-1-carboxamide (0.526 g) was obtained. melting point: 85° C.

Example 30

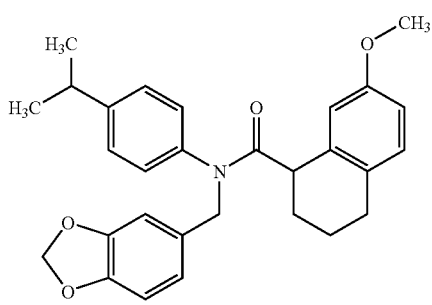

By the reaction and treatment in the same manner as in Example 1 using 7-methoxy-1,2,3,4-tetrahydronaphthalene-1-carboxylic acid (1.0 g) and [(1,3-dioxaindan-5-yl)methyl](4-isopropylphenyl)amine (1.3 g) as starting materials, N-[(1,3-dioxaindan-5-yl)methyl]-N-(4-isopropylphenyl)-7-methoxy-1,2,3,4-tetrahydronaphthalene-1-carboxamide (1.3 g) was obtained. melting point: 97-98° C.

Example 31

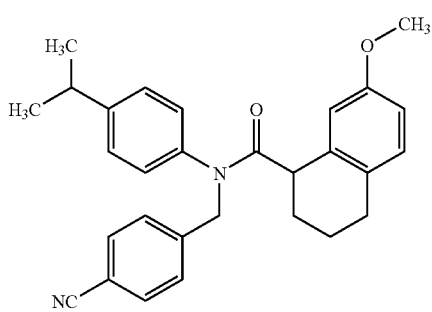

By the reaction and treatment in the same manner as in Example 1 using 7-methoxy-1,2,3,4-tetrahydronaphthalene-1-carboxylic acid (0.63 g) and [(4-cyanophenyl)methyl](4-isopropylphenyl)amine (0.83 g) as starting materials, N-[(4-cyanophenyl)methyl]-N-(4-isopropylphenyl)-7-methoxy-1,2,3,4-tetrahydronaphthalene-1-carboxamide (0.63 g) was obtained. melting point: 137-138° C.

Example 32

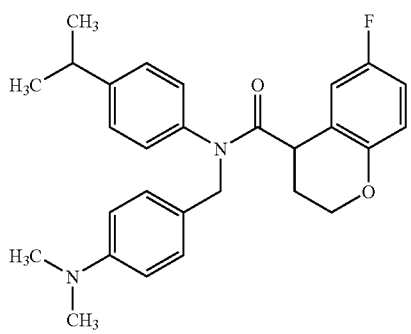

By the reaction and treatment in the same manner as in Example 1 using 6-fluorochroman-4-carboxylic acid (1.96 g) and [(4-dimethylaminophenyl)methyl] (4-isopropylphenyl)amine (2.68 g) as starting materials, N-[(4-dimethylaminophenyl)methyl]-6-fluoro-N-(4-isopropylphenyl)chroman-4-carboxamide (2.89 g) was obtained. melting point: 95-98° C.

Example 33

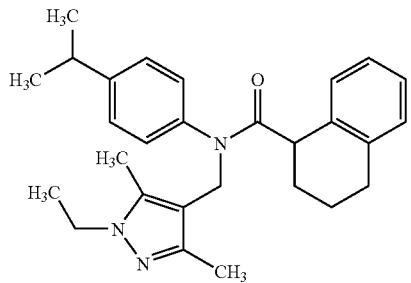

By the reaction and treatment in the same manner as in Example 4 using 1,2,3,4-tetrahydronaphthalene-1-carboxylic acid (0.5 g) and [(1-ethyl-3,5-dimethylpyrazol-4-yl)methyl](4-isopropylphenyl)amine (0.65 g) as starting materials, N-[(1-ethyl-3,5-dimethylpyrazol-4-yl)methyl]-N-(4-isopropylphenyl)-1,2,3,4-tetrahydronaphthalene-1-carboxamide (0.31 g) was obtained. Oxalic acid was added to this compound. By recrystallization from ethyl acetate, N-[(1-ethyl-3,5-dimethylpyrazol-4-yl)methyl]-N-(4-isopropylphenyl)-1,2,3,4-tetrahydronaphthalene-1-carboxamide ½ oxalate ½ hydrate (0.03 g) was obtained. melting point: 142-143° C.

Example 34

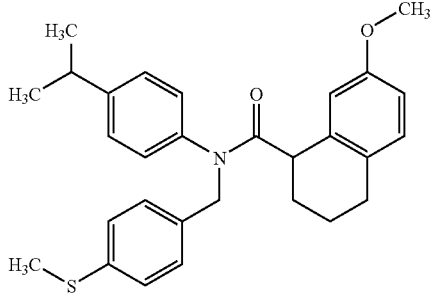

By the reaction and treatment in the same manner as in Example 12 using 7-methoxy-1,2,3,4-tetrahydronaphthalene-1-carboxylic acid (1.5 g) and (4-isopropylphenyl)[(4-methylthiophenyl)methyl]amine (2.0 g) as starting materials, N-(4-isopropylphenyl)-7-methoxy-N-[(4-methylthiophenyl)methyl]-1,2,3,4-tetrahydronaphthalene-1-carboxamide (1.4 g) was obtained.

$^1$H-NMR (CDCl$_3$) δ: 1.23 (6H, d, J=7.3 Hz), 1.43-1.45 (1H, m), 1.86-2.01 (3.H, m), 2.25 (3H, s), 2.47 (3H, s), 2.53-2.61 (1H, m), 2.71-2.97 (2H, m), 3.70 (3H, s), 3.72 (1H, t, J=8.6 Hz), 4.70 (1H, d, J=14 Hz), 5.04 (1H, d, J=14 Hz), 6.65 (1H, d, J=2.7 Hz), 6.67 (1H, dd, J=2.7, 8.6 Hz), 6.93-6.99 (3H, m), 7.16-7.22 (6H, m).

Example 35

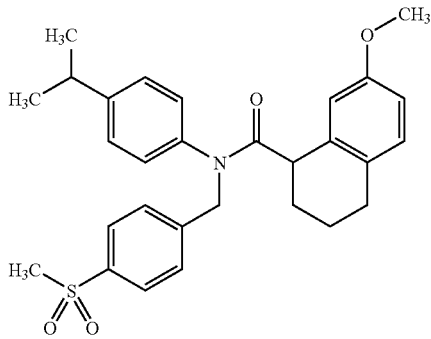

N-(4-Isopropylphenyl)-7-methoxy-N-[(4-methylthiophenyl)methyl]-1,2,3,4-tetrahydronaphthalene-1-carboxamide (1.0 g) was dissolved in acetic acid (10 mL), and 30% aqueous hydrogen peroxide (5.5 mL) was added at room temperature. The mixture was stirred with heating at 100° C. for 3 hr. Water was added to the reaction mixture, and the precipitated solid was purified by silica gel column chromatography to give crude crystals. The crystals were recrystallized from ethyl acetate to give N-(4-isopropylphenyl)-N-[(4-methylsulfonylphenyl)methyl]-7-methoxy-1,2,3,4-tetrahydronaphthalene-1-carboxamide (0.61 g). melting point: 131-132° C.

Example 36

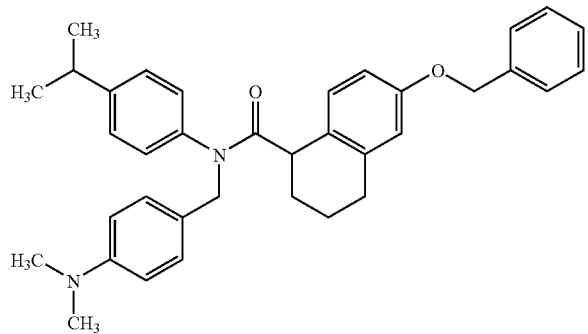

By the reaction and treatment in the same manner as in Example 1 using 6-benzyloxy-1,2,3,4-tetrahydronaphthalene-1-carboxylic acid (1.1 g) and [(4-dimethylaminophenyl)methyl](4-isopropylphenyl)amine (1.05 g) as starting materials, 6-benzyloxy-N-[(4-dimethylaminophenyl)methyl]-N-(4-isopropylphenyl)-1,2,3,4-tetrahydronaphthalene-1-carboxamide (0.23 g) was obtained. melting point: 107-109° C.

Example 37

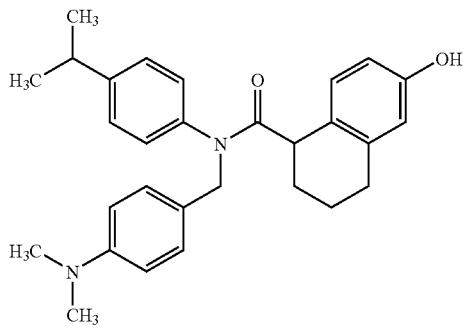

To a solution of 6-benzyloxy-N-[(4-dimethylaminophenyl)methyl]-N-(4-isopropylphenyl)-1,2,3,4-tetrahydronaphthalene-1-carboxamide (0.75 g) in methanol (8.6 mL) were added 10% palladium-carbon (0.09 g) and ammonium formate (0.44 g), and the mixture was stirred at room temperature for 24 hr. The reaction mixture was filtrated, and the solvent was evaporated. The obtained crude crystals were recrystallized from a mixed solvent of ethyl acetate and hexane to give N-[(4-dimethylaminophenyl)methyl]-6-hydroxy-N-(4-isopropylphenyl)-1,2,3,4-tetrahydronaphthalene-1-carboxamide (0.23 g). melting point: 169-171° C.

Example 38

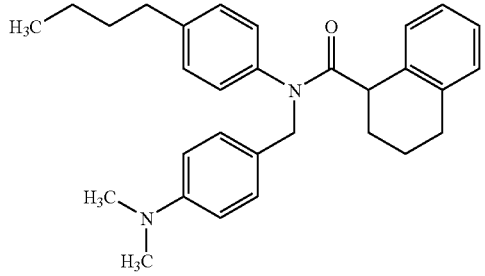

By the reaction and treatment in the same manner as in Example 12 using 1,2,3,4-tetrahydronaphthalene-1-carboxylic acid (0.45 g) and (4-butylphenyl)[(4-dimethylaminophenyl)-methyl]amine (0.6 g) as starting materials, N-(4-butylphenyl)-N-[(4-dimethylaminophenyl)methyl]-1,2,3,4-tetrahydronaphthalene-1-carboxamide (0.35 g) was obtained.

$^1$H-NMR (CDCl$_3$) δ: (0.92 (3H, t, J=7.3 Hz), 1.20-1.70 (5H, m), 1.80-2.10 (3H, m), 2.58 (2H, t, J=7.3 Hz), 2.50-2.70 (1H, m), 2.75-3.00 (1H, m), 2.94 (6H, s), 3.70-3.80 (1H, m), 4.72 (1H, d, J=13.9 Hz), 4.93 (1H, d, J=13.9 Hz), 6.64 (2H, d, J=8.6 Hz), 6.90-7.20 (10H, m).

Example 39

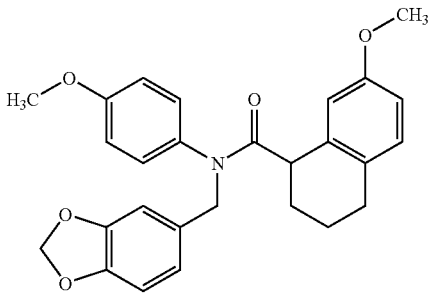

By the reaction and treatment in the same manner as in Example 12 using 7-methoxy-1,2,3,4-tetrahydronaphthalene-1-carboxylic acid (0.75 g) and [(1,3-dioxaindan-5-yl)methyl](4-methoxyphenyl)amine (0.93 g) as starting materials, N-[(1,3-dioxaindan-5-yl)methyl]-N-(4-methoxyphenyl)-7-methoxy-1,2,3,4-tetrahydronaphthalene-1-carboxamide (0.15 g) was obtained.

$^1$H-NMR (CDCl$_3$) δ: 1.43-1.45 (1H, m), 1.86-2.01 (3H, m), 2.52-2.63 (1H, m), 2.70-2.90 (2H, m), 3.73 (3H, s), 3.79 (3H, s), 3.72 (1H, t, J=8.6 hz), 4.63 (1H, d, J=14 Hz), 5.00 (1H, d, J=14 Hz), 5.93 (2H, s), 6.50 (1H, d, J=2.0 Hz), 6.61-6.99 (9H, m).

Example 40

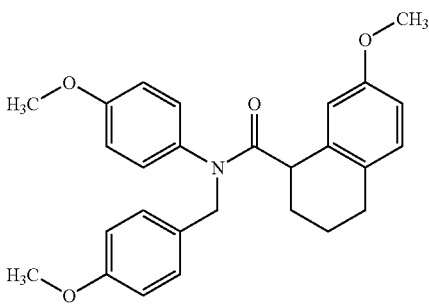

By the reaction and treatment in the same manner as in Example 1 using 7-methoxy-1,2,3,4-tetrahydronaphthalene-1-carboxylic acid (1.5 g) and [(4-methoxyphenyl)methyl](4-methoxyphenyl)amine (0.88 g) as starting materials, N-[(4-methoxyphenyl)methyl]-N-(4-methoxyphenyl)-7-methoxy-1,2,3,4-tetrahydronaphthalene-1-carboxamide (0.72 g) was obtained. melting point: 89-90° C.

Example 41

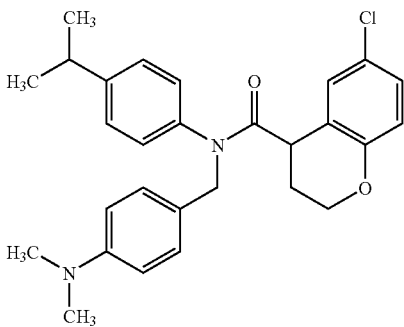

By the reaction and treatment in the same manner as in Example 12 using 6-chlorochroman-4-carboxylic acid (0.66 g) and [(4-dimethylaminophenyl)methyl](4-isopropylphenyl)amine (0.83 g) as starting materials, 6-chloro-N-[(4-dimethylaminophenyl)methyl]-N-(4-isopropylphenyl)chroman-4-carboxamide (0.36 g) was obtained.

$^1$H-NMR (CDCl$_3$) δ: 1.25 (6H, d, J=6.9 Hz), 1.80-2.00 (1H, m), 2.10-2.20 (1H, m), 2.80-3.00 (1H, m), 2.94 (6H, s), 3.65-3.75 (1H, m), 3.90-4.05 (1H, m), 4.40-4.50 (1H, m), 4.73 (1H, d, J=13.8 Hz), 4.88 (1H, d, J=13.8 Hz), 6.60-7.30 (11H, m).

Example 42

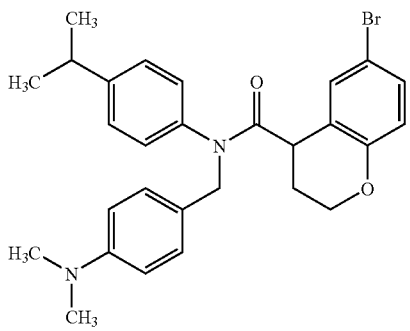

By the reaction and treatment in the same manner as in Example 12 using 6-bromochroman-4-carboxylic acid (0.54 g) and [(4-dimethylaminophenyl)methyl](4-isopropylphenyl)amine (0.57 g) as starting materials, 6-bromo-N-[(4-dimethylaminophenyl)methyl]-N-(4-isopropylphenyl)chroman-4-carboxamide (0.52 g) was obtained.

$^1$H-NMR (CDCl$_3$) δ: 1.24 (6H, d, J=6.9 Hz), 1.81-1.95 (1H, m), 2.07-2.23 (1H, m), 2.81-2.98 (1H, m), 2.93 (6H, s), 3.71 (1H, t, J=6.2 Hz), 3.91-4.03 (1H, m), 4.38-4.50 (1H, m), 4.71 (1H, d, J=13.9 Hz), 4.89 (1H, d, J=13.9 Hz), 6.60-6.72 (3H, m), 6.91-7.25 (8H, m).

Example 43

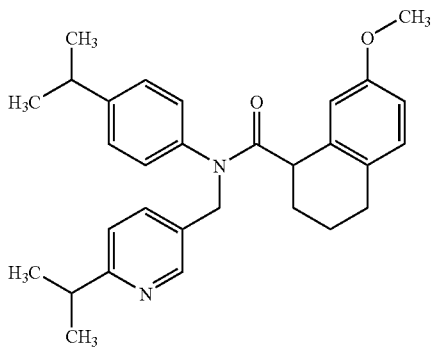

By the reaction and treatment in the same manner as in Example 12 using 7-methoxy-1,2,3,4-tetrahydronaphthalene-1-carboxylic acid (0.31 g) and (4-isopropylphenyl)[(6-isopropylpyridin-3-yl)methyl]amine (0.46 g) as starting materials, N-(4-isopropylphenyl)-N-[(6-isopropylpyridin-3-yl)methyl]-7-methoxy-1,2,3,4-tetrahydronaphthalene-1-carboxamide (0.12 g) was obtained.

$^1$H-NMR (CDCl$_3$) δ: 1.19 (6H, d, J=6.9 Hz), 1.37 (6H, d, J=6.9 Hz), 1.28-1.45 (1H, m), 1.78-1.97 (3H, m), 2.47-2.71 (2H, m), 2.92 (1H, sept, J=6.9 Hz), 3.50 (1H, sept, J=6.9 Hz), 3.70 (3H, s), 3.61-3.75 (1H, m), 5.02 (1H, d, J=13.9 Hz), 5.13 (1H, d, J=13.9 Hz), 6.46 (1H, d, J=2.4 Hz), 6.71 (1H, dd, J=2.4, 8.4 Hz), 6.96 (1H, d, J=8.4 Hz), 7.28-7.41 (4H, m), 8.01 (1H, dd, J=3.6, 8.1 Hz), 8.40 (1H, dd, J=1.8, 8.4 Hz), 8.61 (1H, d, J=1.5 Hz).

Example 44

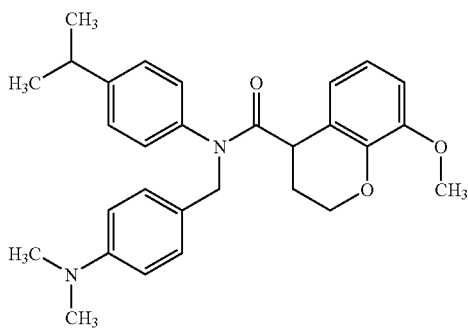

By the reaction and treatment in the same manner as in Example 12 using 8-methoxychroman-4-carboxylic acid, (0.64 g) and [(4-dimethylaminophenyl)methyl](4-isopropylphenyl)amine (0.83 g) as starting materials, N-[(4-dimethylaminophenyl)methyl]-N-(4-isopropylphenyl)-8-methoxychroman-4-carboxamide (0.69 g) was obtained.

$^1$H-NMR (CDCl$_3$) δ: 1.24 (6H, d, J=6.9 Hz), 1.90-2.00 (1H, m), 2.15-2.30 (1H, m), 2.80-3.00 (1H, m), 2.94 (6H, s), 3.77 (1H, t, J=6.3 Hz), 3.84 (3H, s), 4.00-4.20 (1H, m), 4.50-4.65 (1H, m), 4.71 (1H, d, J=13.9 Hz), 4.91 (1H, d, J=13.9 Hz), 6.55-7.25 (11H, m).

Example 45

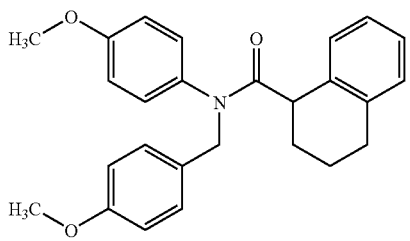

By the reaction and treatment in the same manner as in Example 12 using 1,2,3,4-tetrahydronaphthalene-1-carboxylic acid (0.70 g) and [(4-methoxyphenyl)methyl](4-methoxyphenyl)amine (0.97 g) as starting materials, N-[(4-methoxyphenyl)methyl]-N-(4-methoxyphenyl)-1,2,3,4-tetrahydronaphthalene-1-carboxamide (1.33 g) was obtained.

$^1$H-NMR (CDCl$_3$) δ: 1.47-1.52 (1H, m), 1.86-2.03 (3H, m), 3.78 (3H, s), 3.80 (3H, s), 4.76 (1H, d, J=13.9 Hz), 4.94 (1H, d, J=13.9 Hz), 6.80-7.16 (12H, m)

Example 46

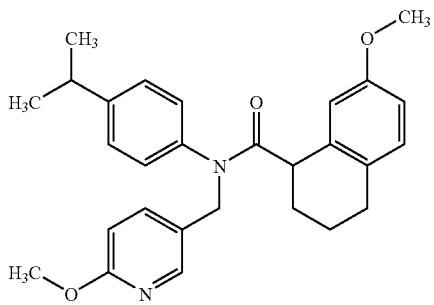

By the reaction and treatment in the same manner as in Example 12 using 7-methoxy-1,2,3,4-tetrahydronaphthalene-1-carboxylic acid (0.50 g) and (4-isopropylphenyl)[(6-methoxypyridin-3-yl)methyl]amine (0.62 g) as starting materials, N-(4-isopropylphenyl)-N-[(6-methoxypyridin-3-yl)methyl]-7-methoxy-1,2,3,4-tetrahydronaphthalene-1-carboxamide was obtained. This was dissolved in ether, and 4N-hydrochloric acid/dioxane was added. The precipitated solid was collected by filtration to give N-(4-isopropylphenyl)-N-[(6-methoxypyridin-3-yl)methyl]-7-methoxy-1,2,3,4-tetrahydronaphthalene-1-carboxamide monohydrochloride (0.47 g).

melting point: 114-117° C.

Example 47

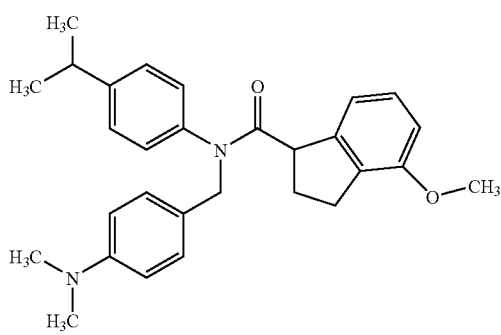

By the reaction and treatment in the same manner as in Example 12 using 4-methoxyindan-1-carboxylic acid (0.20 g) and [(4-dimethylaminophenyl)methyl](4-isopropylphenyl)amine (0.27 g) as starting materials, N-[(4-dimethylaminophenyl)methyl]-N-(4-isopropylphenyl)-4-methoxyindan-1-carboxamide (0.24 g) was obtained.

$^1$H-NMR (CDCl$_3$) δ: 1.23 (6H, d, J=6.9 Hz), 2.08-2.09 (1H, m), 2.31-2.38 (1H, m), 2.63-2.72 (1H, m), 2.86-2.92 (1H, m), 2.94 (6H, s), 3.79 (3H, s), 3.94-4.00 (1H, m), 4.71 (1H, d, J=13.9 Hz), 4.93 (1H, d, J=13.9 Hz), 6.63-6.68 (3H, m), 6.75 (1H, d, J=7.5 Hz), 6.95-6.98 (3H, m), 7.01-7.18 (4H, m)

Example 48

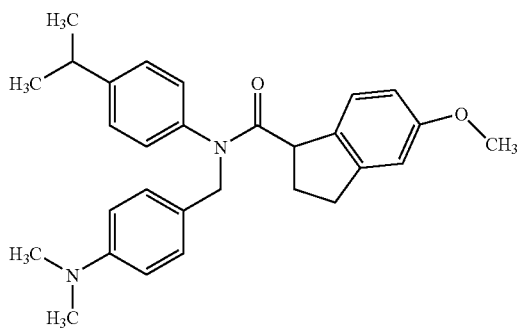

By the reaction and treatment in the same manner as in Example 12 using 5-methoxyindan-1-carboxylic acid (0.50 g) and [(4-dimethylaminophenyl)methyl](4-isopropylphenyl)amine (0.80 g) as starting materials, N-[(4-dimethylaminophenyl)methyl]-N-(4-isopropylphenyl)-5-methoxyindan-1-carboxamide (1.00 g) was obtained.

$^1$H-NMR (CDCl$_3$) δ: 1.23 (6H, d, J=6.9), 2.08-2.09 (1H, m), 2.31-2.38 (1H, m), 2.63-2.77 (1H, m), 2.86-2.93 (1H, m), 2.93 (6H, s), 3.76 (3H, s), 3.90 (1H, t, J=8.6 hz), 4.71 (1H, d,

J=13.9 Hz), 4.92 (1H, d, J=13.9 Hz), 6.63-6.73 (4H, m), 6.95-7.02 (3H, m), 7.01 (2H, d, J=8.7 Hz), 7.17 (2H, d, J=8.3 Hz).

Example 49

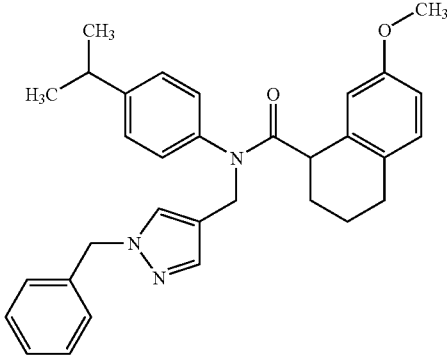

By the reaction and treatment in the same manner as in Example 12 using 7-methoxy-1,2,3,4-tetrahydronaphthalene-1-carboxylic acid (1.5 g) and [(1-benzylpyrazol-4-yl)methyl](4-isopropylphenyl)amine (2.22 g) as starting materials, N-[(1-benzylpyrazol-4-yl)methyl]-N-(4-isopropylphenyl)-7-methoxy-1,2,3,4-tetrahydronaphthalene-1-carboxamide (1.64 g) was obtained.

$^1$H-NMR (CDCl$_3$) δ: 1.27 (6H, d, J=6.9 Hz), 1.37-1.53 (1H, m), 1.77-2.07 (3H, m), 2.52-2.66 (1H, m), 2.69-2.83 (1H, m), 2.91 (1H, sept, J=6.9 Hz), 3.60-3.73 (1H, m), 3.65 (3H, s), 4.58 (1H, d, J=13.9 Hz), 4.85 (1H, d, J=13.9 Hz), 5.24 (2H, s), 6.45 (1H, d, J=2.4 Hz), 6.67 (1H, dd, J=2.4, 8.4 Hz), 6.95 (1H, d, J=8.4 Hz), 7.03 (2H, d, J=8.4 Hz), 7.13-7.45 (9H, m).

Example 50

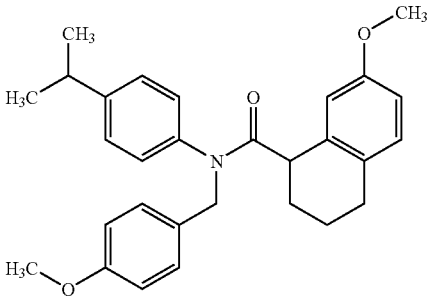

By the reaction and treatment in the same manner as in Example 4 using 7-methoxy-1,2,3,4-tetrahydronaphthalene-1-carboxylic acid (0.31 g) and (4-isopropylphenyl)[(4-methoxyphenyl)methyl]amine (0.38 g) as starting materials, N-(4-isopropylphenyl)-N-[(4-methoxyphenyl)methyl]-7-methoxy-1,2,3,4-tetrahydronaphthalene-1-carboxamide (0.37 g) was obtained. melting point: 83-85° C.

Example 51

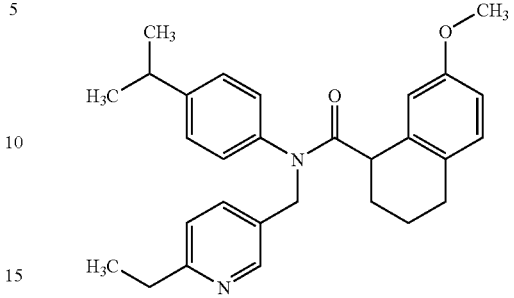

By the reaction and treatment in the same manner as in Example 12 using 7-methoxy-1,2,3,4-tetrahydronaphthalene-1-carboxylic acid (0.58 g) and [(6-ethylpyridin-3-yl)methyl](4-isopropylphenyl)amine (0.71 g) as starting materials, N-[(6-ethylpyridin-3-yl)methyl]-N-(4-isopropylphenyl)-7-methoxy-1,2,3,4-tetrahydronaphthalene-1-carboxamide (0.69 g) was obtained.

$^1$H-NMR (CDCl$_3$) δ: 1.23 (6H, d, J=6.9 Hz), 1.28 (3H, t, J=7.7 Hz), 1.40-1.57 (1H, m), 1.70-2.05 (3H, m), 2.50-2.64 (1H, m), 2.71-2.95 (4H, m), 3.70 (3H, s), 3.64-3.79 (1H, m), 4.80 (1H, d, J=13.9 Hz), 4.96 (1H, d, J=13.9 Hz), 6.47 (1H, d, J=2.4 Hz), 6.67 (1H, dd, J=2.4, 8.4 Hz), 6.96 (1H, d, J=8.4 Hz), 7.00 (2H, d, J=8.4 Hz), 7.12 (1H, d, J=8.4 Hz), 7.21 (2H, d, J=8.4 Hz), 7.68 (1H, dd, J=2.4, 8.4 Hz), 8.29 (1H, d, J=2.4 Hz).

Example 52

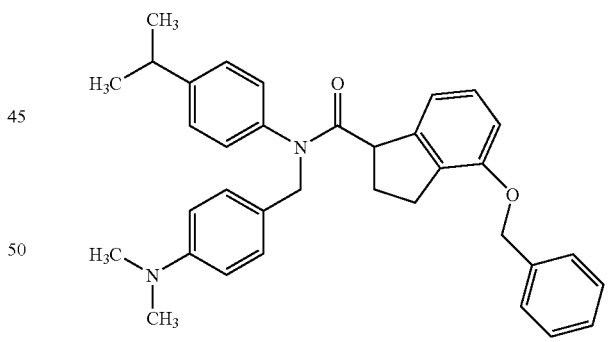

By the reaction and treatment in the same manner as in Example 12 using 4-benzyloxyindan-1-carboxylic acid (0.7 g) and [(4-dimethylaminophenyl)methyl](4-isopropylphenyl)amine (0.7 g) as starting materials, 4-benzyloxy-N-[(4-dimethylaminophenyl)methyl]-N-(4-isopropylphenyl)indan-1-carboxamide (1.5 g) was obtained.

$^1$H-NMR (CDCl$_3$) δ: 1.23 (6H, d, J=6.9 Hz), 2.00-2.20 (1H, m), 2.30-2.45 (1H, m), 2.65-2.80 (1H, m), 2.85-3.00 (1H, m), 2.94 (6H, s), 3.05-3.20 (1H, m), 3.95-4.05 (1H, m), 4.72 (1H, d, J=13.8 Hz), 4.94 (1H, d, J=13.8 Hz), 5.06 (2H, s), 6.60-6.80 (4H, m), 6.90-7.45 (12H, m)

Example 53

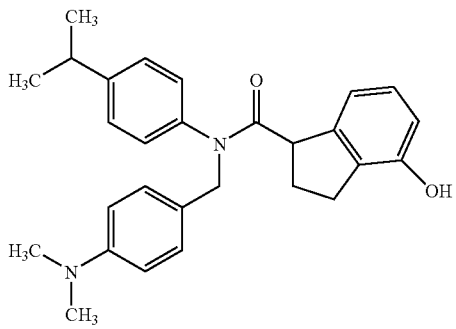

By the reaction and treatment in the same manner as in Example 37 using 4-benzyloxy-N-[(4-dimethylaminophenyl)methyl]-N-(4-isopropylphenyl)indan-1-carboxamide (1.19 g) as a starting material, N-[(4-dimethylaminophenyl)methyl]-4-hydroxy-N-(4-isopropylphenyl)indan-1-carboxamide (0.57 g) was obtained. melting point: 158-160° C.

Example 54

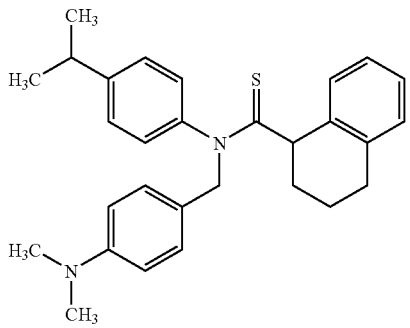

To a solution of N-[(4-dimethylaminophenyl)methyl]-N-(4-isopropylphenyl)-1,2,3,4-tetrahydronaphthalene-1-carboxamide (0.79 g) in toluene (10 mL) was added Lawesson's reagent (0.9 g), and the mixture was heated under reflux for 5 hr. The reaction mixture was partitioned between water and ethyl acetate. The organic layer was washed with saturated brine and dried over anhydrous magnesium sulfate. The solvent was evaporated, and the residue was purified by silica gel column chromatography to give N-[(4-dimethylaminophenyl)methyl]-N-(4-isopropylphenyl)-1,2,3,4-tetrahydronaphthalene-1-carbothioamide (0.19 g). melting point: 123-125° C.

Example 55

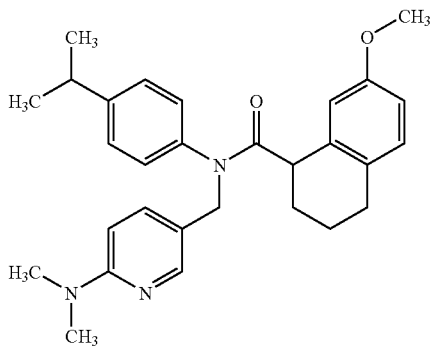

By the reaction and treatment in the same manner as in Example 12 using 7-methoxy-1,2,3,4-tetrahydronaphthalene-1-carboxylic acid (0.31 g) and [(6-dimethylaminopyridin-3-yl)methyl](4-isopropylphenyl)amine (0.24 g) as starting materials, N-[(6-dimethylaminopyridin-3-yl)methyl]-N-(4-isopropylphenyl)-7-methoxy-1,2,3,4-tetrahydronaphthalene-1-carboxamide was obtained. This was dissolved in ether, and 4 mol/L-hydrochloric acid/dioxane (0.30 mL) was added. The solvent was evaporated. The obtained crude crystals were recrystallized from ethyl acetate-hexane to give N-[(6-dimethylaminopyridin-3-yl)methyl]-N-(4-isopropylphenyl)-7-methoxy-1,2,3,4-tetrahydronaphthalene-1-carboxamide hydrochloride ½ hydrate (0.43 g). melting point: 158-160° C.

Example 56

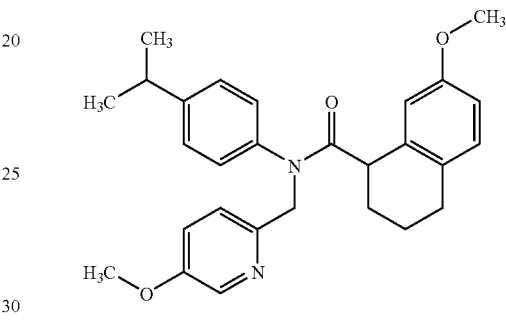

By the reaction and treatment in the same manner as in Example 12 using 7-methoxy-1,2,3,4-tetrahydronaphthalene-1-carboxylic acid (0.31 g) and (4-isopropylphenyl)[(5-methoxypyridin-2-yl)methyl]amine (0.38 g) as starting materials, N-(4-isopropylphenyl)-N-[(5-methoxypyridin-2-yl)methyl]-7-methoxy-1,2,3,4-tetrahydronaphthalene-1-carboxamide was obtained. This is dissolved in ether, and 4 mol/L-hydrochloric acid/dioxane (0.40 mL) was added. The solvent was evaporated, and ether was added to the residue. The precipitated crystals were collected by filtration to give N-(4-isopropylphenyl)-N-[(5-methoxypyridin-2-yl)methyl]-7-methoxy-1,2,3,4-tetrahydronaphthalene-1-carboxamide hydrochloride ½ hydrate (0.54 g). melting point: 108-110° C.

Example 57

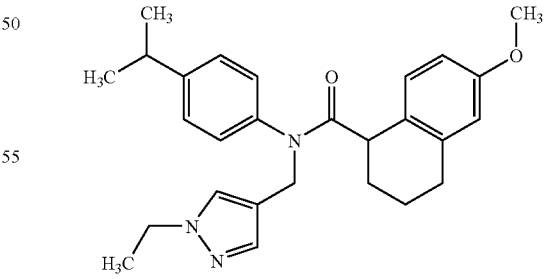

By the reaction and treatment in the same manner as in Example 4 using 6-methoxy-1,2,3,4-tetrahydronaphthalene-1-carboxylic acid (0.31 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-6-methoxy-1,2,3,4-tetrahydronaphthalene-1-carboxamide (0.45 g) was obtained. melting point: 111-113° C.

Example 58

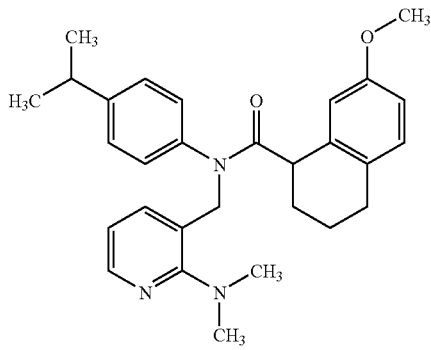

By the reaction and treatment in the same manner as in Example 12 using 7-methoxy-1,2,3,4-tetrahydronaphthalene-1-carboxylic acid (0.31 g) and [(2-dimethylaminopyridin-3-yl)methyl](4-isopropylphenyl)amine (0.40 g) as starting materials, N-[(2-dimethylaminopyridin-3-yl)methyl]-N-(4-isopropylphenyl)-7-methoxy-1,2,3,4-tetrahydronaphthalene-1-carboxamide (0.58 g) was obtained.

$^1$H-NMR (CDCl$_3$) δ: 1.17 (6H, d, J=6.9 Hz), 1.31-1.48 (1H, m), 1.70-2.05 (3H, m), 2.48-2.68 (2H, m), 2.89 (1H, sept, J=6.9 Hz), 3.04 (6H, s), 3.60-3.76 (4H, m), 4.93 (1H, d, J=13.9 Hz), 5.12 (1H, d, J=13.9 Hz), 6.49 (1H, d, J=2.4 Hz), 6.72 (1H, dd, J=2.4, 8.4 Hz), 6.97 (1H, d, J=8.4 Hz), 7.14 (1H, dd, J=6.0, 7.3 Hz), 7.32 (2H, d, J=8.4 Hz), 7.38 (2H, d, J=8.4 Hz), 7.95 (1H, d, J=7.4 Hz), 8.07 (1H, dd, J=1.3, 5.8 Hz).

Example 59

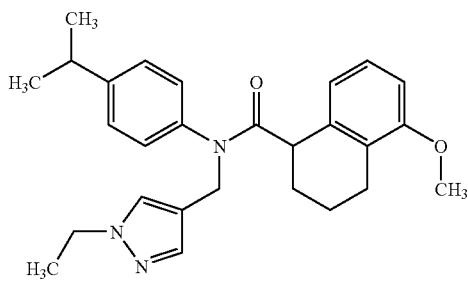

By the reaction and treatment in the same manner as in Example 12 using 5-methoxy-1,2,3,4-tetrahydronaphthalene-1-carboxylic acid (0.31 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-5-methoxy-1,2,3,4-tetrahydronaphthalene-1-carboxamide (0.52 g) was obtained.

$^1$H-NMR (CDCl$_3$) δ: 1.25 (6H, d, J=6.9 Hz), 1.37-1.52 (1H, m), 1.45 (3H, t, J=7.3 Hz), 1.67-2.05 (3H, m), 2.57-2.71 (2H, m), 2.92 (1H, sept, J=6.9 Hz), 3.70 (1H, t, J=6.2 Hz), 3.77 (3H, s), 4.11 (2H, q, J=7.3 Hz), 4.58 (1H, d, J=13.9 Hz), 4.84 (1H, d, J=13.9 Hz), 6.54 (1H, d, J=7.7 Hz), 6.65 (1H, d, J=7.7 Hz), 6.98-7.10 (3H, m), 7.22 (2H, d, J=8.4 Hz), 7.33 (1H, s), 7.41 (1H, s).

Example 60

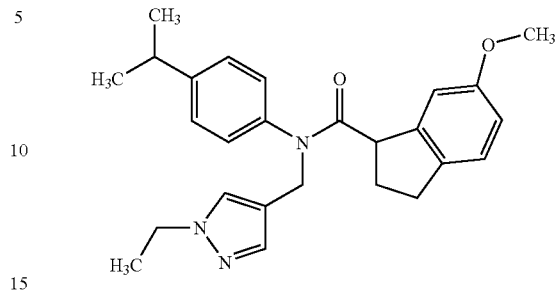

By the reaction and treatment in the same manner as in Example 12 using 6-methoxyindan-1-carboxylic acid (0.29 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-6-methoxyindan-1-carboxamide (0.35 g) was obtained.

$^1$H-NMR (CDCl$_3$) δ: 1.25 (6H, d, J=6.9 Hz), 1.45 (3H, t, J=7.3 Hz), 2.03-2.15 (1H, m), 2.26-2.39 (1H, m), 2.61-2.73 (1H, m), 2.87-3.03 (2H, m), 3.74 (3H, s), 3.93 (1H, t, J=8.1 Hz), 4.12 (2H, q, J=7.3 Hz), 4.66 (1H, d, J=13.9 Hz), 4.79 (1H, d, J=13.9 Hz), 6.68 (1H, d, J=2.4 Hz), 6.69 (1H, dd, J=2.4, 8.4 Hz), 7.00-7.10 (3H, m), 7.23 (2H, d, J=8.4 Hz), 7.32 (1H, s), 7.40 (1H, s).

Example 61

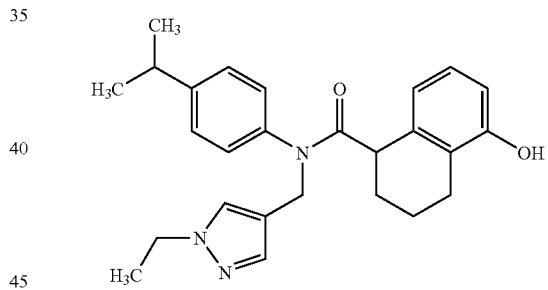

By the reaction and treatment in the same manner as in Example 12 using 5-benzyloxy-1,2,3,4-tetrahydronaphthalene-1-carboxylic acid (0.56 g) and [(1-ethylpyrazol-4-yl)methyl](4-isopropylphenyl)amine (0.49 g) as starting materials, 5-benzyloxy-N-[(1-ethylpyrazol-4-yl)methyl]-N-(4-isopropylphenyl)-1,2,3,4-tetrahydronaphthalene-1-carboxamide (0.72 g) was obtained.

$^1$H-NMR (CDCl$_3$) δ: 1.25 (6H, d, J=6.9 Hz), 1.39-1.55 (1H, m), 1.45 (3H, t, J=7.3 Hz), 1.78-2.09 (3H, m), 2.68-2.80 (2H, m), 2.92 (1H, sept, J=6.9 Hz), 3.72 (1H, t, J=6.2 Hz), 4.13 (2H, q, J=7.3 Hz), 4.58 (1H, d, J=13.9 Hz), 4.84 (1H, d, J=13.9 Hz), 5.03 (2H, s), 6.56 (1H, d, J=7.7 Hz), 6.70 (1H, d, J=7.7 Hz), 6.98-7.12 (3H, m), 7.20-7.42 (9H, m).

By the reaction and treatment in the same manner as in Example 37 using 5-benzyloxy-N-[(1-ethylpyrazol-4-yl)methyl]-N-(4-isopropylphenyl)-1,2,3,4-tetrahydronaphthalene-1-carboxamide (0.72 g), N-[(1-ethylpyrazol-4-yl)methyl]-5-hydroxy-N-(4-isopropylphenyl)-1,2,3,4-tetrahydronaphthalene-1-carboxamide (0.33 g) was obtained. melting point: 212-215° C.

Example 62

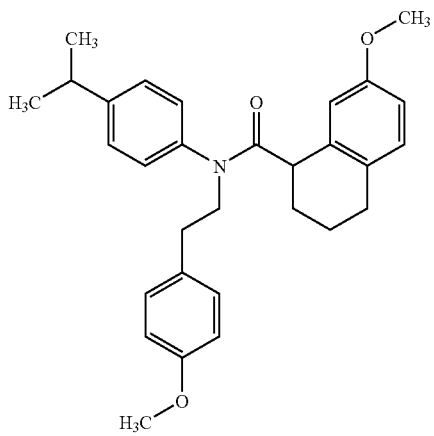

By the reaction and treatment in the same manner as in Example 6 using N-(4-isopropylphenyl)-7-methoxy-1,2,3,4-tetrahydronaphthalene-1-carboxamide (0.49 g) and 1-methanesulfonyloxy-2-(4-methoxyphenyl)ethane (0.38 g) as starting materials, N-(4-isopropylphenyl)-N-[2-(4-methoxyphenyl)ethyl]-7-methoxy-1,2,3,4-tetrahydronaphthalene-1-carboxamide (0.15 g) was obtained.

$^1$H-NMR (CDCl$_3$) δ: 1.25 (6H, d, J=6.9 Hz), 1.38-1.57 (1H, m), 1.78-2.09 (3H, m), 2.51-2.63 (1H, m), 2.69-2.97 (4H, m), 3.65-4.15 (9H, m), 6.51 (1H, d, J=2.4 Hz), 6.67 (1H, dd, J=2.4, 8.4 Hz), 6.75-6.88 (2H, m), 6.96 (1H, d, J=8.4 Hz), 7.06-7.29 (6H, m).

Example 63

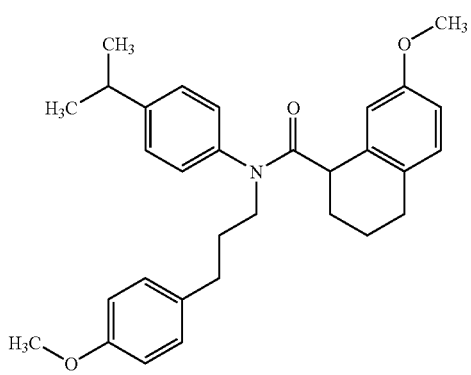

By the reaction and treatment in the same manner as in Example 6 using N-(4-isopropylphenyl)-7-methoxy-1,2,3,4-tetrahydronaphthalene-1-carboxamide (0.49 g) and 1-methanesulfonyloxy-3-(4-methoxyphenyl)propane (0.40 g) as starting materials, N-(4-isopropylphenyl)-N-[3-(4-methoxyphenyl)propyl]-7-methoxy-1,2,3,4-tetrahydronaphthalene-1-carboxamide (0.41 g) was obtained.

$^1$H-NMR (CDCl$_3$) δ: 1.24 (6H, d, J=6.9 Hz), 1.40-1.53 (1H, m), 1.81-2.09 (5H, m), 2.51-2.64 (3H, m), 2.70-2.85 (1H, m), 2.93 (1H, sept, J=6.9 Hz), 3.68-3.87 (9H, m), 6.57 (1H, d, J=2.4 Hz), 6.67 (1H, dd, J=2.4, 8.4 Hz), 6.80 (2H, d, J=8.4 Hz), 6.95 (1H, d, J=8.4 Hz), 7.08 (2H, d, J=8.4 Hz), 7.14-7.33 (4H, m).

Example 64

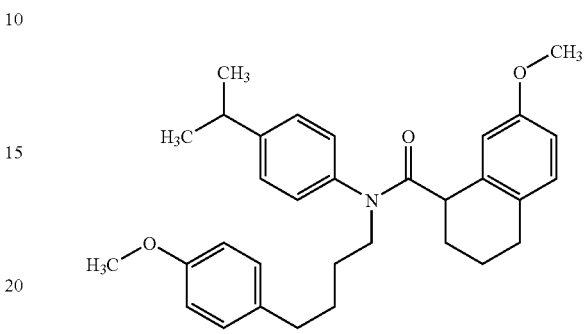

By the reaction and treatment in the same manner as in Example 6 using N-(4-isopropylphenyl)-7-methoxy-1,2,3,4-tetrahydronaphthalene-1-carboxamide (0.49 g) and 1-methanesulfonyloxy-4-(4-methoxyphenyl)butane (0.43 g) as starting materials, N-(4-isopropylphenyl)-N-[4-(4-methoxyphenyl)butyl]-7-methoxy-1,2,3,4-tetrahydronaphthalene-1-carboxamide (0.25 g) was obtained.

$^1$H-NMR (CDCl$_3$) δ: 1.25 (6H, d, J=6.9 Hz), 1.40-1.68 (5H, m), 1.80-2.05 (3H, m), 2.50-2.62 (3H, m), 2.71-2.83 (1H, m), 2.93 (1H, sept, J=6.9 Hz), 3.64-3.88 (9H, m), 6.56 (1H, d, J=2.4 Hz), 6.67 (1H, dd, J=2.4, 8.4 Hz), 6.80 (2H, d, J=8.4 Hz), 6.95 (1H, d, J=8.4 Hz), 7.05 (2H, d, J=8.4 Hz), 7.13 (2H, d, J=8.4 Hz), 7.24 (2H, d, J=8.4 Hz).

Example 65

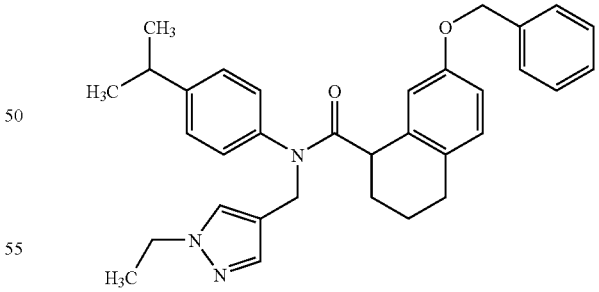

By the reaction and treatment in the same manner as in Example 4 using 7-benzyloxy-1,2,3,4-tetrahydronaphthalene-1-carboxylic acid (0.56 g) and [(1-ethylpyrazol-4-yl)methyl](4-isopropylphenyl)amine (0.49 g) as starting materials, 7-benzyloxy-N-[(1-ethylpyrazol-4-yl)methyl]-N-(4-isopropylphenyl)-1,2,3,4-tetrahydronaphthalene-1-carboxamide (0.61 g) was obtained. melting point: 100-101° C.

Example 66

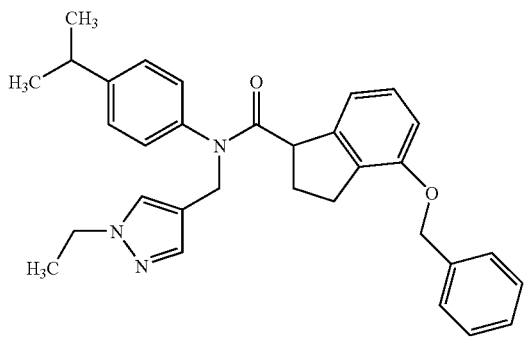

By the reaction and treatment in the same manner as in Example 4 using 4-benzyloxyindan-1-carboxylic acid (0.54 g) and [(1-ethylpyrazol-4-yl)methyl](4-isopropylphenyl)amine (0.49 g) as starting materials, 4-benzyloxy-N-[(1-ethylpyrazol-4-yl)methyl]-N-(4-isopropylphenyl)indan-1-carboxamide (0.79 g) was obtained.

$^1$H-NMR (CDCl$_3$) δ: 1.25 (6H, d, J=6.9 Hz), 1.45 (3H, t, J=7.3 Hz), 2.04-2.18 (1H, m), 2.24-2.39 (1H, m), 2.65-2.80 (1H, m), 2.92 (1H, sept, J=6.9 Hz), 3.06-3.20 (1H, m), 3.98 (1H, t, J=6.2 Hz), 4.12 (2H, q, J=7.3 Hz), 4.65 (1H, d, J=13.9 Hz), 4.79 (1H, d, J=13.9 Hz), 5.06 (2H, s), 6.67 (1H, d, J=7.7 Hz), 6.70 (1H, d, J=7.7 Hz), 7.00-7.10 (3H, m), 7.20-7.43 (9H, m).

Example 67

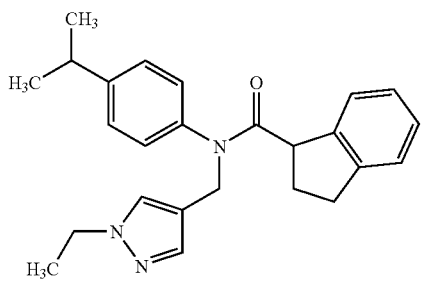

By the reaction and treatment in the same manner as in Example 4 using indan-1-carboxylic acid (0.24 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)indan-1-carboxamide (0.23 g) was obtained. melting point: 83-84° C.

Example 68

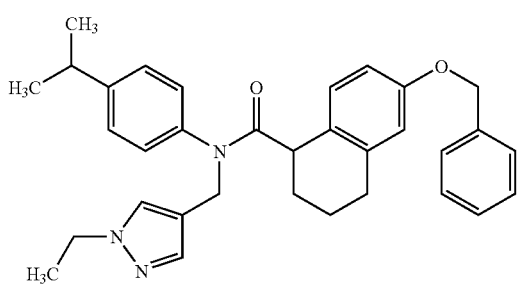

By the reaction and treatment in the same manner as in Example 4 using 6-benzyloxy-1,2,3,4-tetrahydronaphthalene-1-carboxylic acid (0.56 g) and [(1-ethylpyrazol-4-yl)methyl](4-isopropylphenyl)amine (0.49 g) as starting materials, 6-benzyloxy-N-[(1-ethylpyrazol-4-yl)methyl]-N-(4-isopropylphenyl)-1,2,3,4-tetrahydronaphthalene-1-carboxamide (0.65 g) was obtained. melting point: 122-124° C.

Example 69

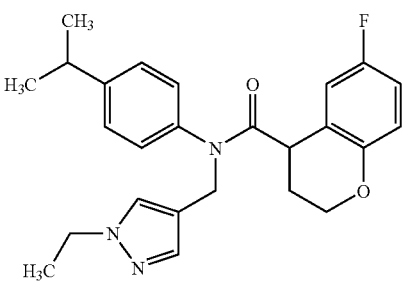

By the reaction and treatment in the same manner as in Example 12 using 6-fluorochroman-4-carboxylic acid (0.29 g) and [(1-ethylpyrazol-4-yl)methyl](4-isopropylphenyl)amine (0.37 g) as starting materials, N-[(1-ethylpyrazol-4-yl)methyl]-6-fluoro-N-(4-isopropylphenyl)chroman-4-carboxamide (0.42 g) was obtained.

$^1$H-NMR (CDCl$_3$) δ: 1.27 (6H, d, J=6.9 Hz), 1.46 (3H, t, J=7.3 Hz), 1.84-1.97 (1H, m), 2.08.2.20 (1H, m), 2.94 (1H, sept, J=6.9 Hz), 3.72 (1H, t, J=6.2 Hz), 3.89-4.00 (1H, m), 4.12 (2H, q, J=7.3 Hz), 4.35-4.45 (1H, m), 4.62 (1H, d, J=13.9 Hz), 4.79 (1H, d, J=13.9 Hz), 6.55 (1H, dd, J=2.4, 8.4 Hz), 6.69-6.83 (2H, m), 7.04 (2H, d, J=8.4 Hz), 7.21-7.31 (3H, s), 7.40 (1H, s).

Example 70

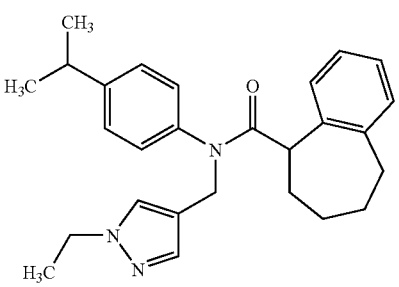

By the reaction and treatment in the same manner as in Example 12 using 6,7,8,9-tetrahydro-5H-benzocycloheptene-5-carboxylic acid (0.29 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-6,7,8,9-tetrahydro-5H-benzocycloheptene-5-carboxamide (0.36 g) was obtained.

$^1$H-NMR (CDCl$_3$) δ: 1.22 (6H, d, J=6.9 Hz), 1.47 (3H, t, J=7.3 Hz), 1.60-1.74 (4H, m), 1.79-1.91 (1H, m), 1.92-2.02 (1H, m), 2.12-2.24 (1H, m), 2.48-2.60 (1H, m), 2.85 (1H, sept, J=6.9 Hz), 3.66 (1H, dd, J=1.5, 9.6 Hz), 4.14 (2H, q, J=7.3 Hz), 4.63 (1H, d, J=13.9 Hz), 4.83 (1H, d, J=13.9 Hz), 6.61-6.77 (2H, m), 6.93-7.13 (6H, m), 7.32 (1H, s), 7.45 (1H, s).

Example 71

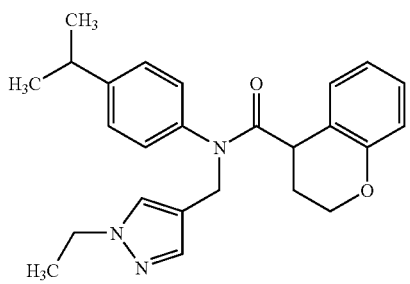

By the reaction and treatment in the same manner as in Example 12 using chroman-4-carboxylic acid (0.27 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)chroman-4-carboxamide (0.52 g) was obtained.

$^1$H-NMR (CDCl$_3$) δ: 1.24 (6H, d, J=6.9 Hz), 1.45 (3H, t, J=7.3 Hz), 1.86-1.98 (1H, m), 2.10-2.22 (1H, m), 2.94 (1H, sept, J=6.9 Hz), 3.76 (1H, t, J=6.2 Hz), 3.92-4.03 (1H, m), 4.13 (2H, q, J=7.3 Hz), 4.39-4.49 (1H, m), 4.62 (1H, d, J=13.9 Hz), 4.80 (1H, d, J=13.9 Hz), 6.74-6.89 (3H, m), 7.00-7.12 (3H, m), 7.25 (2H, d, J=8.4 Hz), 7.32 (1H, s), 7.38 (1H, s).

Example 72

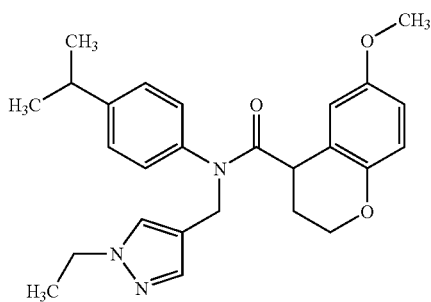

By the reaction and treatment in the same manner as in Example 12 using 6-methoxychroman-4-carboxylic acid (0.31 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-6-methoxychroman-4-carboxamide (0.39 g) was obtained.

$^1$H-NMR (CDCl$_3$) δ: 1.25 (6H, d, J=6.9 Hz), 1.45 (3H, t, J=7.3 Hz), 1.85-1.97 (1H, m), 2.12.2.24 (1H, m), 2.94 (1H, sept, J=6.9 Hz), 3.67 (3H, s), 3.74 (1H, t, J=6.2 Hz), 3.87-3.99 (1H, m), 4.12 (2H, q, J=7.3 Hz), 4.33-4.45 (1H, m), 4.57 (1H, d, J=13.9 Hz), 4.85 (1H, d, J=13.9 Hz), 6.40 (1H, d, J=2.4 Hz), 6.62-6.76 (2H, m), 7.06 (2H, d, J=8.4 Hz), 7.25 (2H, d, J=8.4 Hz), 7.32 (1H, s), 7.41 (1H, s).

Example 73

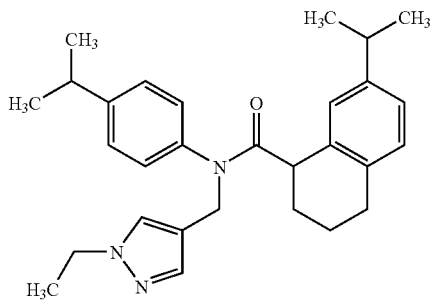

By the reaction and treatment in the same manner as in Example 12 using 7-isopropyl-1,2,3,4-tetrahydronaphthalene-1-carboxylic acid (0.33 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-7-isopropyl-1,2,3,4-tetrahydronaphthalene-1-carboxamide (0.46 g) was obtained.

$^1$H-NMR (CDCl$_3$) δ: 1.17 (6H, dd, J=2.6, 6.9 Hz), 1.25 (6H, d, J=6.9 Hz), 1.41-1.57 (1H, m), 1.46 (3H, t, J=7.3 Hz), 1.82-2.07 (3H, m), 2.68-2.80 (2H, m), 2.92 (1H, sept, J=6.9 Hz), 3.71 (1H, t, J=6.2 Hz), 4.12 (2H, q, J=7.3 Hz), 4.43 (1H, d, J=13.9 Hz), 5.01 (1H, d, J=13.9 Hz), 6.74 (1H, s), 6.95 (1H, d, J=(0.8 Hz), 7.07 (2H, d, J=8.4 Hz), 7.22 (2H, d, J=8.4 Hz), 7.36 (1H, s), 7.46 (1H, s).

Example 74

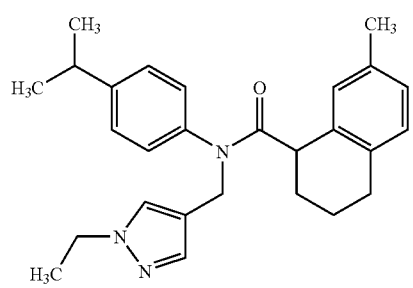

By the reaction and treatment in the same manner as in Example 4 using 7-methyl-1,2,3,4-tetrahydronaphthalene-1-carboxylic acid (0.29 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-7-methyl-1,2,3,4-tetrahydronaphthalene-1-carboxamide (0.41 g) was obtained. melting point: 110-112° C.

Example 75

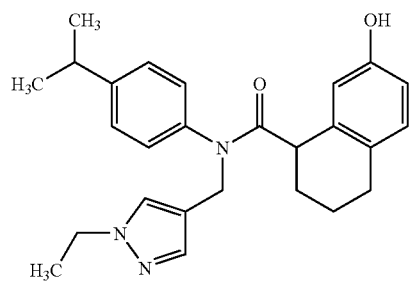

By the reaction and treatment in the same manner as in Example 37 using 7-benzyloxy-N-[(1-ethylpyrazol-4-yl)methyl]-N-(4-isopropylphenyl)-1,2,3,4-tetrahydronaphthalene-1-carboxamide (0.48 g), N-[(1-ethylpyrazol-4-yl)methyl]-7-hydroxy-N-(4-isopropylphenyl)-1,2,3,4-tetrahydronaphthalene-1-carboxamide (0.34 g) was obtained. melting point: 169-170° C.

Example 76

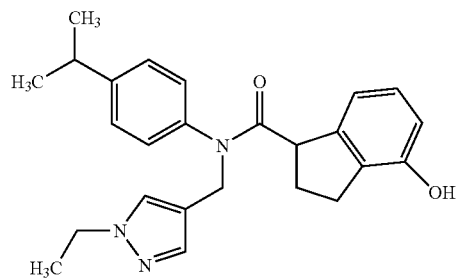

By the reaction and treatment in the same manner as in Example 37 using 4-benzyloxy-N-[(1-ethylpyrazol-4-yl)methyl]-N-(4-isopropylphenyl)indan-1-carboxamide (0.70 g), N-[(1-ethylpyrazol-4-yl)methyl]-4-hydroxy-N-(4-isopropylphenyl)indan-1-carboxamide (0.51 g) was obtained. melting point: 205-206° C.

Example 77

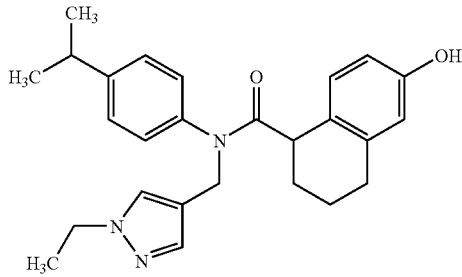

By the reaction and treatment in the same manner as in Example 37 using 6-benzyloxy-N-[(1-ethylpyrazol-4-yl)methyl]-N-(4-isopropylphenyl)-1,2,3,4-tetrahydronaphthalene-1-carboxamide (0.56 g), N-[(1-ethylpyrazol-4-yl)methyl]-6-hydroxy-N-(4-isopropylphenyl)-1,2,3,4-tetrahydronaphthalene-1-carboxamide (0.42 g) was obtained. melting point: 146-147° C.

Example 78

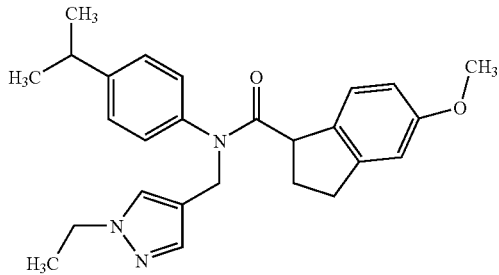

By the reaction and treatment in the same manner as in Example 4 using 5-methoxyindan-1-carboxylic acid (0.29 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-5-methoxyindan-1-carboxamide (0.47 g) was obtained. melting point: 115-116° C.

Example 79

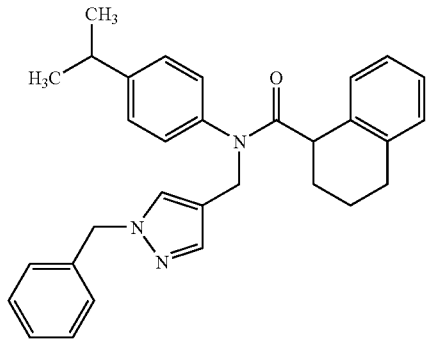

By the reaction and treatment in the same manner as in Example 12 using 1,2,3,4-tetrahydronaphthalene-1-carboxylic acid (0.26 g) and [(1-benzylpyrazol-4-yl)methyl](4-isopropylphenyl)amine (0.46 g) as starting materials, N-[(1-benzylpyrazol-4-yl)methyl]-N-(4-isopropylphenyl)-1,2,3,4-tetrahydronaphthalene-1-carboxamide (0.55 g) was obtained.

$^1$H-NMR (CDCl$_3$) δ: 1.24 (6H, d, J=6.9 Hz), 1.39-1.55 (1H, m), 1.82-2.02 (3H, m), 2.58-2.70 (1H, m), 2.78-2.98 (2H, m), 3.71 (1H, t, J=6.2 Hz), 4.61 (1H, d, J=13.9 Hz), 4.83 (1H, d, J=13.9 Hz), 5.26 (2H, s), 6.88 (1H, d, J=8.4 Hz), 6.98-7.13 (5H, m), 7.16-7.24 (4H, m), 7.28-7.43 (2H, m).

Example 80

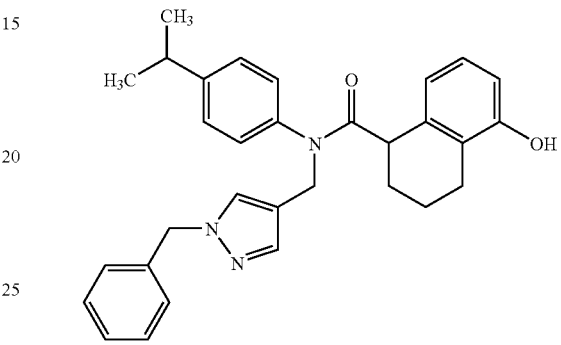

By the reaction and treatment in the same manner as in Example 12 using 5-benzyloxy-1,2,3,4-tetrahydronaphthalene-1-carboxylic acid (0.56 g) and [(1-benzylpyrazol-4-yl)methyl](4-isopropylphenyl)amine (0.61 g) as starting materials, 5-benzyloxy-N-[(1-benzylpyrazol-4-yl)methyl]-N-(4-isopropylphenyl)-1,2,3,4-tetrahydronaphthalene-1-carboxamide (0.67 g) was obtained.

$^1$H-NMR (CDCl$_3$) δ: 1.24 (6H, d, J=6.9 Hz), 1.38-1.53 (1H, m), 1.77-2.07 (3H, m), 2.67-2.77 (2H, m), 2.91 (1H, sept, J=6.9 Hz), 3.70 (1H, t, J=6.2 Hz), 4.58 (1H, d, J=13.9 Hz), 4.84 (1H, d, J=13.9 Hz), 5.02 (2H, s), 5.26 (2H, s), 6.54 (1H, d, J=7.7 Hz), 6.69 (1H, d, J=7.7 Hz), 6.93-7.07 (3H, m), 7.13-7.47 (14H, m).

By the reaction and treatment in the same manner as in Example 37 using 5-benzyloxy-N-[(1-benzylpyrazol-4-yl)methyl]-N-(4-isopropylphenyl)-1,2,3,4-tetrahydronaphthalene-1-carboxamide (0.66 g), N-[(1-benzylpyrazol-4-yl)methyl]-5-hydroxy-N-(4-isopropylphenyl)-1,2,3,4-tetrahydronaphthalene-1-carboxamide (0.47 g) was obtained. melting point: 130.1° C.

Example 81

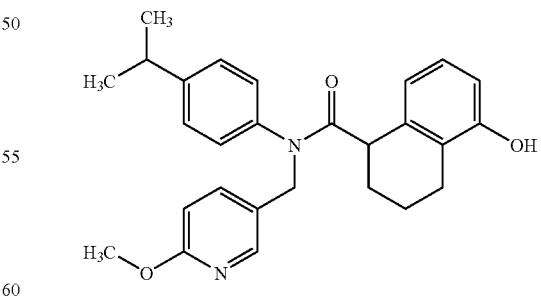

By the reaction and treatment in the same manner as in Example 12 using 5-benzyloxy-1,2,3,4-tetrahydronaphthalene-1-carboxylic acid (0.39 g) and (4-isopropylphenyl)[(6-methoxypyridin-3-yl)methyl]amine (0.35 g) as starting materials, 5-benzyloxy-N-(4-isopropylphenyl)-N-[(6-methoxypyridin-3-yl)methyl]-1,2,3,4-tetrahydronaphthalene-1-carboxamide (0.36 g) was obtained.

¹H-NMR (CDCl₃) δ: 1.23 (6H, d, J=6.9 Hz), 1.40-1.57 (1H, m), 1.78-2.10 (3H, m), 2.70-2.80 (1H, m), 2.90 (1H, sept, J=6.9 Hz), 3.74 (1H, t, J=6.2 Hz), 3.93 (3H, s), 4.79 (1H, d, J=13.9 Hz), 4.89 (1H, d, J=13.9 Hz), 5.03 (2H, s), 6.62 (1H, d, J=7.5 Hz), 6.67-6.75 (2H, m), 6.97-7.12 (3H, m), 7.17-7.47 (7H, m), 7.63 (1H, dd, J=2.4, 8.4 Hz), 7.89 (1H, d, J=2.4 Hz).

By the reaction and treatment in the same manner as in Example 37 using 5-benzyloxy-N-(4-isopropylphenyl)-N-[(6-methoxypyridin-3-yl)methyl]-1,2,3,4-tetrahydronaphthalene-1-carboxamide (0.36 g), 5-hydroxy-N-(4-isopropylphenyl)-N-[(6-methoxypyridin-3-yl)methyl]-1,2,3,4-tetrahydronaphthalene-1-carboxamide (0.25 g) was obtained. melting point: 157.9° C.

Example 82

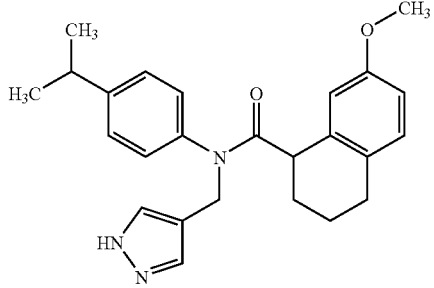

1-(tert-Butyloxycarbonyl)-4-(hydroxymethyl)pyrazole- (3.98 g) was dissolved in methylene chloride (50 mL), and methanesulfonyl chloride (1.63 mL) was added under ice-cooling. The mixture was stirred at room temperature for one day. The reaction mixture was concentrated and partitioned between water and chloroform. The organic layer was washed with saturated brine and dried over anhydrous sodium sulfate. The solvent was evaporated to give a residue (4.20 g). A white amorphous solid (5.20 g) obtained by the reaction and treatment in the same manner as in Example 6 using the residue and N-(4-isopropylphenyl)-7-methoxy-1,2,3,4-tetrahydronaphthalene-1-carboxamide (5.96 g) was dissolved in 4 mol/L-HCl/dioxane (50 mL). The mixture was stirred at room temperature for 3 hr, and the reaction mixture was concentrated under reduced pressure. Ethyl acetate and hexane were added to the residue. The precipitated solid was collected by filtration to give N-(4-isopropylphenyl)-7-methoxy-N-[(pyrazol-4-yl)methyl]-N-1,2,3,4-tetrahydronaphthalene-1-carboxamide hydrochloride (4.17 g).

¹H-NMR (CDCl₃) δ: 1.19 (6H, d, J=6.9 Hz), 1.25-1.42 (1H, m), 1.78-1.98 (3H, m), 2.46-2.71 (2H, m), 2.91 (1H, sept, J=6.9 Hz), 3.60 (1H, t, J=6.2 Hz), 3.66 (3H, s), 4.70 (1H, d, J=13.9 Hz), 4.81 (1H, d, J=13.9 Hz), 5.24 (2H, s), 6.42 (1H, d, J=2.4 Hz), 6.69 (1H, dd, J=2.4, 8.4 Hz), 6.95 (1H, d, J=8.4 Hz), 7.24 (2H, d, J=8.4 Hz), 7.34 (2H, d, J=8.4 Hz), 7.83 (2H, s).

Example 83

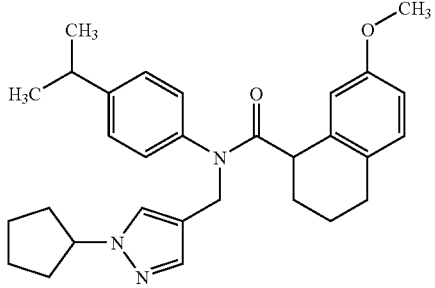

N-(4-Isopropylphenyl)-7-methoxy-N-[(pyrazol-4-yl)methyl]-1,2,3,4-tetrahydronaphthalene-1-carboxamide (0.44 g) and cyclopentyl bromide (0.12 mL) were dissolved in DMF (5 mL), and sodium hydride (0.09 g) was added under ice-cooling. The mixture was stirred at the same temperature for 30 min and then at room temperature for 5 hr. The reaction mixture was concentrated under reduced pressure and partitioned between water and ethyl acetate. The organic layer was washed with saturated brine and dried over anhydrous sodium sulfate. The solvent was evaporated, and the residue was purified by silica gel column chromatography to give N-[(1-cyclopentylpyrazol-4-yl)methyl]-N-(4-isopropylphenyl)-7-methoxy-1,2,3,4-tetrahydronaphthalene-1-carboxamide (0.38 g).

¹H-NMR (CDCl₃) δ: 1.24 (6H, d, J=6.9 Hz), 1.38-1.57 (1H, m), 1.62-2.20 (11H, m), 2.52-2.65 (1H, m), 2.70-2.84 (1H, m), 2.89 (1H, sept, J=6.9 Hz), 3.66 (3H, s), 3.70 (1H, t, J=6.2 Hz), 4.50 (1H, d, J=13.9 Hz), 4.60 (1H, quint, J=6.9 Hz), 4.92 (1H, d, J=13.9 Hz), 6.43 (1H, d, J=2.4 Hz), 6.66 (1H, dd, J=2.4, 8.4 Hz), 6.94 (1H, d, J=8.4 Hz), 7.05 (2H, d, J=8.4 Hz), 7.22 (2H, d, J=8.4 Hz), 7.34 (2H, s), 7.44 (2H, s).

Example 84

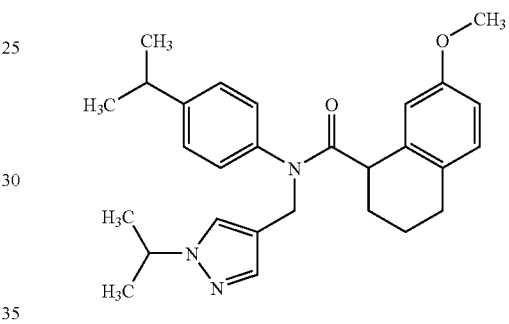

By the reaction and treatment in the same manner as in Example 83 using N-(4-isopropylphenyl)-7-methoxy-N-[(pyrazol-4-yl)methyl]-1,2,3,4-tetrahydronaphthalene-1-carboxamide (0.44 g) and isopropyl iodide (0.11 mL) as starting materials, N-(4-isopropylphenyl)-N-[(1-isopropylpyrazol-4-yl)methyl]-7-methoxy-1,2,3,4-tetrahydronaphthalene-1-carboxamide (0.26 g) was obtained.

¹H-NMR (CDCl₃) δ: 1.24 (6H, d, J=6.9 Hz), 1.36-1.53 (1H, m), 1.47 (6H, d, J=6.9 Hz), 1.79-2.06 (3H, m), 2.52-2.65 (1H, m), 2.70-2.84 (1H, m), 2.92 (1H, sept, J=6.9 Hz), 3.68 (3H, s), 3.70 (1H, t, J=6.2 Hz), 4.44 (1H, quint, J=6.9 Hz), 4.50 (1H, d, J=13.9 Hz), 4.94 (1H, d, J=13.9 Hz), 6.43 (1H, d, J=2.4 Hz), 6.66 (1H, dd, J=2.4, 8.4 Hz), 6.94 (1H, d, J=8.4 Hz), 7.05 (2H, d, J=8.4 Hz), 7.22 (2H, d, J=8.4 Hz), 7.35 (2H, s), 7.44 (2H, s).

Example 85

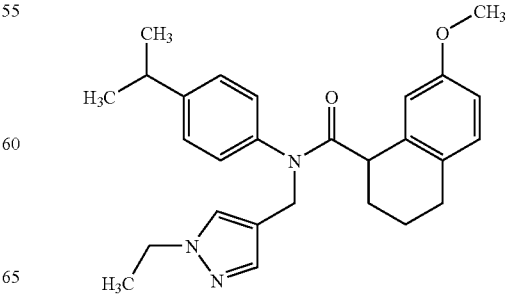

By the reaction and treatment in the same manner as in Example 83 using N-(4-isopropylphenyl)-7-methoxy-N-[(pyrazol-4-yl)methyl]-1,2,3,4-tetrahydronaphthalene-1-carboxamide (0.44 g) and ethyl iodide (0.09 mL) as starting materials, N-[(1-ethylpyrazol-4-yl)methyl]-N-(4-isopropylphenyl)-7-methoxy-1,2,3,4-tetrahydronaphthalene-1-carboxamide (0.31 g) was obtained. This was dissolved in ethyl acetate, and oxalic acid (0.07 g) was added. The precipitated solid was collected by filtration to give N-[(1-ethylpyrazol-4-yl)methyl]-N-(4-isopropylphenyl)-7-methoxy-1,2,3,4-tetrahydronaphthalene-1-carboxamide oxalate (0.06 g).

$^1$H-NMR (CDCl$_3$) δ: 1.24 (6H, d, J=6.9 Hz), 1.36-1.53 (1H, m), 1.32 (3H, t, J=6.9 Hz), 1.77-1.98 (3H, m), 2.47-2.70 (2H, m), 2.90 (1H, sept, J=6.9 Hz), 3.59 (1H, t, J=6.2 Hz), 3.64 (3H, s), 4.07 (2H, q, J=6.9 Hz), 4.56 (1H, d, J=13.9 Hz), 4.80 (1H, d, J=13.9 Hz), 6.41 (1H, d, J=2.4 Hz), 6.69 (1H, dd, J=2.4, 8.4 Hz), 6.94 (1H, d, J=8.4 Hz), 7.19 (2H, d, J=8.4 Hz), 7.27 (1H, s), 7.33 (2H, d, J=8.4 Hz), 7.53 (1H, s).

Example 86

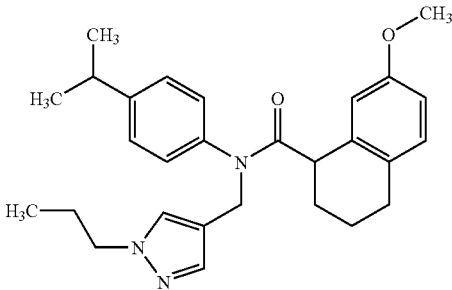

By the reaction and treatment in the same manner as in Example 83 using N-(4-isopropylphenyl)-7-methoxy-N-[(pyrazol-4-yl)methyl]-1,2,3,4-tetrahydronaphthalene-1-carboxamide (0.44 g) and propyl iodide (0.01 mL) as starting materials, N-(4-isopropylphenyl)-N-[(1-propylpyrazol-4-yl)methyl]-7-methoxy-1,2,3,4-tetrahydronaphthalene-1-carboxamide (0.31 g) was obtained.

$^1$H-NMR (CDCl$_3$) δ: 0.88 (3H, t, J=6.9 Hz), 1.24 (6H, d, J=6.9 Hz), 1.38-1.54 (1H, m), 1.77-2.04 (5H, m), 2.52-2.64 (1H, m), 2.70-2.84 (1H, m), 2.92 (1H, sept, J=6.9 Hz), 3.65-3.75 (1H, m), 3.68 (3H, s), 4.02 (2H, t, J=6.9 Hz), 4.07 (2H, q, J=6.9 Hz), 4.55 (1H, d, J=13.9 Hz), 4.88 (1H, d, J=13.9 Hz), 6.44 (1H, d, J=2.4 Hz), 6.66 (1H, dd, J=2.4, 8.4 Hz), 6.95 (1H, d, J=8.4 Hz), 6.98 (2H, d, J=8.4 Hz), 7.22 (2H, d, J=8.4 Hz), 7.35 (1H, s), 7.40 (1H, s).

Example 87

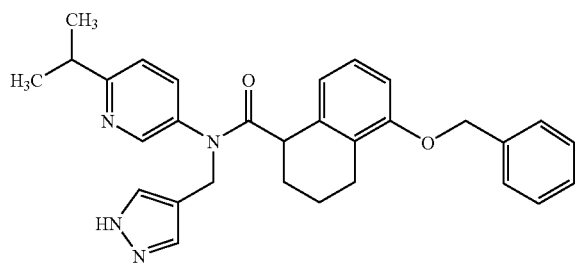

By the reaction and treatment in the same manner as in Example 82 using 1-(tert-butyloxycarbonyl)-4-(hydroxymethyl)pyrazole (578 mg) and 5-benzyloxy-N-(6-isopropylpyridin-3-yl)-1,2,3,4-tetrahydronaphthalene-1-carboxamide (1.17 g) as starting materials, 5-benzyloxy-N-(6-isopropylpyridin-3-yl)-N-[(pyrazol-4-yl)methyl]-1,2,3,4-tetrahydronaphthalene-1-carboxamide hydrochloride (790 mg) was obtained. melting point: 184.7° C.

Example 88

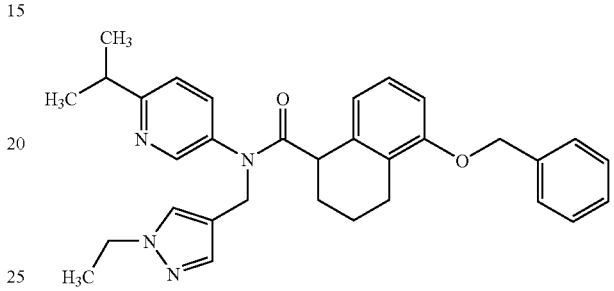

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.79 g) and ethyl iodide (0.12 mL) as starting materials, 5-benzyloxy-N-[(1-ethylpyrazol-4-yl)methyl]-N-(6-isopropylpyridin-3-yl)-1,2,3,4-tetrahydronaphthalene-1-carboxamide (0.43 g) was obtained.

$^1$H-NMR (CDCl$_3$) δ: 1.31 (6H, d, J=6.9 Hz), 1.45 (3H, t, J=7.3 Hz), 1.40-1.57 (1H, m), 1.75-2.07 (3H, m), 2.65-2.77 (2H, m), 2.72 (1H, sept, J=6.9 Hz), 3.64 (1H, t, J=6.2 Hz), 4.14 (2H, q, J=7.3 Hz), 4.61 (1H, d, J=13.9 Hz), 4.85 (1H, d, J=13.9 Hz), 5.03 (2H, s), 6.53 (1H, d, J=7.7 Hz), 6.72 (1H, d, J=7.7 Hz), 7.03 (1H, t, J=7.7 Hz), 7.24-7.43 (8H, m), 8.39 (1H, d, J=1.5 Hz).

Example 89

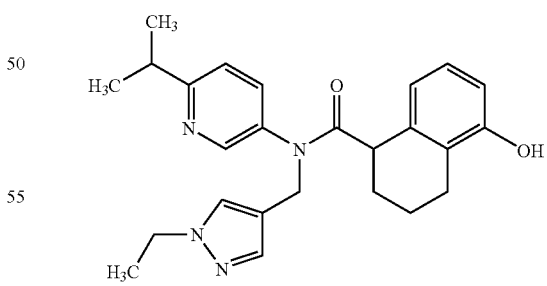

By the reaction and treatment in the same manner as in Example 37 using 5-benzyloxy-N-[(1-ethylpyrazol-4-yl)methyl]-N-(6-isopropylpyridin-3-yl)-1,2,3,4-tetrahydronaphthalene-1-carboxamide (0.43 g), N-[(1-ethylpyrazol-4-yl)methyl]-5-hydroxy-N-(6-isopropylpyridin-3-yl)-1,2,3,4-tetrahydronaphthalene-1-carboxamide (0.33 g) was obtained. melting point: 172.8° C.

Example 90

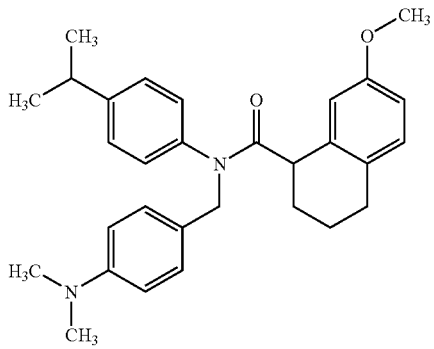

To a solution of N-[(4-dimethylaminophenyl)methyl]-N-(4-isopropylphenyl)-7-methoxy-1,2,3,4-tetrahydronaphthalene-1-carboxamide (29.9 g) in ethanol (300 mL) was added 4 mol/L-HCl/dioxane (17.5 mL) at 0° C. The precipitated white solid was collected by filtration and recrystallized from ethanol:water (2:3) to give N-[(4-dimethylaminophenyl)methyl]-N-(4-isopropylphenyl)-7-methoxy-1,2,3,4-tetrahydronaphthalene-1-carboxamide hydrochloride ½ hydrate (24.1 g). melting point: 146.9° C.

Example 91

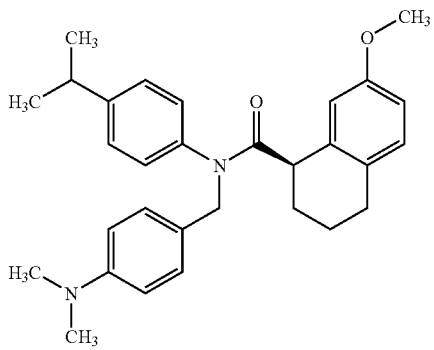

(R)-7-Methoxy-1,2,3,4-tetrahydronaphthalene-1-carboxylic acid (0.65 g) and [(4-dimethylaminophenyl)methyl](4-isopropylphenyl)amine (1.0 g) were reacted and treated in the same manner as in Example 12. The obtained solid was dissolved in ethyl acetate. Thereto was added 4 mol/L-HCl/ethyl acetate (1 mL). The solvent was evaporated under reduced pressure. The precipitated solid was recrystallized twice from ethanol to give (R)—N-[(4-dimethylaminophenyl)methyl]-N-(4-isopropylphenyl)-7-methoxy-1,2,3,4-tetrahydronaphthalene-1-carboxamide hydrochloride ½ ethanol (0.20 g).
melting point: 151-159° C.
optical purity 99.8% e.e.
Analysis Conditions
  column: CHIRALCEL OD (DAICEL)
  developing solvent: hexane/isopropanol=85/15
  flow rate: 0.5 mL/min
  UV detection: 254 nm
  retention time: 26 min
$[\alpha]_D$+113.5° (24° C., methanol, c=1.0)

Example 92

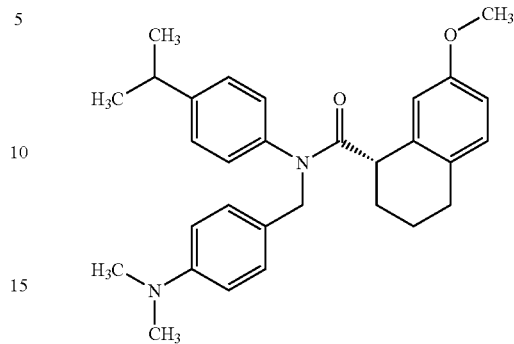

By the reaction and treatment in the same manner as in Example 91 using (S)-7-methoxy-1,2,3,4-tetrahydronaphthalene-1-carboxylic acid (0.95 g) and [(4-dimethylaminophenyl)methyl](4-isopropylphenyl)amine (1.48 g) as starting materials, (S)—N-[(4-dimethylaminophenyl)methyl]-N-(4-isopropylphenyl)-7-methoxy-1,2,3,4-tetrahydronaphthalene-1-carboxamide hydrochloride ½ ethanol (1.09 g) was obtained. melting point: 154-159° C.
optical purity 99.5% e.e.
Analysis Conditions
  column: CHIRALCEL OD (DAICEL)
  developing solvent: hexane/isopropanol=85/15
  flow rate: 0.5 mL/min
  UV detection: 254 nm
  retention time: 21.5 min
$[\alpha]_D$=−113.1° (20° C., methanol, c=1.0)

Example 93

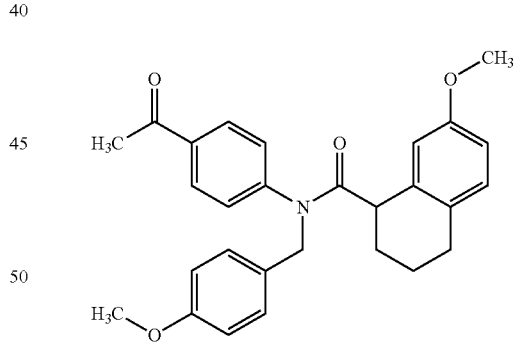

By the reaction and treatment in the same manner as in Example 12 using 7-methoxy-1,2,3,4-tetrahydronaphthalene-1-carboxylic acid (0.63 g) and (4-acetylphenyl)[(4-methoxyphenyl)methyl]amine (0.78 g) as starting materials, N-(4-acetylphenyl)-7-methoxy-N-[(4-methoxyphenyl)methyl]-1,2,3,4-tetrahydronaphthalene-1-carboxamide (0.33 g) was obtained.
$^1$H-NMR (CDCl$_3$) δ: 1.39-1.57 (1H, m), 1.81-2.08 (3H, m), 2.59 (3H, s), 2.70-2.85 (1H, m), 3.60-3.70 (1H, m), 3.72 (3H, s), 3.79 (3H, s), 4.75 (1H, d, J=13.9 Hz), 5.07 (1H, d, J=13.9 Hz), 6.50 (1H, d, J=2.4 Hz), 6.69 (1H, dd, J=2.4, 8.4 Hz), 6.76-6.86 (2H, m), 6.97 (2H, d, J=8.4 Hz), 7.10-7.22 (4H, m), 7.90-7.98 (2H, m).

Example 94

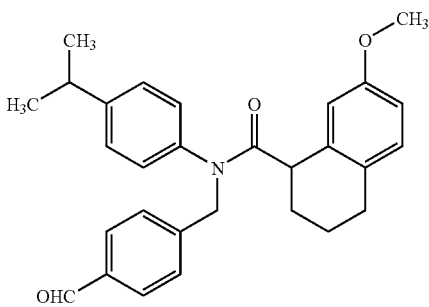

By the reaction and treatment in the same manner as in Example 12 using 7-methoxy-1,2,3,4-tetrahydronaphthalene-1-carboxylic acid (0.41 g) and {[4-(diethoxymethyl)phenyl]-methyl}(4-isopropylphenyl)amine (0.65 g) as starting materials. The obtained residue was dissolved in a mixed solvent (15 mL) of methanol:1 mol/L-hydrochloric acid (1:2) and heated under reflux for 3 hr. The reaction mixture was concentrated under reduced pressure and partitioned between water and ethyl acetate. The organic layer was washed with saturated brine and dried over anhydrous magnesium sulfate. The solvent was evaporated and the residue was purified by silica gel column chromatography to give N-[(4-formylphenyl)methyl]-N-(4-isopropylphenyl)-7-methoxy-1,2,3,4-tetrahydronaphthalene-1-carboxamide (0.42 g).

$^1$H-NMR (CDCl$_3$) δ: 1.23 (6H, d, J=6.9 Hz), 1.40-1.58 (1H, m), 1.85-2.10 (3H, m), 2.50-2.63 (1H, m), 2.70-2.85 (1H, m), 2.89 (1H, sept, J=6.9 Hz), 3.71 (3H, s), 3.75-3.84 (1H, m), 4.89 (1H, d, J=13.9 Hz), 5.10 (1H, d, J=13.9 Hz), 6.53 (1H, d, J=2.4 Hz), 6.68 (1H, dd, J=2.4, 8.4 Hz), 6.96 (1H, d, J=8.4 Hz), 7.02 (2H, d, J=8.4 Hz), 7.20 (2H, d, J=8.4 Hz), 7.45 (2H, d, J=8.4 Hz), 7.81 (2H, d, J=8.4 Hz), 9.98 (1H, s).

Example 95

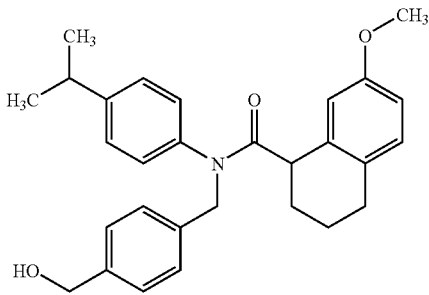

N-[(4-Formylphenyl)methyl]-N-(4-isopropylphenyl)-7-methoxy-1,2,3,4-tetrahydronaphthalene-1-carboxamide (0.42 g) was dissolved in a mixed solvent (10 mL) of ethanol:tetrahydrofuran (2:1), and sodium borohydride (0.15 g) was added under ice-cooling. The mixture was stirred at room temperature for 3 hr. The reaction mixture was partitioned between water and ethyl acetate. The organic layer was washed with saturated brine and dried over sodium sulfate. The solvent was evaporated, and the residue was purified by silica gel column chromatography to give N-{[4-(hydroxymethyl)phenyl]methyl}-N-(4-isopropylphenyl)-7-methoxy-1,2,3,4-tetrahydronaphthalene-1-carboxamide (0.25 g). melting point: 143.2° C.

$^1$H-NMR (CDCl$_3$) δ: 1.23 (6H, d, J=6.9 Hz), 1.40-1.58 (1H, m), 1.82-2.10 (3H, m), 2.51-2.65 (1H, m), 2.72-2.87 (1H, m), 2.89 (1H, sept, J=6.9 Hz), 3.71 (3H, s), 3.68-3.79 (1H, m), 4.68 (2H, s), 4.75 (1H, d, J=13.9 Hz), 5.08 (1H, d, J=13.9 Hz), 6.52 (1H, d, J=2.4 Hz), 6.68 (1H, dd, J=2.4, 8.4 Hz), 6.92-7.06 (3H, m), 7.18 (2H, d, J=8.4 Hz), 7.26-7.37 (4H, m).

Example 96

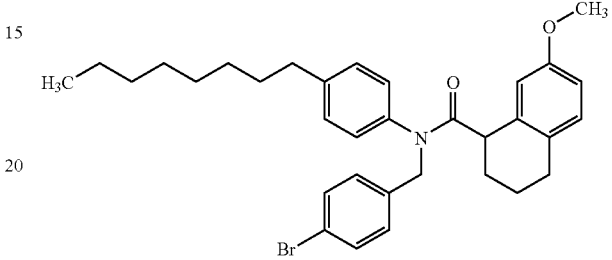

By the reaction and treatment in the same manner as in Example 12 using 7-methoxy-1,2,3,4-tetrahydronaphthalene-1-carboxylic acid (0.62 g) and [(4-bromophenyl)methyl](4-octylphenyl)amine (1.12 g) as starting materials, N-[(4-bromophenyl)methyl]-7-methoxy-N-(4-octylphenyl)-1,2,3,4-tetrahydronaphthalene-1-carboxamide (1.15 g) was obtained.

$^1$H-NMR (CDCl$_3$) δ: 0.87 (3H, t, J=4.5 Hz), 1.20-1.38 (12H, m), 1.42-1.58 (1H, m), 1.82-2.08 (3H, m), 2.52-2.65 (3H, m), 2.71-2.85 (1H, m), 3.70 (3H, s), 3.67-3.81 (1H, m), 4.72 (1H, d, J=14.1 Hz), 5.00 (1H, d, J=14.0 Hz), 6.48 (1H, d, J=2.5 Hz), 6.68 (1H, dd, J=2.6, 8.4 Hz), 6.91-7.01 (3H, m), 7.10-7.18 (4H, m), 7.37-7.45 (2H, m).

Example 97

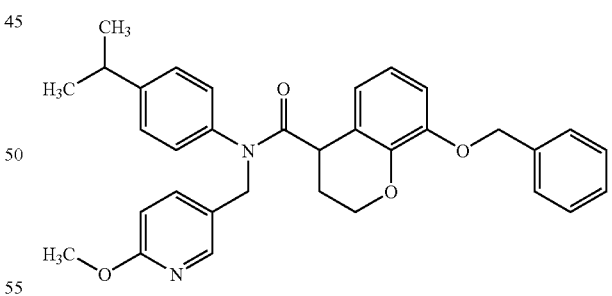

By the reaction and treatment in the same manner as in Example 12 using 8-(benzyloxy)chroman-4-carboxylic acid (0.47 g) and (4-isopropylphenyl)[(6-methoxypyridin-3-yl)methyl]amine 0.43 g) as starting materials, 8-benzyloxy-N-(4-isopropylphenyl)-N-[(6-methoxypyridin-3-yl)methyl]chroman-4-carboxamide (0.61 g) was obtained.

$^1$H-NMR (CDCl$_3$) δ: 1.25 (6H, d, J=6.9 Hz), 1.88-2.02 (1H, m), 2.11-2.24 (1H, m), 2.91 (1H, sept, J=6.9 Hz), 3.79 (1H, t, J=6.3 Hz), 3.92 (3H, s), 4.05-4.16 (1H, m), 4.51-4.61 (1H, m), 4.78 (1H, d, J=13.9 Hz), 4.87 (1H, d, J=13.9 Hz), 5.12 (2H, s), 6.48-6.57 (1H, m), 6.65-6.75 (3H, m), 6.98 (2H, d, J=8.4 Hz), 7.19-7.43 (7H, m), 7.60 (1H, dd, J=2.4, 8.4 Hz), 7.88 (1H, d, J=2.4 Hz).

Example 98

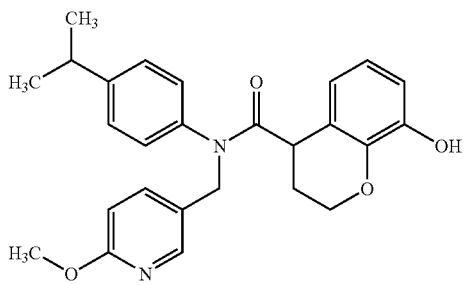

By the reaction and treatment in the same manner as in Example 17 using 8-benzyloxy-N-(4-isopropylphenyl)-N-[(6-methoxypyridin-3-yl)methyl]chroman-4-carboxamide (0.58 g) as a starting material, 8-hydroxy-N-(4-isopropylphenyl)-N-[(6-methoxypyridin-3-yl)methyl]chroman-4-carboxamide (0.35 g) was obtained.
melting point: 141.2° C.

Example 99

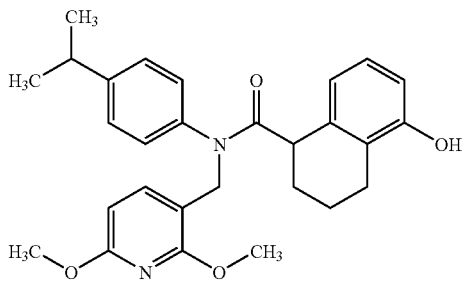

By the reaction and treatment in the same manner as in Example 12 using 5-benzyloxy-1,2,3,4-tetrahydronaphthalene-1-carboxylic acid (0.42 g) and [(2,6-dimethoxypyridin-3-yl)methyl](4-isopropylphenyl)amine (0.43 g) as starting materials, 5-benzyloxy-N-[(2,6-dimethoxypyridin-3-yl)methyl]-N-(4-isopropylphenyl)-1,2,3,4-tetrahydronaphthalene-1-carboxamide (0.71 g) was obtained.

By the reaction and treatment in the same manner as in Example 17 using this compound (0.70 g), N-[(2,6-dimethoxypyridin-3-yl)methyl]-5-hydroxy-N-(4-isopropylphenyl)-1,2,3,4-tetrahydronaphthalene-1-carboxamide (0.41 g) was obtained. melting point: 190.5° C.

Example 100

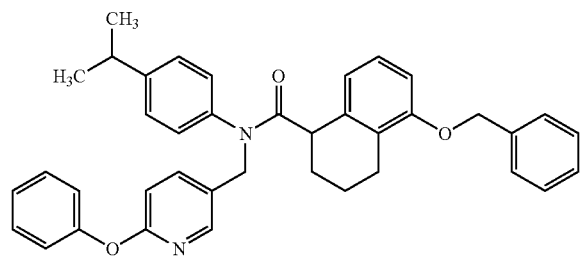

By the reaction and treatment in the same manner as in Example 12 using 5-benzyloxy-1,2,3,4-tetrahydronaphthalene-1-carboxylic acid (0.42 g) and (4-isopropylphenyl)[(6-phenoxypyridin-3-yl)methyl]amine (0.47 g) as starting materials, 5-benzyloxy-N-(4-isopropylphenyl)-N-[(6-phenoxypyridin-3-yl)methyl]-1,2,3,4-tetrahydronaphthalene-1-carboxamide (0.42 g) was obtained.
$^1$H-NMR (CDCl$_3$) δ: 1.22 (6H, d, J=6.9 Hz), 1.38-1.55 (1H, m), 1.77-2.09 (3H, m), 2.67-2.87 (2H, m), 2.88 (1H, sept, J=6.9 Hz), 3.70-3.80 (1H, m), 4.82 (1H, d, J=14.2 Hz), 4.90 (1H, d, J=14.2 Hz), 5.01 (2H, s), 6.62 (1H, d, J=7.7 Hz), 6.74 (1H, d, J=8.5 Hz), 6.85 (1H, d, J=8.5 Hz), 6.97-7.42 (15H, m), 7.71-7.79 (1H, m), 7.94 (1H, d, J=2.3 Hz).

Example 101

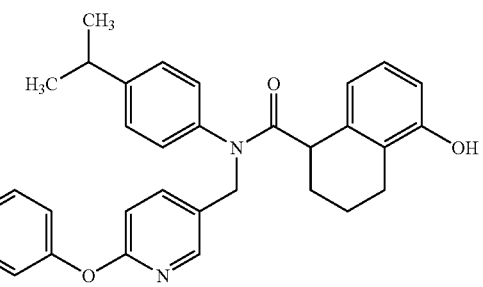

To a solution of 5-benzyloxy-N-(4-isopropylphenyl)-N-[(6-phenoxypyridin-3-yl)methyl]-1,2,3,4-tetrahydronaphthalene-1-carboxamide (0.42 g) in methanol (3 mL) were added 10% palladium carbon (0.05 g) and ammonium formate (0.23 g), and the mixture was stirred at room temperature for one day. The reaction mixture was filtrated, and the solvent was evaporated. The residue was purified by silica gel column chromatography to give 5-hydroxy-N-(4-isopropylphenyl)-N-[(6-phenoxypyridin-3-yl)methyl]-1,2,3,4-tetrahydronaphthalene-1-carboxamide. This compound was dissolved in ethyl acetate, and 4 mol/L-hydrochloric acid/dioxane (0.20 mL) was added. The precipitated solid was collected by filtration to give 5-hydroxy-N-(4-isopropylphenyl)-N-[(6-phenoxypyridin-3-yl)methyl]-1,2,3,4-tetrahydronaphthalene-1-carboxamide hydrochloride (0.11 g).
$^1$H-NMR (DMSO-d$_6$) δ: 1.19 (6H, d, J=6.9 Hz), 1.27-1.43 (1H, m), 1.73-2.00 (3H, m), 2.67-2.87 (2H, m), 2.89 (1H, sept, J=6.9 Hz), 3.51-3.71 (1H, m), 4.79 (1H, d, J=14.7 Hz), 4.92 (1H, d, J=14.7 Hz), 6.46 (1H, d, J=7.5 Hz), 6.62 (1H, d, J=7.8 Hz), 6.84-6.92 (1H, m), 7.00 (1H, d, J=8.4 Hz), 7.07-7.47 (9H, m), 7.70 (1H, dd, J=2.4, 8.4 Hz), 7.91 (1H, d, J=2.1 Hz).

Example 102

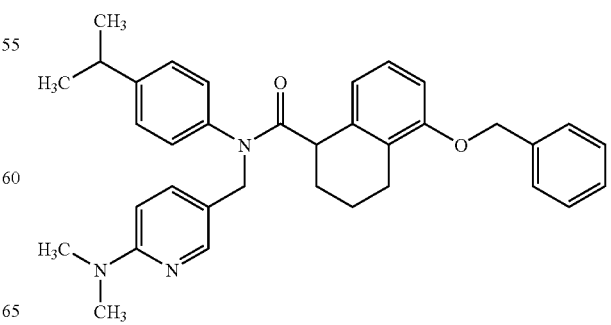

By the reaction and treatment in the same manner as in Example 12 using 5-benzyloxy-1,2,3,4-tetrahydronaphthalene-1-carboxylic acid (0.56 g) and [(6-dimethylaminopyridin-3-yl)methyl](4-isopropylphenyl)amine (0.54 g) as starting materials, 5-benzyloxy-N-[(6-dimethylaminopyridin-3-yl)methyl]-N-(4-isopropylphenyl)-1,2,3,4-tetrahydronaphthalene-1-carboxamide (0.83 g) was obtained.

¹H-NMR (CDCl₃) δ: 1.23 (6H, d, J=6.9 Hz), 1.38-1.53 (1H, m), 1.77-2.10 (3H, m), 2.61-2.78 (2H, m), 2.89 (1H, sept, J=6.9 Hz), 3.08 (6H, s), 3.67-3.77 (1H, m), 4.71 (1H, d, J=14.1 Hz), 4.85 (1H, d, J=14.1 Hz), 5.03 (2H, s), 6.48 (1H, d, J=8.7 Hz), 6.64 (1H, d, J=7.8 Hz), 6.71 (1H, d, J=8.1 Hz), 6.95-7.09 (3H, m), 7.19 (2H, d, J=8.4 Hz), 7.23-7.44 (5H, m), 7.54 (1H, dd, J=2.4, 8.7 Hz), 7.86 (1H, d, J=2.1 Hz).

Example 103

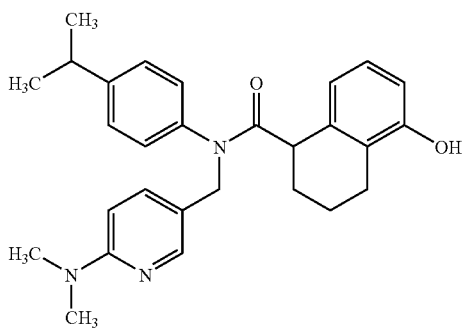

By the reaction and treatment in the same manner as in Example 17 using 5-benzyloxy-N-[(6-dimethylaminopyridin-3-yl)methyl]-N-(4-isopropylphenyl)-1,2,3,4-tetrahydronaphthalene-1-carboxamide (0.83 g) as a starting material, N-[(6-dimethylaminopyridin-3-yl)methyl]-5-hydroxy-N-(4-isopropylphenyl)-1,2,3,4-tetrahydronaphthalene-1-carboxamide (0.33 g) was obtained. melting point: 186.6° C.

Example 104

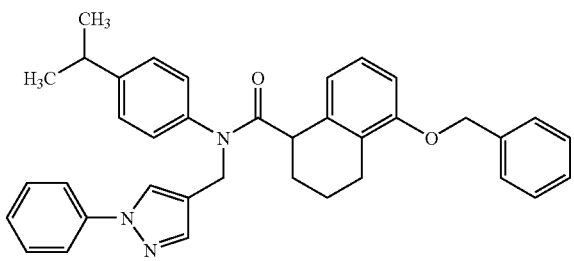

By the reaction and treatment in the same manner as in Example 12 using 5-benzyloxy-1,2,3,4-tetrahydronaphthalene-1-carboxylic acid (0.85 g) and (4-isopropylphenyl)[(1-phenylpyrazol-4-yl)methyl]amine (0.87 g) as starting materials, 5-benzyloxy-N-(4-isopropylphenyl)-N-[(1-phenyl-pyrazol-4-yl)methyl]-1,2,3,4-tetrahydronaphthalene-1-carboxamide (1.21 g) was obtained.

¹H-NMR (CDCl₃) δ: 1.25 (6H, d, J=6.9 Hz), 1.41-1.57 (1H, m), 1.80-2.10 (3H, m), 2.65-2.84 (2H, m), 2.93 (1H, sept, J=6.9 Hz), 3.71-3.82 (1H, m), 4.70 (1H, d, J=14.4 Hz), 4.92 (1H, d, J=14.4 Hz), 5.03 (2H, s), 6.60 (1H, d, J=7.7 Hz), 6.71 (1H, d, J=8.1 Hz), 7.00-7.16 (3H, m), 7.22-7.48 (10H, m), 7.58 (1H, s), 7.66 (2H, d, J=7.6 Hz), 7.95 (1H, s).

Example 105

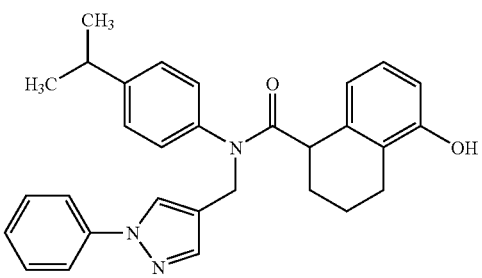

To a solution of 5-benzyloxy-N-(4-isopropylphenyl)-N-[(1-phenylpyrazol-4-yl)methyl]-1,2,3,4-tetrahydronaphthalene-1-carboxamide (1.04 g) in methanol (10 mL) were added 10% palladium carbon (0.10 g) and ammonium formate (0.59 g), and the mixture was stirred at room temperature for one day. The reaction mixture was filtrated, and the solvent was evaporated. The residue was purified by silica gel column chromatography to give 5-hydroxy-N-(4-isopropylphenyl)-N-[(1-phenylpyrazol-4-yl)methyl]-1,2,3,4-tetrahydronaphthalene-1-carboxamide (0.76 g).

¹H-NMR (CDCl₃) δ: 1.25 (6H, d, J=6.9 Hz), 1.36-1.51 (1H, m), 1.78-2.08 (3H, m), 2.50-2.71 (2H, m), 2.93 (1H, sept, J=6.9 Hz), 3.70-3.81 (1H, m), 4.72 (1H, d, J=14.4 Hz), 4.94 (1H, d, J=14.4 Hz), 6.36 (1H, d, J=7.8 Hz), 6.42 (1H, d, J=7.5 Hz), 6.75 (1H, d, J=7.8 Hz), 7.12 (1H, d, J=8.4 Hz), 7.21-7.33 (3H, m), 7.39-7.49 (2H, m), 7.53 (1H, brs), 7.59 (1H, s), 7.69 (2H, d, J=7.5 Hz), 8.01 (1H, s).

Example 106

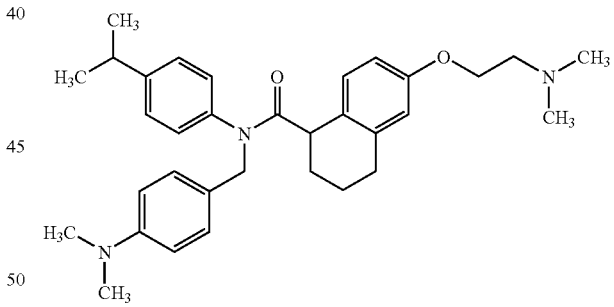

To a solution of N-[(4-dimethylaminophenyl)methyl]-6-hydroxy-N-(4-isopropylphenyl)-1,2,3,4-tetrahydronaphthalene-1-carboxamide (0.66 g) in dimethylformamide (10 mL) were added 2-chloro-N,N-dimethylethylamine hydrochloride (0.26 g) and potassium carbonate (0.62 g), and the mixture was stirred with heating at 50° C. for 3 hr. The reaction mixture was partitioned between water and ethyl acetate. The organic layer was washed with saturated brine and dried over magnesium sulfate. The solvent was evaporated, and the residue was purified by silica gel column chromatography to give 6-[2-(dimethylamino)ethoxy]-N-[(4-dimethylaminophenyl)methyl]-N-(4-isopropylphenyl)-1,2,3,4-tetrahydronaphthalene-1-carboxamide ⅕ hydrate (0.1 g). melting point: 132.6° C.

MS (ESI) m/z: 514 [MH]⁺

Example 107

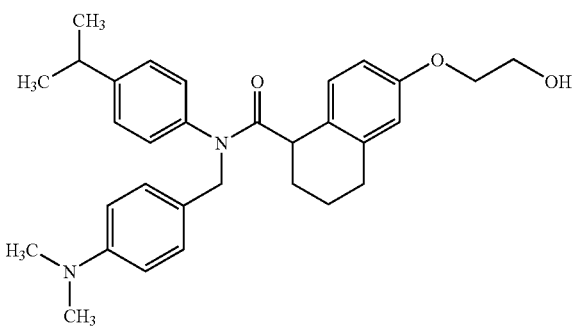

By the reaction and treatment in the same manner as in Example 106 using N-[(4-dimethylaminophenyl)methyl]-6-hydroxy-N-(4-isopropylphenyl)-1,2,3,4-tetrahydronaphthalene-1-carboxamide (0.66 g) and 2-bromoethanol (0.16 mL) as starting materials, N-[(4-dimethylaminophenyl)methyl]-6-(2-hydroxyethoxy)-N-(4-isopropylphenyl)-1,2,3,4-tetrahydronaphthalene-1-carboxamide (0.28 g) was obtained.
melting point: 141.4° C.

Example 108

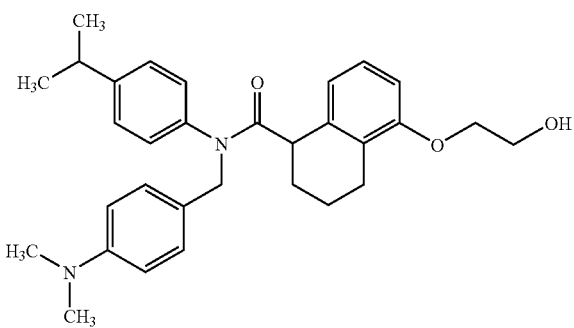

By the reaction and treatment in the same manner as in Example 106 using N-[(4-dimethylaminophenyl)methyl]-5-hydroxy-N-(4-isopropylphenyl)-1,2,3,4-tetrahydronaphthalene-1-carboxamide (0.66 g) and 2-bromoethanol (0.32 mL) as starting materials, N-[(4-dimethylaminophenyl)methyl]-5-(2-hydroxyethoxy)-N-(4-isopropylphenyl)-1,2,3,4-tetrahydronaphthalene-1-carboxamide (0.49 g) was obtained.
$^1$H-NMR (CDCl$_3$) δ: 1.20-1.30 (6H, m), 1.35-1.50 (1H, m), 1.70-2.10 (3H, m), 2.60-2.70 (2H, m), 2.80-3.00 (1H, m), 2.94 (6H, s), 3.65-3.75 (1H, m), 3.85-4.00 (2H, m), 4.00-4.10 (2H, m), 4.72 (1H, d, J=13.8 Hz), 4.91 (1H, d, J=13.8 Hz), 6.60-6.70 (4H, m), 6.90-7.20 (7H, m).

Example 109

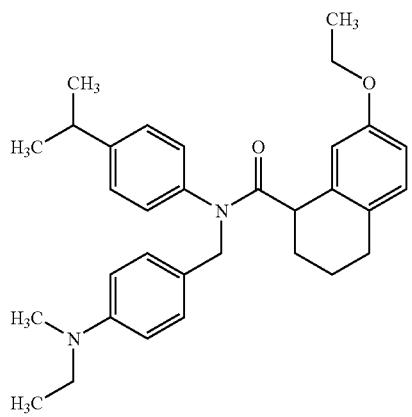

By the reaction and treatment in the same manner as in Example 106 using N-[(4-dimethylaminophenyl)methyl]-7-hydroxy-N-(4-isopropylphenyl)-1,2,3,4-tetrahydronaphthalene-1-carboxamide (0.5 g) and ethyl iodide (0.14 mL) as starting materials, 7-ethoxy-N-{[4-(ethylmethylamino)phenyl]methyl}-N-(4-isopropylphenyl)-1,2,3,4-tetrahydronaphthalene-1-carboxamide (0.1 g) was obtained.
$^1$H-NMR (CDCl$_3$) δ: 1.12 (3H, t, J=7.2 Hz), 1.23 (6H, d, J=6.9 Hz), 1.37 (3H, t, J=6.9 Hz), 1.30-1.55 (1H, m), 1.80-2.10 (3H, m), 2.50-2.65 (1H, m), 2.70-3.00 (2H, m), 2.90 (3H, s), 3.39 (2H, q, J=7.2 Hz), 3.60-3.70 (1H, m), 3.75-4.00 (2H, m), 4.53 (1H, d, J=13.8 Hz), 5.08 (1H, d, J=13.8 Hz), 6.45-6.70 (4H, m), 6.85-7.20 (7H, m).

Example 110

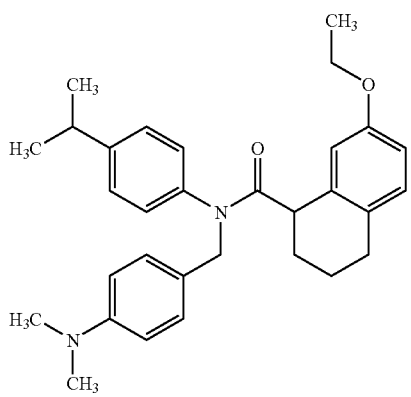

N-[(4-Dimethylaminophenyl)methyl]-7-hydroxy-N-(4-isopropylphenyl)-1,2,3,4-tetrahydronaphthalene-1-carboxamide (0.5 g) and ethyl iodide (0.14 mL) were dissolved in dimethylformamide (5 mL), and sodium hydride (0.07 g) was added under ice-cooling. The mixture was stirred at room temperature for 24 hr. The reaction mixture was partitioned between water and ethyl acetate. The organic layer was washed with saturated brine and dried over magnesium sulfate. The solvent was evaporated, and the residue was purified by silica gel column chromatography to give N-[(4-dimethylaminophenyl)methyl]-7-ethoxy-N-(4-isopropylphenyl)-1,2,3,4-tetrahydronaphthalene-1-carboxamide (0.27 g).
$^1$H-NMR (CDCl$_3$) δ: 1.23 (6H, d, J=6.9 Hz), 1.37 (3H, t, J=7.0 Hz), 1.30-1.60 (1H, m), 1.80-2.10 (3H, m), 2.50-2.65 (1H, m), 2.70-3.00 (2H, m), 2.94 (6H, s), 3.60-3.75 (1H, m), 3.75-3.95 (2H, m), 4.54 (1H, d, J=13.9 Hz), 5.09 (1H, d, J=13.9 Hz), 6.45-6.55 (1H, m), 6.60-6.70 (3H, m), 6.85-7.00 (3H, m), 7.05-7.20 (4H, m).

Example 111

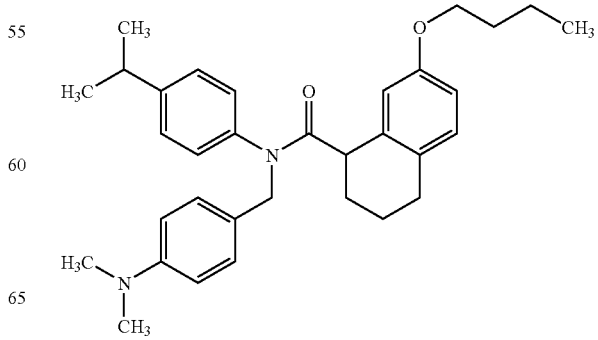

By the reaction and treatment in the same manner as in Example 110 using N-[(4-dimethylaminophenyl)methyl]-7-hydroxy-N-(4-isopropylphenyl)-1,2,3,4-tetrahydronaphthalene-1-carboxamide (0.5 g) and butyl bromide (0.18 mL) as starting materials, 7-butoxy-N-[(4-dimethylaminophenyl)methyl]-N-(4-isopropylphenyl)-1,2,3,4-tetrahydronaphthalene-1-carboxamide (0.15 g) was obtained.

¹H-NMR (CDCl₃) δ: (0.98 (3H, t, J=7.3 Hz), 1.23 (6H, d, J=6.9 Hz) 1.40-1.60 (3H, m), 1.65-2.10 (5H, m), 2.50-2.65 (1H, m), 2.70-3.00 (2H, m), 2.94 (6H, s), 3.65-3.70 (1H, m), 3.75-3.90 (2H, m), 4.54 (1H, d, J=13.9 Hz), 5.10 (1H, d, J=13.9 Hz), 6.45-6.55 (1H, m), 6.60-6.70 (3H, m), 6.85-7.00 (3H, m), 7.10-7.20 (4H, m).

Example 112

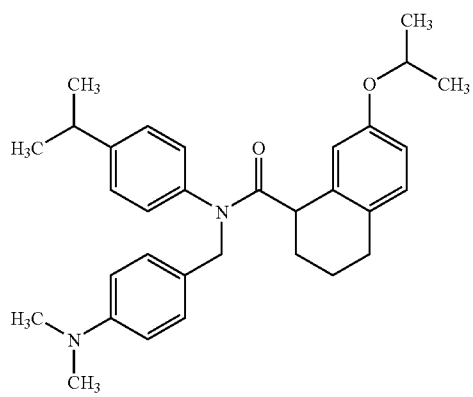

By the reaction and treatment in the same manner as in Example 106 using N-[(4-dimethylaminophenyl)methyl]-7-hydroxy-N-(4-isopropylphenyl)-1,2,3,4-tetrahydronaphthalene-1-carboxamide (0.5 g) and 2-iodopropane (0.17 mL) as starting materials, N-[(4-dimethylaminophenyl)methyl]-7-isopropoxy-N-(4-isopropylphenyl)-1,2,3,4-tetrahydronaphthalene-1-carboxamide (35 mg) was obtained.

¹H-NMR (CDCl₃) δ: 1.10-1.35 (12H, m), 1.35-1.55 (1H, m), 1.80-2.10 (3H, m), 2.50-2.65 (1H, m), 2.70-3.00 (2H, m), 2.94 (6H, s), 3.60-3.80 (1H, m), 4.30-4.45 (1H, m), 4.53 (1H, d, J=13.8 Hz), 5.10 (1H, d, J=13.8 Hz), 6.45-6.55 (1H, m), 6.60-6.75 (3H, m), 6.85-7.05 (3H, m), 7.10-7.25 (4H, m).

Example 113

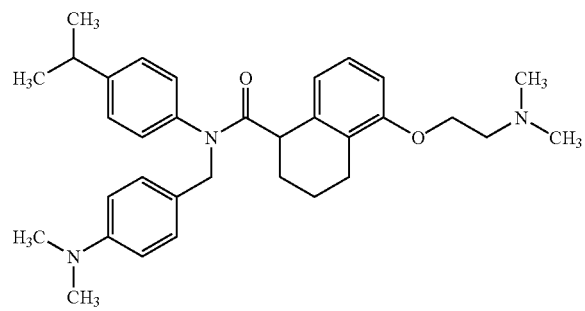

By the reaction and treatment in the same manner as in Example 106 using N-[(4-dimethylaminophenyl)methyl]-5-hydroxy-N-(4-isopropylphenyl)-1,2,3,4-tetrahydronaphthalene-1-carboxamide (0.66 g) and 2-chloro-N,N-dimethylethylamine hydrochloride (0.32 g) as starting materials, 5-[2-(dimethylamino)ethoxy]-N-[(4-dimethylaminophenyl)methyl]-N-(4-isopropylphenyl)-1,2,3,4-tetrahydronaphthalene-1-carboxamide (0.54 g) was obtained. This compound was dissolved in ethyl acetate, and oxalic acid was added. The precipitated solid was subjected to recrystallization from ethyl acetate to give 5-[2-(dimethylamino)ethoxy]-N-[(4-dimethylaminophenyl)methyl]-N-(4-isopropylphenyl)-1,2,3,4-tetrahydronaphthalene-1-carboxamide oxalate ¼ hydrate (93.8 mg).

melting point: 155.7° C.

Example 114

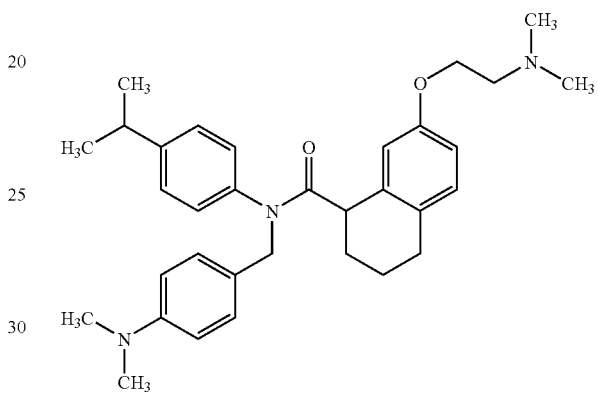

By the reaction and treatment in the same manner as in Example 110 using N-[(4-dimethylaminophenyl)methyl]-7-hydroxy-N-(4-isopropylphenyl)-1,2,3,4-tetrahydronaphthalene-1-carboxamide (0.5 g), 2-chloro-N,N-dimethylethylamine hydrochloride (0.36 g) and sodium iodide (0.51 g) as starting materials, 7-[2-(dimethylamino)ethoxy]-N-[(4-dimethylaminophenyl)methyl]-N-(4-isopropylphenyl)-1,2,3,4-tetrahydronaphthalene-1-carboxamide (36 mg) was obtained.

¹H-NMR (CDCl₃) δ: 1.23 (6H, d, J=6.9 Hz), 1.40-1.55 (1H, m), 1.70-2.05 (5H, m), 2.33 (6H, s), 2.50-2.95 (3H, m), 2.94 (6H, s), 3.60-3.70 (1H, m), 3.85-4.05 (2H, m), 4.64 (1H, d, J=13.9 Hz), 4.99 (1H, d, J=13.9 Hz), 6.50-6.75 (4H, m), 6.90-7.20 (7H, m).

Example 115

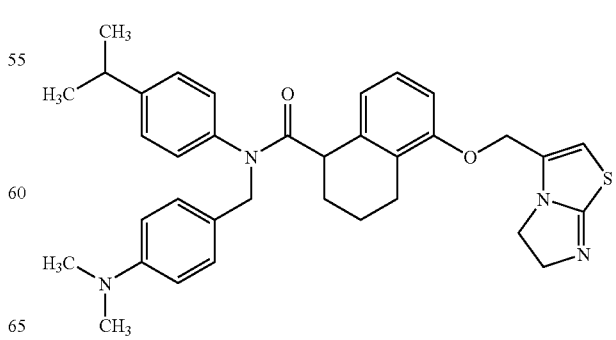

By the reaction and treatment in the same manner as in Example 106 using N-[(4-dimethylaminophenyl)methyl]-5-hydroxy-N-(4-isopropylphenyl)-1,2,3,4-tetrahydronaphthalene-1-carboxamide (0.66 g) and (5,6-dihydroimidazo[2,1-b]thiazol-3-yl)methyl chloride (0.38 g) as starting materials, 5-[(5,6-dihydroimidazo[2,1-b]thiazol-3-yl)methoxy]-N-[(4-dimethylaminophenyl)methyl]-N-(4-isopropylphenyl)-1,2,3,4-tetrahydronaphthalene-1-carboxamide (0.16 g) was obtained.

$^1$H-NMR (CDCl$_3$) δ: 1.23 (6H, d, J=6.9 Hz), 1.40-1.50 (1H, m), 1.75-2.10 (3H, m), 2.64 (2H, t, J=6.6 Hz), 2.85-2.95 (1H, m), 2.94 (6H, s), 2.65-2.75 (1H, m), 3.84 (2H, t, J=9.3 Hz), 4.23 (2H, t, J=9.3 Hz), 4.61 (2H, s), 4.72 (1H, d, J=14.1 Hz), 4.91 (1H, d, J=14.1 Hz), 5.67 (1H, s), 6.60-6.75 (4H, m), 6.90-7.20 (7H, m).

Example 116

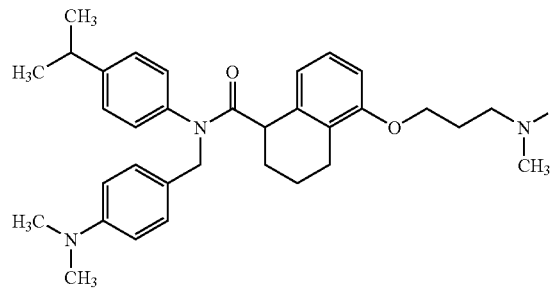

By the reaction and treatment in the same manner as in Example 106 using N-[(4-dimethylaminophenyl)methyl]-5-hydroxy-N-(4-isopropylphenyl)-1,2,3,4-tetrahydronaphthalene-1-carboxamide (0.66 g) and 3-chloro-N,N-dimethylpropylamine hydrochloride (0.32 g) as starting materials, N-[(4-dimethylaminophenyl)-methyl]-5-[3-(dimethylamino)propoxy]-N-(4-isopropylphenyl)-1,2,3,4-tetrahydronaphthalene-1-carboxamide (0.5 g) was obtained. Oxalic acid was added to this compound. By recrystallization from isopropyl alcohol, N-[(4-dimethylaminophenyl)methyl]-5-[3-(dimethylamino)propoxy]-N-(4-isopropylphenyl)-1,2,3,4-tetrahydronaphthalene-1-carboxamide oxalate ⅘ hydrate (0.18 g) was obtained.

melting point: 100.8° C.

Example 117

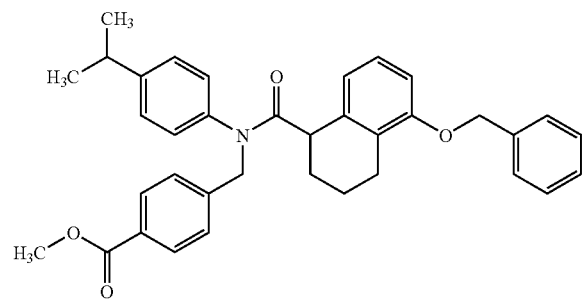

By the reaction and treatment in the same manner as in Example 12 using 5-benzyloxy-1,2,3,4-tetrahydronaphthalene-1-carboxylic acid (2.3 g) and methyl 4-{[(4-isopropylphenyl)amino]methyl}benzoate (2.3 g) as starting materials, methyl 4-{[N-(5-benzyloxy-1,2,3,4-tetrahydronaphthalen-1-ylcarbonyl)-N-(4-isopropylphenyl)amino]methyl}benzoate (2.56 g) was obtained.

$^1$H-NMR (CDCl$_3$) δ: 1.22 (6H, d, J=6.9 Hz), 1.40-1.60 (1H, m), 1.80-2.10 (3H, m), 2.70-2.76 (2H, m), 2.80-2.95 (1H, m), 3.72-3.82 (1H, m), 3.92 (3H, s), 4.90 (1H, d, J=14.2 Hz), 5.04 (1H, d, J=14.2 Hz), 5.03 (2H, s), 6.64 (1H, d, J=7.7 Hz), 6.73 (1H, d, J=8.1 Hz), 6.95-7.45 (12H, m), 7.97 (2H, d, J=8.3 Hz).

Example 118

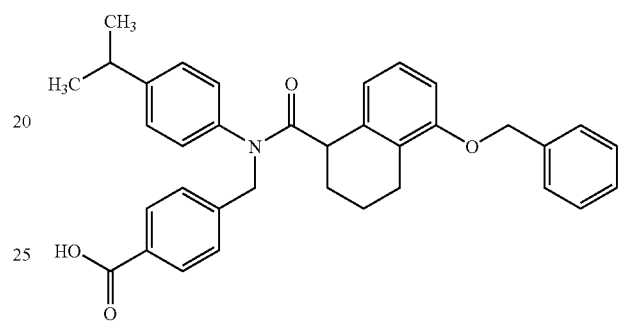

Methanol (14 mL) and 1 mol/L-aqueous sodium hydroxide solution (7 mL) were added to methyl 4-{[N-(5-benzyloxy-1,2,3,4-tetrahydronaphthalen-1-ylcarbonyl)-N-(4-isopropylphenyl)amino]methyl}benzoate (2.56 g), and the mixture was stirred with heating at 50-60° C. After the completion of the reaction, the reaction mixture was neutralized with conc. hydrochloric acid and extracted with ethyl acetate. The organic layer was washed with saturated brine and dried over magnesium sulfate. The solvent was evaporated, and the residue was purified by silica gel column chromatography to give 4-{[N-(5-benzyloxy-1,2,3,4-tetrahydronaphthalen-1-ylcarbonyl)-N-(4-isopropylphenyl)amino]methyl}benzoic acid (2 g).

$^1$H-NMR (CDCl$_3$) δ: 1.25 (6H, d, J=6.9 Hz), 1.40-1.60 (1H, m), 1.80-2.15 (3H, m), 2.70-2.80 (2H, m), 2.82-2.95 (1H, m), 3.72-3.85 (1H, m), 4.94 (1H, d, J=14.1 Hz), 5.06 (1H, d, J=14.1 Hz), 5.03 (2H, s), 6.66 (1H, d, J=7.8 Hz), 6.73 (1H, d, J=8.1 Hz), 6.90-7.50 (12H, m), 8.04 (2H, d, J=8.4 Hz).

Example 119

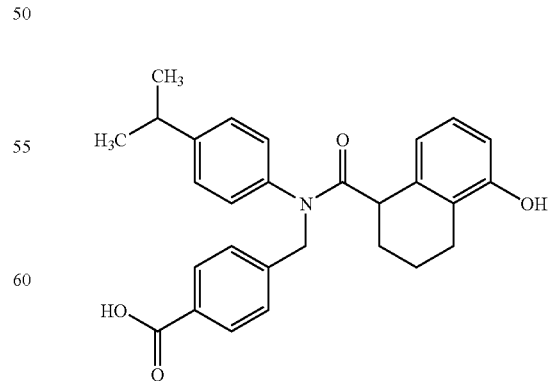

By the reaction and treatment in the same manner as in Example 17 using 4-{[N-(5-benzyloxy-1,2,3,4-tetrahydronaphthalen-1-ylcarbonyl)-N-(4-isopropylphenyl)amino]methyl}benzoic acid (2 g) as a starting material, 4-{[N-(5-hydroxy-1,2,3,4-tetrahydronaphthalen-1-ylcarbonyl)-N-(4-isopropylphenyl)amino]methyl}benzoic acid dihydrate (0.13 g) was obtained. melting point: 231.4° C.

Example 120

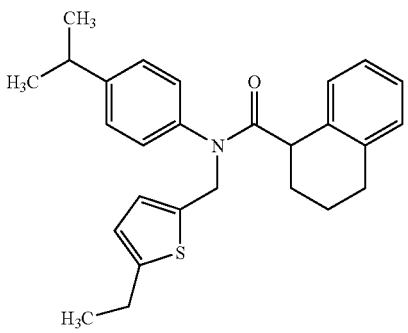

By the reaction and treatment in the same manner as in Example 12 using 1,2,3,4-tetrahydronaphthalene-1-carboxylic acid (0.7 g) and [(5-ethylthiophen-2-yl)methyl](4-isopropylphenyl)amine (1.04 g) as starting materials, N-[(5-ethylthiophen-2-yl) methyl]-N-(4-isopropylphenyl)-1,2,3,4-tetrahydronaphthalene-1-carboxamide (0.18 g) was obtained.

MS (ESI) m/z: 418 [MH]$^+$ $^1$H-NMR (CDCl$_3$) δ: 1.24 (6H, d, J=6.9 Hz), 1.30 (3H, t, J=7.5 Hz), 1.40-1.60 (1H, m), 1.80-2.10 (3H, m), 2.55-2.70 (1H, m), 2.82 (2H, q, J=7.5 Hz), 2.72-3.00 (2H, m), 3.65-3.80 (1H, m), 4.90 (1H, d, J=14.6 Hz), 5.03 (1H, d, J=14.6 Hz), 6.56 (1H, d, J=3.4 Hz), 6.62 (1H, d, J=3.4 Hz), 6.90-7.30 (8H, m).

Example 121

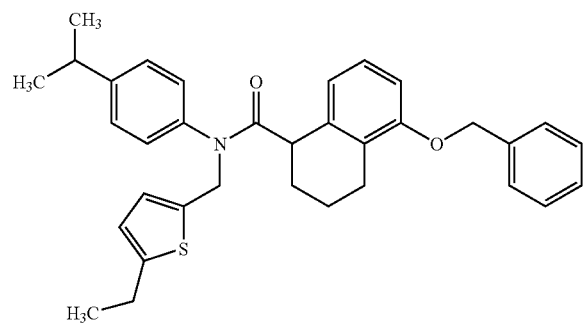

By the reaction and treatment in the same manner as in Example 12 using 5-benzyloxy-1,2,3,4-tetrahydronaphthalene-1-carboxylic acid (1.13 g) and [(5-ethylthiophen-2-yl)methyl](4-isopropylphenyl)amine (1.04 g) as starting materials, 5-benzyloxy-N-[(5-ethylthiophen-2-yl)methyl]-N-(4-isopropylphenyl)-1,2,3,4-tetrahydronaphthalene-1-carboxamide (1.01 g) was obtained.

$^1$H-NMR (CDCl$_3$) δ: 1.24 (6H, d, J=6.9 Hz), 1.29 (3H, t, J=7.5 Hz), 1.35-1.55 (1H, m), 1.80-2.10 (3H, m), 2.81 (2H, q, J=7.5 Hz), 2.60-3.00 (3H, m), 3.70-3.80 (1H, m), 4.90 (1H, d, J=14.4 Hz), 5.03 (1H, d, J=14.4 Hz), 5.03 (2H, s), 6.50-6.75 (4H, m), 7.00-7.12 (3H, m), 7.15-7.50 (7H, m).

Example 122

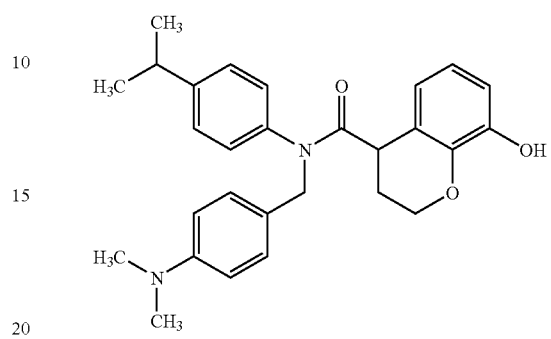

By the reaction and treatment in the same manner as in Example 12 using 8-benzyloxychroman-4-carboxylic acid (0.54 g) and [(4-dimethylaminophenyl)methyl](4-isopropylphenyl)amine (0.51 g) as starting materials, 8-benzyloxy-N-[(4-dimethylaminophenyl)methyl]-N-(4-isopropylphenyl)chroman-4-carboxamide (1 g) was obtained.

MS (ESI) m/z: 535 [MH]$^+$

By the reaction and treatment in the same manner as in Example 17 using this compound, N-[(4-dimethylaminophenyl)methyl]-8-hydroxy-N-(4-isopropylphenyl)chroman-4-carboxamide (0.7 g) was obtained.

$^1$H-NMR (CDCl$_3$) δ: 1.24 (6H, d, J=6.9 Hz), 1.90-2.30 (2H, m), 2.85-3.10 (1H, m), 2.94 (6H, s), 3.70-3.85 (1H, m), 4.00-4.20 (1H, m), 5.00-5.15 (1H, m), 4.70 (1H, d, J=13.8 Hz), 4.90 (1H, d, J=13.8 Hz), 5.47 (1H, s), 6.45-6.85 (5H, m), 6.90-7.30 (6H, m).

Example 123

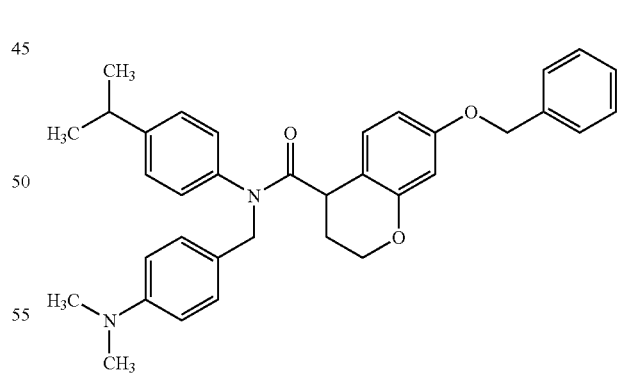

By the reaction and treatment in the same manner as in Example 12 using 7-benzyloxychroman-4-carboxylic acid (0.6 g) and [(4-dimethylaminophenyl)methyl](4-isopropylphenyl)amine (0.57 g) as starting materials, 7-benzyloxy-N-[(4-dimethylaminophenyl)methyl]-N-(4-isopropylphenyl)chroman-4-carboxamide (1.2 g) was obtained.

$^1$H-NMR (CDCl$_3$) δ: 1.24 (6H, d, J=6.9 Hz), 1.80-2.00 (1H, m), 2.05-2.25 (1H, m), 2.85-3.05 (1H, m), 2.94 (6H, s), 3.65-3.75 (1H, m), 3.90-4.05 (1H, m), 4.40-4.55 (1H, m), 4.69 (1H, d, J=13.9 Hz), 4.91 (1H, d, J=13.9 Hz), 4.99 (2H, s), 6.40-7.45 (16H, m).

Example 124

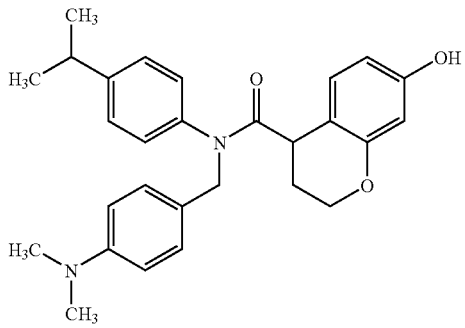

By the reaction and treatment in the same manner as in Example 17 using 7-benzyloxy-N-[(4-dimethylaminophenyl)methyl]-N-(4-isopropylphenyl)chroman-4-carboxamide (1.0 g) as a starting material, N-[(4-dimethylaminophenyl)methyl]-7-hydroxy-N-(4-isopropylphenyl)chroman-4-carboxamide (0.54 g) was obtained. melting point: 173.1° C.

$^1$H-NMR (CDCl$_3$) δ: 1.24 (6H, d, J=6.9 Hz), 1.80-2.00 (1H, m), 2.10-2.25 (1H, m), 2.94 (6H, s), 2.80-3.05 (1H, m), 3.65-3.75 (1H, m), 3.85-4.00 (1H, m), 4.35-4.50 (1H, m), 4.77 (1H, d, J=13.9 Hz), 4.86 (1H, d, J=13.9 Hz), 5.87 (1H, s), 6.18 (1H, d, J=2.5 Hz), 6.26 (1H, dd, J=2.5 Hz, 8.3 Hz), 6.60-7.30 (9H, m).

Example 125

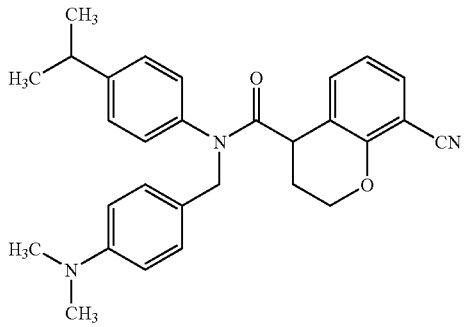

By the reaction and treatment in the same manner as in Example 12 using 8-cyanochroman-4-carboxylic acid (0.7 g) and [(4-dimethylaminophenyl)methyl](4-isopropylphenyl)amine (0.92 g) as starting materials, 8-cyano-N-[(4-dimethylaminophenyl)methyl]-N-(4-isopropylphenyl)chroman-4-carboxamide (1.0 g) was obtained. melting point: 178.8° C.

$^1$H-NMR (CDCl$_3$) δ: 1.25 (6H, d, J=6.9 Hz), 1.80-2.30 (2H, m), 2.80-3.10 (1H, m) 2.94 (6H, s), 3.65-3.80 (1H, m), 4.10-4.25 (1H, m), 4.55-4.70 (1H, m), 4.72 (1H, d, J=13.8 Hz), 4.85 (1H, d, J=13.8 Hz), 6.60-7.50 (11H, m).

Example 126

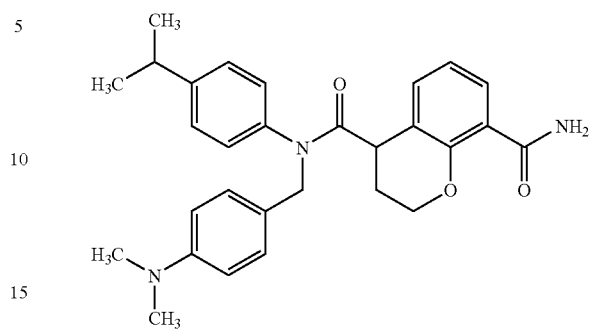

8-Cyano-N-[(4-dimethylaminophenyl)methyl]-N-(4-isopropylphenyl)chroman-4-carboxamide (0.9 g) was dissolved in acetone (12.8 mL), and 1 mol/L-aqueous sodium hydroxide solution (6.4 mL) and 30% aqueous hydrogen peroxide (3.8 mL) were added. The mixture was heated under reflux for 2 hr. The reaction mixture was partitioned between water and ethyl acetate. The organic layer was washed with saturated brine and dried over magnesium sulfate. The solvent was evaporated, and the residue was purified by silica gel column chromatography to give 8-carbamoyl-N-[(4-dimethylaminophenyl)methyl]-N-(4-isopropylphenyl)chroman-4-carboxamide (21 mg).

MS (ESI) m/z: 472 [MH]$^+$ $^1$H-NMR (CDCl$_3$) δ: 1.25 (6H, d, J=6.9 Hz), 1.90-2.25 (2H, m), 2.80-3.10 (1H, m), 2.94 (6H, s), 3.75-3.90 (1H, m), 4.10-4.30 (1H, m), 4.60-4.80 (1H, m), 4.72 (1H, d, J=13.9 Hz), 4.88 (1H, d, J=13.9 Hz), 5.87 (1H, brs), 6.55-6.70 (2H, m), 6.85-7.30 (8H, m), 7.73 (1H, brs), 8.04 (1H, dd, J=1.6, 7.7 Hz).

Example 127

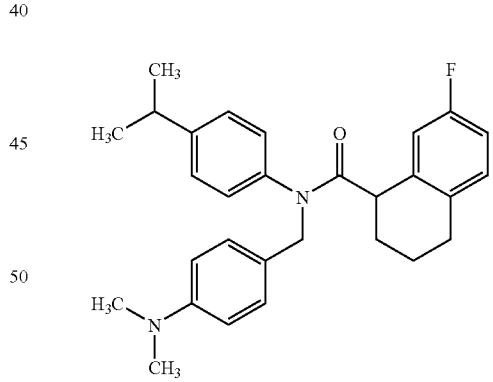

By the reaction and treatment in the same manner as in Example 12 using 7-fluoro-1,2,3,4-tetrahydronaphthalene-1-carboxylic acid (0.41 g) and [(4-dimethylaminophenyl)methyl](4-isopropylphenyl)amine (0.57 g) as starting materials, N-[(4-dimethylaminophenyl)methyl]-7-fluoro-N-(4-isopropylphenyl)-1,2,3,4-tetrahydronaphthalene-1-carboxamide (0.85 g) was obtained. This compound was dissolved in ethyl acetate, and 4 mol/L-HCl/dioxane was added. The precipitated solid was collected by filtration to give N-[(4-dimethylaminophenyl)methyl]-7-fluoro-N-(4-isopropylphenyl)-1,2,3,4-tetrahydronaphthalene-1-carboxamide hydrochloride (0.85 g). melting point: 165.6° C.

¹H-NMR (DMSO-d₆) δ: 1.19 (6H, d, J=6.9 Hz), 1.30-1.50 (1H, m), 1.70-2.00 (3H, m), 2.40-2.75 (2H, m), 2.75-3.05 (1H, m), 2.99 (6H, s), 3.40-3.90 (1H, m), 4.75 (1H, d, J=14.7 Hz), 4.92 (1H, d, J=14.7 Hz), 6.70-6.85 (1H, m), 6.90-7.35 (10H, m).

Example 128

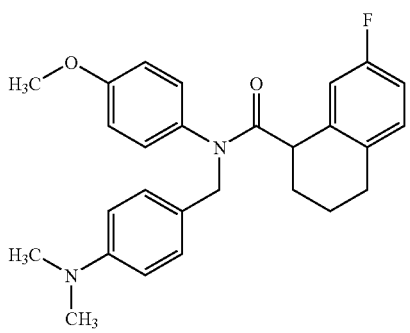

By the reaction and treatment in the same manner as in Example 12 using 7-fluoro-1,2,3,4-tetrahydronaphthalene-1-carboxylic acid (0.41 g) and [(4-dimethylaminophenyl)methyl](4-methoxyphenyl)amine (0.54 g) as starting materials, N-[(4-dimethylaminophenyl)methyl]-7-fluoro-N-(4-methoxyphenyl)-1,2,3,4-tetrahydronaphthalene-1-carboxamide was obtained. This compound was dissolved in ethyl acetate, and 4 mol/L-HCl/dioxane was added. The precipitated solid was collected by filtration to give N-[(4-dimethylaminophenyl)methyl]-7-fluoro-N-(4-methoxyphenyl)-1,2,3,4-tetrahydronaphthalene-1-carboxamide hydrochloride ½ hydrate (0.52 g). melting point: 125.4° C.

Example 129

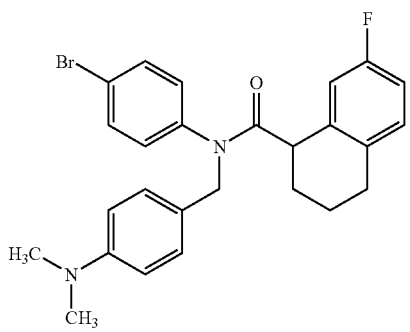

By the reaction and treatment in the same manner as in Example 12 using 7-fluoro-1,2,3,4-tetrahydronaphthalene-1-carboxylic acid (0.41 g) and (4-bromophenyl)[(4-dimethylaminophenyl)methyl]amine (0.64 g) as starting materials, N-(4-bromophenyl)-N-[(4-dimethylaminophenyl)methyl]-7-fluoro-1,2,3,4-tetrahydronaphthalene-1-carboxamide (0.26 g) was obtained.

¹H-NMR (CDCl₃) δ: 1.40-1.70 (1H, m), 1.75-2.10 (3H, m), 2.55-2.90 (2H, m), 2.95 (6H, s), 3.55-3.70 (1H, m), 4.71 (1H, d, J=14.1 Hz), 4.92 (1H, d, J=14.1 Hz), 6.60-7.20 (9H, m), 7.40-7.60 (2H, m).

Example 130

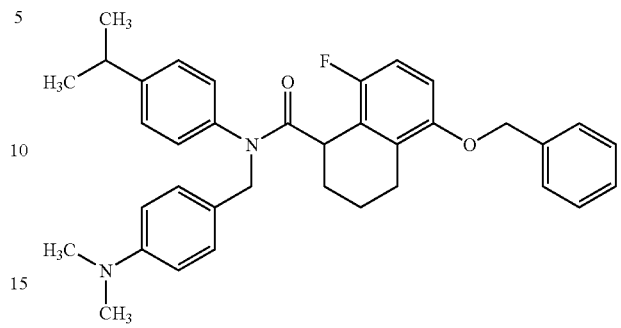

By the reaction and treatment in the same manner as in Example 12 using 5-benzyloxy-8-fluoro-1,2,3,4-tetrahydronaphthalene-1-carboxylic acid (0.5 g) and [(4-dimethylaminophenyl)methyl](4-isopropylphenyl)amine (0.45 g) as starting materials, 5-benzyloxy-N-[(4-dimethylaminophenyl)methyl]-8-fluoro-N-(4-isopropylphenyl)-1,2,3,4-tetrahydronaphthalene-1-carboxamide (0.73 g) was obtained.

¹H-NMR (CDCl₃) δ: 1.23 (6H, d, J=6.9 Hz), 1.40-2.10 (4H, m), 2.55-2.95 (3H, m), 2.94 (6H, s), 3.70-3.85 (1H, m), 4.71 (1H, d, J=14.6 Hz), 4.86 (1H, d, J=14.6 Hz), 5.01 (2H, s), 6.60-6.85 (4H, m), 7.00-7.45 (11H, m).

Example 131

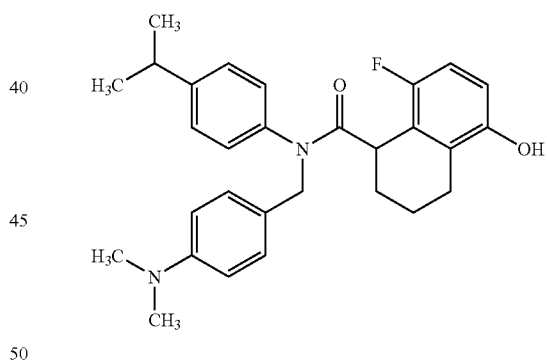

By the reaction and treatment in the same manner as in Example 17 using 5-benzyloxy-N-[(4-dimethylaminophenyl)methyl]-8-fluoro-N-(4-isopropylphenyl)-1,2,3,4-tetrahydronaphthalene-1-carboxamide (0.73 g) as a starting material, N-[(4-dimethylaminophenyl)methyl]-8-fluoro-5-hydroxy-N-(4-isopropylphenyl)-1,2,3,4-tetrahydronaphthalene-1-carboxamide (0.19 g) was obtained.

melting point: 209.0° C.

¹H-NMR (CDCl₃) δ: 1.23 (6H, d, J=6.9 Hz), 1.40-1.60 (1H, m), 1.65-2.05 (3H, m), 2.40-2.55 (1H, m), 2.60-2.80 (1H, m), 2.85-3.00 (1H, m), 2.94 (6H, s), 3.70-3.80 (1H, m), 4.67 (1H, d, J=14.1 Hz), 4.98 (1H, d, J=14.1 Hz), 6.20-6.30 (1H, m), 6.40-6.55 (1H, m), 6.60-6.70 (2H, m), 6.90-7.20 (6H, m), 7.61 (1H, s).

Example 132

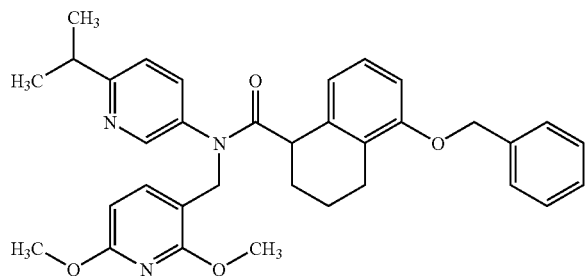

5-Benzyloxy-N-(6-isopropylpyridin-3-yl)-1,2,3,4-tetrahydronaphthalene-1-carboxamide (2.03 g) was dissolved in dimethylformamide (27 mL), and sodium hydride (0.20 g) was added under ice-cooling. The mixture was stirred at the same temperature for 30 min. A solution of 3-chloromethyl-2,6-dimethoxypyridine (0.95 g) in dimethylformamide (6 mL) was added dropwise to the reaction mixture, and the mixture was stirred at room temperature for 3 hr. The reaction mixture was partitioned between water and ethyl acetate. The organic layer was washed with saturated brine and dried over anhydrous magnesium sulfate. The solvent was evaporated, and the residue was purified by silica gel column chromatography to give 5-benzyloxy-N-[(2,6-dimethoxypyridin-3-yl)methyl]-N-(6-isopropylpyridin-3-yl)-1,2,3,4-tetrahydronaphthalene-1-carboxamide (1.43 g).

$^1$H-NMR (CDCl$_3$) δ: 1.29 (6H, d, J=6.9 Hz), 1.40-1.65 (1H, m), 1.75-2.15 (3H, m), 2.60-2.80 (2H, m), 2.95-3.15 (1H, m), 3.55-3.75 (1H, m), 3.69 (3H, s), 3.89 (3H, s), 4.78 (1H, d, J=14.1 Hz), 4.97 (1H, d, J=14.1 Hz), 5.03 (2H, s), 6.25 (1H, d, J=8.0 Hz), 6.63 (1H, d, J=7.7 Hz), 6.72 (1H, d, J=8.0 Hz), 7.06 (1H, t, J=7.9 Hz), 7.14 (1H, d, J=8.3 Hz), 7.25-7.45 (6H, m), 7.55 (1H, d, J=8.0 Hz), 8.30 (1H, d, J=2.3 Hz).

Example 133

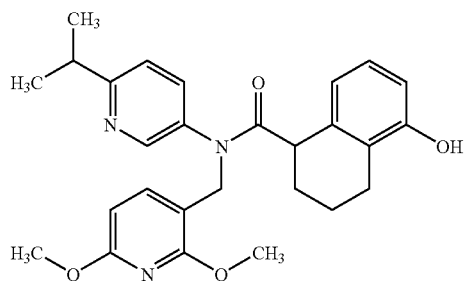

To a solution of 5-benzyloxy-N-[(2,6-dimethoxypyridin-3-yl)methyl]-N-(6-isopropylpyridin-3-yl)-1,2,3,4-tetrahydronaphthalene-1-carboxamide (0.83 g) in trifluoroacetic acid (2.4 mL) was added thioanisole (0.49 mL), and the mixture was stirred at room temperature for one day. The reaction mixture was poured into saturated aqueous sodium hydrogencarbonate and partitioned with ethyl acetate. The organic layer was washed with saturated brine and dried over anhydrous magnesium sulfate. The solvent was evaporated, and the residue was purified by silica gel column chromatography to give N-[(2,6-dimethoxypyridin-3-yl)methyl]-5-hydroxy-N-(6-isopropylpyridin-3-yl)-1,2,3,4-tetrahydronaphthalene-1-carboxamide (0.36 g).

melting point: 164.0° C.

$^1$H-NMR (CDCl$_3$) δ: 1.29 (6H, d, J=6.9 Hz), 1.35-1.60 (1H, m), 1.75-2.10 (3H, m), 2.45-2.70 (2H, m), 2.95-3.15 (1H, m), 3.60-3.75 (1H, m), 3.70 (3H, s), 3.89 (3H, s), 4.82 (1H, d, J=14.1 Hz), 4.95 (1H, d, J=14.1 Hz), 6.08 (1H, s), 6.26 (1H, d, J=8.1 Hz), 6.44 (1H, d, J=7.8 Hz), 6.51 (1H, d, J=7.8 Hz), 6.87 (1H, t, J=7.8 Hz), 7.16 (1H, d, J=8.1 Hz), 7.34 (1H, dd, J=2.4 Hz, 8.1 Hz), 7.54 (1H, d, J=8.1 Hz), 8.31 (1H, d, J=2.4 Hz).

Example 134

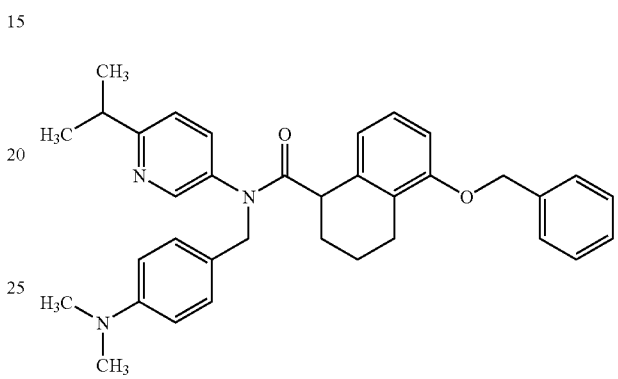

By the reaction and treatment in the same manner as in Example 12 using 5-benzyloxy-1,2,3,4-tetrahydronaphthalene-1-carboxylic acid (0.5 g) and [(4-dimethylaminophenyl)methyl](6-isopropylpyridin-3-yl)amine (0.48 g) as starting materials, 5-benzyloxy-N-[(4-dimethylaminophenyl)methyl]-N-(6-isopropylpyridin-3-yl)-1,2,3,4-tetrahydronaphthalene-1-carboxamide (0.39 g) was obtained.

$^1$H-NMR (CDCl$_3$) δ: 1.29 (6H, d, J=6.9 Hz), 1.40-2.10 (4H, m), 2.60-3.10 (3H, m), 2.94 (6H, s), 3.55-3.70 (1H, m), 4.72 (1H, d, J=14.6 Hz), 4.96 (1H, d, J=14.6 Hz), 5.04 (2H, s), 6.50-7.50 (14H, m), 8.30 (1H, d, J=2.4 Hz).

Example 135

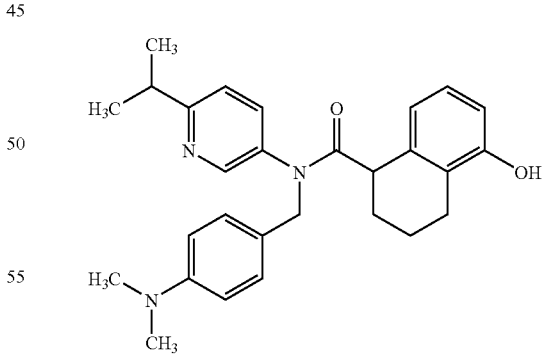

By the reaction and treatment in the same manner as in Example 17 using 5-benzyloxy-N-[(4-dimethylaminophenyl)methyl]-N-(6-isopropylpyridin-3-yl)-1,2,3,4-tetrahydronaphthalene-1-carboxamide (0.39 g) as a starting material, N-[(4-dimethylaminophenyl)methyl]-5-hydroxy-N-(6-isopropylpyridin-3-yl)-1,2,3,4-tetrahydronaphthalene-1-carboxamide (60 mg) was obtained.

MS (ESI) m/z: 444 [MH]$^+$

¹H-NMR (CDCl₃) δ: 1.29 (6H, d, J=6.9 Hz), 1.40-1.70 (1H, m), 1.75-2.15 (3H, m), 2.50-2.70 (2H, m), 2.95 (6H, s), 3.00-3.10 (1H, m), 3.55-3.70 (1H, m), 4.79 (1H, d, J=14.1 Hz), 4.89 (1H, d, J=14.1 Hz), 5.72 (1H, s), 6.40-7.30 (9H, m), 8.30 (1H, d, J=2.1 Hz).

Example 136

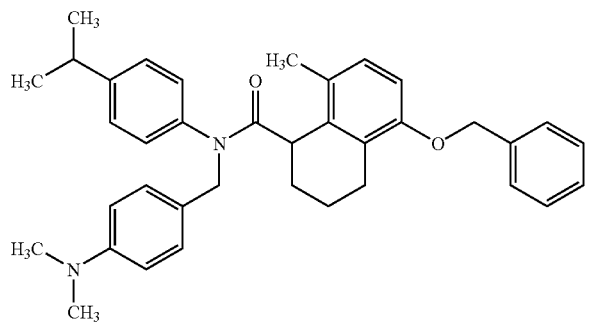

By the reaction and treatment in the same manner as in Example 12 using 5-benzyloxy-8-methyl-1,2,3,4-tetrahydronaphthalene-1-carboxylic acid (0.5 g) and [(4-dimethylaminophenyl)methyl](4-isopropylphenyl)amine (0.45 g) as starting materials, 5-benzyloxy-N-[(4-dimethylaminophenyl)methyl]-N-(4-isopropylphenyl)-8-methyl-1,2,3,4-tetrahydronaphthalene-1-carboxamide (0.6 g) was obtained.

¹H-NMR (CDCl₃) δ: 1.25 (6H, d, J=6.9 Hz), 1.50-1.75 (2H, m), 1.90-2.05 (2H, m), 2.11 (3H, s), 2.45-2.60 (1H, m), 2.85-3.05 (2H, m), 2.93 (6H, s), 3.60-3.65 (1H, m), 4.64 (1H, d, J=13.9 Hz), 4.87 (1H, d, J=13.9 Hz), 5.02 (2H, s), 6.55-6.70 (3H, m), 6.85-7.45 (12H, m).

Example 137

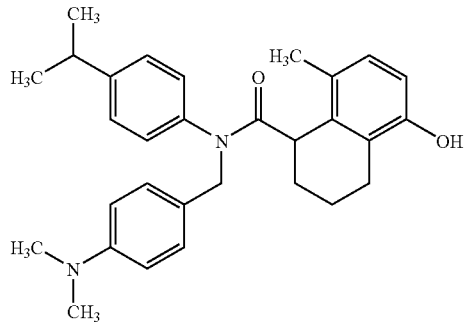

By the reaction and treatment in the same manner as in Example 133 using 5-benzyloxy-N-[(4-dimethylaminophenyl)methyl]-N-(4-isopropylphenyl)-8-methyl-1,2,3,4-tetrahydronaphthalene-1-carboxamide (0.5 g) as a starting material, N-[(4-dimethylaminophenyl)methyl]-5-hydroxy-N-(4-isopropylphenyl)-8-methyl-1,2,3,4-tetrahydronaphthalene-1-carboxamide (0.34 g) was obtained. melting point: 189.5° C.

¹H-NMR (CDCl₃) δ: 1.25 (6H, d, J=6.9 Hz), 1.50-1.75 (2H, m), 1.90-2.10 (2H, m), 2.09 (3H, s), 2.30-2.50 (1H, m), 2.70-3.00 (2H, m), 2.93 (6H, s), 3.60-3.70 (1H, m), 4.72 (1H, d, J=13.8 Hz), 4.83 (1H, d, J=13.8 Hz), 5.72 (1H, s), 6.35-6.75 (4H, m), 7.00-7.30 (6H, m).

Example 138

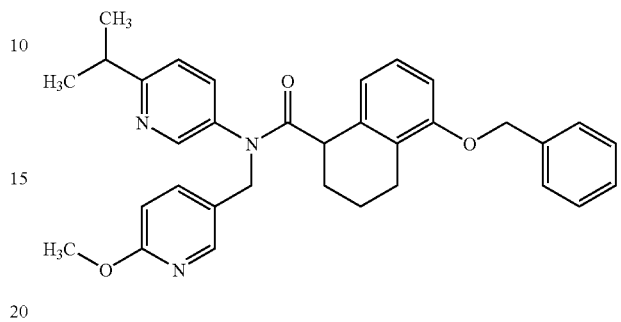

By the reaction and treatment in the same manner as in Example 132 using 5-chloromethyl-2-methoxypyridine (0.63 g) and 5-benzyloxy-N-(6-isopropylpyridin-3-yl)-1,2,3,4-tetrahydronaphthalene-1-carboxamide (0.87 g) as starting materials, 5-benzyloxy-N-(6-isopropylpyridin-3-yl)-N-[(6-methoxypyridin-3-yl)methyl]-1,2,3,4-tetrahydronaphthalene-1-carboxamide (1.23 g) was obtained.

¹H-NMR (CDCl₃) δ: 1.29 (6H, d, J=7.0 Hz), 1.40-1.60 (1H, m), 1.80-2.15 (3H, m), 2.65-2.80 (2H, m), 3.00-3.20 (1H, m), 3.60-3.75 (1H, m), 3.92 (3H, s), 4.81 (1H, d, J=14.3 Hz), 4.90 (1H, d, J=14.3 Hz), 5.04 (2H, s), 6.50-6.80 (3H, m), 7.00-7.50 (7H, m), 7.60-7.70 (1H, m), 7.87 (1H, d, J=2.2 Hz), 8.02 (1H, s), 8.32 (1H, d, J=2.3 Hz).

Example 139

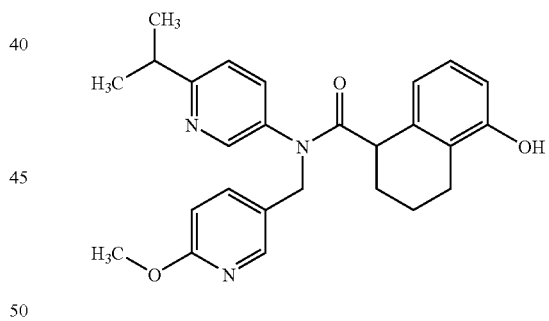

To a solution of 5-benzyloxy-N-(6-isopropylpyridin-3-yl)-N-[(6-methoxypyridin-3-yl)methyl]-1,2,3,4-tetrahydronaphthalene-1-carboxamide (1.23 g) in trifluoroacetic acid (7 mL) was added thioanisole (1.40 mL), and the mixture was stirred at room temperature for one day. The reaction mixture was partitioned between saturated aqueous sodium hydrogencarbonate and ethyl acetate. The organic layer was washed with saturated brine and dried over anhydrous magnesium sulfate. The solvent was evaporated, and the residue was dissolved in ethyl acetate. Thereto was added 4 mol/L-HCl/dioxane (0.63 mL), and the precipitated solid was collected by filtration to give 5-hydroxy-N-(6-isopropylpyridin-3-yl)-N-[(6-methoxypyridin-3-yl)methyl]-1,2,3,4-tetrahydronaphthalene-1-carboxamide dihydrochloride (0.43 g).

MS (ESI) m/z: 432 [MH]⁺

¹H-NMR (DMSO-d₆) δ: 1.31 (6H, d, J=6.9 Hz), 1.35-1.60 (1H, m), 1.70-2.00 (3H, m), 2.30-2.60 (2H, m), 3.20-3.45

(1H, m), 3.45-3.70 (1H, m), 3.83 (3H, s), 4.60-5.10 (2H, m), 6.45-6.70 (2H, m), 6.80-7.00 (2H, m), 7.30-8.25 (4H, m), 8.80 (1H, s).

Example 140

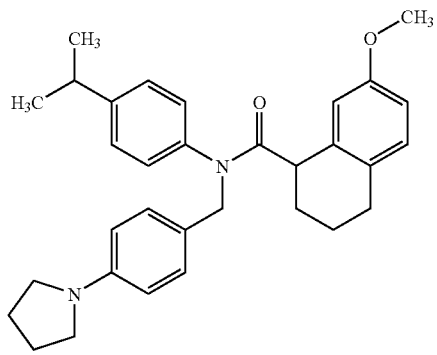

By the reaction and treatment in the same manner as in Example 12 using 7-methoxy-1,2,3,4-tetrahydronaphthalene-1-carboxylic acid (0.39 g) and (4-isopropylphenyl) [(4-pyrrolidinophenyl)methyl]amine (0.56 g) as starting materials, N-(4-isopropylphenyl)-7-methoxy-N-[(4-pyrrolidinophenyl)methyl]-1,2,3,4-tetrahydronaphthalene-1-carboxamide (0.3 g) was obtained.

$^1$H-NMR (CDCl$_3$) δ: 1.25 (6H, d, J=6.3 Hz), 1.35-1.60 (1H, m), 1.80-2.10 (7H, m), 2.50-2.65 (1H, m), 2.70-2.95 (2H, m), 3.20-3.35 (4H, m), 3.69 (3H, s), 3.60-3.80 (1H, m), 4.56 (1H, d, J=13.8 Hz), 5.07 (1H, d, J=13.8 Hz), 6.40-7.20 (11H, m).

Example 141

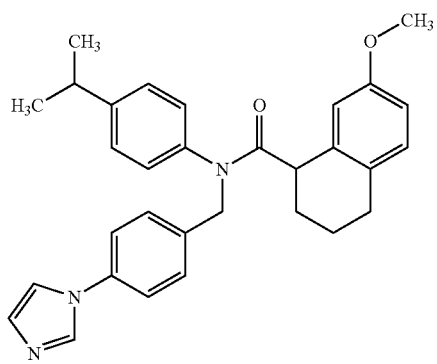

By the reaction and treatment in the same manner as in Example 12 using 7-methoxy-1,2,3,4-tetrahydronaphthalene-1-carboxylic acid (0.39 g) and {[4-(imidazol-1-yl)phenyl]methyl}(4-isopropylphenyl)amine (0.55 g) as starting materials, N-{[4-(imidazol-1-yl)phenyl]methyl}-N-(4-isopropylphenyl)-7-methoxy-1,2,3,4-tetrahydronaphthalene-1-carboxamide ½ hydrate (0.28 g) was obtained.

melting point: 110.7° C.

$^1$H-NMR (CDCl$_3$) δ: 1.24 (6H, d, J=6.9 Hz), 1.40-1.60 (1H, m), 1.80-2.10 (3H, m), 2.50-2.68 (1H, m), 2.70-3.00 (2H, m), 3.72 (3H, s), 3.65-3.80 (1H, m), 4.84 (1H, d, J=14.2 Hz), 5.06 (1H, d, J=14.2 Hz), 6.52 (1H, d, J=2.5 Hz), 6.60-6.70 (1H, m), 6.90-7.10 (3H, m), 7.15-7.50 (8H, m), 7.86 (1H, s).

Example 142

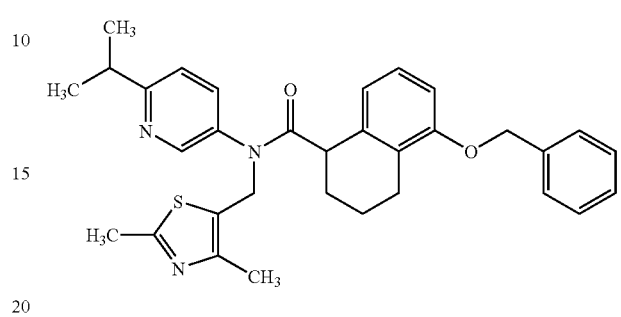

2,4-Dimethyl-5-(hydroxymethyl)thiazole (0.65 g) was dissolved in methylene chloride (15 mL), and methanesulfonyl chloride (0.37 mL) was added under ice-cooling. The mixture was stirred at room temperature for one day. The reaction mixture was concentrated, and the residue was partitioned between water and chloroform. The organic layer was washed with saturated brine and dried over anhydrous sodium sulfate. The solvent was evaporated. By the reaction and treatment of the obtained residue and 5-benzyloxy-N-(6-isopropylpyridin-3-yl)-1,2,3,4-tetrahydronaphthalene-1-carboxamide (1.8 g) in the same manner as in Example 132, 5-benzyloxy-N-[(2,4-dimethylthiazol-5-yl)methyl]-N-(6-isopropylpyridin-3-yl)-1,2,3,4-tetrahydronaphthalene-1-carboxamide (1.64 g) was obtained.

$^1$H-NMR (CDCl$_3$) δ: 1.30 (6H, d, J=6.9 Hz), 1.40-1.70 (1H, m), 1.80-2.10 (3H, m), 2.00 (3H, s), 2.60-2.80, (2H, m), 2.64 (3H, s), 3.00-3.20 (1H, m), 3.60-3.75 (1H, m), 4.93 (1H, d, J=15.0 Hz), 5.01 (1H, d, J=15.0 Hz), 5.04 (2H, s), 6.61 (1H, d, J=7.5 Hz), 6.73 (1H, d, J=8.1 Hz), 7.00-7.50 (8H, m), 8.37 (1H, d, J=2.4 Hz).

Example 143

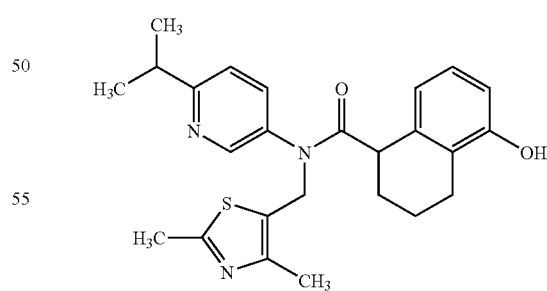

By the reaction and treatment in the same manner as in Example 139 using 5-benzyloxy-N-[(2,4-dimethylthiazol-5-yl)methyl]-N-(6-isopropylpyridin-3-yl)-1,2,3,4-tetrahydronaphthalene-1-carboxamide (1.64 g) as a starting material, N-[(2,4-dimethylthiazol-5-yl)methyl]-5-hydroxy-N-(6-isopropylpyridin-3-yl)-1,2,3,4-tetrahydronaphthalene-1-carboxamide dihydrochloride 5/2 hydrate (0.72 g) was obtained.

MS (ESI) m/z: 436 [MH]+

¹H-NMR (DMSO-d₆) δ: 1.27 (6H, d, J=6.9 Hz), 1.10-1.50 (1H, m), 1.65-2.05 (3H, m), 1.94 (3H, s), 2.35-2.55 (2H, m), 2.65 (3H, s), 3.10-3.30 (1H, m), 3.45-3.60 (1H, m), 4.92 (1H, d, J=15.4 Hz), 5.02 (1H, d, J=15.4 Hz), 6.46 (1H, d, J=7.6 Hz), 6.63 (1H, d, J=7.9 Hz), 6.90 (1H, t, J=7.8 Hz), 7.59 (1H, d, J=8.2 Hz), 7.89 (1H, d, J=8.3 Hz), 8.56 (1H, s).

Example 144

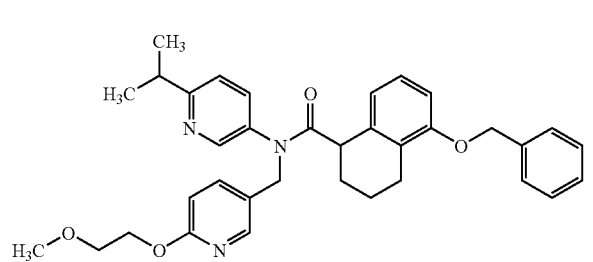

By the reaction and treatment in the same manner as in Example 142 using 5-benzyloxy-N-(6-isopropylpyridin-3-yl)-1,2,3,4-tetrahydronaphthalene-1-carboxamide (1.2 g) and 3-hydroxymethyl-6-(2-methoxyethoxy)pyridine (0.55 g) as starting materials, 5-benzyloxy-N-(6-isopropylpyridin-3-yl)-N-{[6-(2-methoxyethoxy)pyridin-3-yl]methyl}-1,2,3,4-tetrahydronaphthalene-1-carboxamide (1.07 g) was obtained.

¹H-NMR (CDCl₃) δ: 1.29 (6H, d, J=6.9 Hz), 1.40-1.60 (1H, m), 1.80-2.10 (3H, m), 2.65-2.80 (2H, m), 2.95-3.15 (1H, m), 3.45 (3H, s), 3.60-3.70 (1H, m), 3.70-3.80 (2H, m), 4.40-4.50 (2H, m), 4.80 (1H, d, J=15 Hz), 4.90 (1H, d, J=15 Hz), 5.03 (2H, s), 6.57 (1H, d, J=7.8 Hz), 6.73 (1H, d, J=7.8 Hz), 6.78 (1H, d, J=8.4 Hz), 7.06 (1H, t, J=7.8 Hz), 7.17 (1H, d, J=8.4 Hz), 7.20-7.45 (6H, m), 7.60 (1H, dd, J=2.4 Hz, 8.7 Hz), 7.85 (1H, d, J=2.1 Hz), 8.33 (1H, d, J=2.4 Hz).

Example 145

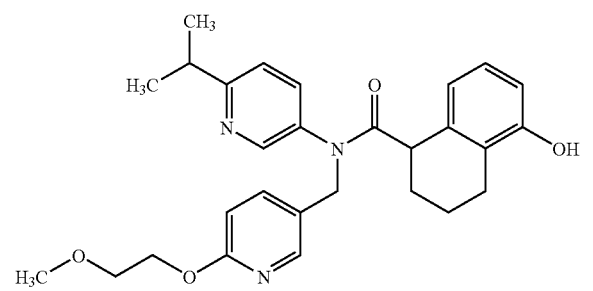

By the reaction and treatment in the same manner as in Example 133 using 5-benzyloxy-N-(6-isopropylpyridin-3-yl)-N-{[6-(2-methoxyethoxy)pyridin-3-yl]methyl}-1,2,3,4-tetrahydronaphthalene-1-carboxamide (1.07 g) as a starting material, 5-hydroxy-N-(6-isopropylpyridin-3-yl)-N-{[6-(2-methoxyethoxy)pyridin-3-yl]methyl}-1,2,3,4-tetrahydronaphthalene-1-carboxamide (0.72 g) was obtained.

¹H-NMR (CDCl₃) δ: 1.16 (6H, d, J=6.9 Hz), 1.40-1.55 (1H, m), 1.75-2.10 (4H, m), 2.50-2.65 (2H, m), 3.00-3.20 (1H, m), 3.45 (3H, s), 3.60-3.70 (1H, m), 3.70-3.80 (2H, m), 4.40-4.50 (2H, m), 4.83 (1H, d, J=14.4 Hz), 4.90 (1H, d, J=14.4 Hz), 6.30-6.45 (2H, m), 6.70-6.90 (2H, m), 7.10-7.35 (2H, m), 7.61 (1H, dd, J=2.4 Hz, 8.5 Hz), 7.86 (1H, d, J=2.2 Hz), 8.34 (1H, d, J=2.3 Hz).

Example 146

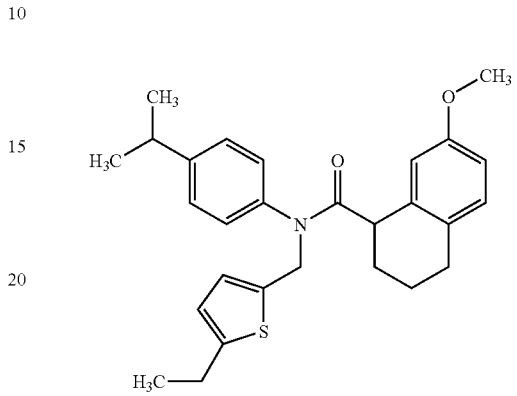

By the reaction and treatment in the same manner as in Example 12 using 7-methoxy-1,2,3,4-tetrahydronaphthalene-1-carboxylic acid (0.82 g) and [(5-ethylthiophen-2-yl)methyl](4-isopropylphenyl)amine (1.04 g) as starting materials, N-[(5-ethylthiophen-2-yl)methyl]-N-(4-isopropylphenyl)-7-methoxy-1,2,3,4-tetrahydronaphthalene-1-carboxamide (0.26 g) was obtained. MS (ESI)m/z: 448 [MH]+

¹H-NMR (CDCl₃) δ: 1.24 (6H, d, J=7.0 Hz), 1.29 (3H, t, J=7.6 Hz), 1.35-1.55 (1H, m), 1.80-2.10 (3H, m), 2.50-2.65 (1H, m), 2.70-3.00 (2H, m), 2.80 (2H, q, J=7.6 Hz), 3.70 (3H, s), 3.60-3.80 (1H, m), 4.73 (1H, d, J=14.6 Hz), 5.19 (1H, d, J=14.6 Hz), 6.50-6.70 (4H, m), 6.90-7.30 (5H, m).

Example 147

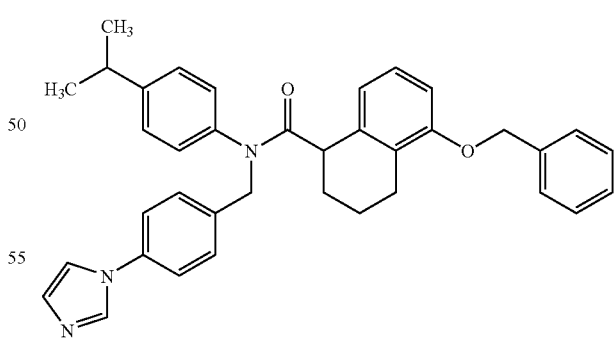

By the reaction and treatment in the same manner as in Example 12 using 5-benzyloxy-1,2,3,4-tetrahydronaphthalene-1-carboxylic acid (0.54 g) and {[4-(imidazol-1-yl)phenyl]methyl}(4-isopropylphenyl)amine (0.55 g) as starting materials, 5-benzyloxy-N-{[4-(imidazol-1-yl)phenyl]methyl-}-N-(4-isopropylphenyl)-1,2,3,4-tetrahydronaphthalene-1-carboxamide (0.62 g) was obtained.

¹H-NMR (CDCl₃) δ: 1.24 (6H, d, J=7.2 Hz), 1.40-1.60 (1H, m), 1.80-2.15 (3H, m), 2.70-2.80 (2H, m), 2.80-3.00 (1H, m), 3.70-3.85 (1H, m), 4.93 (1H, d, J=14.1 Hz), 5.01 (1H, d, J=14.1 Hz), 5.04 (2H, s), 6.65 (1H, d, J=7.8 Hz), 6.73 (1H, d, J=7.8 Hz), 6.95-7.50 (16H, m), 7.87 (1H, s).

Example 148

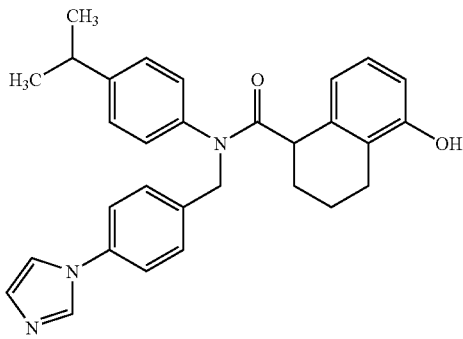

By the reaction and treatment in the same manner as in Example 133 using 5-benzyloxy-N-{[4-(imidazol-1-yl)phenyl]methyl}-N-(4-isopropylphenyl)-1,2,3,4-tetrahydronaphthalene-1-carboxamide (0.62 g) as a starting material, 5-hydroxy-N-{[4-(imidazol-1-yl)phenyl]methyl}-N-(4-isopropylphenyl)-1,2,3,4-tetrahydronaphthalene-1-carboxamide (0.36 g) was obtained.

¹H-NMR (CDCl₃) δ: 1.24 (6H, d, J=6.9 Hz), 1.40-1.60 (1H, m), 1.80-2.15 (3H, m), 2.50-2.75 (2H, m), 2.85-3.00 (1H, m), 3.70-3.85 (1H, m), 4.97 (2H, s), 6.45-6.60 (2H, m), 6.80-7.10 (4H, m), 7.15-7.45 (7H, m), 7.89 (1H, s).

Example 149

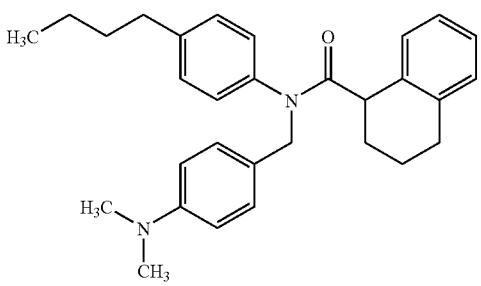

By the reaction and treatment in the same manner as in Example 12 using 1,2,3,4-tetrahydronaphthalene-1-carboxylic acid (0.70 g) and (4-butylphenyl)[(4-dimethylaminophenyl)methyl]amine (0.54 g) as starting materials, N-(4-butylphenyl)-N-[(4-dimethylaminophenyl)methyl]-1,2,3,4-tetrahydronaphthalene-1-carboxamide (0.81 g) was obtained.

¹H-NMR (CDCl₃) δ: (0.92 (3H, t, J=7.4 Hz), 1.26-1.37 (2H, m), 1.50-1.52 (1H, m), 1.55-1.64 (2H, m), 1.89-1.91 (1H, m), 1.95-2.04 (2H, m), 2.58 (2H, t, J=7.4 Hz), 2.65-2.67 (1H, m), 2.82-2.85 (1H, m), 2.94 (6H, s), 3.70-3.75 (1H, m), 4.72 (1H, d, J=13.9 Hz), 4.93 (1H, d, J=13.9 Hz), 6.63 (2H, m), 6.94-7.13 (10H, m).

Example 150

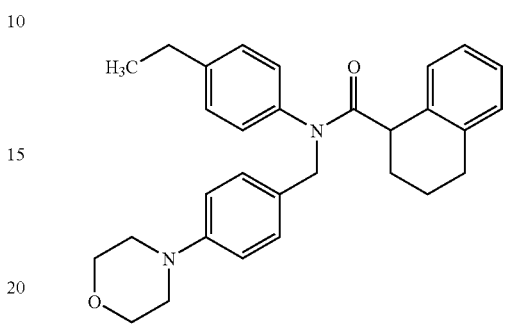

By the reaction and treatment in the same manner as in Example 12 using 1,2,3,4-tetrahydronaphthalene-1-carboxylic acid (0.34 g) and (4-ethylphenyl)[(4-morpholinophenyl)methyl]amine (0.59 g) as starting materials, N-(4-ethylphenyl)-N-[(4-morpholinophenyl)methyl]-1,2,3,4-tetrahydronaphthalene-1-carboxamide (0.60 g) was obtained.

¹H-NMR (CDCl₃) δ: 1.22 (3H, t, J=7.8 Hz), 1.47-1.51 (1H, m), 1.87-1.91 (1H, m), 1.94-2.05 (2H, m), 2.63 (2H, q, J=7.8 Hz), 2.59-2.67 (1H, m), 2.80-2.85 (1H, m), 3.16 (4H, t, J=4.8 Hz), 3.71-3.76 (1H, m), 3.87 (4H, t, J=4.8 Hz), 4.75 (1H, d, J=13.8 Hz), 4.94 (1H, d, J=13.8 Hz), 6.81-6.84 (2H, m), 6.95-7.17 (10H, m).

Example 151

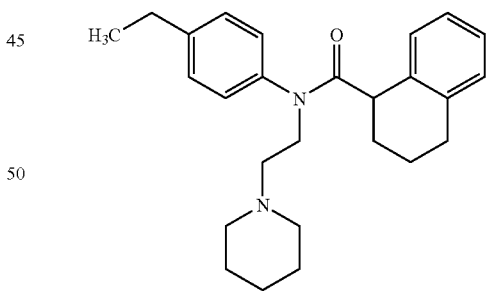

By the reaction and treatment in the same manner as in Example 12 using 1,2,3,4-tetrahydronaphthalene-1-carboxylic acid (0.34 g) and (4-ethylphenyl)(2-piperidinoethyl)amine (0.47 g) as starting materials, N-(4-ethylphenyl)-N-(2-piperidinoethyl)-1,2,3,4-tetrahydronaphthalene-1-carboxamide (0.65 g) was obtained.

¹H-NMR (CDCl₃) δ: 1.22-1.28 (4H, m), 1.43-1.60 (7H, m), 1.94-2.01 (2H, m), 2.39-2.56 (6H, m), 2.63-2.70 (3H, m), 2.78-2.90 (1H, m), 3.61-3.75 (2H, m), 4.10-4.17 (1H, m), 7.00-7.13 (3H, m), 7.18-7.28 (5H, m).

Example 152

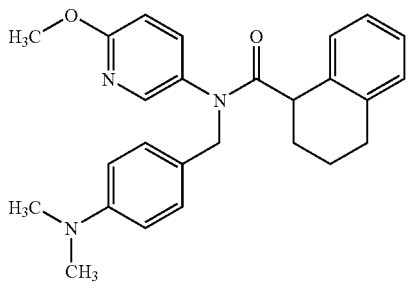

By the reaction and treatment in the same manner as in Example 12 using 1,2,3,4-tetrahydronaphthalene-1-carboxylic acid (0.70 g) and [(4-dimethylaminophenyl)methyl](6-methoxypyridin-3-yl)amine (0.49 g) as starting materials, N-[(4-dimethylaminophenyl)methyl]-N-(6-methoxypyridin-3-yl)-1,2,3,4-tetrahydronaphthalene-1-carboxamide (0.54 g) was obtained.

$^1$H-NMR (CDCl$_3$) δ: 1.45-1.54 (1H, m), 1.86-2.02 (3H, m), 2.63-2.71 (1H, m), 2.80-2.91 (1H, m), 2.94 (6H, s), 3.66-3.71 (1H, m), 3.91 (3H, s), 4.71 (1H, d, J=13.9 Hz), 4.92 (1H, d, J=13.9 Hz), 6.62-6.66 (3H, m), 6.95-6.98 (1H, m), 7.03-7.12 (5H, m), 7.19 (1H, dd, J=2.7, 8.7 Hz), 7.89 (1H, d, J=2.5 Hz).

Example 153

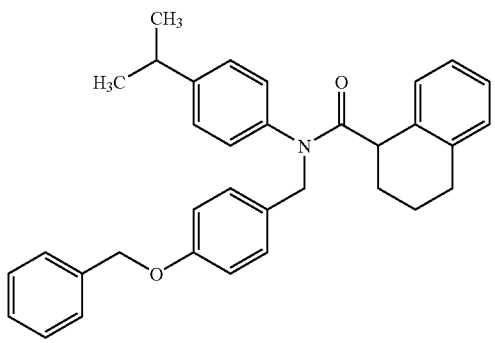

By the reaction and treatment in the same manner as in Example 12 using 1,2,3,4-tetrahydronaphthalene-1-carboxylic acid (0.34 g) and [(4-benzyloxyphenyl)methyl](4-isopropylphenyl)amine (0.66 g) as starting materials, N-[(4-benzyloxyphenyl)methyl]-N-(4-isopropylphenyl)-1,2,3,4-tetrahydronaphthalene-1-carboxamide (0.52 g) was obtained. melting point: 120-121° C.

Example 154

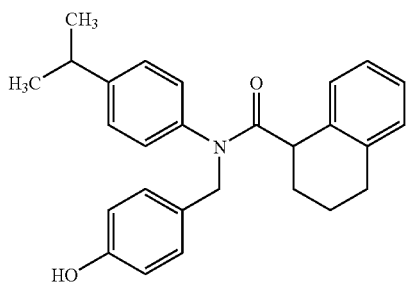

By the reaction and treatment in the same manner as in Example 17 using N-[(4-benzyloxyphenyl)methyl]-N-(4-isopropylphenyl)-1,2,3,4-tetrahydronaphthalene-1-carboxamide (0.39 g) as a starting material, N-[(4-hydroxyphenyl)methyl]-N-(4-isopropylphenyl)-1,2,3,4-tetrahydronaphthalene-1-carboxamide (0.23 g) was obtained. melting point: 156° C.

Example 155

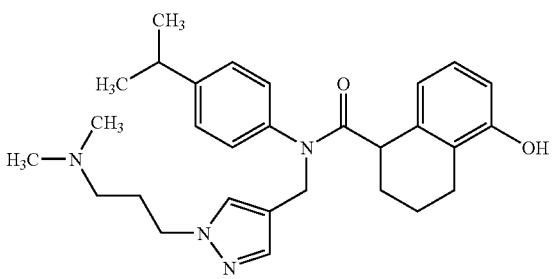

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.52 g) and 3-chloro-N,N-dimethylpropylamine hydrochloride (0.49 g) as starting materials, 5-benzyloxy-N-(4-isopropylphenyl)-N-({1-[3-(dimethylamino)propyl]pyrazol-4-yl}methyl)-1,2,3,4-tetrahydronaphthalene-1-carboxamide (1.1 g) was obtained. By the reaction and treatment in the same manner as in Example 105 using this compound, N-({1-[3-(dimethylamino)propyl]pyrazol-4-yl}methyl)-5-hydroxy-N-(4-isopropylphenyl)-1,2,3,4-tetrahydronaphthalene-1-carboxamide (0.73 g) was obtained.

$^1$H-NMR (CDCl$_3$) δ: 1.24 (6H, d, J=6.9 Hz), 1.43-1.46 (1H, m), 1.81-2.05 (5H, m), 2.21-2.27 (8H, m), 2.57-2.62 (2H, m), 2.92 (1H, sept, J=6.9 Hz), 3.68-3.73 (1H, m), 4.13 (2H, t, J=6.9 Hz), 4.61 (1H, d, J=14.3 Hz), 4.83 (1H, d, J=14.3 Hz), 6.36 (1H, d, J=7.8 Hz), 6.43 (1H, d, J=7.8 Hz), 6.81 (1H, t, J=7.8 Hz), 7.06 (2H, d, J=8.3 Hz), 7.22 (2H, d, J=8.3 Hz), 7.36 (1H, s), 7.42 (1H, s).

Example 156

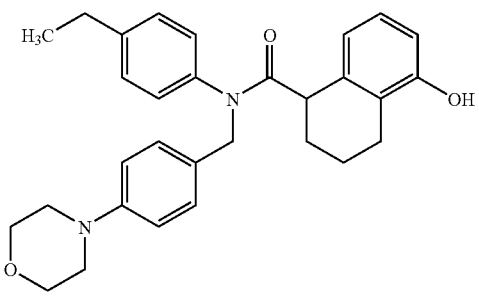

By the reaction and treatment in the same manner as in Example 12 using 5-benzyloxy-1,2,3,4-tetrahydronaphthalene-1-carboxylic acid (0.63 g) and (4-ethylphenyl)[(4-morpholinophenyl)methyl]amine (0.56 g) as starting materials, 5-benzyloxy-N-(4-ethylphenyl)-N-[(4-morpholinophenyl)methyl]-1,2,3,4-tetrahydronaphthalene-1-carboxamide (0.75 g) was obtained. By the reaction and treatment in the same manner as in Example 17 using this compound, N-(4-ethylphenyl)-5-hydroxy-N-[(4-morpholinophenyl)methyl]-1,2,3,4-tetrahydronaphthalene-1-carboxamide (0.51 g) was obtained. melting point: 200° C.

Example 157

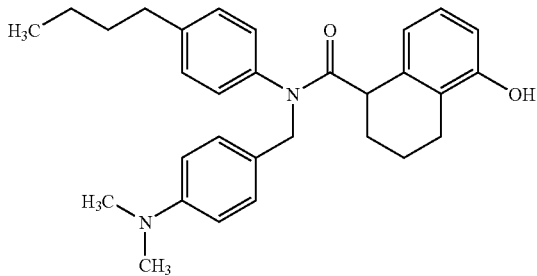

By the reaction and treatment in the same manner as in Example 12 using 5-benzyloxy-1,2,3,4-tetrahydronaphthalene-1-carboxylic acid (0.66 g) and (4-butylphenyl)[(4-dimethylaminophenyl)methyl]amine (0.55 g) as starting materials, 5-benzyloxy-N-(4-butylphenyl)-N-[(4-dimethylaminophenyl)methyl]-1,2,3,4-tetrahydronaphthalene-1-carboxamide (0.98 g) was obtained. By the reaction and treatment in the same manner as in Example 17 using this compound, N-(4-butylphenyl)-N-[(4-dimethylaminophenyl)methyl]-5-hydroxy-1,2,3,4-tetrahydronaphthalene-1-carboxamide (0.44 g) was obtained. melting point: 138° C.

Example 158

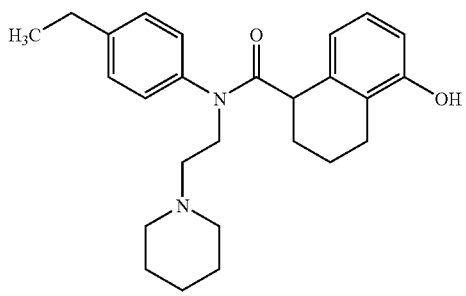

By the reaction and treatment in the same manner as in Example 12 using 5-benzyloxy-1,2,3,4-tetrahydronaphthalene-1-carboxylic acid (0.72 g) and (4-ethylphenyl) (2-piperidinoethyl)amine (0.50 g) as starting materials, 5-benzyloxy-N-(4-ethylphenyl)-N-(2-piperidinoethyl)-1,2,3,4-tetrahydronaphthalene-1-carboxamide (1.19 g) was obtained. By the reaction and treatment in the same manner as in Example 105 using this compound, N-(4-ethylphenyl)-5-hydroxy-N-(2-piperidinoethyl)-1,2,3,4-tetrahydronaphthalene-1-carboxamide (0.77 g) was obtained.

$^1$H-NMR (CDCl$_3$) δ: 1.35-2.00 (9H, m), 2.42-2.57 (7H, m), 2.67 (2H, q, J=7.6 Hz), 3.48 (1H, s), 3.65-3.75 (3H, m), 4.06-4.13 (1H, m), 6.34 (1H, d, J=7.8 Hz), 6.66 (1H, d, J=7.8 Hz), 6.81 (1H, d, J=7.8 Hz), 7.21-7.26 (4H, m).

Example 159

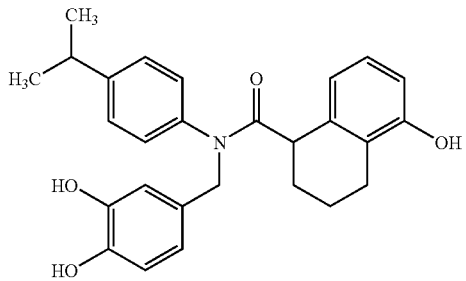

By the reaction and treatment in the same manner as in Example 12 using 5-benzyloxy-1,2,3,4-tetrahydronaphthalene-1-carboxylic acid (1.94 g) and [(3,4-dibenzyloxyphenyl)methyl](4-isopropylphenyl)amine (2.5 g) as starting materials, 5-benzyloxy-N-[(3,4-dibenzyloxyphenyl)methyl]-N-(4-isopropylphenyl)-1,2,3,4-tetrahydronaphthalene-1-carboxamide (2.64 g) was obtained. By the reaction and treatment in the same manner as in Example 17 using this compound, N-[(3,4-dihydroxyphenyl)methyl]-5-hydroxy-N-(4-isopropylphenyl)-1,2,3,4-tetrahydronaphthalene-1-carboxamide (1.35 g) was obtained.

$^1$H-NMR (CDCl$_3$) δ: 1.23 (6H, m), 137-1.42 (1H, m), 1.82-1.97 (6H, m), 2.35-2.43 (1H, m), 2.48-2.55 (1H, m), 2.89 (1H, sept, J=6.9 Hz), 3.71-3.76 (1H, m), 4.70 (1H, d, J=13.8 Hz), 4.82 (1H, d, J=13.8 Hz), 6.30 (1H, dd, J=2.0, 8.0 Hz), 6.47 (1H, d, J=8.0 Hz), 6.61 (2H, t, J=7.7 Hz), 6.90-6.98 (4H, m), 7.17 (2H, d, J=8.4 Hz).

Example 160

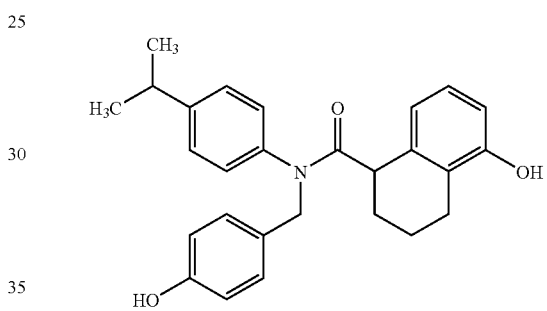

By the reaction and treatment in the same manner as in Example 12 using 5-benzyloxy-1,2,3,4-tetrahydronaphthalene-1-carboxylic acid (0.59 g) and [(4-benzyloxyphenyl)methyl](4-isopropylphenyl)amine (0.58 g) as starting materials, 5-benzyloxy-N-[(4-benzyloxyphenyl)methyl]-N-(4-isopropylphenyl)-1,2,3,4-tetrahydronaphthalene-1-carboxamide (0.74 g) was obtained. By the reaction and treatment in the same manner as in Example 17 using this compound, 5-hydroxy-N-[(4-hydroxyphenyl)methyl]-N-(4-isopropylphenyl)-1,2,3,4-tetrahydronaphthalene-1-carboxamide (0.33 g) was obtained. melting point: 241-243° C.

Example 161

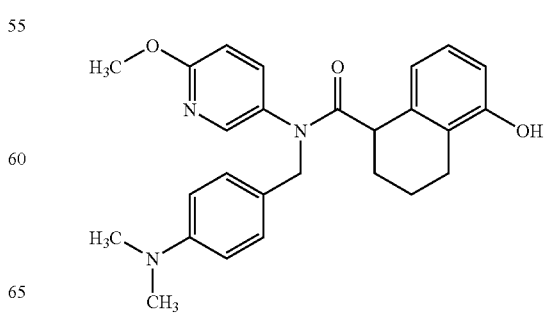

By the reaction and treatment in the same manner as in Example 12 using 5-benzyloxy-1,2,3,4-tetrahydronaphthalene-1-carboxylic acid (1.0 g) and [(4-dimethylaminophenyl)methyl](6-methoxypyridin-3-yl)amine (0.91 g) as starting materials, 5-benzyloxy-N-[(4-dimethylaminophenyl)methyl]-N-(6-methoxypyridin-3-yl)-1,2,3,4-tetrahydronaphthalene-1-carboxamide (1.35 g) was obtained. By the reaction and treatment in the same manner as in Example 105 using this compound, N-[(4-dimethylaminophenyl)methyl]-5-hydroxy-N-(6-methoxypyridin-3-yl)-1,2,3,4-tetrahydronaphthalene-1-carboxamide (0.34 g) was obtained.

$^1$H-NMR (CDCl$_3$) δ: 1.45-1.5 (1H, m), 1.81-2.05 (3H, m), 2.59-2.62 (2H, m), 2.94 (6H, s), 3.65-3.70 (1H, m), 3.92 (3H, m), 4.83 (2H, s), 6.38 (1H, d, J=7.8 Hz), 6.46 (1H, d, J=7.8 Hz), 6.64-6.71 (3H, m), 6.82 (1H, d, J=7.8 Hz), 7.05-7.09 (2H, m), 7.19-7.22 (2H, m), 7.91 (1H, brs).

Example 162

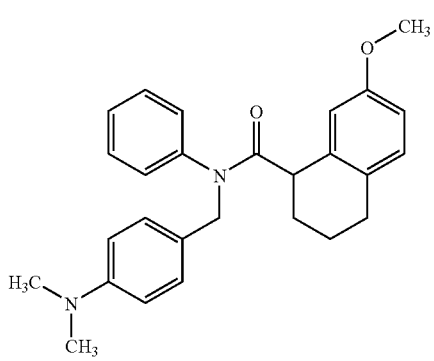

Aniline (93.1 mg) was dissolved in dichloroethane (5 mL), and 4-dimethylaminobenzaldehyde (149 mg), acetic acid (0.06 mL) and sodium triacetoxy borohydride (0.42 g) were added. The mixture was stirred at room temperature for one day. Saturated aqueous sodium hydrogencarbonate (2 mL) was added to the reaction solution, and the mixture was stirred for a while, after which the aqueous layer was absorbed using a diatomaceous earth column. The obtained organic layer was concentrated under reduced pressure, and dichloromethane (5 mL) was added to the residue. To this solution was added a solution of 7-methoxy-1,2,3,4-tetrahydronaphthalene-1-carboxylic acid chloride (0.23 g) in dichloromethane (5 mL), and the mixture was stirred at room temperature for one day. Saturated aqueous sodium hydrogencarbonate (2 mL) was added to the reaction solution. The mixture was stirred for a while, after which the aqueous layer was absorbed using a diatomaceous earth column. The obtained organic layer was concentrated under reduced pressure, and the residue was purified by silica gel column chromatography to give N-[(4-dimethylaminophenyl)methyl]-7-methoxy-N-phenyl-1,2,3,4-tetrahydronaphthalene-1-carboxamide (260 mg).

$^1$H-NMR (CDCl$_3$) δ: 1.42-1.54 (1H, m), 1.83-2.04 (3H, m), 2.53-2.86 (2H, m), 2.93 (6H, s), 3.65-3.72 (1H, m), 3.70 (3H, s), 4.62 (1H, d, J=13.9 Hz), 5.08 (1H, d, J=13.9 Hz), 6.53 (1H, d, J=2.5 Hz), 6.62-6.69 (3H, m), 6.95 (1H, d, J=8.4 Hz), 7.05-7.13 (3H, m), 7.30-7.34 (4H, m).

Example 163

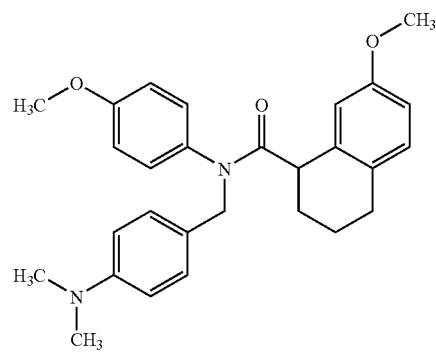

By the reaction and treatment in the same manner as in Example 162 using 4-methoxyaniline (0.12 g) as a starting material instead of aniline, N-[(4-dimethylaminophenyl)methyl]-7-methoxy-N-(4-methoxyphenyl)-1,2,3,4-tetrahydronaphthalene-1-carboxamide (0.12 g) was obtained.

$^1$H-NMR (CDCl$_3$) δ: 1.43-1.55 (1H, m), 1.80-2.05 (3H, m), 2.56-2.62 (1H, m), 2.70-2.85 (1H, m), 2.93 (6H, s), 3.66-3.70 (1H, m), 3.70 (3H, s), 3.79 (3H, s), 4.57 (1H, d, J=13.8 Hz), 5.05 (1H, d, J=13.8 Hz), 6.51 (1H, d, J=2.5 Hz), 6.62-6.69 (3H, m), 6.81-6.85 (2H, m), 6.93-6.97 (3H, m), 7.09-7.13 (2H, m).

Example 164

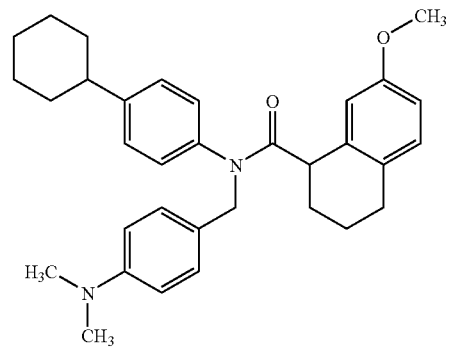

By the reaction and treatment in the same manner as in Example 162 using 4-cyclohexylaniline (0.18 g) as a starting material instead of aniline, N-(4-cyclohexylphenyl)-N-[(4-dimethylaminophenyl)methyl]-7-methoxy-1,2,3,4-tetrahydronaphthalene-1-carboxamide (0.088 g) was obtained.

$^1$H-NMR (CDCl$_3$) δ: 1.34-2.03 (14H, m), 2.44-2.61 (2H, m), 2.71-2.85 (1H, m), 2.93 (6H, s), 3.68-3.72 (1H, m), 3.68 (3H, s), 4.58 (1H, d, J=13.9 Hz), 5.06 (1H, d, J=13.9 Hz), 6.51 (1H, d, J=2.5 Hz)., 6.63-6.68 (3H, m), 6.93-6.98 (3H, m), 7.12-7.16 (4H, m).

Example 165

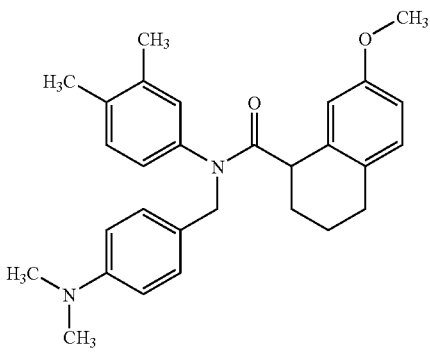

By the reaction and treatment in the same manner as in Example 162 using 3,4-dimethylaniline (0.12 g) as a starting material instead of aniline, N-[(4-dimethylaminophenyl)methyl]-N-(3,4-dimethylphenyl)-7-methoxy-1,2,3,4-tetrahydronaphthalene-1-carboxamide (0.29 g) was obtained.

$^1$H-NMR (CDCl$_3$) δ: 1.35-1.51 (1H, m), 1.86-2.02 (3H, m), 2.21 (3H, s), 2.23 (3H, s), 2.51-2.63 (1H, m), 2.69-2.83 (1H, m), 2.93 (6H, s), 3.69 (3H, s), 3.69-3.74 (1H, m), 4.50-4.65 (1H, m), 4.96-5.08 (1H, m), 6.52 (1H, d, J=2.4 Hz), 6.62-6.68 (3H, m), 6.73-6.76 (1H, m), 6.86 (1H, d, J=1.7 Hz), 6.94 (1H, d, J=8.5 Hz), 7.05 (1H, d, J=8.5 Hz), 7.06-7.12 (2H, m).

Example 166

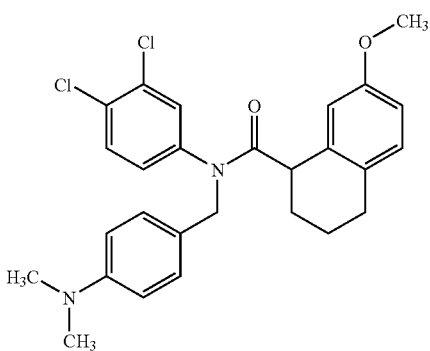

By the reaction and treatment in the same manner as in Example 162 using 3,4-dichloroaniline (0.16 g) as a starting material instead of aniline, N-(3,4-dichlorophenyl)-N-[(4-dimethylaminophenyl)methyl]-7-methoxy-1,2,3,4-tetrahydronaphthalene-1-carboxamide (0.14 g) was obtained.

$^1$H-NMR (CDCl$_3$) δ: 1.42-1.56 (1H, m), 1.80-2.03 (3H, m), 2.55-2.82 (2H, m), 2.94 (6H, s), 3.60-3.69 (1H, m), 3.71 (3H, s), 3.58-3.70 (1H, m), 4.97-5.05 (1H, m), 6.45-6.46 (1H, m), 6.62-6.71 (3H, m), 6.85-6.88 (1H, m), 6.96-6.98 (1H, m), 7.05-7.09 (2H, m), 7.20 (1H, brs), 7.39 (1H, d, J=8.4 Hz).

Example 167

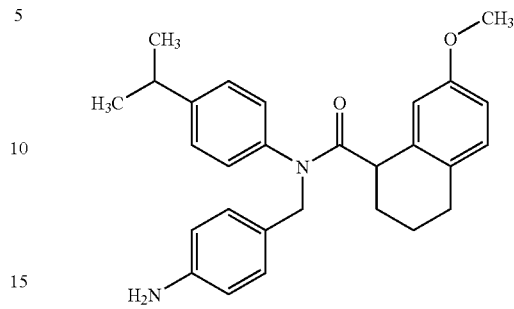

N-(4-Isopropylphenyl)-7-methoxy-N-[(4-nitrophenyl)methyl]-1,2,3,4-tetrahydronaphthalene-1-carboxamide (1.2 g) was dissolved in ethanol (8.1 mL), and stannic chloride (1.5 g) and conc. hydrochloric acid (2.7 mL) were added. The mixture was heated under reflux for 3 hr. The reaction mixture was concentrated under reduced pressure, and the residue was partitioned between water and ethyl acetate. The organic layer was washed with saturated aqueous sodium hydrogencarbonate and dried over magnesium sulfate. The solvent was evaporated under reduced pressure, and the obtained solid was recrystallized from a mixed solvent of chloroform and diisopropyl ether to give N-[(4-aminophenyl)methyl]-N-(4-isopropylphenyl)-7-methoxy-1,2,3,4-tetrahydronaphthalene-1-carboxamide (1.0 g).

melting point: 115-117° C.

Example 168

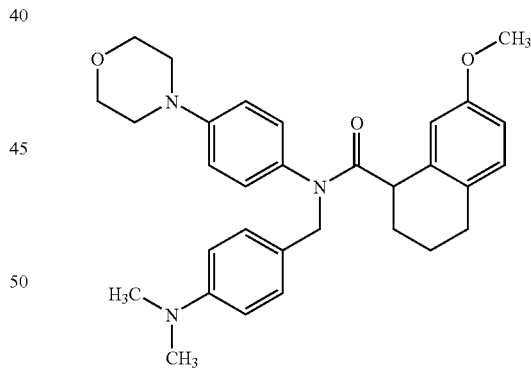

By the reaction and treatment in the same manner as in Example 162 using 4-morpholinoaniline (0.18 g) as a starting material instead of aniline, N-[(4-dimethylaminophenyl)methyl]-7-methoxy-N-(4-morpholinophenyl)-1,2,3,4-tetrahydronaphthalene-1-carboxamide (0.33 g) was obtained.

$^1$H-NMR (CDCl$_3$) δ: 1.40-1.47 (1H, m), 1.82-2.05 (3H, m), 2.56-2.84 (2H, m), 2.93 (6H, s), 3.13-3.16 (4H, m), 3.66-3.73 (1H, m), 3.69 (3H, s), 3.83-3.86 (4H, m), 4.57 (1H, d, J=13.8 Hz), 5.05 (1H, d, J=13.8 Hz), 6.52 (1H, s), 6.62-6.68 (3H, m), 6.80-6.83 (2H, m), 6.93-7.02 (3H, m), 7.13 (2H, d, J=8.4 Hz).

Example 169

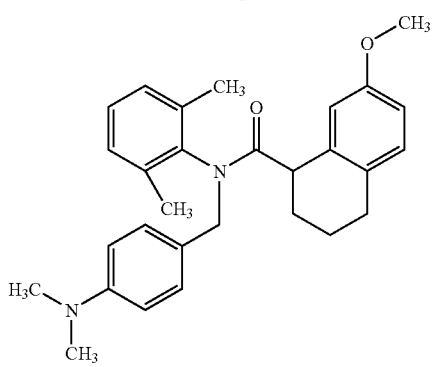

By the reaction and treatment in the same manner as in Example 162 using 2,6-dimethylaniline (0.12 g) as a starting material instead of aniline, N-[(4-dimethylaminophenyl)methyl]-N-(2,6-dimethylphenyl)-7-methoxy-1,2,3,4-tetrahydronaphthalene-1-carboxamide (0.16 g) was obtained.

$^1$H-NMR (CDCl$_3$) δ: 1.24-1.28 (1H, m), 1.89-2.10 (3H, m), 2.10 (6H, s), 2.40-2.45 (1H, m), 2.76-2.83 (1H, m), 2.90 (6H, s), 3.72-3.78 (3H, m), 3.77 (3H, s), 6.49 (1H, s), 6.66 (2H, d, J8.6=Hz), 6.80-6.88 (4H, m), 7.00-7.05 (2H, m), 7.08-7.11 (1H, m).

Example 170

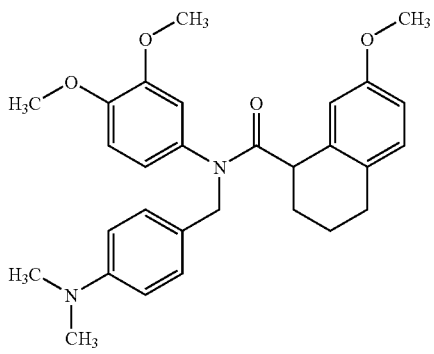

By the reaction and treatment in the same manner as in Example 162 using 3,4-dimethoxyaniline (0.15 g) as a starting material instead of aniline, N-(3,4-dimethoxyphenyl)-N-[(4-dimethylaminophenyl)methyl]-7-methoxy-1,2,3,4-tetrahydronaphthalene-1-carboxamide (0.18 g) was obtained.

$^1$H-NMR (CDCl$_3$) δ: 1.40-1.51 (1H, m), 1.82-2.05 (3H, m), 2.56-2.62 (1H, m), 2.72-2.81 (1H, m), 2.93 (6H, s), 3.66-3.74 (1H, m), 3.69 (6H, s), 3.87 (3H, s), 4.53-4.63 (1H, m), 5.00-5.10 (1H, m), 6.45 (1H, d, J=2.1 Hz), 6.52 (1H, d, J=2.1 Hz), 6.63-6.69 (4H, m), 6.78 (1H, d, J=8.7 Hz), 6.95 (1H, d, J=8.4 Hz), 7.12 (2H, d, J=8.7 Hz).

Example 171

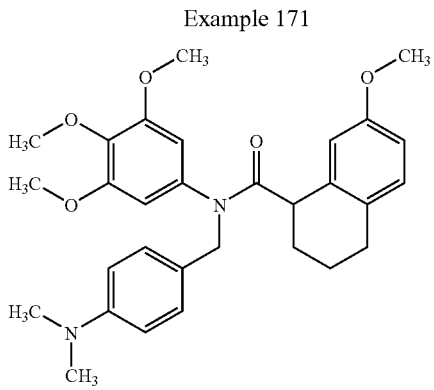

By the reaction and treatment in the same manner as in Example 162 using 3,4,5-trimethoxyaniline (0.18 g) as a starting material instead of aniline, N-[(4-dimethylaminophenyl)methyl]-7-methoxy-N-(3,4,5-trimethoxyphenyl)-1,2,3,4-tetrahydronaphthalene-1-carboxamide (0.22 g) was obtained.

$^1$H-NMR (CDCl$_3$) δ: 1.42-1.59 (1H, m), 1.80-2.05 (3H, m), 2.52-2.64 (1H, m), 2.71-2.85 (1H, m), 2.92 (6H, s), 3.67-3.85 (13H, m), 4.58 (1H, d, J=13.8 Hz), 5.04 (1H, d, J=13.8 Hz), 6.22 (2H, s), 6.51 (1H, d, J=2.4 Hz), 6.63-69.73 (3H, m), 6.96 (1H, d, J=8.4 Hz), 7.14-7.16 (2H, m).

Example 172

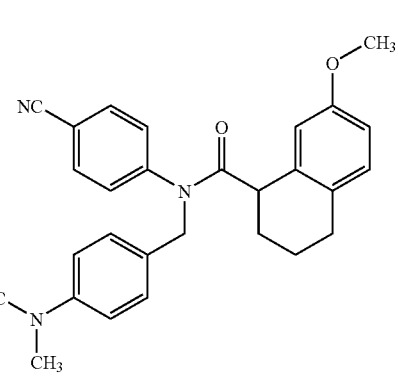

By the reaction and treatment in the same manner as in Example 162 using 4-cyanoaniline (0.12 g) as a starting material instead of aniline, N-(4-cyanophenyl)-N-[(4-dimethylaminophenyl)methyl]-7-methoxy-1,2,3,4-tetrahydronaphthalene-1-carboxamide (0.097 g) was obtained.

$^1$H-NMR (CDCl$_3$) δ: 1.20-1.27 (1H, m), 1.79-2.05 (3H, m), 2.55-2.65 (1H, m), 2.70-2.84 (1H, m), 2.94 (6H, s), 3.55-3.66 (1H, m), 3.72 (3H, s), 4.72 (1H, d, J=14.1 Hz), 5.03 (1H, d, J=14.1 Hz), 6.47 (1H, d, J=2.4 Hz), 6.62 (2H, d, J=8.1 Hz), 6.70 (1H, dd, J=2.4, 8.1 Hz), 6.97 (1H, d, J=8.1 Hz), 7.05 (2H, d, J=8.1 Hz), 7.18-7.20 (2H, m), 7.63-7.66 (2H, m).

Example 173

By the reaction and treatment in the same manner as in Example 162 using 2-fluoroaniline (0.11 g) as a starting material instead of aniline, N-[(4-dimethylaminophenyl)methyl]-N-(2-fluorophenyl)-7-methoxy-1,2,3,4-tetrahydronaphthalene-1-carboxamide (0.41 g) was obtained.

¹H-NMR (CDCl₃) δ: 1.42-1.54 (1H, m), 1.79-2.08 (3H, m), 2.55-2.61 (1H, m), 2.71-2.85 (1H, m), 2.92 (6H, s), 3.58-3.68 (1H, m), 3.69 (1.5H, s), 3.76 (1.5H, s), 4.16 (0.5H, d, J=14.1 Hz), 4.39 (0.5H, d, J=14.1 Hz), 5.28 (0.5H, d, J=14.1 Hz), 5.52 (0.5H, d, J=14.1 Hz), 6.48-6.49 (0.5H, m), 6.59-6.70 (3.5H, m), 6.93-7.25 (7H, m).

Example 174

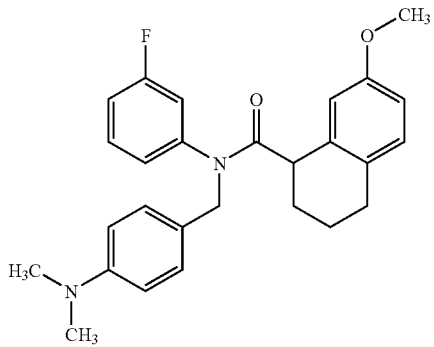

By the reaction and treatment in the same manner as in Example 162 using 3-fluoroaniline (0.11 g) as a starting material instead of aniline, N-[(4-dimethylaminophenyl)methyl]-N-(3-fluorophenyl)-7-methoxy-1,2,3,4-tetrahydronaphthalene-1-carboxamide (0.26 g) was obtained.

¹H-NMR (CDCl₃) δ: 1.42-1.50 (1H, m), 1.86-2.02 (3H, m), 2.56-2.83 (2H, m), 2.93 (6H, s), 3.65-3.69 (1H, m), 3.70 (3H, s), 4.62 (1H, d, J=13.9 Hz), 5.04 (1H, d, J=13.9 Hz), 6.48 (1H, d, J=2.4 Hz), 6.62-6.70 (3H, m), 6.80-7.11 (6H, m), 7.26-7.31 (1H, m).

Example 175

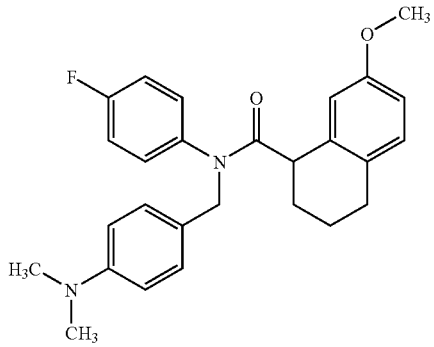

By the reaction and treatment in the same manner as in Example 162 using 4-fluoroaniline (0.11 g) as a starting material instead of aniline, N-[(4-dimethylaminophenyl)methyl]-N-(4-fluorophenyl)-7-methoxy-1,2,3,4-tetrahydronaphthalene-1-carboxamide (0.36 g) was obtained.

¹H-NMR (CDCl₃) δ: 1.38-1.56 (1H, m), 1.79-2.05 (3H, m), 2.52-2.65 (1H, m), 2.71-2.82 (1H, m), 2.93 (6H, s), 3.61-3.67 (1H, m), 3.71 (3H, s), 4.60 (1H, d, J=13.8 Hz), 5.04 (1H, d, J=13.8 Hz), 6.49 (1H, d, J=2.4 Hz), 6.61-6.70 (3H, m), 6.94-7.10 (7H, m).

Example 176

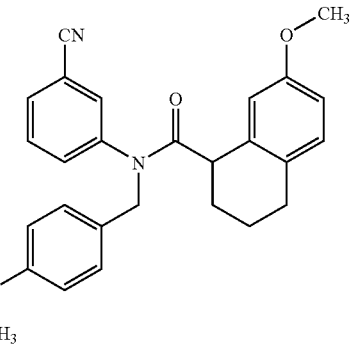

By the reaction and treatment in the same manner as in Example 162 using 3-cyanoaniline (0.12 g) as a starting material instead of aniline, N-(3-cyanophenyl)-N-[(4-dimethylaminophenyl)methyl]-7-methoxy-1,2,3,4-tetrahydronaphthalene-1-carboxamide (0.14 g) was obtained.

¹H-NMR (CDCl₃) δ: 1.42-1.51 (1H, m), 1.79-2.05 (3H, m), 2.54-2.83 (2H, m), 2.94 (6H, s), 3.48-3.62 (1H, m), 3.73 (3H, s), 4.67 (1H, d, J=14.1 Hz), 5.01 (1H, d, J=14.1 Hz), 6.47 (1H, d, J=2.4 Hz), 6.62 (2H, d, J=8.7 Hz), 6.70 (1H, dd, J=2.4, 8.1 Hz), 6.97 (1H, d, J=8.1 Hz), 7.05 (2H, d, J=8.7 Hz), 7.26-7.35 (2H, m), 7.46 (1H, t, J=7.8 Hz), 7.60 (1H, d, J=7.8 Hz).

Example 177

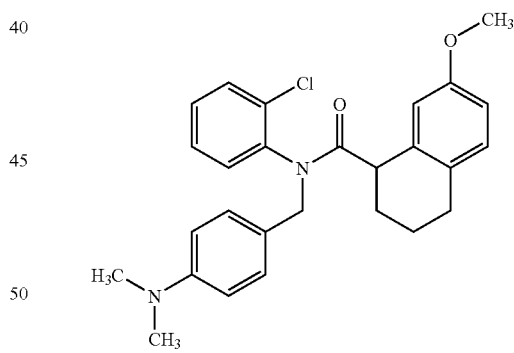

By the reaction and treatment in the same manner as in Example 162 using 2-chloroaniline (0.12 g) as a starting material instead of aniline, N-(2-chlorophenyl)-N-[(4-dimethylaminophenyl)methyl]-7-methoxy-1,2,3,4-tetrahydronaphthalene-1-carboxamide (0.24 g) was obtained.

¹H-NMR (CDCl₃) δ: 1.40-1.55 (1H, m), 1.73-2.12 (3H, m), 2.50-2.65 (1H, m), 2.70-2.84 (1H, m), 2.93 (6H, s), 3.40-3.52 (1H, m), 3.64 (1.5H, s), 3.76 (1.5H, s), 3.85 (0.5H, d, J=14.0 Hz), 3.97 (0.5H, d, J=14.1 Hz) 5.64 (0.5H, d, J=14.1 Hz), 5.80 (0.5H, d, J=14.0 Hz), 6.46-6.47 (0.5H, m), 6.60-6.71 (3H, m), 6.81-6.82 (1H, m), 6.88-6.98 (1.5H, m), 7.04-7.16 (3H, m), 7.24-7.32 (1H, m), 7.50-7.55 (1H, m).

Example 178

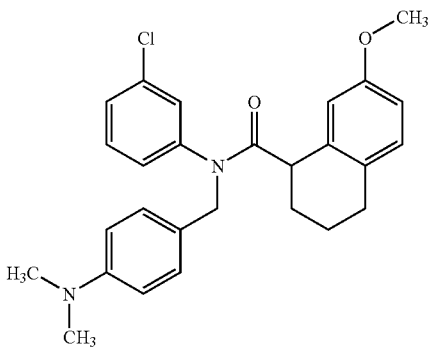

By the reaction and treatment in the same manner as in Example 162 using 3-chloroaniline (0.12 g) as a starting material instead of aniline, N-(3-chlorophenyl)-N-[(4-dimethylaminophenyl)methyl]-7-methoxy-1,2,3,4-tetrahydronaphthalene-1-carboxamide (0.23 g) was obtained.

$^1$H-NMR (CDCl$_3$) δ: 1.42-1.51 (1H, m), 1.79-2.05 (3H, m), 2.54-2.83 (2H, m), 2.93 (6H, s), 3.63-3.68 (1H, m), 3.69 (3H, s), 4.62 (1H, d, J=14.0 Hz), 5.03 (1H, d, J=14.0 Hz), 6.48 (1H, d, J=2.5 Hz), 6.62-6.70 (3H, m), 6.91-7.11 (6H, m), 7.23-7.29 (1H, m).

Example 179

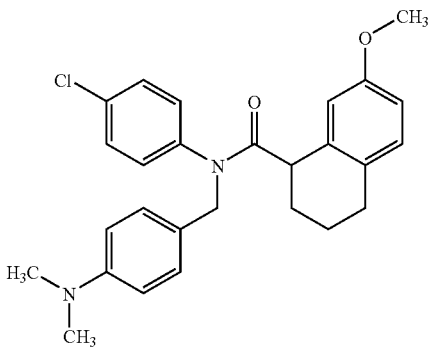

By the reaction and treatment in the same manner as in Example 162 using 4-chloroaniline (0.12 g) as a starting material instead of aniline, N-(4-chlorophenyl)-N-[(4-dimethylaminophenyl)methyl]-7-methoxy-1,2,3,4-tetrahydronaphthalene-1-carboxamide (0.30 g) was obtained.

$^1$H-NMR (CDCl$_3$) δ: 1.45-1.53 (1H, m), 1.78-2.03 (3H, m), 2.55-2.82 (2H, m), 2.93 (6H, s), 3.61-3.68 (1H, m), 3.71 (3H, s), 4.61 (1H, d, J=13.9 Hz), 5.03 (1H, d, J=13.9 Hz), 6.48 (1H, d, J=2.4 Hz), 6.61-6.70 (3H, m), 6.94-7.07 (3H, m), 7.07-7.10 (2H, m), 7.21-7.32 (2H, m).

Example 180

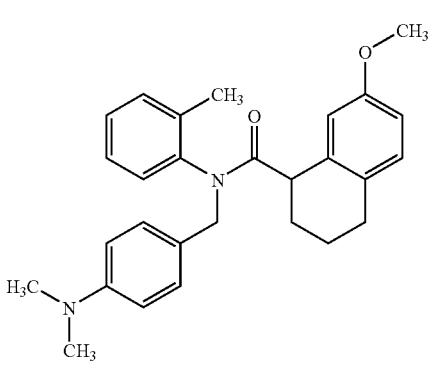

By the reaction and treatment in the same manner as in Example 162 using o-toluidine (0.11 g) as a starting material instead of aniline, N-[(4-dimethylaminophenyl)methyl]-7-methoxy-N-(2-methylphenyl)-1,2,3,4-tetrahydronaphthalene-1-carboxamide (0.22 g) was obtained.

$^1$H-NMR (CDCl$_3$) δ: 1.37-1.50 (1H, m), 1.81-2.10 (3H, m), 2.26 (3H, s), 2.53-2.61 (1H, m), 2.70-2.82 (1H, m), 2.93 (6H, s), 2.42-2.53 (1H, m), 3.61 (1.8H, s), 3.74 (1.2H, s), 3.97 (0.6H, d, J=13.5 Hz), 4.33 (0.4H, d, J=13.5 Hz), 5.19 (0.4H, d, J=13.5 Hz), 5.58 (0.6H, d, J=13.5 Hz), 6.48-7.26 (11H, m).

Example 181

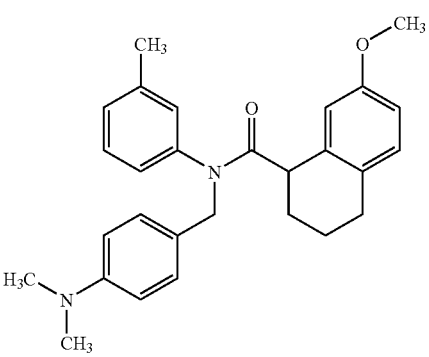

By the reaction and treatment in the same manner as in Example 162 using m-toluidine (0.11 g) as a starting material instead of aniline, N-[(4-dimethylaminophenyl)methyl]-7-methoxy-N-(3-methylphenyl)-1,2,3,4-tetrahydronaphthalene-1-carboxamide (0.23 g) was obtained.

$^1$H-NMR (DMSO-d$_6$) δ: 1.30-1.40 (1H, m), 1.80-1.95 (3H, m), 2.29 (3H, s), 2.50-2.72 (2H, m), 2.86 (6H, s), 3.61-3.67 (1H, m), 3.67 (3H, s), 4.64 (1H, d, J=13.9 Hz), 4.83 (1H, d, J=13.9 Hz), 6.45 (1H, d, J=2.4 Hz), 6.63 (2H, d, J=8.4 Hz), 6.70 (1H, dd, J=2.4, 8.4 Hz), 6.92-7.02 (4H, m), 7.08 (1H, s), 7.15 (1H, d, J=7.5 Hz), 7.26-7.31 (1H, m).

Example 182

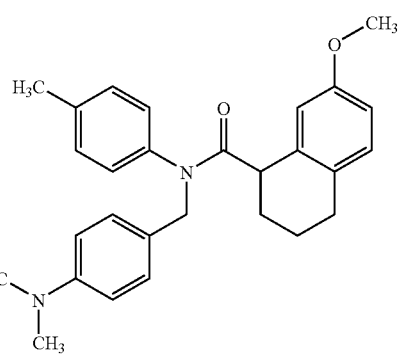

By the reaction and treatment in the same manner as in Example 162 using p-toluidine (0.11 g) as a starting material instead of aniline, N-[(4-dimethylaminophenyl)methyl]-7-methoxy-N-(4-methylphenyl)-1,2,3,4-tetrahydronaphthalene-1-carboxamide (0.27 g) was obtained.

$^1$H-NMR (DMSO-$d_6$) δ: 1.30-1.40 (1H, m), 1.79-1.97 (3H, m), 2.29 (3H, s), 2.48-2.68 (2H, m), 2.86 (6H, s), 3.57-3.62 (1H, m), 3.67 (3H, s), 4.63 (1H, d, J=13.9 Hz), 4.83 (1H, d, J=13.9 Hz), 6.45-6.46 (1H, m), 6.60-6.70 (3H, m), 6.95-7.25 (7H, m).

Example 183

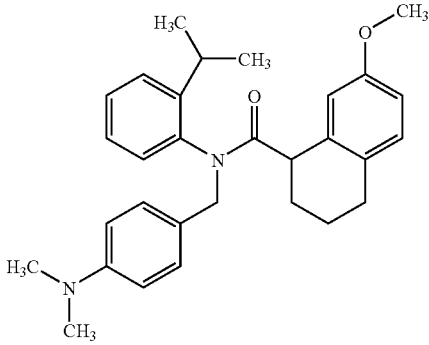

By the reaction and treatment in the same manner as in Example 162 using 2-isopropylaniline (0.14 g) as a starting material instead of aniline, N-[(4-dimethylaminophenyl)methyl]-N-(2-isopropylphenyl)-7-methoxy-1,2,3,4-tetrahydronaphthalene-1-carboxamide (0.12 g) was obtained.

$^1$H-NMR (DMSO-$d_6$) δ: 1.01-1.05 (3H, m), 1.13-1.23 (3H, m), 1.23-1.40 (1H, m), 1.71-1.98 (3H, m), 2.51-2.70 (3H, m), 2.85 (6H, m), 2.92-3.05 (0.5H, m), 3.13-3.23 (0.5H, m), 3.61 (1.5H, s), 3.70 (1.5H, s), 4.09 (0.5H, d, J=14.1 Hz), 4.26 (0.5H, d, J=14.1 Hz), 5.09 (0.5H, d, J=14.1 Hz), 5.32 (0.5H, d, J=14.1 Hz), 6.45 (1H, d, J=2.4 Hz), 6.63 (2H, d, J=8.6 Hz), 6.64-6.73 (1H, m), 6.85-7.04 (4H, m), 7.14-7.18 (1H, m), 7.31-7.39 (1H, m), 7.45-7.49 (1H, m).

Example 184

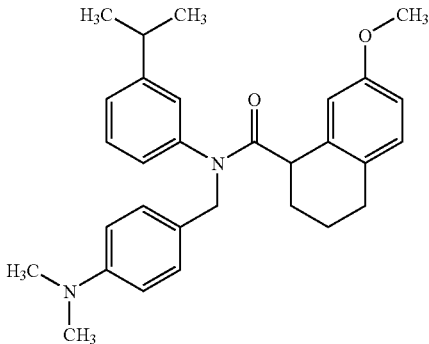

By the reaction and treatment in the same manner as in Example 162 using 3-isopropylaniline (0.14 g) as a starting material instead of aniline, N-[(4-dimethylaminophenyl)methyl]-N-(3-isopropylphenyl)-7-methoxy-1,2,3,4-tetrahydronaphthalene-1-carboxamide (0.28 g) was obtained.

$^1$H-NMR (DMSO-$d_6$) δ: 1.07-1.12 (6H, m), 1.27-1.42 (1H, m), 1.82-1.90 (3H, m), 2.49-2.68 (3H, m), 2.86 (6H, s), 3.56-3.60 (1H, m), 3.66 (3H, s), 4.60 (1H, d, J=14.1 Hz), 4.92 (1H, d, J=14.1 Hz), 6.44 (1H, d, J=2.4 Hz), 6.62-6.71 (3H, m), 6.93-7.02 (5H, m), 7.20 (1H, d, J=7.8 Hz), 7.32 (1H, d, J=7.8 Hz).

Example 185

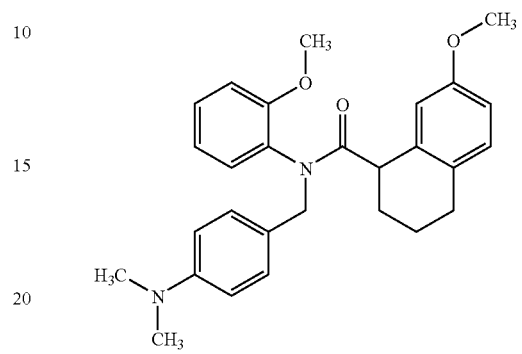

By the reaction and treatment in the same manner as in Example 162 using 2-methoxyaniline (0.12 g) as a starting material instead of aniline, N-[(4-dimethylaminophenyl)methyl)]-7-methoxy-N-(2-methoxyphenyl)-1,2,3,4-tetrahydronaphthalene-1-carboxamide (0.29 g) was obtained.

$^1$H-NMR (DMSO-$d_6$) δ: 1.32-1.42 (1H, m), 1.74-1.92 (3H, m), 2.49-2.68 (2H, m), 2.85 (6H, s), 3.47-3.51 (1H, m), 3.63 (1.5H, s), 3.71 (1.5H, s), 3.82 (1.5H, s), 3.84 (1.5H, s), 3.99 (0.5H, d, J=14.1 Hz), 4.11 (0.5H, d, J=14.1 Hz), 5.17 (0.5H, d, J=14.1 Hz), 5.33 (0.5H, d, J=14.1 Hz), 6.46 (0.5H, d, J=2.4 Hz), 6.60-6.70 (3.5H, m), 6.89-7.03 (5H, m), 7.16 (1H, d, J=8.4 Hz), 7.30-7.35 (1H, m).

Example 186

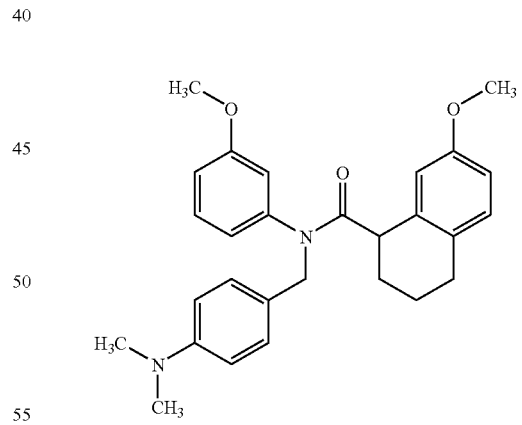

By the reaction and treatment in the same manner as in Example 162 using 3-methoxyaniline (0.12 g) as a starting material instead of aniline, N-[(4-dimethylaminophenyl)methyl]-7-methoxy-N-(3-methoxyphenyl)-1,2,3,4-tetrahydronaphthalene-1-carboxamide (0.20 g) was obtained.

$^1$H-NMR (DMSO-$d_6$) δ: 1.33-1.42 (1H, m), 1.81-1.96 (3H, m), 2.55-2.70 (2H, m), 2.86 (6H, s), 3.65 (3H, s), 3.70 (3H, s), 3.61-3.73 (1H, m), 4.62 (1H, d, J=14.2 Hz), 4.91 (H, d, J=14.2 Hz), 6.46 (H, d, J=2.4 Hz), 6.46-6.76 (5H, m), 6.91-7.02 (4H, m), 7.32 (1H, t, J=8.0 Hz).

Example 187

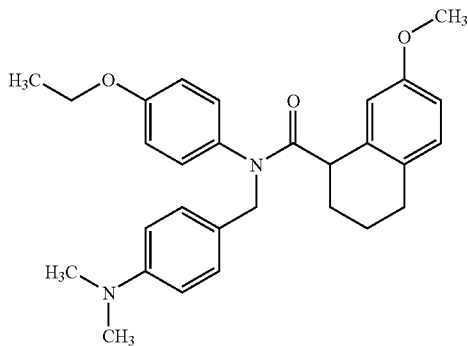

By the reaction and treatment in the same manner as in Example 162 using 4-ethoxyaniline (0.14 g) as a starting material instead of aniline, N-[(4-dimethylaminophenyl)methyl]-N-(4-ethoxyphenyl)-7-methoxy-1,2,3,4-tetrahydronaphthalene-1-carboxamide (0.28 g) was obtained.

$^1$H-NMR (DMSO-d$_6$) δ: 1.25-1.40 (1H, m), 1.27 (3H, t, J=6.9 Hz), 1.78-1.94 (3H, m), 2.54-2.64 (2H, m), 2.86 (6H, s), 3.57-3.63 (1H, m), 3.67 (3H, s), 3.99 (2H, q, J=6.9 Hz), 4.58 (1H, d, J=14.1 Hz), 4.87 (1H, d, J=14.1 Hz), 6.44 (1H, d, J=2.4 Hz), 6.63 (2H, d, J=8.4 Hz), 6.70 (1H, dd, J=2.4, 8.4 Hz), 6.91-7.09 (7H, m).

Example 188

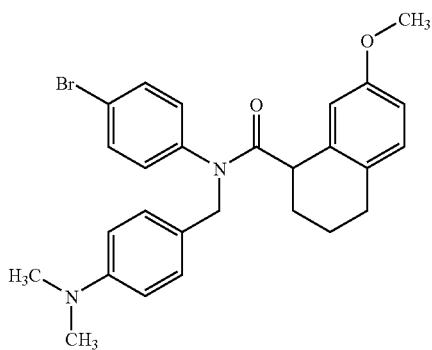

By the reaction and treatment in the same manner as in Example 162 using 4-bromoaniline (0.17 g) as a starting material instead of aniline, N-(4-bromophenyl)-N-[(4-dimethylaminophenyl)methyl]-7-methoxy-1,2,3,4-tetrahydronaphthalene-1-carboxamide (0.25 g) was obtained.

$^1$H-NMR (DMSO-d$_6$) δ: 1.36-1.47 (1H, m), 1.79-1.94 (3H, m), 2.51-2.64 (2H, m), 2.86 (6H, s), 3.55-3.60 (1H, m), 3.67 (3H, s), 4.65 (1H, d, J=14.1 Hz), 4.88 (1H, d, J=14.1 Hz), 6.44 (1H, d, J=2.4 Hz), 6.63 (2H, d, J=8.7 Hz), 6.67-6.73 (1H, m), 6.95-7.03 (3H, m), 7.16 (2H, d, J=8.4 Hz), 7.62 (2H, d, J=8.4 Hz).

Example 189

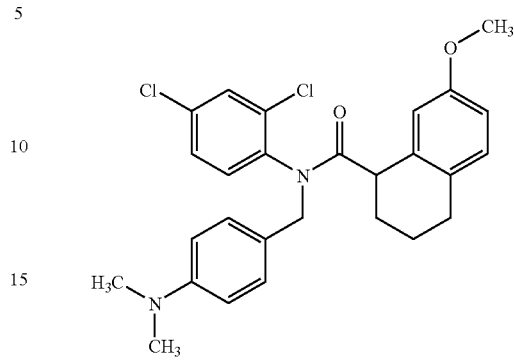

By the reaction and treatment in the same manner as in Example 162 using 2,4-dichloroaniline (0.16 g) as a starting material instead of aniline, N-(2,4-dichlorophenyl)-N-[(4-dimethylaminophenyl)methyl]-7-methoxy-1,2,3,4-tetrahydronaphthalene-1-carboxamide (0.12 g) was obtained.

$^1$H-NMR (CDCl$_3$) δ: 1.42-1.56 (1H, m), 1.75-1.86 (1H, m), 1.97-2.05 (2H, m), 2.56-2.63 (1H, m), 2.72-2.82 (1H, m), 2.94 (6H, s), 3.40-3.48 (1H, m), 3.65 (1.5H, s), 3.75 (1.5H, s), 3.82 (0.5H, d, J=14.0 Hz), 3.92 (0.5H, d, J=14.1 Hz), 5.63 (0.5H, d, J=14.1 Hz), 5.78 (0.5H, d, J=14.0 Hz), 6.41-6.42 (0.5H, m), 6.60-6.82 (4.5H, m), 6.94-7.15 (4H, m), 7.54-7.55 (1H, m).

Example 190

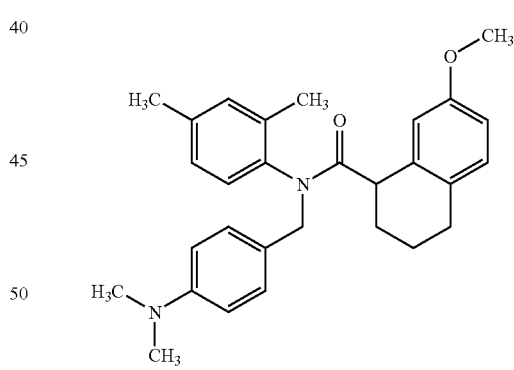

By the reaction and treatment in the same manner as in Example 162 using 2,4-dimethylaniline (0.12 g) as a starting material instead of aniline, N-[(4-dimethylaminophenyl)methyl]-N-(2,4-dimethylphenyl)-7-methoxy-1,2,3,4-tetrahydronaphthalene-1-carboxamide (0.29 g) was obtained.

$^1$H-NMR (CDCl$_3$) δ: 1.40-1.50 (1H, m), 1.80-2.07 (3H, m), 2.20 (1.8H, s), 2.22 (1.2H, s), 2.23 (1.8H, s), 2.30 (1.2H, s), 1.52-1.60 (1H, m), 1.72-1.81 (1H, m), 2.92 (6H, m), 3.45-3.57 (1H, m), 3.60 (1.8H, s), 3.73 (1.2H, s), 3.95 (0.6H, d, J=13.6 Hz), 4.30 (0.4H, d, J=13.7 Hz), 5.24 (0.4H, d, J=13.7 Hz), 5.56 (0.6H, d, J=13.6 Hz), 6.48-7.17 (10H, m).

Example 191

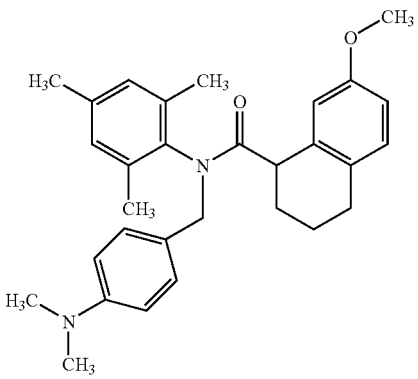

By the reaction and treatment in the same manner as in Example 162 using 2,4,6-trimethylaniline (0.14 g) as a starting material instead of aniline, N-[(4-dimethylaminophenyl)methyl]-7-methoxy-N-(2,4,6-trimethylphenyl)-1,2,3,4-tetrahydronaphthalene-1-carboxamide (0.095 g) was obtained.

$^1$H-NMR (CDCl$_3$) δ: 1.37-1.49 (1H, m), 1.69-1.93 (3H, m), 1.90 (3H, s), 2.12 (3H, s), 2.28 (3H, s), 2.52-2.62 (1H, m), 2.73-2.80 (1H, m), 2.91 (6H, s), 3.41-3.45 (1H, m), 3.69 (3H, s), 4.17 (1H, d, J=13.5 Hz), 5.5 (1H, d, J=13.5 Hz), 6.53-6.69 (4H, m), 6.80-6.84 (1H, m), 6.94 (2H, d, J=8.1 Hz), 7.11-7.25 (2H, m).

Example 192

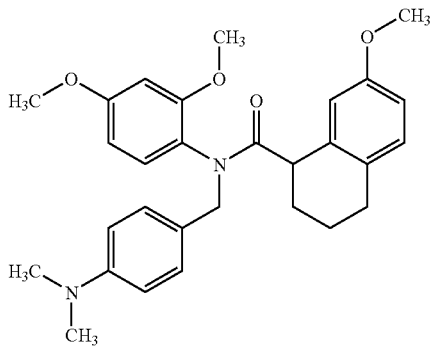

By the reaction and treatment in the same manner as in Example 162 using 2,4-dimethoxyaniline (0.15 g) as a starting material instead of aniline, N-(2,4-dimethoxyphenyl)-N-[(4-dimethylaminophenyl)methyl]-7-methoxy-1,2,3,4-tetrahydronaphthalene-1-carboxamide (0.39 g) was obtained.

$^1$H-NMR (DMSO-d$_6$) δ: 1.37-1.45 (1H, m), 1.74-1.93 (3H, m), 2.55-2.63 (2H, m), 2.85 (3H, s), 2.86 (3H, s), 3.50-3.54 (1H, m), 3.63-3.83 (9H, m), 3.89 (0.5H, d, J=14.1 Hz), 3.99-4.05 (0.5H, m), 5.16 (0.5H, d, J=14.2 Hz), 5.32 (0.5H, d, J=14.1 Hz), 6.44-6.70 (6H, m), 6.77-6.81 (1H, m), 6.92-7.03 (3H, m).

Example 193

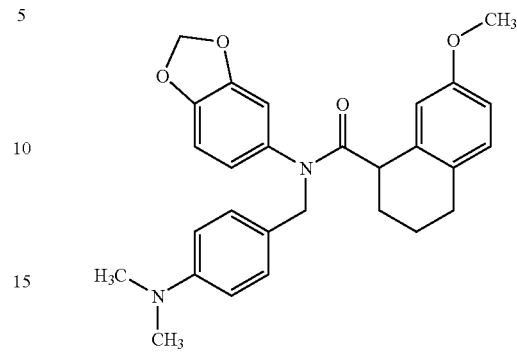

By the reaction and treatment in the same manner as in Example 162 using 5-amino-1,3-dioxaindane (0.14 g) as a starting material instead of aniline, N-(1,3-dioxaindan-5-yl)-N-[(4-dimethylaminophenyl)methyl]-7-methoxy-1,2,3,4-tetrahydronaphthalene-1-carboxamide (0.12 g) was obtained.

$^1$H-NMR (DMSO-d$_6$) δ: 1.37-1.43 (1H, m), 1.79-1.94 (3H, m), 2.55-2.64 (2H, m), 2.87 (6H, s), 3.64-3.66 (1H, m), 3.67 (3H, s), 4.55-4.62 (1H, m), 4.82-4.89 (1H, m), 6.04-6.06 (2H, m), 6.45 (1H, d, J=2.4 Hz), 6.57-6.72 (4H, m), 6.82-6.83 (1H, m), 6.89-7.03 (4H, m).

Example 194

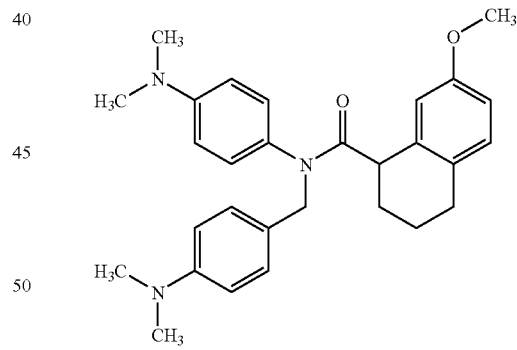

By the reaction and treatment in the same manner as in Example 162 using 4-dimethylaminoaniline (0.14 g) as a starting material instead of aniline, N-(4-dimethylaminophenyl)-N-[(4-dimethylaminophenyl)methyl]-7-methoxy-1,2,3,4-tetrahydronaphthalene-1-carboxamide (0.16 g) was obtained.

$^1$H-NMR (DMSO-d$_6$) δ: 1.30-1.40 (1H, m), 1.78-1.94 (3H, m), 2.56-2.64 (2H, m), 2.87 (12H, s), 3.64-3.68 (1H, m), 3.66 (3H, s), 4.56 (1H, d, J=14.1 Hz), 4.85 (1H, d, J=14.1 Hz), 6.45 (1H, d, J=2.4 Hz), 6.62-6.71 (5H, m), 6.93-7.02 (5H, m).

Example 195

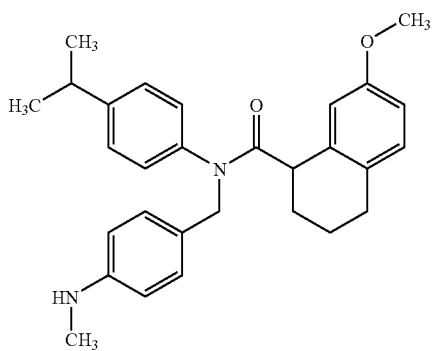

N-[(4-Aminophenyl)methyl]-N-(4-isopropylphenyl)-7-methoxy-1,2,3,4-tetrahydronaphthalene-1-carboxamide (6.47 g) was stirred using di-tert-butyl dicarbonate (in an amount as a solvent) at 80° C. for 2 hr. The reaction mixture was partitioned between saturated aqueous sodium hydrogencarbonate and ethyl acetate. The organic layer was washed with saturated brine and dried over anhydrous magnesium sulfate. The solvent was evaporated, and the residue was purified by silica gel column chromatography to give a solid (6.55 g). From the solid, 2.0 g was dissolved in dimethylformamide (3 mL), and sodium hydride (0.34 g) was added under cooling. The mixture was stirred at the same temperature for 30 min, and methyl iodide (0.28 mL) was added to the reaction mixture, which was followed by stirring for 1 hr. The reaction mixture was poured into iced water and extracted with ethyl acetate. The organic layer was washed with saturated brine and dried over magnesium sulfate. The solvent was evaporated under reduced pressure, and the obtained residue was dissolved in 4 mol/L-HCL/dioxane (5 mL). The mixture was stirred at room temperature for one day. The reaction mixture was partitioned between saturated aqueous sodium hydrogencarbonate and ethyl acetate. The organic layer was washed with saturated brine and dried over magnesium sulfate. The solvent was evaporated under reduced pressure, and the obtained residue was purified by silica gel column chromatography to give N-(4-isopropylphenyl)-7-methoxy-N-[(4-methylaminophenyl)methyl]-1,2,3,4-tetrahydronaphthalene-1-carboxamide (1.45 g).

$^1$H-NMR (DMSO-$d_6$) δ: 1.17 (3H, d, J=6.9 Hz), 1.19 (3H, d, J=6.9 Hz), 1.30-1.39 (1H, m), 1.80-1.94 (3H, m), 2.50-2.64 (2H, m), 2.61 (3H, s), 2.88 (1H, sept, J=6.9 Hz), 3.55-3.60 (1H, m), 3.67 (3H, s), 4.56 (1H, d, J=14.1 Hz), 4.87 (1H, d, J=14.1 Hz), 6.43-6.46 (3H, m), 6.68-6.72 (1H, m), 6.91-6.97 (3H, m), 7.10 (2H, d, J=8.4 Hz), 7.28 (2H, d, J=8.4 Hz).

Example 196

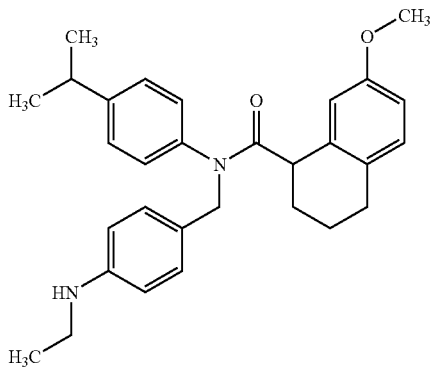

By the reaction and treatment in the same manner as in Example 162 using N-[(4-aminophenyl)methyl]-N-(4-isopropylphenyl)-7-methoxy-1,2,3,4-tetrahydronaphthalene-1-carboxamide (0.33 g) and ethyl iodide (0.07 mL) as starting materials, N-[(4-ethylaminophenyl)methyl]-N-(4-isopropylphenyl)-7-methoxy-1,2,3,4-tetrahydronaphthalene-1-carboxamide (0.29 g) was obtained.

$^1$H-NMR (DMSO-$d_6$) δ: 1.13-1.18 (9H, m), 1.31-1.35 (1H, m), 1.83-1.93 (3H, m), 2.49-2.70 (2H, m), 2.86 (1H, sept, J=6.9 Hz), 2.99 (2H, q, J=7.1 Hz), 3.39-3.58 (1H, m), 3.68 (3H, s), 4.57 (1H, d, J=14.2 Hz), 4.90 (1H, d, J=14.2 Hz), 6.47-6.50 (3H, m), 6.69 (1H, dd, J=2.5, 8.4 Hz), 6.92-6.96 (3H, m), 7.11 (2H, d, J=8.3 Hz), 7.26 (2H, d, J=8.3 Hz).

Example 197

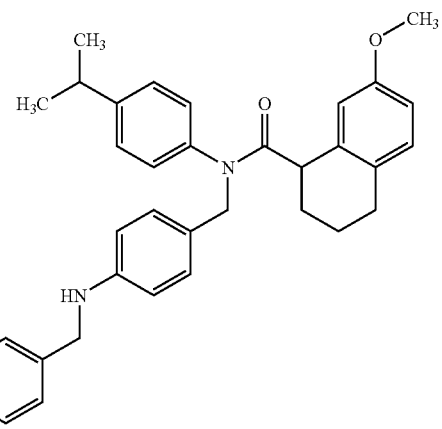

By the reaction and treatment in the same manner as in Example 162 using N-[(4-aminophenyl)methyl]-N-(4-isopropylphenyl)-7-methoxy-1,2,3,4-tetrahydronaphthalene-1-carboxamide (0.33 g) and benzyl bromide (0.1 mL) as starting materials, N-[(4-benzylaminophenyl)methyl]-N-(4-isopropylphenyl)-7-methoxy-1,2,3,4-tetrahydronaphthalene-1-carboxamide (0.13 g) was obtained.

melting point: 135-138° C.

Example 198

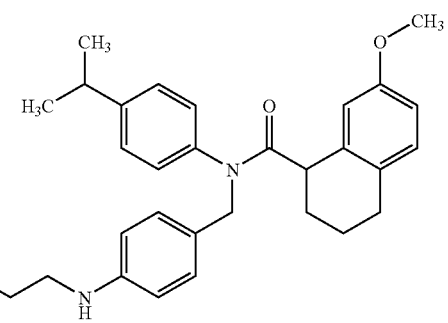

By the reaction and treatment in the same manner as in Example 162 using N-[(4-aminophenyl)methyl]-N-(4-isopropylphenyl)-7-methoxy-1,2,3,4-tetrahydronaphthalene-1-carboxamide (0.41 g) and pentyl bromide (0.14 mL) as starting materials, N-(4-isopropylphenyl)-7-methoxy-N-[(4-pentylaminophenyl)methyl]-1,2,3,4-tetrahydronaphthalene-1-carboxamide (0.19 g) was obtained.

$^1$H-NMR (CDCl$_3$) δ: (0.90-(0.95 (3H, m), 1.23 (6H, d, J=6.9 Hz), 1.36-1.64 (7H, m), 1.85-2.04 (3H, m), 2.54-2.61 (1H, m), 2.71-2.92 (2H, m), 3.08 (2H, t, J=7.1 Hz), 3.59 (1H, brs), 3.66-3.71 (1H, m), 3.69 (3H, s), 4.55 (1H, d, J=13.9 Hz), 5.05 (1H, d, J=13.9 Hz), 6.49-6.53 (3H, m), 6.67 (1H, dd, J=2.6, 8.3 Hz), 6.93-6.98 (3H, m), 7.05-7.08 (2H, m), 7.16 (2H, d, J=8.3 Hz).

Example 199

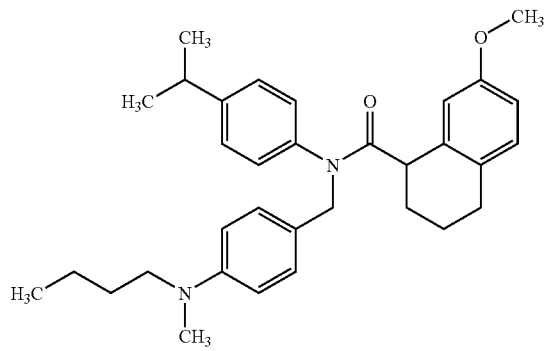

N-(4-Isopropylphenyl)-7-methoxy-N-[(4-methylaminophenyl)methyl]-1,2,3,4-tetrahydronaphthalene-1-carboxamide (0.77 g) was dissolved in ethanol (8 mL), and butyl aldehyde (250 mg) and sodium cyanoborohydride (0.22 g) were added. Acetic acid was added to this solution to pH 5-6, and the mixture was stirred at room temperature for 2 hr. The reaction mixture was partitioned between saturated aqueous sodium hydrogencarbonate and ethyl acetate. The organic layer was washed with saturated brine and dried over magnesium sulfate. The solvent was evaporated under reduced pressure and the obtained residue was purified by silica gel column chromatography to give N-{[4-(butylmethylamino)phenyl]methyl}-N-(4-isopropylphenyl)-7-methoxy-1,2,3,4-tetrahydronaphthalene-1-carboxamide (0.51 g).

$^1$H-NMR (CDCl$_3$) δ: 0.94 (3H, t, J=7.3 Hz), 1.22 (6H, d, J=6.9 Hz), 1.22-1.57 (5H, m), 1.87-2.02 (3H, m), 2.52-2.60 (1H, m), 2.73-2.86 (2H, m), 2.89 (3H, s), 3.25 (2H, t, J=6.9 Hz), 3.67 (3H, s), 3.67-3.73 (1H, m), 4.54 (1H, d, J=13.8 Hz), 5.08 (1H, d, J=13.8 Hz), 6.53 (1H, d, J=2.4 Hz), 6.58 (2H, d, J=8.7 Hz), 6.65 (1H, dd, J=2.4, 8.4 Hz), 6.92 (1H, d, J=8.4 Hz), 6.99 (2H, d, J=8.4 Hz), 7.11-7.22 (4H, m).

Example 200

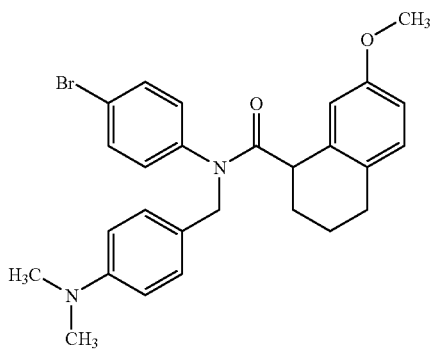

7-Methoxy-1,2,3,4-tetrahydronaphthalene-1-carboxylic acid (0.47 g) and (4-bromophenyl)[(4-dimethylaminophenyl)methyl]-amine (0.70 g) as starting materials were reacted and treated in the same manner as in Example 12. The obtained solid was dissolved in ethyl acetate (4 mL). Thereto was added 4 mol/L-HCl/ethyl acetate (0.35 mL), and the precipitated solid was collected by filtration to give N-(4-bromophenyl)-N-[(4-dimethylaminophenyl)methyl]-7-methoxy-1,2,3,4-tetrahydronaphthalene-1-carboxamide hydrochloride (0.65 g). melting point: 104-113° C.

Example 201

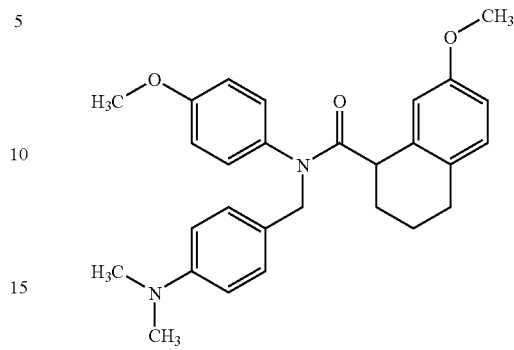

By the reaction and treatment in the same manner as in Example 200 using 7-methoxy-1,2,3,4-tetrahydronaphthalene-1-carboxylic acid (0.50 g) and [(4-dimethylaminophenyl)methyl](4-methoxyphenyl)amine (0.62 g) as starting materials, N-[(4-dimethylaminophenyl)methyl]-7-methoxy-N-(4-methoxyphenyl)-1,2,3,4-tetrahydronaphthalene-1-carboxamide hydrochloride (0.79 g) was obtained. melting point: 152° C.

Example 202

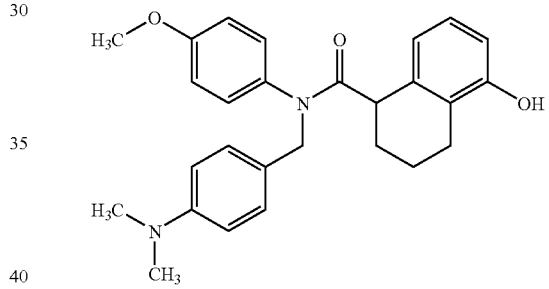

By the reaction and treatment in the same manner as in Example 12 using 5-benzyloxy-1,2,3,4-tetrahydronaphthalene-1-carboxylic acid (0.57 g) and [(4-dimethylaminophenyl)methyl]-4-methoxyphenyl)amine (0.51 g) as starting materials, 5-benzyloxy-N-[(4-dimethylaminophenyl)methyl]-N-(4-methoxyphenyl)-1,2,3,4-tetrahydronaphthalene-1-carboxamide (0.83 g) was obtained. By the reaction and treatment in the same manner as in Example 17 using this compound, N-[(4-dimethylaminophenyl)methyl]-5-hydroxy-N-(4-methoxyphenyl)-1,2,3,4-tetrahydronaphthalene-1-carboxamide (0.33 g) was obtained. melting point: 195-197° C.

Example 203

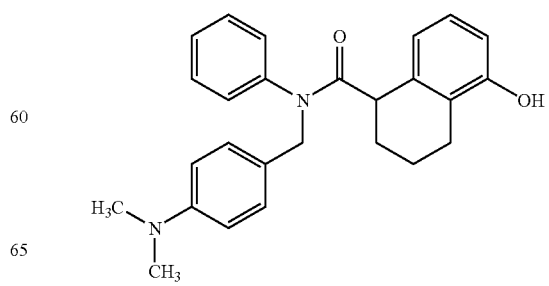

By the reaction and treatment in the same manner as in Example 12 using 5-benzyloxy-1,2,3,4-tetrahydronaphthalene-1-carboxylic acid (0.57 g) and [(4-dimethylaminophenyl)methyl]phenylamine (0.61 g) as starting materials, 5-benzyloxy-N-[(4-dimethylaminophenyl)methyl]-N-phenyl-1,2,3,4-tetrahydronaphthalene-1-carboxamide (0.80 g) was obtained. By the reaction and treatment in the same manner as in Example 17 using this compound, N-[(4-dimethylaminophenyl)methyl]-5-hydroxy-N-phenyl-1,2,3,4-tetrahydronaphthalene-1-carboxamide (0.083 g) was obtained. melting point: 138-143° C.

Example 204

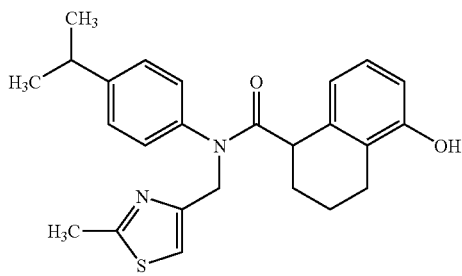

By the reaction and treatment in the same manner as in Example 132 using 5 benzyloxy-N-(4-isopropylphenyl)-1,2,3,4-tetrahydronaphthalene-1-carboxamide (0.65 g) and 4-(chloromethyl)-2-methylthiazole (0.30 g) as starting materials, 5-benzyloxy-N-(4-isopropylphenyl)-N-[(2-methylthiazol-4-yl)methyl]-1,2,3,4-tetrahydronaphthalene-1-carboxamide (0.58 g) was obtained. By the reaction and treatment in the same manner as in Example 133 using this compound (0.51 g), 5 hydroxy-N-(4-isopropylphenyl)-N-[(2-methylthiazol-4-yl)methyl]-1,2,3,4-tetrahydronaphthalene-1-carboxamide (0.22 g) was obtained.

$^1$H-NMR (CDCl$_3$) δ: 1.22 (6H, d, J=6.9 Hz), 1.38-1.48 (1H, m), 1.82-1.90 (1H, m), 1.92-2.00 (2H, m), 2.58-2.60 (2H, m), 2.68 (3H, s), 2.89 (1H, sept, J=6.9 Hz), 3.80-3.84 (1H, m), 5.01 (2H, s), 6.23 (1H, d, J=7.8 Hz), 6.48 (1H, d, J=7.8 Hz), 6.72 (1H, d, J=7.8 Hz), 7.11 (1H, s), 7.17-7.25 (4H, m), 7.69 (1H, s).

Example 205

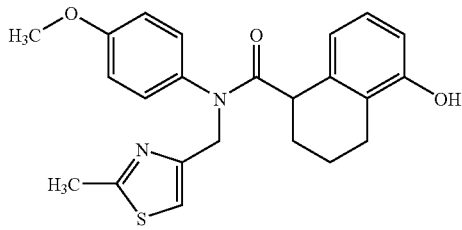

By the reaction and treatment in the same manner as in Example 132 using 5 benzyloxy-N-(4-methoxyphenyl)-1,2,3,4-tetrahydronaphthalene-1-carboxamide (0.63 g) and 4-(chloromethyl)-2-methylthiazole (0.30 g) as starting materials, 5 benzyloxy-N-(4-methoxyphenyl)-N-[(2-methylthiazol-4-yl)methyl]-1,2,3,4-tetrahydronaphthalene-1-carboxamide (0.64 g) was obtained. By the reaction and treatment in the same manner as in Example 133 using this compound (0.50 g), 5-hydroxy-N-(4-methoxyphenyl)-N-1(2-methylthiazol-4-yl)methyl]-1,2,3,4-tetrahydronaphthalene-1-carboxamide (0.31 g) was obtained.

$^1$H-NMR (CDCl$_3$) δ: 1.39-1.45 (1H, m), 1.79-1.84 (1H, m), 1.90-2.00 (2H, m), 2.55-2.59 (2H, m), 2.69 (3H, s), 3.78-3.83 (1H, m), 3.79 (3H, s), 4.97 (1H, d, J=14.9 Hz), 5.02 (1H, d, J=14.9 Hz), 6.25 (1H, d, J=7.8 Hz), 6.48 (1H, d, J=7.8 Hz), 6.74 (1H, t, J=7.8 Hz), 6.86-6.88 (2H, m), 7.08 (1H, s), 7.13-7.23 (2H, m), 7.34 (1H, s).

Example 206

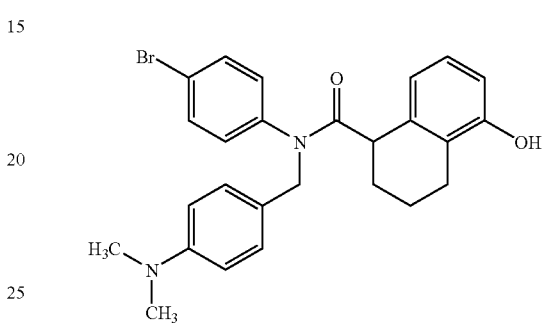

By the reaction and treatment in the same manner as in Example 12 using 5-benzyloxy-1,2,3,4-tetrahydronaphthalene-1-carboxylic acid (0.57 g) and (4-bromophenyl)[(4-dimethylaminophenyl)methyl]amine (0.61 g) as starting materials, 5-benzyloxy-N-(4-bromophenyl)-N-[(4-dimethylaminophenyl)methyl[-1,2,3,4-tetrahydronaphthalene-1-carboxamide (1.14 g) was obtained. By the reaction and treatment in the same manner as in Example 133 using this compound, N-(4-bromophenyl)-N-[(dimethylaminophenyl)methyl]-5-hydroxy-1,2,3,4-tetrahydronaphthalene-1-carboxamide (0.23 g) was obtained. melting point: 218-220° C.

Example 207

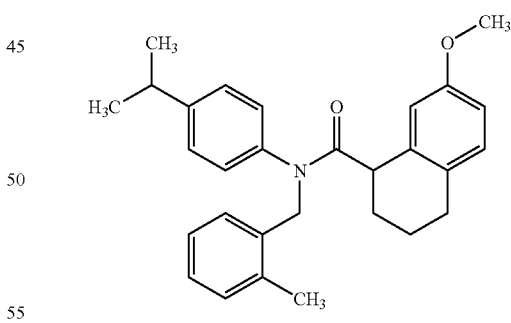

To a solution of 2-tolualdehyde (120 mg) in 1,2-dichloroethane (5 mL) were added 4-isopropylaniline (171 μL), acetic acid (57.2 μL) and sodium triacetoxyborohydride (445 mg), and the mixture was stirred for one day. Saturated aqueous sodium hydrogencarbonate (2 mL) was added to the reaction solution, and the mixture was applied to ExtruteNT-3 (Merck) column and eluted with ethyl acetate (10 mL) 10 min later. The obtained solution was treated with Sep-Pak Plus Silica (Waters), and the obtained solution was concentrated under reduced pressure. The obtained residue was dissolved in methylene chloride (5 mL), and 4-dimethylaminopyridine (30 mg), 7-methoxy-1,2,3,4-tetrahydronaphthalene-1-carboxylic acid (250 mg) and N-cyclohexylcarbodiimide-N'-methylpolystyrene HL (1.5 g) were added. The mixture was stirred for one day, and the reaction mixture was filtrated under reduced pressure. The solvent was evaporated under reduced pressure, and THF (5 mL) and Ambersep 900 OH (800 mg) were added. The mixture was stirred for 3 hr. The reaction mixture was filtrated under reduced pressure. Amberlyst 15 (1 g) was added, and the mixture was stirred for one day. The reaction mixture was filtrated under reduced pressure, and the solvent was evaporated under reduced pressure. The residue was purified by silica gel column chromatography to give N-(4-isopropylphenyl)-7-methoxy-N-(2-tolylethyl)-1,2,3,4-tetrahydronaphthalene-1-carboxamide (106 mg).

MS (ESI) m/z: 428 [MH]$^+$

Example 208

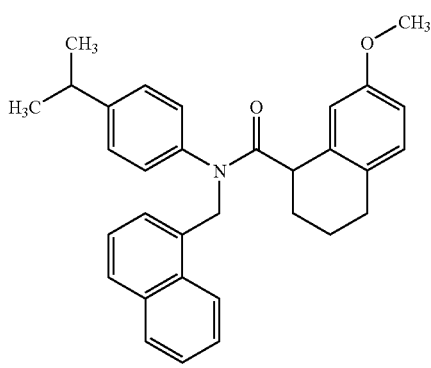

By the reaction and treatment in the same manner as in Example 207 using 1-naphthaldehyde (156 mg) as a starting material instead of 2-tolualdehyde, N-(4-isopropylphenyl)-7-methoxy-N-[(1-naphthyl)methyl]-1,2,3,4-tetrahydronaphthalene-1-carboxamide (258.9 mg) was obtained.

MS (ESI) m/z: 464 [MH]$^+$

Example 209

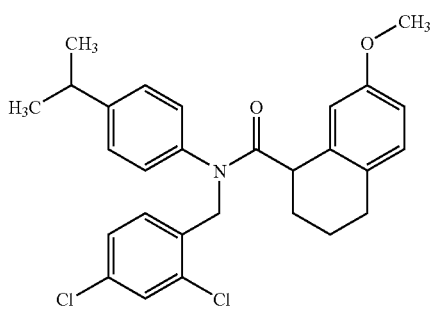

By the reaction and treatment in the same manner as in Example 207 using 2,4-dichlorobenzaldehyde (175 mg) as a starting material instead of 2-tolualdehyde, N-[(2,4-dichlorophenyl)methyl]-N-(4-isopropylphenyl)-7-methoxy-1,2,3,4-tetrahydronaphthalene-1-carboxamide (258.8 mg) was obtained.

MS (ESI) m/z: 482 [MH]$^+$

Example 210

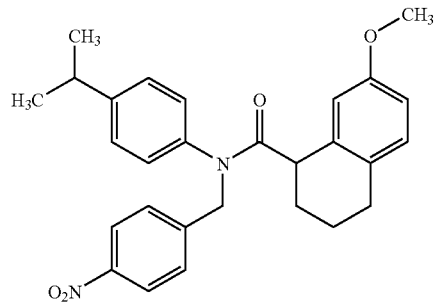

By the reaction and treatment in the same manner as in Example 207 using 4-nitrobenzaldehyde (151 mg) as a starting material instead of 2-tolualdehyde, N-(4-isopropylphenyl)-7-methoxy-N-[(4-nitrophenyl)methyl]-1,2,3,4-tetrahydronaphthalene-1-carboxamide (218.9 mg) was obtained.

MS (ESI) m/z: 459 [MH]$^+$

Example 211

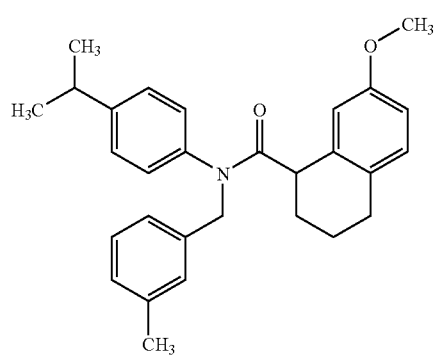

By the reaction and treatment in the same manner as in Example 207 using 3-tolualdehyde (120 mg) as a starting material instead of 2-tolualdehyde, N-(4-isopropylphenyl)-7-methoxy-N-(3-tolylmethyl)-1,2,3,4-tetrahydronaphthalene-1-carboxamide (145.4 mg) was obtained. MS (ESI) m/z: 428 [MH]$^+$ Example 212

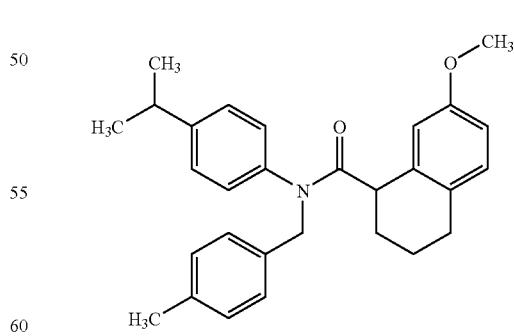

By the reaction and treatment in the same manner as in Example 207 using 4-tolualdehyde (120 mg) as a starting material instead of 2-tolualdehyde, N-(4-isopropylphenyl)-7-methoxy-N-(4-tolylmethyl)-1,2,3,4-tetrahydronaphthalene-1-carboxamide (116.4 mg) was obtained.

MS (ESI) m/z: 428 [MH]$^+$

Example 213

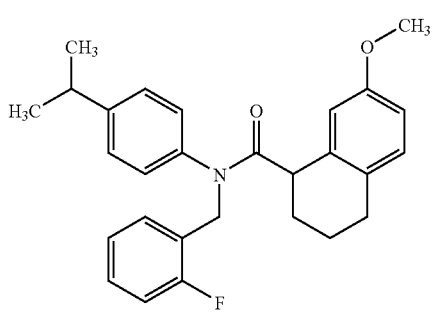

By the reaction and treatment in the same manner as in Example 207 using 2-fluorobenzaldehyde (124 mg) as a starting material instead of 2-tolualdehyde, N-[(2-fluorophenyl)methyl]-N-(4-isopropylphenyl)-7-methoxy-1,2,3,4-tetrahydronaphthalene-1-carboxamide (148 mg) was obtained.
MS (ESI) m/z: 432 [MH]+

Example 214

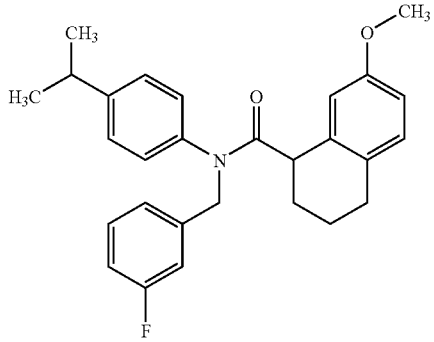

By the reaction and treatment in the same manner as in Example 207 using 3-fluorobenzaldehyde (124 mg) as a starting material instead of 2-tolualdehyde, N-[(3-fluorophenyl)methyl]-N-(4-isopropylphenyl)-7-methoxy-1,2,3,4-tetrahydronaphthalene-1-carboxamide (190.9 mg) was obtained.
MS (ESI) m/z: 432 [MH]+

Example 215

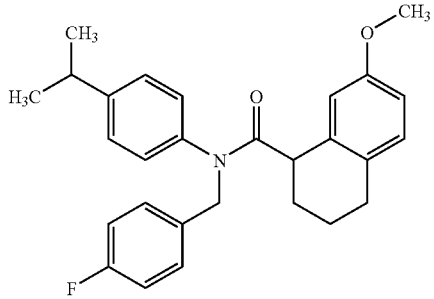

By the reaction and treatment in the same manner as in Example 207 using 4-fluorobenzaldehyde (124 mg) as a starting material instead of 2-tolualdehyde, N-[(4-fluorophenyl)methyl]-N-(4-isopropylphenyl)-7-methoxy-1,2,3,4-tetrahydronaphthalene-1-carboxamide (184.2 mg) was obtained.
MS (ESI) m/z: 432 [MH]+

Example 216

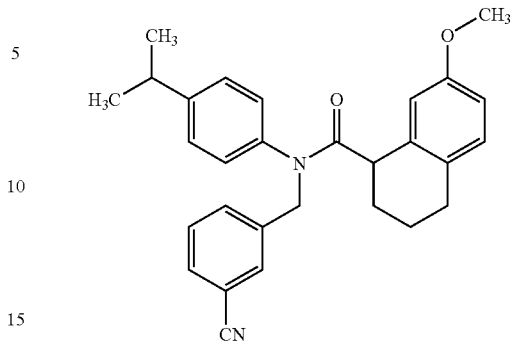

By the reaction and treatment in the same manner as in Example 207 using 3-cyanobenzaldehyde (131 mg) as a starting material instead of 2-tolualdehyde, N-[(3-cyanophenyl)methyl]-N-(4-isopropylphenyl)-7-methoxy-1,2,3,4-tetrahydronaphthalene-1-carboxamide (191 mg) was obtained.
MS (ESI) m/z: 439 [MH]+

Example 217

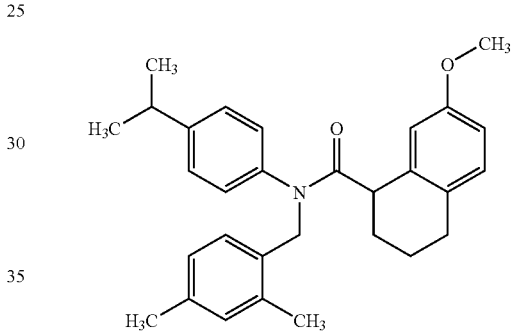

By the reaction and treatment in the same manner as in Example 207 using 2,4-dimethylbenzaldehyde (134 mg) as a starting material instead of 2-tolualdehyde, N-[(2,4-dimethylphenyl)methyl]-N-(4-isopropylphenyl)-7-methoxy-1,2,3,4-tetrahydronaphthalene-1-carboxamide (119.4 mg) was obtained.
MS (ESI) m/z: 442 [MH]+

Example 218

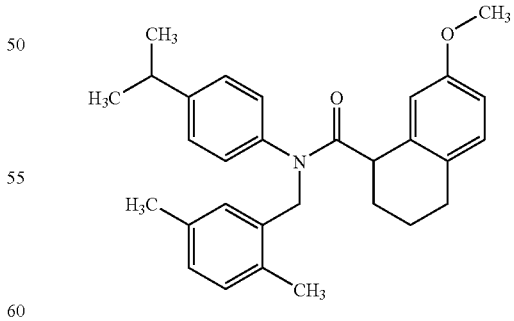

By the reaction and treatment in the same manner as in Example 207 using 2,5-dimethylbenzaldehyde (134 mg) as a starting material instead of 2-tolualdehyde, N-[(2,5-dimethylphenyl)methyl]-N-(4-isopropylphenyl)-7-methoxy-1,2,3,4-tetrahydronaphthalene-1-carboxamide (123.3 mg) was obtained.
MS (ESI) m/z: 442 [MH]+

Example 219

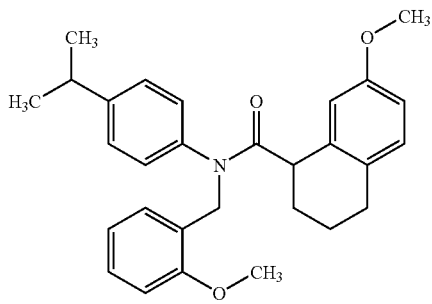

By the reaction and treatment in the same manner as in Example 207 using 2-methoxybenzaldehyde (136 mg) as a starting material instead of 2-tolualdehyde, N-(4-isopropylphenyl)-7-methoxy-N-[(2-methoxyphenyl)methyl]-1,2,3,4-tetrahydronaphthalene-1-carboxamide (190.9 mg) was obtained.
MS (ESI) m/z: 444 [MH]$^+$

Example 220

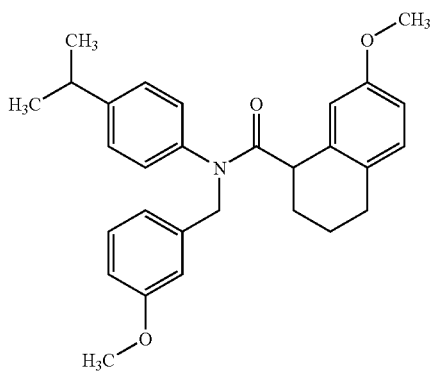

By the reaction and treatment in the same manner as in Example 207 using 3-methoxybenzaldehyde (136 mg) as a starting material instead of 2-tolualdehyde, N-(4-isopropylphenyl)-N-[(3-methoxyphenyl)methyl]-7-methoxy-1,2,3,4-tetrahydronaphthalene-1-carboxamide (173.1 mg) was obtained.
MS (ESI) m/z: 444 [MH]$^+$

Example 221

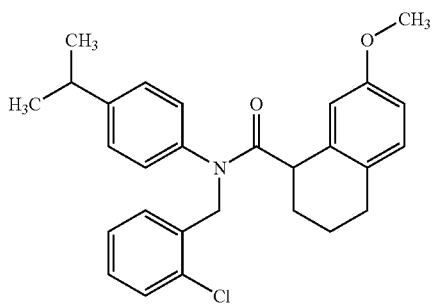

By the reaction and treatment in the same manner as in Example 207 using 2-chlorobenzaldehyde (141 mg) as a starting material instead of 2-tolualdehyde, N-[(2-chlorophenyl)methyl]-N-(4-isopropylphenyl)-7-methoxy-1,2,3,4-tetrahydronaphthalene-1-carboxamide (117.5 mg) was obtained.
MS (ESI) m/z: 448 [MH]$^+$

Example 222

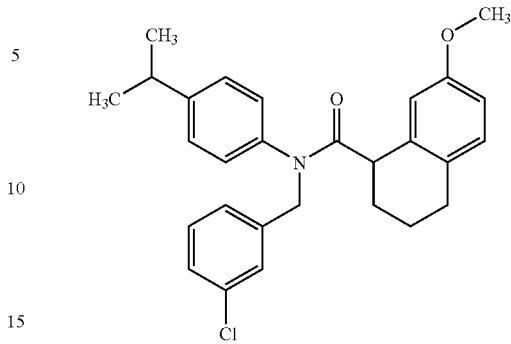

By the reaction and treatment in the same manner as in Example 207 using 3-chlorobenzaldehyde (141 mg) as a starting material instead of 2-tolualdehyde, N-[(3-chlorophenyl)methyl]-N-(4-isopropylphenyl)-7-methoxy-1,2,3,4-tetrahydronaphthalene-1-carboxamide (197.6 mg) was obtained.
MS (ESI) m/z: 448 [MH]$^+$

Example 223

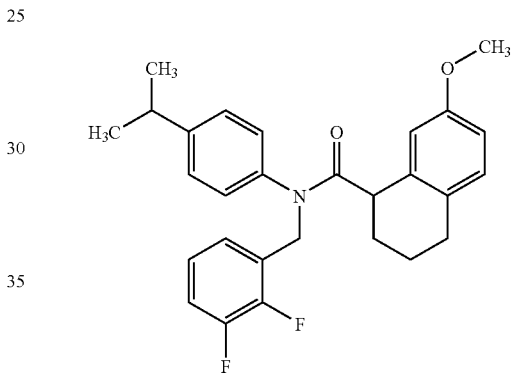

By the reaction and treatment in the same manner as in Example 207 using 2,3-difluorobenzaldehyde (142 mg) as a starting material instead of 2-tolualdehyde, N-[(2,3-difluorophenyl)methyl]-N-(4-isopropylphenyl)-7-methoxy-1,2,3,4-tetrahydronaphthalene-1-carboxamide (130.2 mg) was obtained.
MS (ESI) m/z: 450 [MH]$^+$

Example 224

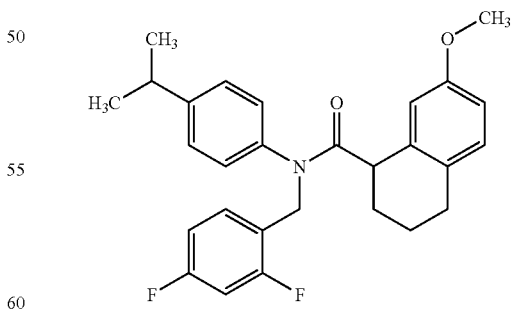

By the reaction and treatment in the same manner as in Example 207 using 2,4-difluorobenzaldehyde (142 mg) as a starting material instead of 2-tolualdehyde, N-[(2,4-difluorophenyl)methyl]-N-(4-isopropylphenyl)-7-methoxy-1,2,3,4-tetrahydronaphthalene-1-carboxamide (179.1 mg) was obtained.
MS (ESI) m/z: 450 [MH]$^+$

Example 225

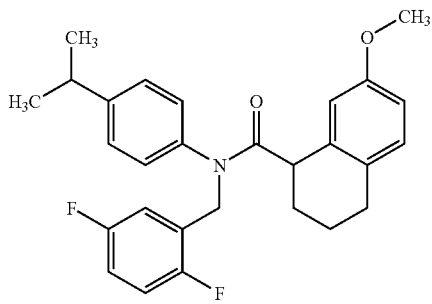

By the reaction and treatment in the same manner as in Example 207 using 2,5-difluorobenzaldehyde (142 mg) as a starting material instead of 2-tolualdehyde, N-[(2,5-difluorophenyl)methyl]-N-(4-isopropylphenyl)-7-methoxy-1,2,3,4-tetrahydronaphthalene-1-carboxamide (212.6 mg) was obtained.

MS (ESI) m/z: 450[MH]$^+$

Example 226

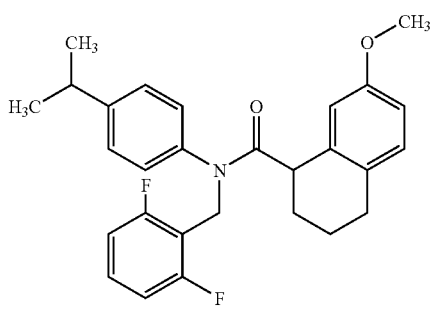

By the reaction and treatment in the same manner as in Example 207 using 2,6-difluorobenzaldehyde (142 mg) as a starting material instead of 2-tolualdehyde, N-[(2,6-difluorophenyl)methyl]-N-(4-isopropylphenyl)-7-methoxy-1,2,3,4-tetrahydronaphthalene-1-carboxamide (87.8 mg) was obtained.

MS (ESI) m/z: 450 [MH]$^+$

Example 227

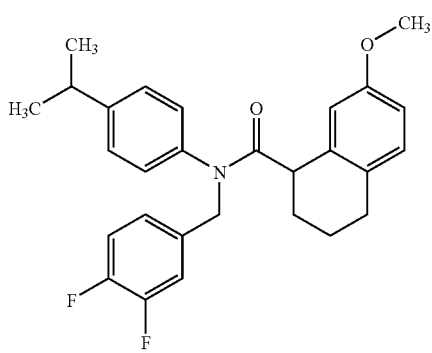

By the reaction and treatment in the same manner as in Example 207 using 3,4-difluorobenzaldehyde (142 mg) as a starting material instead of 2-tolualdehyde, N-[(3,4-difluorophenyl)methyl]-N-(4-isopropylphenyl)-7-methoxy-1,2,3,4-tetrahydronaphthalene-1-carboxamide (126.6 mg) was obtained.

MS (ESI) m/z: 450 [MH]$^+$

Example 228

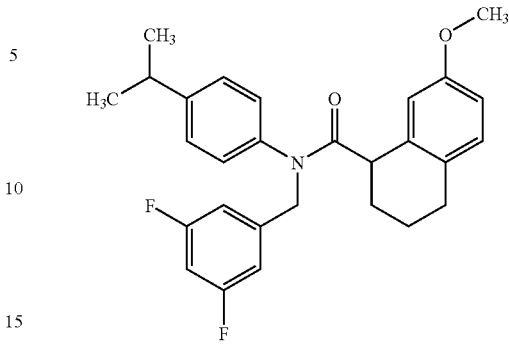

By the reaction and treatment in the same manner as in Example 207 using 3,5-difluorobenzaldehyde (142 mg) as a starting material instead of 2-tolualdehyde, N-[(3,5-difluorophenyl)methyl]-N-(4-isopropylphenyl)-7-methoxy-1,2,3,4-tetrahydronaphthalene-1-carboxamide (151 mg) was obtained.

MS (ESI) m/z: 450 [MH]$^+$

Example 229

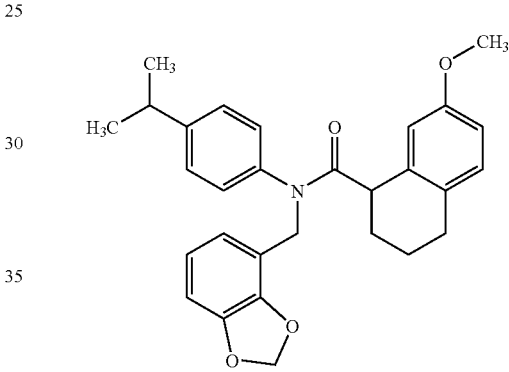

By the reaction and treatment in the same manner as in Example 207 using 2,3-methylenedioxybenzaldehyde (150 mg) as a starting material instead of 2-tolualdehyde, N-[(1,3-dioxaindan-4-yl)methyl]-N-(4-isopropylphenyl)-7-methoxy-1,2,3,4-tetrahydronaphthalene-1-carboxamide (184.4 mg) was obtained.

MS (ESI) m/z: 458 [MH]$^+$

Example 230

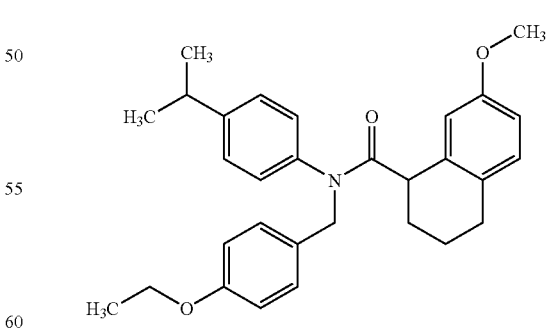

By the reaction and treatment in the same manner as in Example 207 using 4-ethoxybenzaldehyde (150 mg) as a starting material instead of 2-tolualdehyde, N-[(4-ethoxyphenyl)methyl]-N-(4-isopropylphenyl)-7-methoxy-1,2,3,4-tetrahydronaphthalene-1-carboxamide (177.4 mg) was obtained.

MS (ESI) m/z: 458 [MH]$^+$

Example 231

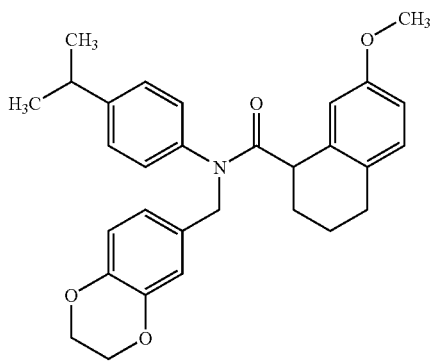

By the reaction and treatment in the same manner as in Example 207 using 3,4-ethylenedioxybenzaldehyde (164 mg) as a starting material instead of 2-tolualdehyde, N-(4-isopropylphenyl)-7-methoxy-N-[(4-oxachroman-6-yl)methyl]-1,2,3,4-tetrahydronaphthalene-1-carboxamide (167.6 mg) was obtained.

MS (ESI) m/z: 472 [MH]+

Example 232

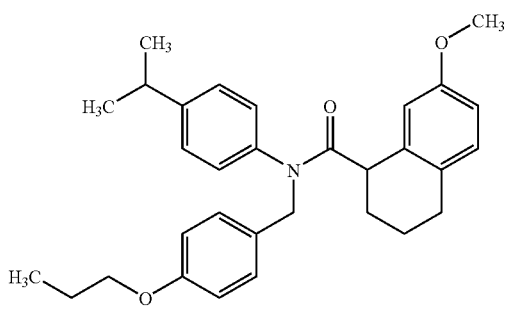

By the reaction and treatment in the same manner as in Example 207 using 4-propoxybenzaldehyde (164 mg) as a starting material instead of 2-tolualdehyde, N-(4-isopropylphenyl)-7-methoxy-N-[(4-propoxyphenyl)methyl]-1,2,3,4-tetrahydronaphthalene-1-carboxamide (172.6 mg) was obtained.

MS (ESI) m/z: 472 [MH]+

Example 233

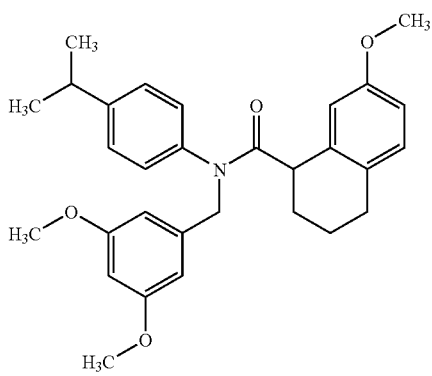

By the reaction and treatment in the same manner as in Example 207 using 3,5-dimethoxybenzaldehyde (166 mg) as a starting material instead of 2-tolualdehyde, N-[(3,5-dimethoxyphenyl)methyl]-N-(4-isopropylphenyl)-7-methoxy-1,2,3,4-tetrahydronaphthalene-1-carboxamide (199.9 mg) was obtained.

MS (ESI) m/z: 474 [MH]+

Example 234

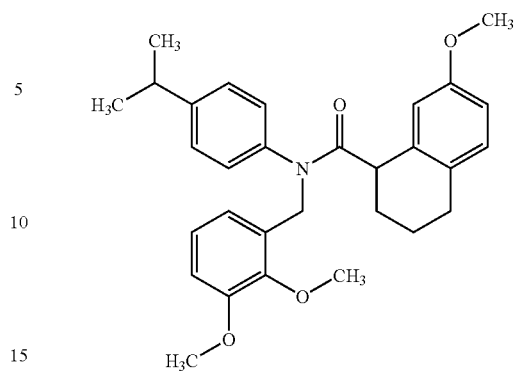

By the reaction and treatment in the same manner as in Example 207 using 2,3-dimethoxybenzaldehyde (166 mg) as a starting material instead of 2-tolualdehyde, N-[(2,3-dimethoxyphenyl)methyl]-N-(4-isopropylphenyl)-7-methoxy-1,2,3,4-tetrahydronaphthalene-1-carboxamide (332 mg) was obtained.

MS (ESI) m/z: 474 [MH]+

Example 235

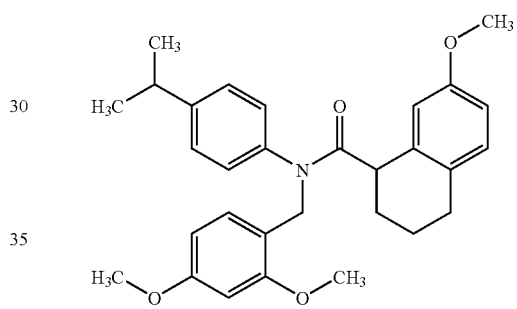

By the reaction and treatment in the same manner as in Example 207 using 2,4-dimethoxybenzaldehyde (166 mg) as a starting material instead of 2-tolualdehyde, N-[(2,4-dimethoxyphenyl)methyl]-N-(4-isopropylphenyl)-7-methoxy-1,2,3,4-tetrahydronaphthalene-1-carboxamide (69.3 mg) was obtained.

MS (ESI) m/z: 474 [MH]+

Example 236

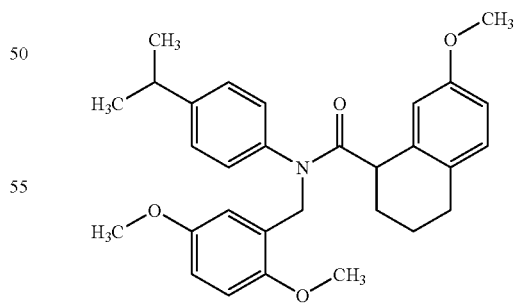

By the reaction and treatment in the same manner as in Example 207 using 2,5-dimethoxybenzaldehyde (166 mg) as a starting material instead of 2-tolualdehyde, N-[(2,5-dimethoxyphenyl)methyl]-N-(4-isopropylphenyl)-7-methoxy-1,2,3,4-tetrahydronaphthalene-1-carboxamide (122.5 mg) was obtained.

MS (ESI) m/z: 474 [MH]+

Example 237

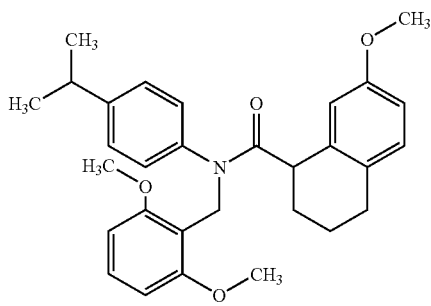

By the reaction and treatment in the same manner as in Example 207 using 2,6-dimethoxybenzaldehyde (166 mg) as a starting material instead of 2-tolualdehyde, N-[(2,6-dimethoxyphenyl)methyl]-N-(4-isopropylphenyl)-7-methoxy-1,2,3,4-tetrahydronaphthalene-1-carboxamide (248.9 mg) was obtained.

MS (ESI) m/z: 474 [MH]$^+$

Example 238

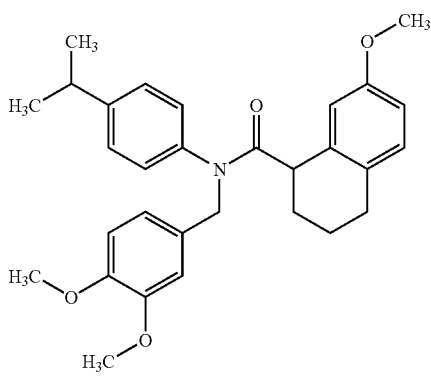

By the reaction and treatment in the same manner as in Example 207 using 3,4-dimethoxybenzaldehyde (166 mg) as a starting material instead of 2-tolualdehyde, N-[(3,4-dimethoxyphenyl)methyl]-N-(4-isopropylphenyl)-7-methoxy-1,2,3,4-tetrahydronaphthalene-1-carboxamide (96.1 mg) was obtained.

MS (ESI) m/z: 474 [MH]$^+$

Example 239

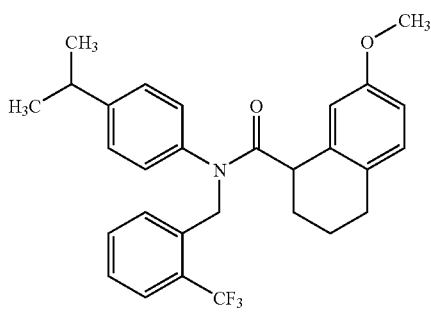

By the reaction and treatment in the same manner as in Example 207 using 2-trifluoromethylbenzaldehyde (174 mg) as a starting material instead of 2-tolualdehyde, N-(4-isopropylphenyl)-7-methoxy-N-[(2-trifluoromethylphenyl)methyl]-1,2,3,4-tetrahydronaphthalene-1-carboxamide (179.1 mg) was obtained.

MS (ESI) m/z: 482 [MH]$^+$

Example 240

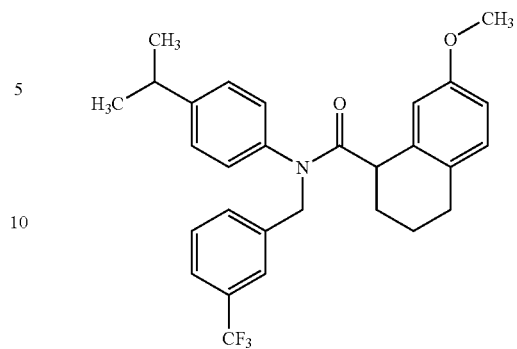

By the reaction and treatment in the same manner as in Example 207 using 3-trifluoromethylbenzaldehyde (174 mg) as a starting material instead of 2-tolualdehyde, N-(4-isopropylphenyl)-7-methoxy-N-[(3-trifluoromethylphenyl)methyl]-1,2,3,4-tetrahydronaphthalene-1-carboxamide (186.2 mg) was obtained.

MS (ESI) m/z: 482 [MH]$^+$

Example 241

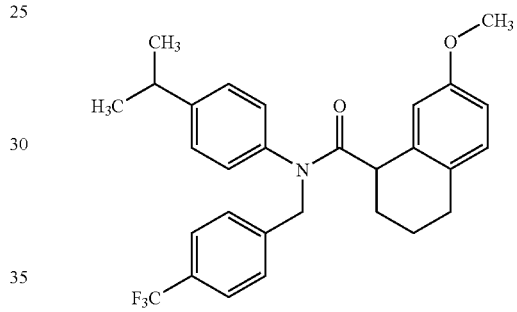

By the reaction and treatment in the same manner as in Example 207 using 4-trifluoromethylbenzaldehyde (174 mg) as a starting material instead of 2-tolualdehyde, N-(4-isopropylphenyl)-7-methoxy-N-[(4-trifluoromethylphenyl)methyl]-1,2,3,4-tetrahydronaphthalene-1-carboxamide (207.9 mg) was obtained.

MS (ESI) m/z: 482 [MH]$^+$

Example 242

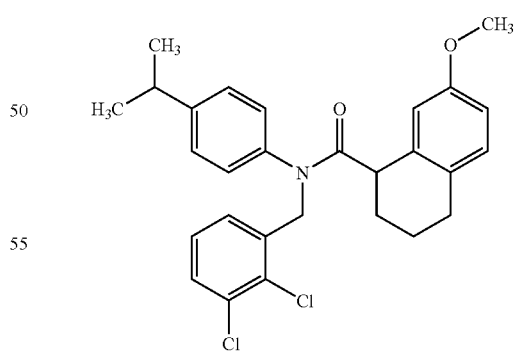

By the reaction and treatment in the same manner as in Example 207 using 2,3-dichlorobenzaldehyde (175 mg) as a starting material instead of 2-tolualdehyde, N-[(2,3-dichlorophenyl)methyl]-N-(4-isopropylphenyl)-7-methoxy-1,2,3,4-tetrahydronaphthalene-1-carboxamide (302.3 mg) was obtained.

MS (ESI) m/z: 482 [MH]$^+$

Example 243

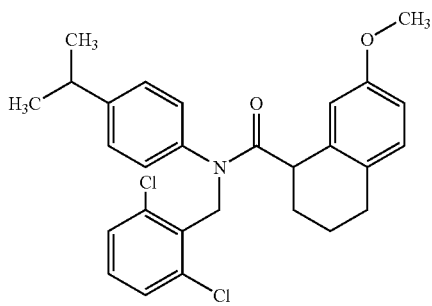

By the reaction and treatment in the same manner as in Example 207 using 2,6-dichlorobenzaldehyde (175 mg) as a starting material instead of 2-tolualdehyde, N-[(2,6-dichlorophenyl)methyl]-N-(4-isopropylphenyl)-7-methoxy-1,2,3,4-tetrahydronaphthalene-1-carboxamide (93.1 mg) was obtained.

MS (ESI) m/z: 482 [MH]$^+$

Example 244

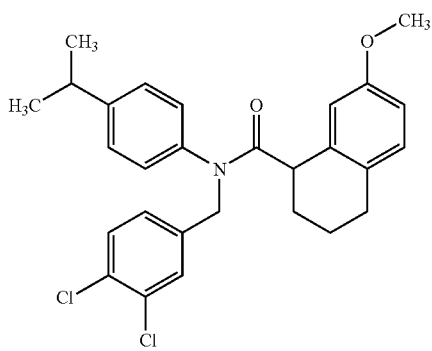

By the reaction and treatment in the same manner as in Example 207 using 3,4-dichlorobenzaldehyde (175 mg) as a starting material instead of 2-tolualdehyde, N-[(3,4-dichlorophenyl)methyl]-N-(4-isopropylphenyl)-7-methoxy-1,2,3,4-tetrahydronaphthalene-1-carboxamide (288.2 mg) was obtained.

MS (ESI) m/z: 482 [MH]$^+$

Example 245

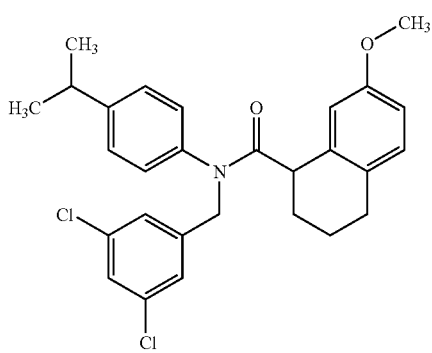

By the reaction and treatment in the same manner as in Example 207 using 3,5-dichlorobenzaldehyde (175 mg) as a starting material instead of 2-tolualdehyde, N-[(3,5-dichlorophenyl)methyl]-N-(4-isopropylphenyl)-7-methoxy-1,2,3,4-tetrahydronaphthalene-1-carboxamide (304.4 mg) was obtained.

MS (ESI) m/z: 482 [MH]$^+$

Example 246

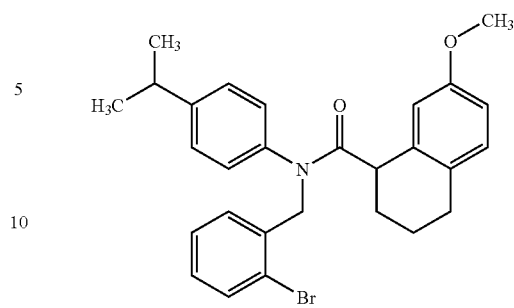

By the reaction and treatment in the same manner as in Example 207 using 2-bromobenzaldehyde (185 mg) as a starting material instead of 2-tolualdehyde, N-[(2-bromophenyl)methyl]-N-(4-isopropylphenyl)-7-methoxy-1,2,3,4-tetrahydronaphthalene-1-carboxamide (157.6 mg) was obtained.

MS (ESI) m/z: 492 [MH]$^+$

Example 247

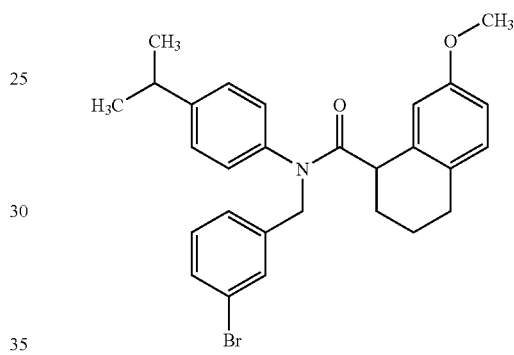

By the reaction and treatment in the same manner as in Example 207 using 3-bromobenzaldehyde (185 mg) as a starting material instead of 2-tolualdehyde, N-[(3-bromophenyl)methyl]-N-(4-isopropylphenyl)-7-methoxy-1,2,3,4-tetrahydronaphthalene-1-carboxamide (214.4 mg) was obtained.

MS (ESI) m/z: 492 [MH]$^+$

Example 248

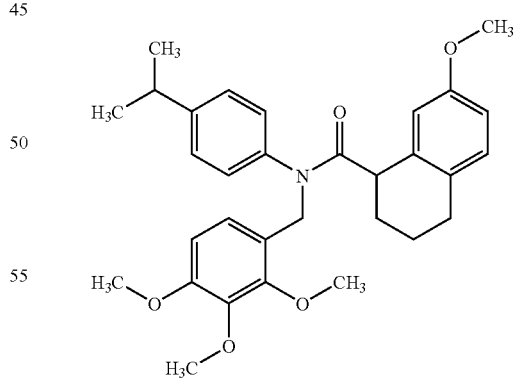

By the reaction and treatment in the same manner as in Example 207 using 2,3,4-trimethoxybenzaldehyde (196 mg) as a starting material instead of 2-tolualdehyde, N-(4-isopropylphenyl)-7-methoxy-N-[(2,3,4-trimethoxyphenyl)methyl]-1,2,3,4-tetrahydronaphthalene-1-carboxamide (365.1 mg) was obtained.

MS (ESI) m/z: 504 [MH]$^+$

Example 249

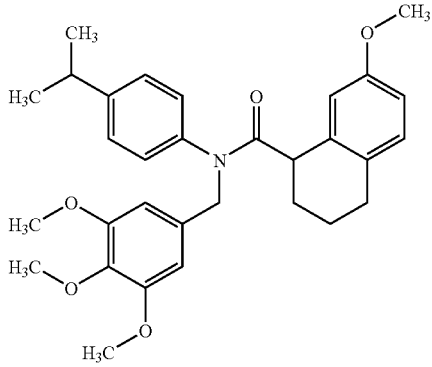

By the reaction and treatment in the same manner as in Example 207 using 3,4,5-trimethoxybenzaldehyde (196 mg) as a starting material instead of 2-tolualdehyde, N-(4-isopropylphenyl)-7-methoxy-N-[(3,4,5-trimethoxyphenyl)methyl]-1,2,3,4-tetrahydronaphthalene-1-carboxamide (139.3 mg) was obtained.

MS (ESI) m/z: 504 [MH]$^+$

Example 250

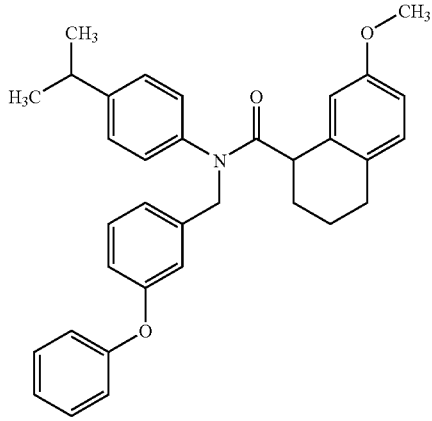

By the reaction and treatment in the same manner as in Example 207 using 3-phenoxybenzaldehyde (198 mg) as a starting material instead of 2-tolualdehyde, N-(4-isopropylphenyl)-7-methoxy-N-[(3-phenoxyphenyl)methyl]-1,2,3,4-tetrahydronaphthalene-1-carboxamide (153.8 mg) was obtained.

MS (ESI) m/z: 506 [MH]$^+$

Example 251

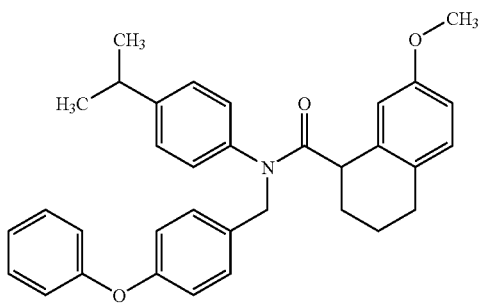

By the reaction and treatment in the same manner as in Example 207 using 4-phenoxybenzaldehyde (198 mg) as a starting material instead of 2-tolualdehyde, N-(4-isopropylphenyl)-7-methoxy-N-[(4-phenoxyphenyl)methyl]-1,2,3,4-tetrahydronaphthalene-1-carboxamide (188.1 mg) was obtained.

MS (ESI) m/z: 506 [MH]$^+$

Example 252

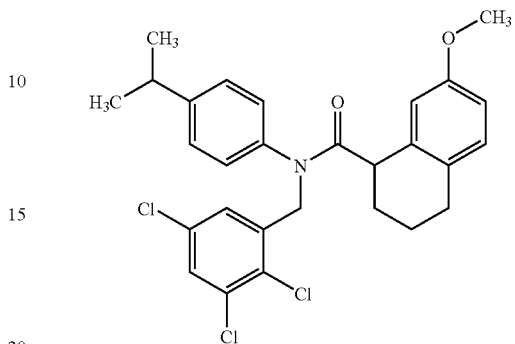

By the reaction and treatment in the same manner as in Example 207 using 2,3,5-trichlorobenzaldehyde (209 mg) as a starting material instead of 2-tolualdehyde, N-(4-isopropylphenyl)-7-methoxy-N-[(2,3,5-trichlorophenyl)methyl]-1,2,3,4-tetrahydronaphthalene-1-carboxamide (400.7 mg) was obtained.

MS (ESI) m/z: 516 [MH]$^+$

Example 253

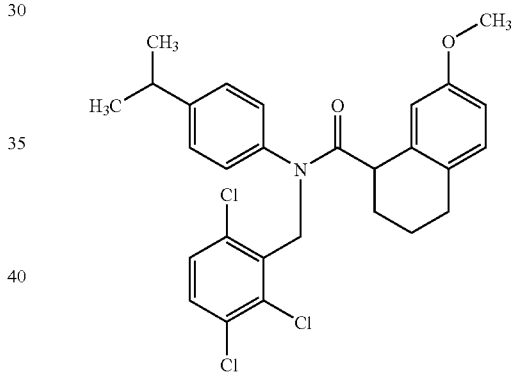

By the reaction and treatment in the same manner as in Example 207 using 2,3,6-trichlorobenzaldehyde (209 mg) as a starting material instead of 2-tolualdehyde, N-(4-isopropylphenyl)-7-methoxy-N-[(2,3,6-trichlorophenyl)methyl]-1,2,3,4-tetrahydronaphthalene-1-carboxamide (112.7 mg) was obtained.

MS (ESI) m/z: 516 [MH]$^+$

Example 254

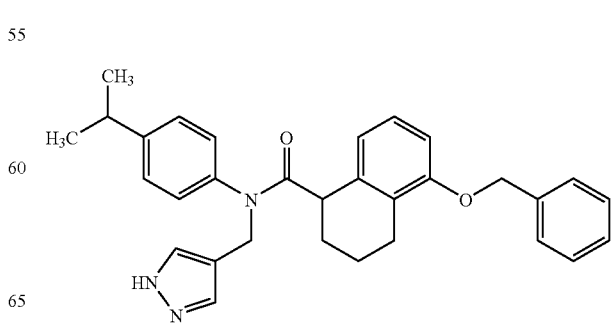

By the reaction and treatment in the same manner as in Example 82 using 5-benzyloxy-N-(4-isopropylphenyl)-1,2,3,4-tetrahydronaphthalene-1-carboxamide (5.94 g) and 1-(tert-butoxycarbonyl)-4-(hydroxymethyl)pyrazole (2.95 g) as starting materials, 5-benzyloxy-N-(4-isopropylphenyl)-N-[(pyrazol-4-yl)methyl]-1,2,3,4-tetrahydronaphthalene-1-carboxamide (3.00 g) was obtained.

¹H-NMR (CDCl₃) δ: 1.25 (6H, d, J=7.0 Hz), 1.44-1.50 (1H, m), 1.82-2.05 (3H, m), 2.69-2.74 (2H, m), 2.87-2.94 (1H, m), 3.70-3.75 (1H, m), 4.69 (1H, d, J=14.4 Hz), 4.86 (1H, d, J=14.4 Hz), 6.58 (1H, d, J=7.8 Hz), 6.70 (1H, d, J=7.8 Hz), 7.01-7.07 (3H, m), 7.21-7.42 (7H, m), 7.51 (2H, s).

Example 255

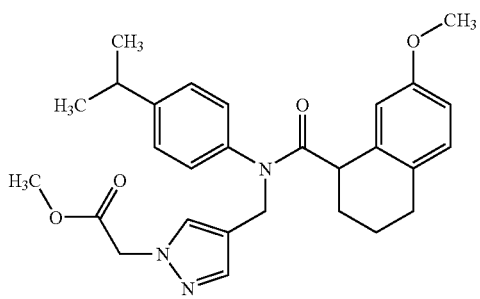

By the reaction and treatment in the same manner as in Example 83 using N-(4-isopropylphenyl)-7-methoxy-N-[(pyrazol-4-yl)methyl]-1,2,3,4-tetrahydronaphthalene-1-carboxamide (1.32 g) and methyl bromoacetate (0.31 mL) as starting materials, methyl 2-(4-{[N-(4-isopropylphenyl)-N-(7-methoxy-1,2,3,4-tetrahydronaphthalene-1-yl)carbonyl)amino]methyl}pyrazol-1-yl)acetate (0.35 g) was obtained.

¹H-NMR (CDCl₃) δ: 1.25 (6H, d, J=6.9 Hz), 1.37-1.53 (1H, m), 1.78-2.07 (3H, m), 2.52-2.62 (1H, m), 2.68-2.85 (1H, m), 2.92 (1H, sept, J=6.9 Hz), 3.64-3.73 (1H, m), 3.69 (3H, s), 3.77 (3H, s), 4.60. (1H, d, J=13.9 Hz), 4.87 (1H, d, J=13.9 Hz), 4.88 (2H, s), 6.45 (1H, d, J=2.4 Hz), 6.66 (1H, dd, J=2.4, 8.4 Hz), 6.95 (1H, d, J=8.4 Hz), 7.06 (2H, d, J=8.4 Hz), 7.23 (2H, d, J=8.4 Hz), 7.42 (1H, s), 7.49 (1H, s).

Example 256

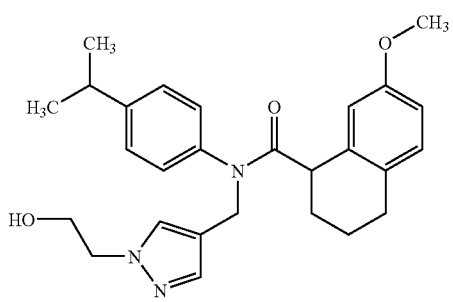

Methyl 2-(4-{[N-(4-isopropylphenyl)-N-(7-methoxy-1,2,3,4-tetrahydronaphthalen-1-ylcarbonyl)amino]methyl}pyrazol-1-yl)acetate (0.34 g) was dissolved in a mixed solvent (10 mL) of ethanol: THF (2: 1), and sodium borohydride (0.11 g) and lithium chloride (0.12 g) were added thereto. The mixture was stirred at 50° C. for 3 hr. The reaction mixture was concentrated under reduced pressure and partitioned between water and ethyl acetate. The organic layer was washed with saturated brine and dried over anhydrous magnesium sulfate. The solvent was evaporated, and the residue was purified by silica gel column chromatography to give N-{[1-(2-hydroxyethyl)pyrazol-4-yl]methyl}-N-(4-isopropylphenyl)-7-methoxy-1,2,3,4-tetrahydronaphthalene-1-carboxamide (0.23 g).

¹H-NMR (CDCl₃) δ: 1.20 (6H, d, J=6.9 Hz), 1.28-1.45 (1H, m), 1.77-1.99 (3H, m), 2.47-2.71 (2H, m), 2.91 (1H, sept, J=6.9 Hz), 3.52-3.62 (1H, m), 3.64 (3H, s), 3.68 (2H, t, J=5.6 Hz), 4.08 (2H, t, J=5.6 Hz), 4.57 (1H, d, J=13.9 Hz), 4.76 (1H, d, J=13.9 Hz), 6.40 (1H, d, J=2.4 Hz), 6.69 (1H, dd, J=2.4, 8.4 Hz), 6.94 (1H, d, J=8.4 Hz), 7.19 (2H, d, J=8.4 Hz), 7.25 (1H, s), 7.33 (2H, d, J=8.4 Hz), 7.52 (1H, s).

Example 257

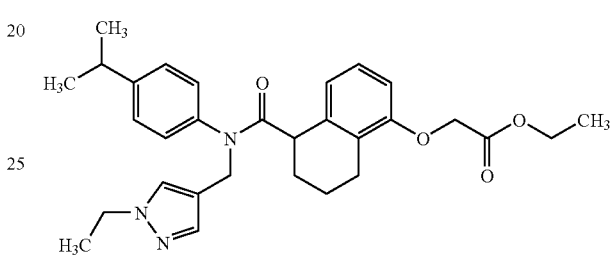

By the reaction and treatment in the same manner as in Example 106 using N-[(1-ethylpyrazol-4-yl)methyl]-5-hydroxy-N-(4-isopropylphenyl)-1,2,3,4-tetrahydronaphthalene-1-carboxamide (1.00 g) and ethyl bromoacetate (0.40 mL) as starting materials, ethyl 2-(5-{N-[(1-ethylpyrazol-4-yl)methyl]-N-(4-isopropylphenyl)carbamoyl}-5,6,7,8-tetrahydronaphthalene-1-yloxy)acetate (1.09 g) was obtained.

¹H-NMR (CDCl₃) δ: 1.25 (6H, d, J=6.9 Hz), 1.28 (3H, t, J=7.1 Hz), 1.45 (3H, t, J=7.1 Hz), 1.39-1.56 (1H, m), 1.78-2.06 (3H, m), 2.61-2.85 (2H, m), 2.92 (1H, sept, J=6.9 Hz), 3.64-3.74 (1H, m), 4.12 (2H, q, J=7.1 Hz), 4.18 (2H, q, J=7.1 Hz), 4.56 (2H, s), 4.59 (1H, d, J=13.9 Hz), 4.83 (1H, d, J=13.9 Hz), 6.53 (1H, d, J=8.1 Hz), 6.59 (1H, d, J=8.1 Hz), 7.01 (1H, t, J=8.1 Hz), 7.05 (2H, d, J=8.4 Hz), 7.22 (2H, d, J=8.4 Hz), 7.33 (1H, s), 7.41 (1H, s).

Example 258

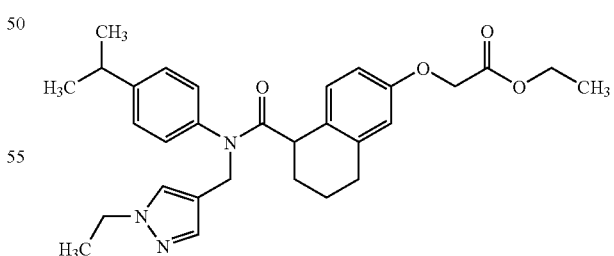

By the reaction and treatment in the same manner as in Example 106 using N-[(1-ethylpyrazol-4-yl)methyl]-6-hydroxy-N-(4-isopropylphenyl)-1,2,3,4-tetrahydronaphthalene-1-carboxamide (1.00 g) as a starting material, ethyl 2-(5-{N-[(1-ethylpyrazol-4-yl)methyl]-N-(4-isopropylphenyl)carbamoyl}-5,6,7,8-tetrahydronaphthalene-2-yloxy)acetate (1.11 g) was obtained.

¹H-NMR (CDCl₃) δ: 1.25 (6H, d, J=6.9 Hz), 1.30 (3H, t, J=7.1 Hz), 1.45 (3H, t, J=7.1 Hz), 1.39-1.57 (1H, m), 1.79-2.02 (3H, m), 2.52-2.67 (1H, m), 2.74-2.89 (1H, m), 2.92 (1H, sept, J=6.9 Hz), 3.59-3.69 (1H, m), 4.12 (2H, q, J=7.1 Hz), 4.25 (2H, q, J=7.1 Hz), 4.54 (2H, s), 4.59 (1H, d, J=13.9 Hz), 4.81 (1H, d, J=13.9 Hz), 6.58 (1H, d, J=2.4 Hz), 6.65 (1H, dd, J=2.4, 8.4 Hz), 6.82 (1H, d, J=8.4 Hz), 7.04 (2H, d, J=8.4 Hz), 7.22 (2H, d, J=8.4 Hz), 7.33 (1H, s), 7.40 (1H, s).

Example 259

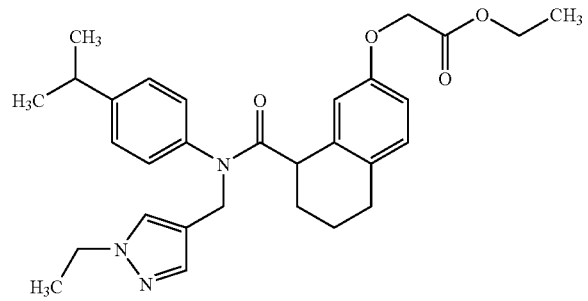

By the reaction and treatment in the same manner as in Example 106 using N-[(1-ethylpyrazol-4-yl)methyl]-7-hydroxy-N-(4-isopropylphenyl)-1,2,3,4-tetrahydronaphthalene-1-carboxamide (1.00 g) as a starting material, ethyl 2-(8-{N-[(1-ethylpyrazol-4-yl)methyl]-N-(4-isopropylphenyl)carbamoyl}-5,6,7,8-tetrahydronaphthalene-2-yloxy)acetate (0.94 g) was obtained.

¹H-NMR (CDCl₃) δ: 1.25 (6H, d, J=6.9 Hz), 1.31 (3H, t, J=7.1 Hz), 1.45 (3H, t, J=7.1 Hz), 1.37-1.55 (1H, m), 1.78-2.05 (3H, m), 2.51-2.65 (1H, m), 2.70-2.84 (1H, m), 2.92 (1H, sept, J=6.9 Hz), 3.61-3.72 (1H, m), 4.14 (2H, q, J=7.1 Hz), 4.27 (2H, q, J=7.1 Hz), 4.51 (2H, s), 4.65 (1H, d, J=13.9 Hz), 4.76 (1H, d, J=13.9 Hz), 6.50 (1H, d, J=2.4 Hz), 6.65 (1H, dd, J=2.4, 8.4 Hz), 6.95 (1H, d, J=8.4 Hz), 7.05 (2H, d, J=8.4 Hz), 7.23 (2H, d, J=8.4 Hz), 7.31 (1H, s), 7.42 (1H, s).

Example 260

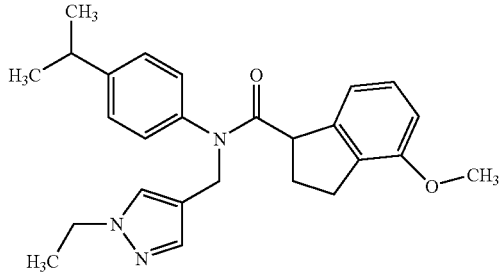

By the reaction and treatment in the same manner as in Example 12 using 4-methoxyindan-1-carboxylic acid (0.29 g) and [(1-ethylpyrazol-4-yl)methyl](4-isopropylphenyl)amine (0.37 g) as starting materials, N-[(1-ethylpyrazol-4-yl)methyl]-N-(4-isopropylphenyl)-4-methoxyindan-1-carboxamide (0.39 g) was obtained.

¹H-NMR (CDCl₃) δ: 1.25 (6H, d, J=6.9 Hz), 1.31 (3H, t, J=7.1 Hz), 2.01-2.17 (1H, m), 2.24-2.39 (1H, m), 2.60-2.75 (1H, m), 2.92 (1H, sept, J=6.9 Hz), 3.00-3.12 (1H, m), 3.79 (3H, s), 3.96 (1H, t, J=6.2 Hz), 4.12 (2H, q, J=7.1 Hz), 4.65 (1H, d, J=13.9 Hz), 4.79 (1H, d, J=13.9 Hz), 6.66 (2H, d, J=8.4 Hz), 6.99-7.16 (3H, m), 7.23 (2H, d, J=8.4 Hz), 7.31 (1H, s), 7.39 (1H, s).

Example 261

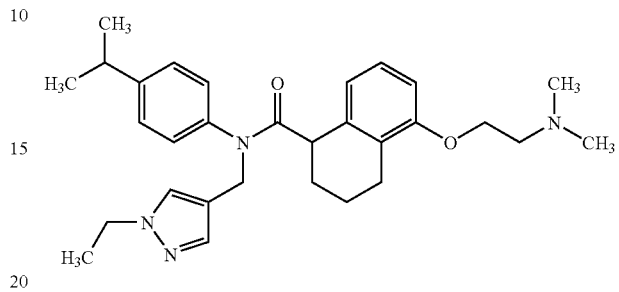

By the reaction and treatment in the same manner as in Example 106 using N-[(1-ethylpyrazol-4-yl)methyl]-5-hydroxy-N-(4-isopropylphenyl)-1,2,3,4-tetrahydronaphthalene-1-carboxamide (0.42 g) and 2-chloro-N,N-dimethylethylamine hydrochloride (0.22 g) as starting materials, 5-[2-(dimethylamino)ethyloxy]-N-[(1-ethylpyrazol-4-yl)methyl]-N-(4-isopropylphenyl)-1,2,3,4-tetrahydronaphthalene-1-carboxamide (0.15 g) was obtained.

¹H-NMR (CDCl₃) δ: 1.25 (6H, d, J=6.9 Hz), 1.45 (3H, t, J=7.1 Hz), 1.39-1.53 (1H, m), 1.71-2.07 (3H, m), 2.35 (6H, s), 2.56-2.69 (2H, m), 2.75 (2H, t, J=5.8 Hz), 2.92 (1H, sept, J=6.9 Hz), 3.66-3.75 (1H, m), 4.04 (2H, t, J=5.8 Hz), 4.12 (2H, q, J=7.1 Hz), 4.58 (1H, d, J=13.9 Hz), 4.83 (1H, d, J=13.9 Hz), 6.54 (1H, d, J=8.1 Hz), 6.64 (1H, d, J=8.1 Hz), 6.98-7.10 (3H, m), 7.22 (2H, d, J=8.4 Hz), 7.33 (1H, s), 7.41 (1H, s).

Example 262

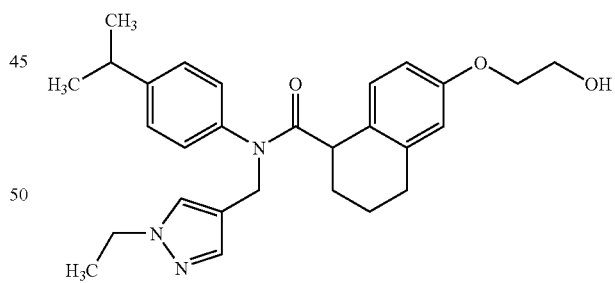

By the reaction and treatment in the same manner as in Example 256 using ethyl 2-(5-{N-[(1-ethylpyrazol-4-yl)methyl]-N-(4-isopropylphenyl)carbamoyl}-5,6,7,8-tetrahydronaphthalene-2-yloxy)acetate (0.56 g) as a starting material, N-[(1-ethylpyrazol-4-yl)methyl]-6-(2-hydroxyethoxy)-N-(4-isopropylphenyl)-1,2,3,4-tetrahydronaphthalene-1-carboxamide (0.46 g) was obtained. melting point: 137.3° C.

¹H-NMR (CDCl₃) δ: 1.25 (6H, d, J=6.9 Hz), 1.45 (3H, t, J=7.3 Hz), 1.40-1.55 (1H, m), 1.80-2.12 (3H, m), 2.53-2.68 (1H, m), 2.77-3.00 (2H, m), 3.59-3.69 (1H, m), 3.87-3.95 (2H, m), 3.97-4.05 (2H, m), 4.13 (2H, q, J=7.3 Hz), 4.60 (1H, d, J=13.9 Hz), 4.81 (1H, d, J=13.9 Hz), 6.60 (1H, d, J=2.4

Hz), 6.65 (1H, dd, J=2.4, 8.4 Hz), 6.82 (1H, d, J=8.4 Hz), 7.04 (2H, d, J=8.4 Hz), 7.23 (2H, d, J=8.4 Hz), 7.33 (1H, s), 7.40 (1H, s).

Example 263

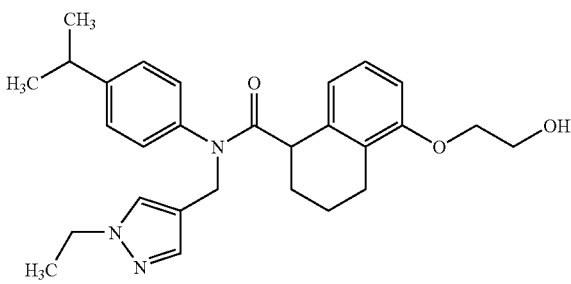

By the reaction and treatment in the same manner as in Example 256 using ethyl 2-(5-{N-[(1-ethylpyrazol-4-yl)methyl]-N-(4-isopropylphenyl)carbamoyl}-5,6,7,8-tetrahydronaphthalene-1-yloxy)acetate (0.60 g) as starting materials, N-[(1-ethylpyrazol-4-yl)methyl]-5-(2-hydroxyethoxy)-N-(4-isopropylphenyl)-1,2,3,4-tetrahydronaphthalene-1-carboxamide (0.46 g) was obtained.

¹H-NMR (CDCl₃) δ: 1.25 (6H, d, J=6.9 Hz), 1.45 (3H, t, J=7.1 Hz), 1.39-1.55 (1H, m), 1.77-2.19 (3H, m), 2.60-2.72 (2H, m), 2.92 (1H, sept, J=6.9 Hz), 3.66-3.73 (1H, m), 3.87-3.96 (2H, m), 4.03 (2H, t, J=4.3 Hz), 4.13 (2H, q, J=7.1 Hz), 4.59 (1H, d, J=13.9 Hz), 4.83 (1H, d, J=13.9 Hz), 6.57 (1H, d, J=8.1 Hz), 6.65 (1H, d, J=8.1 Hz), 6.97-7.10 (3H, m), 7.22 (2H, d, J=8.4 Hz), 7.33 (1H, s), 7.40 (1H, s).

Example 264

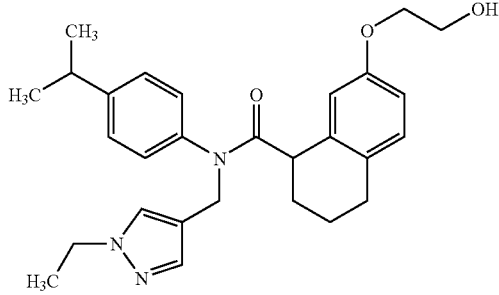

By the reaction and treatment in the same manner as in Example 256 using ethyl 2-(8-{N-[(1-ethylpyrazol-4-yl)methyl]-N-(4-isopropylphenyl)carbamoyl}-5,6,7,8-tetrahydronaphthalene-2-yloxy)acetate (0.47 g) as starting materials, N-[(1-ethylpyrazol-4-yl)methyl]-7-(2-hydroxyethoxy)-N-(4-isopropylphenyl)-1,2,3,4-tetrahydronaphthalene-1-carboxamide (0.40 g) was obtained.

¹H-NMR (CDCl₃) δ: 1.25 (6H, d, J=6.9 Hz), 1.45 (3H, t, J=7.1 Hz), 1.39-1.55 (1H, m), 1.69-2.05 (3H, m), 2.51-2.84 (3H, m), 2.93 (1H, sept, J=6.9 Hz), 3.63-3.72 (1H, m), 3.82-3.98 (4H, m), 4.13 (2H, q, J=7.1 Hz), 4.43 (1H, d, J=13.9 Hz), 4.99 (1H, d, J=13.9 Hz), 6.41 (1H, d, J=2.4 Hz), 6.66 (1H, dd, J=2.4, 8.4 Hz), 6.94 (1H, d, J=8.4 Hz), 7.08 (2H, d, J=8.4 Hz), 7.24 (2H, d, J=8.4 Hz), 7.44 (2H, s).

Example 265

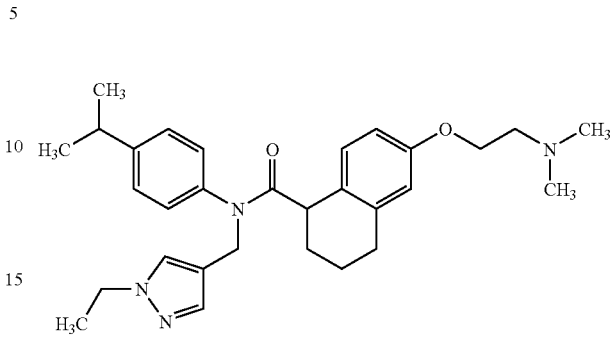

By the reaction and treatment in the same manner as in Example 106 using N-[(1-ethylpyrazol-4-yl)methyl]-6-hydroxy-N-(4-isopropylphenyl)-1,2,3,4-tetrahydronaphthalene-1-carboxamide (0.42 g) and 2-chloro-N,N-dimethylethylamine hydrochloride (0.22 g) as starting materials, 6-[2-(dimethylamino)ethoxy]-N-[(1-ethylpyrazol-4-yl)methyl]-N-(4-isopropylphenyl)-1,2,3,4-tetrahydronaphthalene-1-carboxamide (0.19 g) was obtained.

¹H-NMR (CDCl₃) δ: 1.25 (6H, d, J=6.9 Hz), 1.43 (3H, t, J=7.1 Hz), 1.40-1.53 (1H, m), 1.69-2.04 (3H, m), 2.31 (6H, s), 2.52-2.67 (1H, m), 2.69 (2H, t, J=5.8 Hz), 2.73-2.90 (1H, m), 2.92 (1H, sept, J=6.9 Hz), 3.60-3.70 (1H, m), 4.00 (2H, t, J=5.8 Hz), 4.12 (2H, q, J=7.1 Hz), 4.58 (1H, d, J=13.9 Hz), 4.82 (1H, d, J=13.9 Hz), 6.59 (1H, d, J=2.4 Hz), 6.66 (1H, dd, J=2.4, 8.4 Hz), 6.80 (1H, d, J=8.4 Hz), 7.04 (2H, d, J=8.4 Hz), 7.22 (2H, d, J=8.4 Hz), 7.32 (1H, s), 7.40 (1H, s).

Example 266

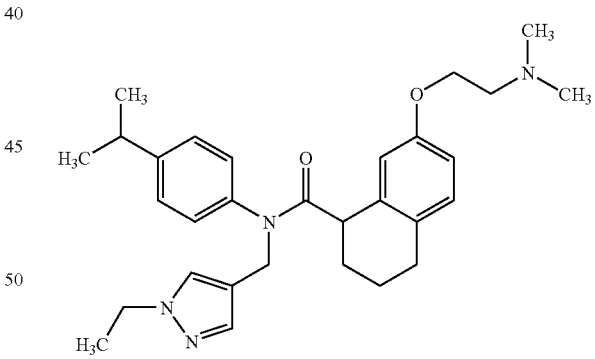

By the reaction and treatment in the same manner as in Example 106 using N-[(1-ethylpyrazol-4-yl)methyl]-7-hydroxy-N-(4-isopropylphenyl)-1,2,3,4-tetrahydronaphthalene-1-carboxamide (0.42 g) and 2-chloro-N,N-dimethylethylamine hydrochloride (0.22 g) as starting materials, 7-[2-(dimethylamino)ethoxy]-N-[(1-ethylpyrazol-4-yl)methyl]-N-(4-isopropylphenyl)-1,2,3,4-tetrahydronaphthalene-1-carboxamide (0.15 g) was obtained.

¹H-NMR (CDCl₃) δ: 1.25 (6H, d, J=6.9 Hz), 1.43 (3H, t, J=7.1 Hz), 1.39-1.56 (1H, m), 1.77-2.07 (3H, m), 2.33 (6H, s), 2.50-2.83 (4H, m), 2.92 (1H, sept, J=6.9 Hz), 3.63-3.73 (1H, m), 3.94 (2H, t, J=5.8 Hz), 4.13 (2H, q, J=7.1 Hz), 4.63 (1H, d, J=13.9 Hz), 4.78 (1H, d, J=13.9 Hz), 6.48 (1H, d, J=2.4

Hz), 6.68 (1H, dd, J=2.4, 8.4 Hz), 6.94 (1H, d, J=8.4 Hz), 7.06 (2H, d, J=8.4 Hz), 7.23 (2H, d, J=8.4 Hz), 7.32 (1H, s), 7.41 (1H, s).

Example 267

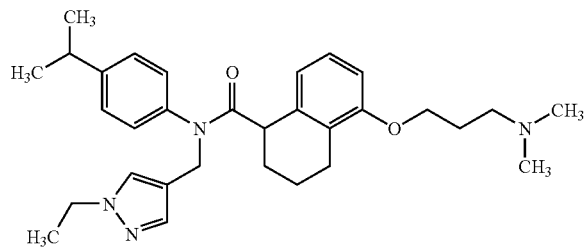

By the reaction and treatment in the same manner as in Example 106 using N-[(1-ethylpyrazol-4-yl)methyl]-5-hydroxy-N-(4-isopropylphenyl)-1,2,3,4-tetrahydronaphthalene-1-carboxamide (0.42 g) and 3-chloro-N,N-dimethylpropylamine hydrochloride (0.24 g) as starting materials, 5-[3-(dimethylamino)propoxy]-N-[(1-ethylpyrazol-4-yl)methyl]-N-(4-isopropylphenyl)-1,2,3,4-tetrahydronaphthalene-1-carboxamide was obtained. This was dissolved in ethyl acetate, and oxalic acid (0.12 g) was added. The precipitated solid was collected by filtration to give 5-[3-(dimethylamino)propoxy]-N-[(1-ethylpyrazol-4-yl)methyl]-N-(4-isopropylphenyl)-1,2,3,4-tetrahydronaphthalene-1-carboxamide 3/2 oxalate (0.36 g). melting point: 142.6° C.

$^1$H-NMR (CDCl$_3$) δ: 1.25 (6H, d, J=6.9 Hz), 1.44 (3H, t, J=7.1 Hz), 1.36-1.57 (1H, m), 1.72-2.07 (3H, m), 2.14-2.31 (2H, m), 2.52-2.67 (2H, m), 2.88 (6H, s), 2.92 (1H, sept, J=6.9 Hz), 3.20-3.47 (2H, m), 3.67-3.78 (1H, m), 3.92-4.08 (2H, m), 4.14 (2H, q, J=7.1 Hz), 4.58 (1H, d, J=13.9 Hz), 4.80 (1H, d, J=13.9 Hz), 6.53 (1H, d, J=8.1 Hz), 6.59 (1H, d, J=8.1 Hz), 6.96-7.10 (3H, m), 7.24 (2H, d, J=8.4 Hz), 7.36 (1H, s), 7.40 (1H, s).

Example 268

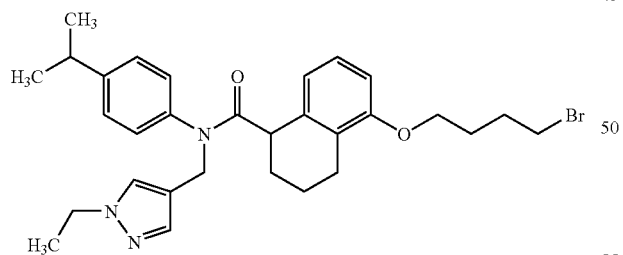

By the reaction and treatment in the same manner as in Example 106 using N-[1-ethylpyrazol-4-yl)methyl]-5-hydroxy-N-(4-isopropylphenyl)-1,2,3,4-tetrahydronaphthalene-1-carboxamide (0.46 g) and 1,4-dibromobutane (1.33 mL) as starting materials, 5-(4-bromobutoxy)-N-[(1-ethylpyrazol-4-yl)methyl]-N-(4-isopropylphenyl)-1,2,3,4-tetrahydronaphthalene-1-carboxamide (0.52 g) was obtained.

$^1$H-NMR (CDCl$_3$) δ: 1.25 (6H, d, J=6.9 Hz), 1.38-1.51 (1H, m), 1.45 (3H, t, J=7.1 Hz), 1.66-2.10 (7H, m), 2.57-2.69 (2H, m), 2.92 (1H, sept, J=6.9 Hz), 3.48 (2H, t, J=5.8 Hz), 3.65-3.75 (1H, m), 3.94 (2H, t, J=5.8 Hz), 4.13 (2H, q, J=7.1 Hz), 4.58 (1H, d, J=13.9 Hz), 4.84 (1H, d, J=13.9 Hz), 6.54 (1H, d, J=8.4 Hz), 6.62 (1H, d, J=8.4 Hz), 6.96-7.09 (3H, m), 7.22 (2H, d, J=8.4 Hz), 7.33 (1H, s), 7.41 (1H, s).

Example 269

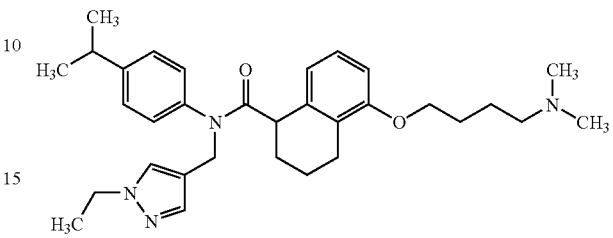

To a solution of 5-(4-bromobutoxy)-N-[(1-ethylpyrazol-4-yl)methyl]-N-(4-isopropylphenyl)-1,2,3,4-tetrahydronaphthalene-1-carboxamide (0.52 g) in acetonitrile (10 mL) were added dimethylamine hydrochloride (0.69 g) and potassium carbonate (1.30 g), and the mixture was heated under reflux for 1.5 hr. The reaction mixture was concentrated under reduced pressure, and the residue was partitioned between water and chloroform. The organic layer was washed with saturated brine and dried over anhydrous sodium sulfate. The solvent was evaporated, and the residue was purified by silica gel column chromatography to give 5-[4-(dimethylamino)butoxy]-N-[(1-ethylpyrazol-4-yl)methyl]-N-(4-isopropylphenyl)-1,2,3,4-tetrahydronaphthalene-1-carboxamide (0.27 g).

$^1$H-NMR (CDCl$_3$) δ: 1.24 (6H, d, J=6.9 Hz), 1.38-1.57 (1H, m), 1.45 (3H, t, J=7.1 Hz), 1.64-2.07 (7H, m), 2.31 (6H, s), 2.39-2.71 (4H, m), 2.92 (1H, sept, J=6.9 Hz), 3.65-3.76 (1H, m), 3.92 (2H, t, J=5.8 Hz), 4.12 (2H, q, J=7.1 Hz), 4.58 (1H, d, J=13.9 Hz), 4.83 (1H, d, J=13.9 Hz), 6.53 (1H, d, J=8.0 Hz), 6.62 (1H, d, J=8.0 Hz), 6.96-7.10 (3H, m), 7.22 (2H, d, J=8.4 Hz), 7.33 (1H, s), 7.41 (1H, s).

Example 270

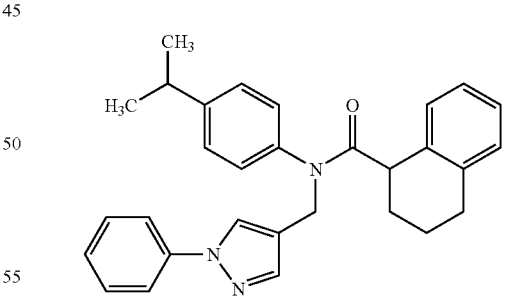

By the reaction and treatment in the same manner as in Example 12 using 1,2,3,4-tetrahydronaphthalene-1-carboxylic acid (0.35 g) and (4-isopropylphenyl)[(1-phenylpyrazol-4-yl)methyl]amine (0.58 g) as starting materials, N-(4-isopropylphenyl)-N-[(1-phenylpyrazol-4-yl)methyl]-1,2,3,4-tetrahydronaphthalene-1-carboxamide (0.42 g) was obtained.

$^1$H-NMR (CDCl$_3$) δ: 1.25 (6H, d, J=6.9 Hz), 1.41-1.60 (1H, m), 1.83-2.09 (3H, m), 2.59-2.72 (1H, m), 2.79-3.00 (2H, m), 3.70-3.81 (1H, m), 4.72 (1H, d, J=14.4 Hz), 4.89

(1H, d, J=14.4 Hz), 6.90-6.99 (1H, m), 7.00-7.17 (5H, m), 7.21-7.31 (3H, m), 7.37-7.47 (2H, m), 7.58 (1H, s), 7.66 (2H, d, J=9.0 Hz), 7.94 (1H, s).

Example 271

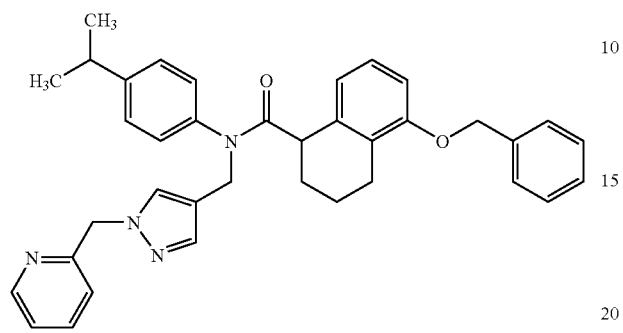

To a solution of 5-benzyloxy-N-(4-isopropylphenyl)-N-[(pyrazol-4-yl)methyl]-1,2,3,4-tetrahydronaphthalene-1-carboxamide (0.27 g) in methylene chloride (2 mL) were added tetra-n-butylammonium hydrogensulfate (0.66 g), 2-(chloromethyl)pyridine hydrochloride (0.19 g) and 1 mol/L-aqueous sodium hydroxide solution (2.26 mL), and the mixture was stirred at room temperature for one day. The reaction mixture was partitioned between water and chloroform. The organic layer was washed with saturated brine and dried over anhydrous magnesium sulfate. The solvent was evaporated and the residue was purified by silica gel column chromatography to give 5-benzyloxy-N-(4-isopropylphenyl)-N-{[1-(2-pyridylmethyl)pyrazol-4-yl]methyl}-1,2,3,4-tetrahydronaphthalene-1-carboxamide (0.19 g).

$^1$H-NMR (CDCl$_3$) δ: 1.24 (6H, d, J=6.9 Hz), 1.38-1.56 (1H, m), 1.78-2.07 (3H, m), 2.61-2.82 (2H, m), 2.91 (1H, sept, J=6.9 Hz), 3.67-3.77 (1H, m), 4.64 (1H, d, J=14.4 Hz), 4.86 (1H, d, J=14.4 Hz), 5.01 (2H, s), 5.40 (2H, s), 6.59 (1H, d, J=7.7 Hz), 6.69 (1H, d, J=8.2 Hz), 6.87-7.08 (4H, m), 7.15-7.49 (10H, m), 7.57-7.66 (1H, m), 8.56 (1H, d, J=5.7 Hz).

Example 272

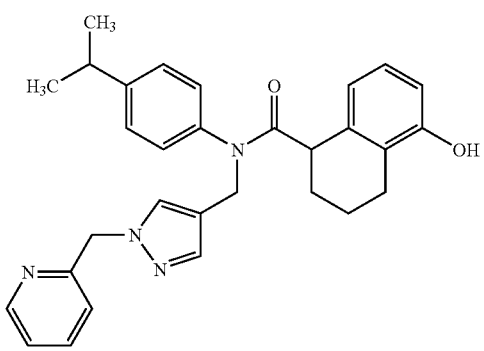

By the reaction and treatment in the same manner as in Example 101 using 5-benzyloxy-N-(4-isopropylphenyl)-N-{[1-(2-pyridylmethyl)pyrazol-4-yl]methyl}-1,2,3,4-tetrahydronaphthalene-1-carboxamide (0.19 g) as a starting material, 5-hydroxy-N-(4-isopropylphenyl)-N-{[1-(2-pyridylmethyl)pyrazol-4-yl]methyl}-1,2,3,4-tetrahydronaphthalene-1-carboxamide hydrochloride (0.08 g) was obtained. MS (ESI) m/z: 481 [MH]$^+$ $^1$H-NMR (DMSO-d$_6$) δ: 1.19 (6H, d, J=6.9 Hz), 1.27-1.42 (1H, m), 1.70-2.00 (3H, m), 2.37-2.57 (2H, m), 2.91 (1H, sept, J=6.9 Hz), 3.50-3.60 (1H, m), 4.66 (1H, d, J=14.7 Hz), 4.73 (1H, d, J=14.7 Hz), 5.56 (2H, s), 6.41 (1H, d, J=7.5 Hz), 6.60 (1H, d, J=7.8 Hz), 6.85 (1H, t, J=7.8 Hz), 7.10-7.22 (3H, m), 7.27-7.37 (3H, m), 7.59-7.68 (1H, m), 7.74 (1H, s), 8.14 (1H, m), 8.73 (1H, d, J=4.5 Hz).

Example 273

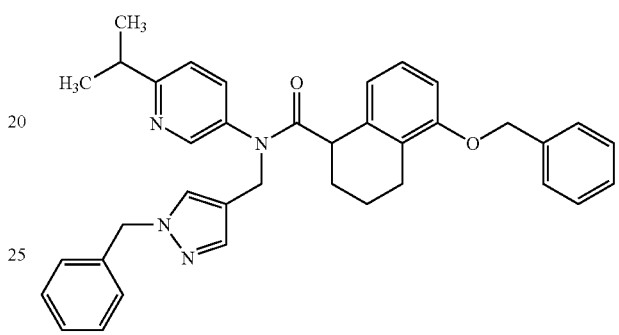

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.36 g) and benzyl bromide (0.18 mL) as starting materials, 5-benzyloxy-N-[(1-benzylpyrazol-4-yl)methyl]-N-(6-isopropylpyridin-3-yl)-1,2,3,4-tetrahydronaphthalene-1-carboxamide (0.34 g) was obtained.

$^1$H-NMR (CDCl$_3$) δ: 1.30 (6H, d, J=6.9 Hz), 1.38-1.54 (1H, m), 1.76-2.06 (3H, m), 2.61-2.78 (2H, m), 3.08 (1H, sept, J=6.9 Hz), 3.58-3.68 (1H, m), 4.60 (1H, d, J=14.7 Hz), 4.84 (1H, d, J=14.7 Hz), 5.01 (2H, s), 5.24 (2H, s), 6.52 (1H, d, J=7.8 Hz), 6.70 (1H, d, J=8.1 Hz), 6.98 (1H, t, J=8.0 Hz), 7.11-7.18 (3H, m), 7.22-7.43 (11H, m), 8.38 (1H, d, J=2.4 Hz).

Example 274

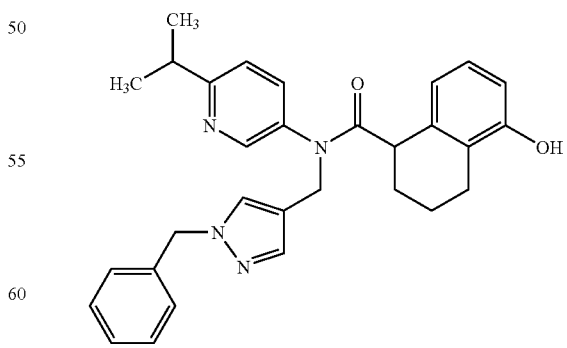

By the reaction and treatment in the same manner as in Example 101 using 5-benzyloxy-N-[(1-benzylpyrazol-4-yl)methyl]-N-(6-isopropylpyridin-3-yl)-1,2,3,4-tetrahydronaphthalene-1-5-carboxamide (0.34 g) as starting materials, N-[(1-benzylpyrazol-4-yl)methyl]-5-hydroxy-N-(6-isopropylpyridin-3-yl)-1,2,3,4-tetrahydronaphthalene-1-carboxamide hydrochloride (0.27 g) was obtained.

¹H-NMR (DMSO-d₆) δ: 1.31 (6H, d, J=6.9 Hz), 1.37-1.55 (1H, m), 1.72-1.95 (3H, m), 2.37-2.58 (3H, m), 3.23-3.39 (1H, m), 4.63-4.90 (2H, m), 5.27 (2H, s), 6.46 (1H, d, J=7.5 Hz), 6.64 (1H, d, J=7.8 Hz), 6.87 (1H, t, J=7.8 Hz), 7.05-7.15 (2H, m), 7.23-7.38 (4H, m), 7.60-7.88 (2H, m), 8.03-8.18 (1H, m), 8.69-8.82 (1H, m).

Example 275

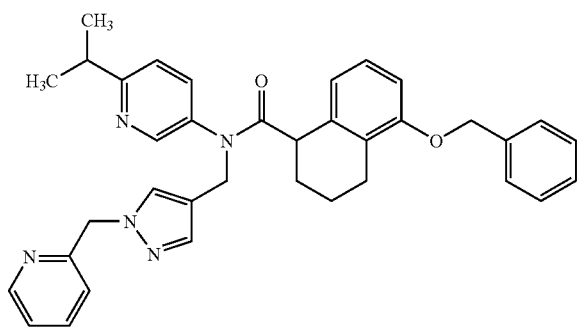

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-(chloromethyl)pyridine hydrochloride (0.49 g) as starting materials, 5-benzyloxy-N-(6-isopropylpyridin-3-yl)-N-{[1-(2-pyridylmethyl)pyrazol-4-yl]methyl}-1,2,3,4-tetrahydronaphthalene-1-carboxamide (0.74 g) was obtained.

¹H-NMR (CDCl₃) δ: 1.31 (6H, d, J=6.9 Hz), 1.38-1.57 (1H, m), 1.78-2.07 (3H, m), 2.61-2.82 (2H, m), 3.08 (1H, sept, J=6.9 Hz), 3.58-3.67 (1H, m), 4.66 (1H, d, J=14.4 Hz), 4.86 (1H, d, J=14.7 Hz), 5.03 (2H, s), 5.41 (2H, s), 6.54 (H, d, J=7.8 Hz), 6.71 (1H, d, J=8.1 Hz), 6.90-7.03 (2H, m), 7.15-7.50 (10H, m), 7.58-7.67 (1H, m), 8.39 (1H, d, J=2.4 Hz), 8.57 (1H, dd, J=(0.6, 4.8 Hz).

Example 276

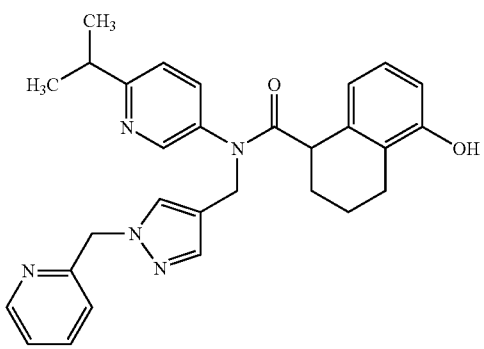

By the reaction and treatment in the same manner as in Example 139 using 5-benzyloxy-N-(6-isopropylpyridin-3-yl)-N-[(1-(2-pyridylmethyl)pyrazol-4-yl)methyl]-1,2,3,4-tetrahydronaphthalene-1-carboxamide (0.72 g) as a starting material, 5-hydroxy-N-(6-isopropylpyridin-3-yl)-N-{[1-(2-pyridylmethyl)pyrazol-4-yl]methyl}-1,2,3,4-tetrahydronaphthalene-1-carboxamide dihydrochloride (0.56 g) was obtained.

MS (ESI) m/z: 482 [MH]⁺

¹H-NMR (DMSO-d₆) δ: 1.30 (6H, d, J=6.9 Hz), 1.37-1.55 (1H, m), 1.70-1.95 (3H, m), 2.34-2.58 (2H, m), 3.24-3.65 (2H, m), 4.50-5.05 (2H, m), 5.62 (2H, s), 6.49 (1H, d, J=7.7 Hz), 6.54 (1H, d, J=7.9 Hz), 6.87 (1H, t, J=7.8 Hz), 7.23 (1H, d, J=7.9 Hz), 7.31-7.43 (1H, m), 7.63-7.90 (3H, m), 8.05-8.29 (2H, m), 8.63-0.79 (2H, m).

Example 277

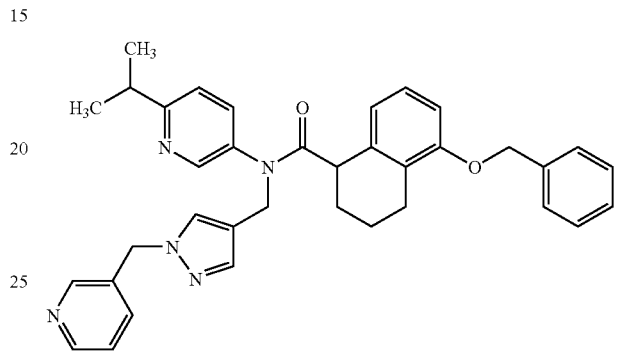

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 3-(chloromethyl)pyridine hydrochloride (0.49 g) as starting materials, 5-benzyloxy-N-(6-isopropylpyridin-3-yl)-N-{[1-(3-pyridylmethyl)pyrazol-4-yl]methyl}-1,2,3,4-tetrahydronaphthalene-1-carboxamide (0.68 g) was obtained.

¹H-NMR (CDCl₃) δ: 1.31 (6H, d, J=6.9 Hz), 1.38-1.55 (1H, m), 1.75-2.07 (3H, m), 2.60-2.82 (2H, m), 3.09 (1H, sept, J=6.9 Hz), 3.57-3.67 (1H, m), 4.61 (1H, d, J=14.5 Hz), 4.84 (1H, d, J=14.5 Hz), 5.03 (2H, s), 5.28 (2H, s), 6.49 (1H, d, J=7.7 Hz), 6.71 (1H, d, J=8.1 Hz), 7.00 (1H, t, J=7.9 Hz), 7.18 (1H, d, J=8.3 Hz), 7.23-7.51 (10H, m), 8.38 (1H, d, J=2.4 Hz), 8.50 (1H, d, J=2.0 Hz), 8.57 (1H, dd, J=1.6, 4.8 Hz).

Example 278

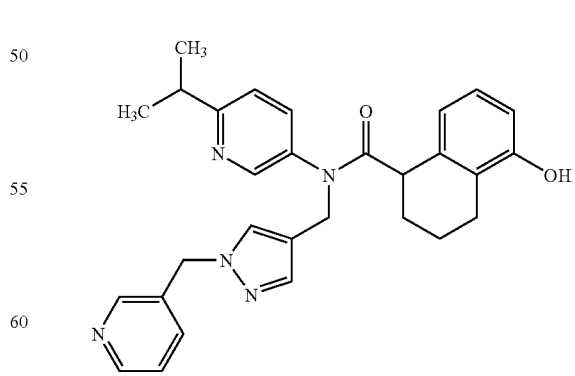

By the reaction and treatment in the same manner as in Example 139 using 5-benzyloxy-N-(6-isopropylpyridin-3-yl)-N-{[1-(3-pyridylmethyl)pyrazol-4-yl]methyl}-1,2,3,4-tetrahydronaphthalene-1-carboxamide (0.66 g) as a starting material, 5-hydroxy-N-(6-isopropylpyridin-3-yl)-N-{[1-(3-pyridylmethyl)pyrazol-4-yl]methyl}-1,2,3,4-tetrahydronaphthalene-1-carboxamide dihydrochloride (0.51 g) was obtained.

MS (ESI) m/z: 482 [MH]+

$^1$H-NMR (DMSO-d$_6$) δ: 1.30 (6H, d, J=6.9 Hz), 1.33-1.53 (1H, m), 1.69-1.93 (3H, m), 2.36-2.61 (2H, m), 3.20-3.64 (2H, m), 4.60-4.96 (2H, m), 5.55 (2H, s), 6.47 (1H, d, J=7.6 Hz), 6.65 (1H, d, J=7.8 Hz), 6.87 (1H, t, J=7.8 Hz), 7.30-7.44 (1H, m), 7.68-7.92 (2H, m), 7.98-8.16 (2H, m), 8.27 (1H, d, J=8.1 Hz), 8.61-0.82 (2H, m), 8.88 (1H, d, J=5.1 Hz).

Example 279

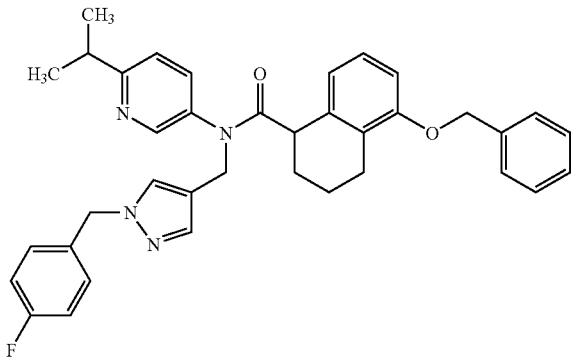

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-fluorobenzyl chloride (0.36 mL) as starting materials, 5-benzyloxy-N-({1-[(4-fluorophenyl)methyl]pyrazol-4-yl}methyl)-N-(6-isopropylpyridin-3-yl)-1,2,3,4-tetrahydronaphthalene-1-carboxamide (0.76 g) was obtained.

$^1$H-NMR (CDCl$_3$) δ: 1.30 (6H, d, J=6.9 Hz), 1.37-1.53 (1H, m), 1.77-2.07 (3H, m), 2.60-2.81 (2H, m), 3.08 (1H, sept, J=6.9 Hz), 3.57-3.66 (1H, m), 4.60 (1H, d, J=14.5 Hz), 4.84 (1H, d, J=14.5 Hz), 5.03 (2H, s), 5.22 (2H, s), 6.49 (1H, d, J=7.7 Hz), 6.71 (1H, d, J=8.1 Hz), 6.92-7.05 (3H, m), 7.11-7.20 (3H, m), 7.24-7.44 (8H, m), 8.36 (1H, d, J=2.4 Hz).

Example 280

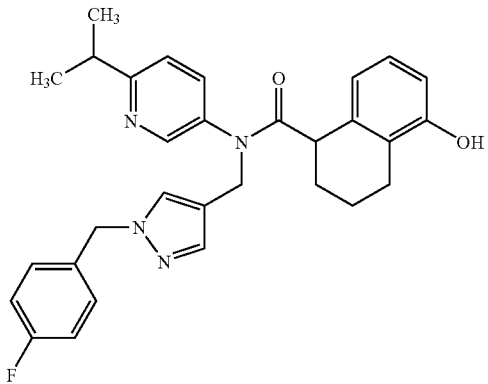

By the reaction and treatment in the same manner as in Example 139 using 5-benzyloxy-N-({1-[(4-fluorophenyl)methyl]pyrazol-4-yl}methyl)-N-(6-isopropylpyridin-3-yl)-1,2,3,4-tetrahydronaphthalene-1-carboxamide (0.76 g) as a starting material, N-({1-[(4-fluorophenyl)methyl]pyrazol-4-yl}methyl)-5-hydroxy-N-(6-isopropylpyridin-3-yl)-1,2,3,4-tetrahydronaphthalene-1-carboxamide hydrochloride (0.59 g) was obtained.

MS (ESI) m/z: 499 [MH]+

$^1$H-NMR (DMSO-d$_6$) δ: 1.29 (6H, d, J=6.9 Hz), 1.33-1.50 (1H, m), 1.68-1.94 (3H, m), 2.34-2.60 (2H, m), 3.20-3.63 (2H, m), 4.60-4.87 (2H, m), 5.26 (2H, s), 6.45 (1H, d, J=7.6 Hz), 6.63 (1H, d, J=7.8 Hz), 6.86 (1H, t, J=7.8 Hz), 7.07-7.22 (4H, m), 7.25-7.37 (1H, m), 7.57-7.78 (2H, m), 7.92-8.10 (1H, m), 8.59-8.75 (1H, m).

Example 281

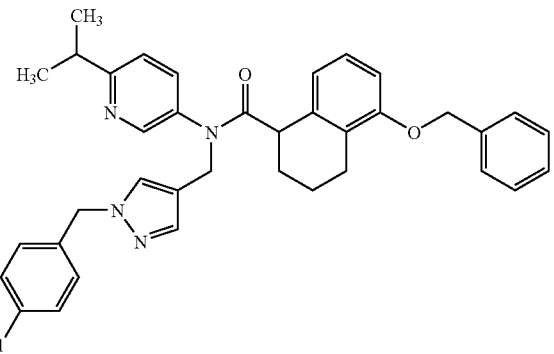

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-chlorobenzyl chloride (0.48 g) as starting materials, 5-benzyloxy-N-({1-[(4-chlorophenyl)methyl]pyrazol-4-yl}methyl)-N-(6-isopropylpyridin-3-yl)-1,2,3,4-tetrahydronaphthalene-1-carboxamide (0.76 g) was obtained.

$^1$H-NMR (CDCl$_3$) δ: 1.31 (6H, d, J=6.9 Hz), 1.37-1.57 (1H, m), 1.77-2.07 (3H, m), 2.60-2.82 (2H, m), 3.09 (1H, sept, J=6.9 Hz), 3.57-3.67 (1H, m), 4.59 (1H, d, J=14.5 Hz), 4.84 (1H, d, J=14.5 Hz), 5.03 (2H, s), 5.22 (2H, s), 6.49 (1H, d, J=7.7 Hz), 6.72 (1H, d, J=8.1 Hz), 6.97 (1H, t, J=7.9 Hz), 7.11 (2H, d, J=8.4 Hz), 7.17 (1H, d, J=8.3 Hz), 7.24-7.43 (10H, m), 8.37 (1H, d, J=2.4 Hz).

Example 282

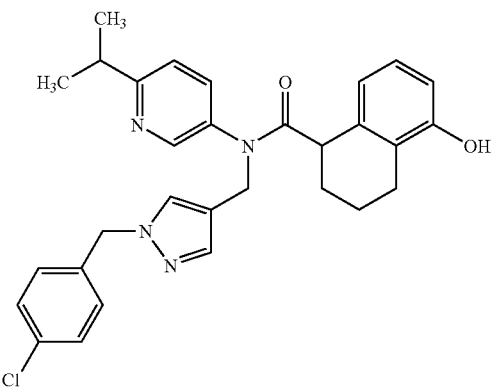

By the reaction and treatment in the same manner as in Example 139 using 5-benzyloxy-N-({1-[(4-chlorophenyl)methyl]pyrazol-4-yl}methyl)-N-(6-isopropylpyridin-3-yl)-1,2,3,4-tetrahydronaphthalene-1-carboxamide (0.76 g) as a starting material, N-({1-[(4-chlorophenyl)methyl]pyrazol-4-yl}methyl)-5-hydroxy-N-(6-isopropylpyridin-3-yl)-1,2,3,4-tetrahydronaphthalene-1-carboxamide hydrochloride (0.65 g) was obtained.

MS (ESI) m/z: 515 [MH]+

$^1$H-NMR (DMSO-d$_6$) δ: 1.29 (6H, d, J=6.9 Hz), 1.36-1.53 (1H, m), 1.67-1.95 (3H, m), 2.33-2.57 (2H, m), 3.17-3.67 (2H, m), 4.59-4.89 (2H, m), 5.27 (2H, s), 6.45 (1H, d, J=7.8 Hz), 6.63 (1H, d, J=7.8 Hz), 6.86 (1H, t, J=7.8 Hz), 7.15 (2H, d, J=8.4 Hz), 7.22-7.36 (1H, m), 7.41 (2H, d, J=8.4 Hz), 7.57-7.78 (2H, m), 7.90-8.08 (1H, m), 8.58-8.72 (1H, m).

Example 283

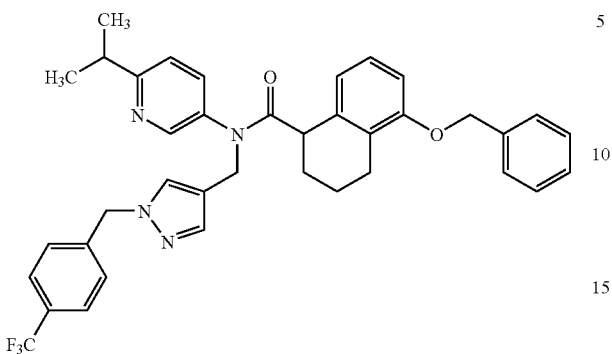

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-(trifluoromethyl)benzyl chloride (0.48 g) as starting materials, 5-benzyloxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide (0.84 g) was obtained.

$^1$H-NMR (CDCl$_3$) δ: 1.30 (6H, d, J=6.9 Hz), 1.37-1.57 (1H, m), 1.78-2.07 (3H, m), 2.60-2.82 (2H, m), 3.09 (1H, sept, J=6.9 Hz), 3.58-3.68 (1H, m), 4.61 (1H, d, J=14.5 Hz), 4.85 (1H, d, J=14.5 Hz), 5.03 (2H, s), 5.31 (2H, s), 6.49 (1H, d, J=7.7 Hz), 6.71 (1H, d, J=8.1 Hz), 6.96 (1H, t, J=7.9 Hz), 7.18 (1H, d, J=8.3 Hz), 7.23-7.46 (10H, m), 7.60 (2H, d, J=8.2 Hz), 8.38 (1H, d, J=2.4 Hz).

Example 284

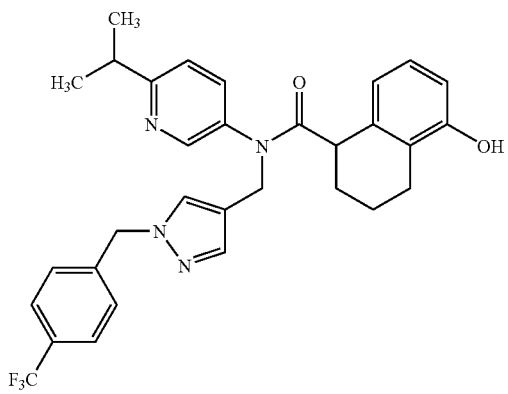

By the reaction and treatment in the same manner as in Example 139 using 5-benzyloxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide (0.83 g) as a starting material, 5-hydroxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide hydrochloride (0.67 g) was obtained. MS (ESI) m/z: 549 [MH]$^+$ $^1$H-NMR (DMSO-d$_6$) δ: 1.27 (6H, d, J=6.9 Hz), 1.33-1.50 (1H, m), 1.70-1.96 (3H, m), 2.34-2.59 (2H, m), 3.12-3.67 (2H, m), 4.64-4.87 (2H, m), 5.40 (2H, s), 6.45 (1H, d, J=7.5 Hz), 6.62 (1H, d, J=7.8 Hz), 6.84 (1H, t, J=7.7 Hz), 7.22-7.40 (3H, m), 7.57-7.77 (4H, m), 7.89-8.05 (1H, m), 8.56-8.71 (1H, m).

Example 285

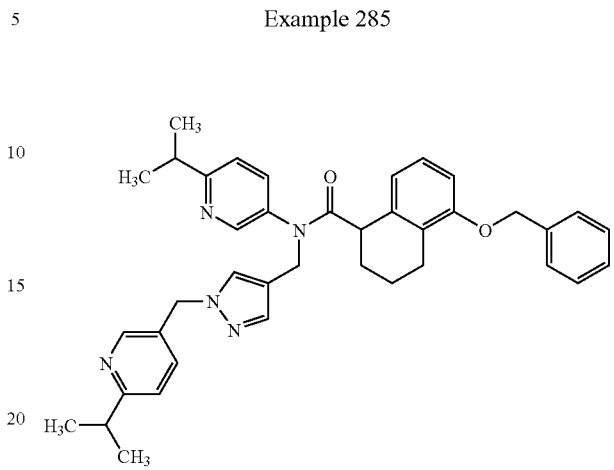

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 3-chloromethyl-6-isopropylpyridine (0.51 g) as starting materials, 5-benzyloxy-N-(6-isopropylpyridin-3-yl)-N-({1-[(6-isopropylpyridin-3-yl)methyl]pyrazol-4-yl}methyl)-1,2,3,4-tetrahydronaphthalene-1-carboxamide (0.77 g) was obtained.

$^1$H-NMR (CDCl$_3$) δ: 1.28 (6H, d, J=6.9 Hz), 1.31 (6H, d, J=6.9 Hz), 1.37-1.54 (1H, m), 1.77-2.07 (3H, m), 2.60-2.82 (2H, m), 2.99-3.17 (2H, m), 3.57-3.67 (1H, m), 4.61 (1H, d, J=14.7 Hz), 4.83 (1H, d, J=14.4 Hz), 5.03 (2H, s), 5.24 (2H, s), 6.50 (1H, d, J=7.8 Hz), 6.71 (1H, d, J=8.1 Hz), 6.99 (1H, t, J=8.0 Hz), 7.10-7.19 (2H, m), 7.25-7.45 (9H, m), 8.38 (1H, d, J=2.4 Hz), 8.42 (1H, d, J=2.1 Hz).

Example 286

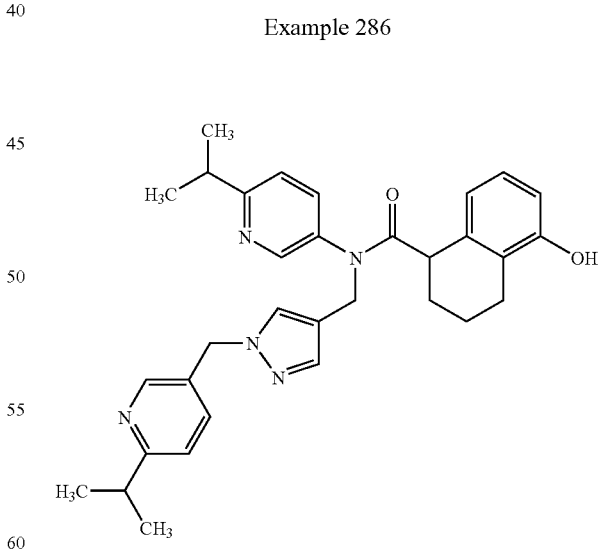

By the reaction and treatment in the same manner as in Example 139 using 5-benzyloxy-N-(6-isopropylpyridin-3-yl)-N-({1-[(6-isopropylpyridin-3-yl)methyl]pyrazol-4-yl}methyl)-1,2,3,4-tetrahydronaphthalene-1-carboxamide (0.76 g) as a starting material, 5-hydroxy-N-(6-isopropylpyridin-3-yl)-N-({1-[(6-isopropylpyridin-3-yl)methyl]pyrazol-4-yl}methyl)-1,2,3,4-tetrahydronaphthalene-1-carboxamide dihydrochloride (0.57 g) was obtained. MS (ESI) m/z: 524 [MH]$^+$ $^1$H-NMR (DMSO-d$_6$) δ: 1.30 (6H, d, J=6.9 Hz), 1.35 (6H, d, J=6.9 Hz), 1.37-1.50 (1H, m), 1.70-1.97 (3H, m), 2.34-2.60 (2H, m), 3.23-3.62 (3H, m), 4.63-4.88 (2H, m), 5.52 (2H, s), 6.47 (1H, d, J=7.5 Hz), 6.64 (1H, d, J=8.1 Hz), 6.87 (1H, t, J=7.8 Hz), 7.30-7.45 (1H, m), 7.72-7.89 (2H, m), 7.96-8.16 (2H, m), 8.25 (1H, dd, J=1.8, 8.1 Hz), 8.58-8.78 (2H, m).

Example 287

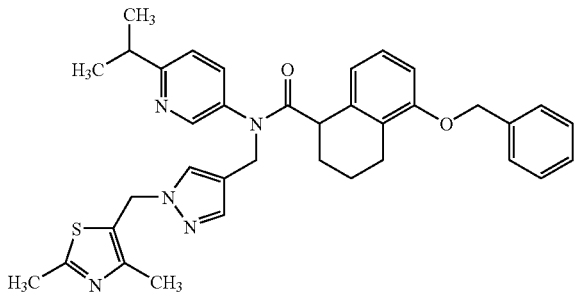

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 5-(chloromethyl)-2,4-dimethylthiazole (0.49 g) as starting materials, 5-benzyloxy-N-({1-[(2,4-dimethylthiazol-5-yl)methyl]pyrazol-4-yl}methyl)-N-(6-isopropylpyridin-3-yl)-1,2,3,4-tetrahydronaphthalene-1-carboxamide (0.92 g) was obtained.

$^1$H-NMR (CDCl$_3$) δ: 1.31 (6H, d, J=6.9 Hz), 1.37-1.57 (1H, m), 1.77-2.09 (3H, m), 2.34 (3H, s), 2.39 (3H, s), 2.67-2.83 (2H, m), 3.09 (1H, sept, J=6.9 Hz), 3.57-3.67 (1H, m), 4.59 (1H, d, J=14.4 Hz), 4.82 (1H, d, J=14.4 Hz), 5.03 (2H, s), 5.31 (2H, s), 6.50 (1H, d, J=7.5 Hz), 6.72 (1H, d, J=8.1 Hz), 7.01 (1H, t, J=8.0 Hz), 7.18 (1H, d, J=8.4 Hz), 7.24-7.42 (8H, m), 8.36 (1H, d, J=2.4 Hz).

Example 288

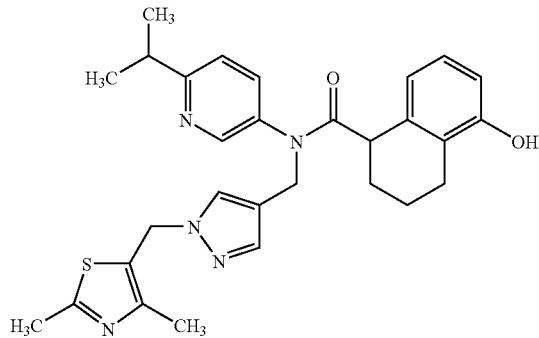

By the reaction and treatment in the same manner as in Example 139 using 5-benzyloxy-N-({1-[(2,4-dimethylthiazol-5-yl) methyl]pyrazol-4-yl}methyl)-N-(6-isopropylpyridin-3-yl)-1,2,3,4-tetrahydronaphthalene-1-carboxamide (0.91 g) as a starting material, N-({1-[(2,4-dimethylthiazol-5-yl)methyl]pyrazol-4-yl}methyl)-5-hydroxy-N-(6-isopropylpyridin-3-yl)-1,2,3,4-tetrahydronaphthalene-1-carboxamide hydrochloride (0.35 g) was obtained.

MS (ESI) m/z: 516 [MH]$^+$ $^1$H-NMR (DMSO-d$_6$) δ: 1.29 (6H, d, J=6.9 Hz), 1.34-1.50 (1H, m), 1.70-1.95 (3H, m), 2.34 (3H, s), 2.37-2.57 (2H, m), 2.62 (3H, s), 3.17-3.67 (2H, m), 4.60-4.85 (2H, m), 5.43 (2H, s), 6.44 (1H, d, J=7.7 Hz), 6.63 (1H, d, J=7.9 Hz), 6.87 (1H, t, J=7.8 Hz), 7.25-7.39 (1H, m), 7.60-7.80 (2H, m), 7.92-8.07 (1H, m), 8.57-8.72 (1H, m).

Example 289

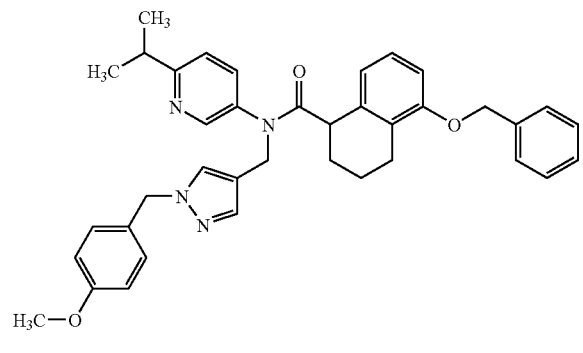

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-methoxybenzyl chloride (0.41 mL) as starting materials, 5-benzyloxy-N-(6-isopropylpyridin-3-yl)-N-({1-[(4-methoxyphenyl)methyl]pyrazol-4-yl}methyl)-1,2,3,4-tetrahydronaphthalene-1-carboxamide (0.69 g) was obtained.

$^1$H-NMR (CDCl$_3$) δ: 1.30 (6H, d, J=6.9 Hz), 1.37-1.53 (1H, m), 1.75-2.07 (3H, m), 2.60-2.82 (2H, m), 3.08 (1H, sept, J=6.9 Hz), 3.57-3.67 (1H, m), 3.79 (3H, s), 4.59 (1H, d, J=14.4 Hz), 4.83 (1H, d, J=14.4 Hz), 5.03 (2H, s), 5.19 (2H, s), 6.50 (1H, d, J=7.5 Hz), 6.71 (1H, d, J=8.1 Hz), 6.86 (2H, d, J=6.3 Hz), 6.99 (1H, t, J=8.1 Hz), 7.10-7.18 (3H, m), 7.23-7.45 (8H, m), 8.37 (1H, d, J=2.4 Hz).

Example 290

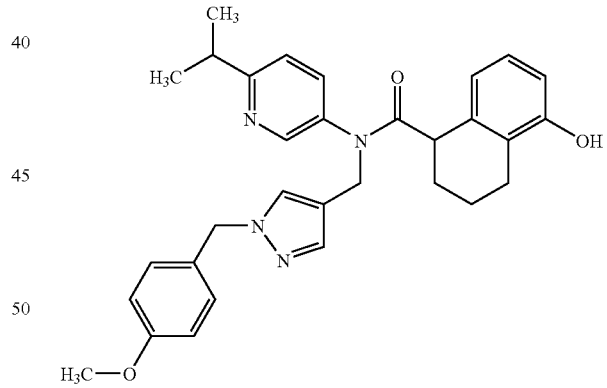

By the reaction and treatment in the same manner as in Example 101 using 5-benzyloxy-N-(6-isopropylpyridin-3-yl)-N-({1-[(4-methoxyphenyl)methyl]pyrazol-4-yl}methyl)-1,2,3,4-tetrahydronaphthalene-1-carboxamide (0.69 g) as a starting material, 5-hydroxy-N-(6-isopropylpyridin-3-yl)-N-({1-[(4-methoxyphenyl)methyl]pyrazol-4-yl}methyl)-1,2,3,4-tetrahydronaphthalene-1-carboxamide hydrochloride (0.54 g) was obtained.

MS (ESI) m/z: 511 [MH]$^+$ $^1$H-NMR (DMSO-d$_6$) δ: 1.27 (6H, d, J=6.9 Hz), 1.31-1.50 (1H, m), 1.70-1.96 (3H, m), 2.35-2.60 (2H, m), 3.10-3.70 (2H, m), 3.73 (3H, s), 4.61-4.85 (2H, m), 5.18 (2H, s), 6.43 (1H, d, J=7.57 Hz), 6.62 (1H, d, J=7.9 Hz), 6.80-6.92 (3H, m), 7.11 (2H, d, J=8.4 Hz), 7.22-7.34 (1H, m), 7.51-7.68 (2H, m), 7.83-7.97 (1H, m), 8.52-8.67 (1H, m).

Example 291

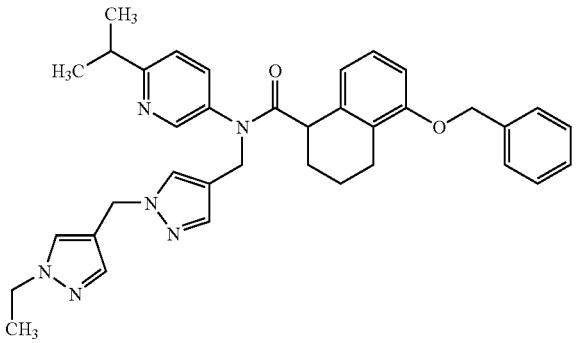

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-chloromethyl-1-ethylpyrazole (0.43 g) as starting materials, 5-benzyloxy-N-({1-[(1-ethylpyrazol-4-yl)methyl]pyrazol-4-yl}methyl)-N-(6-isopropylpyridin-3-yl)-1,2,3,4-tetrahydronaphthalene-1-carboxamide (0.58 g) was obtained.

$^1$H-NMR (CDCl$_3$) δ: 1.30 (6H, d, J=6.9 Hz), 1.46 (3H, t, J=7.2 Hz), 1.38-1.55 (1H, m), 1.73-2.07 (3H, m), 2.60-2.80 (2H, m), 3.08 (1H, sept, J=6.9 Hz), 3.57-3.66 (1H, m), 4.14 (2H, q, J=7.2 Hz), 4.58 (2H, s), 4.65 (1H, d, J=14.7 Hz), 4.78 (1H, d, J=14.4 Hz), 5.02 (2H, s), 6.16 (1H, s), 6.52 (1H, d, J=7.7 Hz), 6.72 (1H, d, J=5.1 Hz), 7.03 (1H, t, J=7.9 Hz), 7.17 (1H, d, J=8.3 Hz), 7.23-7.56 (9H, m), 8.35 (1H, d, J=2.4 Hz).

Example 292

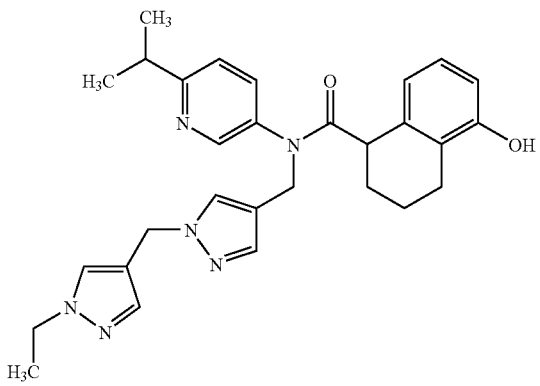

By the reaction and treatment in the same manner as in Example 139 using 5-benzyloxy-N-({1-[(1-ethylpyrazol-4-yl)methyl]pyrazol-4-yl}methyl)-N-(6-isopropylpyridin-3-yl)-1,2,3,4-tetrahydronaphthalene-1-carboxamide (0.44 g) as a starting material, N-({1-[(1-ethylpyrazol-4-yl)methyl]pyrazol-4-yl}methyl)-5-hydroxy-N-(6-isopropylpyridin-3-yl)-1,2,3,4-tetrahydronaphthalene-1-carboxamide hydrochloride (0.34 g) was obtained. MS (ESI) m/z: 499 [MH]$^+$ $^1$H-NMR (DMSO-d$_6$) δ: 1.28 (6H, d, J=6.9 Hz), 1.32 (3H, t, J=7.2 Hz), 1.38-1.50 (1H, m), 1.70-1.96 (3H, m), 2.36-2.58 (2H, m), 3.08-3.50 (2H, m), 4.08 (2H, q, J=7.2 Hz), 4.58-4.81 (2H, m), 5.10 (2H, s), 6.43 (1H, d, J=7.5 Hz), 6.62 (1H, d, J=8.1 Hz), 6.87 (1H, t, J=7.7 Hz), 7.18-7.36 (2H, m), 7.48-7.68 (3H, m), 7.82-7.97 (1H, m), 8.50-8.63 (1H, m).

Example 293

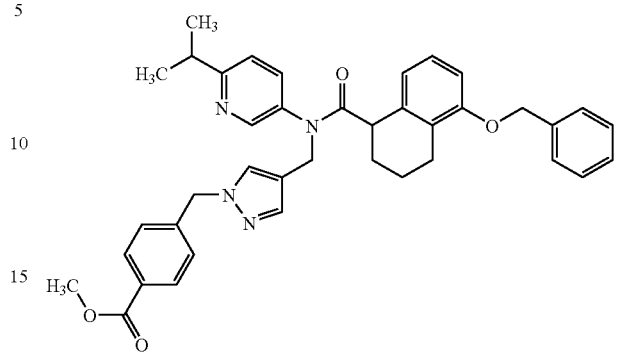

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.66 g) and methyl 4-(bromomethyl)benzoate (0.31 g) as starting materials, methyl 4-[(4-{[N-(5-benzyloxy-1,2,3,4-tetrahydronaphthalene-1-ylcarbonyl)-N-(6-isopropylpyridin-3-yl)amino]methyl}pyrazol-1-yl)methyl]benzoate (0.61 g) was obtained.

$^1$H-NMR (CDCl$_3$) δ: 1.31 (6H, d, J=6.9 Hz), 1.37-1.54 (1H, m), 1.77-2.08 (3H, m), 2.60-2.82 (2H, m), 3.09 (1H, sept, J=6.9 Hz), 3.58-3.68 (1H, m), 3.91 (3H, s), 4.62 (1H, d, J=14.5 Hz), 4.85 (1H, d, J=14.5 Hz), 5.03 (2H, s), 5.31 (2H, s), 6.50 (1H, d, J=7.7 Hz), 6.71 (1H, d, J=8.1 Hz), 6.98 (1H, t, J=7.9 Hz), 7.14-7.46 (12H, m), 8.01 (1H, dd, J=1.7, 8.3 Hz), 8.38 (1H, d, J=2.4 Hz).

Example 294

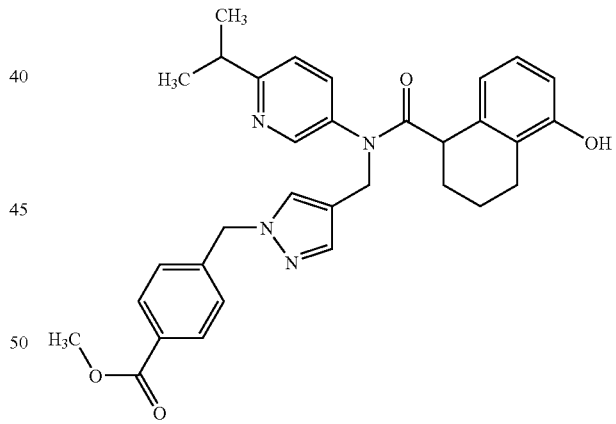

By the reaction and treatment in the same manner as in Example 101 using methyl 4-[(4-{[N-(5-benzyloxy-1,2,3,4-tetrahydronaphthalene-1-ylcarbonyl)-N-(6-isopropylpyridin-3-yl)amino]methyl}pyrazol-1-yl)methyl]benzoate (0.61 g) as a starting material, methyl 4-[(4-{[N-(5-hydroxy-1,2,3,4-tetrahydronaphthalene-1-ylcarbonyl)-N-(6-isopropylpyridin-3-yl)amino]methyl}pyrazol-1-yl)methyl]benzoate hydrochloride (0.51 g) was obtained.

MS (ESI) m/z: 539 [MH]$^+$ $^1$H-NMR (DMSO-d$_6$) δ: 1.28 (6H, d, J=6.9 Hz), 1.35-1.50 (1H, m), 1.72-1.97 (3H, m), 2.36-2.60 (2H, m), 3.15-3.70 (2H, m), 3.85 (3H, s), 4.65-4.90 (2H, m), 5.38 (2H, s), 6.45 (1H, d, J=7.6 Hz), 6.62 (1H, d, J=7.8 Hz), 6.85 (1H, t, J=7.8

Hz), 7.21 (2H, d, J=8.3 Hz), 7.29-7.42 (1H, m), 7.58-7.75 (1H, m), 7.90-8.02 (4H, m), 8.58-8.71 (1H, m).

Example 295

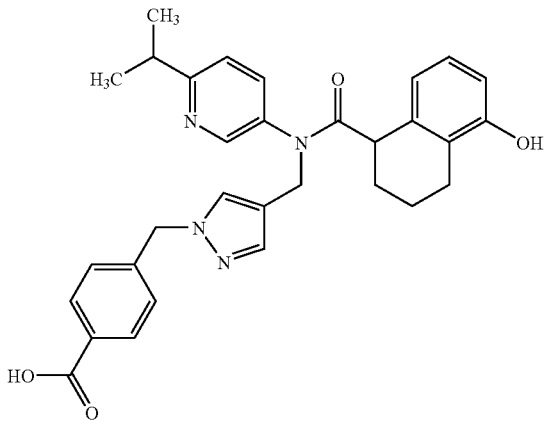

Methyl 4-[(4-{[N-(5-hydroxy-1,2,3,4-tetrahydronaphthalene-1-ylcarbonyl)-N-(6-isopropylpyridin-3-yl)amino]methyl}pyrazol-1-yl)methyl]benzoate (0.36 g) was dissolved in a mixed solvent (4 mL) of ethanol: 1 mol/L-aqueous sodium hydroxide solution (1:1), and the mixture was stirred at room temperature for one day. The reaction mixture was concentrated under reduced pressure, and the residue was partitioned between water and toluene. Citric acid was added to the aqueous layer until the mixture is acidified. The aqueous layer was extracted with ethyl acetate. The organic layer was washed with saturated brine and dried over anhydrous magnesium sulfate. The solvent was evaporated, and the residue was dissolved in ethyl acetate. Thereto was added 4 mol/L-HCl/dioxane. The precipitated solid was collected by filtration to give 4-[(4-{[N-(5-hydroxy-1,2,3,4-tetrahydronaphthalene-1-ylcarbonyl)-N-(6-isopropylpyridin-3-yl)amino]methyl}pyrazol-1-yl)methyl]benzoic acid hydrochloride (0.27 g).

MS (ESI) m/z: 525 [MH]$^+$ $^1$H-NMR (DMSO-d$_6$) δ: 1.26 (6H, d, J=6.9 Hz), 1.33-1.51 (1H, m), 1.70-1.98 (3H, m), 2.34-2.60 (2H, m), 3.07-3.60 (2H, m), 4.65-4.89 (2H, m), 5.37 (2H, s), 6.44 (1H, d, J=7.5 Hz), 6.61 (1H, d, J=7.8 Hz), 6.85 (1H, t, J=7.7 Hz), 7.18 (2H, d, J=7.9 Hz), 7.27-7.40 (1H, m), 7.52-7.73 (2H, m), 7.80-7.97 (3H, m), 8.50-8.68 (1H, m).

Example 296

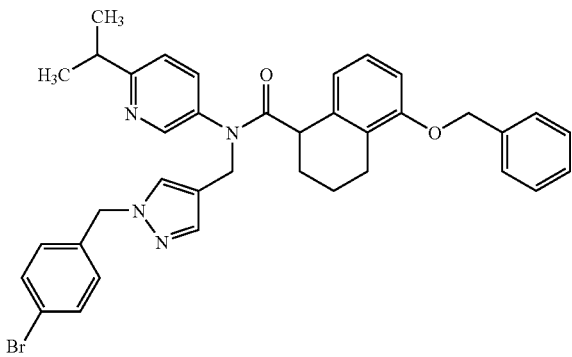

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-bromobenzyl chloride (0.75 g) as starting materials, 5-benzyloxy-N-({1-[(4-bromophenyl)methyl]pyrazol-4-yl}methyl)-N-(6-isopropylpyridin-3-yl)-1,2,3,4-tetrahydronaphthalene-1-carboxamide (0.83 g) was obtained.

$^1$H-NMR (CDCl$_3$) δ: 1.31 (6H, d, J=6.9 Hz), 1.38-1.54 (1H, m), 1.75-2.07 (3H, m), 2.61-2.82 (2H, m), 3.09 (1H, sept, J=6.9 Hz), 3.57-3.67 (1H, m), 4.59 (1H, d, J=14.4 Hz), 4.84 (1H, d, J=14.7 Hz), 5.03 (2H, s), 5.20 (2H, s), 6.48 (1H, d, J=7.5 Hz), 6.72 (1H, d, J=8.1 Hz), 6.97 (1H, t, J=7.8 Hz), 7.05 (2H, d, J=8.1 Hz), 7.17 (1H, d, J=8.1 Hz), 7.25-7.49 (10H, m), 8.37 (1H, d, J=2.4 Hz).

Example 297

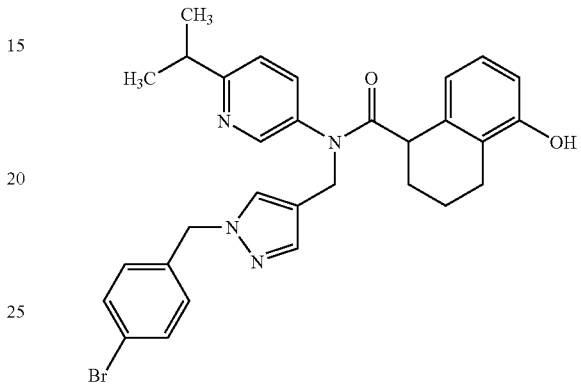

By the reaction and treatment in the same manner as in Example 139 using 5-benzyloxy-N-({1-[(4-bromophenyl)methyl]pyrazol-4-yl}methyl)-N-(6-isopropylpyridin-3-yl)-1,2,3,4-tetrahydronaphthalene-1-carboxamide (0.83 g) as a starting material, N-({1-[(4-bromophenyl)methyl]pyrazol-4-yl}methyl)-5-hydroxy-N-(6-isopropylpyridin-3-yl)-1,2,3,4-tetrahydronaphthalene-1-carboxamide hydrochloride (0.68 g) was obtained.

MS (ESI) m/z: 559, 561 [MH]$^+$ $^1$H-NMR (DMSO-d$_6$) δ: 1.29 (6H, d, J=6.9 Hz), 1.34-1.52 (1H, m), 1.69-1.95 (3H, m), 2.34-2.58 (2H, m), 3.18-3.66 (2H, m), 4.62-4.90 (2H, m), 5.26 (2H, s), 6.44 (1H, d, J=7.6 Hz), 6.63 (1H, d, J=7.8 Hz), 6.86 (1H, t, J=7.8 Hz), 7.08 (2H, d, J=8.4 Hz), 7.23-7.42 (1H, m), 7.54 (2H, d, J=8.3 Hz), 7.59-7.79 (2H, m), 7.92-8.10 (1H, m), 8.60-8.79 (1H, m).

Example 298

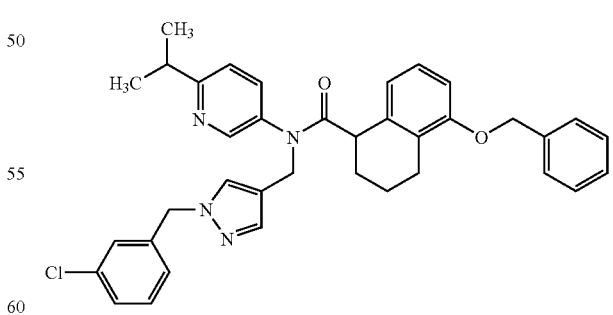

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 3-chlorobenzyl chloride (0.38 mL) as starting materials, 5-benzyloxy-N-({1-[(3-chlorophenyl)methyl]pyrazol-4-yl}methyl)-N-(6- isopropylpyridin-3-yl)-1,2,3,4-tetrahydronaphthalene-1-carboxamide (0.77 g) was obtained.

¹H-NMR (CDCl₃) δ: 1.30 (6H, d, J=6.9 Hz), 1.38-1.56 (1H, m), 1.87-2.07 (3H, m), 2.62-2.83 (2H, m), 3.09 (1H, sept, J=6.9 Hz), 3.58-3.68 (1H, m), 4.62 (1H, d, J=14.4 Hz), 4.84 (1H, d, J=14.4 Hz), 5.03 (2H, s), 5.23 (2H, s), 6.51 (1H, d, J=7.5 Hz), 6.71 (1H, d, J=8.1 Hz), 6.93-7.19 (3H, m), 7.24-7.47 (11H, m), 8.40 (1H, d, J=2.4 Hz).

Example 299

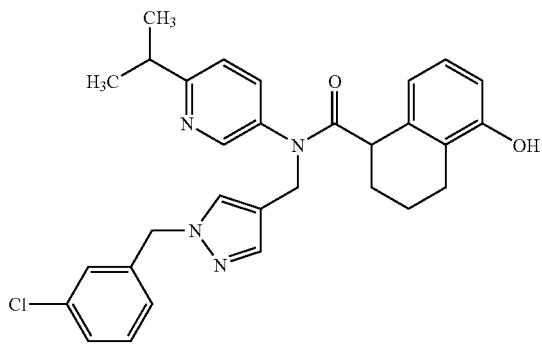

By the reaction and treatment in the same manner as in Example 139 using 5-benzyloxy-N-({1-[(3-chlorophenyl)methyl]pyrazol-4-yl}methyl)-N-(6-isopropylpyridin-3-yl)-1,2,3,4-tetrahydronaphthalene-1-carboxamide (0.77 g) as a starting material, N-({1-[(3-chlorophenyl)methyl]pyrazol-4-yl}methyl)-5-hydroxy-N-(6-isopropylpyridin-3-yl)-1,2,3,4-tetrahydronaphthalene-1-carboxamide hydrochloride (0.62 g) was obtained.

MS (ESI) m/z: 515 [MH]⁺

¹H-NMR (DMSO-d₆) δ: 1.30 (6H, d, J=6.9 Hz), 1.34-1.54 (1H, m), 1.70-1.96 (3H, m), 2.37-2.62 (2H, m), 3.21-3.70 (2H, m), 4.60-4.92 (2H, m), 5.30 (2H, s), 6.46 (1H, d, J=7.6 Hz), 6.63 (1H, d, J=7.8 Hz), 6.86 (1H, t, J=7.8 Hz), 7.02-7.12 (1H, m), 7.20 (1H, s), 7.27-7.44 (3H, m), 7.62-7.82 (2H, m), 7.93-8.12 (1H, m), 8.63-8.85 (1H, m).

Example 300

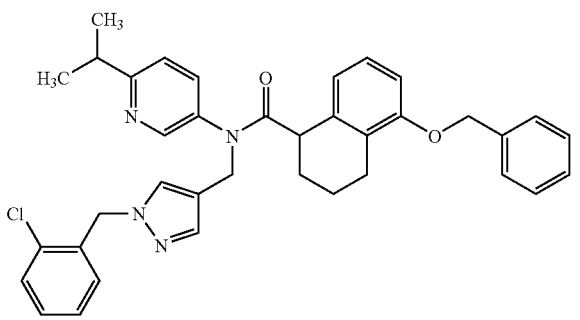

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-chlorobenzyl chloride (0.38 mL) as starting materials, 5-benzyloxy-N-({1-[(2-chlorophenyl)methyl]pyrazol-4-yl}methyl)-N-(6- isopropylpyridin-3-yl)-1,2,3,4-tetrahydronaphthalene-1-carboxamide (0.77 g) was obtained.

¹H-NMR (CDCl₃) δ: 1.30 (6H, d, J=6.9 Hz), 1.38-1.55 (1H, m), 1.76-2.08 (3H, m), 2.61-2.82 (2H, m), 3.08 (1H, sept, J=6.9 Hz), 3.57-3.67 (1H, m), 4.66 (1H, d, J=14.4 Hz), 4.84 (1H, d, J=14.4 Hz), 5.03 (2H, s), 5.38 (2H, s), 6.53 (1H, d, J=7.5 Hz), 6.71 (1H, d, J=8.1 Hz), 6.96-7.06 (2H, m), 7.13-7.45 (12H, m), 8.38 (1H, d, J=2.4 Hz).

Example 301

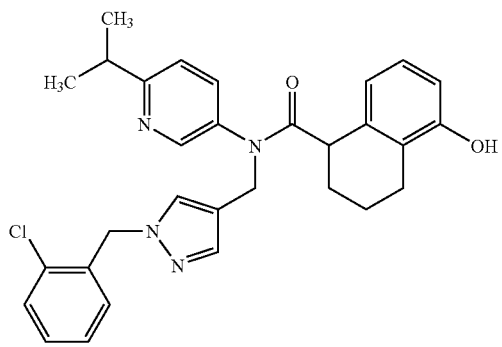

By the reaction and treatment in the same manner as in Example 139 using 5-benzyloxy-N-({1-[(2-chlorophenyl)methyl]pyrazol-4-yl}methyl)-N-(6-isopropylpyridin-3-yl)-1,2,3,4-tetrahydronaphthalene-1-carboxamide (0.76 g) as a starting material, N-({1-[(2-chlorophenyl)methyl]pyrazol-4-yl}methyl)-5-hydroxy-N-(6-isopropylpyridin-3-yl)-1,2,3,4-tetrahydronaphthalene-1-carboxamide hydrochloride (0.61 g) was obtained.

MS (ESI) m/z: 515 [MH]⁺

¹H-NMR (DMSO-d₆) δ: 1.30 (6H, d, J=6.9 Hz), 1.32-1.53 (1H, m), 1.70-1.98 (3H, m), 2.36-2.61 (2H, m), 3.21-3.67 (2H, m), 4.64-4.90 (2H, m), 5.37 (2H, s), 6.47 (1H, d, J=7.6 Hz), 6.64 (1H, d, J=7.9 Hz), 6.79-6.91 (2H, m), 7.23-7.50 (4H, m), 7.57-7.85 (2H, m), 7.93-8.17 (1H, m), 8.62-8.94 (1H, m).

Example 302

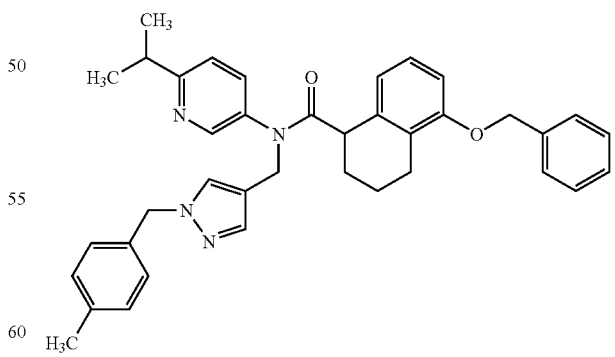

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-methylbenzyl chloride (0.42 g) as starting materials, 5-benzyloxy- N-(6-isopropylpyridin-3-yl)-N-({1-[(4-methylphenyl)methyl]pyrazol-4-yl}methyl)-1,2,3,4-tetrahydronaphthalene-1-carboxamide (0.66 g) was obtained.

¹H-NMR (CDCl₃) δ: 1.30 (6H, d, J=6.9 Hz), 1.38-1.53 (1H, m), 1.77-2.07 (3H, m), 2.33 (3H, s), 2.62-2.80 (2H, m), 3.08 (1H, sept, J=6.9 Hz), 3.57-3.64 (1H, m), 4.60 (1H, d, J=14.4 Hz), 4.84 (1H, d, J=14.7 Hz), 5.03 (2H, s), 5.21 (2H, s), 6.50 (1H, d, J=7.8 Hz), 6.71 (1H, d, J=8.1 Hz), 6.99 (1H, t, J=8.0 Hz), 7.03-7.18 (5H, m), 7.24-7.42 (8H, m), 8.37 (1H, d, J=2.4 Hz).

Example 303

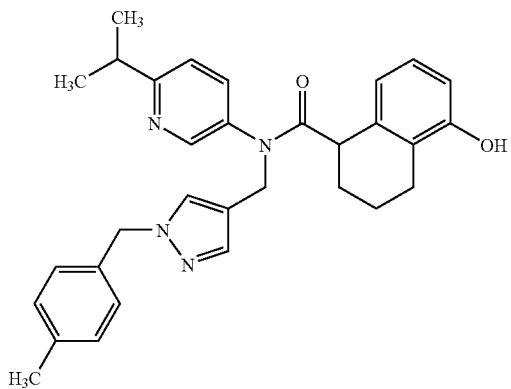

By the reaction and treatment in the same manner as in Example 139 using 5-benzyloxy-N-(6-isopropylpyridin-3-yl)-N-({1-[(4-methylphenyl)methyl]pyrazol-4-yl}methyl)-1,2,3,4-tetrahydronaphthalene-1-carboxamide (0.66 g) as starting materials, 5-hydroxy-N-(6-isopropylpyridin-3-yl)-N-({1-[(4-methylphenyl)methyl]pyrazol-4-yl}methyl)-1,2,3,4-tetrahydronaphthalene-1-carboxamide hydrochloride (0.55 g) was obtained.

MS (ESI) m/z: 495 [MH]⁺

¹H-NMR (DMSO-d₆) δ: 1.31 (6H, d, J=6.9 Hz), 1.35-1.52 (1H, m), 1.68-1.95 (3H, m), 2.27 (3H, s), 2.34-2.58 (2H, m), 3.25-3.63 (2H, m), 4.65-4.91 (2H, m), 5.21 (2H, s), 6.45 (1H, d, J=7.6 Hz), 6.64 (1H, d, J=7.8 Hz), 6.86 (1H, t, J=7.8 Hz), 7.03 (2H, d, J=8.0 Hz), 7.14 (2H, d, J=7.9 Hz), 7.25-7.40 (1H, m), 7.64-7.86 (2H, m), 7.99-8.17 (1H, m), 8.66-8.82 (1H, m).

Example 304

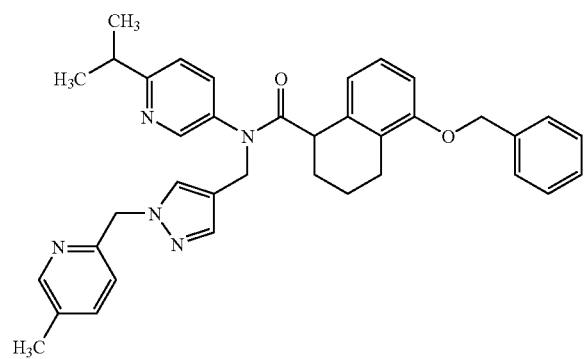

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-(chloromethyl)-5-methylpyridine (0.43 g) as starting materials, 5-benzyloxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide (0.71 g) was obtained.

¹H-NMR (CDCl₃) δ: 1.30 (6H, d, J=6.9 Hz), 1.40-1.57 (1H, m), 1.74-2.09 (3H, m), 2.32 (3H, s), 2.61-2.80 (2H, m), 3.08 (1H, sept, J=6.9 Hz), 3.58-3.67 (1H, m), 4.65 (1H, d, J=14.5 Hz), 4.85 (1H, d, J=14.5 Hz), 5.03 (2H, s), 5.36 (2H, s), 6.54 (1H, d, J=7.7 Hz), 6.71 (1H, d, J=8.1 Hz), 6.89 (1H, d, J=8.0 Hz), 7.01 (1H, t, J=7.9 Hz), 7.17 (1H, d, J=8.3 Hz), 7.24-7.49 (9H, m), 8.38 (2H, s).

Example 305

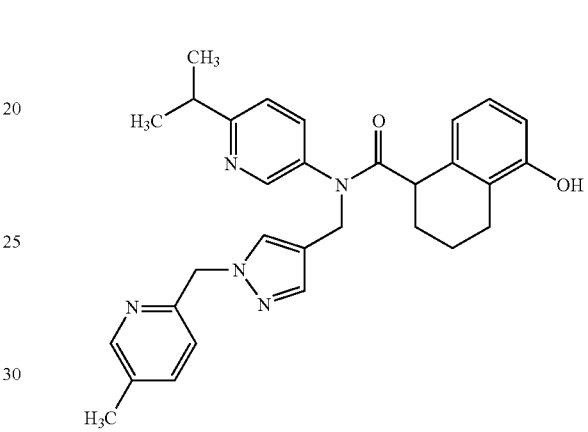

By the reaction and treatment in the same manner as in Example 139 using 5-benzyloxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide (0.71 g) as a starting material, 5-hydroxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide dihydrochloride (0.62 g) was obtained. MS (ESI) m/z: 496 [MH]⁺

¹H-NMR (DMSO-d₆) δ: 1.31 (6H, d, J=6.9 Hz), 1.33-1.55 (1H, m), 1.71-1.97 (3H, m), 2.43 (3H, s), 2.36-2.59 (2H, m), 3.29-3.64 (2H, m), 4.62-4.91 (2H, m), 5.67 (2H, s), 6.49 (1H, d, J=7.7 Hz), 6.65 (1H, d, J=7.9 Hz), 6.88 (1H, t, J=7.8 Hz), 7.28-7.41 (2H, m), 7.72-7.96 (2H, m), 8.12-8.29 (2H, m), 8.63-8.80 (2H, m).

Example 306

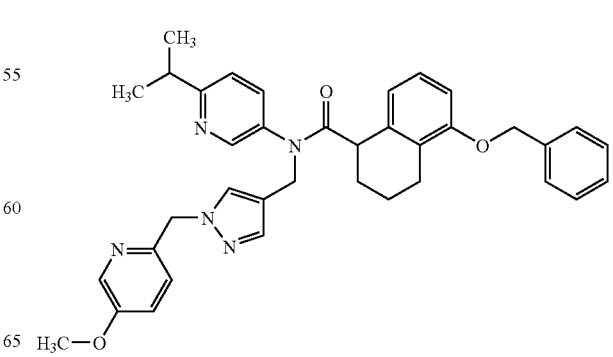

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 6-chloromethyl-3-methoxypyridine (0.47 g) as starting materials, 5-benzyloxy-N-(6-isopropylpyridin-3-yl)-N-({1-[(5-methoxypyridin-2-yl)methyl]pyrazol-4-yl}methyl)-1,2,3,4-tetrahydronaphthalene-1-carboxamide (0.63 g) was obtained.

$^1$H-NMR (CDCl$_3$) δ: 1.30 (6H, d, J=6.9 Hz), 1.41-1.57 (1H, m), 1.76-2.09 (3H, m), 2.61-2.82 (2H, m), 3.08 (1H, sept, J=6.9 Hz), 3.68-3.77 (1H, m), 3.84 (3H, s), 4.65 (1H, d, J=14.5 Hz), 4.84 (1H, d, J=14.5 Hz), 5.03 (2H, s), 5.33 (2H, s), 6.54 (1H, d, J=7.7 Hz), 6.71 (1H, d, J=8.1 Hz), 6.95-7.05 (2H, m), 7.11-7.19 (2H, m), 7.25-7.47 (8H, m), 8.25 (1H, d, J=2.9 Hz), 8.37 (1H, d, J=2.4 Hz).

Example 307

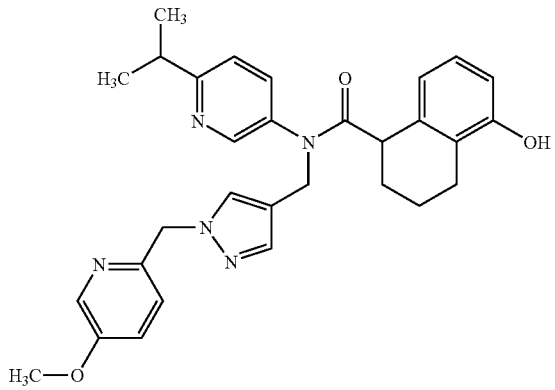

By the reaction and treatment in the same manner as in Example 101 using 5-benzyloxy-N-(6-isopropylpyridin-3-yl)-N-({1-[(5-methoxypyridin-2-yl)methyl]pyrazol-4-yl}methyl)-1,2,3,4-tetrahydronaphthalene-1-carboxamide (0.61 g) as a starting material, 5-hydroxy-N-(6-isopropylpyridin-3-yl)-N-({1-[(5-methoxypyridin-2-yl)methyl]pyrazol-4-yl}methyl)-1,2,3,4-tetrahydronaphthalene-1-carboxamide dihydrochloride (0.46 g) was obtained. MS (ESI) m/z: 512 [MH]$^+$ $^1$H-NMR (DMSO-d$_6$) δ: 1.31 (6H, d, J=6.9 Hz), 1.37-1.54 (1H, m), 1.71-1.95 (3H, m), 2.36-2.60 (2H, m), 3.31-3.65 (2H, m), 3.89 (3H, s), 4.67-4.90 (2H, m), 5.49 (2H, s), 6.49 (1H, d, J=7.6 Hz), 6.65 (1H, d, J=7.8 Hz), 6.88 (1H, t, J=7.8 Hz), 7.24 (1H, d, J=8.8 Hz), 7.29-7.42 (1H, m), 7.71-7.96 (3H, m), 8.13-8.29 (1H, m), 8.44 (1H, d, J=2.7 Hz), 8.70-8.84 (1H, m).

Example 308

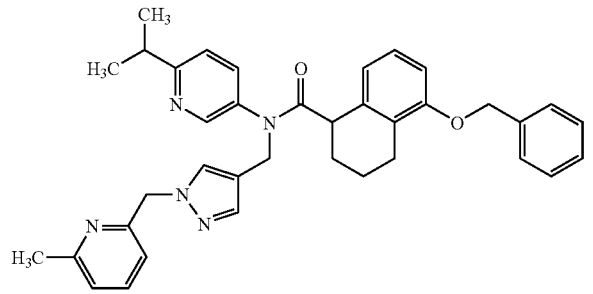

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-chloromethyl-6-methylpyridine (0.43 g) as starting materials, 5-benzyloxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide (0.75 g) was obtained.

$^1$H-NMR (CDCl$_3$) δ: 1.30 (6H, d, J=6.9 Hz), 1.38-1.56 (1H, m), 1.77-2.10 (3H, m), 2.55 (3H, s), 2.62-2.83 (2H, m), 3.08 (1H, sept, J=6.9 Hz), 3.58-3.68 (1H, m), 4.66 (1H, d, J=1.4 Hz), 4.86 (1H, d, J=14.7 Hz), 5.03 (2H, s), 5.37 (2H, s), 6.54 (1H, d, J=7.8 Hz), 6.64-6.75 (2H, m), 6.94-7.08 (2H, m), 7.18 (1H, d, J=8.1 Hz), 7.25-7.55 (9H, m), 8.39 (1H, d, J=2.4 Hz).

Example 309

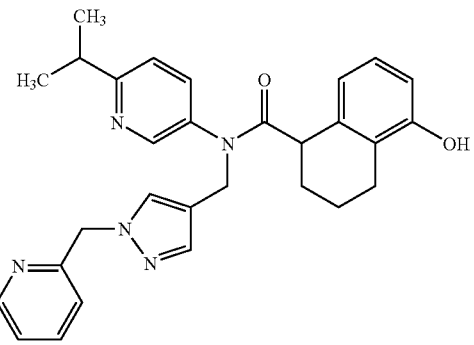

By the reaction and treatment in the same manner as in Example 139 using 5-benzyloxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide (0.74 g) as a starting material, 5-hydroxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide dihydrochloride (0.63 g) was obtained. MS (ESI) m/z: 496 [MH]$^+$ $^1$H-NMR (DMSO-d$_6$) δ: 1.29 (6H, d, J=6.9 Hz), 1.32-1.53 (1H, m), 1.70-1.99 (3H, m), 2.34-2.58 (2H, m), 2.72 (3H, s), 3.15-3.34 (1H, m), 3.45-3.62 (1H, m), 4.72 (1H, d, J=15.6 Hz), 4.83 (1H, d, J=14.7 Hz), 5.68 (2H, s), 6.48 (1H, d, J=7.5 Hz), 6.63 (1H, d, J=7.8 Hz), 6.88 (1H, t, J=7.8 Hz), 7.07 (1H, d, J=8.1 Hz), 7.29-7.48 (1H, m), 7.61-8.32 (5H, m), 8.57-8.74 (1H, m).

Example 310

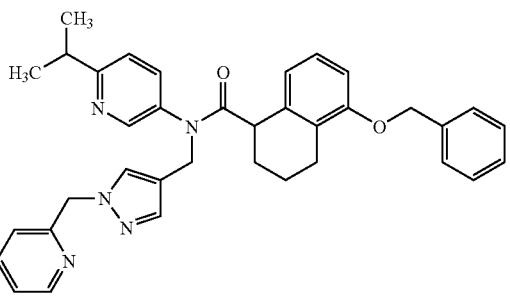

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-(chloromethyl)-4-methylpyridine (0.53 g) as starting materials, 5-benzyloxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide (0.67 g) was obtained.

$^1$H-NMR (CDCl$_3$) δ: 1.30 (6H, d, J=6.9 Hz), 1.38-1.57 (1H, m), 1.75-2.08 (3H, m), 2.31 (3H, s), 2.60-2.82 (2H, m), 3.08 (1H, sept, J=6.9 Hz), 3.57-3.69 (1H, m), 4.67 (1H, d, J=14.4 Hz), 4.85 (1H, d, J=14.4 Hz), 5.03 (2H, s), 5.36 (2H, s), 6.55 (1H, d, J=7.5 Hz), 6.72 (1H, d, J=7.8 Hz), 6.80 (1H, s), 6.93-7.06 (2H, m), 7.13-7.50 (9H, m), 8.33-8.46 (2H, m).

Example 311

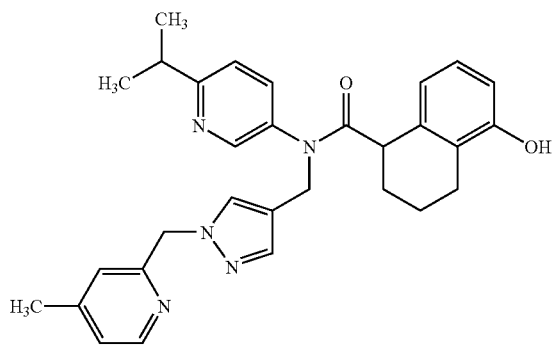

By the reaction and treatment in the same manner as in Example 139 using 5-benzyloxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide (0.67 g) as a starting material, 5-hydroxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide dihydrochloride (0.57 g) was obtained. MS (ESI) m/z: 496 [MH]$^+$ $^1$H-NMR (DMSO-d$_6$) δ: 1.30 (6H, d, J=6.9 Hz), 1.35-1.51 (1H, m), 1.70-1.97 (3H, m), 2.36-2.62 (5H, m), 3.19-3.39 (1H, m), 3.45-3.64 (1H, m), 4.71 (1H, d, J=14.0 Hz), 4.85 (1H, d, J=14.1 Hz), 5.69 (2H, s), 6.49 (1H, d, J=7.7 Hz), 6.64 (1H, d, J=7.9 Hz), 6.87 (1H, t, J=7.8 Hz), 7.25-7.47 (2H, m), 7.63-8.20 (4H, m), 8.62-8.80 (2H, m).

Example 312

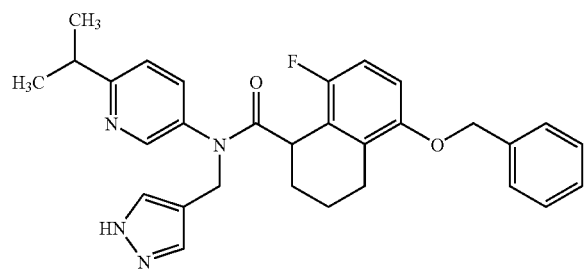

By the reaction and treatment in the same manner as in Example 82 using 1-(tert-butyloxycarbonyl)-4-(hydroxymethyl)pyrazole (1.41 g) and 5-benzyloxy-8-fluoro-N-(6-isopropylpyridin-3-yl)-1,2,3,4-tetrahydronaphthalene-1-carboxamide (2.83 g) as starting materials, 5-benzyloxy-8-fluoro-N-(6-isopropylpyridin-3-yl)-N-[(pyrazol-4-yl)methyl]-1,2,3,4-tetrahydronaphthalene-1-carboxamide hydrochloride (1.62 g) was obtained.

melting point: 194.7° C.

Example 313

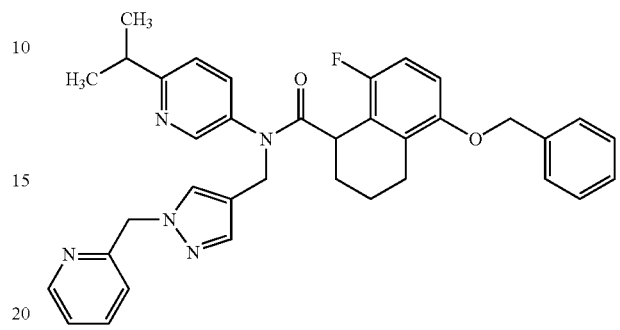

By the reaction and treatment in the same manner as in Example 271 using 5-benzyloxy-8-fluoro-N-(6-isopropylpyridin-3-yl)-N-[(pyrazol-4-yl)methyl]-1,2,3,4-tetrahydronaphthalene-1-carboxamide (0.79 g) and 2-(chloromethyl)pyridine hydrochloride (0.49 g) as starting materials, 5-benzyloxy-8-fluoro-N-(6-isopropylpyridin-3-yl)-N-{[1-(2-pyridylmethyl)pyrazol-4-yl]methyl}-1,2,3,4-tetrahydronaphthalene-1-carboxamide (0.69 g) was obtained.

$^1$H-NMR (CDCl$_3$) δ: 1.32 (6H, d, J=6.9 Hz), 1.43-1.58 (1H, m), 1.65-2.02 (3H, m), 2.55-2.82 (2H, m), 3.10 (1H, sept, J=6.9 Hz), 3.60-3.70 (1H, m), 4.57 (1H, d, J=14.6 Hz), 4.87 (1H, d, J=14.6 Hz), 5.00 (2H, s), 5.41 (2H, s), 6.61-6.77 (2H, m), 6.90 (1H, d, J=7.9 Hz), 7.14-7.48 (10H, m), 8.59-8.68 (1H, m), 8.43 (1H, d, J=2.4 Hz), 8.53-8.60 (1H, m).

Example 314

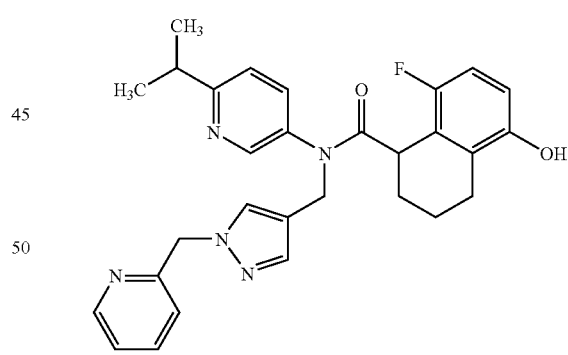

By the reaction and treatment in the same manner as in Example 139 using 5-benzyloxy-8-fluoro-N-(6-isopropylpyridin-3-yl)-N-{[1-(2-pyridylmethyl)pyrazol-4-yl]methyl}-1,2,3,4-tetrahydronaphthalene-1-carboxamide (0.69 g) as a starting material, 8-fluoro-5-hydroxy-N-(6-isopropylpyridin-3-yl)-N-{[1-(2-pyridylmethyl)pyrazol-4-yl]methyl}-1,2,3,4-tetrahydronaphthalene-1-carboxamide dihydrochloride (0.69 g) was obtained. MS (ESI) m/z: 500 [MH]$^+$ $^1$H-NMR (DMSO-d$_6$) δ: 1.32 (6H, d, J=6.9 Hz), 1.38-1.57 (1H, m), 1.63-1.92 (3H, m), 2.33-2.60 (2H, m), 3.26-3.44 (1H, m), 3.50-3.65 (1H, m), 4.60 (1H, d, J=14.7 Hz), 4.87 (1H, d, J=15.0 Hz), 5.64 (2H, s), 6.58-6.78 (2H, m), 7.23 (1H, d, J=7.8 Hz), 7.36 (1H, s), 7.64-7.87 (3H, m), 8.00-8.13 (1H, m), 8.19-8.36 (1H, m), 8.44-8.58 (1H, m), 8.78 (1H, d, J=5.1 Hz).

Example 315

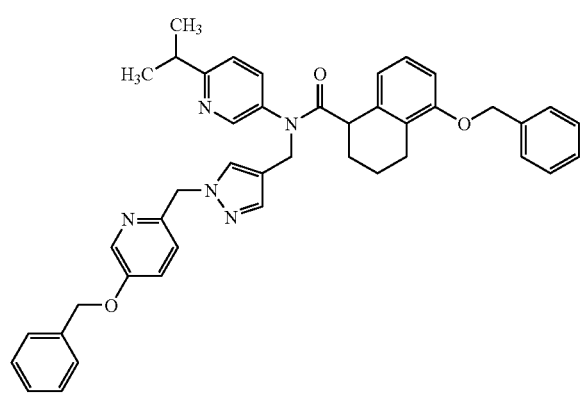

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 3-(benzyloxy)-6-(chloromethyl)pyridine (0.81 g) as starting materials, 5-benzyloxy-N-({1-[(5-(benzyloxy)pyridin-2-yl)methyl]pyrazol-4-yl}methyl)-N-(6-isopropylpyridin-3-yl)-1,2,3,4-tetrahydronaphthalene-1-carboxamide (0.75 g) was obtained.

$^1$H-NMR (CDCl$_3$) δ: 1.30 (6H, d, J=6.9 Hz), 1.37-1.54 (1H, m), 1.77-2.07 (3H, m), 2.60-2.80 (2H, m), 3.08 (1H, sept, J=6.9 Hz), 3.57-3.67 (1H, m), 4.65 (1H, d, J=14.7 Hz), 4.84 (1H, d, J=14.7 Hz), 5.02 (2H, s), 5.09 (2H, s), 5.33 (2H, s), 6.54 (1H, d, J=7.5 Hz), 6.71 (1H, d, J=8.1 Hz), 6.98 (2H, t, J=8.3 Hz), 7.13-7.48 (15H, m), 8.32 (1H, d, J=2.7 Hz), 8.37 (1H, d, J=2.4 Hz).

Example 316

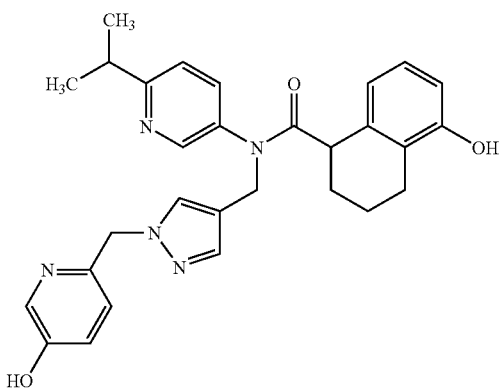

By the reaction and treatment in the same manner as in Example 101 using 5-benzyloxy-N-({1-[(5-(benzyloxy)pyridin-2-yl)methyl]pyrazol-4-yl}methyl)-N-(6-isopropylpyridin-3-yl)-1,2,3,4-tetrahydronaphthalene-1-carboxamide (0.74 g) as a starting material, 5-hydroxy-N-({1-[(5-hydroxypyridin-2-yl)methyl]pyrazol-4-yl}methyl)-N-(6-isopropylpyridin-3-yl)-1,2,3,4-tetrahydronaphthalene-1-carboxamide dihydrochloride (0.57 g) was obtained. MS (ESI) m/z: 498 [MH]$^+$ $^1$H-NMR (DMSO-d$_6$) δ: 1.31 (6H, d, J=6.9 Hz), 1.38-1.57 (1H, m), 1.70-1.97 (3H, m), 2.33-2.63 (2H, m), 3.26-3.67 (2H, m), 4.62-4.93 (2H, m), 5.56 (2H, s), 6.48 (1H, d, J=7.6 Hz), 6.65 (1H, d, J=7.8 Hz), 6.88 (1H, t, J=7.8 Hz), 7.28-7.44 (2H, m), 7.68-7.95 (3H, m), 8.08-8.23 (1H, m), 8.37 (1H, d, J=2.7 Hz), 8.67-8.83 (1H, m).

Example 317

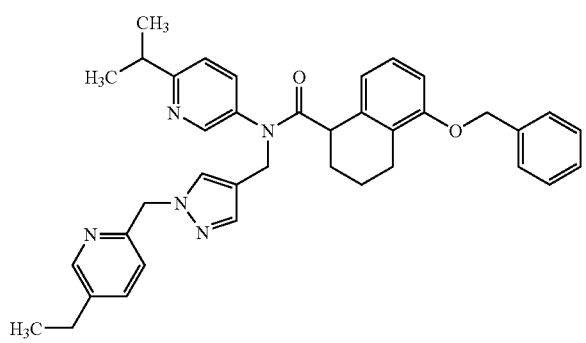

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-chloromethyl-5-ethylpyridine (0.58 g) as starting materials, 5-benzyloxy-N-({1-[(5-ethylpyridin-2-yl)methyl]pyrazol-4-yl}methyl)-N-(6-isopropylpyridin-3-yl)-1,2,3,4-tetrahydronaphthalene-1-carboxamide (0.75 g) was obtained.

$^1$H-NMR (CDCl$_3$) δ: 1.23 (3H, t, J=7.6 Hz), 1.30 (6H, d, J=6.9 Hz), 1.37-1.55 (1H, m), 1.77-2.07 (3H, m), 2.63 (2H, q, J=7.6 Hz), 2.65-2.82 (2H, m), 3.08 (1H, sept, J=6.9 Hz), 3.58-3.68 (1H, m), 4.66 (1H, d, J=14.5 Hz), 4.85 (1H, d, J=14.5 Hz), 5.03 (2H, s), 5.37 (2H, s), 6.55 (1H, d, J=7.7 Hz), 6.71 (1H, d, J=8.0 Hz), 6.91 (1H, d, J=8.0 Hz), 7.01 (1H, t, J=8.2 Hz), 7.17 (1H, d, J=8.4 Hz), 7.25-7.50 (9H, m), 8.38 (1H, d, J=2.3 Hz), 8.40 (1H, d, J=1.9 Hz).

Example 318

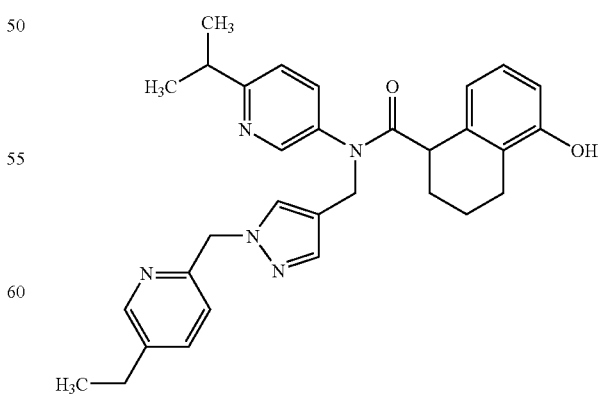

By the reaction and treatment in the same manner as in Example 271 using 5-benzyloxy-N-({1-[(5-ethylpyridin-2- yl)methyl]pyrazol-4-yl}methyl)-N-(6-isopropylpyridin-3-yl)-1,2,3,4-tetrahydronaphthalene-1-carboxamide (0.75 g) as a starting material, N-({1-[(5-ethylpyridin-2-yl)methyl]pyrazol-4-yl}methyl)-5-hydroxy-N-(6-isopropylpyridin-3-yl)-1,2,3,4-tetrahydronaphthalene-1-carboxamide dihydrochloride (0.61 g) was obtained.

MS (ESI) m/z: 510 [MH]+

1H-NMR (DMSO-d6) δ: 1.22 (3H, t, J=7.5 Hz), 1.29 (6H, d, J=6.9 Hz), 1.32-1.53 (1H, m), 1.70-1.97 (3H, m), 2.33-2.57 (2H, m), 2.74 (2H, q, J=7.5 Hz), 3.20-3.37 (1H, m), 3.43-3.63 (1H, m), 4.62-4.90 (2H, m), 5.63 (2H, s), 6.48 (1H, d, J=7.5 Hz), 6.64 (1H, d, J=7.8 Hz), 6.87 (1H, t, J=7.8 Hz), 7.28 (1H, d, J=8.1 Hz), 7.32-7.42 (1H, m), 7.65-7.91 (2H, m), 8.02-8.27 (2H, m), 8.57-8.77 (2H, m).

Example 319

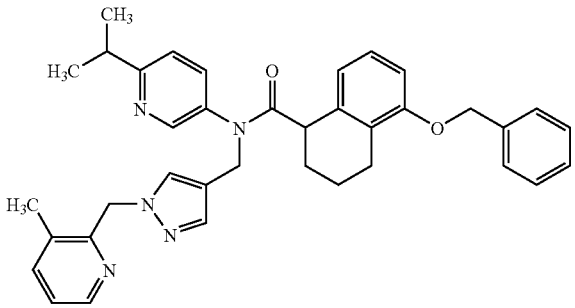

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-chloromethyl-3-methylpyridine (0.53 g) as starting materials, 5-benzyloxy-N-(6-isopropylpyridin-3-yl)-N-({1-[(3-methylpyridin-2-yl)methyl]pyrazol-4-yl}methyl)-1,2,3,4-tetrahydronaphthalene-1-carboxamide (0.75 g) was obtained.

1H-NMR (CDCl3) δ: 1.30 (6H, d, J=6.9 Hz), 1.38-1.54 (1H, m), 1.72-2.07 (3H, m), 2.30 (3H, s), 2.59-2.79 (2H, m), 3.08 (1H, sept, J=6.9 Hz), 3.56-3.66 (1H, m), 4.63 (1H, d, J=14.4 Hz), 4.81 (1H, d, J=14.4 Hz), 5.03 (2H, s), 5.42 (2H, s), 6.54 (1H, d, J=7.8 Hz), 6.71 (1H, d, J=8.1 Hz), 6.93-7.03 (1H, m), 7.09-7.19 (2H, m), 7.23-7.50 (9H, m), 8.36 (1H, d, J=2.1 Hz), 8.42 (1H, dd, J=1.2, 4.8 Hz).

Example 320

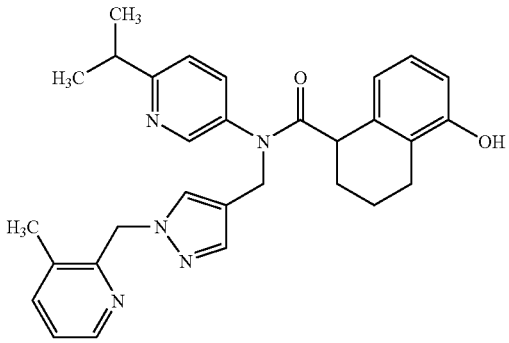

By the reaction and treatment in the same manner as in Example 139 using 5-benzyloxy-N-(6-isopropylpyridin-3-yl)-N-({1-[(3-methylpyridin-2-yl)methyl]pyrazol-4-yl}methyl)-1,2,3,4-tetrahydronaphthalene-1-carboxamide (0.74 g) as a starting material, 5-hydroxy-N-(6-isopropylpyridin-3-yl)-N-({1-[(3-methylpyridin-2-yl)methyl]pyrazol-4-yl}methyl)-1,2,3,4-tetrahydronaphthalene-1-carboxamide dihydrochloride (0.65 g) was obtained.

MS (ESI) m/z: 496 [MH]+

1H-NMR (DMSO-d6) δ: 1.29 (6H, d, J=6.9 Hz), 1.32-1.52 (1H, m), 1.70-1.97 (3H, m), 2.30 (3H, s), 2.38-2.60 (2H, m), 3.17-3.33 (1H, m), 3.43-3.60 (1H, m), 4.60-4.86 (2H, m), 5.70 (2H, s), 6.46 (1H, d, J=7.5 Hz), 6.63 (1H, d, J=7.8 Hz), 6.87 (1H, t, J=7.8 Hz), 7.23-7.37 (1H, m,), 7.58-8.09 (4H, m), 8.25 (1H, d, J=7.8 Hz), 8.54-8.70 (2H, m).

Example 321

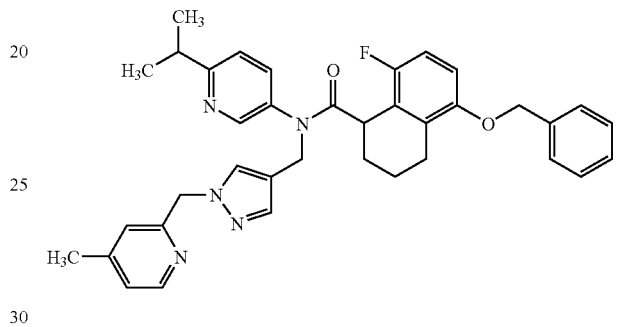

By the reaction and treatment in the same manner as in Example 271 using 5-benzyloxy-8-fluoro-N-(6-isopropylpyridin-3-yl)-N-[(pyrazol-4-yl)methyl]-1,2,3,4-tetrahydronaphthalene-1-carboxamide hydrochloride (0.81 g) and 2-chloromethyl-4-methylpyridine (0.54 g) as starting materials, 5-benzyloxy-8-fluoro-N-(6-isopropylpyridin-3-yl)-N-({1-[(4-methylpyridin-2-yl)methyl]pyrazol-4-yl}methyl)-1,2,3,4-tetrahydronaphthalene-1-carboxamide (0.77 g) was obtained.

1H-NMR (CDCl3) δ: 1.31 (6H, d, J=6.9 Hz), 1.43-1.57 (1H, m), 1.67-2.03 (3H, m), 2.31 (3H, s), 2.57-2.84 (2H, m), 3.09 (1H, sept, J=6.9 Hz), 3.60-3.72 (1H, m), 4.58 (1H, d, J=14.4 Hz), 4.87 (1H, d, J=14.4 Hz), 5.00 (2H, s), 5.36 (2H, s), 6.62-6.77 (3H, m), 7.02 (1H, d, J=4.8 Hz), 7.19 (1H, d, J=8.1 Hz), 7.24-8.07 (8H, m), 8.35-8.45 (2H, m).

Example 322

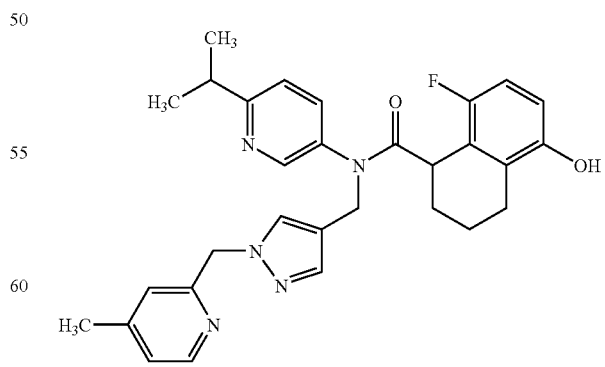

By the reaction and treatment in the same manner as in Example 139 using 5-benzyloxy-8-fluoro-N-(6-isopropylpyridin-3-yl)-N-({1-[(4-methylpyridin-2-yl)methyl]pyrazol-4- yl}methyl)-1,2,3,4-tetrahydronaphthalene-1-carboxamide (0.76 g) as a starting material, 8-fluoro-5-hydroxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide dihydrochloride (0.64 g) was obtained.

MS (ESI) m/z: 514 [MH]$^+$ $^1$H-NMR (DMSO-d$_6$) δ: 1.30 (6H, d, J=6.9 Hz), 1.38-1.56 (1H, m), 1.61-1.93 (3H, m), 2.33-2.59 (5H, m), 3.18-3.37 (1H, m), 3.50-3.63 (1H, m), 4.59 (1H, d, J=14.7 Hz), 4.84 (1H, d, J=14.7 Hz), 5.68 (2H, s), 6.60-6.77 (3H, m), 7.26 (1H, s), 7.36 (1H, m), 7.63-8.05 (4H, m), 8.41-8.53 (1H, m), 8.73 (1H, d, J=6.0 Hz).

Example 323

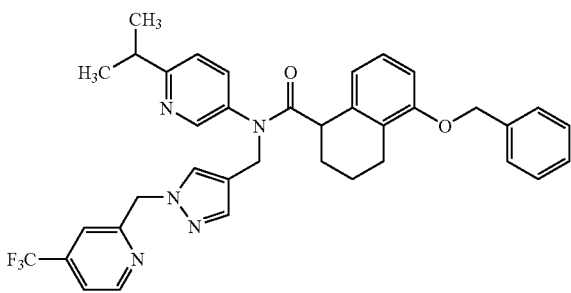

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-chloromethyl-4-trifluoromethylpyridine (0.67 g) as starting materials, 5-benzyloxy-N-(6-isopropylpyridin-3-yl)-N-({1-[(4-trifluoromethylpyridin-2-yl)methyl]pyrazol-4-yl}methyl)-1,2,3,4-tetrahydronaphthalene-1-carboxamide (0.79 g) was obtained.

$^1$H-NMR (CDCl$_3$) δ: 1.31 (6H, d, J=6.9 Hz), 1.40-1.57 (1H, m), 1.75-2.07 (3H, m), 2.59-2.81 (2H, m), 3.09 (1H, sept, J=6.9 Hz), 3.59-3.68 (1H, m), 4.69 (1H, d, J=14.7 Hz), 4.85 (1H, d, J=14.7 Hz), 5.03 (2H, s), 5.48 (2H, s), 6.54 (1H, d, J=7.8 Hz), 6.72 (1H, d, J=8.1 Hz), 7.00 (1H, t, J=7.8 Hz), 7.10-7.47 (10H, m), 7.55 (1H, s), 8.42 (1H, d, J=2.4 Hz), 8.76 (1H, d, J=5.1 Hz).

Example 324

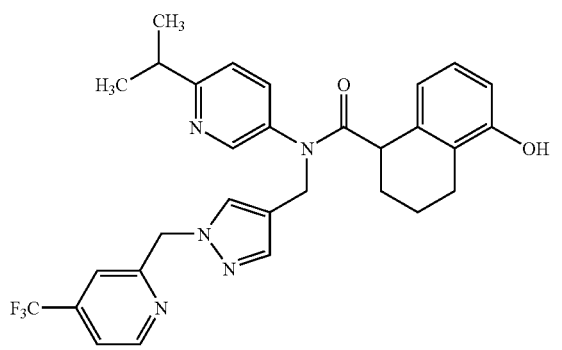

By the reaction and treatment in the same manner as in Example 139 using 5-benzyloxy-N-(6-isopropylpyridin-3-yl)-N-({1-[(4-trifluoromethylpyridin-2-yl)methyl]pyrazol-4-yl}methyl)-1,2,3,4-tetrahydronaphthalene-1-carboxamide (0.78 g) as a starting material, 5-hydroxy-N-(6-isopropylpyridin-3-yl)-N-({1-[(4-trifluoromethylpyridin-2-yl)methyl]pyrazol-4-yl}methyl)-1,2,3,4-tetrahydronaphthalene-1-carboxamide dihydrochloride (0.63 g) was obtained. MS (ESI) m/z: 550 [MH]+

$^1$H-NMR (DMSO-d$_6$) δ: 1.29 (6H, d, J=6.9 Hz), 1.35-1.53 (1H, m), 1.68-1.95 (3H, m), 2.35-2.59 (2H, m), 3.16-3.34 (1H, m), 3.44-3.62 (1H, m), 4.63-4.92 (2H, m), 5.53 (2H, s), 6.46 (1H, d, J=7.5 Hz), 6.63 (1H, d, J=7.8 Hz), 6.85 (1H, t, J=7.8 Hz), 7.28-7.42 (2H, m), 7.60-8.06 (4H, m), 8.58-8.75 (1H, m), 8.84 (1H, d, J=5.1 Hz).

Example 325

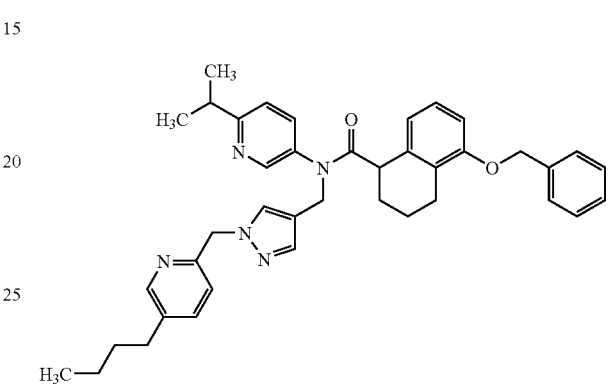

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 5-butyl-2-chloromethylpyridine (0.66 g) as starting materials, 5-benzyloxy-N-({1-[(5-butylpyridin-2-yl)methyl]pyrazol-4-yl}methyl)-N-(6-isopropylpyridin-3-yl)-1,2,3,4-tetrahydronaphthalene-1-carboxamide (0.76 g) was obtained.

$^1$H-NMR (CDCl$_3$) δ: 0.92 (3H, t, J=7.2 Hz), 1.21-1.68 (11H, m), 1.78-2.07 (3H, m), 2.59 (2H, t, J=7.2 Hz), 2.67-2.79 (2H, m), 3.08 (1H, sept, J=6.9 Hz), 3.57-3.67 (1H, m), 4.66 (1H, d, J=14.4 Hz), 4.85 (1H, d, J=14.4 Hz), 5.03 (2H, s), 5.34 (2H, s), 6.55 (1H, d, J=7.8 Hz), 6.71 (1H, d, J=8.1 Hz), 6.89 (1H, d, J=7.8 Hz), 7.01 (1H, t, J=7.8 Hz), 7.17 (1H, d, J=8.1 Hz), 7.24-7.48 (10H, m), 8.38 (1H, s).

Example 326

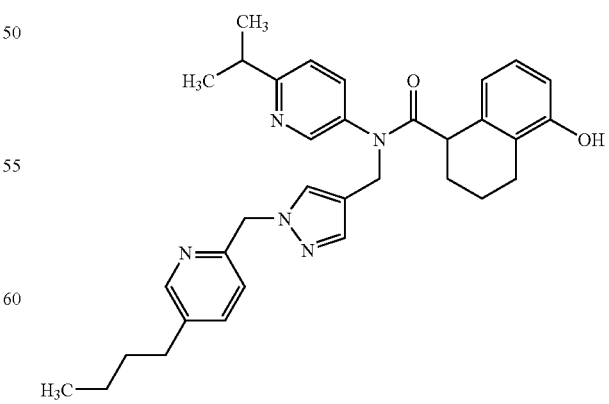

By the reaction and treatment in the same manner as in Example 139 using 5-benzyloxy-N-({1-[(5-butylpyridin-2- yl)methyl]pyrazol-4-yl}methyl)-N-(6-isopropylpyridin-3-yl)-1,2,3,4-tetrahydronaphthalene-1-carboxamide (0.76 g) as a starting material, N-({1-[(5-butylpyridin-5-yl)methyl]pyrazol-4-yl}methyl)-5-hydroxy-N-(6-isopropylpyridin-3-yl)-1,2,3,4-tetrahydronaphthalene-1-carboxamide dihydrochloride (0.62 g) was obtained.

MS (ESI) m/z: 538 [MH]⁺

¹H-NMR (DMSO-d₆) δ: 0.90 (3H, t, J=7.2 Hz), 1.18-1.63 (11H, m), 1.71-1.97 (3H, m), 2.37-2.60 (2H, m), 2.70 (2H, t, J=7.2 Hz), 3.13-3.32 (1H, m), 3.43-3.61 (1H, m), 4.72 (1H, d, J=13.5 Hz), 4.82 (1H, d, J=14.7 Hz), 5.59 (2H, s), 6.47 (1H, d, J=7.5 Hz), 6.63 (1H, d, J=7.8 Hz), 6.87 (1H, t, J=7.8 Hz), 7.21 (1H, d, J=8.1 Hz), 7.29-7.42 (1H, m), 7.58-8.19 (4H, m), 8.55-8.72 (2H, m).

Example 327

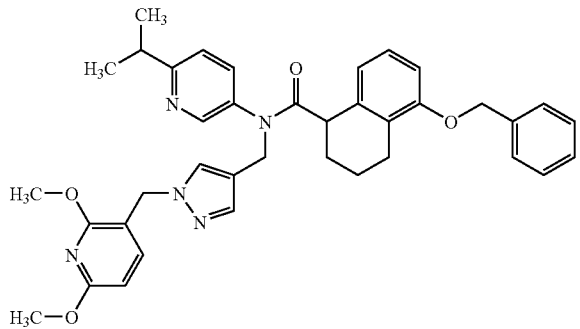

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 3-chloromethyl-2,6-dimethoxypyridine (0.56 g) as starting materials, 5-benzyloxy-N-({1-[(2,6-dimethoxypyridin-3-yl)methyl]pyrazol-4-yl}methyl)-N-(6-isopropylpyridin-3-yl)-1,2,3,4-tetrahydronaphthalene-1-carboxamide (0.69 g) was obtained.

¹H-NMR (CDCl₃) δ: 1.30 (6H, d, J=6.9 Hz), 1.38-1.55 (1H, m), 1.76-2.08 (3H, m), 2.60-2.81 (2H, m), 3.08 (1H, sept, J=6.9 Hz), 3.57-3.67 (1H, m), 3.90 (3H, s), 3.94 (3H, s), 4.63 (1H, d, J=14.4 Hz), 4.80 (1H, d, J=14.4 Hz), 5.03 (2H, s), 5.15 (2H, s), 6.27 (1H, d, J=8.1 Hz), 6.53 (1H, d, J=7.8 Hz), 6.72 (1H, d, J=8.1 Hz), 7.01 (1H, t, J=7.8 Hz), 7.16 (1H, d, J=8.1 Hz), 7.23-7.44 (9H, m), 8.37 (1H, d, J=2.4 Hz).

Example 328

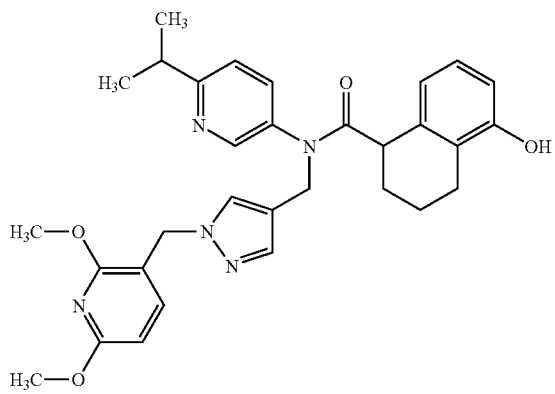

By the reaction and treatment in the same manner as in Example 139 using 5-benzyloxy-N-({1-[(2,6-dimethoxypyridin-3-yl)methyl]pyrazol-4-yl}methyl)-N-(6-isopropylpyridin-3-yl)-1,2,3,4-tetrahydronaphthalene-1-carboxamide (0.68 g) as a starting material, N-({1-[(2,6-dimethoxypyridin-3-yl)methyl]pyrazol-4-yl}methyl)-5-hydroxy-N-(6-isopropylpyridin-3-yl)-1,2,3,4-tetrahydronaphthalene-1-carboxamide dihydrochloride (0.16 g) was obtained. MS (ESI) m/z: 542 [MH]⁺

¹H-NMR (DMSO-d₆) δ: 1.26 (6H, d, J=6.9 Hz), 1.30-1.50 (1H, m), 1.69-1.95 (3H, m), 2.32-2.59 (2H, m), 3.07-3.26 (1H, m), 3.40-3.57 (1H, m), 3.85 (3H, s), 3.88 (3H, s), 4.58-4.85 (2H, m), 5.12 (2H, s), 6.35 (1H, d, J=8.1 Hz), 6.43 (1H, d, J=7.5 Hz), 6.62 (1H, d, J=7.8 Hz), 6.86 (1H, t, J=7.7 Hz), 7.26 (2H, d, J=8.1 Hz), 7.43-7.62 (2H, m), 7.75-7.92 (1H, m), 8.43-8.63 (1H, m).

Example 329

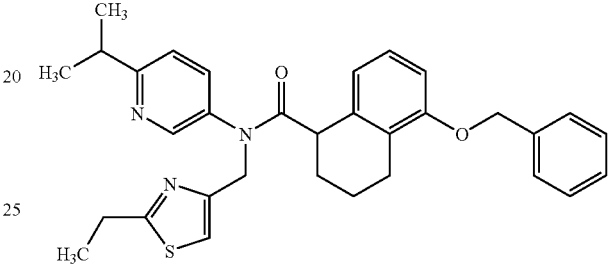

By the reaction and treatment in the same manner as in Example 132 using 5-benzyloxy-N-(6-isopropylpyridin-3-yl)-1,2,3,4-tetrahydronaphthalene-1-carboxamide (1.20 g) and 4-chloromethyl-2-ethylthiazole (0.49 g) as starting materials, 5-benzyloxy-N-[(2-ethylthiazol-4-yl)methyl]-N-(6-isopropylpyridin-3-yl)-1,2,3,4-tetrahydronaphthalene-1-carboxamide (1.30 g) was obtained.

¹H-NMR (CDCl₃) δ: 1.29 (6H, d, J=6.9 Hz), 1.38 (3H, t, J=7.5 Hz), 1.45-1.57 (1H, m), 1.83-2.08 (3H, m), 2.60-2.81 (2H, m), 3.01 (2H, q, J=7.5 Hz), 3.07 (1H, sept, J=6.9 Hz), 3.68-3.78 (1H, m), 4.88 (1H, d, J=14.7 Hz), 5.02 (2H, s), 5.09 (1H, d, J=14.7 Hz), 6.63 (1H, d, J=7.8 Hz), 6.71 (1H, d, J=8.1 Hz), 7.03 (1H, t, J=7.8 Hz), 7.10 (1H, s), 7.20 (1H, d, J=8.1 Hz), 7.23-7.45 (5H, m), 7.60 (1H, dd, J=2.7, 8.4 Hz), 8.47 (1H, d, J=2.4 Hz).

Example 330

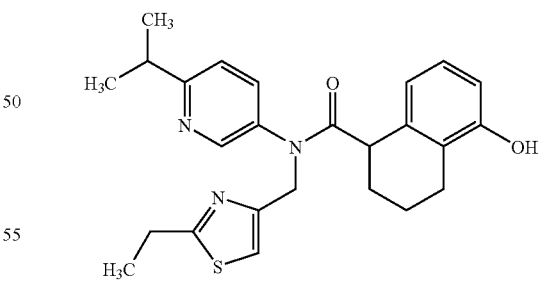

By the reaction and treatment in the same manner as in Example 139 using 5-benzyloxy-N-[(2-ethylthiazol-4-yl)methyl]-N-(6-isopropylpyridin-3-yl)-1,2,3,4-tetrahydronaphthalene-1-carboxamide (1.28 g) as a starting material, N-[(2-ethylthiazol-4-yl)methyl]-5-hydroxy-N-(6-isopropylpyridin-3-yl)-1,2,3,4-tetrahydronaphthalene-1-carboxamide hydrochloride (0.85 g) was obtained.

MS (ESI) m/z: 436 [MH]⁺

¹H-NMR (DMSO-d₆) δ: 1.24-1.57 (10H, m), 1.73-2.00 (3H, m), 2.32-2.60 (2H, m), 2.98 (2H, q, J=7.4 Hz), 3.19-3.45

(1H, m), 3.52-3.70 (1H, m), 4.80-5.11 (2H, m), 6.40-6.58 (1H, m), 6.63 (1H, d, J=7.8 Hz), 6.87 (1H, t, J=7.8 Hz), 7.30-8.02 (2H, m), 8.22-8.48 (1H, m), 8.80-8.93 (1H, m).

Example 331

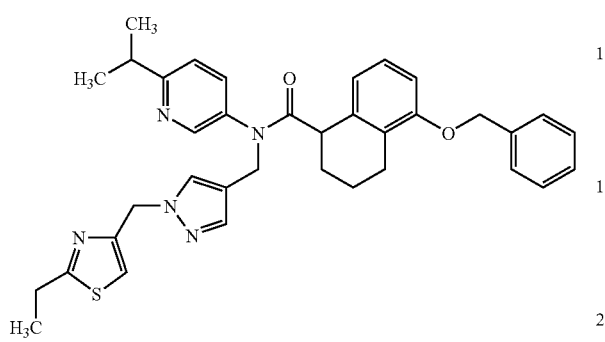

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 4-chloromethyl-2-ethylthiazole (0.49 g) as starting materials, 5-benzyloxy-N-({1-[(2-ethylthiazol-4-yl)methyl]pyrazol-4-yl}methyl)-N-(6-isopropylpyridin-3-yl)-1,2,3,4-tetrahydronaphthalene-1-carboxamide (0.66 g) was obtained.

$^1$H-NMR (CDCl$_3$) δ: 1.31 (6H, d, J=6.9 Hz), 1.37 (3H, t, J=7.5 Hz), 1.41-1.57 (1H, m), 1.77-2.08 (3H, m), 2.60-2.80 (2H, m), 3.01 (2H, q, J=7.5 Hz), 3.09 (1H, sept, J=6.9 Hz), 3.59-3.68 (1H, m), 4.66 (1H, d, J=14.4 Hz), 4.84 (1H, d, J=14.7 Hz), 5.03 (2H, s), 5.26 (2H, s), 6.55 (1H, d, J=7.8 Hz), 6.72 (1H, d, J=8.1 Hz), 6.82 (1H, s), 7.03 (1H, t, J=7.8 Hz), 7.18 (1H, d, J=8.4 Hz), 7.22-7.50 (8H, m), 8.38 (1H, d, J=2.4 Hz).

Example 332

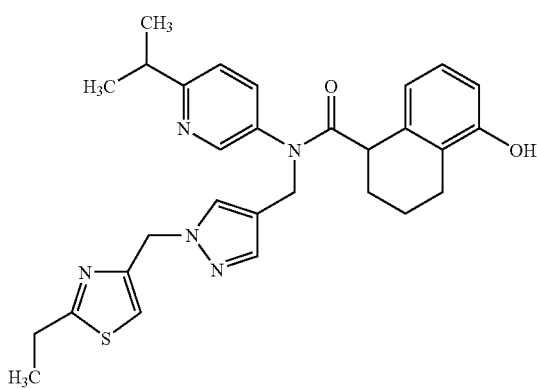

By the reaction and treatment in the same manner as in Example 139 using 5-benzyloxy-N-({1-[(2-ethylthiazol-4-yl)methyl]pyrazol-4-yl}methyl)-N-(6-isopropylpyridin-3-yl)-1,2,3,4-tetrahydronaphthalene-1-carboxamide (0.65 g) as a starting material, N-({1-[(2-ethylthiazol-4-yl)methyl]pyrazol-4-yl}methyl)-5-hydroxy-N-(6-isopropylpyridin-3-yl)-1,2,3,4-tetrahydronaphthalene-1-carboxamide hydrochloride (0.56 g) was obtained. MS (ESI) m/z: 516 [MH]+

$^1$H-NMR (DMSO-d$_6$) δ: 1.18-1.52 (10H, m), 1.70-1.97 (3H, m), 2.34-2.60 (2H, m), 2.95 (2H, q, J=7.5 Hz), 3.18-3.39 (1H, m), 3.45-3.62 (1H, m), 4.60-4.88 (2H, m), 5.32 (2H, s), 6.47 (1H, d, J=7.5 Hz), 6.63 (1H, d, J=7.8 Hz), 6.87 (1H, t, J=7.8 Hz), 7.14 (1H, s), 7.22-7.38 (1H, m), 7.57-7.81 (2H, m), 7.97-8.13 (1H, m), 8.60-8.88 (1H, m).

Example 333

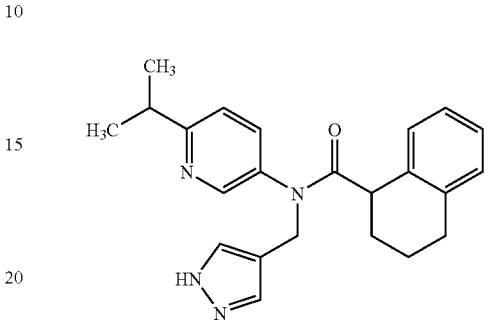

By the reaction and treatment in the same manner as in Example 82 using 1-(tert-butyloxycarbonyl)-4-(hydroxymethyl)pyrazole (1.74 g) and N-(6-isopropylpyridin-3-yl)-1,2,3,4-tetrahydronaphthalene-1-carboxamide (2.15 g) as starting materials, N-(6-isopropylpyridin-3-yl)-N-[(pyrazol-4-yl)methyl]-1,2,3,4-tetrahydronaphthalene-1-carboxamide hydrochloride (1.99 g) was obtained. melting point: 217.3° C.

$^1$H-NMR (CDCl$_3$) δ: 1.36 (6H, d, J=6.9 Hz), 1.42-1.60 (1H, m), 1.75-2.00 (3H, m), 2.55-2.80 (2H, m), 3.52 (1H, sept, J=6.9 Hz), 3.60-3.77 (1H, m), 4.70-5.02 (2H, m), 6.98-7.18 (4H, m), 7.85 (2H, s), 8.00 (1H, d, J=8.7 Hz), 8.33-8.53 (1H, m), 8.98 (1H, d, J=2.1 Hz).

Example 334

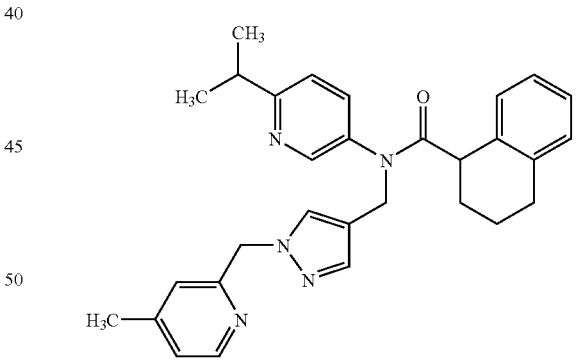

To a solution of N-(6-isopropylpyridin-3-yl)-N-[(pyrazol-4-yl)methyl]-1,2,3,4-tetrahydronaphthalene-1-carboxamide hydrochloride (0.99 g) in methylene chloride (10 mL) were added tetra-n-butylammonium hydrogensulfate (0.82 g), 2-chloromethyl-4-methylpyridine hydrochloride (0.86 g) and 1 mol/L-aqueous sodium hydroxide solution (24.0 mL). The mixture was stirred at room temperature for one day. The reaction mixture was partitioned between water and chloroform. The organic layer was washed with saturated brine and dried over anhydrous magnesium sulfate. The solvent was evaporated, and the residue was purified by silica gel column chromatography to give N-(6-isopropylpyridin-3-yl)-N-({1-[(4-methylpyridin-2-yl)methyl]pyrazol-4-yl}methyl)-1,2,3, 4-tetrahydronaphthalene-1-carboxamide. This compound was dissolved in ethyl acetate, and 4 mol/L-HCl/dioxane (2.4 mL) was added. The precipitated solid was collected by filtration to give N-(6-isopropylpyridin-3-yl)-N-({1-[(4-methylpyridin-2-yl)methyl]pyrazol-4-yl}methyl)-1,2,3,4-tetrahydronaphthalene-1-carboxamide dihydrochloride (0.61 g).

MS (ESI) m/z: 480 [MH]$^+$ $^1$H-NMR (DMSO-d$_6$) δ: 1.31 (6H, d, J=6.9 Hz), 1.38-1.60 (1H, m), 1.72-2.00 (3H, m), 2.50 (3H, s), 2.57-2.80 (2H, m), 3.23-3.42 (1H, m), 3.53-3.68 (1H, m), 4.60-4.94 (2H, m), 5.45 (2H, s), 6.95-7.20 (5H, m), 7.27-7.43 (1H, m), 7.60-7.93 (3H, m), 8.01-8.22 (1H, m), 8.40 (1H, d, J=2.7 Hz), 8.67-8.85 (1H, m).

Example 335

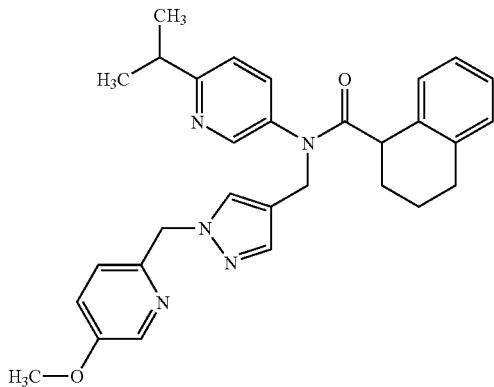

By the reaction and treatment in the same manner as in Example 334 using N-(6-isopropylpyridin-3-yl)-N-[(pyrazol-4-yl)methyl]-1,2,3,4-tetrahydronaphthalene-1-carboxamide hydrochloride (0.95 g) and 2-chloromethyl-5-methoxypyridine (0.83 g) as starting materials, N-(6-isopropylpyridin-3-yl)-N-({1-[(5-methoxypyridin-2-yl)methyl]pyrazol-4-yl}methyl)-1,2,3,4-tetrahydronaphthalene-1-carboxamide dihydrochloride (0.97 g) was obtained.

MS (ESI) m/z: 496 [MH]$^+$ $^1$H-NMR (DMSO-d$_6$) δ: 1.31 (6H, d, J=6.9 Hz), 1.37-1.59 (1H, m), 1.77-2.02 (3H, m), 2.46-2.82 (5H, m), 3.21-3.42 (1H, m), 3.52-3.71 (1H, m), 4.60-4.98 (2H, m), 5.70 (2H, s), 6.98-7.17 (4H, m), 7.28-7.52 (2H, m), 7.75 (2H, d, J=5.4 Hz), 7.85-8.00 (1H, m), 8.09-8.26 (1H, m), 8.74 (2H, d, J=6.0 Hz).

Example 336

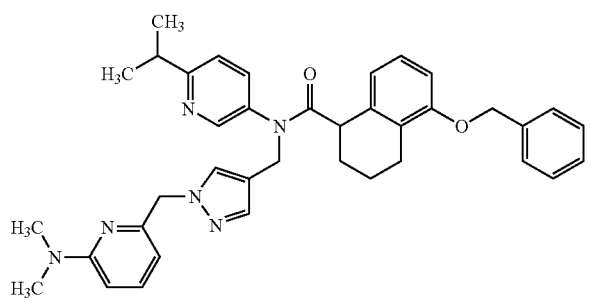

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide (0.78 g) and 6-chloromethyl-2-(dimethylamino)pyridine (0.46 g) as starting materials, 5-benzyloxy-N-({1-[(6-dimethylaminopyridin-2-yl)methyl]pyrazol-4-yl}methyl)-N-(6-isopropylpyridin-3-yl)-1,2,3,4-tetrahydronaphthalene-1-carboxamide (0.43 g) was obtained.

$^1$H-NMR (CDCl$_3$) δ: 1.30 (6H, d, J=6.9 Hz), 1.39-1.63 (1H, m), 1.77-2.08 (3H, m), 2.60-2.83 (2H, m), 3.05 (6H, s), 3.08 (1H, sept, J=6.9 Hz), 3.57-3.67 (1H, m), 4.66 (1H, d, J=14.4 Hz), 4.85 (1H, d, J=14.4 Hz), 5.03 (2H, s), 5.22 (2H, s), 6.19 (1H, d, J=7.2 Hz), 6.40 (1H, d, J=8.4 Hz), 6.55 (1H, d, J=7.5 Hz), 6.71 (1H, d, J=8.1 Hz), 7.01 (1H, t, J=8.0 Hz), 7.16 (1H, d, J=8.4 Hz), 7.23-7.44 (8H, m), 7.51 (1H, s), 8.40 (1H, d, J=2.1 Hz).

Example 337

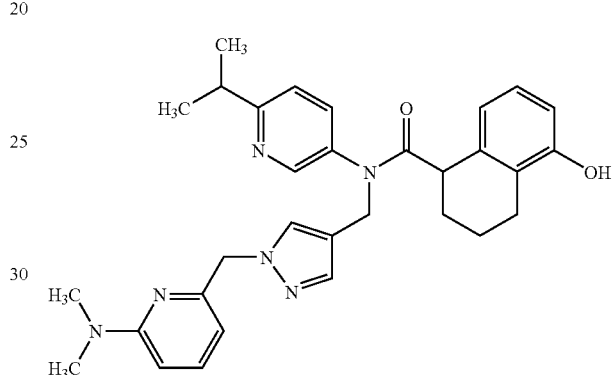

By the reaction and treatment in the same manner as in Example 101 using 5-benzyloxy-N-({1-[(6-dimethylaminopyridin-2-yl)methyl]pyrazol-4-yl}methyl)-N-(6-isopropylpyridin-3-yl)-1,2,3,4-tetrahydronaphthalene-1-carboxamide (0.43 g) as a starting material, N-({1-[(6-dimethylaminopyridin-2-yl)methyl]pyrazol-4-yl}methyl)-5-hydroxy-N-(6-isopropylpyridin-3-yl)-1,2,3,4-tetrahydronaphthalene-1-carboxamide dihydrochloride (0.30 g) was obtained. MS (ESI) m/z: 525 [MH]$^+$ $^1$H-NMR (DMSO-d$_6$) δ: 1.28 (6H, d, J=6.9 Hz), 1.33-1.51 (1H, m), 1.70-1.96 (3H, m), 2.35-2.60 (2H, m), 3.15-3.32 (1H, m), 3.17 (6H, m), 3.43-3.64 (1H, m), 4.72 (1H, d, J=14.1 Hz), 4.81 (1H, d, J=14.4 Hz), 5.46 (2H, s), 6.09 (1H, d, J=7.2 Hz), 6.46 (1H, d, J=7.5 Hz), 6.63 (1H, d, J=7.8 Hz), 6.82-6.97 (2H, m), 7.30-7.43 (1H, m), 7.57-7.85 (3H, m), 7.90-8.07 (1H, m), 8.55-8.68 (1H, m).

Example 338

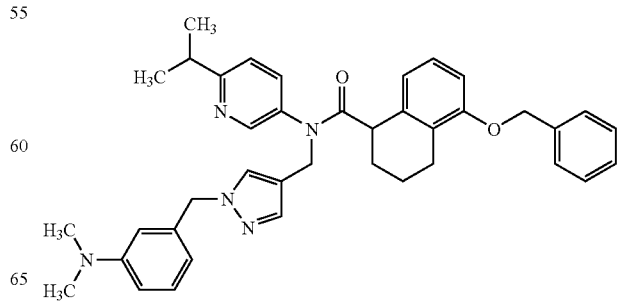

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 3-(dimethylamino)benzyl chloride (0.51 g) as starting materials, 5-benzyloxy-N-({1-[3-(dimethylaminophenyl)methyl]pyrazol-4-yl}methyl)-N-(6-isopropylpyridin-3-yl)-1,2,3,4-tetrahydronaphthalene-1-carboxamide (0.46 g) was obtained.

¹H-NMR (CDCl₃) δ: 1.30 (6H, d, J=6.9 Hz), 1.39-1.55 (1H, m), 1.75-2.07 (3H, m), 2.58-2.80 (2H, m), 2.93 (6H, s), 3.08 (1H, sept, J=6.9 Hz), 3.57-3.67 (1H, m), 4.61 (1H, d, J=14.4 Hz), 4.84 (1H, d, J=14.7 Hz), 5.03 (2H, s), 5.20 (2H, s), 6.47-6.59 (3H, m), 6.62-6.75 (2H, m), 6.95-7.04 (1H, m), 7.11-7.45 (10H, m), 8.38 (1H, d, J=2.4 Hz).

Example 339

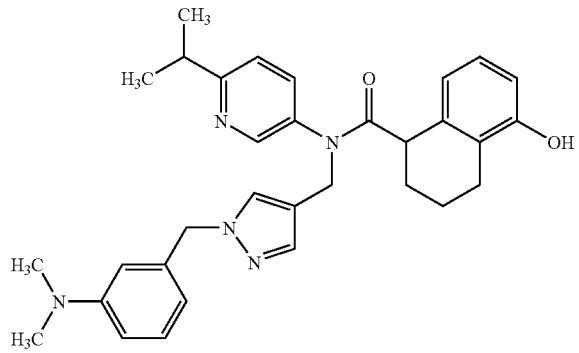

By the reaction and treatment in the same manner as in Example 101 using 5-benzyloxy-N-({1-[3-(dimethylaminophenyl)methyl]pyrazol-4-yl}methyl)-N-(6-isopropylpyridin-3-yl)-1,2,3,4-tetrahydronaphthalene-1-carboxamide (0.46 g) as a starting material, N-({1-[3-(dimethylaminophenyl)methyl]pyrazol-4-yl}methyl)-5-hydroxy-N-(6-isopropylpyridin-3-yl)-1,2,3,4-tetrahydronaphthalene-1-carboxamide dihydrochloride (0.33 g) was obtained. MS (ESI) m/z: 524 [MH]⁺

¹H-NMR (DMSO-d₆) δ: 1.28 (6H, d, J=6.9 Hz), 1.33-1.50 (1H, m), 1.67-1.93 (3H, m), 2.33-2.57 (2H, m), 3.00 (6H, s), 3.11-3.31 (1H, m), 3.42-3.63 (1H, m), 4.60-4.86 (2H, m), 5.28 (2H, s), 6.45 (1H, d, J=7.8 Hz), 6.63 (1H, d, J=7.8 Hz), 6.75-6.90 (2H, m), 7.17-7.41 (4H, m), 7.57-7.75 (2H, m), 7.85-8.03 (1H, m), 8.53-8.71 (1H, m).

Example 340

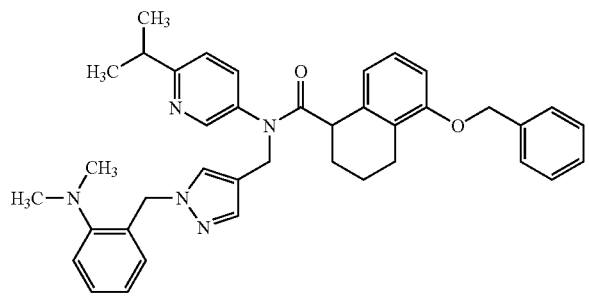

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 2-(dimethylamino)benzyl chloride (0.51 g) as starting materials, 5-benzyloxy-N-({1-[(2-(dimethylamino)phenyl)methyl]pyrazol-4-yl}methyl)-N-(6-isopropylpyridin-3-yl)-1,2,3,4-tetrahydronaphthalene-1-carboxamide (0.43 g) was obtained.

¹H-NMR (CDCl₃) δ: 1.30 (6H, d, J=6.9 Hz), 1.36-1.56 (1H, m), 1.68-2.07 (3H, m), 2.66 (6H, s), 2.65-2.81 (2H, m), 3.08 (1H, sept, J=6.9 Hz), 3.57-3.67 (1H, m), 4.64 (1H, d, J=14.4 Hz), 4.84 (1H, d, J=14.4 Hz), 5.02 (2H, s), 5.40 (2H, s), 6.52 (1H, d, J=7.8 Hz), 6.71 (1H, d, J=8.1 Hz), 6.88 (1H, d, J=6.6 Hz), 6.94-7.06 (2H, m), 7.16 (2H, d, J=8.1 Hz), 7.22-7.45 (9H, m), 8.38 (1H, d, J=2.4 Hz).

Example 341

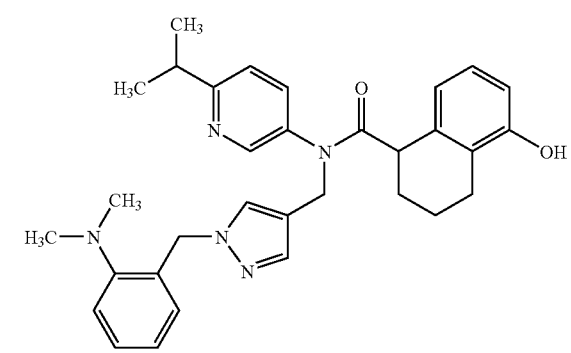

By the reaction and treatment in the same manner as in Example 101 using 5-benzyloxy-N-({1-[(2-(dimethylamino)phenyl)methyl]pyrazol-4-yl}methyl)-N-(6-isopropylpyridin-3-yl)-1,2,3,4-tetrahydronaphthalene-1-carboxamide (0.43 g) as a starting material, N-({1-[(2-(dimethylamino)phenyl)methyl]pyrazol-4-yl}methyl)-5-hydroxy-N-(6-isopropylpyridin-3-yl)-1,2,3,4-tetrahydronaphthalene-1-carboxamide dihydrochloride (0.32 g) was obtained. MS (ESI) m/z: 524 [MH]⁺

¹H-NMR (DMSO-d₆) δ: 1.28 (6H, d, J=6.9 Hz), 1.31-1.52 (1H, m), 1.70-1.96 (3H, m), 2.33-2.59 (2H, m), 3.08 (6H, s), 3.15-3.33 (1H, m), 3.44-3.61 (1H, m), 4.62-4.87 (2H, m), 5.68 (2H, s), 6.46 (1H, d, J=7.5 Hz), 6.63 (1H, d, J=7.8 Hz), 6.87 (1H, d, J=7.8 Hz), 7.00 (1H, d, J=7.2 Hz), 7.27-7.51 (3H, m), 7.60-8.05 (4H, m), 8.57-8.70 (1H, m).

Example 342

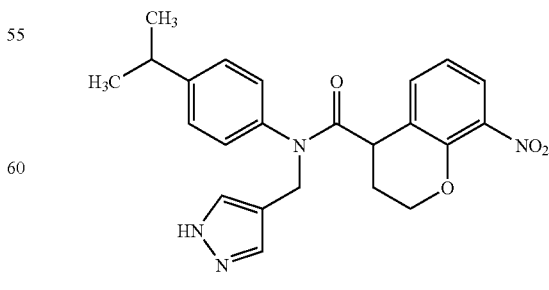

By the reaction and treatment in the same manner as in Example 82 using N-(4-isopropylphenyl)-8-nitrochroman-4- carboxamide (4.1 g) and 1-(tert-butyloxycarbonyl)-4-(hydroxymethyl)pyrazole (2.4 g) as starting materials, N-(4-isopropylphenyl)-8-nitro-N-[(pyrazol-4-yl)methyl]chroman-4-carboxamide (2.9 g) was obtained.

¹H-NMR (CDCl₃) δ: 1.27 (6H, d, J=6.9 Hz), 1.90-2.25 (2H, m), 2.85-3.05 (1H, m), 3.60-3.85 (2H, m), 4.05-4.25 (1H, m), 4.50-4.70 (1H, m), 4.72 (1H, d, J=14.4 Hz), 4.80 (1H, d, J=14.4 Hz), 6.87 (1H, t, J=7.9 Hz), 7.00-7.15 (3H, m), 7.20-7.35 (2H, m), 7.49 (2H, s), 7.70 (1H, d, J=1.4 Hz).

Example 343

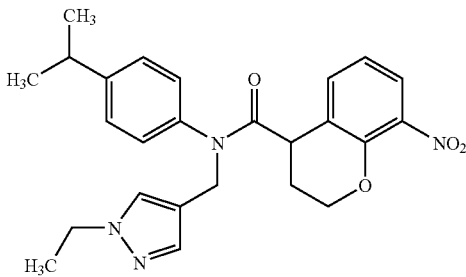

By the reaction and treatment in the same manner as in Example 271 using N-(4-isopropylphenyl)-8-nitro-N-[(pyrazol-4-yl)methyl]chroman-4-carboxamide (2.9 g) and ethyl iodide (1.1 mL) as starting materials, N-[(1-ethylpyrazol-4-yl)methyl]-N-(4-isopropylphenyl)-8-nitrochroman-4-carboxamide (2.9 g) was obtained.

¹H-NMR (CDCl₃) δ: 1.27 (6H, d, J=6.9 Hz), 1.45 (3H, t, J=7.2 Hz), 1.90-2.05 (1H, m), 2.10-2.20 (1H, m), 2.85-3.05 (1H, m), 3.70-3.80 (1H, m), 4.13 (2H, q, J=7.2 Hz), 4.05-4.25 (1H, m), 4.50-4.65 (1H, m), 4.64 (1H, d, J=14.1 Hz), 4.75 (1H, d, J=14.1 Hz), 6.87 (1H, t, J=7.8 Hz), 6.95-7.10 (3H, m), 7.20-7.40 (4H, m) 7.65-7.75 (1H, m).

Example 344

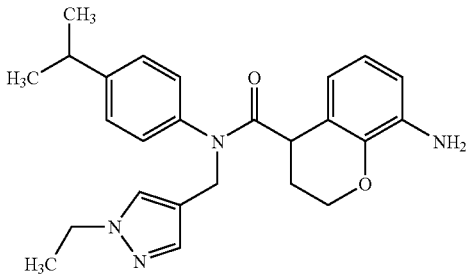

To a mixed solvent of ethanol (43 mL) and water (18 mL) were added iron (0.43 g) and ammonium chloride (0.06 g), and a solution of N-[(1-ethylpyrazol-4-yl)methyl]-N-(4-isopropylphenyl)-8-nitrochroman-4-carboxamide (0.9 g) in ethanol (10 mL) was added dropwise with heating and stirring at 50° C.-70° C. After stirring at 50° C.-70° C. for 3 hr, the reaction mixture was partitioned between water and ethyl acetate. The organic layer was washed with saturated brine and dried over magnesium sulfate. The solvent was evaporated, and the residue was purified by silica gel column chromatography to give 8-amino-N-[(1-ethylpyrazol-4-yl)methyl]-N-(4-isopropylphenyl)chroman-4-carboxamide (0.66 g).

¹H-NMR (CDCl₃) δ: 1.27 (6H, d, J=6.9 Hz), 1.45 (3H, t, J=7.3 Hz), 1.85-2.00 (1H, m), 2.10-2.25 (1H, m), 2.85-3.00 (1H, m), 3.60-3.80 (3H, m), 4.00-4.20 (1H, m), 4.12 (2H, q, J=7.3 Hz), 4.45-4.55 (1H, m), 4.60 (1H, d, J=14.4 Hz), 4.81 (1H, d, J=14.4 Hz), 6.30 (1H, d, J=7.5 Hz), 6.50-6.56 (1H, m), 6.63 (1H, t, J=7.6 Hz), 6.95-7.40 (6H, m).

Example 345

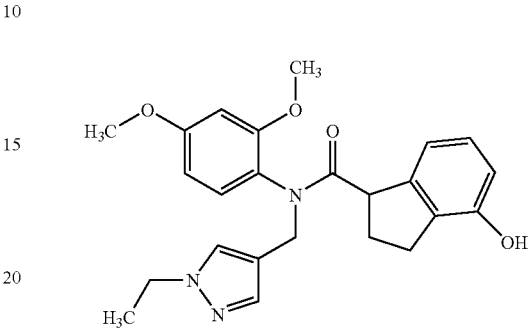

By the reaction and treatment in the same manner as in Example 82 using 4-benzyloxy-N-(2,4-dimethoxyphenyl)indan-1-carboxamide (0.96 g) and 1-(tert-butyloxycarbonyl)-4-(hydroxymethyl)pyrazole (0.47 g) as starting materials, 4-benzyloxy-N-(2,4-dimethoxyphenyl)-N-[(pyrazol-4-yl)methyl]indan-1-carboxamide (0.43 g) was obtained. By the reaction and treatment in the same manner as in Example 271 using this compound (0.43 g) and ethyl iodide (0.28 mL), 4-benzyloxy-N-(2,4-dimethoxyphenyl)-N-[(1-ethylpyrazol-4-yl)methyl]indan-1-carboxamide (0.36 g) was obtained. By the reaction and treatment in the same manner as in Example 17 using this compound (0.36 g), N-(2,4-dimethoxyphenyl)-N-[(1-ethylpyrazol-4-yl)methyl]-4-hydroxyindan-1-carboxamide (0.21 g) was obtained.

MS (ESI) m/z: 422 [MH]⁺

¹H-NMR (CDCl₃) δ: 1.44 (3H, t, J=7.2 Hz), 2.00-2.50 (2H, m), 2.55-2.80 (1H, m), 2.90-3.20 (1H, m), 3.55-4.40 (8H, m), 4.11 (2H, q, J=7.2 Hz), 5.00-5.25 (1H, m), 5.90-7.50 (9H, m).

Example 346

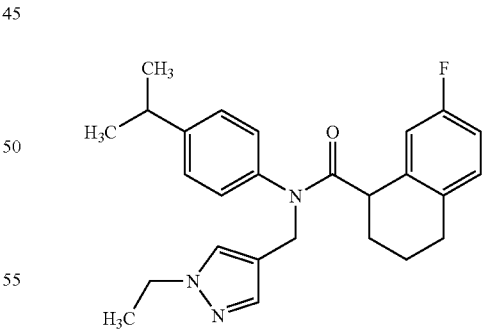

By the reaction and treatment in the same manner as in Example 12 using 7-fluoro-1,2,3,4-tetrahydronaphthalene-1-carboxylic acid (0.41 g) and [(1-ethylpyrazol-4-yl)methyl](4-isopropylphenyl)amine (0.51 g) as starting materials, N-[(1-ethylpyrazol-4-yl)methyl]-7-fluoro-N-(4-isopropylphenyl)-1,2,3,4-tetrahydronaphthalene-1-carboxamide (0.33 g) was obtained.

¹H-NMR (CDCl₃) δ: 1.26 (6H, d, J=6.9 Hz), 1.40-1.60 (1H, m), 1.46 (3H, t, J=7.2 Hz), 1.80-2.15 (3H, m), 2.55-3.05

(3H, m), 3.60-3.75 (1H, m), 4.14 (2H, q, J=7.2 Hz), 4.59 (1H, d, J=14.4 Hz), 4.83 (1H, d, J=14.4 Hz), 6.55-6.65 (1H, m), 6.75-6.85 (1H, m), 6.95-7.10 (3H, m), 7.20-7.40 (2H, m), 7.31 (1H, s), 7.43 (1H, s).

Example 347

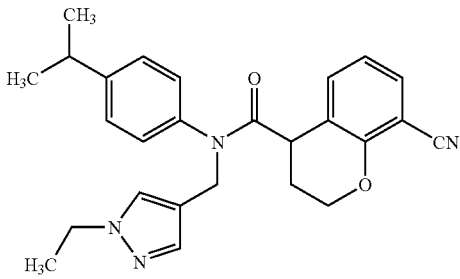

By the reaction and treatment in the same manner as in Example 12 using 8-cyanochroman-4-carboxylic acid (0.7 g) and [(1-ethylpyrazol-4-yl)methyl](4-isopropylphenyl)amine (0.84 g) as starting materials, 8-cyano-N-[(1-ethylpyrazol-4-yl)methyl]-N-(4-isopropylphenyl)chroman-4-carboxamide (1.2 g) was obtained.

$^1$H-NMR (CDCl$_3$) δ: 1.27 (6H, d, J=7.0 Hz), 1.45 (3H, t, J=7.4 Hz), 1.85-2.20 (2H, m), 2.85-3.05 (1H, m), 3.70-3.80 (1H, m), 4.05-4.25 (1H, m), 4.12 (2H, q, J=7.4 Hz), 4.63 (1H, d, J=14.3 Hz), 4.75 (1H, d, J=14.3 Hz), 4.50-4.70 (1H, m), 6.85 (1H, t, J=7.7 Hz), 7.00-7.15 (3H, m), 7.20-7.50 (5H, m).

Example 348

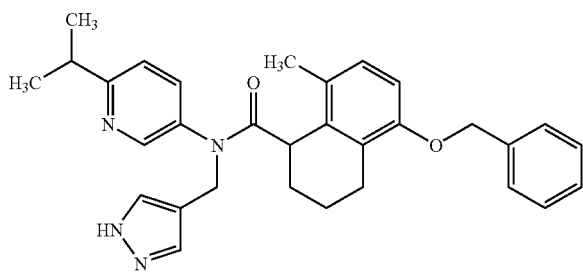

By the reaction and treatment in the same manner as in Example 82 using 5-benzyloxy-N-(6-isopropylpyridin-3-yl)-8-methyl-1,2,3,4-tetrahydronaphthalene-1-carboxamide (1.75 g) and 1-(tert-butyloxycarbonyl)-4-(hydroxymethyl) pyrazole (0.84 g) as starting materials, 5-benzyloxy-N-(6-isopropylpyridin-3-yl)-8-methyl-N-[(pyrazol-4-yl)methyl]-1,2,3,4-tetrahydronaphthalene-1-carboxamide (1.22 g) was obtained.

MS (ESI) m/z: 495 [MH]$^+$ $^1$H-NMR (CDCl$_3$) δ: 1.33 (6H, d, J=6.9 Hz), 1.50-1.80 (2H, m), 1.82-2.10 (2H, m), 2.05 (3H, s), 2.45-2.60 (1H, m), 2.80-3.20 (2H, m), 3.50-3.60 (1H, m), 4.57 (1H, d, J=14.5 Hz), 4.86 (1H, d, J=14.5 Hz), 5.01 (2H, s), 6.68 (1H, d, J=8.3 Hz), 6.88 (1H, d, J=8.2 Hz), 7.20-7.55 (9H, m), 8.45 (1H, d, J=2.4 Hz).

Example 349

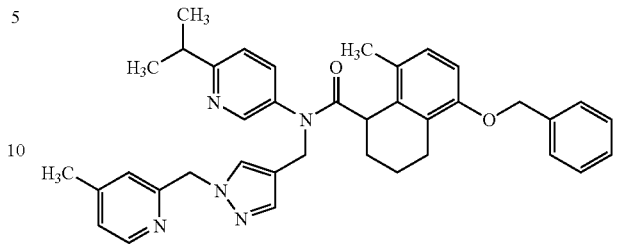

By the reaction and treatment in the same manner as in Example 271 using 5-benzyloxy-N-(6-isopropylpyridin-3-yl)-8-methyl-N-[(pyrazol-4-yl)methyl]-1,2,3,4-tetrahydronaphthalene-1-carboxamide (0.5 g) and 2-chloromethyl-4-methylpyridine hydrochloride (0.36 g) as starting materials, 5-benzyloxy-N-(6-isopropylpyridin-3-yl)-N-({1-[(4-methylpyridin-2-yl)methyl]pyrazol-4-yl}methyl)-8-methyl-1,2,3,4-tetrahydronaphthalene-1-carboxamide (0.45 g) was obtained.

$^1$H-NMR (CDCl$_3$) δ: 1.33 (6H, d, J=6.9 Hz), 1.55-1.75 (2H, m), 1.80-2.00 (2H, m) 2.03 (3H, s), 2.31 (3H, s), 2.45-2.60 (1H, m), 2.85-3.00 (1H, m), 3.02-3.20 (1H, m), 3.50-3.60 (1H, m), 4.54 (1H, d, J=14.5 Hz), 4.82 (1H, d, J=14.5 Hz), 5.01 (2H, s), 5.35 (2H, s), 6.67 (1H, d, J=8.3 Hz), 6.79 (1H, s), 6.87 (1H, d, J=8.3 Hz), 7.02 (1H, d, J=4.8 Hz), 7.15-7.50 (9H, m), 8.41 (1H, d, J=5.0 Hz), 8.46 (1H, d, J=2.4 Hz).

Example 350

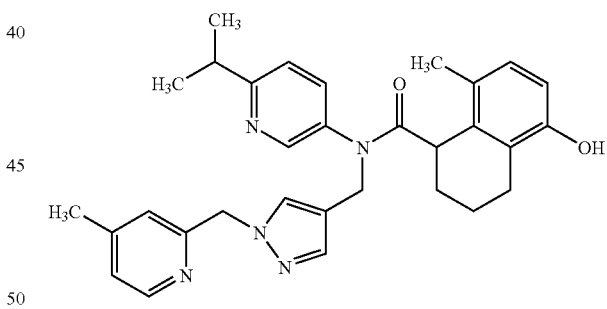

By the reaction and treatment in the same manner as in Example 139 using 5-benzyloxy-N-(6-isopropylpyridin-3-yl)-N-({1-[(4-methylpyridin-2-yl)methyl]pyrazol-4-yl}methyl)-8-methyl-1,2,3,4-tetrahydronaphthalene-1-carboxamide (0.45 g) as starting materials, 5-hydroxy-N-(6-isopropylpyridin-3-yl)-N-({1-[(4-methylpyridin-2-yl)methyl]pyrazol-4-yl}methyl)-8-methyl-1,2,3,4-tetrahydronaphthalene-1-carboxamide dihydrochloride (0.27 g) was obtained. MS (ESI) m/z: 510 [MH]$^+$ $^1$H-NMR (DMSO-d$_6$) δ: 1.28 (6H, d, J=6.9 Hz), 1.40-2.05 (4H, m), 1.92 (3H, s), 2.20-2.70 (5H, m), 3.10-3.25 (1H, m), 3.40-3.50 (1H, m), 4.60 (1H, d, J=14.4 Hz), 4.75 (1H, d, J=14.4 Hz), 5.60 (2H, s), 6.54 (1H, d, J=7.2 Hz), 6.70 (1H, d, J=8.1 Hz), 7.17 (1H, brs), 7.34 (1H, brs), 7.50-7.95 (4H, m), 8.51 (1H, brs), 8.67 (1H, d, J=5.7 Hz).

Example 351

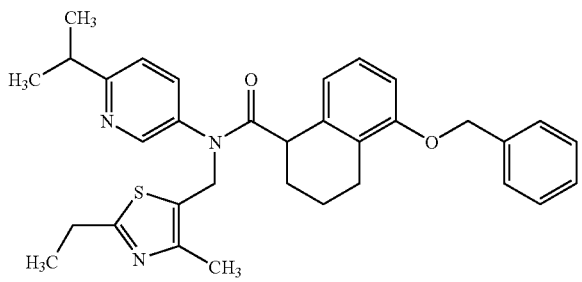

By the reaction and treatment in the same manner as in Example 142 using 2-ethyl-5-hydroxymethyl-4-methylthiazole (0.63 g) and 5-benzyloxy-N-(6-isopropylpyridin-3-yl)-1,2,3,4-tetrahydronaphthalene-1-carboxamide (1.8 g) as starting materials, 5-benzyloxy-N-[(2-ethyl-4-methylthiazol-5-yl)methyl]-N-(6-isopropylpyridin-3-yl)-1,2,3,4-tetrahydronaphthalene-1-carboxamide (1.3 g) was obtained.

MS (ESI) m/z: 540 [MH]$^+$

Example 352

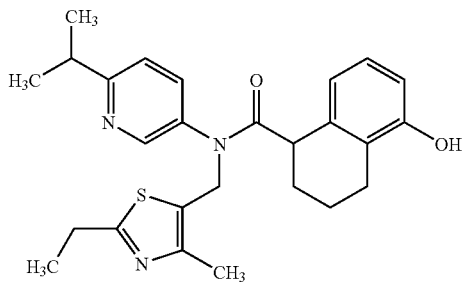

By the reaction and treatment in the same manner as in Example 139 using 5-benzyloxy-N-[(2-ethyl-4-methylthiazol-5-yl)methyl]-N-(6-isopropylpyridin-3-yl)-1,2,3,4-tetrahydronaphthalene-1-carboxamide (1.3 g) as a starting material, N-[(2-ethyl-4-methylthiazol-5-yl)methyl]-5-hydroxy-N-(6-isopropylpyridin-3-yl)-1,2,3,4-tetrahydronaphthalene-1-carboxamide hydrochloride (0.83 g) was obtained.

MS (ESI) m/z: 450 [MH]$^+$ $^1$H-NMR (DMSO-$d_6$) δ: 1.26 (6H, d, J=6.9 Hz), 1.26 (3H, t, J=7.5 Hz), 1.30-1.50 (1H, m), 1.70-2.00 (3H, m), 1.94 (3H, s), 2.35-2.60 (2H, m), 2.94 (2H, q, J=7.5 Hz), 3.10-3.25 (1H, m), 3.40-3.60 (1H, m), 4.92 (1H, d, J=14.6 Hz), 5.04 (1H, d, J=14.6 Hz), 6.45 (1H, d, J=7.5 Hz), 6.63 (1H, d, J=7.8 Hz), 6.89 (1H, t, J=7.8 Hz), 7.56 (1H, d, J=8.1 Hz), 7.75-7.90 (1H, m), 8.52 (1H, brs).

Example 353

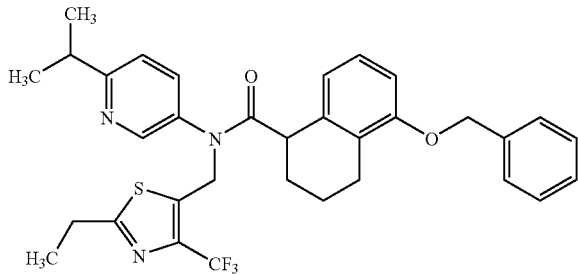

By the reaction and treatment in the same manner as in Example 142 using 2-ethyl-5-hydroxymethyl-4-trifluoromethylthiazole (0.63 g) and 5-benzyloxy-N-(6-isopropylpyridin-3-yl)-1,2,3,4-tetrahydronaphthalene-1-carboxamide (1.2 g) as starting materials, 5-benzyloxy-N-[(2-ethyl-4-trifluoromethylthiazol-5-yl)methyl]-N-(6-isopropylpyridin-3-yl)-1,2,3,4-tetrahydronaphthalene-1-carboxamide (0.4 g) was obtained.

$^1$H-NMR (CDCl$_3$) δ: 1.30 (6H, d, J=6.9 Hz), 1.40 (3H, t, J=7.5 Hz), 1.45-1.65 (1H, m), 1.80-2.10 (3H, m), 2.65-2.80 (2H, m), 3.02 (2H, q, J=7.5 Hz), 2.95-3.20 (1H, m), 3.65-3.80 (1H, m), 5.04 (2H, s), 5.19 (2H, s), 6.59 (1H, d, J=7.8 Hz), 6.75 (1H, d, J=7.8 Hz), 7.08 (1H, t, J=7.8 Hz), 7.20-7.45 (7H, m), 8.37 (1H, d, J=2.4 Hz).

Example 354

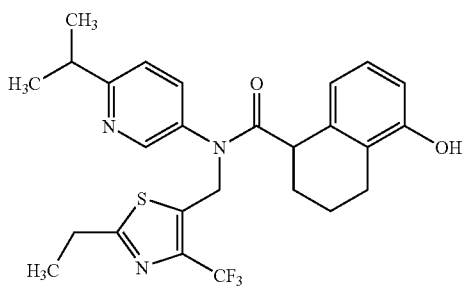

By the reaction and treatment in the same manner as in Example 133 using 5-benzyloxy-N-[(2-ethyl-4-trifluoromethylthiazol-5-yl)methyl]-N-(6-isopropylpyridin-3-yl)-1,2,3,4-tetrahydronaphthalene-1-carboxamide (0.4 g) as a starting material, N-[(2-ethyl-4-trifluoromethylthiazol-5-yl)methyl]-5-hydroxy-N-(6-isopropylpyridin-3-yl)-1,2,3,4-tetrahydronaphthalene-1-carboxamide (0.22 g) was obtained.

melting point: 164.0° C.

$^1$H-NMR (CDCl$_3$) δ: 1.30 (6H, d, J=7.0 Hz), 1.40 (3H, t, J=7.6 Hz), 1.45-1.70 (1H, m), 1.80-2.20 (3H, m), 2.50-2.75 (2H, m), 3.03 (2H, q, J=7.6 Hz), 3.00-3.20 (1H, m), 3.65-3.80 (1H, m), 5.19 (2H, s), 5.58 (1H, s), 6.45-6.60 (2H, m), 6.93 (1H, t, J=7.8 Hz), 7.20-7.50 (2H, m), 8.37 (1H, d, J=2.4 Hz).

Example 355

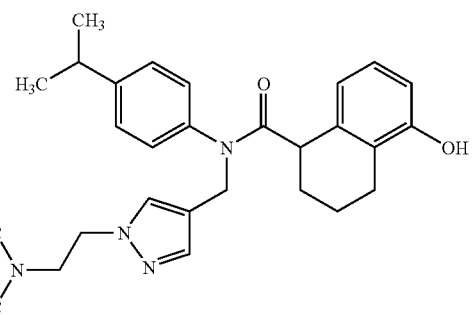

To a solution of 5-benzyloxy-N-(4-isopropylphenyl)-N-[(pyrazol-4-yl)methyl]-1,2,3,4-tetrahydronaphthalene-1-carboxamide (0.35 g) in dimethylformamide were added 2-chloro-N,N-dimethylethylamine hydrochloride (0.12 g) and sodium hydride (0.035 g), and the mixture was stirred for one day. The reaction mixture was partitioned between water and ethyl acetate. The organic layer was washed with saturated brine and dried over magnesium sulfate. The solvent was evaporated, and the obtained residue was reacted and treated in the same manner as in Example 17 to give N-({1-[2-(dimethylamino)ethyl]pyrazol-4-yl}methyl)-5-hydroxy-N-(4-isopropylphenyl)-1,2,3,4-tetrahydronaphthalene-1-carboxamide (0.18 g). melting point: 92° C.

Example 356

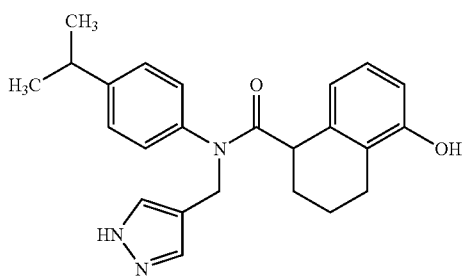

By the reaction and treatment in the same manner as in Example 17 using 5-benzyloxy-N-(4-isopropylphenyl)-N-[(pyrazol-4-yl)methyl]-1,2,3,4-tetrahydronaphthalene-1-carboxamide (0.36 g) as a starting material, 5-hydroxy-N-(4-isopropylphenyl)-N-[(pyrazol-4-yl)methyl]-1,2,3,4-tetrahydronaphthalene-1-carboxamide (0.14 g) was obtained. melting point: 247° C.

Example 357

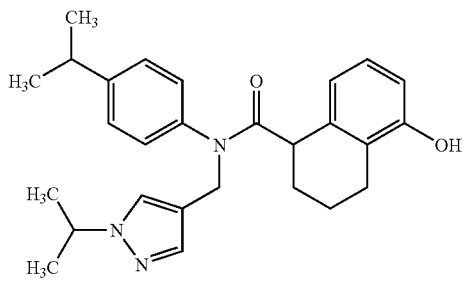

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.41 g) and isopropyl iodide (0.16 mg) as starting materials, 5-benzyloxy-N-(4-isopropylphenyl)-N-[(1-isopropylpyrazol-4-yl)methyl]-1,2,3,4-tetrahydronaphthalene-1-carboxamide (0.47 g) was obtained. By the reaction and treatment of this compound, in the same manner as in Example 17 5-hydroxy-N-(4-isopropylphenyl)-N-[(1-isopropylpyrazol-4-yl)methyl]-1,2,3,4-tetrahydronaphthalene-1-carboxamide (0.22 g) was obtained. melting point: 185° C.

Example 358

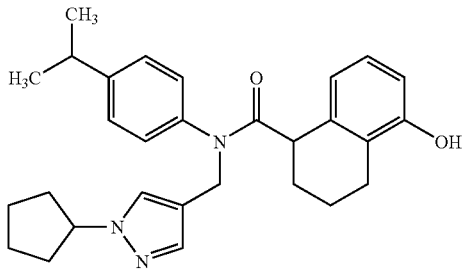

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.50 mg) and bromocyclopentane (0.12 mL) as starting materials, 5-benzyloxy-N-[(1-cyclopentylpyrazol-4-yl)methyl]-N-(4-isopropylphenyl)-1,2,3,4-tetrahydronaphthalene-1-carboxamide (0.54 g) was obtained. By the reaction and treatment of this compound in the same manner as in Example 17, N-[(1-cyclopentylpyrazol-4-yl)methyl]-5-hydroxy-N-(4-isopropylphenyl)-1,2,3,4-tetrahydronaphthalene-1-carboxamide (0.27 g) was obtained. melting point: 173° C.

Example 359

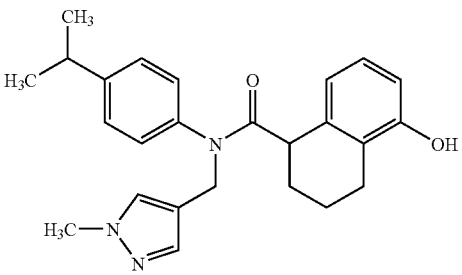

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.52 g) and methyl iodide (0.073 mL) as starting materials, 5-benzyloxy-N-(4-isopropylphenyl)-N-[(1-methylpyrazol-4-yl)methyl]-1,2,3,4-tetrahydronaphthalene-1-carboxamide (0.49 g) was obtained. By the reaction and treatment of this compound in the same manner as in Example 17, 5-hydroxy-N-(4-isopropylphenyl)-N-[(1-methylpyrazol-4-yl)methyl]-1,2,3,4-tetrahydronaphthalene-1-carboxamide (0.33 g) was obtained. melting point: 215° C.

Example 360

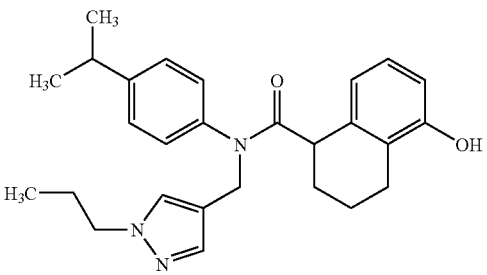

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.50 g) and 1-bromopropane (0.1 mL) as starting materials, 5-benzyloxy-N-(4-isopropylphenyl)-N-[(1-propylpyrazol-4-yl)methyl]-1,2,3,4-tetrahydronaphthalene-1-carboxamide (0.52 g) was obtained. By the reaction and treatment of this compound in the same manner as in Example 17, 5-hydroxy-N-(4-isopropylphenyl)-N-[(1-propylpyrazol-4-yl)methyl]-1,2,3,4-tetrahydronaphthalene-1-carboxamide (0.31 g) was obtained. melting point: 161° C.

Example 361

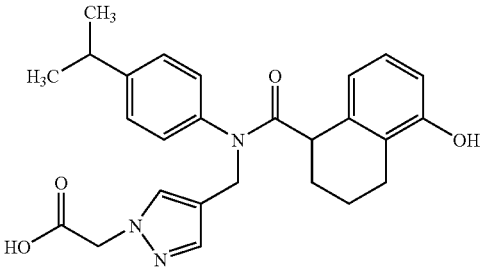

By the reaction and treatment in the same manner as in Example 83 using 5-benzyloxy-N-(4-isopropylphenyl)-N-

[(pyrazol-4-yl)methyl]-1,2,3,4-tetrahydronaphthalene-1-carboxamide (1.12 g) and ethyl bromoacetate (0.31 mL), ethyl 2-(4-{[N-(5-benzyloxy-1,2,3,4-tetrahydronaphthalen-1-ylcarbonyl)-N-(4-isopropylphenyl)amino]methyl}pyrazol-1-yl)acetate (0.66 g) was obtained. This compound was dissolved in ethanol (20 mL), and 1 mol/L-aqueous sodium hydroxide solution (1.22 mL) was added. The mixture was stirred at room temperature for 1 hr. To the reaction mixture was added 1 mol/L-hydrochloric acid (1.22 mL), and the mixture was extracted with ethyl acetate. The organic layer was washed with saturated brine and dried over anhydrous magnesium sulfate. The solvent was evaporated. By the reaction and treatment of the obtained residue in the same manner as in Example 17 (0.58 g), 2-(4-{[N-(5-benzyloxy-1,2,3,4-tetrahydronaphthalen-1-ylcarbonyl)-N-(4-isopropylphenyl)amino]methyl}pyrazol-1-yl)acetic acid (0.23 g) was obtained. melting point: 180-182° C.

Example 362

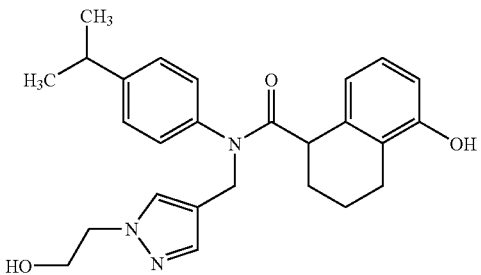

Ethyl 2-(4-{[N-(5-benzyloxy-1,2,3,4-tetrahydronaphthalen-1-ylcarbonyl)-N-(4-isopropylphenyl)amino]methyl}pyrazol-1-yl)acetate (1.0 g) was dissolved in tetrahydrofuran:ethanol (1:2) solution (10 mL), and lithium chloride (0.30 g) and sodium borohydride (0.27 g) were added. The mixture was stirred at room temperature for 3 hr. The reaction mixture was partitioned between water and ethyl acetate. The organic layer was washed with saturated brine and dried over magnesium sulfate. The solvent was evaporated, and the obtained residue (0.91 g) was reacted and treated in the same manner as in Example 17 to give 5-hydroxy-N-{[1-(2-hydroxyethyl)pyrazol-4-yl]methyl}-N-(4-isopropylphenyl)-1,2,3,4-tetrahydronaphthalene-1-carboxamide (0.25 g). melting point: 110-114° C.

Example 363

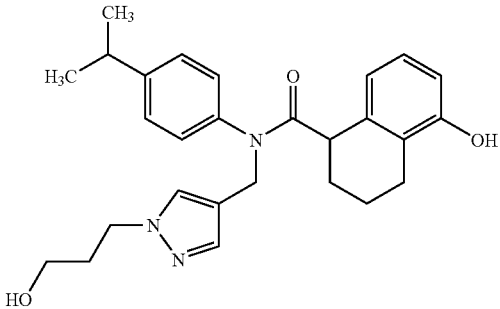

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (1.02 g) and 1-bromo-3-(2-oxanyloxy)propane (0.45 mL) as starting materials, 5-benzyloxy-N-(4-isopropylphenyl)-N-({1-[3-(2-oxanyloxy)propyl]pyrazol-4-yl}methyl)-1,2,3,4-tetrahydronaphthalene-1-carboxamide (1.65 g) was obtained. This compound was dissolved in methanol (30 mL), and 4 mol/L-HCl/dioxane (0.1 mL) was added. The mixture was stirred at room temperature for 2 hr. Into the reaction mixture was poured saturated aqueous sodium hydrogencarbonate (2 mL). The reaction mixture was concentrated under reduced pressure and partitioned between water and ethyl acetate. The organic layer was washed with saturated brine and dried over magnesium sulfate. The solvent was evaporated. By the reaction and treatment of the obtained residue (0.94 g) in the same manner as in Example 105, 5-hydroxy-N-{[1-(3-hydroxypropyl)pyrazol-4-yl]methyl}-N-(4-isopropylphenyl)-1,2,3,4-tetrahydronaphthalene-1-carboxamide (0.58 g) was obtained.

$^1$H-NMR (CDCl$_3$) δ: 2.48 (6H, d, J=6.9 Hz), 1.41-1.44 (1H, m), 1.82-1.98 (5H, m), 2.57 (2H, brs), 2.92 (1H, sept, J=6.9 Hz), 3.48-3.52 (2H, m), 3.68-3.73 (1H, m), 4.19 (2H, t, J=6.2 Hz), 4.57 (1H, d, J=14.3 Hz), 4.83 (1H, d, J=14.3 Hz), 6.40 (2H, t, J=8.7 Hz), 6.80 (1H, t, J=7.8 Hz), 7.07 (2H, d, J=8.1 Hz), 7.22-7.26 (2H, m), 7.34 (1H, s), 7.47 (1H, s), 8.14 (1H, brs).

Example 364

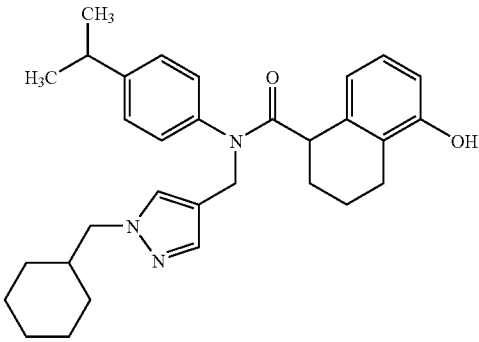

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.33 g) and (bromomethyl)cyclohexane (0.142 mL) as starting materials, 5-benzyloxy-N-{[1-(cyclohexylmethyl)pyrazol-4-yl]methyl}-N-(4-isopropylphenyl)-1,2,3,4-tetrahydronaphthalene-1-carboxamide (0.26 g) was obtained. By the reaction and treatment of this compound in the same manner as in Example 105, N-{[1-(cyclohexylmethyl)pyrazol-4-yl]methyl}-5-hydroxy-N-(4-isopropylphenyl)-1,2,3,4-tetrahydronaphthalene-1-carboxamide (0.18 g) was obtained.

$^1$H-NMR (DMSO-d$_6$) δ: (0.84-(0.92 (2H, m), 1.11-1.44 (12H, m), 1.63-1.77 (6H, m), 1.91-1.99 (1H, m), 2.43-2.52 (2H, m), 2.89 (1H, sept, J=6.9 Hz), 3.50-3.55 (1H, m), 3.86 (2H, d, J=7.2 Hz), 4.65 (2H, s), 6.40 (1H, d, J=7.8 Hz), 6.59 (1H, d, J=7.8 Hz), 6.86 (1H, t, J=7.8 Hz), 7.12 (2H, d, J=8.4 Hz), 7.21 (1H, s), 7.28 (2H, d, J=8.4 Hz), 7.41 (1H, s).

Example 365

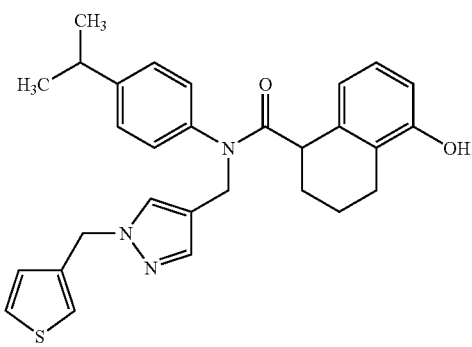

By the reaction and treatment in the same manner as in Example 83 using 5-benzyloxy-N-(4-isopropylphenyl)-N-[(pyrazol-4-yl)methyl]-1,2,3,4-tetrahydronaphthalene-1-carboxamide (0.37 g) and 3-(chloromethyl)thiophene (0.21 g) as starting materials, 5-benzyloxy-N-(4-isopropylphenyl)-N-{[1-(3-thienylmethyl)pyrazol-4-yl]methyl}-1,2,3,4-tetrahydronaphthalene-1-carboxamide (0.16 g) was obtained. By the reaction and treatment of this compound (0.11 g), in the same manner as in Example 133, 5-hydroxy-N-(4-isopropylphenyl)-N-{[1-(3-thienylmethyl)pyrazol-4-yl]methyl}-1,2,3,4-tetrahydronaphthalene-1-carboxamide (0.054 g) was obtained.

$^1$H-NMR (CDCl$_3$) δ: 1.24 (6H, d, J=6.9 Hz), 1.38-1.45 (1H, m), 1.76-2.01 (3H, m), 2.55-2.60 (2H, m), 2.92 (1H, sept, J=6.9 Hz), 3.67-3.72 (1H, m), 4.67 (1H, d, J=14.4 Hz), 4.79 (1H, d, J=14.4 Hz), 5.23 (2H, s), 6.33 (1H, d, J=7.8 Hz); 6.38 (1H, d, J=7.8 Hz), 6.74 (1H, t, J=7.8 Hz), 6.94-6.96 (1H, m), 7.04 (2H, d, J=8.1 Hz), 7.11-7.12 (1H, m), 7.20-7.30 (3H, m), 7.41 (2H, s), 7.53 (1H, brs).

Example 366

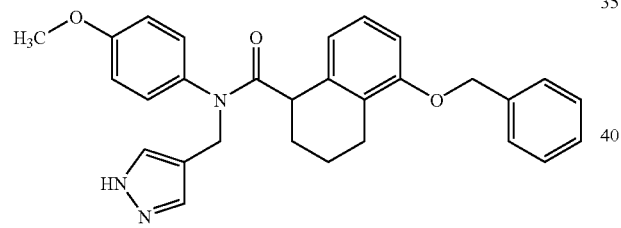

By the reaction and treatment in the same manner as in Example 82 using 5-benzyloxy-N-(4-methoxyphenyl)-1,2,3,4-tetrahydronaphthalene-1-carboxamide (2.98 g) and 1-(tert-butoxycarbonyl)-4-(hydroxymethyl)pyrazole (1.83 g) as starting materials, 5-benzyloxy-N-(4-methoxyphenyl)-N-[(pyrazol-4-yl)methyl]-1,2,3,4-tetrahydronaphthalene-1-carboxamide (1.74 g) was obtained.

MS (ESI) m/z: 468 [MH]$^+$

Example 367

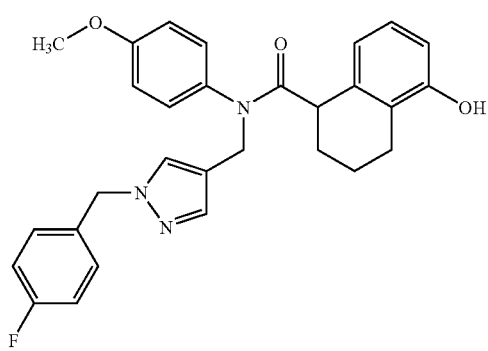

By the reaction and treatment in the same manner as in Example 83 using 5-benzyloxy-N-(4-methoxyphenyl)-N-[(pyrazol-4-yl)methyl]-1,2,3,4-tetrahydronaphthalene-1-carboxamide (0.56 g) and 4-fluorobenzyl chloride (0.172 mL) as starting materials, 5-benzyloxy-N-{[1-(4-fluorobenzyl)pyrazol-4-yl]methyl}-N-(4-methoxyphenyl)-1,2,3,4-tetrahydronaphthalene-1-carboxamide (0.60 g) was obtained. By the reaction and treatment of this compound in the same manner as in Example 133, N-{[1-(4-fluorobenzyl)pyrazol-4-yl]methyl}-5-hydroxy-N-(4-methoxyphenyl)-1,2,3,4-tetrahydronaphthalene-1-carboxamide (0.42 g) was obtained.

melting point: 143-146° C.

Example 368

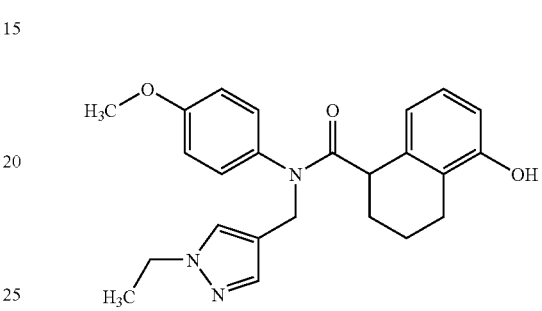

By the reaction and treatment in the same manner as in example 83 using 5-benzyloxy-N-(4-methoxyphenyl)-N-[(pyrazol-4-yl)methyl]-1,2,3,4-tetrahydronaphthalene-1-carboxamide (0.62 g) and ethyl iodide (0.13 mL) as starting materials, 5-benzyloxy-N-[(1-ethylpyrazol-4-yl)methyl]-N-(4-methoxyphenyl)-1,2,3,4-tetrahydronaphthalene-1-carboxamide (0.55 g) was obtained. By the reaction and treatment of this compound (0.40 g) in the same manner as in Example 133, N-[(1-ethylpyrazol-4-yl)methyl]-5-hydroxy-N-(4-methoxyphenyl)-1,2,3,4-tetrahydronaphthalene-1-carboxamide (0.30 g) was obtained. melting point: 211-213° C.

Example 369

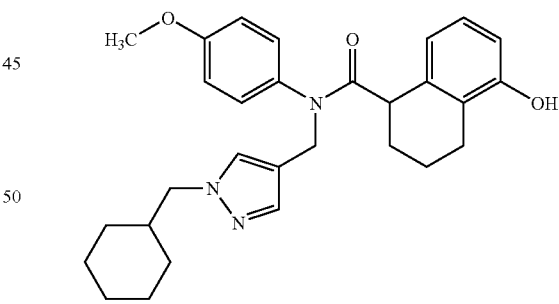

By the reaction and treatment in the same manner as in Example 83 using 5-benzyloxy-N-(4-methoxyphenyl)-N-[(pyrazol-4-yl)methyl]-1,2,3,4-tetrahydronaphthalene-1-carboxamide (0.56 g) and (bromomethyl)cyclohexane (0.20 mL) as starting materials, 5-benzyloxy-N-{[1-(cyclohexylmethyl)pyrazol-4-yl]methyl}-N-(4-methoxyphenyl)-1,2,3,4-tetrahydronaphthalene-1-carboxamide (0.55 g) was obtained. By the reaction and treatment in the same manner as in Example 133 using this compound (0.45 g), N-{[1-(cyclohexylmethyl)pyrazol-4-yl]methyl}-5-hydroxy-N-(4-methoxyphenyl)-1,2,3,4-tetrahydronaphthalene-1-carboxamide (0.36 g) was obtained.

¹H-NMR (DMSO-d₆) δ: 0.84-0.92 (2H, m), 1.12-1.23 (3H, m), 1.32-1.46 (3H, m), 1.63-1.75 (6H, m), 1.90-1.94 (1H, m), 2.40-2.56 (2H, m), 3.53-3.58 (1H, m), 3.74 (3H, s), 3.83 (2H, d, J=1 (0.8 Hz), 4.60 (1H, d, J=14.7 Hz), 4.66 (1H, d, J=14.7 Hz), 6.40 (1H, d, J=7.8 Hz), 6.62 (1H, d, J=7.8 Hz), 6.86 (1H, t, J=78 Hz), 6.93-6.96 (2H, m), 7.10-7.13 (2H, m), 7.20 (1H, s), 7.41 (1H, s), 9.19 (1H, s).

Example 370

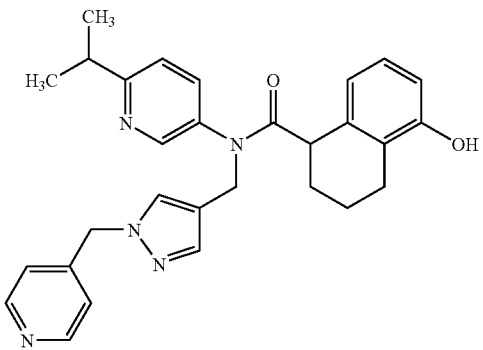

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.77 g) and 4-(chloromethyl)pyridine (0.49 g) as starting materials, 5-benzyloxy-N-(6-isopropylpyridin-3-yl)-N-{[1-(4-pyridylmethyl)pyrazol-4-yl]methyl}-1,2,3,4-tetrahydronaphthalene-1-carboxamide (0.67 g) was obtained. By the reaction and treatment of this compound in the same manner as in Example 139, 5-hydroxy-N-(6-isopropylpyridin-3-yl)-N-{[1-(4-pyridylmethyl)pyrazol-4-yl]methyl}-1,2,3,4-tetrahydronaphthalene-1-carboxamide dihydrochloride (0.58 g) was obtained.

MS (ESI) m/z: 482 [MH]⁺

¹H-NMR (DMSO-d₆) δ: 1.28 (6H, d, J=6.9 Hz), 1.35-1.43 (1H, m), 1.80-2.00 (3H, m), 2.38-2.55 (2H, m), 3.22-3.28 (1H, m), 3.53 (1H, brs), 4.73 (1H, d, J=14.3 Hz), 4.84 (1H, d, J=14.3 Hz), 5.68 (2H, s), 6.47 (1H, d, J=7.8 Hz), 6.64 (1H, d, J=7.8 Hz), 6.87 (1H, d, J=7.8 Hz), 7.43 (1H, s), 7.57 (2H, d, J=6.6 Hz), 7.66-7.69 (1H, m), 7.83 (1H, s), 8.00 (1H, brs), 8.61 (1H, brs), 8.89 (2H, d, J=6.6 Hz).

Example 371

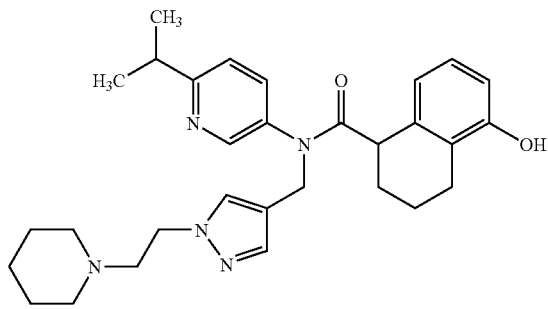

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.77 g) and 1-(2-chloroethyl)piperidine hydrochloride (0.55 g) as starting materials, 5-benzyloxy-N-(6-isopropylpyridin-3-yl)-N-{[1-(2-piperidinoethyl)pyrazol-4-yl]methyl}-1,2,3,4-tetrahydronaphthalene-1-carboxamide (0.76 g) was obtained. By the reaction and treatment of this compound in the same manner as in Example 139, 5-hydroxy-N-(6-isopropylpyridin-3-yl)-N-{[1-(2-piperidinoethyl)pyrazol-4-yl]methyl}-1,2,3,4-tetrahydronaphthalene-1-carboxamide dihydrochloride (0.54 g) was obtained.

MS (ESI) m/z: 502 [MH]⁺

¹H-NMR (DMSO-d₆) δ: 1.31 (6H, d, J=6.9 Hz), 1.32-1.40 (1H, m), 1.65-1.91 (7H, m), 2.47-2.52 (3H, m), 2.81-2.86 (2H, m), 3.18-3.57 (5H, m), 4.61 (2H, d, J=6.6 Hz), 4.63-4.87 (2H, m), 5.10 (2H, brs), 6.49 (1H, d, J=7.8 Hz), 6.66 (1H, d, J=7.8 Hz), 6.88 (1H, t, J=7.8 Hz), 7.36 (1H, brs), 7.76 (2H, brs), 8.15 (1H, brs), 8.68 (1H, brs), 11.1 (1H, brs).

Example 372

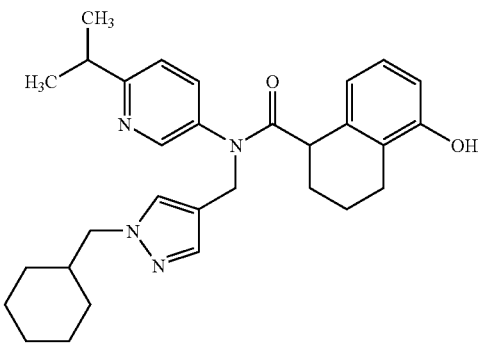

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.72 g) and (bromomethyl)cyclohexane (0.25 mL) as starting materials, 5-benzyloxy-N-{[1-(cyclohexylmethyl)pyrazol-4-yl]methyl}-N-(6-isopropylpyridin-3-yl)-1,2,3,4-tetrahydronaphthalene-1-carboxamide (0.86 g) was obtained. By the reaction and treatment of this compound in the same manner as in Example 139, N-{[1-(cyclohexylmethyl)pyrazol-4-yl]methyl}-5-hydroxy-N-(6-isopropylpyridin-3-yl)-1,2,3,4-tetrahydronaphthalene-1-carboxamide hydrochloride (0.63 g) was obtained.

MS (ESI) m/z: 487 [MH]⁺

¹H-NMR (DMSO-d₆) δ: 0.83-1.91 (21H, m), 2.46-2.52 (2H, m), 3.23 (1H, brs), 3.52 (1H, brs), 3.86 (2H, d, J=7.1 Hz), 4.74 (2H, brs), 6.45 (1H, d, J=7.8 Hz), 6.63 (1H, d, J=7.8 Hz), 6.88 (1H, t, J=7.8 Hz), 7.26 (1H, brs), 7.49 (1H, brs), 7.65 (1H, brs), 7.93 (1H, brs), 8.61 (1H, brs).

Example 373

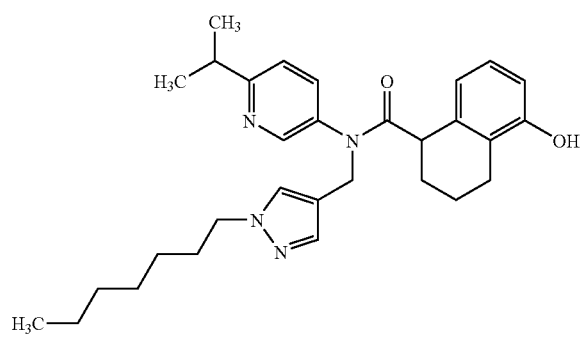

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.72 g) and 1-bromoheptane (0.283 mL) as starting materials, 5-benzyloxy-N-[(1-heptylpyrazol-4-yl)methyl]-N-(6-isopropylpyridin-3-yl)-1,2,3,4-tetrahydronaphthalene-1-carboxamide (0.86 g) was obtained. By the reaction and treatment of this compound in the same manner as in Example 139, N-[(1-heptylpyrazol-4-yl)methyl]-5-hydroxy-N-(6-isopropylpyridin-3-yl)-1,2,3,4-tetrahydronaphthalene-1-carboxamide hydrochloride (0.62 g) was obtained.

MS (ESI) m/z: 489 [MH]$^+$ $^1$H-NMR (DMSO-d$_6$) δ: 0.82-(0.87 (3H, m), 1.10-1.43 (15H, m), 1.63-1.91 (5H, m), 2.46-2.54 (2H, m), 3.31 (1H, brs), 3.54 (1H, brs), 4.02 (2H, t, J=6.9 Hz), 4.72-4.77 (2H, m), 6.47 (1H, d, J=7.8 Hz), 6.64 (1H, d, J=7.8 Hz), 6.88 (1H, t, J=7.8 Hz), 7.27 (1H, brs), 7.55 (1H, brs), 7.74 (1H, brs), 8.03 (1H, brs), 8.68 (1H, brs).

Example 374

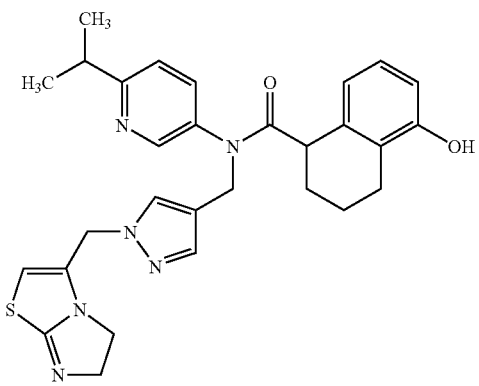

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.72 g) and 3-chloromethyl-5,6-dihydroimidazo[2,1-b]thiazole hydrochloride (0.38 g) as starting materials, 5-benzyloxy-N-({1-[(5,6-dihydroimidazo[2,1-b]thiazol-3-yl)methyl]pyrazol-4-yl}methyl)-N-(6-isopropylpyridin-3-yl)-1,2,3,4-tetrahydronaphthalene-1-carboxamide (0.92 g) was obtained. By the reaction and treatment of this compound in the same manner as in Example 139, N-({1-[(5,6-dihydroimidazo[2,1-b]thiazol-3-yl)methyl]pyrazol-4-yl}methyl)-5-hydroxy-N-(6-isopropylpyridin-3-yl)-1,2,3,4-tetrahydronaphthalene-1-carboxamide dihydrochloride (0.50 g) was obtained.

MS (ESI) m/z: 529 [MH]$^+$ $^1$H-NMR (DMSO-d$_6$) δ: 1.28 (6H, d, J=6.8 Hz), 1.34-1.44 (1H, m), 1.80-1.91 (3H, m), 2.46-2.55 (2H, m), 3.21 (1H, brs), 3.51 (1H, brs), 4.11-4.29 (4H, m), 4.66-4.81 (2H, m), 5.35 (2H, m), 6.45 (1H, d, J=7.8 Hz), 6.64 (1H, d, J=7.8 Hz), 6.81-6.91 (2H, m), 7.37 (1H, brs), 7.59-7.61 (1H, m), 7.74 (1H, brs), 7.93 (1H, brs), 8.85 (1H, brs), 9.98 (1H, brs).

Example 375

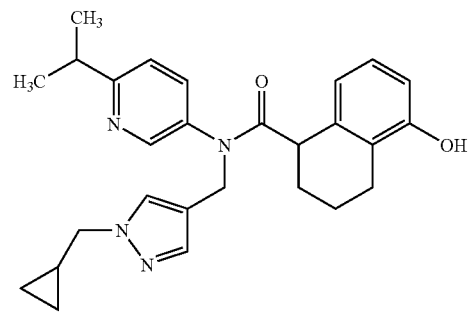

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.72 g) and (bromomethyl)cyclopropane (0.174 mL) as starting materials, 5-benzyloxy-N-{[1-(cyclopropylmethyl)pyrazol-4-yl]methyl}-N-(6-isopropylpyridin-3-yl)-1,2,3,4-tetrahydronaphthalene-1-carboxamide (0.80 g) was obtained. By the reaction and treatment of this compound in the same manner as in Example 139, N-{[1-(cyclopropylmethyl)pyrazol-4-yl]methyl}-5-hydroxy-N-(6-isopropylpyridin-3-yl)-1,2,3,4-tetrahydronaphthalene-1-carboxamide hydrochloride (0.58 g) was obtained.

MS (ESI) m/z: 445 [MH]$^+$ $^1$H-NMR (DMSO-d$_6$) δ: 0.26-(0.30 (2H, m), 0.45-(0.51 (2H, m), 1.12-1.20 (1H, m), 1.32 (6H, d, J=6.9 Hz), 1.40-1.50 (1H, m), 1.81-1.91 (3H, m), 2.47-2.51 (2H, m), 3.34 (1H, brs), 3.55 (1H, brs), 3.91 (2H, d, J=6.9 Hz), 4.76 (2H, brs), 6.49 (1H, d, J=7.8 Hz), 6.65 (1H, d, J=7.8 Hz), 6.89 (1H, t, J=7.8 Hz), 7.28 (1H, brs), 7.59 (1H, brs), 7.79 (1H, brs), 8.07 (1H, brs), 8.70 (1H, brs).

Example 376

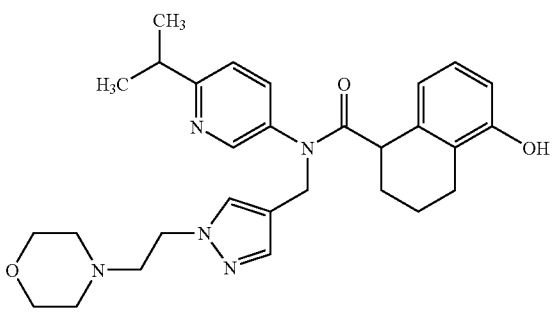

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.72 g) and 4-(2-chloroethyl)morpholine hydrochloride (0.33 g) as starting materials, 5-benzyloxy-N-{[1-(2-morpholinoethyl)pyrazol-4-yl]methyl}-N-(6-isopropylpyridin-3-yl)-1,2,3,4-tetrahydronaphthalene-1-carboxamide (0.69 g) was obtained. By the reaction and treatment of this compound in the same manner as in Example 139, 5-hydroxy-N-{[1-(2-morpholinoethyl)pyrazol-4-yl]methyl}-N-(6-isopropylpyridin-3-yl)-1,2,3,4-tetrahydronaphthalene-1-carboxamide hydrochloride (0.34 g) was obtained.

MS (ESI) m/z: 504 [MH]+

1H-NMR (DMSO-d6) δ: 1.30 (6H, d, J=6.9 Hz), 1.40-1.50 (1H, m), 1.81-1.91 (3H, m), 2.43-2.54 (2H, m), 3.05 (1H, brs), 3.24 (1H, brs), 3.52-3.57 (4H, m), 3.81-3.89 (4H, m), 4.58-5.20 (6H, m), 6.48 (1H, d, J=7.8 Hz), 6.64 (1H, d, J=7.8 Hz), 6.90 (1H, t, J=7.8 Hz), 7.35 (1H, brs), 7.47-7.73 (2H, m), 8.05 (1H, brs), 8.63 (1H, brs), 11.7 (1H, brs).

Example 377

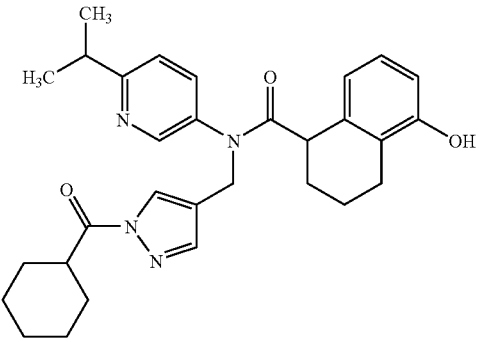

To a solution of 5-benzyloxy-N-(6-isopropylpyridin-3-yl)-N-[(pyrazol-4-yl)methyl]-1,2,3,4-tetrahydronaphthalene-1-carboxamide hydrochloride (0.72 g) in dimethylformamide (5 mL) were added triethylamine (0.23 mL) and cyclohexanecarbonyl chloride (0.22 mL), and the mixture was stirred at room temperature for one day. The reaction mixture was partitioned between water and ethyl acetate. The organic layer was washed with saturated brine and dried over magnesium sulfate. The solvent was evaporated, and the residue was purified by silica gel column chromatography to give 5-benzyloxy-N-{[1-(cyclohexylcarbonyl)pyrazol-4-yl]methyl}-N-(6-isopropylpyridin-3-yl)-1,2,3,4-tetrahydronaphthalene-1-carboxamide (0.67 g). By the reaction and treatment of this compound in the same manner as in Example 139, N-{[1-(cyclohexanecarbonyl)pyrazol-4-yl]methyl}-5-hydroxy-N-(6-isopropylpyridin-3-yl)-1,2,3,4-tetrahydronaphthalene-1-carboxamide hydrochloride (0.23 g) was obtained.

MS (ESI) m/z: 501 [MH]+

1H-NMR (DMSO-d6) δ: 1.15-2.00 (20H, m), 2.43 (2H, brs), 2.58-2.64 (1H, m), 3.40-3.44 (1H, m), 3.66 (1H, brs), 4.73-7.89 (2H, m), 6.89 (1H, d, J=7.8 Hz), 7.01 (1H, d, J=7.8 Hz), 7.16 (1H, t, J=7.8 Hz), 7.57-7.66 (2H, m), 7.86-7.89 (2H, m), 8.25-8.26 (1H, m), 8.87 (1H, brs).

Example 378

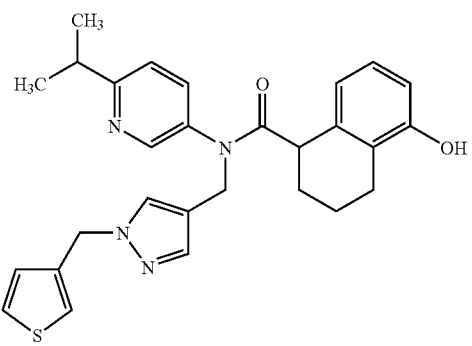

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.83 g) and 3-(chloromethyl)thiophene (0.27 g) as starting materials, 5-benzyloxy-N-{[1-(3-thienylmethyl)pyrazol-4-yl]methyl}-N-(6-isopropylpyridin-3-yl)-1,2,3,4-tetrahydronaphthalene-1-carboxamide (0.48 g) was obtained. By the reaction and treatment of this compound in the same manner as in Example 139, 5-hydroxy-N-(6-isopropylpyridin-3-yl)-N-{[1-(3-thienylmethyl)pyrazol-4-yl]methyl}-1,2,3,4-tetrahydronaphthalene-1-carboxamide hydrochloride (0.39 g) was obtained.

MS (ESI) m/z: 487 [MH]+

1H-NMR (DMSO-d6) δ: 1.30 (6H, d, J=6.8 Hz), 1.42 (1H, m), 1.79-1.91 (3H, m), 2.46-2.51 (2H, m), 3.30 (1H, brs), 3.53-3.57 (1H, m), 4.76 (2H, m), 5.26 (2H, s), 6.45 (1H, d, J=7.8 Hz), 6.64 (1H, d, J=7.8 Hz), 6.87-6.94 (2H, m), 7.24-7.28 (2H, m), 7.49-7.52 (1H, m), 7.61 (1H, brs), 7.73 (1H, brs), 8.02 (1H, brs), 8.68 (1H, brs).

Example 379

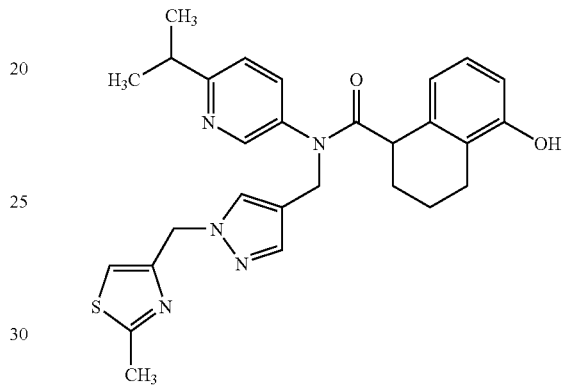

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.83 g) and 4-(chloromethyl)-2-methylthiazole (0.55 g) as starting materials, 5-benzyloxy-N-({1-[(2-methylthiazol-4-yl)methyl]pyrazol-4-yl}methyl)-N-(6-isopropylpyridin-3-yl)-1,2,3,4-tetrahydronaphthalene-1-carboxamide (0.73 g) was obtained. By the reaction and treatment of this compound in the same manner as in Example 139, 5-hydroxy-N-(6-isopropylpyridin-3-yl)-N-({1-[(2-methylthiazol-4-yl)methyl]pyrazol-4-yl}methyl)-1,2,3,4-tetrahydronaphthalene-1-carboxamide hydrochloride (0.62 g) was obtained.

MS (ESI) m/z: 502 [MH]+

1H-NMR (DMSO-d6) δ: 1.33 (6H, d, J=6.9 Hz), 1.41-1.50 (1H, m), 1.83-1.91 (3H, m), 2.41-2.50 (2H, m), 2.63 (3H, s), 3.40-3.45 (1H, m), 3.57 (1H, brs), 4.70-4.85 (2H, m), 5.31 (2H, s), 6.49 (1H, d, J=7.8 Hz), 6.66 (1H, d, J=7.8 Hz), 6.88 (1H, d, J=7.8 Hz), 7.19 (1H, s), 7.32 (1H, brs), 7.67-7.70 (1H, m), 7.87-7.89 (1H, m), 8.21 (1H, brs), 8.80 (1H, brs).

Example 380

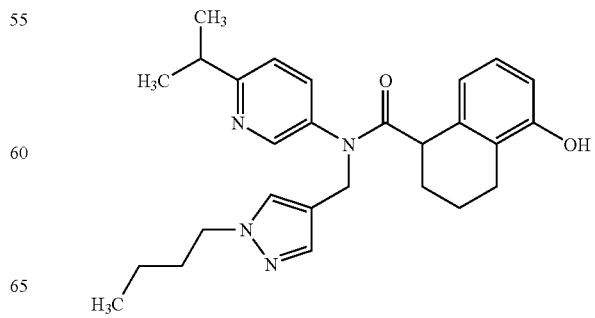

By the reaction and treatment in the same manner as in Example 271 using 5-benzyloxy-N-(6-isopropylpyridin-3-yl)-N-[(pyrazol-4-yl)methyl]-1,2,3,4-tetrahydronaphtha-lene-1-carboxamide hydrochloride (0.83 g) and 1-bromobutane (0.322 mL) as starting materials, 5-benzyloxy-N-[(1-butylpyrazol-4-yl)methyl]-N-(6-isopropylpyridin-3-yl)-1,2,3,4-tetrahydronaphthalene-1-carboxamide (0.66 g) was obtained. By the reaction and treatment of this compound in the same manner as in Example 139, N-[(1-butylpyrazol-4-yl)methyl]-5-hydroxy-N-(6-isopropylpyridin-3-yl)-1,2,3,4-tetrahydronaphthalene-1-carboxamide hydrochloride (0.41 g) was obtained. MS (ESI) m/z: 447 [MH]+

¹H-NMR (DMSO-d₆) δ: 0.82-0.84 (3H, m), 1.07-1.20 (2H, m), 1.35 (6H, d, J=6.9 Hz), 1.40-1.51 (1H, m), 1.62-1.92 (5H, m), 2.47-2.52 (2H, m), 3.43-3.57 (2H, m), 3.99-4.06 (2H, m), 4.70-5.20 (2H, m), 6.50 (1H, d, J=7.7 Hz), 6.68 (1H, d, J=7.7 Hz), 6.89 (1H, t, J=7.7 Hz), 7.33 (1H, brs), 7.60 (1H, brs), 7.92-7.95 (1H, m), 8.25 (1H, brs), 8.82 (1H, brs).

Example 381

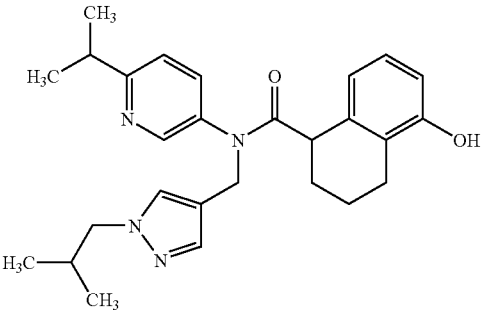

By the reaction and treatment in the same manner as in Example 271 using 5-benzyloxy-N-(6-isopropylpyridin-3-yl)-N-[(pyrazol-4-yl)methyl]-1,2,3,4-tetrahydronaphtha-lene-1-carboxamide hydrochloride (0.83 g) and isobutyl bromide (0.326 mL) as starting materials, 5-benzyloxy-N-(6-isopropylpyridin-3-yl)-N-{[1-(2-methylpropyl)pyrazol-4-yl]methyl}-1,2,3,4-tetrahydronaphthalene-1-carboxamide (0.16 g) was obtained. By the reaction and treatment of this compound in the same manner as in Example 19, 5-hydroxy-N-(6-isopropylpyridin-3-yl)-N-{[1-(2-methylpropyl)pyrazol-4-yl]methyl}-1,2,3,4-tetrahydronaphthalene-1-carboxamide hydrochloride (0.11 g) was obtained.

MS (ESI) m/z: 447 [MH]+

¹H-NMR (DMSO-d₆) δ: 0.75 (6H, d, J=6.9 Hz), 1.29 (6H, d, J=6.9 Hz), 1.35-1.47 (1H, m), 1.81-1.94 (3H, m), 2.46-2.52 (3H, m), 3.29 (1H, brs), 3.50-3.60 (1H, m), 3.83 (2H, d, J=6.9 Hz), 4.76 (2H, brs), 6.47 (1H, d, J=7.8 Hz), 6.64 (1H, d, J=7.8 Hz), 6.88 (1H, t, J=7.8 Hz), 7.24-7.31 (1H, m), 7.51 (1H, brs), 7.74 (1H, brs), 8.02 (1H, brs), 8.67 (1H, brs).

Example 382

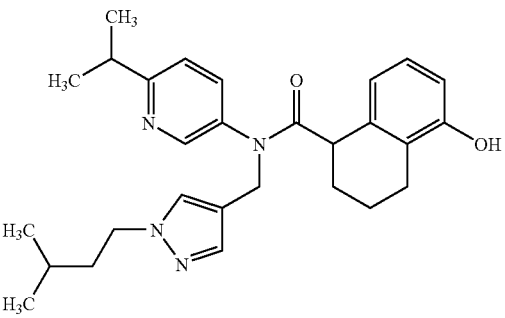

By the reaction and treatment in the same manner as in Example 271 using 5-benzyloxy-N-(6-isopropylpyridin-3-yl)-N-[(pyrazol-4-yl)methyl]-1,2,3,4-tetrahydronaphtha-lene-1-carboxamide hydrochloride (0.83 g) and 1-bromo-3-methylbutane (0.359 mL) as starting materials, 5-benzyloxy-N-(6-isopropylpyridin-3-yl)-N-{[1-(3-methylbutyl)pyrazol-4-yl]methyl}-1,2,3,4-tetrahydronaphthalene-1-carboxamide (0.60 g) was obtained. By the reaction and treatment of this compound in the same manner as in Example 139, 5-hydroxy-N-(6-isopropylpyridin-3-yl)-N-{[1-(3-methylbutyl)pyrazol-4-yl]methyl}-1,2,3,4-tetrahydronaphthalene-1-carboxamide hydrochloride (0.45 g) was obtained.

MS (ESI) m/z: 461 [MH]+

¹H-NMR (DMSO-d₆) δ: 0.85 (6H, d, J=6.6 Hz), 1.34 (6H, d, J=6.9 Hz), 1.43-1.54 (1H, m), 1.56-1.63 (2H, m), 1.85-1.92 (3H, m), 2.43-2.52 (3H, m), 3.41-3.65 (2H, m), 4.02-4.08 (2H, m), 4.70-5.20 (2H, m), 6.49 (1H, d, J=7.8 Hz), 6.67 (1H, d, J=7.8 Hz), 6.89 (1H, t, J=7.8 Hz), 7.22-7.31 (1H, m), 7.61 (1H, brs), 7.90-7.92 (1H, m), 8.22 (1H, brs), 8.81 (1H, brs).

Example 383

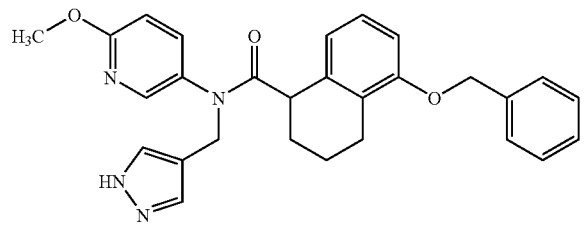

By the reaction and treatment in the same manner as in Example 82 using 5-benzyloxy-N-(6-methoxypyridin-3-yl)-1,2,3,4-tetrahydronaphthalene-1-carboxamide (20.0 g) and 1-(tert-butoxycarbonyl)-4-(hydroxymethyl)pyrazole (12.0 g), 5-benzyloxy-N-(6-methoxypyridin-3-yl)-N-[(pyrazol-4-yl)methyl]-1,2,3,4-tetrahydronaphthalene-1-carboxamide hydrochloride (18.8 g) was obtained. MS (ESI) m/z: 469 [MH]+

¹H-NMR (DMSO-d₆) δ: 1.38-1.49 (1H, m), 1.75-1.82 (2H, m), 1.90-2.00 (1H, m), 2.52-2.55 (2H, m), 3.57 (1H, t, J=6.8 Hz), 3.84 (3H, s), 4.71 (2H, s), 5.08 (2H, s), 6.59-6.62 (1H, m), 6.83-6.90 (2H, m), 7.02-7.07 (1H, m), 7.31-7.46 (7H, m), 7.60-7.64 (1H, m), 8.04 (1H, d, J=2.4 Hz).

Example 384

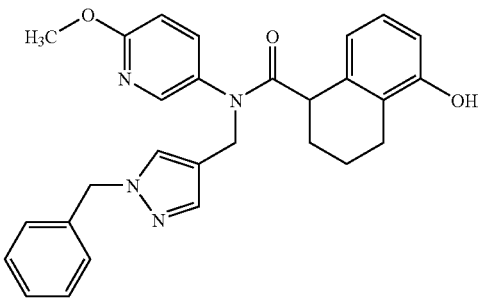

By the reaction and treatment in the same manner as in Example 83 using 5-benzyloxy-N-(6-methoxypyridin-3-yl)-N-[(pyrazol-4-yl)methyl]-1,2,3,4-tetrahydronaphthalene-1-carboxamide hydrochloride (0.94 g) and benzyl bromide (0.285 mL) as starting materials, 5-benzyloxy-N-[(1-benzylpyrazol-4-yl)methyl]-N-(6-methoxypyridin-3-yl)-1,2,3,4-tetrahydronaphthalene-1-carboxamide (0.31 g) was obtained. By the reaction and treatment of this compound in the same manner as in Example 139, N-[(1-benzylpyrazol-4-yl)methyl]-5-hydroxy-N-(6-methoxypyridin-3-yl)-1,2,3,4-tetrahydronaphthalene-1-carboxamide hydrochloride (0.087 g) was obtained.

MS (ESI) m/z: 469[MH]+

1H-NMR (DMSO-d6) δ: 1.36-1.43(1H,m), 1.75-1.79(2H,m), 1.86-2.00(1H,m), 2.43-2.57(2H,m), 3.49-3.55(1H,m), 3.85(3H,s), 4.68(2H,s), 5.28(2H,s), 6.40(1H,d,J=7.8 Hz), 6.60(1H,d,J=7.8 Hz), 6.82-6.88(2H,m), 7.09(2H,d,J=6.5 Hz), 7.25-7.36(4H,m), 7.57-7.62(2H,m), 8.01(1H,d,J=2.4 Hz), 9.20(1H,brs).

Example 385

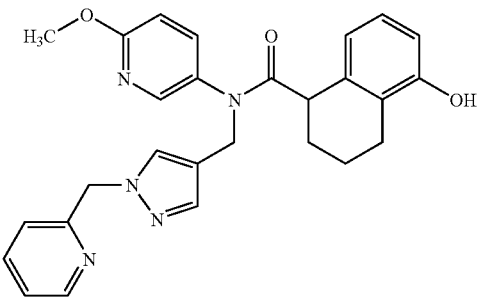

By the reaction and treatment in the same manner as in Example 83 using 5-benzyloxy-N-(6-methoxypyridin-3-yl)-N-[(pyrazol-4-yl)methyl]-1,2,3,4-tetrahydronaphthalene-1-carboxamide hydrochloride (0.94 g) and 2-(chloromethyl)pyridine hydrochloride (0.33 g) as starting materials, 5-benzyloxy-N-(6-methoxypyridin-3-yl)-N-{[1-(2-pyridylmethyl)pyrazol-4-yl]methyl}-1,2,3,4-tetrahydronaphthalene-1-carboxamide (0.28 g) was obtained. By the reaction and treatment of this compound in the same manner as in Example 139, 5-hydroxy-N-(6-methoxypyridin-3-yl)-N-{[1-(2-pyridylmethyl)pyrazol-4-yl]methyl}-1,2,3,4-tetrahydronaphthalene-1-carboxamide dihydrochloride (0.085 g) was obtained.

MS (ESI) m/z: 470[MH]+

1H-NMR (DMSO-d6) δ: 1.35-1.43(1H,m), 1.74-1.80(2H,m), 1.87-1.95(1H,m), 2.43-2.56(2H,m), 3.50-3.55(1H,m), 3.85(3H,s), 4.65-5.00(3H,m), 5.51(2H,m), 6.43(1H,d,J=7.8 Hz), 6.61(1H,d,J=7.8 Hz), 6.83-6.90(2H,m), 7.03(1H,d,J=7.8 Hz), 7.34(1H,s), 7.55(1H,t,J=6.3 Hz), 7.64(1H,dd,J=2.7, 8.7 Hz), 7.73(1H,s), 8.00-8.07(2H,m), 8.66-8.67(1H,m).

Example 386

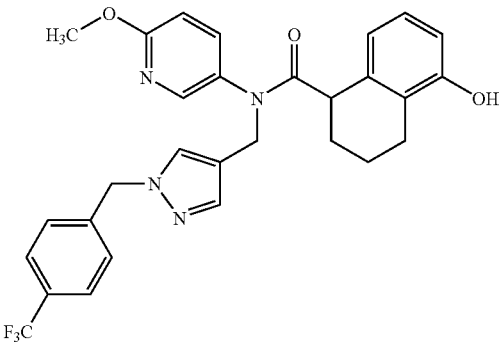

By the reaction and treatment in the same manner as in Example 271 using 5-benzyloxy-N-[(pyrazol-4-yl)methyl]-N-(6-methoxypyridin-3-yl)-1,2,3,4-tetrahydronaphthalene-1-carboxamide hydrochloride (0.936 g) and 4-(trifluoromethyl)benzyl chloride (0.592 mL) as starting materials, 5-benzyloxy-N-(6-methoxypyridin-3-yl)-N-{[1-(4-trifluoromethylbenzyl)pyrazol-4-yl]methyl}-1,2,3,4-tetrahydronaphthalene-1-carboxamide (1.25 g) was obtained. By the reaction and treatment of this compound in the same manner as in Example 133, 5-hydroxy-N-(6-methoxypyridin-3-yl)-N-{[1-(4-trifluoromethylbenzyl)pyrazol-4-yl]methyl}-1,2,3,4-tetrahydronaphthalene-1-carboxamide (0.53 g) was obtained. melting point: 199-200° C.

Example 387

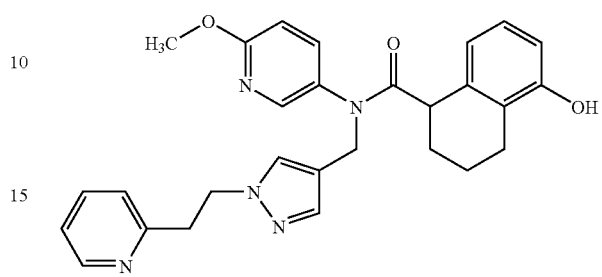

By the reaction and treatment in the same manner as in Example 271 using 5-benzyloxy-N-[(pyrazol-4-yl)methyl]-N-(6-methoxypyridin-3-yl)-1,2,3,4-tetrahydronaphthalene-1-carboxamide hydrochloride (0.70 g) and 2-(2-chloroethyl)pyridine (0.42 g) as starting materials, 5-benzyloxy-N-(6-methoxypyridin-3-yl)-N-({1-[2-(2-pyridyl)ethyl]pyrazol-4-yl}methyl)-1,2,3,4-tetrahydronaphthalene-1-carboxamide (0.45 g) was obtained. By the reaction and treatment of this compound in the same manner as in Example 139, 5-hydroxy-N-(6-methoxypyridin-3-yl)-N-({1-[2-(2-pyridyl)ethyl]pyrazol-4-yl}methyl)-1,2,3,4-tetrahydronaphthalene-1-carboxamide dihydrochloride (0.31 g) was obtained.

MS (ESI) m/z: 484[MH]+

1H-NMR (DMSO-d6) δ: 1.37-1.41(1H,m), 1.71-1.77(2H,m), 1.87-1.92(1H,m), 2.44-2.52(2H,m), 3.47-3.57(3H,m), 3.86(3H,s), 4.54-4.68(4H,m), 6.40(1H,d,J=7.7 Hz), 6.63(1H,d,J=7.7 Hz), 6.86-6.91(2H,m), 7.12(1H,s), 7.53-7.58(2H,m), 7.72(1H,d,J=8.0 Hz), 7.86-7.90(1H,m), 7.94(1H,d,J=2.5 Hz), 8.38-8.41(1H,m), 8.81(1H,d,J=4.9 Hz).

Example 388

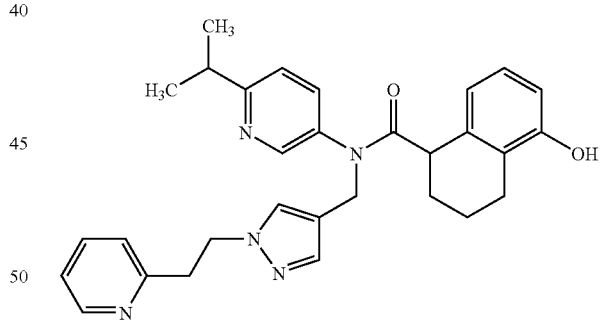

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.83 g) and 2-(2-chloroethyl)pyridine (0.42 g) as starting materials, 5-benzyloxy-N-(6-isopropylpyridin-3-yl)-N-({1-[2-(2-pyridyl)ethyl]pyrazol-4-yl}methyl)-1,2,3,4-tetrahydronaphthalene-1-carboxamide (0.56 g) was obtained. By the reaction and treatment of this compound in the same manner as in Example 139, 5-hydroxy-N-(6-isopropylpyridin-3-yl)-N-({1-[2-(2-pyridyl)ethyl]pyrazol-4-yl}methyl)-1,2,3,4-tetrahydronaphthalene-1-carboxamide dihydrochloride (0.41 g) was obtained.

MS (ESI) m/z: 496[MH]+

1H-NMR (DMSO-d6) δ: 1.32(6H,d,J=6.9 Hz), 1.37-1.46(1H,m), 1.79-1.92(3H,m), 2.44-2.56(2H,m), 3.34(1H,brs), 3.51-3.60(1H,m), 3.58(2H,t,J=6.6 Hz), 4.61(2H,t,J=6.6 Hz), 4.73-4.78(2H,m), 6.46(1H,d,J=7.8 Hz), 6.66(1H,d,J=7.8 Hz), 6.90(1H,t,J=7.8 Hz), 7.20(1H,brs), 7.61(1H,brs), 7.76(2H,d,J=7.7Hz), 7.86-7.92(1H,m), 8.04(1H,brs), 8.46(1H,t,J=7.7 Hz), 8.63(1H,brs), 8.82(1H,d,J=5.0 Hz).

Example 389

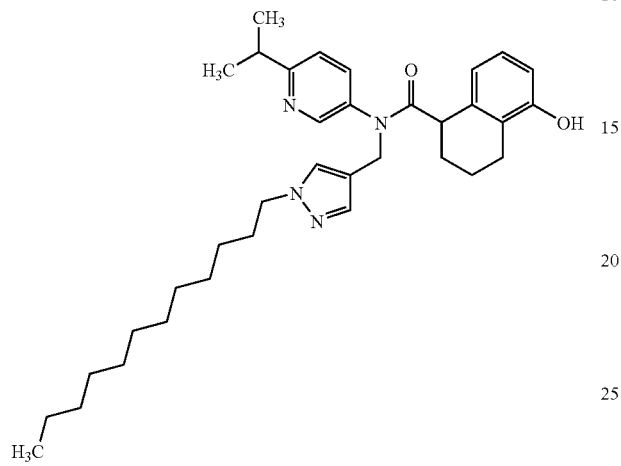

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.96 g) and dodecyl bromide (0.719 mL) as starting materials, 5-benzyloxy-N-[(1-dodecylpyrazol-4-yl)methyl]-N-(6-isopropylpyridin-3-yl)-1,2,3,4-tetrahydronaphthalene-1-carboxamide (1.29 g) was obtained. By the reaction and treatment of this compound in the same manner as in Example 139, N-[(1-dodecylpyrazol-4-yl)methyl]-5-hydroxy-N-(6-isopropylpyridin-3-yl)-1,2,3,4-tetrahydronaphthalene-1-carboxamide hydrochloride (0.54 g) was obtained. MS (ESI) m/z: 559[MH]+

$^1$H-NMR (DMSO-d$_6$) δ: 0.82-0.87(3H,m), 1.12-1.45(19H,m), 1.32(6H,d,J=6.9 Hz), 1.64-1.73(2H,m), 1.82-1.92(3H,m), 2.40-2.56(2H,m), 3.30-3.40(1H,m), 3.55(1H,brs), 4.02(2H,t,J=6.7 Hz), 4.74-4.82(2H,m), 6.48(1H,d,J=7.8 Hz), 6.66(1H,d,J=7.8 Hz), 6.89(1H,t,J=7.8 Hz), 7.28(1H,brs), 7.56(1H,brs), 7.78(1H,brs), 8.07(1H,brs), 8.72(1H,brs).

Example 390

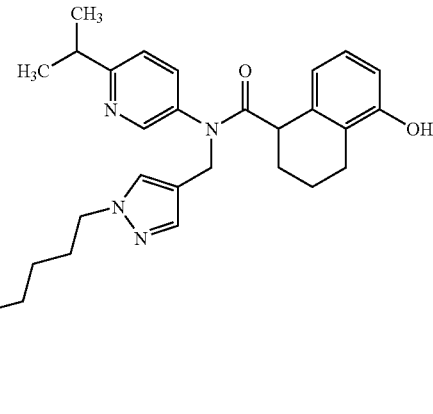

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.96 g) and nonyl bromide (0.57 mL) as starting materials, 5-benzyloxy-N-(6-isopropylpyridin-3-yl)-N-[(1-nonylpyrazol-4-yl)methyl]-1,2,3,4-tetrahydronaphthalene-1-carboxamide (1.20 g) was obtained. By the reaction and treatment of this compound in the same manner as in Example 139, 5-hydroxy-N-(6-isopropylpyridin-3-yl)-N-[(1-nonylpyrazol-4-yl)methyl]-1,2,3,4-tetrahydronaphthalene-1-carboxamide hydrochloride (0.81 g) was obtained.
MS (ESI) m/z: 517[MH]+

$^1$H-NMR (DMSO-d$_6$) δ: 0.85(3H,t,J=6.6 Hz), 1.12-1.45(13H,m), 1.31(6H,d,J=6.9 Hz), 1.68(2H,tt,J=6.9 Hz), 1.81-1.91(3H,m), 2.40-2.55(2H,m), 3.33(1H,brs), 3.54(1H,brs), 4.02(2H,t,J=6.9 Hz), 4.69-4.81(2H,m), 6.47(1H,d,J=7.8 Hz), 6.65(1H,d,J=7.8 Hz), 6.88(1H,t,J=7.8 Hz), 7.27(1H,brs), 7.55(1H,brs), 7.76(1H,brs), 8.05(1H,brs), 8.69(1H,brs).

Example 391

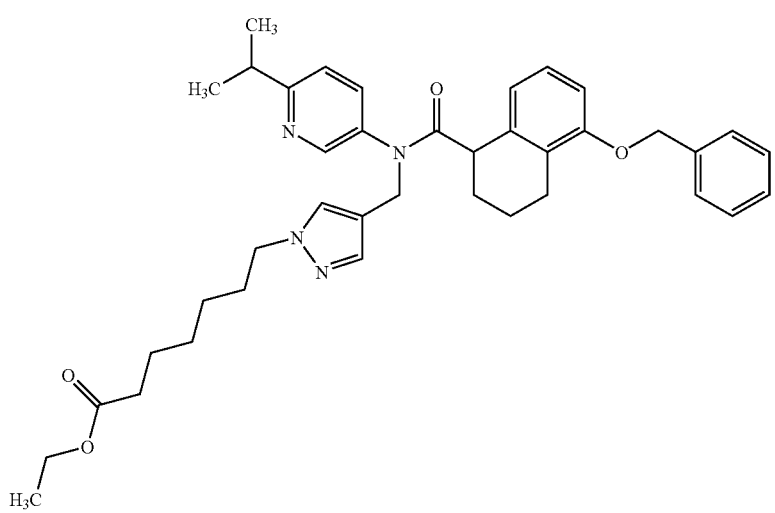

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (3.26 g) and ethyl 7-bromoheptanoate (2.0 mL) as starting materials, ethyl 7-(4-{[N-(5-benzyloxy-1,2,3,4-tetrahydronaphthalen-1-ylcarbonyl)-N-(6-isopropylpyridin-3-yl)amino]methyl}pyrazol-1-yl)heptanoate (4.25 g) was obtained.

MS (ESI) m/z: 637[MH]+

Example 392

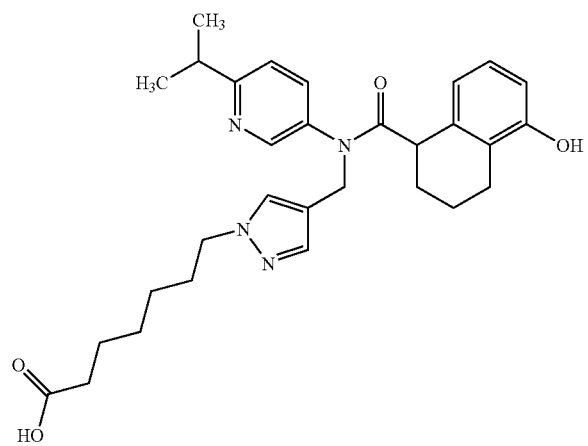

Ethyl 7-(4-{[N-(5-benzyloxy-1,2,3,4-tetrahydronaphthalen-1-ylcarbonyl)-N-(6-isopropylpyridin-3-yl)amino]methyl}pyrazol-1-yl)heptanoate (2.0 g) was dissolved in ethanol (100 mL), and 1 mol/L-aqueous sodium hydroxide solution (6.60 mL) was added. The mixture was stirred at room temperature for 1 hr. To the reaction mixture was added 1 mol/L-hydrochloric acid (6.60 mL), and the mixture was extracted with ethyl acetate. The organic layer was washed with saturated brine and dried over anhydrous magnesium sulfate. The solvent was evaporated, and the residue was purified by silica gel column chromatography to give 7-(4-{[N-(5-benzyloxy-1,2,3,4-tetrahydronaphthalen-1-ylcarbonyl)-N-(6-isopropylpyridin-3-yl)amino]methyl}pyrazol-1-yl)heptanoic acid (1.80 g). By the reaction and treatment of this compound in the same manner as in Example 139, 7-(4-{[N-(5-hydroxy-1,2,3,4-tetrahydronaphthalen-1-ylcarbonyl)-N-(6-isopropylpyridin-3-yl)amino]methyl}pyrazol-1-yl)heptanoic acid hydrochloride (0.84 g) was obtained.

MS (ESI) m/z: 519[MH]+

$^1$H-NMR (DMSO-$d_6$) δ: 1.13-1.51(7H,m), 1.32(6H,d, J=6.8 Hz), 1.64-1.73(2H,m), 1.80-1.99(3H,m), 2.18(2H,t, J=7.2 Hz), 2.40-2.57(2H,m), 3.36(1H,brs), 3.55(1H,brs), 4.02(2H,t,J=6.9 Hz), 4.68-4.81(2H,m), 6.48(1H,d,J=7.8 Hz), 6.65(1H,d,J=7.8 Hz), 6.89(1H,t,J=7.8 Hz), 7.28(1H,brs), 7.56(1H,brs), 7.80(1H,brs), 8.08(1H,brs), 8.74(1H,brs).

Example 393

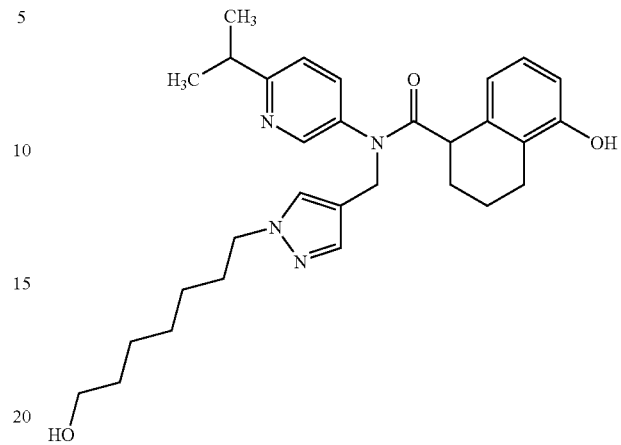

By the reaction and treatment in the same manner as in Example 256 using ethyl 7-(4-{[N-(5-benzyloxy-1,2,3,4-tetrahydronaphthalen-1-ylcarbonyl)-N-(6-isopropylpyridin-3-yl)amino]methyl}pyrazol-1-yl)heptanoate (2.2 g) as a starting material, 5-benzyloxy-N-{[1-(7-hydroxyheptyl)pyrazol-4-yl]methyl}-N-(6-isopropylpyridin-3-yl)-1,2,3,4-tetrahydronaphthalene-1-carboxamide (1.30 g) was obtained. By the reaction and treatment of this compound in the same manner as in Example 139, 5-hydroxy-N-{[1-(7-hydroxyheptyl)pyrazol-4-yl]methyl}-N-(6-isopropylpyridin-3-yl)-1,2,3,4-tetrahydronaphthalene-1-carboxamide hydrochloride (0.48 g) was obtained.

MS (ESI) m/z: 505[MH]+

$^1$H-NMR (DMSO-$d_6$) δ: 1.04-1.40(15H,m), 1.64-1.73(2H,m), 1.85-1.91(3H,m), 2.50-2.52(2H,m), 3.36(2H,t,J=6.4 Hz), 3.36-3.40(1H,m), 3.56(1H,brs), 4.02(2H,t,J=6.4 Hz), 4.79(2H,brs), 6.48(1H,d,J=7.8 Hz), 6.66(1H,d,J=7.8 Hz), 6.89(1H,t,J=7.8 Hz), 7.29(1H,brs), 7.57(1H,brs), 7.85(1H,brs), 8.13(1H,brs), 8.77(1H,brs).

Example 394

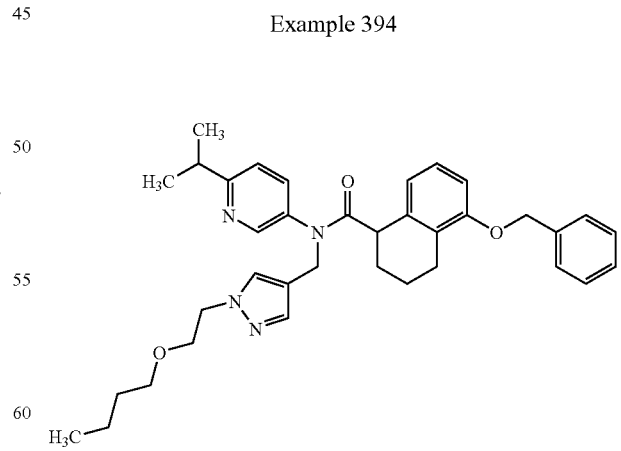

To a solution of ethylene glycol monobutyl ether (1 mL) and triethylamine (1.6 mL) in dichloromethane (20 mL) was added methanesulfonyl chloride (0.88 mL) under ice-cooling, and the mixture was stirred at room temperature for one day. The reaction mixture was partitioned between water and chloroform, washed with saturated brine and dried over magnesium sulfate. The solvent was evaporated, and the obtained residue and 5-benzyloxy-N-(6-isopropylpyridin-3-yl)-N-[(pyrazol-4-yl)methyl]-1,2,3,4-tetrahydronaphthalene-1-carboxamide hydrochloride (1.0 g) were reacted and treated in the same manner as in Example 83 to give 5-benzyloxy-N-{[1-(2-butoxyethyl)pyrazol-4-yl]methyl}-N-(6-isopropylpyridin-3-yl)-1,2,3,4-tetrahydronaphthalene-1-carboxamide (0.58 g).

MS (ESI) m/z: 581[MH]$^+$

Example 395

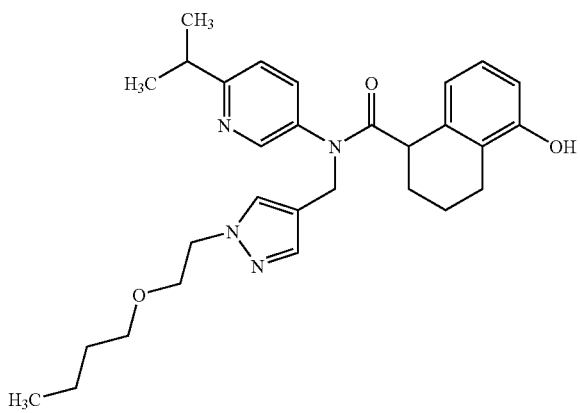

By the reaction and treatment in the same manner as in Example 139 using 5-benzyloxy-N-{[1-(2-butoxyethyl) pyrazol-4-yl]methyl}-N-(6-isopropylpyridin-3-yl)-1,2,3,4-tetrahydronaphthalene-1-carboxamide (0.58 g) as a starting material, N-{[1-(2-butoxyethyl)pyrazol-4-yl]methyl}-5-hydroxy-N-(6-isopropylpyridin-3-yl)-1,2,3,4-tetrahydronaphthalene-1-carboxamide hydrochloride (0.25 g) was obtained.

MS (ESI) m/z: 491[MH]$^+$ $^1$H-NMR (DMSO-d$_6$) δ: 0.82(3H,t,J=7.3 Hz), 1.15-1.24 (2H,m), 1.29(6H,d,J=6.6 Hz), 1.36-1.43(3H,m), 1.81-1.91 (3H,m), 2.41-2.51(2H,m), 3.21-3.32(1H,m), 3.32(2H,t,J=6.6 Hz), 3.53(1H,brs), 3.65(2H,t,J=5.4 Hz), 4.18(2H,t,J=5.4 Hz), 4.70-4.77(2H,m), 6.47(1H,d,J=7.8 Hz), 6.63(1H,d,J=7.8 Hz), 6.89(1H,t,J=7.8 Hz), 7.27(1H,brs), 7.55(1H,brs), 7.68 (1H,brs), 7.96(1H,brs), 8.63(1H,brs).

Example 396

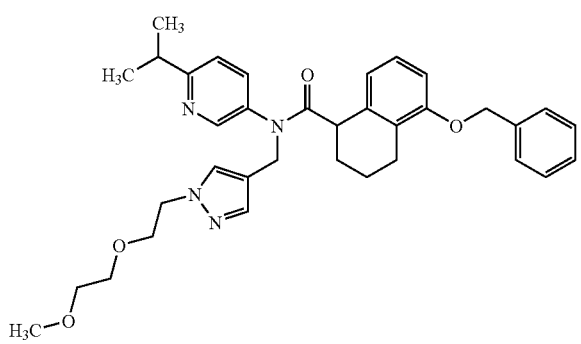

By the reaction and treatment in the same manner as in Example 394 using diethylene glycol monomethyl ether (1 mL) and 5-benzyloxy-N-(6-isopropylpyridin-3-yl)-N-[(pyrazol-4-yl)methyl]-1,2,3,4-tetrahydronaphthalene-1-carboxamide (1.0 g) as starting materials, 5-benzyloxy-N-(6-isopropylpyridin-3-yl)-N-({1-[2-(2-methoxyethoxy)ethyl] pyrazol-4-yl}methyl)-1,2,3,4-tetrahydronaphthalene-1-carboxamide (0.76 g) was obtained.

MS (ESI) m/z: 583[MH]+

Example 397

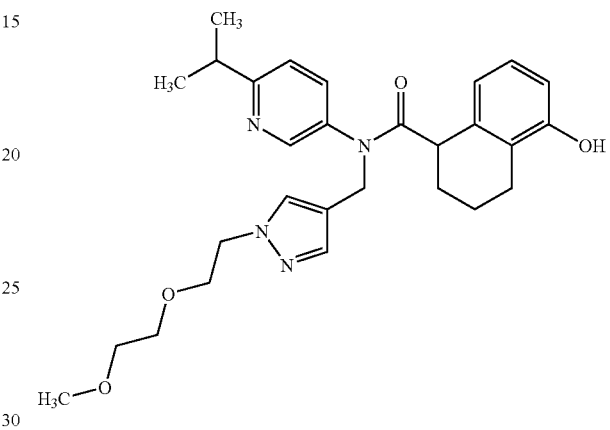

By the reaction and treatment in the same manner as in Example 139 using 5-benzyloxy-N-(6-isopropylpyridin-3-yl)-N-({1-[2-(2-methoxyethoxy)ethyl]pyrazol-4-yl} methyl)-1,2,3,4-tetrahydronaphthalene-1-carboxamide (0.76 g) as a starting material, 5-hydroxy-N-(6-isopropylpyridin-3-yl)-N-({1-[2-(2-methoxyethoxy)ethyl]pyrazol-4-yl}methyl)-1,2,3,4-tetrahydronaphthalene-1-carboxamide hydrochloride (0.20 g) was obtained.

MS (ESI) m/z: 493[MH]$^+$ $^1$H-NMR (DMSO-d$_6$) δ: 1.31(6H,d,J=6.9 Hz), 1.40(1H, m), 1.81-1.91(3H,m), 2.51(2H,m), 3.19(3H,s), 3.28-3.32 (1H,m), 3.36-3.39(2H,m), 3.44-3.47(2H,m), 3.48-3.52(1H, m), 3.70(2H,t,J=5.4 Hz), 4.19(2H,t,J=5.4 Hz), 4.71-4.78(2H, m), 6.49(1H,d,J=7.8 Hz), 6.64(1H,d,J=7.8 Hz), 6.89(1H,t, J=7.8 Hz), 7.28(1H,brs), 7.58(1H,brs), 7.76(1H,brs), 8.04 (1H,brs), 8.70(1H,brs).

Example 398

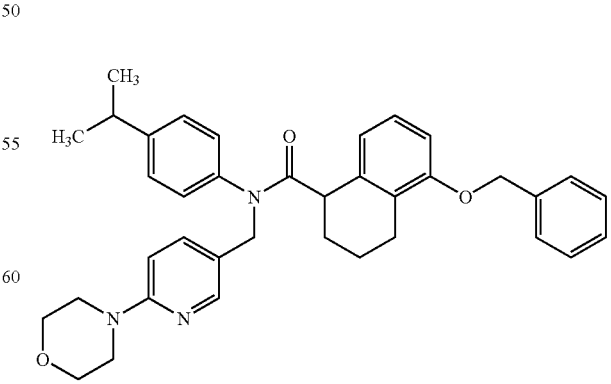

By the reaction and treatment in the same manner as in Example 12 using 5-benzyloxy-1,2,3,4-tetrahydronaphthalene-1-carboxylic acid (0.56 g) and (4-isopropylphenyl)[(6-morpholinopyridin-3-yl)methyl]amine (0.62 g) as starting materials, 5-benzyloxy-N-(4-isopropylphenyl)-N-[(6-morpholinopyridin-3-yl)methyl]-1,2,3,4-tetrahydronaphthalene-1-carboxamide (0.90 g) was obtained.

$^1$H-NMR (CDCl$_3$) δ: 1.21(6H,d,J=6.9 Hz), 1.31-1.51(1H, m), 1.73-2.09(3H,m), 2.49-2.70(2H,m), 2.90(1H,sept,J=6.9 Hz), 3.49(4H,t,J=5.0 Hz), 3.68-3.79(1H,m), 3.83(4H,t,J=4.8 Hz), 4.73(1H,d,J=14.1 Hz), 4.86(1H,d,J=14.1 Hz), 5.03(2H, s), 6.55-6.65(2H,m), 6.71(1H,d,J=8.1 Hz), 6.97-7.10(3H,m), 7.17-7.45(7H,m), 7.69(1H,dd,J=2.1, 8.7 Hz), 7.93(1H,d, J=2.1 Hz).

Example 399

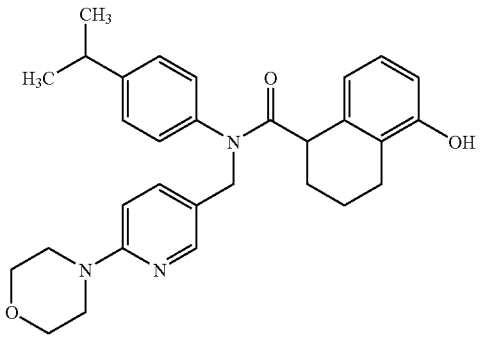

By the reaction and treatment in the same manner as in Example 105 using 5-benzyloxy-N-(4-isopropylphenyl)-N-[(6-morpholinopyridin-3-yl)methyl]-1,2,3,4-tetrahydronaphthalene-1-carboxamide (0.88 g) as a starting material, 5-hydroxy-N-(4-isopropylphenyl)-N-[(6-morpholinopyridin-3-yl)methyl]-1,2,3,4-tetrahydronaphthalene-1-carboxamide (0.51 g) was obtained.

$^1$H-NMR (CDCl$_3$) δ: 1.21(6H,d,J=6.9 Hz), 1.32-1.51(1H, m), 1.73-2.08(3H,m), 2.49-2.69(2H,m), 2.88(1H,sept,J=6.9 Hz), 3.36-3.58(4H,m), 3.69-3.90(5H,m), 4.78(1H,d,J=14.2 Hz), 4.85(1H,d,J=14.2 Hz), 6.34(1H,d,J=7.9 Hz), 6.46(1H,d, J=7.7 Hz), 6.62(1H,d,J=8.8 Hz), 6.78(1H,t,J=7.8 Hz), 7.02 (2H,d,J=7.9 Hz), 7.20(2H,d,J=8.3 Hz), 7.59(1H,dd,J=2.1, 8.7 Hz), 7.93(1H,d,J=2.0 Hz), 7.90-8.38(1H,brs).

Example 400

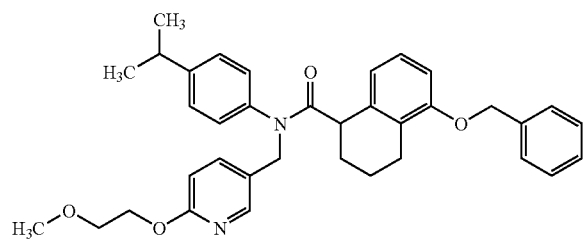

By the reaction and treatment in the same manner as in Example 12 using 5-benzyloxy-1,2,3,4-tetrahydronaphthalene-1-carboxylic acid (0.56 g) and (4-isopropylphenyl)([6-(2-methoxyethoxy)pyridin-3-yl]methyl)amine (0.60 g) as starting materials, 5-benzyloxy-N-(4-isopropylphenyl)-N-([6-(2-methoxyethoxy)pyridin-3-yl]methyl)-1,2,3,4-tetrahydronaphthalene-1-carboxamide (0.52 g) was obtained.

$^1$H-NMR (CDCl$_3$) δ: 1.23(6H,d,J=6.9 Hz), 1.40-1.59(1H, m), 1.77-2.10(3H,m), 2.67-2.79(2H,m), 2.90(1H,sept,J=6.9 Hz), 3.45(3H,s), 3.68-3.81(3H,m), 4.39-4.50(2H,m), 4.78 (1H,d,J=14.1 Hz), 4.89(1H,d,J=14.1 Hz), 5.03(2H,s), 6.61 (1H,d,J=7.8 Hz), 6.72(1H,d,J=8.1 Hz), 6.77(1H,d,J=8.7 Hz), 6.98(2H,d,J=8.4 Hz), 7.06(1H,t,J=8.1 Hz), 7.17-7.44(7H,m), 7.61(1H,dd,J=2.4, 8.4 Hz), 7.86(1H,d,J=2.4 Hz).

Example 401

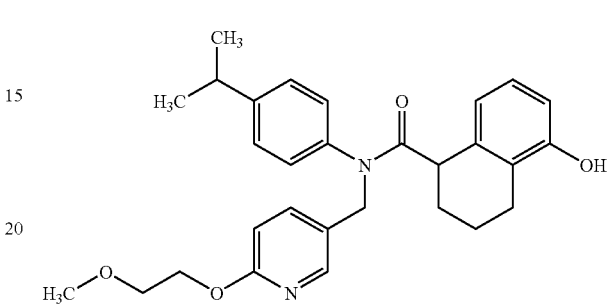

By the reaction and treatment in the same manner as in Example 17 using 5-benzyloxy-N-(4-isopropylphenyl)-N-{[6-(2-methoxyethoxy)pyridin-3-yl]methyl}-1,2,3,4-tetrahydronaphthalene-1-carboxamide (0.88 g) as a starting material, 5-hydroxy-N-(4-isopropylphenyl)-N-{[6-(2-methoxyethoxy)pyridin-3-yl]methyl}-1,2,3,4-tetrahydronaphthalene-1-carboxamide (0.35 g) was obtained. melting point: 153° C.

Example 402

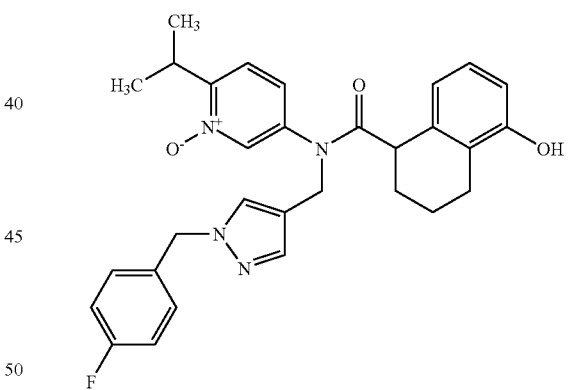

To a solution of N-({1-[(4-fluorophenyl)methyl]pyrazol-4-yl}methyl)-5-hydroxy-N-(6-isopropylpyridin-3-yl)-1,2,3,4-tetrahydronaphthalene-1-carboxamide (0.55 g) in chloroform (10 mL) was added m-chloroperbenzoic acid (0.29 g), and the mixture was stirred at room temperature for 2 hr. The reaction mixture was partitioned between water and chloroform. The organic layer was washed with saturated brine and dried over anhydrous magnesium sulfate. The solvent was evaporated and the residue was purified by silica gel column chromatography to give N-({1-[(4-fluorophenyl)methyl]pyrazol-4-yl}methyl)-5-hydroxy-N-(6-isopropyl-1-oxidopyridin-3-yl)-1,2,3,4-tetrahydronaphthalene-1-carboxamide hydrochloride (0.13 g).

MS (ESI) m/z: 515[MH]$^+$ $^1$H-NMR (CDCl$_3$) δ: 1.31(6H,d,J=6.9 Hz), 1.38-1.57(1H, m), 1.78-2.05(3H,m), 2.48-2.67(2H,m), 3.57-3.80(2H,m), 4.61(1H,d,J=14.7 Hz), 4.82(1H,d,J=15.0 Hz), 5.23(2H,s), 6.33(1H,d,J=7.8 Hz), 6.49(1H,d,J=7.8 Hz), 6.80(1H,t, J=8.0Hz), 6.95-7.10(3H,m), 7.13-7.29(4H,m), 7.42(2H,d, J=2.1 Hz), 8.15-8.30(1H,brs).

Example 403

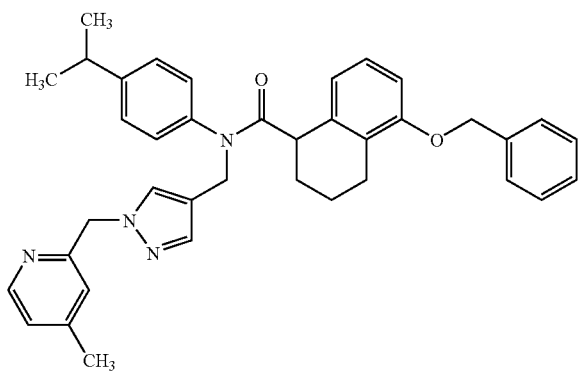

By the reaction and treatment in the same manner as in Example 271 using 5-benzyloxy-N-(4-isopropylphenyl)-N-[(pyrazol-4-yl)methyl]-1,2,3,4-tetrahydronaphthalene-1-carboxamide (0.62 g) and 2-(chloromethyl)-4-methylpyridine hydrochloride (0.46 g) as starting materials, 5-benzyloxy-N-(4-isopropylphenyl)-N-({1-[(4-methylpyridin-2-yl)methyl]pyrazol-4-yl}methyl)-1,2,3,4-tetrahydronaphthalene-1-carboxamide (0.53 g) was obtained.

$^1$H-NMR (CDCl$_3$) δ: 1.24(6H,d,J=6.9 Hz), 1.35-1.53(1H, m), 1.75-2.08(3H,m), 2.30(3H,s), 2.60-2.80(2H,m), 2.91 (1H,sept,J=6.9 Hz), 3.65-3.77(1H,m), 4.65(1H,d,J=14.4 Hz), 4.85(1H,d,J=14.4 Hz), 5.02(2H,s), 5.37(2H,s), 6.58(1H,d, J=7.8 Hz), 6.70(1H,d,J=8.1 Hz), 6.76(1H,s), 6.92-7.09(4H, m), 7.17-7.51(9H,m), 8.41(1H,d,J=4.8 Hz).

Example 404

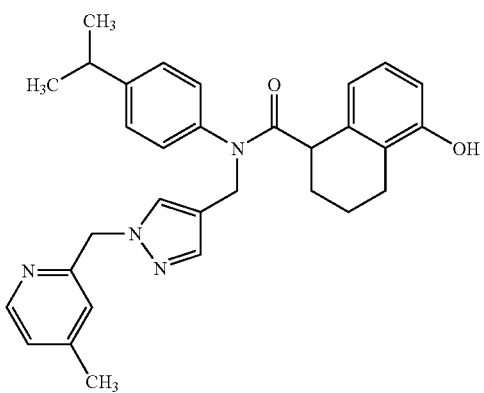

By the reaction and treatment in the same manner as in Example 133 using 5-benzyloxy-N-(4-isopropylphenyl)-N-({1-[(4-methylpyridin-2-yl)methyl]pyrazol-4-yl}methyl)-1,2,3,4-tetrahydronaphthalene-1-carboxamide (0.53 g) as a starting material, 5-hydroxy-N-(4-isopropylphenyl)-N-({1-[(4-methylpyridin-2-yl)methyl]pyrazol-4-yl}methyl)-1,2,3,4-tetrahydronaphthalene-1-carboxamide (0.50 g) was obtained.

$^1$H-NMR (CDCl$_3$) δ: 1.24(6H,d,J=6.9 Hz), 1.35-2.08(4H, m), 2.30(3H,s), 2.49-2.68(2H,m), 2.91(1H,sept,J=6.9 Hz), 3.64-3.76(1H,m), 4.68(1H,d,J=14.4 Hz), 4.83(1H,d,J=14.4 Hz), 5.03-5.18(1H,brs), 5.38(2H,s), 6.45(2H,t,J=7.8 Hz), 6.73-6.86(2H,m), 6.98-7.12(3H,m), 7.18-7.32(2H,m), 7.46 (1H,s), 7.50(1H,s), 8.42(1H,d,J=5.1 Hz).

Example 405

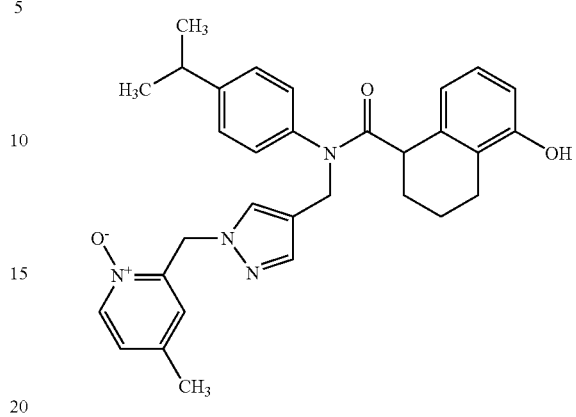

By the reaction and treatment in the same manner as in Example 402 using 5-hydroxy-N-(4-isopropylphenyl)-N-({1-[4-methylpyridin-2-yl]methyl}pyrazol-4-yl)methyl)-1,2,3,4-tetrahydronaphthalene-1-carboxamide (0.50 g) as a starting material, 5-hydroxy-N-(4-isopropylphenyl)-N-({1-[(4-methyl-1-oxidopyridin-2-yl)methyl]pyrazol-4-yl}methyl)-1,2,3,4-tetrahydronaphthalene-1-carboxamide (0.16 g) was obtained.

$^1$H-NMR (CDCl$_3$) δ: 1.24(6H,d,J=6.9 Hz), 1.35-1.52(1H, m), 1.76-2.07(3H,m), 2.27(3H,s), 2.52-2.67(2H,m), 2.92 (1H,sept,J=6.9 Hz), 3.66-3.80(1H,m), 4.69(1H,d,J=14.5 Hz), 4.88(1H,d,J=14.5 Hz), 5.56(2H,s), 6.43(2H,d,J=7.9 Hz), 6.51(1H,d,J=1.6 Hz), 6.78(1H,t,J=7.8 Hz), 7.00-7.17(3H,m), 7.20-7.31(2H,m), 7.54(1H,s), 7.58(1H,s), 8.18(1H,d,J=6.6 Hz).

Example 406

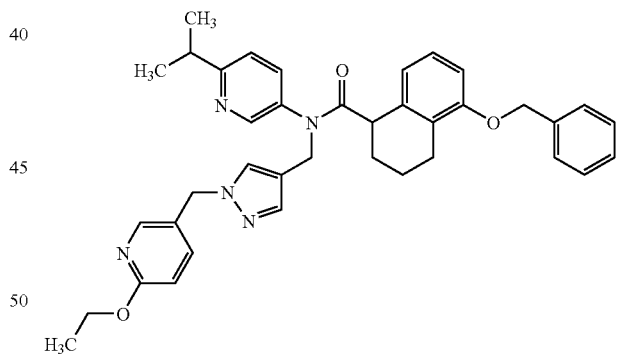

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 5-chloromethyl-2-ethoxypyridine (0.51 g) as starting materials, 5-benzyloxy-N-({1-[(6-ethoxypyridin-3-yl)methyl]pyrazol-4-yl}methyl)-N-(6-isopropylpyridin-3-yl)-1,2,3,4-tetrahydronaphthalene-1-carboxamide (0.67 g) was obtained.

$^1$H-NMR (CDCl$_3$) δ: 1.30(6H,d,J=6.9 Hz), 1.38(3H,t, J=7.1 Hz), 1.39-1.57(1H,m), 1.78-2.08(3H,m), 2.60-2.80 (2H,m), 3.08(1H,sept,J=6.9 Hz), 3.57-3.67(1H,m), 4.35(2H, q,J=7.1 Hz), 4.59(1H,d,J=14.4 Hz), 4.83(1H,d,J=14.4 Hz), 5.03(2H,s), 5.17(2H,s), 6.49(1H,d,J=7.8 Hz), 6.65-6.77(2H, m), 7.01(1H,t,J=8.0 Hz), 7.17(1H,d,J=8.4 Hz), 7.22-7.48 (9H,m), 8.04(1H,d,J=2.4 Hz), 8.36(1H,d,J=2.4 Hz).

Example 407

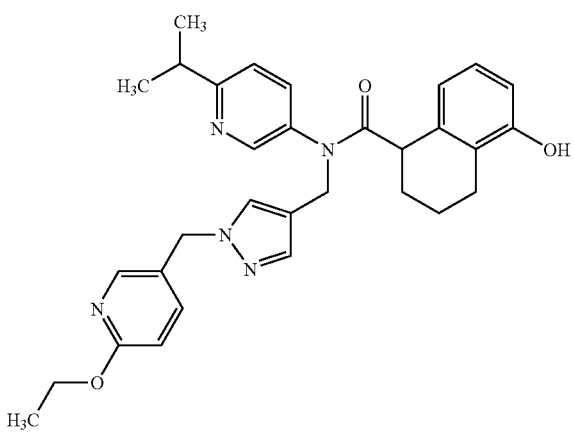

By the reaction and treatment in the same manner as in Example 101 using 5-benzyloxy-N-({1-[(6-ethoxypyridin-3-yl)methyl]pyrazol-4-yl}methyl)-N-(6-isopropylpyridin-3-yl)-1,2,3,4-tetrahydronaphthalene-1-carboxamide (0.66 g) as a starting material, N-({1-[(6-ethoxypyridin-3-yl)methyl]pyrazol-4-yl}methyl)-5-hydroxy-N-(6-isopropylpyridin-3-yl)-1,2,3,4-tetrahydronaphthalene-1-carboxamide dihydrochloride (0.54 g) was obtained.

MS (ESI) m/z: 526[MH]$^+$

Example 408

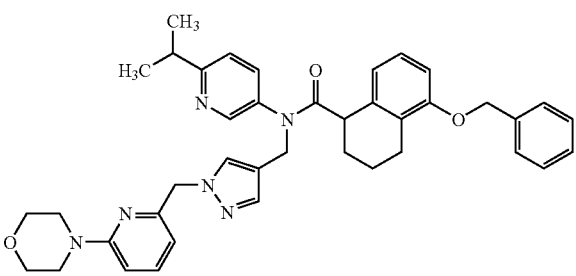

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.65 g) and 6-chloromethyl-2-morpholinopyridine (0.29 g) as starting materials, 5-benzyloxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide (0.44 g) was obtained.

$^1$H-NMR (CDCl$_3$) δ: 1.30(6H,d,J=6.9 Hz), 1.39-1.57(1H,m), 1.77-2.08(3H,m), 2.60-2.81(2H,m), 3.09(1H,sept,J=6.9 Hz), 3.49(4H,t,J=4.8 Hz), 3.58-3.69(1H,m), 3.80(4H,t,J=5.0 Hz), 4.66(1H,d,J=14.4 Hz), 4.85(1H,d,J=14.4 Hz), 5.03(2H,s), 5.23(2H,s), 6.28(1H,d,J=7.2 Hz), 6.46-6.58(2H,m), 6.71(1H,d,J=8.1 Hz), 7.00(1H,t,J=7.8 Hz), 7.18(1H,d,J=8.4 Hz), 7.25-7.51(9H,m), 8.39(1H,d,J=2.4 Hz).

Example 409

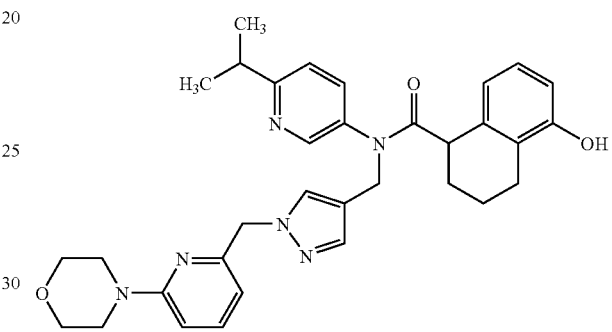

By the reaction and treatment in the same manner as in Example 101 using 5-benzyloxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide (0.44 g) as a starting material, 5-hydroxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide dihydrochloride (0.30 g) was obtained. MS (ESI) m/z: 567[MH]$^+$ $^1$H-NMR (DMSO-d$_6$) δ: 1.30(6H,d,J=6.9 Hz), 1.34-1.52(1H,m), 1.68-1.93(3H,m), 2.34-2.58(2H,m), 3.20-3.70(10H,m), 5.30(2H,s), 6.13(1H,d,J=7.2 Hz), 6.47(1H,d,J=7.8 Hz), 6.64(1H,d,J=7.8 Hz), 6.78-6.90(2H,m), 7.27-7.44(1H,m), 7.61(1H,t,J=7.8 Hz), 7.67-7.83(2H,m), 7.97-8.17(1H,m), 8.61-8.80(1H,m).

Example 410

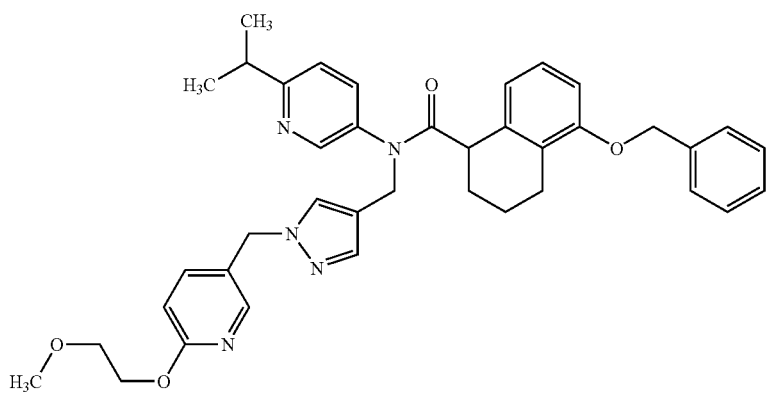

By the reaction and treatment in the same manner as in Example, 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 5-chloromethyl-2-(2-methoxyethoxy)pyridine (0.61 g) as starting materials, 5-benzyloxy-N-(6-isopropylpyridin-3-yl)-N-[(1-{[6-(2-methoxyethoxy)pyridin-3-yl]methyl}pyrazol-4-yl)methyl]-1,2,3,4-tetrahydronaphthalene-1-carboxamide (0.77 g) was obtained.

¹H-NMR (CDCl₃) δ: 1.31(6H,d,J=6.9 Hz), 1.40-1.57(1H, m), 1.75-2.05(3H,m), 2.60-2.80(2H,m), 3.08(1H,sept,J=6.9 Hz), 3.39-3.49(3H,m), 3.55-3.65(1H,m), 3.68-3.78(2H,m), 4.42-4.51(2H,m), 4.59(1H,d,J=14.7 Hz), 4.83(1H,d,J=14.4 Hz), 5.03(2H,s), 5.17(2H,s), 6.49(1H,d,J=7.8 Hz), 6.72(1H, d,J=8.1 Hz), 6.80(1H,t,J=9.3 Hz), 7.01(1H,t,J=7.8 Hz), 7.17 (1H,d,J=8.4 Hz), 7.24-7.48(9H,m), 8.03(1H,d,J=2.4 Hz), 8.37(1H,d,J=2.4 Hz).

Example 411

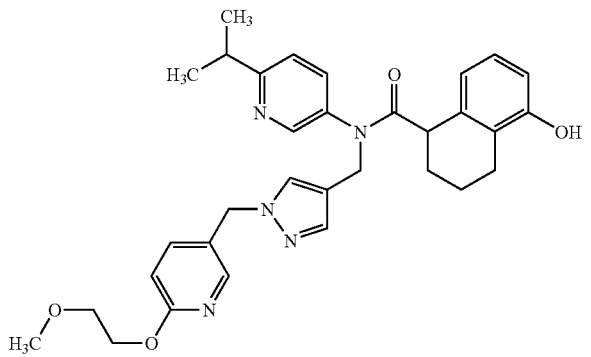

By the reaction and treatment in the same manner as in Example 101 using 5-benzyloxy-N-(6-isopropylpyridin-3-yl)-N-[(1-{[6-(2-methoxyethoxy)pyridin-3-yl]methyl}pyrazol-4-yl)methyl]-1,2,3,4-tetrahydronaphthalene-1-carboxamide (0.76 g) as a starting material, 5-hydroxy-N-(6-isopropylpyridin-3-yl)-N-[(1-{[6-(2-methoxyethoxy)pyridin-3-yl]methyl}pyrazol-4-yl)methyl]-1,2,3,4-tetrahydronaphthalene-1-carboxamide dihydrochloride (0.55 g) was obtained.

MS (ESI) m/z: 556[MH]⁺

¹H-NMR (DMSO-d₆) δ: 1.31(6H,d,J=6.9 Hz), 1.34-1.53 (1H,m), 1.68-1.93(3H,m), 2.35-2.60(2H,m), 3.29-3.67(7H, m), 4.29-4.39(2H,m), 4.63-4.90(2H,m), 5.22(2H,s), 6.45 (1H,d,J=7.6 Hz), 6.64(1H,d,J=7.8 Hz), 6.77-6.90(2H,m), 7.22-7.38(1H,m), 7.55(1H,dd,J=2.4, 8.5 Hz), 7.60-7.89(2H, m), 8.00-8.16(2H,m), 8.67-8.82(1H,m).

Example 412

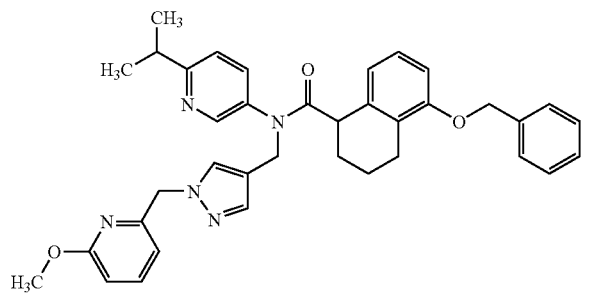

By the reaction and treatment in the same manner as in Example 271 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and 6-chloromethyl-2-methoxypyridine (0.47 g) as starting materials, 5-benzyloxy-N-(6-isopropylpyridin-3-yl)-N-({1-[(6-methoxypyridin-2-yl)methyl]pyrazol-4-yl}methyl)-1,2,3,4-tetrahydronaphthalene-1-carboxamide (0.44 g) was obtained.

¹H-NMR (CDCl₃) δ: 1.31(6H,d,J=6.9 Hz), 1.40-1.60(1H, m), 1.77-2.08(3H,m), 2.61-2.82(2H,m), 3.09(1H,sept,J=6.9 Hz), 3.60-3.70(1H,m), 3.88(3H,s), 4.66(1H,d,J=14.7 Hz), 4.86(1H,d,J=14.4 Hz), 5.03(2H,s), 5.28(2H,s), 6.53(2H,t, J=6.6 Hz), 6.64(1H,d,J=8.4 Hz), 6.71(1H,d,J=8.1 Hz), 7.00 (1H,t,J=7.8 Hz), 7.18(1H,d,J=8.4 Hz), 7.25-7.56(9H,m), 8.39(1H,d,J=2.1 Hz).

Example 413

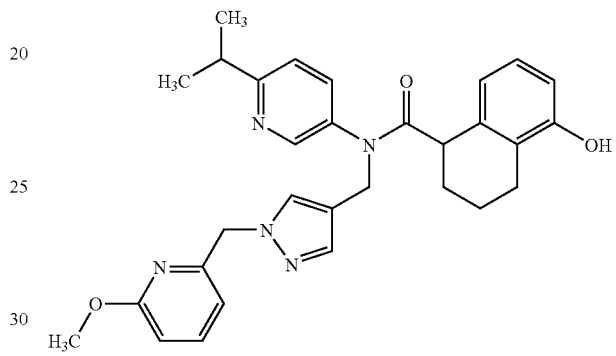

By the reaction and treatment in the same manner as in Example 101 using 5-benzyloxy-N-(6-isopropylpyridin-3-yl)-N-({1-[(6-methoxypyridin-2-yl)methyl]pyrazol-4-yl}methyl)-1,2,3,4-tetrahydronaphthalene-1-carboxamide (0.43 g) as a starting material, 5-hydroxy-N-(6-isopropylpyridin-3-yl)-N-(({1-[(6-methoxypyridin-2-yl)methyl]pyrazol-4-yl}methyl)-1,2,3,4-tetrahydronaphthalene-1-carboxamide dihydrochloride (0.34 g) was obtained. MS (ESI) m/z: 512[MH]+

¹H-NMR (DMSO-d₆) δ: 1.27(6H,d,J=6.9 Hz), 1.31-1.53 (1H,m), 1.69-1.99(3H,m), 2.34-2.60(2H,m), 3.13-3.32(1H, m), 3.43-3.62(1H,m), 3.80(3H,s), 4.65-4.90(2H,m), 5.29(2H,s), 6.39(1H,d,J=7.2 Hz), 6.46(1H,d,J=7.8 Hz), 6.62 (1H,d,J=7.8 Hz), 6.73(1H,d,J=8.4 Hz), 6.86(1H,t,J=7.8 Hz), 7.25-7.44(1H,m), 7.55-8.05(4H,m), 8.49-8.73(1H,m).

Example 414

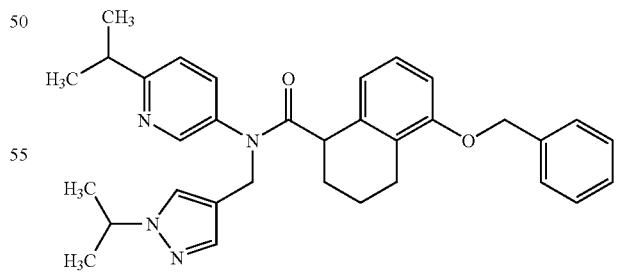

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide hydrochloride (0.78 g) and isopropyl iodide (0.30 mL) as starting materials, 5-benzyloxy-N-[(1-isopropylpyrazol-4-yl)methyl]-N-(6-isopropylpyridin-3-yl)-1,2,3,4-tetrahydronaphthalene-1-carboxamide (0.68 g) was obtained.

¹H-NMR (CDCl₃) δ: 1.31(6H,d,J=6.9 Hz), 1.39-1.58(7H, m), 1.78-2.07(3H,m), 2.62-2.83(2H,m), 3.09(1H,sept,J=6.9 Hz), 3.58-3.68(1H,m), 4.47(1H,sept,J=6.6 Hz), 4.58(1H,d, J=14.7 Hz), 4.90(1H,d,J=14.4 Hz), 5.03(2H,s), 6.52(1H,d, J=7.8 Hz), 6.72(1H,d,J=8.1 Hz), 7.02(1H,t,J=7.8 Hz), 7.19 (1H,d,J=8.1 Hz), 7.25-7.47(8H,m), 8.38(1H,d,J=2.4 Hz).

Example 415

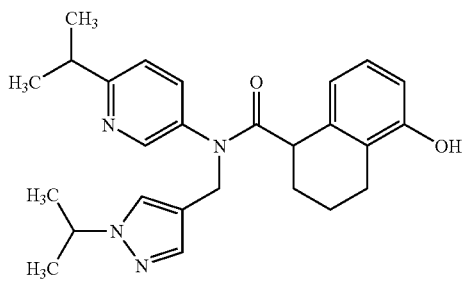

By the reaction and treatment in the same manner as in Example 101 using 5-benzyloxy-N-[(1-isopropylpyrazol-4-yl)methyl]-N-(6-isopropylpyridin-3-yl)-1,2,3,4-tetrahydronaphthalene-1-carboxamide (0.67 g) as a starting material, 5-hydroxy-N-[(1-isopropylpyrazol-4-yl)methyl]-N-(6-isopropylpyridin-3-yl)-1,2,3,4-tetrahydronaphthalene-1-carboxamide (0.52 g) was obtained.

MS (ESI) m/z: 433[MH]⁺

¹H-NMR (DMSO-d₆) δ: 1.22-1.60(13H,m), 1.72-1.98 (3H,m), 2.36-2.64(2H,m), 3.21-3.63(2H,m), 4.30-5.07(3H, m), 6.46(1H,d,J=7.6 Hz), 6.63(1H,d,J=7.8 Hz), 6.88(1H,t, J=7.8 Hz), 7.20-7.37(1H,m), 7.47-7.63(1H,m), 7.68-7.87 (1H,m), 7.97-8.13(1H,m), 8.59-8.80(1H,m).

Example 416

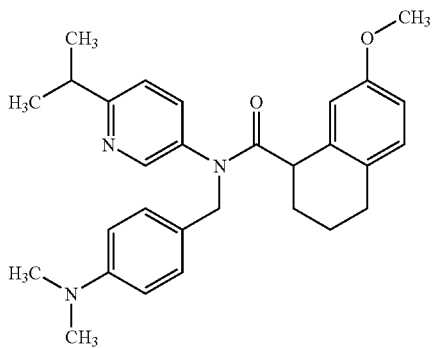

By the reaction and treatment in the same manner as in Example 12 using 7-methoxy-1,2,3,4-tetrahydronaphthalene-1-carboxylic acid (0.41 g) and [(4-dimethylaminophenyl)methyl](6-isopropylpyridin-3-yl)amine (0.54 g) as starting materials, N-[(4-dimethylaminophenyl)methyl]-N-(6-isopropylpyridin-3-yl)-7-methoxy-1,2,3,4-tetrahydronaphthalene-1-carboxamide (0.13 g) was obtained.

MS (ESI) m/z: 458[MH]⁺

¹H-NMR (CDCl₃) δ: 1.29(6H,d,J=6.9 Hz), 1.40-1.65(1H, m), 1.80-2.10(3H,m), 2.50-2.85(2H,m), 2.93(6H,s), 3.00-3.15(1H,m), 3.55-3.65(1H,m), 3.69(3H,s), 4.60(1H,d,J=13.8 Hz), 5.07(1H,d,J=13.8 Hz), 6.48(1H,d,J=2.4 Hz), 6.55-6.75 (3H,m), 6.90-7.30(5H,m), 8.29(1H,d,J=2.4 Hz).

Example 417

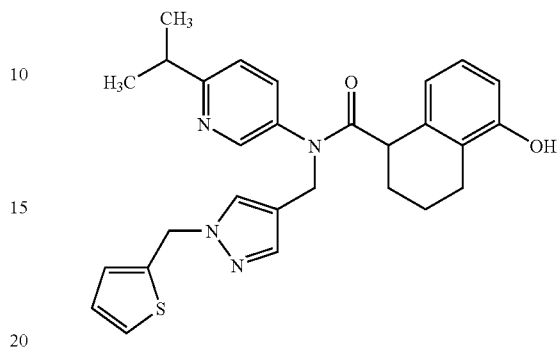

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide (0.96 g) and 2-(chloromethyl)thiophene (0.25 g) as a starting material, 5-benzyloxy-N-(6-isopropylpyridin-3-yl)-N-{[1-(2-thienylmethyl)pyrazol-4-yl]methyl}-1,2,3,4-tetrahydronaphthalene-1-carboxamide (0.95 g) was obtained. By the reaction and treatment of this compound in the same manner as in Example 133, 5-hydroxy-N-(6-isopropylpyridin-3-yl)-N-{[1-(2-thienylmethyl)pyrazol-4-yl]methyl}-1,2,3,4-tetrahydronaphthalene-1-carboxamide (0.41 g) was obtained. melting point: 125-129° C.

Example 418

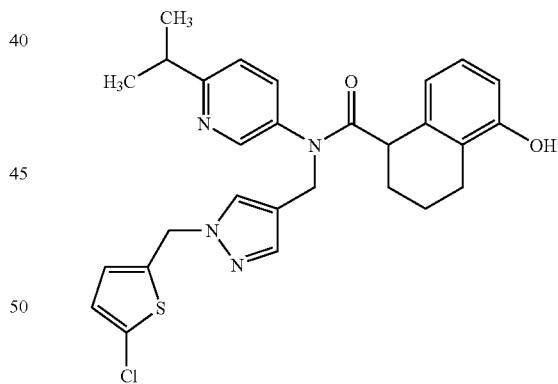

By the reaction and treatment in the same manner as in Example 83 using 5-benzyloxy-N-(6-isopropylpyridin-3-yl)-N-[(pyrazol-4-yl)methyl]-1,2,3,4-tetrahydronaphthalene-1-carboxamide (1.44 g) and 2-chloro-5-(chloromethyl) thiophene (0.79 g) as starting materials, 5-benzyloxy-N-({1-[(5-chlorothiophen-2-yl)methyl]pyrazol-4-yl}methyl)-N-(6-isopropylpyridin-3-yl)-1,2,3,4-tetrahydronaphthalene-1-carboxamide (1.37 g) was obtained. By the reaction and treatment of this compound in the same manner as in Example 133, N-({1-[(5-chlorothiophen-2-yl)methyl]pyrazol-4-yl}methyl)-5-hydroxy-N-(6-isopropylpyridin-3-yl)-1,2,3,4-tetrahydronaphthalene-1-carboxamide (0.37 g) was obtained. melting point: 98-101° C.

Example 419

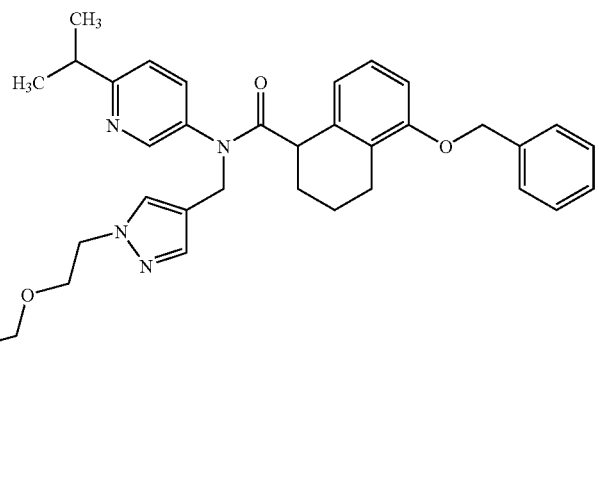

By the reaction and treatment of diethylene glycol monobutyl ether (1.0 mL) and 5-benzyloxy-N-(6-isopropylpyridin-3-yl)-N-[(pyrazol-4-yl)methyl]-1,2,3,4-tetrahydronaphthalene-1-carboxamide (0.96 g) in the same manner as in Example 394, 5-benzyloxy-N-({1-[2-(2-butoxyethoxy)ethyl]pyrazol-4-yl}methyl)-N-(6-isopropylpyridin-3-yl)-1,2,3,4-tetrahydronaphthalene-1-carboxamide (1.94 g) was obtained.

MS (ESI) m/z: 625[MH]$^+$

Example 420

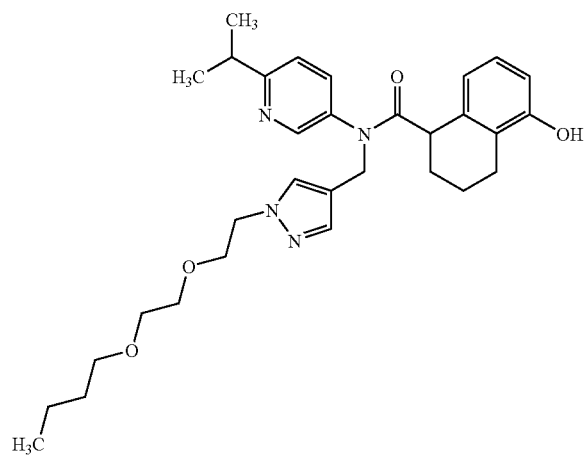

By the reaction and treatment in the same manner as in Example 139 using 5-benzyloxy-N-(6-isopropylpyridin-3-yl)-N-({1-[2-(2-butoxyethoxy)ethyl]pyrazol-4-yl}methyl)-1,2,3,4-tetrahydronaphthalene-1-carboxamide (1.94 g) as a starting material, N-({1-[2-(2-butoxyethoxy)ethyl]pyrazol-4-yl}methyl)-5-hydroxy-N-(6-isopropylpyridin-3-yl)-1,2,3,4-tetrahydronaphthalene-1-carboxamide hydrochloride (0.48 g) was obtained.

MS (ESI) m/z: 535[MH]$^+$ $^1$H-NMR (DMSO-d$_6$) δ: (0.85(3H,t,J=7.2 Hz), 1.21-1.48 (11H,m), 1.80-1.85(3H,m), 2.51(2H,brs), 3.26(2H,t,J=6.5 Hz), 3.42-3.58(6H,m), 3.71(2H,t,J=5.2 Hz), 4.20(2H,t,J=5.2 Hz), 4.73-4.82(2H,m), 6.50(1H,d,J=7.7 Hz), 6.67(1H,d, J=7.7 Hz), 6.90(1H,t,J=7.7 Hz), 7.32(1H,brs), 7.61(1H,brs), 7.92(1H,brs), 8.21(1H,brs), 8.81(1H,brs).

Example 421

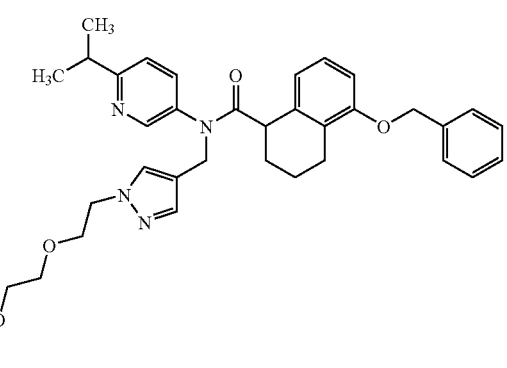

By the reaction and treatment of diethylene glycol monoethyl ether (1.5 mL) and 5-benzyloxy-N-(6-isopropylpyridin-3-yl)-N-[(pyrazol-4-yl)methyl]-1,2,3,4-tetrahydronaphthalene-1-carboxamide (0.72 g) in the same manner as in Example 394, 5-benzyloxy-N-({1-[2-(2-ethoxyethoxy)ethyl]pyrazol-4-yl}methyl)-N-(6-isopropylpyridin-3-yl)-1,2,3,4-tetrahydronaphthalene-1-carboxamide (0.89 g) was obtained.

MS (ESI) m/z: 597[MH]$^+$

Example 422

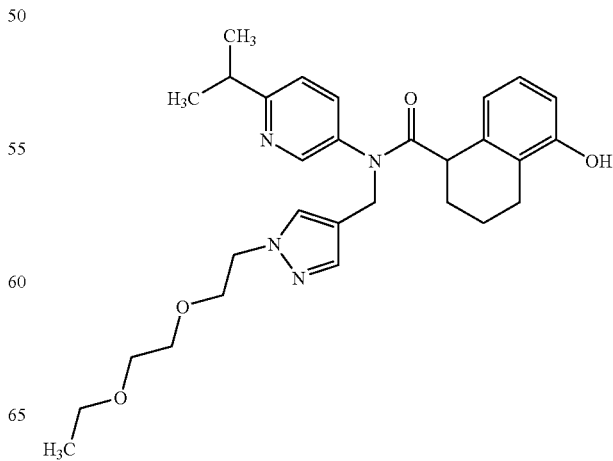

By the reaction and treatment in the same manner as in Example 139 using 5-benzyloxy-N-({1-[2-(2-ethoxyethoxy)ethyl]pyrazol-4-yl}methyl)-N-(6-isopropylpyridin-3-yl)-1,2,3,4-tetrahydronaphthalene-1-carboxamide (0.00 g) as a starting material, 5-hydroxy-N-({1-[2-(2-ethoxyethoxy)ethyl]pyrazol-4-yl}methyl)-N-(6-isopropylpyridin-3-yl)-1,2,3,4-tetrahydronaphthalene-1-carboxamide hydrochloride (0.15 g) was obtained.

MS (ESI) m/z: 507[MH]+

$^1$H-NMR (DMSO-$d_6$) δ: 1.06(3H,t,J=7.0 Hz), 1.32(1H,d, J=6.8 Hz), 1.43-1.48(1H,m), 1.81-1.91(3H,m), 2.50(2H,brs), 3.34-3.55(8H,m), 3.70(2H,t,J=5.3 Hz), 4.19(2H,t,J=5.3 Hz), 4.71-4.79(2H,m), 6.48(1H,d,J=7.7 Hz), 6.65(1H,d,J=7.7 Hz), 6.90(1H,t,J=7.7 Hz), 7.29(1H,brs), 7.59(1H,brs), 7.79(1H,brs), 8.08(1H,brs), 8.72(1H,brs).

Example 423

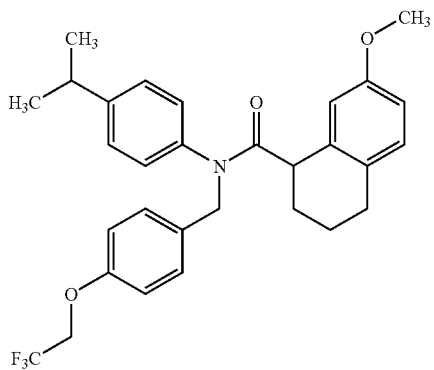

By the reaction and treatment in the same manner as in Example 12 using 7-methoxy-1,2,3,4-tetrahydronaphthalene-1-carboxylic acid (0.64 g) and (4-isopropylphenyl){[4-(2,2,2-trifluoroethoxy)phenyl]methyl}amine (1.0 g) as starting materials, N-(4-isopropylphenyl)-7-methoxy-N-{[4-(2,2,2-trifluoroethoxy)phenyl]methyl}-1,2,3,4-tetrahydronaphthalene-1-carboxamide (0.58 g) was obtained. melting point: 125-127° C.

Example 424

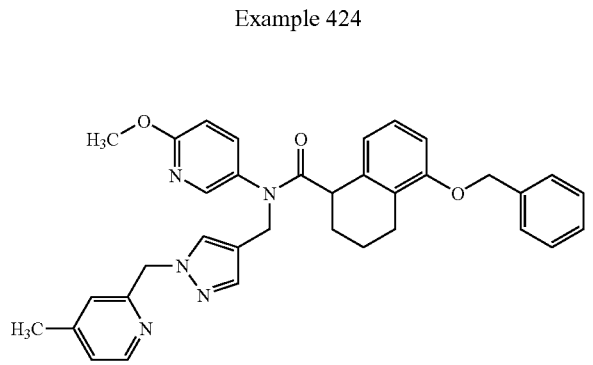

By the reaction and treatment in the same manner as in Example 271 using 5-benzyloxy-N-(6-methoxypyridin-3-yl)-N-[(pyrazol-4-yl)methyl]-1,2,3,4-tetrahydronaphthalene-1-carboxamide (0.94 g) and 2-chloromethyl-4-methylpyridine hydrochloride (0.71 g) as starting materials, 5-benzyloxy-N-(6-methoxypyridin-3-yl)-N-({1-[(4-methylpyridin-2-yl)methyl]pyrazol-4-yl}methyl)-1,2,3,4-tetrahydronaphthalene-1-carboxamide (0.90 g) was obtained.

$^1$H-NMR (CDCl$_3$) δ: 1.39-1.57(1H,m), 1.76-2.12(3H,m), 2.31(3H,s), 2.61-2.82(2H,m), 3.62-3.82(1H,m), 3.93(3H,s), 4.65(1H,d,J=14.4 Hz), 4.84(1H,d,J=14.4 Hz), 5.03(2H,s), 5.36(2H,s), 6.55(1H,d,J=7.8 Hz), 6.68-6.83(3H,m), 6.95-7.07(8H,m), 7.98(1H,d,J=2.4 Hz), 8.41(1H,d,J=5.1 Hz).

Example 425

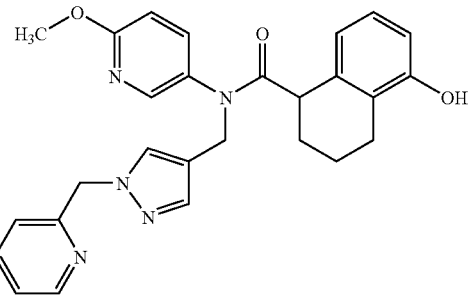

By the reaction and treatment in the same manner as in Example 101 using 5-benzyloxy-N-(6-methoxypyridin-3-yl)-N-({1-[(4-methylpyridin-2-yl)methyl]pyrazol-4-yl}methyl)-1,2,3,4-tetrahydronaphthalene-1-carboxamide (0.90 g) as a starting material, 5-hydroxy-N-(6-methoxypyridin-3-yl)-N-({1-[(4-methylpyridin-2-yl)methyl]pyrazol-4-yl}methyl)-1,2,3,4-tetrahydronaphthalene-1-carboxamide dihydrochloride (0.67 g) was obtained. MS (ESI) m/z: 484 [MH]+

$^1$H-NMR (DMSO-$d_6$) δ: 1.22-1.51(1H,m), 1.80-2.00(3H,m), 2.35-2.62(5H,m), 3.47-3.57(1H,m), 3.84(3H,s), 4.67(1H,d,J=14.6 Hz), 4.76(1H,d,J=14.7 Hz), 5.71(2H,s), 6.45(1H,d,J=7.7 Hz), 6.63(1H,d,J=7.8 Hz), 6.80-6.92(2H,m), 7.24(1H,s), 7.38(1H,s), 7.70(1H,dd,J=2.6, 8.7 Hz), 7.77(1H,d,J=5.8 Hz), 7.85(1H,s), 8.07(1H,d,J=2.4 Hz), 8.74(1H,d,J=5.9 Hz).

Example 426

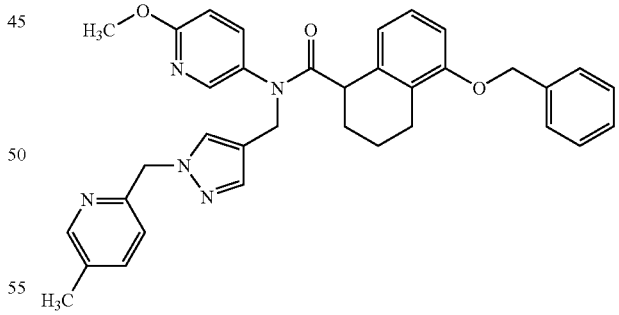

By the reaction and treatment in the same manner as in Example 271 using 5-benzyloxy-N-(6-methoxypyridin-3-yl)-N-[(pyrazol-4-yl)methyl]-1,2,3,4-tetrahydronaphthalene-1-carboxamide (0.94 g) and 2-chloromethyl-5-methylpyridine hydrochloride (0.71 g) as starting materials, 5-benzyloxy-N-(6-methoxypyridin-3-yl)-N-({1-[(5-methylpyridin-2-yl)methyl]pyrazol-4-yl}methyl)-1,2,3,4-tetrahydronaphthalene-1-carboxamide (0.94 g) was obtained.

$^1$H-NMR (CDCl$_3$) δ: 1.39-1.57(1H,m), 1.76-2.12(3H,m), 2.31(3H,s), 2.61-2.82(2H,m), 3.62-3.82(1H,m), 3.93(3H,s), 4.65(1H,d,J=14.4 Hz), 4.84(1H,d,J=14.4 Hz), 5.03(2H,s), 5.35(2H,s), 6.54(1H,d,J=7.7 Hz), 6.64-6.77(2H,m), 6.88(1H, d,J=8.0 Hz), 7.01(1H,t,J=7.9 Hz), 7.23-7.52(9H,m), 7.97 (1H,d,J=2.5 Hz), 8.38(1H,d,J=1.7 Hz).

Example 427

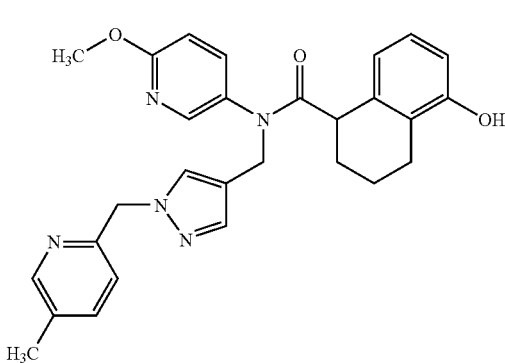

By the reaction and treatment in the same manner as in Example 101 using 5-benzyloxy-N-(6-methoxypyridin-3-yl)-N-({1-[(5-methylpyridin-2-yl)methyl]pyrazol-4-yl}methyl)-1,2,3,4-tetrahydronaphthalene-1-carboxamide (0.94 g) as a starting material, 5-hydroxy-N-(6-methoxypyridin-3-yl)-N-({1-[(5-methylpyridin-2-yl)methyl]pyrazol-4-yl}methyl)-1,2,3,4-tetrahydronaphthalene-1-carboxamide dihydrochloride (0.73 g) was obtained. MS (ESI) m/z: 484 [MH]+

$^1$H-NMR (DMSO-d$_6$) δ: 1.30-1.52(1H,m), 1.68-1.98(3H, m), 2.33-2.57(5H,m), 3.45-3.57(1H,m), 3.85(3H,s), 4.66 (1H,d,J=15.0 Hz), 4.74(1H,d,J=14.7 Hz), 5.61(2H,s), 6.43 (1H,d,J=7.5 Hz), 6.62(1H,d,J=7.8 Hz), 6.79-6.93(2H,m), 7.22(1H,d,J=8.1 Hz), 7.34(1H,s), 7.65(1H,dd,J=2.7, 8.7 Hz), 7.79(1H,s), 8.02-8.18(2H,m), 8.68(1H,s).

Example 428

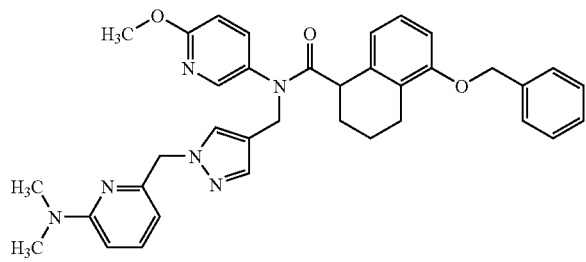

By the reaction and treatment in the same manner as in Example 271 using 5-benzyloxy-N-(6-methoxypyridin-3-yl)-N-[(pyrazol-4-yl)methyl]-1,2,3,4-tetrahydronaphthalene-1-carboxamide (0.94 g) and 6-chloromethyl-2-(dimethylamino)pyridine (0.68 g) as starting materials, 5-benzyloxy-N-({1-[(6-(dimethylamino)pyridin-2-yl)methyl]pyrazol-4-yl}methyl)-N-(6-methoxypyridin-3-yl)-1,2,3,4-tetrahydronaphthalene-1-carboxamide (0.31 g) was obtained. $^1$H-NMR (CDCl$_3$) δ: 1.38-1.67(1H,m), 1.73-2.07 (3H,m), 2.61-2.82(2H,m), 3.04(6H,s), 3.59-3.72(1H,m), 3.93(3H,s), 4.64(1H,d,J=14.4 Hz), 4.83(1H,d,J=14.4 Hz), 5.03(2H,s), 5.21(2H,s), 6.18(1H,d,J=7.2 Hz), 6.40(1H,d, J=8.4 Hz), 6.54(1H,d,J=7.5 Hz), 6.62-6.76(2H,m), 7.01(1H, t,J=8.0 Hz), 7.21-7.52(9H,m), 7.99(1H,d,J=2.4 Hz).

Example 429

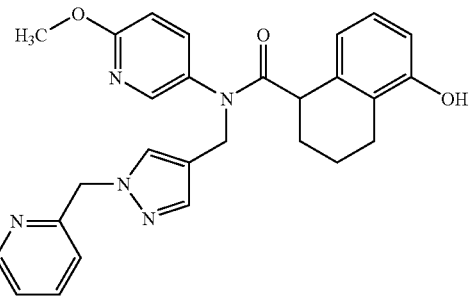

By the reaction and treatment in the same manner as in Example 101 using 5-benzyloxy-N-({1-[(6-(dimethylamino)pyridin-2-yl)methyl]pyrazol-4-yl}methyl)-N-(6-methoxypyridin-3-yl)-1,2,3,4-tetrahydronaphthalene-1-carboxamide (0.31 g) as a starting material, N-({1-[(6-(dimethylamino)pyridin-2-yl)methyl]pyrazol-4-yl}methyl)-5-hydroxy-N-(6-methoxypyridin-3-yl)-1,2,3,4-tetrahydronaphthalene-1-carboxamide dihydrochloride (0.20 g) was obtained. MS (ESI) m/z: 513[MH]+

$^1$H-NMR (DMSO-d$_6$) δ: 1.30-1.50(1H,m), 1.68-2.00(3H, m), 2.34-2.58(2H,m), 3.17(6H,s), 3.30-3.78(1H,m), 3.84(3H,s), 4.67(1H,d,J=14.8 Hz), 4.74(1H,d,J=14.7 Hz), 5.45(2H,s), 6.06(1H,d,J=7.1 Hz), 6.43(1H,d,J=7.6 Hz), 6.61 (1H,d,J=7.8 Hz), 6.80-6.97(3H,m), 7.35(1H,s), 7.60-7.81 (3H,m), 8.06(1H,d,J=2.4 Hz).

Example 430

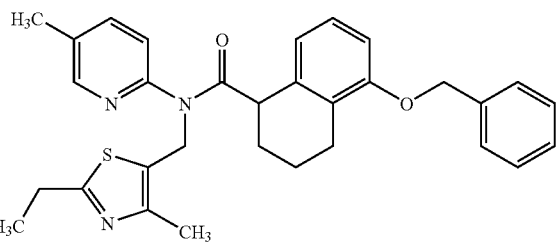

By the reaction and treatment in the same manner as in Example 132 using 5-benzyloxy-N-(5-methylpyridin-2-yl)-1,2,3,4-tetrahydronaphthalene-1-carboxamide (1.43 g) and 5-chloromethyl-2-ethyl-4-methylthiazole (0.68 g) as starting materials, 5-benzyloxy-N-[(2-ethyl-4-methylthiazol-5-yl)methyl]-N-(5-methylpyridin-2-yl)-1,2,3,4-tetrahydronaphthalene-1-carboxamide (0.92 g) was obtained.

$^1$H-NMR (CDCl$_3$) δ: 1.33(3H,t,J=7.5 Hz), 1.40-1.57(1H, m), 1.75-2.12(6H,m), 2.36(3H,s), 2.66-2.80(2H,m), 2.92 (2H,q,J=7.6 Hz), 3.68-3.81(1H,m), 5.03(2H,s), 5.10(1H,d, J=15.0 Hz), 5.17(1H,d,J=15.0 Hz), 6.72(1H, d, J=3.3 Hz), 6.75(1H,d,J=2.7 Hz), 6.88-7.00(1H,m), 7.07(1H,t,J=8.0 Hz), 7.25-7.52(6H,m), 8.40(1H,d,J=2.1 Hz).

Example 431

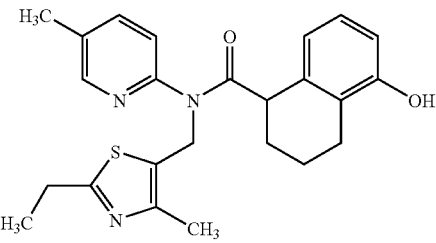

By the reaction and treatment in the same manner as in Example 101 using 5-benzyloxy-N-[(2-ethyl-4-methylthiazol-5-yl)methyl]-N-(5-methylpyridin-2-yl)-1,2,3,4-tetrahydronaphthalene-1-carboxamide (0.92 g) as a starting material, N-[(2-ethyl-4-methylthiazol-5-yl)methyl]-5-hydroxy-N-(5-methylpyridin-2-yl)-1,2,3,4-tetrahydronaphthalene-1-carboxamide hydrochloride (0.57 g) was obtained. MS (ESI) m/z: 422[MH]+

$^1$H-NMR (DMSO-d$_6$) δ: 1.30(3H,t,J=7.5 Hz), 1.35-1.50 (1H,m), 1.73-1.99(3H,m), 2.16(3H,s), 2.34(3H,s), 2.42-2.58 (2H,m), 3.10(2H,q,J=7.5 Hz), 3.62-3.77(1H,m), 5.03(2H,s), 6.44(1H,d,J=7.6 Hz), 6.43(1H,d,J=7.7 Hz), 6.85(1H,t,J=7.8 Hz), 7.40(1H,d,J=8.0 Hz), 7.80(1H,dd,J=2.1, 8.1 Hz), 8.42 (1H,d,J=2.3 Hz).

Example 432

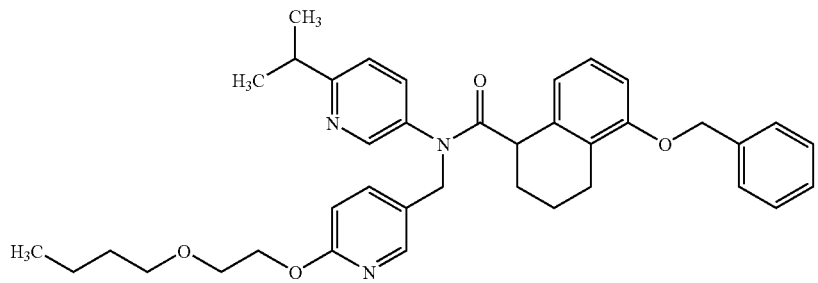

By the reaction and treatment in the same manner as in Example 142 using 5-benzyloxy-N-(6-isopropylpyridin-3-yl)-1,2,3,4-tetrahydronaphthalene-1-carboxamide (0.53 g) and 2-(2-butoxyethoxy)-5-(hydroxymethyl)pyridine (0.30 g) as starting materials, 5-benzyloxy-N-{[6-(2-butoxyethoxy)pyridin-3-yl]methyl}-N-(6-isopropylpyridin-3-yl)-1,2,3,4-tetrahydronaphthalene-1-carboxamide (0.40 g) was obtained.

MS (ESI) m/z: 608[MH]+

Example 433

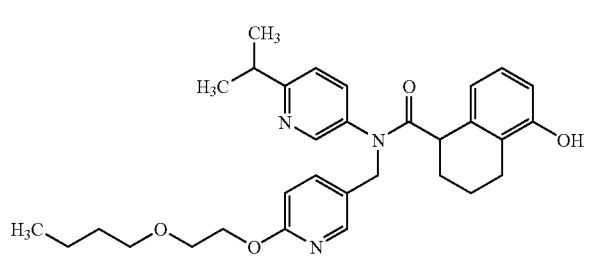

By the reaction and treatment in the same manner as in Example 139 using 5-benzyloxy-N-{[6-(2-butoxyethoxy)pyridin-3-yl]methyl}-N-(6-isopropylpyridin-3-yl)-1,2,3,4-tetrahydronaphthalene-1-carboxamide (0.40 g) as a starting material, N-{[6-(2-butoxyethoxy)pyridin-3-yl]methyl}-5-hydroxy-N-(6-isopropylpyridin-3-yl)-1,2,3,4-tetrahydronaphthalene-1-carboxamide (0.10 g) was obtained. MS (ESI) m/z: 518[MH]+

$^1$H-NMR (CDCl$_3$) δ: 0.92(3H,t,J=7.2 Hz), 1.30(6H,d, J=6.9 Hz), 1.20-2.15(8H,m), 2.50-2.70(2H,m), 3.00-3.20 (1H,m), 3.54(2H,t,J=6.6 Hz), 3.60-3.70(1H,m), 3.75-3.85 (2H,m), 4.40-4.50(2H,m), 4.83(1H,d,J=14.1 Hz), 4.90(1H,d, J=14.1 Hz), 6.35-6.50(2H,m), 6.75-6.90(2H,m), 7.19(1H,d, J=8.4 Hz), 7.25-7.35(1H,m), 7.61(1H,dd,J=2.4, 8.4 Hz), 7.85 (1H,d,J=2.4 Hz), 8.34(1H,d,J=2.4 Hz).

Example 434

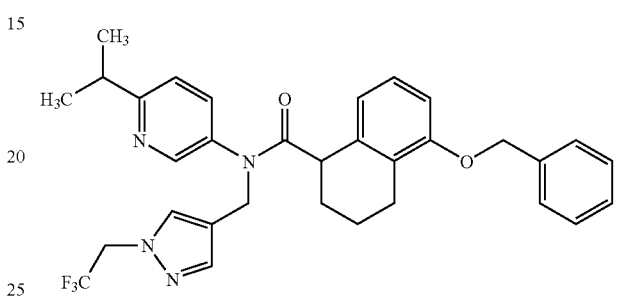

By the reaction and treatment in the same manner as in Example 132 using 5-benzyloxy-N-(6-isopropylpyridin-3-yl)-1,2,3,4-tetrahydronaphthalene-1-carboxamide (2.05 g) and 4-chloromethyl-1-(2,2,2-trifluoroethyl)pyrazole (1.02 g) as starting materials, 5-benzyloxy-N-(6-isopropylpyridin-3-yl)-N-{[1-(2,2,2-trifluoroethyl)pyrazol-4-yl]methyl}-1,2,3,4-tetrahydronaphthalene-1-carboxamide (1.70 g) was obtained.

MS (ESI) m/z: 563[MH]+

$^1$H-NMR (CDCl$_3$) δ: 1.31(6H,d,J=7.2 Hz), 1.40-1.65(1H, m), 1.75-2.10(3H,m), 2.60-2.85(2H,m), 3.00-3.20(1H,m), 3.60-3.70(1H,m), 4.55-4.75(3H,m), 4.87(1H,d,J=14.4 Hz), 5.03(2H,s), 6.51(1H,d,J=7.8 Hz), 6.73(1H,d,J=7.8 Hz), 7.04 (1H,t,J=7.8 Hz), 7.15-7.60(9H,m), 8.39(1H,d,J=2.4 Hz).

Example 435

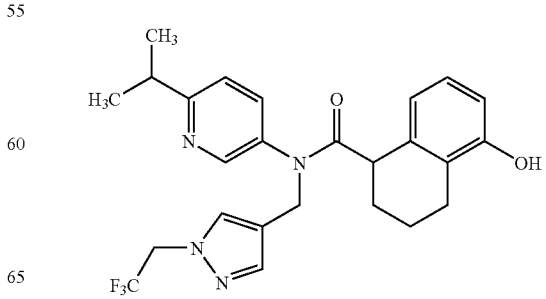

By the reaction and treatment in the same manner as in Example 17 using 5-benzyloxy-N-(6-isopropylpyridin-3-yl)-N-{[1-(2,2,2-trifluoroethyl)pyrazol-4-yl]methyl}-1,2,3,4-tetrahydronaphthalene-1-carboxamide (0.81 g) as a starting material, 5-hydroxy-N-(6-isopropylpyridin-3-yl)-N-{[1-(2,2,2-trifluoroethyl)pyrazol-4-yl]methyl}-1,2,3,4-tetrahydronaphthalene-1-carboxamide (0.23 g) was obtained. melting point: 127.7° C.

MS (ESI) m/z: 473[MH]$^+$ $^1$H-NMR (CDCl$_3$) δ: 1.29(6H,d,J=6.3 Hz), 1.35-1.55(1H,m), 1.75-2.10(3H,m), 2.50-2.70(2H,m), 3.00-3.20(1H,m), 3.60-3.70(1H,m), 4.55-4.75(3H,m), 4.85(1H,d,J=14.5 Hz), 6.35-6.45(2H,m), 6.82(1H,t,J=7.8 Hz), 6.91(1H,brs), 7.20-7.55(4H,m), 8.40(1H,d,J=2.3 Hz).

Formulation Example 1

The compound of the present invention (50 mg) is thoroughly kneaded with lactose (98 mg), cornstarch (45 mg) and hydroxypropyl cellulose (3 mg) in a kneader. The kneaded product is passed through a 200 mesh sieve, dried at 50° C. and passed through a 24 mesh sieve. Talc (3 mg) and magnesium stearate (1 mg) were mixed and, using a 9 mm diameter pounder, tablets weighing 200 mg are obtained. These tablets may be sugar-coated or film-coated as necessary.

Pharmaceutical Preparation Example 1

Tablets containing the following ingredients were produced by a conventional method.

| ingredients | per tablet |
|---|---|
| compound of Example 4 | 10 mg |
| lactose | 125 mg |
| corn starch | 75 mg |
| talc | 4 mg |
| magnesium stearate | 1 mg |
| total weight | 215 mg |

Pharmaceutical Preparation Example 2

Capsules containing the following ingredients were produced by a conventional method.

| ingredients | per capsule |
|---|---|
| compound of Example 4 | 10 mg |
| lactose | 165 mg |
| corn starch | 20 mg |
| talc | 5 mg |
| weight of a capsule | 200 mg |

Pharmaceutical Preparation Example 3

Ointment containing the following ingredients was produced by a conventional method.

| ingredients | dose |
|---|---|
| compound of Example 4 | 0.2 g |
| white petrolatum | 97.8 g |
| liquid paraffin | 2 g |
| total weight | 100 g |

Pharmaceutical Preparation Example 4

Injection containing the following ingredients was produced by a conventional method.

| ingredients | dose |
|---|---|
| compound of Example 4 | 0.2 g |
| sodium chloride | 0.9 g |
| distilled water for injection | suitable amount |
| total weight | 100 g |

Pharmaceutical Preparation Example 5

Eye drop containing the following ingredients was produced by a conventional method.

| ingredients | |
|---|---|
| compound of Example 4 | 0.1 g |
| sodium chloride | 0.3 g |
| sterile purified water | suitable amount |
| total weight | 100 g |

The superior pharmacological effect of the compound of the formula (1) is verified by a series of the following tests.

Test Example 1

C5a Receptor Binding Assay

The C5a receptor binding inhibitory action of C5a and the test compound was evaluated by a receptor binding assay comprising reacting human cell line U-937 (human histiocytic lymphoma line), which expresses the C5a receptor, with [$^{125}$I]-human C5a (Amersham Pharmacia Biotech) in a MultiScreen (MILLIPORE). First, U-937 cell was stimulated with 1 mM dibutyryl cyclic AMP (dcAMP, SIGMA) for 2 days to express the C5a receptor (dcAMP-U937 cell), and suspended in a binding buffer [50 mM HEPES, 1 mM CaCl$_2$, 5 mM MgCl$_2$, 0.5% bovine albumin (BSA, SIGMA), 0.02% NaN$_3$ (pH 7.2)] and stored at −80° C. The binding assay was started by the addition of 1×10$^5$ cells/50 μL of dcAMP-U937 cell suspension dissolved immediately before use, 25 μL of a test compound solution (obtained by dissolving the test compound in N,N-Dimethylformamide to a final concentration of 10 mmol/L and diluting with binding buffer), and 25 μL of [$^{125}$I]-C5a solution (final concentration 200 pM), to each well of the MultiScreen. For calculation of non-specific binding, wells containing a non-labeled C5a (final concentration 20 nM) or binding buffer instead of the test compound were prepared. After incubation at 4° C. for 2 hr, suction filtration and addition of 300 µL of the binding buffer were repeated 4 times to remove non-binding portion. After drying the MultiScreen, the radioactivity on the filter was measured using a gamma counter.

The rate (% inhibition) of inhibition of C5a binding by the test compound was calculated by the following formula using the count value obtained without addition of the test compound as Total, the count value obtained with addition of non-labeled C5a as Non, and the count value obtained with addition of the test compound as Test.

% Inhibition=100−[(Test−Non)/(Total−Non)]×100

Further, the concentration ($IC_{50}$ value) of the test compound, at which binding of [$^{125}$I]-human C5a is inhibited by 50%, was calculated by two-interpolation method. In this evaluation system, $IC_{50}$ value of the compound of Example 4 was 104 nmol/L.

Test Example 2

Action on Increase of Intracellular $Ca^{2+}$ Concentration of C5a Stimulated Neutrophil A neutrophil fraction was separately taken from human peripheral venous blood using Lympholyte-poly (Cedarlane), and suspended in Hank's Balanced Salt Solution (HBSS, GIBCO BRL) supplemented with 1% fetal bovine serum (FBS). Then, Fura 2-AM (final concentration 5 µM, DOJINDO) was added to the neutrophil fraction ($5\times10^6$ cells/mL), and the mixture was incubated at 37° C. for 40 min. The cells were washed by centrifugation and suspended to the concentration of $1\times10^6$ cells/mL. The intracellular $Ca^{2+}$ concentration was measured using a spectrophotofluorometer (CAF-110, JASCO Corporation), and calculated from the ratio (Ex340 value/Ex380 value) of fluorescent intensities at 500 nm upon excitation at 340 nm and 380 nm, the former being Ex340 value, the latter being Ex380 value. To be specific, a neutrophil suspension (450 µL, $1\times10^6$ cells/mL) was dispensed to a cuvette having a stirrer bar at 5 min before the measurement and the suspension was heated to 37° C. Then the cuvette was set on CAF-110 set for 37° C., and the measurement was started. Immediately thereafter, 50 µL of a test compound solution was added. About 45 sec later, 5 µL of recombinant human C5a (final concentration 100 pmol/L) was added and the measurement was continued for about 1 min. Then, Triton X-100 (final concentration 0.2%) was added and the cells were dissolved, and sb2 value, which was the Ex340 value then, and Rmax value, which was the Ex340 value/Ex380 value then, was measured. Then, EGTA (final concentration 3 mmol/L) was added and sf2 value, which was the Ex340 value then, and Rmin value, which was the Ex340/Ex380 value then, was measured. From these measurement results, the intracellular $Ca^{2+}$ concentration was calculated from the following formula.

$$\text{Intracellular } Ca^{2+} \text{ concentration (nmol/L)} = \frac{(Ex340 \text{ value}/Ex80 \text{ value}) - R\text{min value}}{R\text{max value} - (Ex340 \text{ value}/Ex380 \text{ value})} \times 224 \times (sf2/sb2)$$

In the formula, the Ex340 value/Ex380 value is the value at each continuous point over the entire period of measurement.

The rate (% inhibition) of the inhibition of increase in intracellular $Ca^{2+}$ concentration of C5a stimulated neutrophil by the test compound was calculated by the following formula, wherein the peak value of increase in intracellular $Ca^{2+}$ concentration derived by C5a without addition of the test compound is Max, the peak value of intracellular $Ca^{2+}$ concentration without addition of the test compound and without stimulation with C5a is Min, and the peak value of increase in intracellular $Ca^{2+}$ concentration derived by C5a with the addition of the test compound is Test.

% Inhibition=100−[(Test−Min)/(Max−Min)]×100

Further, the concentration ($IC_{50}$ value) of the test compound, at which increase in intracellular $Ca^{2+}$ concentration of C5a-stimulated neutrophil is inhibited by 50%, was calculated by two-interpolation method.

The $IC_{50}$ value of the compound of Example 4 was 5 nmol/L. Moreover, addition of the compound of Example 4 (3 µmol/L) did not induce an increase in intracellular $Ca^{2+}$ and the agonistic action was not found.

Test Example 3

Action of C5a-Stimulated Neutrophil on Production of Reactive Oxygen Species

A neutrophil fraction was separately taken from human peripheral venous blood using Lympholyte-poly (Cedarlane), and suspended in Hank's Balanced Salt Solution (HBSS, GIBCO BRL) containing 1% fetal bovine serum (FBS) and 1 mmol/L of luminol (Wako Pure Chemical Industries, Ltd.). Reactive oxygen species was measured using a luminometer (MicroLumat, Berthold) for 96 well plate. That is, $1\times10^5$ cells/150 µL of neutrophil suspension and 25 µL of a test compound solution (obtained by dissolving the test compound in N,N-Dimethyl formamide to a final concentration of 10 mmol/L and diluting with HBSS supplemented with 1% FBS) were added to a well, which was set in a MicroLumat set for 37° C. and stood for about 5 min. Then, 25 µL of C5a (final concentration 3 nmol/L) was added and luminescence produced by the reaction of the luminol and the reactive oxygen species was measured with the lapse of time for 15 min. The rate (% inhibition) of inhibition of the production of reactive oxygen species in C5a stimulated neutrophil by the test compound was calculated by the following formula, wherein the peak value of the production of reactive oxygen species derived by C5a without addition of the test compound is Max, the peak value of the production of reactive oxygen species without addition of the test compound and without C5a stimulation is Min, and the peak value of the production of reactive oxygen species derived by C5a with the addition of the test compound is Test.

% Inhibition=100−[(Test−Min)/(Max−Min)]×100

In addition, the concentration ($IC_{50}$ value) of the test compound, at which the production of reactive oxygen species in C5a stimulated neutrophil is inhibited by 50%, was calculated by two-interpolation method.

The $IC_{50}$ value of the compound of Example 4 was 10 nmol/L.

Test Example 4

Action on Migrating Ability of C5a-Stimulated Neutrophil

A neutrophil fraction was separately taken from human peripheral venous blood using Lympholyte-poly (Cedarlane) and suspended in RPMI 1640 medium (GIBCO BRL) supplemented with 0.1% bovine serum albumin (BSA). To. this neutrophil fraction ($5\times10^6$ cells/mL) was added Calcein-AM (final concentration 5 µM, FUNAKOSHI), and the mixture was incubated at 37° C. for 30 min. The cells were washed by centrifugation and suspended to a concentration of $1\times10^6$ cells/mL. The migration was evaluated by adding neutrophils to chemotaxicell (pore size: 3 μm, KURABO) and measuring the neutrophils that migrated outside the chemotaxicell. First, 100 pmol/L of C5a solution was added to 24 well plate (500 μL/well) and chemotaxicell was set in the well. Then, neutrophil suspension and test compound solution (200 μL each) were added to the inside of the chemotaxicell and incubated at 37° C., 5% $CO_2$ for 90 min. After the completion of the reaction, chemotaxicell was removed after shaking well and 100 μL of cell lysate solution (10% SDS, 0.01 mol/L HCl) was added. The fluorescent intensity of each well was measured by Cyto Fluor II (Ex: 485, Em: 530). The rate (% inhibition) of the inhibition of migration of C5a-stimulated neutrophil by the test compound was calculated by the following formula, wherein the fluorescence intensity of neutrophil that migrated by C5a stimulation without addition of the test compound is Max, the fluorescent intensity of neutrophil that migrated without addition of test compound and without C5a stimulation is Min, and the fluorescent intensity of neutrophil that migrated by C5a stimulation with the addition of the test compound is Test.

% Inhibition=100−[(Test−Min)/(Max−Min)]×100

Further, the concentration ($IC_{50}$ value) of the test compound, at which migration of C5a-stimulated neutrophil is inhibited by 50%, was calculated by two-interpolation method.

The $IC_{50}$ value of the compound of Example 4 was 100 nmol/L.

Test Example 5

Action on C5a Induced Neutrophil Decrease in Monkey

The test compound is intravenously, subcutaneously or orally administered to cynomolgus monkey. Then human C5a (SIGMA) is intravenously administered. The peripheral neutrophil count is taken with the lapse of time, and suppressive action by the test compound on the decrease in peripheral neutrophil count is evaluated.

Test Example 6

Action on Collagen-Induced Arthritis in Monkey

Type II collagen derived from bovine (purchased from Collagen Research Center) is intradermally inoculated twice to the back of cynomolgus monkey, together with complete Freund's adjuvant H37Rv (purchased from Wako Pure Chemical Industries, Ltd.) on the first day of testing and day 21. The test compound is orally administered from day 22 to day 33 after inoculation. The swelling of four limb joints is observed according to the scores of 0 (no change)-3 (edema of 5 toes). The joint swelling score of each monkey is shown by the total scores of four limbs.

Test Example 7

Toxicity Test

In a single administration toxicity test, the test compound is administered to male and female SD rats (3 per group) and cynomolgus monkey (1 per group) and the toxicity by single administration is evaluated using the presence or absence of death incident, general condition and body weight as indices. In a repeat administration toxicity test, the test compound is repeatedly administered to male and female SD rats (6 per group) and male and female cynomolgus monkeys (2 per group) for 2 weeks and the toxicity of the test compound by repeat administration is evaluated using general condition, body weight, diet intake, hematological test, biochemical test for blood, weight of organs and autopsy (including pathological test of tissues) as indices.

Test Example 8

Evaluation of Bioavailability in Rat

The test compound is intravenously and orally administered to male SD rats (5 per group), and the blood is drawn with the lapse of time. Using high performance liquid chromatography, the drug concentration in plasma is measured. The bioavailability (BA) is calculated by the following formula.

$$\frac{AUC \text{ by oral administration}}{AUC \text{ by intravenous administration}} \times \frac{\text{dose of intreavenous administration}}{\text{dose of oral administration}} \times 100(\%)$$

AUC: plasma concentration−area under time curve

Industrial Applicability

The compound of the formula (1) of the present invention, an optically active form thereof and pharmaceutical acceptable salt thereof have a C5a receptor antagonistic action and are useful as an agent for the prophylaxis or treatment of diseases or syndromes due to inflammation caused by C5a [e.g., autoimmune diseases such as rheumatism, systemic lupus erythematosus and the like, sepsis, adult respiratory distress syndrome, chronic obstructive pulmonary disease, allergic diseases such as asthma and the like, atherosclerosis, cardiac infarction, brain infarction, psoriasis, Alzheimer's disease and serious organ injury (e.g., pneumonia, nephritis, hepatitis and pancreatitis and the like) due to activation of leukocytes caused by ischemia reperfusion, trauma, burn, surgical invasion and the like]. In addition, it is useful as an agent for the prophylaxis or treatment of infectious diseases caused by bacteria or virus that invades via a C5a receptor.

This application is based on a patent application Nos. 280540/2000 and 386813/2000 filed in Japan, the contents of which are hereby incorporated by reference.

What is claimed is:
1. An amide derivative of formula (1)

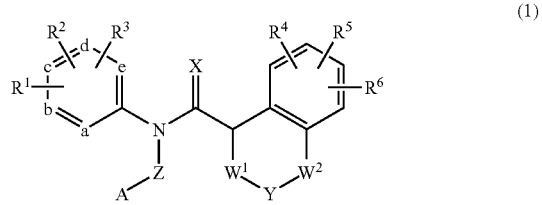

wherein
$R^1$, $R^2$ and $R^3$ are the same or different and each is selected from the group consisting of a hydrogen atom, an unsubstituted alkyl group, a substituted alkyl group, an unsubstituted alkenyl group, a substituted alkenyl group, an unsubstituted alkynyl group, a substituted alkynyl group, an unsubstituted cycloalkyl group, a substituted cycloalkyl group, an unsubstituted aryl group, a substituted aryl group, an unsubstituted heteroaryl group, a substituted heteroaryl group, an unsubstituted arylalkyl group, a substituted arylalkyl group, an unsubstituted heteroarylalkyl group, a substituted heteroarylalkyl group, an unsubstituted alkoxy group, a substituted alkoxy group, an aryloxy group, an arylalkyloxy group, an unsubstituted acyloxy group, a substituted acyloxy group, a halogen atom, a hydroxyl group, a nitro group, a cyano group, an acyl group, a mercapto group, an alkylthio group, an alkylsulfonyl group, an amino group, an alkylamino group, a dialkylamino group, a cyclic amino group, an unsubstituted carbamoyl group, a substituted carbamoyl group, an alkoxycarbonyl group, a carboxyl group, an acylamino group, an unsubstituted sulfamoyl group, a substituted sulfamoyl group, and a haloalkyl group, or any two of $R^1$, $R^2$ and $R^3$ in combination with the adjacent carbon atom may form a ring, a, b, c, d and e are each carbon atom, or 1 or 2 of a, b, c, d and e is(are) nitrogen atom(s), wherein the nitrogen atom may be bonded to an oxygen atom to form an amine oxide, and the rest are carbon atoms, $R^4$, $R^5$ and $R^6$ are the same or different and each is selected from the group consisting of a hydrogen atom, an unsubstituted alkyl group, a substituted alkyl group, an unsubstituted alkenyl group, a substituted alkenyl group, an unsubstituted alkynyl group, a substituted alkynyl group, an unsubstituted cycloalkyl group, a substituted cycloalkyl group, an unsubstituted aryl group, a substituted aryl group, an unsubstituted heteroaryl group, a substituted heteroaryl group, an unsubstituted arylalkyl group, a substituted arylalkyl group, an unsubstituted heteroarylalkyl group, a substituted heteroarylalkyl group, an unsubstituted alkoxy group, a substituted alkoxy group, an aryloxy group, an arylalkyloxy group, an unsubstituted acyloxy group, a substituted acyloxy group, a halogen atom, a hydroxyl group, a nitro group, a cyano group, an acyl group, a mercapto group, an alkylthio group, an alkylsulfonyl group, an amino group, an alkylamino group, a dialkylamino group, a cyclic amino group, an unsubstituted carbamoyl group, a substituted carbamoyl group, an alkoxycarbonyl group, a carboxyl group, an acylamino group, an unsubstituted sulfamoyl group, a substituted sulfamoyl group, a haloalkyl group, and a haloalkyloxy group, A is selected from the group consisting of an unsubstituted cycloalkyl group, a substituted cycloalkyl group, an unsubstituted aryl group, a substituted aryl group, an unsubtituted heteroaryl group, and a substituted heteroaryl group, $W^1$ and $W^2$ are the same or different and each is a bond, an unsubstituted alkylene($C_n$), or a substituted alkylene ($C_n$) wherein n is an integer of 1 to 3, X is oxygen atom or sulfur atom, Y is selected from the group consisting of a bond, an oxygen atom, —CO—, —N($R^7$)— wherein $R^7$ is a hydrogen atom, an unsubstituted alkyl group or a substituted alkyl group, —$SO_m$— wherein m is an integer of 0 to 2, —CON($R^8$)— wherein $R^8$ is a hydrogen atom, an unsubstituted alkyl group or a substituted alkyl group, and —N($R^9$)CO— wherein $R^9$ is a hydrogen atom, an unsubstituted alkyl group or a substituted alkyl group, and Z is an unsubstituted alkylene group or a substituted alkylene group, an optically active form thereof or a pharmaceutically acceptable salt thereof.

2. The amide derivative of claim 1, wherein, in the formula (1), $R^1$, $R^2$ and $R^3$ are the same or different and each is selected from the group consisting of a hydrogen atom, an unsubstituted alkyl group, a substituted alkyl group, an unsubstituted alkenyl group, a substituted alkenyl group, an unsubstituted alkynyl group, a substituted alkynyl group, a cycloalkyl group, an unsubstituted alkoxy group, a substituted alkoxy group, an unsubstituted acyloxy group, a substituted acyloxy group, a halogen atom, a hydroxyl group, a nitro group, a cyano group, an acyl group, a mercapto group, an alkylthio group, an alkylsulfonyl group, an amino group, an alkylamino group, a dialkylamino group, a cyclic amino group, a carbamoyl group, an alkoxycarbonyl group, a carboxyl group, a tetrazolyl group, an oxadiazolyl group, a sulfamoyl group, and a haloalkyl group, a, b, c, d and e are each carbon atom, or 1 or 2 of a, b, c, d and e is(are) nitrogen atom(s) and the rest are carbon atoms, $R^4$, $R^5$ and $R^6$ are the same or different and each is selected from the group consisting of a hydrogen atom, an unsubstituted alkyl group, a substituted alkyl group, an unsubstituted alkenyl group, a substituted alkenyl group, an unsubstituted alkynyl group, a substituted alkynyl group, a cycloalkyl group, an unsubstituted alkoxy group, a substituted alkoxy group, an unsubstituted acyloxy group, a substituted acyloxy group, a halogen atom, a hydroxyl group, a nitro group, a cyano group, an acyl group, a mercapto group, an alkylthio group, an alkylsulfonyl group, an amino group, an alkylamino group, a dialkylamino group, a cyclic amino group, a carbamoyl group, an alkoxycarbonyl group, a carboxyl group, a tetrazolyl group, an oxadiazolyl group, a sulfamoyl group, and a haloalkyl group, A is selected from the group consisting of a cycloalkyl group, an unsubstituted aryl group, a substituted aryl group, an unsubtituted heteroaryl group, and a substituted heteroaryl group, $W^1$ and $W^2$ are the same or different and each is a bond, an unsubstituted alkylene($C_n$), or a substituted alkylene ($C_n$) wherein n is an integer of 1 to 3, X is oxygen atom or sulfur atom, Y is selected from the group consisting of a bond, an oxygen atom, —CO—, —N($R^7$)— wherein $R^7$ is a hydrogen atom, an unsubstituted alkyl group or a substituted alkyl group, —$SO_m$— wherein m is an integer of 0 to 2, —CON($R^8$)— wherein $R^8$ is a hydrogen atom, an unsubstituted alkyl group or a substituted alkyl group, and —N($R^9$)CO— wherein $R^9$ is a hydrogen atom, an unsubstituted alkyl group or a substituted alkyl group, and Z is an unsubstituted alkylene group or a substituted alkylene group, an optically active form thereof or a pharmaceutically acceptable salt thereof.

3. The amide derivative of claim 2, wherein a, b, c, d and e in the formula (1) are all carbon atoms, an optically active form thereof or a pharmaceutically acceptable salt thereof.

4. The amide derivative of claim 1, wherein $R^1$, $R^2$ and $R^3$ in the formula (1) are the same or different and each is selected from the group consisting of a hydrogen atom, an alkyl group having 2 to 4 carbon atoms, and an alkoxy group, an optically active form thereof or a pharmaceutically acceptable salt thereof.

5. The amide derivative of claim 1, wherein $R^1$, $R^2$ and $R^3$ in the formula (1) are the same or different and each is selected from the group consisting of a hydrogen atom, an alkyl group having 2 to 4 carbon atoms, and an alkoxy group having 2 to 4 carbon atoms, an optically active form thereof or a pharmaceutically acceptable salt thereof.

6. The amide derivative of claim 1, wherein $R^1$, $R^2$ and $R^3$ in the formula (1) are the same or different and each is selected from the group consisting of a hydrogen atom, an alkyl group having 2 to 4 carbon atoms, and a methoxy group, an optically active form thereof or a pharmaceutically acceptable salt thereof.

7. The amide derivative of claim 1, wherein $R^4$, $R^5$ and $R^6$ in the formula (1) are the same or different and each is selected from the group consisting of a hydrogen atom, an unsubstituted alkyl group, a substituted alkyl group, an unsubstituted alkoxy group, a substituted alkoxy group, an unsubstituted acyloxy group, a substituted acyloxy group, a halogen atom, a hydroxyl group, an amino group, an alkylamino group, a dialkylamino group, a cyclic amino group, a carboxyl group, a haloalkyl group, and a haloalkyloxy group, an optically active form thereof or a pharmaceutically acceptable salt thereof.

8. The amide derivative of claim 1, wherein $R^4$, $R^5$ and $R^6$ in the formula (1) are the same or different and each is selected from the group consisting of a hydrogen atom, an unsubstituted alkyl group, a substituted alkyl group, an unsubstituted alkoxy group, a substituted alkoxy group, an unsubstituted acyloxy group, a substituted acyloxy group, a halogen atom, a hydroxyl group, an amino group, an alkylamino group, a dialkylamino group, a cyclic amino group, a carboxyl group, and a haloalkyl group, an optically active form thereof or a pharmaceutically acceptable salt thereof.

9. The amide derivative of claim 1, wherein Z of the formula (1) is —$CH_2$—, an optically active form thereof or a pharmaceutically acceptable salt thereof.

10. The amide derivative of claim 1, wherein A of the formula (1) is selected from the group consisting of an unsubstituted aryl group, a substituted aryl group, an unsubstituted heteroaryl group, and a substituted heteroaryl group, an optically active form thereof or a pharmaceutically acceptable salt thereof.

11. The amide derivative of claim 1, wherein A of the formula (1) is selected from the group consisting of an unsubstituted pyridyl group, a substituted pyridyl group, an unsubstituted pyrazolyl group, a substituted pyrazolyl group, an unsubstituted thiazolyl group, a substituted thiazolyl group, an unsubstituted oxazolyl group, a substituted oxazolyl group, an unsubstituted thienyl group, and a substituted thienyl group, an optically active form thereof or a pharmaceutically acceptable salt thereof.

12. The amide derivative of claim 1, wherein A of the formula (1) is a nitrogen-containing heterocyclic group selected from the group consisting of formulae (Aa)-(Ac)

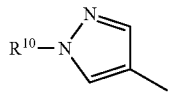
(Aa)

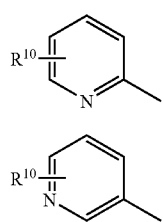
(Ab)

(Ac)

wherein $R^{10}$ is selected from the group consisting of a hydrogen atom, an unsubstituted alkyl group, a substituted alkyl group, an unsubstituted alkenyl group, a substituted alkenyl group, an unsubstituted alkynyl group, a substituted alkynyl group, a cycloalkyl group, an unsubstituted alkoxy group, a substituted alkoxy group, an unsubstituted acyloxy group, a substituted acyloxy group, a halogen atom, a hydroxyl group, a nitro group, a cyano group, an acyl group, a mercapto group, an alkylthio group, an alkylsulfonyl group, an amino group, an alkylamino group, a dialkylamino group, a cyclic amino group, a carbamoyl group, an alkoxycarbonyl group, a carboxyl group, a tetrazolyl group, an oxadiazolyl group, a sulfamoyl group, and a haloalkyl group, an optically active form thereof or a pharmaceutically acceptable salt thereof.

13. The amide derivative of claim 1, wherein X of the formula (1) is oxygen atom, an optically active form thereof or a pharmaceutically acceptable salt thereof.

14. The amide derivative of claim 1, wherein —$W^1$—Y—$W^2$— of the formula (1) is —$(CH_2)_2$—, —$(CH_2)_3$— or —$(CH_2)_2O$—, an optically active form thereof or a pharmaceutically acceptable salt thereof.

15. The amide derivative of claim 1, wherein $R^1$, $R^2$ and $R^3$ of the formula (1) are the same or different and each is selected from the group consisting of a hydrogen atom, an alkyl group having 2 to 4 carbon atoms, and an alkoxy group having 2 to 4 carbon atoms, a, b, c, d and e are each carbon atom, or either b or d is nitrogen atom and the rest are carbon atoms, $R^4$, $R^5$ and $R^6$ are the same or different and each is selected from the group consisting of a hydrogen atom, a methoxy group, a halogen atom, and a hydroxyl group, Z is —$CH_2$—, A is a nitrogen-containing heterocyclic group selected from the group consisting of formulae (Aa')-(Ae')

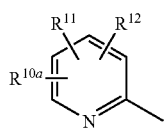
(Aa')

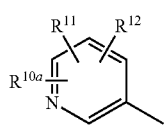
(Ab')

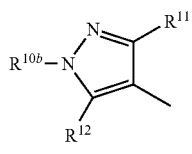
(Ac')

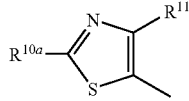
(Ad')

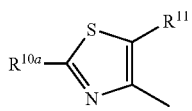

(Ae')

wherein $R^{10a}$, $R^{11}$ and $R^{12}$ are the same or different and each is selected from the group consisting of a hydrogen atom, an unsubstituted alkyl group, a substituted cycloalkyl group, an unsubstituted cycloalkyl group, a substituted aryl group, an unsubstituted aryl group, a substituted heteroaryl group, an unsubstituted heteroaryl group, a substituted arylalkyl group, an unsubstituted arylalkyl group, a substituted heteroarylalkyl group, an unsubstituted heteroarylalkyl group, a substituted alkoxy group, an unsubstituted alkoxy group, an aryloxy group, an arylalkyloxy group, a halogen atom, a hydroxyl group, a nitro group, a cyano group, an alkylthio group, an amino group, an alkylamino group, a dialkylamino group, a cyclic amino group, a haloalkyl group, a haloalkyloxy group, $R^{13}O(CH_2)_jO(CH_2)_kO(CH_2)_lO$— wherein j, k and l are each independently an integer of 2 to 10, $R^{13}$ is selected from the group consisting of a hydrogen atom, an unsubstituted alkyl group, a substituted cycloalkyl group, an unsubstituted cycloalkyl group, a substituted aryl group, an unsubstituted aryl group, a substituted heteroaryl group, an unsubstituted heteroaryl group, a substituted arylalkyl group, an unsubstituted arylalkyl group, a substituted heteroarylalkyl group, an unsubstituted heteroarylalkyl group, and a or haloalkyl group, and $R^{13}O(CH_2)_jO(CH_2)_kO$— wherein j, k and $R^{13}$ are as defined above, $R^{10b}$ is selected from the group consisting of a hydrogen atom, an unsubstituted alkyl group, a substituted cycloalkyl group, an unsubstituted cycloalkyl group, a substituted aryl group, an unsubstituted aryl group, a substituted heteroaryl group, an unsubstituted heteroaryl group, a substituted arylalkyl group, an unsubstituted arylalkyl group, a substituted heteroarylalkyl group, an unsubstituted heteroarylalkyl group, a haloalkyl group, a haloalkyloxy group, $R^{13}O(CH_2)_jO(CH_2)_kO(CH_2)_l$— wherein j, k, l and $R^{13}$ are as defined above, and $R^{13}O(CH_2)_jO(CH_2)_k$— wherein j, k and $R^{13}$ are as defined above, X is oxygen atom, and —$W^1$—Y—$W^2$— is —$(CH_2)_2$— or —$(CH_2)_3$—, an optically active form thereof or a pharmaceutically acceptable salt thereof.

16. An amide derivative, wherein the amide derivative is selected from the group consisting of
N-[(4-dimethylaminophenyl)methyl]-N-(4-ethylphenyl)-1,2,3,4-tetrahydronaphthalene-1-carboxamide,
N-[(4-dimethylaminophenyl)methyl]-N-(4-ethylphenyl)indan-1-carboxamide,
N-[(4-dimethylaminophenyl)methyl]-N-(4-isopropylphenyl)-1,2,3,4-tetrahydronaphthalene-1-carboxamide,
N-[(4-dimethylaminophenyl)methyl]-N-(4-isopropylphenyl)-7-methoxy-1,2,3,4-tetrahydronaphthalene-1-carboxamide,
N-[(4dimethylaminophenyl)methyl]-N-(4-isopropylphenyl)chroman-4-carboxamide,
N-[(4-dimethylaminophenyl)methyl]-5-hydroxy-N-(4-isopropylphenyl)-1,2,3,4-tetrahydronaphthalen-1-carboxamide, N-[(4-dimethylaminophenyl)methyl]-N-(4-isopropylphenyl)-6-methoxyindan-1-carboxamide,
N-[(1-ethylpyrazol-4-yl)methyl]-N-(4-isopropylphenyl)-1,2,3,4-tetrahydronaphthalene-1-carboxamide,
N-[(4-dimethylaminophenyl)methyl]-N-(4-isopropylphenyl)-6-methoxychroman-4-carboxamide,
N-[(1,3-dioxaindan-5-yl)methyl]-N-(4-isopropylphenyl)-7-methoxy-1,2,3,4-tetrahydronaphthalene-1-carboxamide,
N-[(4-dimethylaminophenyl)methyl]-4-hydroxy-N-(4-isopropylphenyl)indan-1-carboxamide,
N-[(1-ethylpyrazol-4-yl)methyl]-5-hydroxy-N-(4-isopropylphenyl)-1,2,3,4-tetrahydronaphthalene-1-carboxamide, and
N-[(1-ethylpyrazol-4-yl)methyl]-4-hydroxy-N-(4-isopropylphenyl)indan-1-carboxamide,
an optically active form thereof or a pharmaceutically acceptable salt thereof.

17. The amide derivative of claim 1, wherein the amide derivative is
N-[(1-ethylpyrazol-4-yl)methyl]-5-hydroxy-N-(6-isopropylpyridin-3-yl)-1,2,3,4-tetrahydronaphthalene-1-carboxamide,
an optically active form thereof or a pharmaceutically acceptable salt thereof.

18. An amide derivative, wherein the amide derivative is selected from the group consisting of
N-[(2,6-dimethoxypyridin-3-yl)methyl]-5-hydroxy-N-(4-isopropylphenyl)-1,2,3,4-tetrahydronaphthalene-1-carboxamide,
5-hydroxy-N-(4-isopropylphenyl)-N-[(6-phenoxypyridin-3-yl)methyl]-1,2,3,4-tetrahydronaphthalene-1-carboxamide,
N-[(6-dimethylaminopyridin-3-yl)methyl]-5-hydroxy-N-(4-isopropylphenyl)-1,2,3,4-tetrahydronaphthalene-1-carboxamide,
N-[(4-dimethylaminophenyl)methyl]-7-ethoxy-N-(4-isopropylphenyl)-1,2,3,4-tetrahydronaphthalene-1-carboxamide,
N-[(5-ethylthiophen-2-yl)methyl]-N-(4-isopropylphenyl)-1,2,3,4-tetrahydronaphthalene-1-carboxamide,
N-[(4-dimethylaminophenyl)methyl]-7-fluoro-N-(4-isopropylphenyl)-1,2,3,4-tetrahydronaphthalene-1-carboxamide,
N-(4-bromophenyl)-N-[(4-dimethylaminophenyl)methyl]-7-fluoro-1,2,3,4-tetrahydronaphthalene-1-carboxamide,
N-[(4-dimethylaminophenyl)methyl]-8-fluoro-5-hydroxy-N-(4-isopropylphenyl)-1,2,3,4-tetrahydronaphthalene-1-carboxamide,
N-[(2,6-dimethoxypyridin-3-yl)methyl]-5-hydroxy-N-(6-isopropylpyridin-3-yl)-1,2,3,4-tetrahydronaphthalene-1-carboxamide,
N-[(4-dimethylaminophenyl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-[(6-methoxypyridin-3-yl)methyl]-1,2,3,4-tetrahydronaphthalene-1-carboxamide,
N-[(2,4-dimethylthiazol-5-yl)methyl]-5-hydroxy-N-(6-isopropylpyridin-3-yl)-1,2,3,4-tetrahydronaphthalene-1-carboxamide,
N-(4-butylphenyl)-N-[(4-dimethylaminophenyl)methyl]-5-hydroxy-1,2,3,4-tetrahydronaphthalene-1-carboxamide,
N-[(4-dimethylaminophenyl)methyl]-7-methoxy-N-(4-methoxyphenyl)-1,2,3,4-tetrahydronaphthalene-1-carboxamide, N-(4-chlorophenyl)-N-[(4dimethylaminophenyl)methyl]-7-methoxy-1,2,3,4-tetrahydronaphthalene-1-carboxamide, N-[(4-dimethylaminophenyl)methyl]-7-methoxy-N-(4-methylphenyl-1,2,3,4-tetrahydronaphthalene-1-carboxamide, N-[(4-dimethylaminophenyl)methyl]-N-(4-ethoxyphenyl)-7-methoxy-1,2,3,4-tetrahydronaphthalene-1-carboxamide, N-(4-bromophenyl)-N-[(4-dimethylaminophenyl)methyl]-7-methoxy-1,2,3,4-tetrahydronaphthalene-1-carboxamide, N-(4-isopropylphenyl)-7-methoxy-N-[(4-methylaminophenyl)methyl]-1,2,3,4-tetrahydronaphthalene-1-carboxamide, N-[(4-dimethylaminophenyl)methyl]-5-hydroxy-N-(4-methoxyphenyl)-1,2,3,4-tetrahydronaphthalene-1-carboxamide, 5-hydroxy-N-(4-isopropylphenyl)-N-[(2-methylthiazol-4-yl)methyl]-1,2,3,4-tethydronaphthalene-1-carboxamide, N-(4-bromophenyl)-N-[(dimethylaminophenyl)methyl]-5-hydroxy-1,2,3,4-tetrahydronaphthalene-1-carboxamide, N-(4-isopropylphenyl)-7-methoxy-N-(2-tolylmethyl)-1,2,3,4-tetrahydronaphthalene-1-carboxamide, N-[(2,4-dichlorophenyl)methyl]-N-(4-isopropylphenyl)-7-methoxy-1,2,3,4-tetrahydronaphthalene-1-carboxamide, N-(4-isopropylphenyl)-7-methoxy-N-[(4-nitrophenyl)methyl]-1,2,3,4-tetrahydronaphthalene-1-carboxamide, N-(4-isopropylphenyl)-7-methoxy-N-[(3-tolyl)methyl]-1,2,3,4-tetrahydronaphthalene-1-carboxamide, N-(4-isopropylphenyl)-7-methoxy-N-[(4-tolyl)methyl]-1,2,3,4-tetrahydronaphthalene-1-carboxamide, N-[(2-fluorophenyl)methyl]-N-(4-isopropylphenyl)-7-methoxy-1,2,3,4-tetrahydronaphthalene-1-carboxamide, N-[(4-fluorophenyl)methyl]-N-(4-isopropylphenyl)-7-methoxy-1,2,3,4-tetrahydronaphthalene-1-carboxamide, N-[(2,4-dimethylphenyl)methyl]-N-(4-isopropylphenyl)-7-methoxy-1,2,3,4-tetrahydronaphthalene-1-carboxamide, N-(4-isopropylphenyl)-7-methoxy-N-[2-methoxyphenyl)methyl]-1,2,3,4-tetrahydronaphthalene-1-carboxamide, N-[(2-chlorophenyl)methyl]-N-(4-isopropylphenyl)-7-methoxy-1,2,3,4-tetrahydronaphthalene-1-carboxamide, N-[(2,4-difluorophenyl)methyl]-N-(4-isopropylphenyl)-7-methoxy-1,2,3,4-tetrahydronaphthalene-1-carboxamide, N-[(2,6-difluorophenyl)methyl]-N-(4-isopropylphenyl)-7-methoxy-1,2,3,4-tetrahydronaphthalene-1-carboxamide, N-[(4-ethoxyphenyl)methyl]-N-(4-isopropylphenyl)-7-methoxy-1,2,3,4-tetrahydronaphthalene-1-carboxamide, N-(4-isopropylphenyl)-7-methoxy-N-[(4-oxachroman-6-yl)methyl]-1,2,3,4-tetrahydronaphthalene-1-carboxamide, N-[(2,3-dimethoxyphenyl)methyl]-N-(4-isopropylphenyl)-7-methoxy-1,2,3,4-tetrahydronaphthalene-1-carboxamide, N-[(2,4-dimethoxyphenyl)methyl]-N-(4-isopropylphenyl)-7-methoxy-1,2,3,4-tetrahydronaphthalene-1-carboxamide, N-(4-isopropylphenyl)-7-methoxy-N-[(2-trifluoromethylphenyl)methyl]-1,2,3,4-tetrahydronaphthalene-1-carboxamide, N-(4-isopropylphenyl)-7-methoxy-N-[(4-trifluoromethylphenyl)methyl]-1,2,3,4-tetrahydronaphthalene-1-carboxamide, N-[(2-bromophenyl)methyl]-N-(4-isopropylphenyl)-7-methoxy-1,2,3,4-tetrahydronaphthalene-1-carboxamide, N-(4-isopropylphenyl)-7-methoxy-N-[(2,3,4-trimethoxyphenyl)methyl]-1,2,3,4-tetrahydronaphthalene-1-carboxamide, 5-hydroxy-N-(4-isopropylphenyl)-N-{[1-(2-pyridylmethyl)pyrazol-4-yl]methyl}-1,2,3,4-tetrahydronaphthalene-1-carboxamide, N-[(1-benzylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(2-pyridylmethyl)pyrazol-4-yl]methyl}-1,2,3,4-tetrahydronaphthalene-1-carboxamide, N-({1-[(4-fluorophenyl)methyl]pyrazol-4-yl}methyl)-5-hydroxy-N-(6-isopropylpyridin-3-yl)-1,2,3,4-tetrahydronaphthalene-1-carboxamide, N-({1-[(4-chlorophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide, 5-hydroxy-N-(6-isopropylpyridin-3-yl)-N-({1-[(4-methoxyphenyl)methyl]pyrazol-4-yl}methyl)-1,2,3,4-tetrahydronaphthalene-1-carboxamide, N-({1-[(4-bromophenyl)methyl]pyrazol-4-yl}methyl)-5-hydroxy-N-(6-isopropylpyridin-3-yl)-1,2,3,4-tetrahydronaphthalene-1-carboxamide, N-({1-[(3-chlorophenyl)methyl]pyrazol-4-yl}methyl)-5-hydroxy-N-(6-isopropylpyridin-3-yl)-1,2,3,4-tetrahydronaphthalene-1-carboxamide, N-({1-[(2-chlorophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[(4-methylphenyl)methyl]pyrazol-4-yl}methyl)-1,2,3,4-tetrahydronaphthalene-1-carboxamide, 5-hydroxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(5-methoxypyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide, 8-fluoro-5-hydroxy-N-(6-isopropylpyridin-3-yl)-N-{[1-(2-pyridylmethyl)pyrazol-4-yl]methyl}-1,2,3,4-tetrahydronaphthalene-1-carboxamide, 5-hydroxy-N-(6-isopropylpyridin-3-yl)-N-({1-[(4-trifluoromethylpyridin-2-yl)methyl]pyrazol-4-yl}methyl)-1,2,3,4-tetrahydronaphthalene-1-carboxamide, N-({1-[(6-dimethylaminopyridin-2-yl)methyl]pyrazol-4-yl}methyl)-5-hydroxy-N-(6-isopropylpyridin-3-yl)-1,2,3,4-tetrahydronaphthalene-1-carboxamide,
N-({1-[3-(dimethylaminophenyl)methyl]pyrazol-4-yl}methyl)-5-hydroxy-N-(6-isopropylpyridin-3-yl)-1,2,3,4-tetrahydronaphthalene-1-carboxamide,
N-[(2-ethyl-4-trifluoromethylthiazol-5-yl)methyl]-5-hydroxy-N-(6-isopropylpyridin-3-yl)-1,2,3,4-tetrahydronaphthalene-1-carboxamide,
5-benzyloxy-N-(4-isopropylphenyl)-N-[(1-isopropylpyrazol-4-yl)methyl]-1,2,3,4-tetrahydronaphthalene-1-carboxamide,
5-hydroxy-N-(4-isopropylphenyl)-N-[1-methylpyrazol-4-yl)methyl]-1,2,3,4-tetrahydronaphthalene-1-carboxamide,
5-benzyloxy-N-(4-isopropylphenyl)-N-[(1-propylpyrazol-4-yl)methyl]-1,2,3,4-tetrahydronaphthalene-1-carboxamide,
N-{[1-(cyclohexylmethyl)pyrazol-4-yl]methyl}-5-hydroxy-N-(4-isopropylphenyl)-1,2,3,4-tetrahydronaphthalene-1-carboxamide,
5-hydroxy-N-(4-isopropylphenyl)-N-{[1-(3-thienylmethyl)pyrazol-4-yl]methyl}-1,2,3,4-tetrahydronaphthalene-1-carboxamide,
N-{[1-(4-fluorobenzyl)pyrazol-4-yl]methyl}-5-hydroxy-N-(4-methoxyphenyl)-1,2,3,4-tetrahydronaphthalene-1-carboxamide,
N-[(1-ethylpyrazol-4-yl)methyl]-5-hydroxy-N-(4-methoxyphenyl)-1,2,3,4-tetrahydronaphthalene-1-carboxamide,
N-{[1-(cyclohexylmethyl)pyrazol-4-yl]methyl}-5-hydroxy-N-(4-methoxyphenyl)-1,2,3,4-tetrahydronaphthalene-1-carboxamide,
5-hydroxy-N-(6-isopropylpyridin-3-yl)-N-{[1-(2-piperidinoethyl)pyrazol-4-yl]methyl}-1,2,3,4-tetrahydronaphthalene-1-carboxamide,
N-{[1-(cyclohexylmethyl)pyrazol-4-yl]methyl}-5-hydroxy-N-(6-isopropylpyridin-3-yl)-1,2,3,4-tetrahydronaphthalene-1-carboxamide,
N-[(1-heptylpyrazol-4-yl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-{[1-(3-thienylmethyl)pyrazol-4-yl]methyl}-1,2,3,4-tetrahydronaphthalene-1-carboxamide,
5-hydroxy-N-(6-isopropylpyridin-3-yl)-N-({1-[(2-methylthiazol-4-yl)methyl]pyrazol-4-yl}methyl)-1,2,3,4-tetrahydronaphthalene-1-carboxamide,
N-[(1-butylpyrazol-4-yl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-{[1-(3-methylbutyl)pyrazol-4-yl]methyl}-1,2,3,4-tetrahydronaphthalene-1-carboxamide,
N-[(1-benzylpyrazol-4-yl)methyl]-5-hydroxy-N-(6-methoxypyridin-3-yl)-1,2,3,4-tetrahydronaphthalene-1-carboxamide,
5-hydroxy-N-(6-isopropylpyridine-3-yl)-N-({1-[2-(2-pyridyl)ethyl]pyrazol-4-yl}methyl)-1,2,3,4-tetrahydronaphthalene-1-carboxamide,
N-[(1-dodecylpyrazol-4-yl)methyl]-5-hydroxy-N-(6-isopropylpyridin-3-yl)-1,2,3,4-tetrahydronaphthalene-1-carboxamide,
5-hydroxy-N-(6-isopropylpyridin-3-yl)-N-[(1-nonylpyrazol-4-yl)methyl]-1,2,3,4-tetrahydronaphthalene-1-carboxamide,
N-{[1-(2-butoxyethyl)pyrazol-4-yl]methyl}-5-hydroxy-N-(6-isopropylpyridin-3-yl)-1,2,3,4-tetrahydronaphthalene-1-carboxamide,
5-hydroxy-N-(6-isopropylpyridin-3-yl)-N-({1-[2-(2-methoxyethoxy)ethyl]pyrazol-4-yl}methyl)-1,2,3,4-tetrahydronaphthalene-1-carboxamide,
5-hydroxy-N-(4-isopropylphenyl)-N-[(6-morpholinopyridin-3-yl)methyl]-1,2,3,4-tetrahydronaphthalene-1-carboxamide,
5-hydroxy-N-(4-isopropylphenyl)-N-({1-[(4-methylpyridin-2-yl)methyl]pyrazol-4-yl}methyl)-1,2,3,4-tetrahydronaphthalene-1-carboxamide,
5-hydroxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide,
5-hydroxy-N-(6-isopropylpyridin-3-yl)-N-({1-[(6-methoxypyridin-2-yl)methyl]pyrazol-4-yl}methyl)-1,2,3,4-tetrahydronaphthalene-1-carboxamide,
5-hydroxy-N-[(1-isopropylpyrazol-4-yl)methyl]-N-(6-isopropylpyridin-3-yl)-1,2,3,4-tetrahydronaphthalene-1-carboxamide,
N-[(4dimethylaminophenyl)methyl]-N-(6-isopropylpyridin-3-yl)-7-methoxy-1,2,3,4-tetrahydronaphthalene-1-carboxamide,
5-hydroxy-N-(6-isopropylpyridin-3-yl)-N-{[1-(2-thienylmethyl)pyrazol-4-yl]methyl}-1,2,3,4-tetrahydronaphthalene-1-carboxamide,
N-({1-[(5-chlorothiophen-2-yl)methyl]pyrazol-4-yl}methyl)-5-hydroxy-N-(6-isopropylpyridin-3-yl)-1,2,3,4-tetrahydronaphthalene-1-carboxamide,
5-benzyloxy-N-({1-[2-(2-butoxyethoxy)ethyl]pyrazol-4-yl}methyl)-N-(6-isopropylpyridin-3-yl)-1,2,3,4-tetrahydronaphthalene-1-carboxamide,
N-({1-[2-(2-butoxyethoxy)ethyl]pyrazol-4-yl}methyl)-5-hydroxy-N-(6-isopropylpyridin-3-yl)-1,2,3,4-tetrahydronaphthalene-1-carboxamide, and
N-({1-[2-(2-ethoxyethoxy)ethyl]pyrazol-4-yl}methyl)-N-(6-isopropylpyridin-3-yl)-5-hydroxy-1,2,3,4-tetrahydronaphthalene-1-carboxamide,
an optically active form thereof or a pharmaceutically acceptable salt thereof.

19. A pharmaceutical composition comprising the amide derivative of claim 1, an optically active form thereof or a pharmaceutically acceptable salt thereof, and a pharmaceutically acceptable additive.

20. A method of treating a disease involving C5a comprising administering to a subject in need thereof an effective amount of the amide derivative of formula (1')

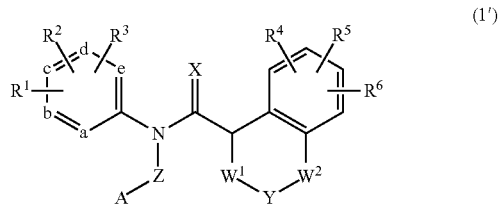

wherein
$R^1$, $R^2$ and $R^3$ are the same or different and each is a hydrogen atom, an unsubstituted alkyl group or an unsubstituted alkoxy group,
a, b, c, d and e are each carbon atom, or 1 or 2 of a, b, c, d and e is(are) nitrogen atom(s) and the rest are carbon atoms, $R^4$, $R^5$ and $R^6$ are the same or different and each is a hydrogen atom or a hydroxyl group, A is a substituted pyridyl group or a substituted pyrazolyl group, $W^1$ is an unsubstituted alkylene($C_3$) group, $W^2$ is a bond, X is an oxygen atom, Y is a bond, Z is an unsubstituted alkylene group, an optically active form thereof or a pharmaceutically acceptable salt thereof, wherein said disease involving C5a is selected from the group consisting of rheumatoid arthritis, systemic lupus erythematosus (SLE), adult respiratory distress syndrome (ARDS), psoriasis and sepsis.

21. The method of claim 20, wherein the disease involving C5a is rheumatoid arthritis.

22. A C5a receptor antagonist comprising the amide derivative of claim 1, an optically active form thereof or a pharmaceutically acceptable salt thereof as an active ingredient.

23. A pharmaceutical composition comprising the amide derivative of claim 16, an optically active form thereof or a pharmaceutically acceptable salt thereof, and a pharmaceutically acceptable additive.

24. A C5a receptor antagonist comprising the amide derivative of claim 16, an optically active form thereof or a pharmaceutically acceptable salt thereof as an active ingredient.

25. A pharmaceutical composition comprising the amide derivative of claim 18, an optically active form thereof or a pharmaceutically acceptable salt thereof, and a pharmaceutically acceptable additive.

26. A C5a receptor antagonist comprising the amide derivative of claim 18, an optically active form thereof or a pharmaceutically acceptable salt thereof as an active ingredient.

27. An amide derivative N-[(1-ethylpyrazol-4-yl)methyl]-5-hydroxy-N-(4-methoxyphenyl)-1,2,3,4-tetrahydronaphthalene-1-carboxamide, an optically active form thereof or a pharmaceutically acceptable salt thereof.

28. A pharmaceutical composition comprising the amide derivative of claim 27, an optically active form thereof or a pharmaceutically acceptable salt thereof, and a pharmaceutically acceptable additive.

29. A method of treating a disease involving C5a comprising administering to a subject in need thereof an effective amount of the amide derivative of claim 27, an optically active form thereof or a pharmaceutically acceptable salt thereof, wherein said disease involving C5a is selected from the group consisting of rheumatoid arthritis, systemic lupus erythematosus (SLE), adult respiratory distress syndrome (ARDS), psoriasis and sepsis.

30. A C5a receptor antagonist comprising the amide derivative of claim 27, an optically active form thereof or a pharmaceutically acceptable salt thereof as an active ingredient.

31. A method for treating rheumatoid arthritis comprising administering to a subject in need thereof an effective amount of an amide derivative N-[(1-ethylpyrazol-4-yl)methyl]-5-hydroxy-N-(4-methoxyphenyl)-1,2,3,4-tetrahydronaphthalene-1-carboxamide or a pharmaceutically acceptable salt thereof.

32. A pharmaceutical composition comprising an amide derivative N-[(1-ethylpyrazol-4-yl)methyl]-5-hydroxy-N-(6-isopropylpyridin-3-yl)-1,2,3,4-tetrahydronaphthalene-1-carboxamide or a pharmaceutically acceptable salt thereof, and a pharmaceutically acceptable additive.

33. A method of treating a disease involving C5a comprising administering to a subject in need thereof an effective amount of an amide derivative N-[(1-ethylpyrazol-4-yl)methyl]-5-hydroxy-N-(6-isopropylpyridin-3-yl)-1,2,3,4-tetrahydronaphthalene-1-carboxamide or a pharmaceutically acceptable salt thereof, wherein said disease involving C5a is selected from the group consisting of rheumatoid arthritis, systemic lupus erythematosus (SLE), adult respiratory distress syndrome (ARDS), psoriasis and sepsis.

34. A C5a receptor antagonist comprising an amide derivative N-[(1-ethylpyrazol-4-yl)methyl]-5-hydroxy-N-(6-isopropylpyridin-3-yl)-1,2,3,4-tetrahydronaphthalene-1-carboxamide or a pharmaceutically acceptable salt thereof as an active ingredient.

35. A method for treating rheumatoid arthritis comprising administering to a subject in need thereof an effective amount of an amide derivative N-[(1-ethylpyrazol-4-yl)methyl]-5-hydroxy-N-(6-isopropylpyridin-3-yl)-1,2,3,4-tetrahydronaphthalene-1-carboxamide or a pharmaceutically acceptable salt thereof.

36. The method of treating a disease involving C5a according to claim 20, wherein amide derivative of formula (1') is selected from the group consisting of N-[(1-ethylpyrazol-4-yl)methyl]-N-(4-isopropylphenyl)-1,2,3,4-tetrahydronaphthalene-1-carboxamide, N-[(1-ethylpyrazol-4-yl)methyl]-5-hydroxy-N-(4-isopropylphenyl)-1,2,3,4-tetrahydronaphthalene-1-carboxamide, N-[(2,6-dimethoxypyridin-3-yl)methyl]-5-hydroxy-N-(4-isopropylphenyl)-1,2,3,4-tetrahydronaphthalene-1-carboxamide, 5-hydroxy-N-(4-isopropylphenyl)-N-[(6-phenoxypyridin-3-yl)methyl]-1,2,3,4-tetrahydronaphthalene-1-carboxamide, N-[(6-dimethylaminopyridin-3-yl)methyl]-5-hydroxy-N-(4-isopropylphenyl)-1,2,3,4-tetrahydronaphthalene-1-carboxamide, N-[(2,6-dimethoxypyridin-3-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-[(6-methoxypyridin-3-yl)methyl]-1,2,3,4-tetrahydronaphthalene-1-carboxamide, 5-hydroxy-N-(4-isopropylphenyl)-N-{[1-(2-pyridylmethyl)pyrazol-4-yl]methyl}-1,2,3,4-tetrahydronaphthalene-1-carboxamide, N-[(1-benzylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(2-pyridylmethyl)pyrazol-4-yl]methyl}-1,2,3,4-tetrahydronaphthalene-1-carboxamide, N-({1-[(4-fluorophenyl)methyl]pyrazol-4-yl}methyl)-5-hydroxy-N-(6-isopropylpyridin-3-yl)-1,2,3,4-tetrahydronaphthalene-1-carboxamide, N-({1-[(4-chlorophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[(4-trifluoromethylphenyl)methyl]pyrazol-4-yl}methyl)-1,2,3,4-tetrahydronaphthalene-1-carboxamide, 5-hydroxy-N-(6-isopropylpyridin-3-yl)-N-({1-[(4-methoxyphenyl)methyl]pyrazol-4-yl}methyl)-1,2,3,4-tetrahydronaphthalene-1-carboxamide, N-({1-[(4-bromophenyl)methyl]pyrazol-4-yl}methyl)-5-hydroxy-N-(6-isopropylpyridin-3-yl)-1,2,3,4-tetrahydronaphthalene-1-carboxamide, N-({1-[(3-chlorophenyl)methyl]pyrazol-4-yl}methyl)-5-hydroxy-N-(6-isopropylpyridin-3-yl)-1,2,3,4-tetrahydronaphthalene-1-carboxamide, N-({1-[(2-chlorophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[(4-methylphenyl)methyl]pyrazol-4-yl}methyl)-1,2,3,4-tetrahydronaphthalene-1-carboxamide, 5-hydroxy-N-(6-isopropylpyridin-3-yl)-N-({1-[(5-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(5-methoxypyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(4-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(4-trifluoromethylpyridin-2-yl)methyl]pyrazol-4-yl}methyl)-1,2,3,4-tetrahydronaphthalene-1-carboxamide, N-({1-[(6-dimethylaminopyridin-2-yl)methyl]pyrazol-4-yl}methyl)-5-hydroxy-N-(6-isopropylpyridin-3-yl)-1,2,3,4-tetrahydronaphthalene-1-carboxamide, N-({1-[3-(dimethylaminophenyl)methyl]pyrazol-4-yl}methyl)-5-hydroxy-N-(6-isopropylpyridin-3-yl)-1,2,3,4-tetrahydronaphthalene-1-carboxamide, 5-hydroxy-N-(4-isopropylphenyl)-N-[(1-methylpyrazol-4-yl)methyl]-1,2,3,4-tetrahydronaphthalene-1-carboxamide, N-{[1-(cyclohexylmethyl)pyrazol-4-yl]methyl}-5-hydroxy-N-(4-isopropylphenyl)-1,2,3,4-tetrahydronaphthalene-1-carboxamide, 5-hydroxy-N-(4-isopropylphenyl)-N-{[1-(3-thienylmethyl)pyrazol-4-yl]methyl}-1,2,3,4-tetrahydronaphthalene-1-carboxamide, N-{[1-(4-fluorobenzyl)pyrazol-4-yl]methyl}-5-hydroxy-N-(4-methoxyphenyl)-1,2,3,4-tetrahydronaphthalene-1-carboxamide, N-[(1-ethylpyrazol-4-yl)methyl]-5-hydroxy-N-(4-methoxyphenyl)-1,2,3,4-tetrahydronaphthalene-1-carboxamide, N-{[1-(cyclohexylmethyl)pyrazol-4-yl]methyl}-5-hydroxy-N-(4-methoxyphenyl)-1,2,3,4-tetrahydronaphthalene-1-carboxamide, 5-hydroxy-N-(6-isopropylpyridin-3-yl)-N-{[1-(2-piperidinoethyl)pyrazol-4-yl]methyl}-1,2,3,4-tetrahydronaphthalene-1-carboxamide, N-{[1-(cyclohexylmethyl)pyrazol-4-yl]methyl}-5-hydroxy-N-(6-isopropylpyridin-3-yl)-1,2,3,4-tetrahydronaphthalene-1-carboxamide, N-[(1-heptylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(3-thienylmethyl)pyrazol-4-yl]methyl}-1,2,3,4-tetrahydronaphthalene-1-carboxamide, 5-hydroxy-N-(6-isopropylpyridin-3-yl)-N-({1-[(2-methylthiazol-4-yl)methyl]pyrazol-4-yl}methyl)-1,2,3,4-tetrahydronaphthalene-1-carboxamide, N-[(1-butylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-{[1-(3-methylbutyl)pyrazol-4-yl]methyl}-1,2,3,4-tetrahydronaphthalene-1-carboxamide, N-[(1-benzylpyrazol-4-yl)methyl]-5-hydroxy-N-(6-methoxypyridin-3-yl)-1,2,3,4-tetrahydronaphthalene-1-carboxamide, 5-hydroxy-N-(6-isopropylpyridine-3-yl)-N-({1-[2-(2-pyridyl)ethyl]pyrazol-4-yl}methyl)-1,2,3,4-tetrahydronaphthalene-1-carboxamide, N-[(1-dodecylpyrazol-4-yl)methyl]-5-hydroxy-N-(6-isopropylpyridin-3-yl)-1,2,3,4-tetrahydronaphthalene-1-carboxamide, 5-hydroxy-N-(6-isopropylpyridin-3-yl)-N-[(1-nonylpyrazol-4-yl)methyl]-1,2,3,4-tetrahydronaphthalene-1-carboxamide, N-{[1-(2-butoxyethyl)pyrazol-4-yl]methyl}-5-hydroxy-N-(6-isopropylpyridin-3-yl)-1,2,3,4-tetrahydronaphthalene-1-carboxamide, 5-hydroxy-N-(6-isopropylpyridin-3-yl)-N-({1-[2-(2-methoxyethoxy)ethyl]pyrazol-4-yl}methyl)-1,2,3,4-tetrahydronaphthalene-1-carboxamide, 5-hydroxy-N-(4-isopropylphenyl)-N-[(6-morpholinopyridin-3-yl)methyl]-1,2,3,4-tetrahydronaphthalene-1-carboxamide, 5-hydroxy-N-(4-isopropylphenyl)-N-({1-[(4-methylpyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-morpholinopyridin-2-yl)methyl]pyrazol-4-yl}methyl)-1,2,3,4-tetrahydronaphthalene-1-carboxamide, 5-hydroxy-N-(6-isopropylpyridin-3-yl)-N-({1-[(6-methoxypyridin-2-yl)methyl]pyrazol-4-yl}methyl)-1,2,3,4-tetrahydronaphthalene-1-carboxamide, 5-hydroxy-N-[(1-isopropylpyrazol-4-yl)methyl]-N-(6-isopropylpyridin-3-yl)-1,2,3,4-tetrahydronaphthalene-1-carboxamide, 5-hydroxy-N-(6-isopropylpyridin-3-yl)-N-{[1-(2-thienylmethyl)pyrazol-4-yl]methyl}-1,2,3,4-tetrahydronaphthalene-1-carboxamide, N-({1-[(5-chlorothiophen-2-yl)methyl]pyrazol-4-yl}methyl)-5-hydroxy-N-(6-isopropylpyridin-3-yl)-1,2,3,4-tetrahydronaphthalene-1-carboxamide, N-({1-[2-(2-butoxyethoxy)ethyl]pyrazol-4-yl}methyl)-5-hydroxy-N-(6-isopropylpyridin-3-yl)-1,2,3,4-tetrahydronaphthalene-1-carboxamide, and N-({1-[2-(2-ethoxyethoxy)ethyl]pyrazol-4-yl}methyl)-N-(6-isopropylpyridin-3-yl)-5-hydroxy-1,2,3,4-tetrahydronaphthalene-1-carboxamide, an optically active form thereof or a pharmaceutically acceptable salt thereof.

37. The method of claim 36, wherein the disease involving C5a is rheumatoid arthritis.

* * * * *